US008569026B2

(12) United States Patent
Chotani et al.

(10) Patent No.: US 8,569,026 B2
(45) Date of Patent: Oct. 29, 2013

(54) SYSTEMS USING CELL CULTURE FOR PRODUCTION OF ISOPRENE

(75) Inventors: Gopal K. Chotani, Cupertino, CA (US); Joseph C. McAuliffe, Sunnyvale, CA (US); Caroline M. Peres, Palo Alto, CA (US); Gregory M. Whited, Belmont, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 866 days.

(21) Appl. No.: 12/560,366

(22) Filed: Sep. 15, 2009

(65) Prior Publication Data

US 2010/0167371 A1 Jul. 1, 2010

Related U.S. Application Data

(60) Provisional application No. 61/097,163, filed on Sep. 15, 2008, provisional application No. 61/187,832, filed on Jun. 17, 2009.

(51) Int. Cl.
*C12P 5/02* (2006.01)
*C12M 1/04* (2006.01)
*C12N 9/16* (2006.01)

(52) U.S. Cl.
USPC .................. 435/167; 435/296.1; 435/196

(58) Field of Classification Search
USPC ........................... 435/167, 296.1, 196
See application file for complete search history.

(56) References Cited

U.S. PATENT DOCUMENTS

| | | | |
|---|---|---|---|
| 4,570,029 A | 2/1986 | Kulprathipanja et al. | |
| 4,652,527 A | 3/1987 | Stirling | |
| 4,683,202 A | 7/1987 | Mullis | |
| 4,703,007 A | 10/1987 | Mulholland et al. | |
| 5,849,970 A | 12/1998 | Fall et al. | |
| 5,874,276 A | 2/1999 | Fowler et al. | |
| 6,022,725 A | 2/2000 | Fowler et al. | |
| 6,106,888 A | 8/2000 | Dale et al. | |
| 6,176,176 B1 | 1/2001 | Dale et al. | |
| 6,268,328 B1 | 7/2001 | Mitchinson et al. | |
| 7,132,527 B2 | 11/2006 | Payne et al. | |
| 7,241,587 B2 | 7/2007 | Dodge et al. | |
| 7,262,041 B2 | 8/2007 | Baldwin et al. | |
| 2008/0038805 A1 | 2/2008 | Melis | |
| 2010/0048964 A1 | 2/2010 | Calabria et al. | |

FOREIGN PATENT DOCUMENTS

| | | |
|---|---|---|
| EP | 0 215 594 A2 | 3/1987 |
| EP | 0 215 594 A3 | 3/1987 |
| EP | 0 215 594 B1 | 3/1987 |
| EP | 0 215 594 B2 | 3/1987 |

(Continued)

OTHER PUBLICATIONS

Karl et al., "Human breath isoprene and its relation to blood cholesterol levels: new measurements and modeling," J Appl Physiol 91:762-770, 2001.*

(Continued)

*Primary Examiner* — Rosanne Kosson
(74) *Attorney, Agent, or Firm* — Morrison & Foerster LLP

(57) ABSTRACT

The invention features methods for producing isoprene from cultured cells. The invention also provides compositions that include these cultured cells. The invention provides isoprene compositions, such as compositions with increased amount of isoprene or increased purity. Additionally, the invention provides methods of producing isoprene by culturing cells under conditions suitable for isoprene production while maintaining cell viability and/or metabolic activity.

20 Claims, 296 Drawing Sheets

(56) References Cited

FOREIGN PATENT DOCUMENTS

| EP | 0 238 023 A2 | 9/1987 |
|---|---|---|
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 137 280 B1 | 3/1992 |
| WO | WO-95/04134 A1 | 2/1995 |
| WO | WO-96/35796 A1 | 11/1996 |
| WO | WO 9802550 A2 * | 1/1998 |
| WO | WO-2004/033646 A2 | 4/2004 |
| WO | WO-2004/033646 A3 | 4/2004 |
| WO | WO-2005/001036 A2 | 1/2005 |
| WO | WO-2005/001036 C1 | 1/2005 |
| WO | WO-2007/140339 A2 | 12/2007 |
| WO | WO-2007/140339 A3 | 12/2007 |
| WO | WO-2007/140339 A8 | 12/2007 |
| WO | WO-2008/003078 A2 | 1/2008 |
| WO | WO-2008/003078 A3 | 1/2008 |
| WO | WO-2008/003078 A8 | 1/2008 |
| WO | WO-2009/076676 A2 | 6/2009 |
| WO | WO-2009/076676 A3 | 6/2009 |
| WO | WO-2010/003007 A2 | 1/2010 |
| WO | WO-2010/003007 A3 | 1/2010 |

OTHER PUBLICATIONS

Anderson, M.S. et al. (Nov. 15, 1989). "Isopentenyl Diphosphate: Dimethylallyl Diphosphate Isomerase. An Improved Purification of the Enzyme and Isolation of the Gene From *Saccharomyces cerevisiae*," *J. Biol. Chem.* 264(32):19169-19175.

Bellion, E. et al. (1993). "Methylamine Utilization in Yeast and Bacteria: Studies Using in vivo NMR," Chapter 32 in *Microbial Growth on $C_1$ Compounds*, Murrell, J.C. et al. eds, Intercept Limited: Andover, UK, pp. 415-432.

Bennett, J.W. et al. eds. (1991). "Gene Cloning and Analysis," Chapter 3 in *More Gene Manipulations in Fungi*, Academic Press, Inc.: San Diego, CA, pp. 70-76.

Boel, E. et al. (1984). "Two Different Types of Intervening Sequences in the Glucoamylase Gene from *Aspergillus niger*," *The EMBO Journal* 3(7):1581-1585.

Bouvier, F. et al. (2005). "Biogenesis, Molecular Regulation and Function of Plant Isoprenoids," *Progress in Lipid Research* 44:357-429.

Brown, L. et al. (Aug. 26, 1996). "Enzymatic Saccharification of Lignocellulosic Biomass," *NREL, Ethanol Project, Chemical Analysis and Testing Task, LAP-009*, pp. 1-8.

Bunge, M. et al. (Apr. 2008). "On-Line Monitoring of Microbial Volatile Metabolites by Proton Transfer Reaction-Mass Spectrometry," *Applied and Environmental Microbiology* 74(7):2179-2186.

Campbell, E.I. et al. (1989). "Improved Transformation Efficiency of *Aspergillus niger* Using the Homologus *niaD* Gene for Nitrate Reductase," *Curr. Genet.* 16:53-56.

Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.

Cho, S. et al. (Sep. 2002). "Adsorptive Ethylene Recovery from LDPE Off-Gas," *Korean J. Chem. Eng.* 19(5):821-826.

Dhe-Paganon, S. et al. (1994). "Mechanism of Mevalonate Pyrophosphate Decarboxylase: Evidence for a Carbocationic Transition State," *Biochemistry* 33(45):13355-13362.

Finkelstein, D.B. (1992). "Transformation," Chapter 6 in *Biotechnology of Filamentous Fungi*, Butterworth-Heinemann: Boston, MA, pp. 113-156.

Fungal Genetics Stock Center (2012). "FGSC Online Catalog of Strains," located at <http://www.fgsc.net/>, last visited on Dec. 27, 2012, 1 page.

GenBank Accession No. AAQ16588, last updated on Feb. 15, 2005, located at <http://www.ncbi.nlm.nih.gov/protein/AAQ16588>, last visited on May 29, 2012, 2 pages.

GenBank Accession No. AAQ84170, last updated on Feb. 15, 2005, located at <http://www.ncbi.nlm.nih.gov/protein/AAQ84170>, last visited on Dec. 22, 2011, 2 pages.

GenBank Accession No. ACD70404, last visited on May 27, 2008, located at <http://www.ncbi.nlm.nih.gov/protein/ACD70404>, last visited on May 29, 2012, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/AY341431>, last visited on Feb. 27, 2012, 2 pages.

GenBank Accession No. BAD98243, last updated on May 10, 2005, located at <http://www.ncbi.nlm.nih.gov/protein/BAD98243>, last visited on Dec. 10, 2012, 2 pages.

GenBank Accession No. CAC35696, last updated on Apr. 15, 2005, located at <http://www.ncbi.nlm.nih.gov/protein/CAC35696>, last visited on Nov. 1, 2011, 1 page.

GenBank Accession No. CAJ29303, last updated on Jan. 10, 2007, located at <http://www.ncbi.nlm.nih.gov/protein/CAJ29303>, last visited on May 29, 2012, 1 page.

GenBank Accession No. CAL69918, last updated on Aug. 14, 2008, located at <http://www.ncbi.nlm.nih.gov/protein/CAL69918>, last visited on May 29, 2012, 2 pages.

GenBank Accession No. D86235, last updated on Oct. 29, 1997, located at <http://www.ncbi.nlm.nih.gov/nuccore/D86235>, last visited on Feb. 27, 2012, 2 pages.

GenBank Accession No. EF175870, last updated on Jan. 13, 2007, located at <http://www.ncbi.nlm.nih.gov/nuccore/EF175870>, last visited on May 29, 2012, 1 page.

GenBank Accession No. NC_003901.1, last updated on Dec. 21, 2012, located at <http://www.ncbi.nlm.nih.gov/nuccore/NC_003901.1>, last visited on Dec. 27, 2012, 515 pages.

GenomeNet (2012). "Steroid Biosynthesis—Reference Pathway," in KEGG: Kyoto Encyclopedia of Genes and Genomes, located at <http://www.genome.jp/kegg/pathway/map/map00100.html>, last visited on Dec. 28, 2012, 1 page.

Goedegebuur, F. et al. (2002). "Cloning and Relational Analysis of 15 Novel Fungal Endoglucanases from Family 12 Glycosyl Hydrolase," *Curr. Genet.* 41:89-98.

Gräwert, T. et al. (2004, e-pub. Sep. 21, 2004). "IspH Protein of *Escherichia coli*: Studies on Iron-Sulfur Cluster Implementation and Catalysis," *J. Am. Chem. Soc.* 126:12847-12855.

Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.

Harkki, A. et al. (Jun. 1989). "A Novel Fungal Expression System: Secretion of Active Calf Chymosin from the Filamentous Fungus *Trichoderma reesei*," *Bio/Technology* 7:596-603.

Harkki, A. et al. (Mar. 1991). "Genetic Engineering of *Trichoderma* to Produce Strains with Novel Cellulase Profiles," *Enzyme Microb. Technol.* 13:227-233.

Hedl, M. et al. (Apr. 2002). "*Enterococcus faecalis* Acetoacetyl-Coenzyme a Thiolase/3-Hydroxy-3-Methylglutaryl-Coenzyme A Reductase, a Dual-Function Protein of Isopentenyl Diphosphate Biosynthesis," *Journal of Bacteriology* 184(8):2116-2122.

Hoeffler, J-F. et al. (2002). "Isoprenoid Biosynthesis via the Methylerythritol Phosphate Pathway. Mechanistic Investigations of the 1-Deoxy-$_D$-Xylulose 5-Phosphate Reductoisomerase," *Eur. J. Biochem.* 269:4446-4457.

(56) References Cited

OTHER PUBLICATIONS

Hunter, B.K. et al. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.

Ilmén, M. et al. (Apr. 1997). "Regulation of Cellulase Gene Expression in the Filamentous Fungus *Trichoderma reesei*," *Applied and Environmental Microbiology* 63(4):1298-1306.

Innis, M.A. et al. (Apr. 1985). "Expression, Glycosylation, and Secretion of an *Aspergillus* Glucoamylase by *Saccharomyces cerevisiae*," *Science* 228:21-26.

International Search Report mailed on Feb. 12, 2010, for PCT Patent Application No. PCT/US2009/057021, filed on Sep. 15, 2009, 5 pages.

International Search Report mailed on Feb. 10, 2010, for PCT Patent Application No. PCT/US2009/057039, filed on Sep. 15, 2009, 5 pages.

Julsing, M.K. et al. (Jul. 2007, e-pub. Apr. 26, 2007). "Functional Analysis of Genes Involved in the Biosynthesis of Isoprene in *Bacillus subtilis*," *Appl. Microbiol. Biotechnol.* 75(6):1377-1384.

Karl, T. et al. (2003). "Dynamic Measurements of Partition Coefficients Using Proton-Transfer-Reaction Mass Spectrometry (PTR-MS)," *International Journal of Mass Spectrometry* 223-224, 383-395.

Kelley, J.M. et al. (1985). "Transformation of *Aspergillus niger* by the *amdS* Gene of *Aspergillus nidulans*," *The EMBO Journal* 4(2):475-479.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Kovach, M.E. et al. (1995). "Four New Derivatives of the Broad-Host-Range Cloning Vector pBBR1MCS, Carrying Different Antibiotic-Resistance Cassettes," *Gene* 166:175-176.

Ladygina, N. et al. (2006). "A Review on Microbial Synthesis of Hydrocarbons," *Process Biochemistry* 41:1001-1014.

Lüttgen, H. et al. (Feb. 1, 2000). "Biosynthesis of Terpenoids: YchB Protein of *Escherichia coli* Phosphorylates the 2-Hydroxy Group of 4-Diphosphocytidyl-2C-Methyl-$_D$-Erythritol," *PNAS* 97(3):1062-1067.

Maury, J. et al. (2005). "Microbial Isoprenoid Production: An Example of Green Chemistry through Metabolic Engineering," *Adv. Biochem. Engin/Biotechnol.* 100:19-51.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Neidhardt, F.C. et al. (Sep. 1974). "Culture Medium for Enterobacteria," *Journal of Bacteriology* 119(3):736-747.

Nevalainen, K.M.H. et al. (1991). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc.: New York, NY, pp. 129-148.

NFPA 69, (2008 Edition). "Standard on Explosion Prevention Systems."

Nunberg, J.H. et al. (Nov. 1984). "Molecular Cloning and Characterization of the Glucoamylase Gene of *Aspergillus awamori*," *Molecular and Cellular Biology* 4(11):2306-2315.

Oulmouden, A. et al. (1991). "Nucleotide Sequence of the *ERG12* Gene of *Saccharomyces cerevisiae* Encoding Mevalonate Kinase," *Curr. Genet.* 19:9-14.

Penttilä, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein, A.L. et al. eds., American Society for Microbiology: Washington, D.C., pp. 615-624.

Pourquié, J. et al. (1988). "Scale Up of Cellulase Production and Utilization," in *Biochemistry and Genetics of Cellulose Degradation*, Aubert, J-P. et al. eds., Academic Press: San Diego, CA, pp. 71-86.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-*C*-Methylerythritol," *PNAS* 96(21):11758-11763.

Rohdich, F. et al. (Jun. 6, 2000). "Biosynthesis of Terpenoids: 4-Diphosphocytidyl-2C-Methyl-$_D$-Erythritol Synthase of *Arabidopsis thaliana*," *PNAS* 97(12):6451-6456.

Schnitzler, J.-P. et al. (2005, e-pub. Jul. 29, 2005). "Biochemical Properties of Isoprene Synthase in Poplar (*Populus* x *canescens*)," *Planta* 222(5):777-786.

Sharkey, T.D. et al. (Feb. 2005). "Evolution of the Isoprene Biosynthetic Pathway in Kudzu[1[w]]," *Plant Physiology* 137:700-712.

Sheir-Neiss, G. et al. (Jul. 1984). "Characterization of the Secreted Cellulases of *Trichoderma reesei* Wild Type and Mutants During Controlled Fermentations," *Applied Microbiology and Biotechnology* 20(1):46-53.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sprenger, G.A. et al. (Nov. 1997). "Identification of a Thiamin-Dependent Synthase in *Escherichia coli* Required for the Formation of the 1-Deoxy-$_D$-Xylulose 5-Phosphate Precursor to Isoprenoids, Thiamin, and Pyridoxol," *Proc. Natl. Acad. Sci. USA* 94:12857-12862.

Sulter, G.J. et al. (1990). "Proliferation and Metabolic Significance of Peroxisomes in *Candida boidinii* During Growth on $_D$-Alanine or Oleic Acid as the Sole Carbon Source," *Archives of Microbiology* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.

Swiss Institute of Bioinformatics (2012). "ExPASy Bioinformatics Resource Portal," located at <http://expasy.org>, last visited on Dec. 27, 2012, 1 page.

Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.

Tsay, Y.H. et al. (Feb. 1991). "Cloning and Characterization of *ERG8*, an Essential Gene of *Saccharomyces cerevisiae* That Encodes Phosphomevalonate Kinase," *Molecular and Cellular Biology* 11(2):620-631.

Van Den Hondel, C.A.M.J.J. et al. (1991). "Heterologous Gene Expression in Filamentous Fungi," Chapter 18 in *More Gene Manipulations in Fungi*, Bennett, J.W. et al. eds., Academic Press, Inc.: San Diego, CA, pp. 396-428.

Wagner, W.P. et al. (Aug. 1999). "Three Distinct Phases of Isoprene Formation During Growth and Sporulation of *Bacillus subtilis*," *Journal of Bacteriology* 181(15):4700-4703.

Ward, M. et al. (Aug. 1993). "Use of *Aspergillus* Overproducing Mutants, Cured for Integrated Plasmid, to Overproduce Heterologous Proteins," *Applied Microbiology and Biotechnology* 39(6):738-743.

Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.

Yamada, K. et al. (1989). "Production of Glycerol from Methanol by a Mutant Strain of *Candida boidinii* No. 2201," *Agric. Biol. Chem.* 53(2):541-543.

Yelton, M.M. et al. (Mar. 1984). "Transformation of *Aspergillus nidulans* by Using a *trpC* Plasmid," *Proc. Natl. Acad. Sci. USA* 81:1470-1474.

(56) References Cited

OTHER PUBLICATIONS

Zabetakis, M.G. (1965). "Flammability Characteristics of Combustible Gases and Vapors," Bulletin 627, Bureau of Mines, U.S. Dept. of the Interior: Washington, D.C.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

Airgas Inc. (May 12, 1996). "Material Safety Data Sheet for Ethylene—$C_2H_4$ (Document #001022)," located at http://terpconnect.umd.edu/~choi/MSDS/Airgas/ETHYLENE.pdf, 9 pages.

OECD SIDS (2005). "Isoprene CAS No. 78-79-5." SIDS Initial Assessment Report for SIAM 20, Paris, France, Apr. 19-22, 2005, UNEP Publications located at http://www.chem.unep.ch/irptc/sids/oecdsids/78795.pdf, 116 pages.

* cited by examiner

Figure 1

1-
*atg*tgtgcgacctcttctcaatttactcagattaccgagcataattcccgtcgttccgcaaactatcagccaaa
cctgtggaatttcgaattcctgcaatccctggagaacgacctgaaagtggaaaagctggaggagaaagc
gaccaaactggaggaagaagttcgctgcatgatcaaccgtgtagacacccagccgctgtccctgctgga
gctgatcgacgatgtgcagcgcctgggtctgacctacaaatttgaaaaagacatcattaaagccctggaa
aacatcgtactgctggacgaaaacaaaaagaacaaatctgacctgcacgcaaccgctctgtctttccgtct
gctgcgtcagcacggtttcgaggtttctcaggatgttttgagcgtttcaaggataaagaaggtggtttcagcg
gtgaactgaaaggtgacgtccaaggcctgctgagcctgtatgaagcgtcttacctgggtttcgagggtgag
aacctgctggaggaggcgcgtaccttttccatcacccacctgaagaacaacctgaaagaaggcattaata
ccaaggttgcagaacaagtgagccacgccctggaactgccatatcaccagcgtctgcaccgtctggagg
cacgttggttcctggataaatacgaaccgaaagaaccgcatcaccagctgctgctggagctggcgaagct
ggattttaacatggtacagaccctgcaccagaaagagctgcaagatctgtcccgctggtggaccgagatg
ggcctggctagcaaactggattttgtacgcgaccgcctgatggaagtttatttctgggcactgggtatggcgc
cagacccgcagtttggtgaatgtcgcaaagctgttactaaaatgtttggtctggtgacgatcatcgatgacgt
gtatgacgtttatggcactctggacgaactgcaactgttcaccgatgctgtagagcgctgggacgttaacgct
attaacaccctgccggactatatgaaactgtgtttcctggcactgtacaacaccgttaacgacacgtcctattc
tattctgaaagagaaaggtcataacaacctgtcctatctgacgaaaagctggcgtgaactgtgcaaagcct
ttctgcaagaggcgaaatggtccaacaacaaaattatcccggctttctccaagtacctggaaaacgccag
cgtttcctcctccggtgtagcgctgctggcgccgtcttacttttccgtatgccagcagcaggaagacatctccg
accacgcgctgcgttccctgaccgacttccatggtctggtgcgttctagctgcgttatcttccgcctgtgcaac
gatctggccacctctgcggcggagctggaacgtggcgagactaccaattctatcattagctacatgcacga
aaacgatggtaccagcgaggaacaggcccgcgaagaactgcgtaaactgatcgacgccgaatggaaa
aagatgaatcgtgaacgcgttagcgactccaccctgctgcctaaagcgttcatggaaatcgcagttaacat
ggcacgtgttcccactgcacctaccagtatggcgatggtctgggtcgcccagactacgcgactgaaaacc
gcatcaaactgctgctgattgacccttttcccgattaaccagctgatgtatgtc
taactgcag
(SEQ ID NO:1)

Figure 3A

1-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgtttttgcgcc
gacatcataacggttctggcaaatattctgaaatgagctgttgacaattaatcatccggctcgtataatgtgtgga
attgtgagcggataacaatttcacacaggaaacagcgccgctgagaaaaagcgaagcggcactgctcttta
acaatttatcagacaatctgtgtgggcactcgaccggaattatcgattaactttattattaaaaattaaagaggtat
atattaatgtatcgattaaataaggaggaataaaccATGtgtgcgacctcttctcaatttactcagattaccgag
cataattcccgtcgttccgcaaactatcagccaaacctgtggaatttcgaattcctgcaatccctggagaacga
cctgaaagtggaaaagctggaggagaaagcgaccaaactggaggaagaagttcgctgcatgatcaaccgt
gtagacacccagccgctgtccctgctggagctgatcgacgatgtgcagcgcctgggtctgacctacaaatttg
aaaaagacatcattaaagccctggaaaacatcgtactgctggacgaaaacaaaaagaacaaatctgacct
gcacgcaaccgctctgtctttccgtctgctgcgtcagcacggtttcgaggtttctcaggatgtttttgagcgtttcaa
ggataaagaaggtggtttcagcggtgaactgaaaggtgacgtccaaggcctgctgagcctgtatgaagcgtct
tacctgggtttcgagggtgagaacctgctggaggaggcgcgtaccttttccatcacccacctgaagaacaacc
tgaaagaaggcattaataccaaggttgcagaacaagtgagccacgccctggaactgccatatcaccagcgt
ctgcaccgtctggaggcacgttggttcctggataaatacgaaccgaaagaaccgcatcaccagctgctgctg
gagctggcgaagctggattttaacatggtacagaccctgcaccagaaagagctgcaagatctgtcccgctgg
tggaccgagatgggcctggctagcaaactggattttgtacgcgaccgcctgatggaagtttattctgggcactg
ggtatggcgccagacccgcagtttggtgaatgtcgcaaagctgttactaaaatgtttggtctggtgacgatcatc
gatgacgtgtatgacgtttatggcactctggacgaactgcaactgttcaccgatgctgtagagcgctgggacgtt
aacgctattaacaccctgccggactatatgaaactgtgtttcctggcactgtacaacaccgttaacgacacgtc
ctattctattctgaaagagaaaggtcataacaacctgtcctatctgacgaaaagctggcgtgaactgtgcaaag
cctttctgcaagaggcgaaatggtccaacaacaaaattatcccggctttctccaagtacctggaaaacgccag
cgtttcctcctccggtgtagcgctgctggcgccgtcttacttttccgtatgccagcagcaggaagacatctccgac
cacgcgctgcgttccctgaccgacttccatggtctggtgcgttctagctgcgttatcttccgcctgtgcaacgatct
ggccacctctgcggcggagctggaacgtggcgagactaccaattctatcattagctacatgcacgaaaacga
tggtaccagcgaggaacaggcccgcgaagaactgcgtaaactgatcgacgccgaatggaaaaagatgaa
tcgtgaacgcgttagcgactccaccctgctgcctaaagcgttcatggaaatcgcagttaacatggcacgtgtttc
ccactgcacctaccagtatggcgatggtctgggtcgcccagactacgcgactgaaaaccgcatcaaactgct
gctgattgaccctttcccgattaaccagctgatgtatgtc*TAA*ctgcagctggtaccatatgggaattcgaagct
ttctagaacaaaaactcatctcagaagaggatctgaatagcgccgtcgaccatcatcatcatcatcattgagttt
aaacggtctccagcttggctgttttggcggatgagagaagattttcagcctgatacagattaaatcagaacgca
gaagcggtctgataaaacagaatttgcctggcggcagtagcgcggtggtcccacctgaccccatgccgaact
cagaagtgaaacgccgtagcgccgatggtagtgtggggtctccccatgcgagagtagggaactgccaggc
atcaaataaaacgaaaggctcagtcgaaagactgggcctttcgttttatctgttgtttgtcggtgaacgctctcctg
agtaggacaaatccgccgggagcggatttgaacgttgcgaagcaacggcccgg

Figure 3B agggtggcgggcaggacgcccgccataaactgccaggcatcaaattaagcagaaggccatcctgac
ggatggccttttttgcgtttctacaaactcttttttgtttatttttctaaatacattcaaatatgtatccgctcatgagac
aataaccctgataaatgcttcaataatattgaaaaaggaagagtatgagtattcaacatttccgtgtcgccc
ttattccctttttttgcggcattttgccttcctgtttttgctcacccagaaacgctggtgaaagtaaaagatgctga
agatcagttgggtgcacgagtgggttacatcgaactggatctcaacagcggtaagatccttgagagttttc
gccccgaagaacgttttccaatgatgagcacttttaaagttctgctatgtggcgcggtattatcccgtgttgac
gccgggcaagagcaactcggtcgccgcatacactattctcagaatgacttggttgagtactcaccagtca
cagaaaagcatcttacggatggcatgacagtaagagaattatgcagtgctgccataaccatgagtgata
acactgcggccaacttacttctgacaacgatcggaggaccgaaggagctaaccgcttttttgcacaacat
gggggatcatgtaactcgccttgatcgttgggaaccggagctgaatgaagccataccaaacgacgagc
gtgacaccacgatgcctgtagcaatggcaacaacgttgcgcaaactattaactggcgaactacttactct
agcttcccggcaacaattaatagactggatggaggcggataaagttgcaggaccacttctgcgctcggc
ccttccggctggctggtttattgctgataaatctggagccggtgagcgtgggtctcgcggtatcattgcagca
ctggggccagatggtaagccctcccgtatcgtagttatctacacgacggggagtcaggcaactatggatg
aacgaaatagacagatcgctgagataggtgcctcactgattaagcattggtaactgtcagaccaagttta
ctcatatatactttagattgatttaaaacttcattttttaatttaaaaggatctaggtgaagatcctttttgataatct
catgaccaaaatcccttaacgtgagttttcgttccactgagcgtcagaccccgtagaaaagatcaaagga
tcttcttgagatcctttttttctgcgcgtaatctgctgcttgcaaacaaaaaaaccaccgctaccagcggtggt
ttgtttgccggatcaagagctaccaactctttttccgaaggtaactggcttcagcagagcgcagataccaa
atactgtccttctagtgtagccgtagttaggccaccacttcaagaactctgtagcaccgcctacatacctcg
ctctgctaatcctgttaccagtggctgctgccagtggcgataagtcgtgtcttaccgggttggactcaagac
gatagttaccggataaggcgcagcggtcgggctgaacggggggttcgtgcacacagcccagcttggag
cgaacgacctacaccgaactgagatacctacagcgtgagctatgagaaagcgccacgcttcccgaag
ggagaaaggcggacaggtatccggtaagcggcagggtcggaacaggagagcgcacgagggagctt
ccaggggggaaacgcctggtatctttatagtcctgtcgggtttcgccacctctgacttgagcgtcgatttttgtg
atgctcgtcaggggggcggagcctatggaaaaacgccagcaacgcggcctttttacggttcctggccttt
gctggccttttgctcacatgttctttcctgcgttatcccctgattctgtggataaccgtattaccgcctttgagtga
gctgataccgctcgccgcagccgaacgaccgagcgcagcgagtcagtgagcgaggaagcggaaga
gcgcctgatgcggtattttctccttacgcatctgtgcggtatttcacaccgcatatggtgcactctcagtacaa
tctgctctgatgccgcatagttaagccagtatacactccgctatcgctacgtgactgggtcatggctgcgcc
ccgacacccgccaacacccgctgacgcgccctgacgggcttgtctgctcccggcatccgcttacagaca
agctgtgaccgtctccgggagctgcatgtgtcagaggttttcaccgtcatcaccgaaacgcgcgaggca
gcagatcaattcgcgcgcgaaggcgaagcggcatgcatttacgttgacaccatcgaatggtgcaaaac
ctttcgcggtatggcatgatagcgcccggaagagagtcaattcagggtggtgaatgtgaaaccagtaac
gttatacgatgtcgcagagtatgccggtgtctcttatcagaccgtttcccgcgtggtgaaccaggccagcc
acgtttctgcgaaaacgcgggaaaaagtggaagcggcgatggcggagctgaattacattcccaaccgc
gtggcacaacaactggcgggcaaacagtcgttgctgattggcgttgccacctccagtctggccctgcacg
cgccgtcgcaaattgtcgcggcgattaaatctcgcgccgatcaactgggtgccagcgtggtggtgtcgat
ggtagaacgaagcggcgtcgaagcctgtaaagcggcggtgcacaatcttctcgcgcaacgcgtcagtg
ggctgatcattaactatccgctggatgaccaggatgccattgctgtggaagctgcct

Figure 3C

Gcactaatgttccggcgttatttcttgatgtctctgaccagacacccatcaacagtattattttctc
ccatgaagacggtacgcgactgggcgtggagcatctggtcgcattgggtcaccagcaaat
cgcgctgttagcgggcccattaagttctgtctcggcgcgtctgcgtctggctggctggcataaa
tatctcactcgcaatcaaattcagccgatagcggaacgggaaggcgactggagtgccatgt
ccggttttcaacaaaccatgcaaatgctgaatgagggcatcgttcccactgcgatgctggttg
ccaacgatcagatggcgctgggcgcaatgcgcgccattaccgagtccgggctgcgcgttg
gtgcggatatctcggtagtgggatacgacgataccgaagacagctcatgttatatcccgccg
tcaaccaccatcaaacaggattttcgcctgctggggcaaaccagcgtggaccgcttgctgc
aactctctcagggccaggcggtgaagggcaatcagctgttgcccgtctcactggtgaaaag
aaaaaccaccctggcgcccaatacgcaaaccgcctctccccgcgcgttggccgattcatta
atgcagctggcacgacaggtttcccgactggaaagcgggcagtgagcgcaacgcaatta
atgtgagttagcgcgaattgatctg
(SEQ ID NO:2)

Figure 5A

1-
ttctcatgtttgacagcttatcatcgataagctttaatgcggtagtttatcacagttaaattgctaacgcagtca
ggcaccgtgtatgaaatctaacaatgcgctcatcgtcatcctcggcaccgtcaccctggatgctgtaggca
taggcttggttatgccggtactgccgggcctcttgcgggatatccggatatagttcctccttcagcaaaaaa
cccctcaagacccgtttagaggccccaaggggttatgctagttattgctcagcggtggcagcagccaact
cagcttcctttcgggctttgttagcagccggatccctgcagttagacatacatcagctggttaatcgggaaa
gggtcaatcagcagcagtttgatgcggttttcagtcgcgtagtctgggcgacccagaccatcgccatactg
gtaggtgcagtgggaaacacgtgccatgttaactgcgatttccatgaacgctttaggcagcagggtggag
tcgctaacgcgttcacgattcatctttttccattcggcgtcgatcagtttacgcagttcttcgcgggcctgttcct
cgctggtaccatcgttttcgtgcatgtagctaatgatagaattggtagtctcgccacgttccagctccgccgc
agaggtggccagatcgttgcacaggcggaagataacgcagctagaacgcaccagaccatggaagtc
ggtcagggaacgcagcgcgtggtcggagatgtcttcctgctgctggcatacggaaaagtaagacggcg
ccagcagcgctacaccggaggaggaaacgctggcgttttccaggtacttggagaaagccgggataattt
tgttgttggaccatttcgcctcttgcagaaaggctttgcacagttcacgccagcttttcgtcagataggacag
gttgttatgacctttctctttcagaatagaataggacgtgtcgttaacggtgttgtacagtgccaggaaacac
agtttcatatagtccggcagggtgttaatagcgttaacgtcccagcgctctacagcatcggtgaacagttgc
agttcgtccagagtgccataaacgtcatacacgtcatcgatgatcgtcaccagaccaaacattttagtaac
agctttgcgacattcaccaaactgcgggtctggcgccatacccagtgcccagaaataaacttccatcagg
cggtcgcgtacaaaatccagtttgctagccaggcccatctcggtccaccagcgggacagatcttgcagct
ctttctggtgcagggtctgtaccatgttaaaatccagcttcgccagctccagcagcagctggtgatgcggtt
ctttcggttcgtatttatccaggaaccaacgtgcctccagacggtgcagacgctggtgatatggcagttcca
gggcgtggctcacttgttctgcaaccttggtattaatgccttctttcaggttgttcttcaggtgggtgatggaaa
aggtacgcgcctcctccagcaggttctcaccctcgaaacccaggtaagacgcttcatacaggctcagca
ggccttggacgtcacctttcagttcaccgctgaaaccaccttctttatccttgaaacgctcaaaaacatcctg
agaaacctcgaaaccgtgctgacgcagcagacggaaagacagagcggttgcgtgcaggtcagatttgt
tcttttgtttcgtccagcagtacgatgttttccagggctttaatgatgtcttttcaaatttgtaggtcagaccca
ggcgctgcacatcgtcgatcagctccagcagggacagcggctgggtgtctacacggttgatcatgcagc
gaacttcttcctccagtttggtcgctttctcctccagcttttccactttcaggtcgttctccagggattgcaggaat
tcgaaattccacaggtttggctgatagtttgcggaacgacgggaattatgctcggtaatctgagtaaattga
gaagaggtcgcacacatatgacgaccttcgatatggccgctgctgtgatgatgatgatgatgatgatg
atggcccatggtatatctccttcttaaagttaaacaaaattattctagagggggaattgttatccgctcacaatt
cccctatagtgagtcgtattaatttcgcgggatcgagatctcgatcctctacgccggacgcatcgtggccgg
catcaccggcgccacaggtgcggttgctggcgcctatatcgccgacatcaccgatggggaagatcggg
ctcgccacttcgggctcatgagcgcttgtttcggcgtgggtatggtggcaggcccgtggccgggggact
gttgggcgccatctccttgcatgcaccattccttgcggcggcggtgctcaacggcctcaacctactactgg
gctgcttcctaatgcaggagtcgcataagggagagcgtcgagatcccggacaccatcgaatggcgcaa
aaccttcgcggtatggcatgatagcgcccggaagagagtcaattcaggtggtgaatgtgaaaccagt
aacgttatacgatgtcgcagagtatgccggtgtctcttatcagaccgtttcccgcgtggtgaaccaggcca
gccacgtttctgcgaaaacgcgggaaaaagtggaagcggcgatggcggagctgaattacattcccaac
cgcgtggcacaacaactggcgggcaaacagtcgttgctgattggcgttgccacctccagtctggccctgc
acgcgccgtcgcaaattgtcgcggcgattaaatct

Figure 5B cgcgccgatcaactgggtgccagcgtggtggtgtcgatggtagaacgaagcggcgtcgaagcctgta
aagcggcggtgcacaatcttctcgcgcaacgcgtcagtgggctgatcattaactatccgctggatgacc
aggatgccattgctgtggaagctgcctgcactaatgttccggcgttatttcttgatgtctctgaccagacac
ccatcaacagtattattttctcccatgaagacggtacgcgactgggcgtggagcatctggtcgcattgggt
caccagcaaatcgcgctgttagcgggcccattaagttctgtctcggcgcgtctgcgtctggctggctggc
ataaatatctcactcgcaatcaaattcagccgatagcggaacgggaaggcgactggagtgccatgtcc
ggttttcaacaaaccatgcaaatgctgaatgagggcatcgttcccactgcgatgctggttgccaacgatc
agatggcgctgggcgcaatgcgcgccattaccgagtccgggctgcgcgttggtgcggatatctcggta
gtgggatacgacgataccgaagacagctcatgttatatcccgccgttaaccaccatcaaacaggatttt
cgcctgctggggcaaaccagcgtggaccgcttgctgcaactctctcagggccaggcggtgaagggca
atcagctgttcccgtctcactggtgaaaagaaaaaccaccctggcgcccaatacgcaaaccgcctct
ccccgcgcgttggccgattcattaatgcagctggcacgacaggtttcccgactggaaagcgggcagtg
agcgcaacgcaattaatgtaagttagctcactcattaggcaccgggatctcgaccgatgcccttgagag
ccttcaacccagtcagctccttccggtgggcgcggggcatgactatcgtcgccgcacttatgactgtcttc
tttatcatgcaactcgtaggacaggtgccggcagcgctctgggtcattttcggcgaggaccgctttcgctg
gagcgcgacgatgatcggcctgtcgcttgcggtattcggaatcttgcacgccctcgctcaagccttcgtc
actggtcccgccaccaaacgtttcggcgagaagcaggccattatcgccggcatggcggccgacgcg
ctgggctacgtcttgctggcgttcgcgacgcgaggctggatggccttccccattatgattcttctcgcttccg
gcggcatcgggatgcccgcgttgcaggccatgctgtccaggcaggtagatgacgaccatcagggaca
gcttcaaggatcgctcgcggctcttaccagccaacttcgatcactggaccgctgatcgtcacggcgattt
atgccgcctcggcgagcacatggaacgggttggcatggattgtaggcgccgccctataccttgtctgcct
ccccgcgttgcgtcgcggtgcatggagccgggccacctcgacctgaatggaagccggcggcacctcg
ctaacggattcaccactccaagaattggagccaatcaattcttgcggagaactgtgaatgcgcaaacc
aaccccttggcagaacatatccatcgcgtccgccatctccagcagccgcacgcggcgcatctcgggca
gcgttgggtcctggccacgggtgcgcatgatcgtgctcctgtcgttgaggacccggctaggctggcggg
gttgccttactggttagcagaatgaatcaccgatacgcgagcgaacgtgaagcgactgctgctgcaaa
acgtctgcgacctgagcaacaacatgaatggtcttcggtttccgtgtttcgtaaagtctggaaacgcgga
agtcagcgccctgcaccattatgttccggatctgcatcgcaggatgctgctggctaccctgtggaacacc
tacatctgtattaacgaagcgctggcattgaccctgagtgattttctctggtcccgccgcatccataccgc
cagttgtttaccctcacaacgttccagtaaccgggcatgttcatcatcagtaacccgtatcgtgagcatcct
ctctcgtttcatcggtatcattaccccatgaacagaaatcccccttacacggaggcatcagtgaccaaa
caggaaaaaaccgcccttaacatggcccgctttatcagaagccagacattaacgcttctggagaaact
caacgagctggacgcggatgaacaggcagacatctgtgaatcgcttcacgaccacgctgatgagcttt
accgcagctgcctcgcgcgtttcggtgatgacggtgaaaacctctgacacatgcagctcccggagacg
gtcacagcttgtctgtaagcggatgccgggagcagacaagcccgtcagggcgcgtcagcgggtgttg
gcgggtgtcggggcgcagccatgacccagtcacgtagcgatagcggagtgtatactggcttaactatg
cggcatcagagcagattgtactgagagtgcaccatatatgcggtgtgaaataccgcacagatgcgtaa
ggagaaaataccgcatcaggcgctcttccgcttcctcgctcactgactcgctgcgctcggtcgttcggctg
cggcgagcggtatcagctcactcaaaggcggtaatacggttatccacagaatcaggggataacgcag
gaaagaacatgtgagcaaaaggccagcaaaaggccaggaaccgtaaaaaggccgcgttgctggc
gtttttccataggctccgcccccctgacgagcatcacaaaaatcgacgctcaagtcaga

Figure 5C ggtggcgaaacccgacaggactataaagataccaggcgtttccccctggaagctccctcgtgcgctctcct
gttccgaccctgccgcttaccggatacctgtccgcctttctcccttcgggaagcgtggcgctttctcatagctca
cgctgtaggtatctcagttcggtgtaggtcgttcgctccaagctgggctgtgtgcacgaaccccccgttcagc
ccgaccgctgcgccttatccggtaactatcgtcttgagtccaacccggtaagacacgacttatcgccactgg
cagcagccactggtaacaggattagcagagcgaggtatgtaggcggtgctacagagttcttgaagtggtg
gcctaactacggctacactagaaggacagtatttggtatctgcgctctgctgaagccagttaccttcggaaa
aagagttggtagctcttgatccggcaaacaaaccaccgctggtagcggtggttttttgtttgcaagcagcag
attacgcgcagaaaaaaaggatctcaagaagatcctttgatcttttctacggggtctgacgctcagtggaac
gaaaactcacgttaagggattttggtcatgagattatcaaaaaggatcttcacctagatccttttaaattaaaa
atgaagttttaaatcaatctaaagtatatatgagtaaacttggtctgacagttaccaatgcttaatcagtgagg
cacctatctcagcgatctgtctatttcgttcatccatagttgcctgactccccgtcgtgtagataactacgatacg
ggagggcttaccatctggccccagtgctgcaatgataccgcgagacccacgctcaccggctccagatttat
cagcaataaaccagccagccggaagggccgagcgcagaagtggtcctgcaactttatccgcctccatcc
agtctattaattgttgccgggaagctagagtaagtagttcgccagttaatagtttgcgcaacgttgttgccattg
ctgcaggcatcgtggtgtcacgctcgtcgtttggtatggcttcattcagctccggttcccaacgatcaaggcg
agttacatgatcccccatgttgtgcaaaaaagcggttagctccttcggtcctccgatcgttgtcagaagtaagt
tggccgcagtgttatcactcatggttatggcagcactgcataattctcttactgtcatgccatccgtaagatgctt
ttctgtgactggtgagtactcaaccaagtcattctgagaatagtgtatgcggcgaccgagttgctcttgcccgg
cgtcaacacgggataataccgcgccacatagcagaactttaaaagtgctcatcattggaaaacgttcttcg
gggcgaaaactctcaaggatcttaccgctgttgagatccagttcgatgtaacccactcgtgcacccaactg
atcttcagcatcttttactttcaccagcgtttctgggtgagcaaaaacaggaaggcaaaatgccgcaaaaa
agggaataagggcgacacggaaatgttgaatactcatactcttcctttttcaatattattgaagcatttatcagg
gttattgtctcatgagcggatacatatttgaatgtatttagaaaaataaacaatagggg ttccgcgcacattt
ccccgaaaagtgccacctgacgtctaagaaaccattattatcatgacattaacctataaaaataggcgtatc
acgaggccctttcgtcttcaagaa (SEQ ID NO:5)

Figure 7A

1-
cccgtcttactgtcgggaattcgcgttggccgattcattaatgcagctggcacgacaggtttcccgactggaa
agcgggcagtgagcgcaacgcaattaatgtgagttagctcactcattaggcaccccaggctttacactttat
gcttccggctcgtatgttgtgtggaattgtgagcggataacaatttcacacaggaaacagctatgaccatgat
tacgccaagcttgtatcgattaaataaggaggaataaaccatgtgtgcgacctcttctcaatttactcagatta
ccgagcataattcccgtcgttccgcaaactatcagccaaacctgtggaatttcgaattcctgcaatccctgga
gaacgacctgaaagtggaaaagctggaggagaaagcgaccaaactggaggaagaagttcgctgcatg
atcaaccgtgtagacacccagccgctgtccctgctggagctgatcgacgatgtgcagcgcctgggtctgac
ctacaaatttgaaaaagacatcattaaagccctggaaaacatcgtactgctggacgaaaacaaaaagaa
caaatctgacctgcacgcaaccgctctgtctttccgtctgctgcgtcagcacggtttcgaggtttctcaggatgt
tttttgagcgtttcaaggataaagaaggtggtttcagcggtgaactgaaaggtgacgtccaaggcctgctga
gcctgtatgaagcgtcttacctgggtttcgagggtgagaacctgctggaggaggcgcgtacctttccatcac
ccacctgaagaacaacctgaaagaaggcattaataccaaggttgcagaacaagtgagccacgccctgg
aactgccatatcaccagcgtctgcaccgtctggaggcacgttggttcctggataaatacgaaccgaaaga
accgcatcaccagctgctgctggagctggcgaagctggattttaacatggtacagaccctgcaccagaaa
gagctgcaagatctgtcccgctggtggaccgagatgggcctggctagcaaactggattttgtacgcgaccg
cctgatggaagtttatttctgggcactgggtatggcgccagacccgcagtttggtgaatgtcgcaaagctgtt
actaaaatgtttggtctggtgacgatcatcgatgacgtgtatgacgtttatggcactctggacgaactgcaact
gttcaccgatgctgtagagcgctgggacgttaacgctattaacaccctgccggactatatgaaactgtgtttc
ctggcactgtacaacaccgttaacgacacgtcctattctattctgaaagagaaaggtcataacaacctgtcc
tatctgacgaaaagctggcgtgaactgtgcaaagcctttctgcaagaggcgaaatggtccaacaacaaa
attatcccggctttctccaagtacctggaaaacgccagcgtttcctcctccggtgtagcgctgctggcgccgt
cttacttttccgtatgccagcagcaggaagacatctccgaccacgcgctgcgttccctgaccgacttccatg
gtctggtgcgttctagctgcgttatcttccgcctgtgcaacgatctggccacctctgcggcggagctggaacgt
ggcgagactaccaattctatcattagctacatgcacgaaaacgatggtaccagcgaggaacaggcccgc
gaagaactgcgtaaactgatcgacgccgaatggaaaaagatgaatcgtgaacgcgttagcgactccacc
ctgctgcctaaagcgttcatggaaatcgcagttaacatggcacgtgtttcccactgcacctaccagtatggc
gatggtctgggtcgcccagactacgcgactgaaaaccgcatcaaactgctgctgattgaccctttcccgatt
aaccagctgatgtatgtctaactgcaggtcgactctagaggatccccgggtaccgagctcgaattcactgg
ccgtcgttttacaacgtcgtgactgggaaaaccctggcgttacccaacttaatcgccttgcagcacatcccc
ctttcgccagctggcgtaatagcgaagaggcccgcaccgatcgcccttcccaacagttgcgcagcctgaa
tggcgaatggcgcctgatgcggtattttctccttacgcatctgtgcggtatttcacaccgcatatggtgcactct
cagtacaatctgctctgatgccgcatagttaagccagccccgacacccgccaacacccgctgacgagctt
agtaaagccctcgctagattttaatgcggatgttgcgattacttcgccaactattgcgataacaagaaaaag
ccagcctttcatgatatatctcccaatttgtgtagggcttattatgcacgcttaaaaataataaaagcagacttg
acctgatagtttggctgtgagcaattatgtgcttagtgcatctaacgcttgagttaagccgcgccgcgaagcg
gcgtcggcttgaacgaattgttagacattatttgccgactaccttggtgatctcgcctttcacgtagtggacaaa
ttcttccaactgatctgcgcgcgaggccaagcgatcttcttcttgtccaagataagcctgtctagcttcaagtat
gacgggctgatactgggccggcaggcgctccattgcccagtcggcagcgacatccttcggcgcgattttgc
cggttactgcgctgtaccaaatgcgggacaacgtaagcactacatttcgctcatcgccagcccagtcgggc
ggcgagttccatag

Figure 7B cgttaaggtttcatttagcgcctcaaatagatcctgttcaggaaccggatcaaagagttcctccgccgctg
gacctaccaaggcaacgctatgttctcttgcttttgtcagcaagatagccagatcaatgtcgatcgtggct
ggctcgaagatacctgcaagaatgtcattgcgctgccattctccaaattgcagttcgcgcttagctggata
acgccacggaatgatgtcgtcgtgcacaacaatggtgacttctacagcgcggagaatctcgctctctcc
aggggaagccgaagtttccaaaaggtcgttgatcaaagctcgccgcgttgtttcatcaagccttacggtc
accgtaaccagcaaatcaatatcactgtgtggcttcaggccgccatccactgcggagccgtacaaatgt
acggccagcaacgtcggttcgagatggcgctcgatgacgccaactacctctgatagttgagtcgatact
tcggcgatcaccgcttccctcatgatgtttaactttgttttagggcgactgccctgctgcgtaacatcgttgct
gctccataacatcaaacatcgacccacggcgtaacgcgcttgctgcttggatgcccgaggcatagact
gtaccccaaaaaaacagtcataacaagccatgaaaaccgccactgcgccgttaccaccgctgcgttc
ggtcaaggttctggaccagttgcgtgagcgcatacgctacttgcattacagcttacgaaccgaacaggc
ttatgtccactgggttcgtgccttcatccgtttccacggtgtgcgtcacccggcaaccttgggcagcagcg
aagtcgaggcatttctgtcctggctggcgaacgagcgcaaggtttcggtctccacgcatcgtcaggcatt
ggcggccttgctgttcttctacggcaaggtgctgtgcacggatctgccctggcttcaggagatcggaaga
cctcggccgtcgcggcgcttgccggtggtgctgaccccggatgaagtggttcgcatcctcggttttctgga
aggcgagcatcgtttgttcgcccagcttctgtatggaacgggcatgcggatcagtgagggtttgcaactg
cgggtcaaggatctggatttcgatcacggcacgatcatcgtgcgggagggcaagggctccaaggatc
gggccttgatgttacccgagagcttggcacccagcctgcgcgagcaggggaattaattcccacgggttt
tgctgcccgcaaacgggctgttctggtgttgctagtttgttatcagaatcgcagatccggcttcagccggttt
gccggctgaaagcgctatttcttccagaattgccatgatttttccccacggggaggcgtcactggctcccgt
gttgtcggcagctttgattcgataagcagcatcgcctgtttcaggctgtctatgtgtgactgttgagctgtaa
caagttgtctcaggtgttcaatttcatgttctagttgctttgttttactggtttcacctgttctattaggtgttacatg
ctgttcatctgttacattgtcgatctgttcatggtgaacagctttgaatgcaccaaaaactcgtaaaagctct
gatgtatctatcttttttacaccgttttcatctgtgcatatggacagttttcccttttgatatgtaacggtgaacagt
tgttctacttttgtttgttagtcttgatgcttcactgatagatacaagagccataagaacctcagatccttccgt
atttagccagtatgttctctagtgtggttcgttgtttttgcgtgagccatgagaacgaaccattgagatcatac
ttactttgcatgtcactcaaaaatttttgcctcaaaactggtgagctgaattttttgcagttaaagcatcgtgtag
tgtttttcttagtccgttatgtaggtaggaatctgatgtaatggttgttggtattttgtcaccattcattttatctggt
tgttctcaagttcggttacgagatccatttgtctatctagttcaacttggaaaatcaacgtatcagtcgggcg
gcctcgcttatcaaccaccaatttcatattgctgtaagtgtttaaatctttacttattggtttcaaaacccattgg
ttaagccttttaaaactcatggtagttattttcaagcattaacatgaacttaaattcatcaaggctaatctctata
tttgccttgtgagtttcttttgtgttagttcttttaataaccactcataaatcctcatagagtatttgttttcaaaag
acttaacatgttccagattatattttatgaatttttttaactggaaaagataaggcaatatctcttcactaaaa
actaattctaattttcgcttgagaacttggcatagtttgtccactggaaaatctcaaagcctttaaccaaag
gattcctgatttccacagttctcgtcatcagctctctggttgctttagctaatacaccataagcattttccctact
gatgttcatcatctgagcgtattggttataagtgaacgataccgtccgttctttccttgtagggttttcaatcgt
ggggttgagtagtgccacacagcataaaattagcttggtttcatgctccgttaagtcatagcgactaatcg
ctagttcatttgctttgaaaacaactaattcagacatacatctcaattggtctaggtgattttaatcactatac
caattgagatgggctagtcaatgataattactagtccttttcctttgagttgtgggtatctgta

Figure 7C

Aattctgctagacctttgctggaaaacttgtaaattctgctagaccctctgtaaattccgctagacctttgtg
tgttttttttgtttatattcaagtggttataatttatagaataaagaaagaataaaaaaagataaaaagaat
agatcccagccctgtgtataactcactactttagtcagttccgcagtattacaaaaggatgtcgcaaac
gctgtttgctcctctacaaaacagaccttaaaaccctaaaggcttaagtagcaccctcgcaagctcgg
gcaaatcgctgaatattccttttgtctccgaccatcaggcacctgagtcgctgtcttttcgtgacattcagtt
cgctgcgctcacggctctggcagtgaatgggggtaaatggcactacaggcgcctttatggattcatgc
aaggaaactacccataatacaagaaaagcccgtcacgggcttctcagggcgtttatggcgggtctg
ctatgtggtgctatctgacttttgctgttcagcagttcctgccctctgattttccagtctgaccacttcggatta
tcccgtgacaggtcattcagactggctaatgcacccagtaaggcagcggtatcatcaacaggctta (SEQ ID NO:7)

Figure 12A

1-
gaattgctccattttcttctgctatcaaaataacagactcgtgattttccaaacgagctttcaaaaaagcctctgcc
ccttgcaaatcggatgcctgtctataaaattcccgatattggttaaacagcggcgcaatggcggccgcatctgat
gtctttgcttggcgaatgttcatcttatttcttcctccctctcaataatttttcattctatcccttttctgtaaagtttatttttc
agaatacttttatcatcatgctttgaaaaaatatcacgataatatccattgttctcacggaagcacacgcaggtca
tttgaacgaatttttttcgacaggaatttgccgggactcaggagcatttaacctaaaaaagcatgacatttcagcat
aatgaacatttactcatgtctattttcgttcttttctgtatgaaaatagttatttcgagtctctacggaaatagcgagag
atgatatacctaaatagagataaaatcatctcaaaaaaatgggtctactaaaatattattccatctattacaataa
attcacagaatagtcttttaagtaagtctactctgaattttttaaaaggagagggtaaagagtgtgtgcgacctctt
ctcaatttactcagattaccgagcataattcccgtcgttccgcaaactatcagccaaacctgtggaatttcgaatt
cctgcaatccctggagaacgacctgaaagtggaaaagctggaggagaaagcgaccaaactggaggaag
aagttcgctgcatgatcaaccgtgtagacacccagccgctgtccctgctggagctgatcgacgatgtgcagcg
cctgggtctgacctacaaatttgaaaaagacatcattaaagccctggaaaacatcgtactgctggacgaaaa
caaaaagaacaaatctgacctgcacgcaaccgctctgtctttccgtctgctgcgtcagcacggtttcgaggtttc
tcaggatgttttgagcgtttcaaggataaagaaggtggtttcagcggtgaactgaaaggtgacgtccaaggcc
tgctgagcctgtatgaagcgtcttacctgggtttcgagggtgagaacctgctggaggaggcgcgtacctttcca
tcacccacctgaagaacaacctgaaagaaggcattaataccaaggttgcagaacaagtgagccacgccct
ggaactgccatatcaccagcgtctgcaccgtctggaggcacgttggttcctggataaatacgaaccgaaaga
accgcatcaccagctgctgctggagctggcgaagctggattttaacatggtacagaccctgcaccagaaaga
gctgcaagatctgtcccgctggtggaccgagatgggcctggctagcaaactggattttgtacgcgaccgcctg
atggaagtttatttctgggcactgggtatggcgccagacccgcagtttggtgaatgtcgcaaagctgttactaaa
atgtttggtctggtgacgatcatcgatgacgtgtatgacgtttatggcactctggacgaactgcaactgttcaccg
atgctgtagagcgctgggacgttaacgctattaacaccctgccggactatatgaaactgtgtttcctggcactgt
acaacaccgttaacgacacgtcctattctattctgaaagagaaaggtcataacaacctgtcctatctgacgaaa
agctggcgtgaactgtgcaaagcctttctgcaagaggcgaaatggtccaacaacaaaattatcccggctttctc
caagtacctggaaaacgccagcgtttcctcctccggtgtagcgctgctggcgccgtcttactttccgtatgccag
cagcaggaagacatctccgaccacgcgctgcgttccctgaccgacttccatggtctggtgcgttctagctgcgtt
atcttccgcctgtgcaacgatctggccacctctgcggcggagctggaacgtggcgagactaccaattctatcat
tagctacatgcacgaaaacgatggtaccagcgaggaacaggcccgcgaagaactgcgtaaactgatcgac
gccgaatggaaaaagatgaatcgtgaacgcgttagcgactccaccctgctgcctaaagcgttcatggaaatc
gcagttaacatggcacgtgtttcccactgcacctaccagtatggcgatggtctgggtcgcccagactacgcga
ctgaaaaccgcatcaaactgctgctgattgacccttcccgattaaccagctgatgtatgtctaaaaaaaaccg
gccttggccccgccggttttttattattttttcttcctccgcatgttcaatccgctccataatcgacggatggctccctct
gaaaattttaacgagaaacggcgggttgacccggctcagtcccgtaacggccaagtcctgaaacgtctcaat
cgccgcttcccggtttccggtcagctcaatgccgtaacggtcggcggcgttttcctgataccgggagacggcatt
cgtaatcggatcctctagagtcgacctgcaggcatgcaagctttgcctcgcgcgtttcggtgatgacggtgaaa
acctctgacacatgcagctcccggagacggtcacagcttgtctgtaagcggatgccgggagcagacaagcc
cgtcagggcgcgtcagcgggtgttggcgggtgtcggggcgcagccatgacccagtcacgtagcgata

Figure 12B gcggagtgtatactggcttaactatgcggcatcagagcagattgtactgagagtgcaccatatgcggtgt
gaaataccgcacagatgcgtaaggagaaaataccgcatcaggcgctcttccgcttcctcgctcactga
ctcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaac
cgtaaaaaggccgcgttgctggcgtttttccataggctccgcccccctgacgagcatcacaaaaatcga
cgctcaagtcagaggtggcgaaacccgacaggactataaagataccaggcgtttccccctggaagct
ccctcgtgcgctctcctgttccgaccctgccgcttaccggatacctgtccgcctttctcccttcgggaagcgt
ggcgctttctcaatgctcacgctgtaggtatctcagttcggtgtaggtcgttcgctccaagctgggctgtgtg
cacgaaccccccgttcagcccgaccgctgcgccttatccggtaactatcgtcttgagtccaacccggta
agacacgacttatcgccactggcagcagccactggtaacaggattagcagagcgaggtatgtaggcg
gtgctacagagttcttgaagtggtggcctaactacggctacactagaaggacagtatttggtatctgcgct
ctgctgaagccagttaccttcggaaaaagagttggtagctcttgatccggcaaacaaaccaccgctggt
agcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaa
aaaggatcgaagtcggttcagaaaaagaaggatatggatctggagctgtaatataaaaaccttcttcaa
ctaacggggcaggttagtgacattagaaaaccgactgtaaaaagtacagtcggcattatctcatattata
aaagccagtcattaggcctatctgacaattcctgaatagagttcataaacaatcctgcatgataaccatc
acaaacagaatgatgtacctgtaaagatagcggtaaatatattgaattacctttattaatgaattttcctgct
gtaataatgggtagaaggtaattactattattattgatatttaagttaaacccagtaaatgaagtccatgga
ataatagaaagagaaaaagcattttcaggtataggtgtttgggaaacaatttaaaagaaccattatattt
ctctacatcagaaaggtataaatcataaaactctttgaagtcattctttacaggagtccaaataccagag
aatgttttagatacaccatcaaaaattgtataaagtggctctaacttatcccaataacctaactctccgtcg
ctattgtaaccagttctaaaagctgtatttgagtttatcaccctgtcactaagaaaataaatgcagggtaa
aatttatatccttcttgttttatgtttcggtataaaacactaatatcaatttctgtggttatactaaaagtcgtttgtt
ggttcaaataatgattaaatatctcttttctcttccaattgtctaaatcaatttattaaagttcatttgatatgcct
cctaaattttatctaaagtgaatttaggaggcttacttgtctgctttcttcattagaatcaatccttttttaaagtc
aatattactgtaacataaatatatattttaaaaatatcccactttatccaattttcgtttgttgaactaatgggtg
ctttagttgaagaataaagaccacattaaaaaatgtggtctttgtgtttttaaaggatttgagcgtacgcg
aaaaatcctttctttcttcttatcttgataataagggtaactattgccggttgtccattcatggctgaactctgc
ttcctctgttgacatgacacacatcatctcaatatccgaatagggcccatcagtctgacgaccaagagag
ccataaacaccaatagccttaacatcatccccatatttatccaatattcgttccttaatttcatgaacaatctt
cattctttcttctctagtcattattattggtccattcactattctcattcccttttcagataattttagatttgcttttcta
aataagaatatttggagagcaccgttcttattcagctattaataactcgtcttcctaagcatccttcaatcctttt
taataacaattatagcatctaatcttcaacaaactggcccgtttgttgaactactctttaataaaataatttttc
cgttcccaattccacattgcaataatagaaaatccatcttcatcggcttttcgtcatcatctgtatgaatcaa
atcgccttcttctgtgtcatcaaggtttaatttttatgtatttcttttaacaaaccaccataggagattaaccttt
acggtgtaaaccttcctccaaatcagacaaacgtttcaaattcttttcttcatcatcggtcataaaatccgta
tcctttacaggatattttgcagtttcgtcaattgccgattgtatatccgatttatatttattttcggtcgaatcattt
gaacttttacatttggatcatagtctaatttcattgccttttccaaaattgaatccattgttt

Figure 12C ttgattcacgtagttttctgttattctaaaataagttggttccacacataccattacatgcatgtgctgattata
agaattatctttattatttattgtcacatccgttgcacgcataaaaccaacaagattttattaatttttttatatt
gcatcattcggcgaaatccttgagccatatctgtcaaactcttatttaattcttcgccatcataaacatttta
actgttaatgtgagaaacaaccaacgaactgttggcttttgtttaataacttcagcaacaacctttgtgac
tgaatgccatgtttcattgctctcctccagttgcacattggacaaagcctggatttgcaaaaccacactcg
ataccactttctttcgcctgtttcacgattttgtttatactctaatatttcagcacaatcttttactctttcagccttt
ttaaattcaagaatatgcagaagttcaaagtaatcaacattagcgattttcttttctctccatggtctcacttt
tccactttttgtcttgtccactaaaacccttgattttcatctgaataaatgctactattaggacacataatatt
aaaagaaaccccccatctatttagttatttgtttagtcacttataactttaacagatggggttttctgtgcaac
caattttaagggttttcaatactttaaaacacatacataccaacacttcaacgcacctttcagcaactaa
aataaaaatgacgttatttctatatgtatcaagataagaaagaacaagttcaaaaccatcaaaaaaag
acaccttttcaggtgcttttttttatttttataaaactcattccctgatctcgacttcgttcttttttttacctctcggttatg
agttagttcaaattcgttcttttttaggttctaaatcgtgttttttcttggaattgtgctgttttatcctttaccttgtcta
caaaccccttaaaaacgttttttaaaggcttttaagccgtctgtacgttccttaag (SEQ ID NO:57)

Figure 13

```
ATGTGTGCAACCTCCTCCCAGTTTACTCAGATTACCGAGCATAATTCT
CGACGATCTGCTAACTACCAGCCGAACCTTTGGAACTTTGAGTTTCT
CCAGTCTCTCGAAAATGACCTGAAGGTGGAAAAGCTCGAGGAGAAG
GCGACCAAACTCGAGGAGGAGGTGCGATGTATGATCAACAGAGTTG
ACACCCAACCCCTGTCTTTGCTGGAGCTGATCGACGATGTGCAGCG
GTTGGGTTTGACTTATAAATTCGAGAAGGACATTATCAAGGCACTGG
AGAACATTGTGCTCCTCGACGAGAACAAGAAGAACAAGTCTGATCTT
CACGCTACCGCTCTCTTTCCGACTTCTTCGACAACACGGCTTCGA
GGTGTCGCAGGACGTCTTCGAGAGATTTAAGGACAAGGAGGGAGGA
TTTAGCGGCGAGCTGAAGGGAGACGTTCAGGGTCTTCTCTCCTTGT
ACGAGGCGTCCTACCTGGGATTCGAGGGAGAGAACCTCCTGGAGG
AAGCTCGTACATTTTCCATCACTCACCTTAAGAATAACCTTAAGGAGG
GAATTAACACCAAGGTGGCCGAGCAGGTTTCTCACGCCCTGGAGCT
CCCCTACCACCAACGGCTCCATAGACTGGAGGCTCGTTGGTTCCTG
GACAAATATGAGCCAAAGGAGCCTCATCATCAGTTGCTGTTGGAGTT
GGCCAAGCTGGACTTCAATATGGTTCAGACGCTGCACCAAAAGGAG
TTGCAGGACCTGTCTCGATGGTGGACCGAGATGGGATTGGCCTCGA
AGCTGGATTTTGTCCGTGACCGACTTATGGAGGTCTATTTTTGGGCC
CTTGGAATGGCGCCTGACCCCAGTTCGGAGAGTGCCGGAAGGCG
GTGACGAAGATGTTCGGTCTTGTGACTATCATCGACGACGTCTACGA
TGTCTACGGCACACTCGACGAGTTGCAGCTGTTCACTGACGCCGTC
GAGCGATGGGATGTGAACGCCATTAATACTCTCCCTGACTATATGAA
GCTGTGCTTCCTGGCTCTGTACAACACTGTCAACGATACCTCGTACT
CTATCCTCAAGGAGAAGGGACACAACAATCTCTCCTACTTGACCAAA
TCCTGGCGAGAACTGTGCAAGGCTTTCTGCAGGAGGCTAAATGGT
CCAATAACAAGATCATTCCTGCTTTTCTAAATACCTGGAAAATGCCT
CGGTGTCGAGCTCTGGCGTCGCCCTTCTGGCCCCTTCCTACTTCTC
CGTCTGCCAGCAGCAGGAGGATATTCCGATCATGCTCTTAGATCGC
TGACCGATTTTCACGGCCTCGTGCGATCTTCCTGCGTGATTTTTCGG
TTGTGTAATGACCTTGCGACCTCTGCTGCTGAGCTGGAACGAGGCG
AGACTACAAATTCCATTATTTCTTACATGCACGAAAACGATGGAACAT
CTGAAGAACAGGCTAGAGAGGAACTGCGAAAGTTGATCGACGCCGA
GTGGAAGAAGATGAACAGAGAGCGGGTGTCCGACTCTACCCTGCTT
CCCAAGGCCTTCATGGAGATCGCCGTGAACATGGCTCGAGTTTCCC
ATTGTACTTACCAGTACGGTGACGGCCTGGGTCGTCCGGACTACGC
TACAGAGAACCGAATCAAGCTGCTGCTCATCGACCCCTTCCCTATCA
ACCAATTGATGTACGTGTAA
```

(SEQ ID NO:8)

Figure 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACC CTTATCGCTG ACCCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTCAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGGA GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCAAAAAC ACTCTGCTGA TAAATCCTGT GACCTAGGTT TATCCATGCC
1501 TTCTAAATTG TCCATAAAAG ATAATGGTAA CAAGGTCGCA TTGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGGTTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAACGA TAGTTTTGCA TCACGATGAG CACGGCTTTT GTAGAAACAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGCAA AAGAACGACA ATTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTG GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCCT CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTCCCCAC CGGCTCGCCT CGTAAGCGCA CAAGGACTGC
6121 TCCCAAAGAT CCTAGGCGGG ATTTGCCGA TTTCGGCCTA AAGGAACCGG AACACGTAGA
6181 AAGCCAGTCC GCAGAAACGC TGCTGACCCC GGATGAATGT CAGCTACTGG GCTATCTGGA
6241 CAAGCGAAAA CGCAAGCGCA AACAGAAAGC AGGTAGCCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```
(SEQ ID NO:11)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTCACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGACGG AGGATTTAGC GGCGAGCTGA ACGGAGACCT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCAGA TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```

(SEQ ID NO:12)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTCTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCCACC AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```
(SEQ ID NO:13)

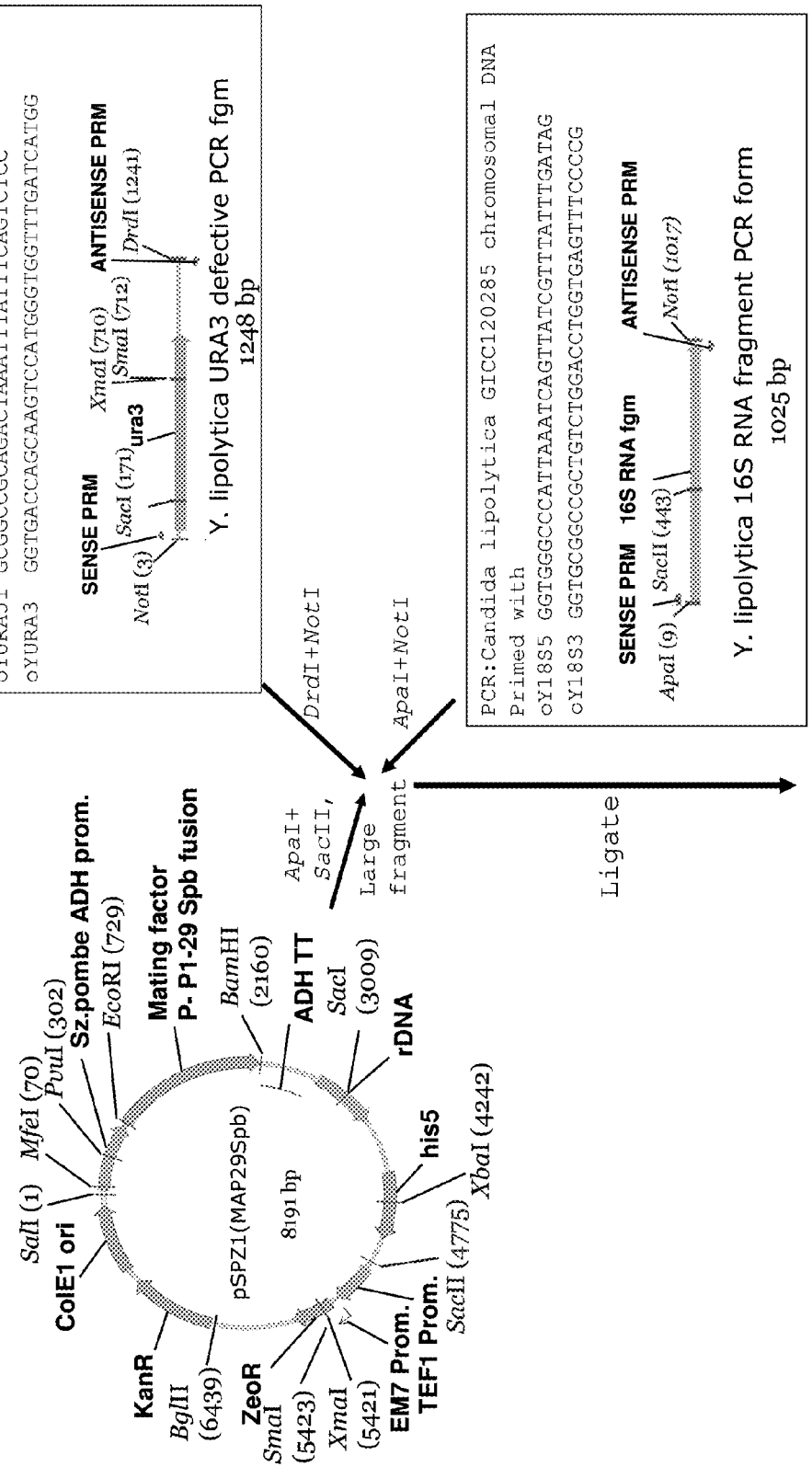
Figure 18A1

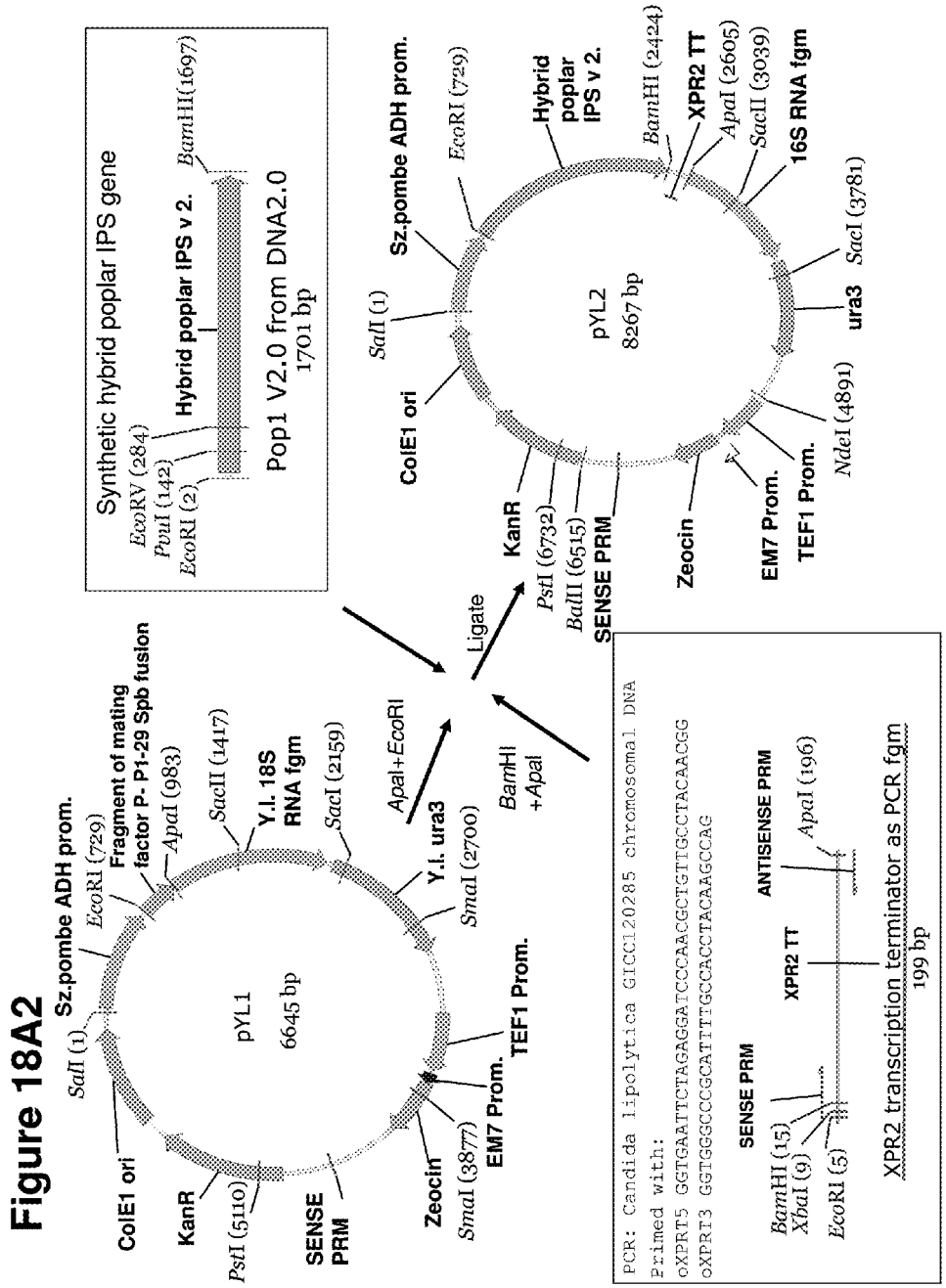
Figure 18A2

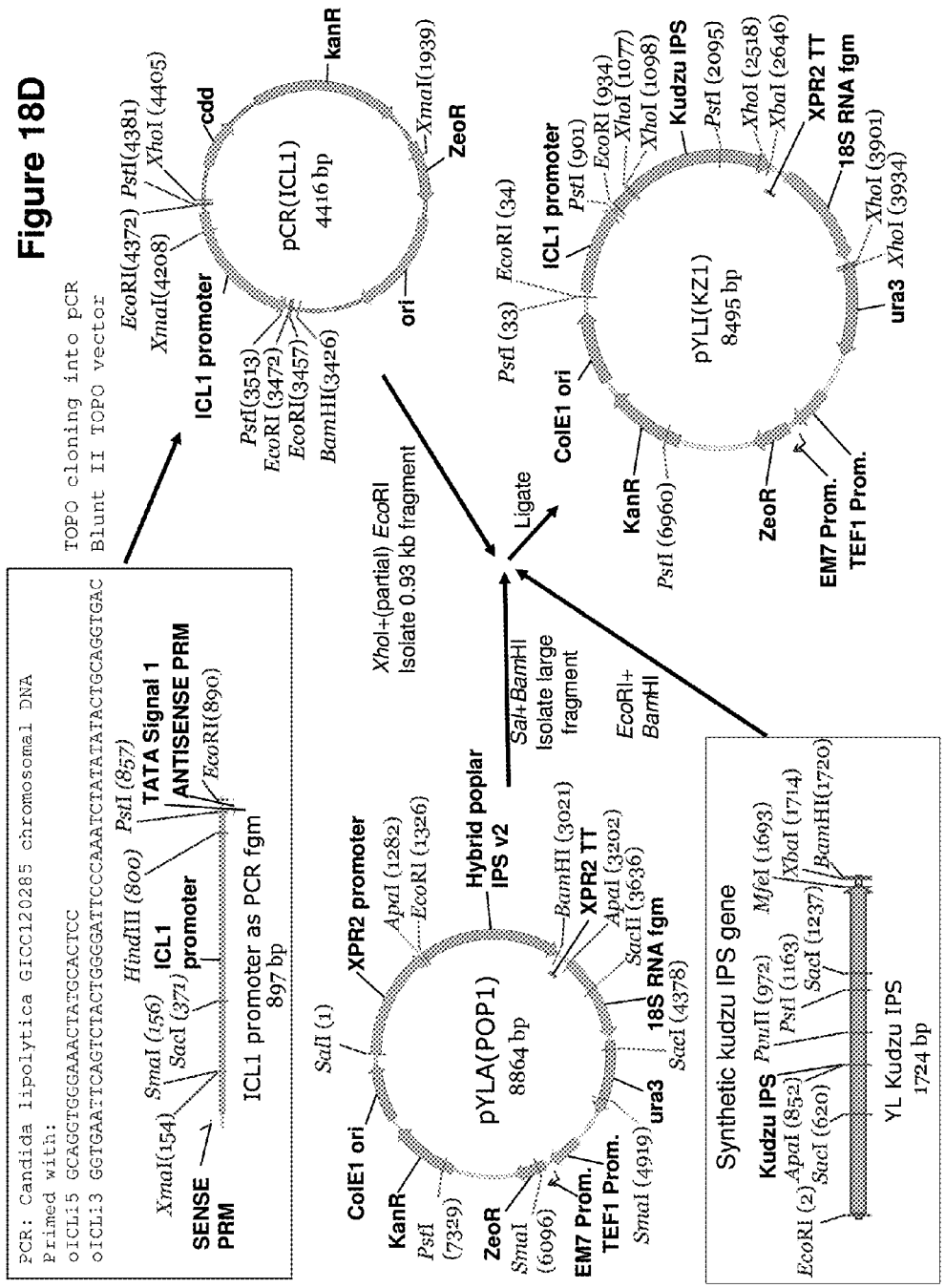

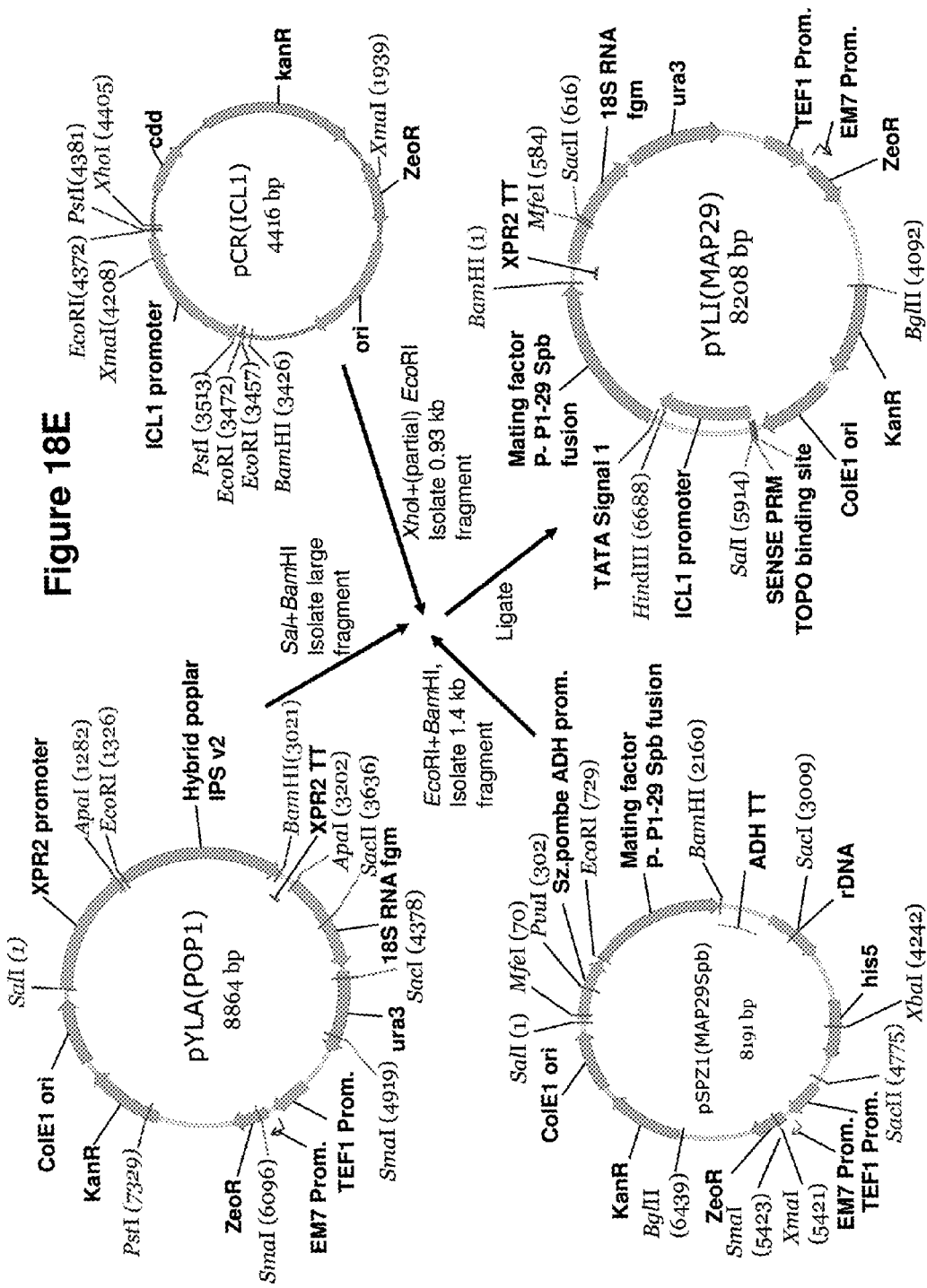

Figure 22A

1-
gctggtaccatatgggaattcgaagctttctagaacaaaaactcatctcagaagaggatctgaatagcgccgtc
gaccatcatcatcatcattgagtttaaacggtctccagcttggctgttttggcggatgagagaagattttcagcc
tgatacagattaaatcagaacgcagaagcggtctgataaaacagaatttgcctggcggcagtagcgcggtggt
cccacctgacccatgccgaactcagaagtgaaacgccgtagcgccgatggtagtgtggggtctccccatgcg
agagtagggaactgccaggcatcaaataaaacgaaaggctcagtcgaaagactgggcctttcgttttatctgtt
gtttgtcggtgaacgctctcctgagtaggacaaatccgccgggagcggatttgaacgttgcgaagcaacggcc
cggagggtggcgggcaggacgcccgccataaactgccaggcatcaaattaagcagaaggccatcctgacg
gatggcctttttgcgttctacaaactcttttgtttatttttctaaatacattcaaatatgtatccgcttaaccggaattgcc
agctggggcgccctctggtaaggttgggaagccctgcaaagtaaactggatggctttctcgccgccaaggatct
gatggcgcaggggatcaagctctgatcaagagacaggatgaggatcgtttcgcatgattgaacaagatggatt
gcacgcaggttctccggccgcttgggtggagaggctattcggctatgactgggcacaacagacaatcggctgct
ctgatgccgccgtgttccggctgtcagcgcaggggcgcccggttcttttgtcaagaccgacctgtccggtgccct
gaatgaactgcaagacgaggcagcgcggctatcgtggctggccacgacgggcgttcttgcgcagctgtgctc
gacgttgtcactgaagcgggaagggactggctgctattgggcgaagtgccggggcaggatctcctgtcatctca
ccttgctcctgccgagaaagtatccatcatggctgatgcaatgcggcggctgcatacgcttgatccggctacctg
cccattcgaccaccaagcgaaacatcgcatcgagcgagcacgtactcggatggaagccggtcttgtcgatca
ggatgatctggacgaagagcatcaggggctcgcgccagccgaactgttcgccaggctcaaggcgagcatgc
ccgacggcgaggatctcgtcgtgacccatggcgatgcctgcttgccgaatatcatggtggaaaatggccgctttt
ctggattcatcgactgtggccggctgggtgtggcggaccgctatcaggacatagcgttggctacccgtgatattg
ctgaagagcttggcggcgaatgggctgaccgcttcctcgtgctttacggtatcgccgctcccgattcgcagcgca
tcgccttctatcgccttcttgacgagttcttctgacatgaccaaaatcccttaacgtgagttttcgttccactgagcgtc
agaccccgtagaaaagatcaaaggatcttcttgagatcctttttttctgcgcgtaatctgctgcttgcaaacaaaaa
aaccaccgctaccagcggtggtttgtttgccggatcaagagctaccaactcttttccgaaggtaactggcttcag
cagagcgcagataccaaatactgtccttctagtgtagccgtagttaggccaccacttcaagaactctgtagcacc
gcctacatacctcgctctgctaatcctgttaccagtggctgctgccagtggcgataagtcgtgtcttaccgggttgg
actcaagacgatagttaccggataaggcgcagcggtcgggctgaacggggggttcgtgcacacagcccagct
tggagcgaacgacctacaccgaactgagatacctacagcgtgagctatgagaaagcgccacgcttcccgaa
gggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgt
caggggggcggagcctatggaaaaacgccagcaacgcggcctttttacggttcctggccttttgctggccttttgc
tcacatgttctttcctgcgttatcccctgattctgtggataaccgtattaccgcctttgagtgagctgataccgctcgcc
gcagccgaacgaccgagcgcagcgagtcagtgagcgaggaagcggaagagcgcctgatgcggtattttctc
cttacgcatctgtgcggtatttcacaccgcatatggtgcactctcagtacaatctgctctgatgccgcatagttaagc
cagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtca
gaggttttcaccgtcatcaccgaaacgcgcgaggcagcagatcaattcgcgcgcgaaggcgaagcggcatg
catttacgttgacaccatcgaatggtgcaaaacctttcgcggtatggcatgatagcgcccggaaga

Figure 22B gagtcaattcagggtggtgaatgtgaaaccagtaacgttatacgatgtcgcagagtatgccggtgtctcttatc
agaccgtttcccgcgtggtgaaccaggccagccacgtttctgcgaaaacgcgggaaaaagtggaagcgg
cgatggcggagctgaattacattcccaaccgcgtggcacaacaactggcgggcaaacagtcgttgctgatt
ggcgttgccacctccagtctggccctgcacgcgccgtcgcaaattgtcgcggcgattaaatctcgcgccgat
caactgggtgccagcgtggtggtgtcgatggtagaacgaagcggcgtcgaagcctgtaaagcggcggtgc
acaatcttctcgcgcaacgcgtcagtgggctgatcattaactatccgctggatgaccaggatgccattgctgtg
gaagctgcctgcactaatgttccggcgttatttcttgatgtctctgaccagacacccatcaacagtattattttctc
ccatgaagacggtacgcgactgggcgtggagcatctggtcgcattgggtcaccagcaaatcgcgctgttag
cgggcccattaagttctgtctcggcgcgtctgcgtctggctggctggcataaatatctcactcgcaatcaaattc
agccgatagcggaacgggaaggcgactggagtgccatgtccggttttcaacaaaccatgcaaatgctgaa
tgagggcatcgttcccactgcgatgctggttgccaacgatcagatggcgctgggcgcaatgcgcgccattac
cgagtccgggctgcgcgttggtgcggatatctcggtagtgggatacgacgataccgaagacagctcatgtta
tatcccgccgtcaaccaccatcaaacaggattttcgcctgctggggcaaaccagcgtggaccgcttgctgca
actctctcagggccaggcggtgaagggcaatcagctgttgcccgtctcactggtgaaaagaaaaaccacc
ctggcgcccaatacgcaaaccgcctctccccgcgcgttggccgattcattaatgcagctggcacgacaggtt
tcccgactggaaagcgggcagtgagcgcaacgcaattaatgtgagttagcgcgaattgatctggtttgacag
cttatcatcgactgcacggtgcaccaatgcttctggcgtcaggcagccatcggaagctgtggtatggctgtgc
aggtcgtaaatcactgcataattcgtgtcgctcaaggcgcactcccgttctggataatgttttttgcgccgacatc
ataacggttctggcaaatattctgaaatgagctgttgacaattaatcatccggctcgtataatgtgtggaattgtg
agcggataacaatttcacacaggaaacagcgccgctgagaaaaagcgaagcggcactgctctttaacaat
ttatcagacaatctgtgtgggcactcgaccggaattatcgattaactttattattaaaaattaaagaggtatatatt
aatgtatcgattaaataaggaggaataaaccatgtgtgcgacctcttctcaatttactcagattaccgagcata
attcccgtcgttccgcaaactatcagccaaacctgtggaatttcgaattcctgcaatccctggagaacgacctg
aaagtggaaaagctggaggagaaagcgaccaaactggaggaagaagttcgctgcatgatcaaccgtgt
agacacccagccgctgtccctgctggagctgatcgacgatgtgcagcgcctgggtctgacctacaaatttga
aaaagacatcattaaagccctggaaaacatcgtactgctggacgaaaacaaaagaacaaatctgacct
gcacgcaaccgctctgtctttccgtctgctgcgtcagcacggtttcgaggtttctcaggatgttttgagcgtttca
aggataaagaaggtggtttcagcggtgaactgaaaggtgacgtccaaggcctgctgagcctgtatgaagcg
tcttacctgggtttcgagggtgagaacctgctggaggaggcgcgtaccttttccatcacccacctgaagaaca
acctgaaagaaggcattaataccaaggttgcagaacaagtgagccacgccctggaactgccatatcacca
gcgtctgcaccgtctggaggcacgttggttcctggataaatacgaaccgaaagaaccgcatcaccagctgc
tgctggagctggcgaagctggattttaacatggtacagaccctgcaccagaaagagctgcaagatctgtccc
gctggtggaccgagatgggcctggctagcaaactggattttgtacgcgaccgcctgatggaagtttatttctgg
gcactgggtatggcgccagacccgcagtttggtgaatgtcgcaaagctgttactaaaatgtttggtctggtgac
gatcatcgatgacgtgtatgacgtttatggcactctggacgaactgcaactgttcaccgatgctgtagagcgct
gggacgttaacgctattaacaccctgccggactatatgaaactgtgtttcctggcactgtacaacaccgttaac
gacacgtcctattctattctgaaagagaaaggtcataacaacctgtcctatctgacgaaaagctggcgtgaa
ctgtgcaaagcctttctgcaagaggcgaaatggtccaacaacaaaattatcccggctttctccaagtacctgg
aaaacgccagcgtttcctcctccggtgtagcgctgctggcgccgtcttacttttccgta

Figure 22C tgccagcagcaggaagacatctccgaccacgcgctgcgttccctgaccgacttccatggtctggtgcgttctag
ctgcgttatcttccgcctgtgcaacgatctggccacctctgcggcggagctggaacgtggcgagactaccaatt
ctatcattagctacatgcacgaaaacgatggtaccagcgaggaacaggcccgcgaagaactgcgtaaactg
atcgacgccgaatggaaaaagatgaatcgtgaacgcgttagcgactccaccctgctgcctaaagcgttcatg
gaaatcgcagttaacatggcacgtgtttcccactgcacctaccagtatggcgatggtctgggtcgcccagacta
cgcgactgaaaaccgcatcaaactgctgctgattgaccctttcccgattaaccagctgatgtatgtctaactgca
tcgcccttaggaggtaaaaaaaaatgactgccgacaacaatagtatgccccatggtgcagtatctagttacgc
caaattagtgcaaaaccaaacacctgaagacattttggaagagtttcctgaaattattccattacaacaaagac
ctaatacccgatctagtgagacgtcaaatgacgaaagcggagaaacatgtttttctggtcatgatgaggagca
aattaagttaatgaatgaaaattgtattgttttggattgggacgataatgctattggtgccggtaccaagaaagttt
gtcatttaatggaaaatattgaaaagggtttactacatcgtgcattctccgtctttattttcaatgaacaaggtgaatt
acttttacaacaaagagccactgaaaaaataactttccctgatctttggactaacacatgctgctctcatccacta
tgtattgatgacgaattaggtttgaagggtaagctagacgataagattaagggcgctattactgcggcggtgag
aaaactagatcatgaattaggtattccagaagatgaaactaagacaaggggtaagtttcacttttaaacagaa
tccattacatggcaccaagcaatgaaccatggggtaacatgaaattgattacatcctattttataagatcaacg
ctaaagaaaacttgactgtcaacccaaacgtcaatgaagttagagacttcaaatgggtttcaccaaatgatttg
aaaactatgtttgctgacccaagttacaagtttacgccttggtttaagattatttgcgagaattacttattcaactggt
gggagcaattagatgacctttctgaagtggaaaatgacaggcaaattcatagaatgctataacaacgcgtcct
gcattcgcccttaggaggtaaaaaaacatgagttttgatattgccaaatacccgaccctggcactggtcgactc
cacccaggagttacgactgttgccgaaagagagtttaccgaaactctgcgacgaactgcgccgctatttactc
gacagcgtgagccgttccagcgggcacttcgcctccgggctgggcacggtcgaactgaccgtggcgctgca
ctatgtctacaacaccccgtttgaccaattgatttgggatgtggggcatcaggcttatccgcataaaattttgacc
ggacgccgcgacaaaatcggcaccatccgtcagaaaggcggtctgcacccgttcccgtggcgcggcgaaa
gcgaatatgacgtattaagcgtcgggcattcatcaacctccatcagtgccggaattggtattgcggttgctgccg
aaaaagaaggcaaaaatcgccgcaccgtctgtgtcattggcgatggcgcgattaccgcaggcatggcgtttg
aagcgatgaatcacgcgggcgatatccgtcctgatatgctggtgattctcaacgacaatgaaatgtcgatttcc
gaaaatgtcggcgcgctcaacaaccatctggcacagctgctttccggtaagcttactcttcactgcgcgaagg
cgggaaaaaagttttctctggcgtgccgccaattaaagagctgctcaaacgcaccgaagaacatattaaagg
catggtagtgcctggcacgttgtttgaagagctgggctttaactacatcggcccggtggacggtcacgatgtgct
ggggcttatcaccacgctaaagaacatgcgcgacctgaaaggcccgcagttcctgcatatcatgaccaaaa
aaggtcgtggttatgaaccggcagaaaaagacccgatcactttccacgccgtgcctaaatttgatccctccag
cggttgtttgccgaaaagtagcggcggtttgccgagctattcaaaaatctttggcgactggttgtgcgaaacggc
agcgaaagacaacaagctgatggcgattactccggcgatgcgtgaaggttccggcatggtcgagttttcacgt
aaattcccggatcgctacttcgacgtggcaattgccgagcaacacgcggtgacctttgctgcgggtctggcgat
tggtgggtacaaacccattgtcgcgatttactccactttcctgcaacgcgcctatgatcaggtgctgcatgacgtg
gcgattcaaaagcttccggtcctgttcgccatcgaccgcgcgggcattgttggtgctgacggtcaaacccatca
gggtgcttttgatctctcttacctgcgctgcataccggaaatggtcattatgaccccgagcgatgaaaacgaatg
tcgccagatgctctataccggctatcactataacgatggcccgtcagcggtgcgctacccgcgtggcaacgcg
gtcgg

Figure 22D cgtggaactgacgccgctggaaaaactaccaattggcaaaggcattgtgaagcgtcgtggcgagaaactgg
cgatccttaactttggtacgctgatgccagaagcggcgaaagtcgccgaatcgctgaacgccacgctggtcg
atatgcgttttgtgaaaccgcttgatgaagcgttaattctggaaatggccgccagccatgaagcgctggtcacc
gtagaagaaaacgccattatgggcggcgcaggcagcggcgtgaacgaagtgctgatggcccatcgtaaac
cagtacccgtgctgaacattggcctgccggacttctttattccgcaaggaactcaggaagaaatgcgcgccga
actcggcctcgatgccgctggtatggaagccaaaatcaaggcctggctggcataactgca (SEQ ID NO:20)

Figure 25A

5'-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgtttttgcgcc
gacatcataacggttctggcaaatattctgaaatgagctgttgacaattaatcatccggctcgtataatgtgtgga
attgtgagcggataacaatttcacacaggaaacagcgccgctgagaaaaagcgaagcggcactgctcttta
acaatttatcagacaatctgtgtgggcactcgaccggaattatcgattaactttattattaaaaattaaagaggtat
atattaatgtatcgattaaataaggaggaataaaccatggatccgagctcggatccactagtaacggccgcca
gtgtgctggaattcgcccttaggaggtaaaaaaacatgtcattaccgttcttaacttctgcaccgggaaaggttat
tattttggtgaacactctgctgtgtacaacaagcctgccgtcgctgctagtgtgtctgcgttgagaacctacctgct
aataagcgagtcatctgcaccagatactattgaattggacttcccggacattagctttaatcataagtggtccatc
aatgatttcaatgccatcaccgaggatcaagtaaactcccaaaaattggccaaggctcaacaagccaccgat
ggcttgtctcaggaactcgttagtcttttggatccgttgttagctcaactatccgaatccttccactaccatgcagcg
ttttgtttcctgtatatgtttgtttgcctatgcccccatgccaagaatattaagttttctttaaagtctactttacccatcgg
tgctgggttgggctcaagcgcctctatttctgtatcactggccttagctatggcctacttggggggggttaataggat
ctaatgacttggaaaagctgtcagaaaacgataagcatatagtgaatcaatgggccttcataggtgaaagtg
tattcacggtaccccttcaggaatagataacgctgtggccacttatggtaatgccctgctatttgaaaaagactc
acataatggaacaataaacacaaacaatttaagttcttagatgatttcccagccattccaatgatcctaacctat
actagaattccaaggtctacaaaagatcttgttgctcgcgttcgtgtgttggtcaccgagaaatttcctgaagttat
gaagccaattctagatgccatgggtgaatgtgccctacaaggcttagagatcatgactaagttaagtaaatgta
aaggcaccgatgacgaggctgtagaaactaataatgaactgtatgaacaactattggaattgataagaataa
atcatggactgcttgtctcaatcggtgtttctcatcctggattagaacttattaaaaatctgagcgatgatttgagaa
ttggctccacaaaacttaccggtgctggtggcggcggttgctctttgactttgttacgaagagacattactcaaga
gcaaattgacagcttcaaaaagaaattgcaagatgattttagttacgagacatttgaaacagacttgggtggga
ctggctgctgtttgttaagcgcaaaaaatttgaataaagatcttaaaatcaaatccctagtattccaattatttgaa
aataaaactaccacaaagcaacaaattgacgatctattattgccaggaaacacgaatttaccatggacttcat
aagctaatttgcgataggcctgcacccttaaggaggaaaaaaacatgtcagagttgagagccttcagtgccc
cagggaaagcgttactagctggtggatatttagttttagatacaaaatatgaagcatttgtagtcggattatcggc
aagaatgcatgctgtagcccatccttacggttcattgcaagggtctgataagtttgaagtgcgtgtgaaaagtaa
acaatttaaagatggggagtggctgtaccatataagtcctaaaagtggcttcattcctgtttcgataggcggatct
aagaacccttcattgaaaaagttatcgctaacgtatttagctactttaaacctaacatggacgactactgcaata
gaaacttgttcgttattgatattttctctgatgatgcctaccattctcaggaggatagcgttaccgaacatcgtggca
acagaagattgagttttcattcgcacagaattgaagaagttcccaaaacagggctgggctcctcggcaggttta
gtcacagttttaactacagctttggcctccttttttgtatcggacctggaaaataatgtagacaaatatagagaagt
tattcataatttagcacaagttgctcattgtcaagctcagggtaaaattggaagcgggtttgatgtagcggcggc
agcatatggatctatcagatatagaagattcccacccgcattaatctctaatttgccagatattggaagtgctactt
acggcagtaaactggcgcatttggttgatgaagaagactggaatattacgattaaaagtaaccatttaccttcg
ggattaactttatggatgggcgatattaagaatggttcagaaacagtaaaactggtccagaaggtaaaaaatt
ggtatgattcgcatatgccagaaagcttgaaaata

Figure 25B tatacagaactcgatcatgcaaattctagatttatggatggactatctaaactagatcgcttacacgagactc
atgacgattacagcgatcagatatttgagtctcttgagaggaatgactgtacctgtcaaaagtatcctgaaat
cacagaagttagagatgcagttgccacaattagacgttcctttagaaaaataactaaagaatctggtgccg
atatcgaacctcccgtacaaactagcttattggatgattgccagaccttaaaaggagttcttacttgcttaatac
ctggtgctggtggttatgacgccattgcagtgattactaagcaagatgttgatcttagggctcaaaccgctaat
gacaaaagattttctaaggttcaatggctggatgtaactcaggctgactggggtgttaggaaagaaaaaga
tccggaaacttatcttgataaataacttaaggtagctgcatgcagaattcgcccttaaggaggaaaaaaaa
atgaccgtttacacagcatccgttaccgcacccgtcaacatcgcaacccttaagtattggggaaaaggg
acacgaagttgaatctgcccaccaattcgtccatatcagtgactttatcgcaagatgacctcagaacgttga
cctctgcggctactgcacctgagtttgaacgcgacactttgtggttaaatggagaaccacacagcatcgac
aatgaaagaactcaaaattgtctgcgcgacctacgccaattaagaaaggaaatggaatcgaaggacgc
ctcattgcccacattatctcaatggaaactccacattgtctccgaaaataactttcctacagcagctggtttag
cttcctccgctgctggctttgctgcattggtctctgcaattgctaagttataccaattaccacagtcaacttcaga
aatatctagaatagcaagaaaggggtctggttcagcttgtagatcgttgtttggcggatacgtggcctggga
aatgggaaaagctgaagatggtcatgattccatggcagtacaaatcgcagacagctctgactggcctcag
atgaaagcttgtgtcctagttgtcagcgatattaaaaaggatgtgagttccactcagggtatgcaattgaccgt
ggcaacctccgaactatttaaagaaagaattgaacatgtcgtaccaaagagatttgaagtcatgcgtaaag
ccattgttgaaaaagatttcgccacctttgcaaaggaaacaatgatggattccaactctttccatgccacatgt
ttggactctttccctccaatattctacatgaatgacacttccaagcgtatcatcagttggtgccacaccattaat
cagttttacggagaaacaatcgttgcatacacgtttgatgcaggtccaaatgctgtgttgtactacttagctga
aaatgagtcgaaactctttgcatttatctataaattgtttggctctgttcctggatgggacaagaaatttactact
gagcagcttgaggctttcaaccatcaatttgaatcatctaactttactgcacgtgaattggatcttgagttgcaa
aaggatgttgccagagtgattttaactcaagtcggttcaggcccacaagaaacaaacgaatctttgattgac
gcaaagactggtctaccaaaggaataagatcaattcgctgcatcgcccttaggaggtaaaaaaaaatga
ctgccgacaacaatagtatgccccatggtgcagtatctagttacgccaaattagtgcaaaaccaaacacct
gaagacattttggaagagtttcctgaaattattccattacaacaaagacctaatacccgatctagtgagacgt
caaatgacgaaagcggagaaacatgttttctggtcatgatgaggagcaaattaagttaatgaatgaaatt
gtattgtttggattgggacgataatgctattggtgccggtaccaagaaagtttgtcatttaatggaaaatattga
aaagggtttactacatcgtgcattctccgtctttattttcaatgaacaaggtgaattacttttacaacaaagagc
cactgaaaaaataactttccctgatctttggactaacacatgctgctctcatccactatgtattgatgacgaatt
aggtttgaagggtaagctagacgataagattaagggcgctattactgcggcggtgagaaaactagatcat
gaattaggtattccagaagatgaaactaagacaaggggtaagtttcacttttaaacagaatccattacatg
gcaccaagcaatgaaccatggggtgaacatgaaattgattacatcctatttataagatcaacgctaaaga
aaacttgactgtcaacccaaacgtcaatgaagttagagacttcaaatgggtttcaccaaatgatttgaaaac
tatgtttgctgacccaagttacaagtttacgccttggtttaagattatttgcgagaattacttattcaactggtggg
agcaattagatgacctttctgaagtggaaaatgacaggcaaattcatagaatgctataacaacgcgtcctg
cattcgcccttaggaggtaaaaaaacatgtgtgcgacctcttctcaatttactcagattaccgagcataattcc
cgtcgttccgcaaactatcagccaaacctgtggaatttcgaattcctgcaatccctggagaacgacctgaa
agtggaaaagctggaggagaaagcgaccaaactggaggaagaagttcgctgcatg

Figure 25C atcaaccgtgtagacacccagccgctgtccctgctggagctgatcgacgatgtgcagcgcctgggtctgacc
tacaaatttgaaaaagacatcattaaagccctggaaaacatcgtactgctggacgaaaacaaaaagaaca
aatctgacctgcacgcaaccgctctgtcttccgtctgctgcgtcagcacggtttcgaggtttctcaggatgttttt
gagcgtttcaaggataaagaaggtggtttcagcggtgaactgaaaggtgacgtccaaggcctgctgagcct
gtatgaagcgtcttacctgggtttcgagggtgagaacctgctggaggaggcgcgtaccttttccatcacccac
ctgaagaacaacctgaaagaaggcattaataccaaggttgcagaacaagtgagccacgccctggaactg
ccatatcaccagcgtctgcaccgtctggaggcacgttggttcctggataaatacgaaccgaaagaaccgca
tcaccagctgctgctggagctggcgaagctggatttaacatggtacagaccctgcaccagaaagagctgc
aagatctgtcccgctggtggaccgagatgggcctggctagcaaactggattttgtacgcgaccgcctgatgg
aagtttatttctgggcactgggtatggcgccagacccgcagtttggtgaatgtcgcaaagctgttactaaaatgt
ttggtctggtgacgatcatcgatgacgtgtatgacgtttatggcactctggacgaactgcaactgttcaccgatg
ctgtagagcgctgggacgttaacgctattaacaccctgccggactatatgaaactgtgtttcctggcactgtac
aacaccgttaacgacacgtcctattctattctgaaagagaaaggtcataacaacctgtcctatctgacgaaaa
gctggcgtgaactgtgcaaagcctttctgcaagaggcgaaatggtccaacaacaaaattatcccggctttctc
caagtacctggaaaacgccagcgtttcctcctccggtgtagcgctgctggcgccgtcttacttttccgtatgcca
gcagcaggaagacatctccgaccacgcgctgcgttccctgaccgacttccatggtctggtgcgttctagctgc
gttatcttccgcctgtgcaacgatctggccacctctgcggcggagctggaacgtggcgagactaccaattcta
tcattagctacatgcacgaaaacgatggtaccagcgaggaacaggcccgcgaagaactgcgtaaactgat
cgacgccgaatggaaaaagatgaatcgtgaacgcgttagcgactccaccctgctgcctaaagcgttcatgg
aaatcgcagttaacatggcacgtgtttcccactgcacctaccagtatggcgatggtctgggtcgcccagacta
cgcgactgaaaaccgcatcaaactgctgctgattgacccttcccgattaaccagctgatgtatgtctaactgc
agctggtaccatatgggaattcgaagctttctagaacaaaaactcatctcagaagaggatctgaatagcgcc
gtcgaccatcatcatcatcatcattgagtttaaacggtctccagcttggctgttttggcggatgagagaagatttt
cagcctgatacagattaaatcagaacgcagaagcggtctgataaaacagaatttgcctggcggcagtagc
gcggtggtcccacctgaccccatgccgaactcagaagtgaaacgccgtagcgccgatggtagtgtggggt
ctccccatgcgagagtagggaactgccaggcatcaaataaaacgaaaggctcagtcgaaagactgggcc
tttcgttttatctgttgtttgtcggtgaacgctctcctgagtaggacaaatccgccgggagcggatttgaacgttgc
gaagcaacggcccggagggtggcgggcaggacgcccgccataaactgccaggcatcaaattaagcag
aaggccatcctgacggatggccttttgcgttttctacaaactctttttgtttattttctaaatacattcaaatatgtatc
cgcttaaccggaattgccagctggggcgccctctggtaaggttgggaagccctgcaaagtaaactggatgg
ctttctcgccgccaaggatctgatggcgcaggggatcaagctctgatcaagagacaggatgaggatcgtttc
gcatgattgaacaagatggattgcacgcaggttctccggccgcttgggtggagaggctattcggctatgactg
ggcacaacagacaatcggctgctctgatgccgccgtgttccggctgtcagcgcaggggcgcccggttctttt
gtcaagaccgacctgtccggtgccctgaatgaactgcaagacgaggcagcgcggctatcgtggctggcca
cgacgggcgttccttgcgcagctgtgctcgacgttgtcactgaagcgggaagggactggctgctattgggcg
aagtgccggggcaggatctcctgtcatctcaccttgctcctgccgagaaagtatccatcatggctgatgcaat
gcggcggctgcatacgcttgatccggctacctgcccattcgaccaccaagcgaaacatcgcatcgagcga
gcacgtactcggatggaagccggtcttgtcgatcaggatgatctggacgaagagcatcaggggctcgcgcc
agccgaactgttcgccaggctcaaggcgagcatgcccgacggcgaggatctcgtcgtgacccat

Figure 25D ggcgatgcctgcttgccgaatatcatggtggaaaatggccgcttttctggattcatcgactgtggccggctgggtgt
ggcggaccgctatcaggacatagcgttggctacccgtgatattgctgaagagcttggcggcgaatgggctgac
cgcttcctcgtgctttacggtatcgccgctcccgattcgcagcgcatcgccttctatcgccttcttgacgagttcttctg
acgcatgaccaaaatcccttaacgtgagttttcgttccactgagcgtcagaccccgtagaaaagatcaaaggat
cttcttgagatcctttttttctgcgcgtaatctgctgcttgcaaacaaaaaaaccaccgctaccagcggtggtttgttt
gccggatcaagagctaccaactcttttccgaaggtaactggcttcagcagagcgcagataccaaatactgtcct
tctagtgtagccgtagttaggccaccacttcaagaactctgtagcaccgcctacatacctcgctctgctaatcctgt
taccagtggctgctgccagtggcgataagtcgtgtcttaccgggttggactcaagacgatagttaccggataagg
cgcagcggtcgggctgaacggggggttcgtgcacacagcccagcttggagcgaacgacctacaccgaactg
agatacctacagcgtgagctatgagaaagcgccacgcttcccgaagggagaaaggcggacaggtatccggt
aagcggcagggtcggaacaggagagcgcacgagggagcttcaggggggaaacgcctggtatctttatagtc
ctgtcgggtttcgccacctctgacttgagcgtcgattttgtgatgctcgtcaggggggcggagcctatggaaaaa
cgccagcaacgcggccttttacggttcctggccttttgctggccttttgctcacatgttctttcctgcgttatcccctgat
tctgtggataaccgtattaccgcctttgagtgagctgataccgctcgccgcagccgaacgaccgagcgcagcg
agtcagtgagcgaggaagcggaagagcgcctgatgcggtattttctccttacgcatctgtgcggtatttcacacc
gcatatggtgcactctcagtacaatctgctctgatgccgcatagttaagccagtatacactccgctatcgctacgtg
actgggtcatggctgcgccccgacacccgccaacacccgctgacgcgccctgacgggcttgtctgctcccggc
atccgcttacagacaagctgtgaccgtctccgggagctgcatgtgtcagaggttttcaccgtcatcaccgaaacg
cgcgaggcagcagatcaattcgcgcgcgaaggcgaagcggcatgcatttacgttgacaccatcgaatggtgc
aaaacctttcgcggtatggcatgatagcgcccggaagagagtcaattcagggtggtgaatgtgaaaccagtaa
cgttatacgatgtcgcagagtatgccggtgtctcttatcagaccgtttcccgcgtggtgaaccaggccagccacgt
ttctgcgaaaacgcgggaaaaagtggaagcggcgatggcggagctgaattacattcccaaccgcgtggcac
aacaactggcgggcaaacagtcgttgctgattggcgttgccacctccagtctggccctgcacgcgccgtcgcaa
attgtcgcggcgattaaatctcgcgccgatcaactgggtgccagcgtggtggtgtcgatggtagaacgaagcgg
cgtcgaagcctgtaaagcggcggtgcacaatcttctcgcgcaacgcgtcagtgggctgatcattaactatccgct
ggatgaccaggatgccattgctgtggaagctgcctgcactaatgttccggcgttatttcttgatgtctctgaccaga
cacccatcaacagtattatttctcccatgaagacggtacgcgactgggcgtggagcatctggtcgcattgggtca
ccagcaaatcgcgctgttagcgggcccattaagttctgtctcggcgcgtctgcgtctggctggctggcataaatat
ctcactcgcaatcaaattcagccgatagcggaacgggaaggcgactggagtgccatgtccggttttcaacaaa
ccatgcaaatgctgaatgagggcatcgttcccactgcgatgctggttgccaacgatcagatggcgctgggcgca
atgcgcgccattaccgagtccgggctgcgcgttggtgcggatatctcggtagtgggatacgacgataccgaag
acagctcatgttatatcccgccgtcaaccaccatcaaacaggattttcgcctgctggggcaaaccagcgtggac
cgcttgctgcaactctctcagggccaggcggtgaagggcaatcagctgttgcccgtctcactggtgaaaagaaa
aaccaccctggcgcccaatacgcaaaccgcctctccccgcgcgttggccgattcattaatgcagctggcacga
caggtttcccgactggaaagcgggcagtgagcgcaacgcaattaatgtgagttagcgcgaattgatctg (SEQ ID NO:33)

Figure 27A

5'-
cccgtcttactgtcgggaattcgcgttggccgattcattaatgcagattctgaaatgagctgttgacaattaatcatc
cggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattatta
aaaattaaagaggtatatattaatgtatcgattaaataaggaggaataaaccatggatccgagctcaggaggta
aaaaaacatgaaaacagtagttattattgatgcattacgaacaccaattggaaaatataaaggcagcttaagtc
aagtaagtgccgtagacttaggaacacatgttacaacacaacttttaaaaagacattccactatttctgaagaaa
ttgatcaagtaatctttggaaatgttttacaagctggaaatggccaaaatcccgcacgacaaatagcaataaac
agcggtttgtctcatgaaattcccgcaatgacggttaatgaggtctgcggatcaggaatgaaggccgttatttgg
cgaaacaattgattcaattaggagaagcggaagttttaattgctggcgggattgagaatatgtcccaagcaccta
aattacaacgttttaattacgaaacagaaagctacgatgcgccttttctagtatgatgtatgatggattaacggatg
cctttagtggtcaggcaatgggcttaactgctgaaaatgtggccgaaaagtatcatgtaactagagaagagcaa
gatcaatttctgtacattcacaattaaaagcagctcaagcacaagcagaagggatattcgctgacgaaatagc
cccattagaagtatcaggaacgcttgtggagaaagatgaagggattcgccctaattcgagcgttgagaagcta
ggaacgcttaaaacagttttaaagaagacggtactgtaacagcagggaatgcatcaaccattaatgatgggg
cttctgctttgattattgcttcacaagaatatgccgaagcacacggtcttccttatttagctattattcgagacagtgtg
gaagtcggtattgatccagcctatatgggaatttcgccgattaaagccattcaaaaactgttagcgcgcaatcaa
cttactacggaagaaattgatctgtatgaaatcaacgaagcatttgcagcaacttcaatcgtggtccaaagaga
actggctttaccagaggaaaaggtcaacatttatggtggcggtatttcattaggtcatgcgattggtgccacaggt
gctcgttattaacgagtttaagttatcaattaaatcaaaaagaaaagaaatatggagtggcttctttatgtatcggc
ggtggcttaggactcgctatgctactagagagacctcagcaaaaaaaaaacagccgattttatcaaatgagtcc
tgaggaacgcctggcttctcttcttaatgaaggccagatttctgctgatacaaaaaaagaatttgaaaatacggct
ttatcttcgcagattgccaatcatatgattgaaaatcaaatcagtgaaacagaagtgccgatgggcgttggcttac
atttaacagtggacgaaactgattatttggtaccaatggcgacagaagagccctcagttattgcggctttgagtaa
tggtgcaaaaatagcacaaggatttaaaacagtgaatcaacaacgcttaatgcgtggacaaatcgttttttacga
tgttgcagatcccgagtcattgattgataaactacaagtaagagaagcggaagtttttcaacaagcagagttaag
ttatccatctatcgttaaacggggcggcggcttaagagatttgcaatatcgtactttgatgaatcatttgtatctgtcg
actttttagtagatgttaaggatgcaatgggggcaaatatcgttaacgctatgttggaaggtgtggccgagttgttcc
gtgaatggtttgcggagcaaaagattttattcagtattttaagtaattatgccacggagtcggttgttacgatgaaaa
cggctattccagtttcacgtttaagtaagggggagcaatggccgggaaattgctgaaaaaattgttttagcttcacg
ctatgcttcattagatccttatcgggcagtcacgcataacaaaggaatcatgaatggcattgaagctgtagttttag
ctacaggaaatgatacacgcgctgttagcgcttcttgtcatgcttttgcggtgaaggaaggtcgctaccaaggctt
gactagttggacgctggatggcgaacaactaattggtgaaatttcagttccgcttgctttagccacggttggcggtg
ccacaaaagtcttacctaaatctcaagcagctgctgatttgttagcagtgacggatgcaaaagaactaagtcga
gtagtagcggctgttggtttggcacaaaatttagcggcgttacgggccttagtctctgaaggaattcaaaaagga
cacatggctctacaagcacgttctttagcgatgacggtcggagctactggtaaagaagttgaggcagtcgctca
acaattaaaacgtcaaaaaacgatgaaccaagaccgagccatggctatttaaatgatttaagaaaacaataa
aggaggtaaaaaaacatgacaattgggat

Figure 27B tgataaaattagtttttttgtgcccccttattatattgatatgacggcactggctgaagccagaaatgtagaccctgg
aaaatttcatattggtattgggcaagaccaaatggcggtgaacccaatcagccaagatattgtgacatttgcagc
caatgccgcagaagcgatcttgaccaaagaagataaagaggccattgatatggtgattgtcgggactgagtcc
agtatcgatgagtcaaaagcggccgcagttgtcttacatcgtttaatggggattcaacctttcgctcgctctttcgaa
atcaaggaagcttgttacggagcaacagcaggcttacagttagctaagaatcacgtagccttacatccagataa
aaaagtcttggtcgtagcggcagatattgcaaaatatggcttaaattctggcggtgagcctacacaaggagctg
gggcggttgcaatgttagttgctagtgaaccgcgcatttggctttaaaagaggataatgtgatgctgacgcaaga
tatctatgacttttggcgtccaacaggccacccgtatcctatggtcgatggtcctttgtcaaacgaaacctacatcc
aatcttttgcccaagtctgggatgaacataaaaaacgaaccggtcttgattttgcagattatgatgctttagcgttcc
atattccttacacaaaaatgggcaaaaaagccttattagcaaaaatctccgaccaaactgaagcagaacagg
aacgaattttagcccgttatgaagaaagtatcgtctatagtcgtcgcgtaggaaacttgtatacgggttcactttatc
tgggactcatttccctttagaaaatgcaacgacttttaaccgcaggcaatcaaattggtttattcagttatggttctgg
tgctgtcgctgaattttcactggtgaattagtagctggttatcaaaatcatttacaaaaagaaactcatttagcactg
ctggataatcggacagaactttctatcgctgaatatgaagccatgtttgcagaaactttagacacagacattgatc
aaacgttagaagatgaattaaaatatagtatttctgctattaataataccgttcgttcttatcgaaactaagagatctg
cagctggtaccatatgggaattcgaagcttgggcccgaacaaaaactcatctcagaagaggatctgaatagcg
ccgtcgaccatcatcatcatcatcattgagtttaaacggtctccagcttggctgttttggcggatgagagaagatttt
cagcctgatacagattaaatcagaacgcagaagcggtctgataaaacagaatttgcctggcggcagtagcgc
ggtggtcccacctgaccccatgccgaactcagaagtgaaacgccgtagcgccgatggtagtgtggggtctccc
catgcgagagtagggaactgccaggcatcaaataaaacgaaaggctcagtcgaaagactgggcctttcgtttt
atctgttgtttgtcggtgaacgctctcctgagtaggacaaatccgccgggagcggatttgaacgttgcgaagcaa
cggcccggagggtggcgggcaggacgcccgccataaactgccaggcatcaaattaagcagaaggccatcc
tgacggatggcctttttgcgtttctacaaactctttttgtttatttttctaaatacattcaaatatgtatccgctcatgagac
aataaccctgataaatgcttcaataatctggcgtaatagcgaagaggcccgcaccgatcgcccttcccaacagt
tgcgcagcctgaatggcgaatggcgcctgatgcggtattttctccttacgcatctgtgcggtatttcacaccgcatat
ggtgcactctcagtacaatctgctctgatgccgcatagttaagccagccccgacacccgccaacacccgctga
cgagcttagtaaagccctcgctagattttaatgcggatgttgcgattacttcgccaactattgcgataacaagaaa
aagccagcctttcatgatatatctcccaatttgtgtagggcttattatgcacgcttaaaaataataaaagcagacttg
acctgatagtttggctgtgagcaattatgtgcttagtgcatctaacgcttgagttaagccgcgccgcgaagcggcg
tcggcttgaacgaattgttagacattatttgccgactaccttggtgatctcgcctttcacgtagtggacaaattcttcc
aactgatctgcgcgcgaggccaagcgatcttcttcttgtccaagataagcctgtctagcttcaagtatgacgggct
gatactgggccggcaggcgctccattgcccagtcggcagcgacatccttcggcgcgattttgccggttactgcgc
tgtaccaaatgcgggacaacgtaagcactacatttcgctcatcgccagcccagtcgggcggcgagttccatag
cgttaaggtttcatttagcgcctcaaatagatcctgttcaggaaccggatcaaagagttcctccgccgctggacct
accaaggcaacgctatgttctcttgcttttgtcagcaagatagccagatcaatgtcgatcgtggctggctcgaaga
tacctgcaagaatgtcattgcgctgccattctccaaattgcagttcgcgcttagctggataacgccacggaatgat
gtcgtcgtgcacaacaatggtgacttctacagcgcggagaatctcgctctctccaggggaagccgaagtttcca
aaaggtcgttgat

Figure 27C caaagctcgccgcgttgtttcatcaagccttacggtcaccgtaaccagcaaatcaatatcactgtgtggcttca
ggccgccatccactgcggagccgtacaaatgtacggccagcaacgtcggttcgagatggcgctcgatgac
gccaactacctctgatagttgagtcgatacttcggcgatcaccgcttccctcatgatgtttaactttgttttagggc
gactgccctgctgcgtaacatcgttgctgctccataacatcaaacatcgacccacggcgtaacgcgcttgctg
cttggatgcccgaggcatagactgtaccccaaaaaaacagtcataacaagccatgaaaaccgccactgc
gccgttaccaccgctgcgttcggtcaaggttctggaccagttgcgtgagcgcatacgctacttgcattacagct
tacgaaccgaacaggcttatgtccactgggttcgtgccttcatccgtttccacggtgtgcgtcacccggcaacc
ttgggcagcagcgaagtcgaggcatttctgtcctggctggcgaacgagcgcaaggtttcggtctccacgcat
cgtcaggcattggcggccttgctgttcttctacggcaaggtgctgtgcacggatctgccctggcttcaggagat
cggaagacctcggccgtcgcggcgcttgccggtggtgctgaccccggatgaagtggttcgcatcctcggtttt
ctggaaggcgagcatcgtttgttcgcccagcttctgtatggaacgggcatgcggatcagtgagggtttgcaac
tgcgggtcaaggatctggatttcgatcacggcacgatcatcgtgcgggagggcaagggctccaaggatcg
ggccttgatgttacccgagagcttggcacccagcctgcgcgagcaggggaattaattcccacgggttttgctg
cccgcaaacgggctgttctggtgttgctagtttgttatcagaatcgcagatccggcttcagccggtttgccggct
gaaagcgctatttcttccagaattgccatgattttttccccacgggaggcgtcactggctcccgtgttgtcggca
gctttgattcgataagcagcatcgcctgtttcaggctgtctatgtgtgactgttgagctgtaacaagttgtctcagg
tgttcaatttcatgttctagttgctttgttttactggtttcacctgttctattaggtgttacatgctgttcatctgttacattgt
cgatctgttcatggtgaacagctttgaatgcaccaaaaactcgtaaaagctctgatgtatctatcttttttacacc
gttttcatctgtgcatatggacagttttcccttttgatatgtaacggtgaacagttgttctactttttgtttgttagtcttgat
gcttcactgatagatacaagagccataagaacctcagatccttccgtatttagccagtatgttctctagtgtggtt
cgttgttttttgcgtgagccatgagaacgaaccattgagatcatacttactttgcatgtcactcaaaaattttgcctc
aaaactggtgagctgaatttttgcagttaaagcatcgtgtagtgtttttcttagtccgttatgtaggtaggaatctga
tgtaatggttgttggtattttgtcaccattcattttatctggttgttctcaagttcggttacgagatccatttgtctatcta
gttcaacttggaaaatcaacgtatcagtcgggcggcctcgcttatcaaccaccaatttcatattgctgtaagtgtt
taaatctttacttattggtttcaaaacccattggttaagccttttaaactcatggtagttattttcaagcattaacatg
aacttaaattcatcaaggctaatctctatatttgccttgtgagttttcttttgtgttagttcttttaataaccactcataaa
tcctcatagagtatttgttttcaaaagacttaacatgttccagattatattttatgaattttttttaactggaaaagataa
ggcaatatctcttcactaaaaactaattctaattttttcgcttgagaacttggcatagtttgtccactggaaaatctc
aaagcctttaaccaaaggattcctgatttccacagttctcgtcatcagctctctggttgcttagctaatacaccat
aagcattttccctactgatgttcatcatctgagcgtattggttataagtgaacgataccgtccgttcttccttgtag
ggttttcaatcgtggggttgagtagtgccacacagcataaaattagcttggtttcatgctccgttaagtcatagcg
actaatcgctagttcatttgctttgaaaacaactaattcagacatacatctcaattggtctaggtgattttaatcact
ataccaattgagatgggctagtcaatgataattactagtcctttttcctttgagttgtgggtatctgtaaattctgcta
gacctttgctggaaaacttgtaaattctgctagaccctctgtaaattccgctagacctttgtgtgttttttttgtttatatt
caagtggttataatttatagaataaagaaagaataaaaaaagataaaaagaatagatcccagccctgtgtat
aactcactactttagtcagttccgcagtattacaaaaggatgtcgcaaacgctgtttgctcctctacaaaacag
accttaaaaccctaaaggcttaagtagcaccctcgcaagctcgggcaaatcgctgaatattccttttgtctccg
acc

Figure 27D

Atcaggcacctgagtcgctgtcttttcgtgacattcagttcgctgcgctcacggctctggcagtgaatgggggtaaat
ggcactacaggcgccttttatggattcatgcaaggaaactacccataatacaagaaaagcccgtcacgggcttctc
agggcgtttatggcgggtctgctatgtggtgctatctgactttttgctgttcagcagttcctgccctctgattttccagtctg
accacttcggattatcccgtgacaggtcattcagactggctaatgcacccagtaaggcagcggtatcatcaacagg
ctta (SEQ ID NO:46)

Figure 29A

5'-
tgtaacctttgctttcaaatgagtagaaataatgcacatccatgtttgtatcgtgcaaataaagtgtttcatccgtagga
aaaaatgactttagtatctgttccgcttttctgatgaaatgtgctccccgacaaaattgaatgaatcatggacatttgc
tggctttgatacagcgaaagcagccgttcctatgttatatatcggatttaacagcaggacaaaaaacaccatgaca
gccatcgtcacccacttattcacacgcacataaacctttcctgacttttggaacagatgatagctcatcaaaaatcc
cgccattgccaaataaatcgtatatggcattactgcaccataatcttttgagatttgattgggatatggcgcaagcag
caagacaagcagtccgataatcagcgtataaaataagcctagtaagatcttatccgttctccaatacagcttgaaa
aacactacattcaacgcaatgggaagagtgatgatgaaaaacagaaacacgaatgcaatcggctccatcccat
ccgggtattccttccaatacgaaaagaaactaaaaatcatttgtacgatcggcaaactgacaacagcaaggtcg
aacgtataaaacttaccctttccgccatgatcacgcggcatcagcatatagtgaaaagccgtcagcagcacatat
ccgtataacaaaaaatgcagcagcggcagcagttcttttccgtcctctcttaagtaagcgctggtgaagtttgttgatt
gcacctggtgaataagttcaacagacactcccgccagcagcacaatccgcaatataacacccgccaagaacat
tgtgcgctgccggtttatttttgggatgatgcaccaaaagatataagcccgccagaacaacaattgaccattgaatc
agcagggtgctttgtctgcttaatataaaataacgttcgaaatgcaatacataatgactgaataactccaacacga
acaacaactccattttcttctgctatcaaaataacagactcgtgattttccaaacgagctttcaaaaaagcctctgcc
ccttgcaaatcggatgcctgtctataaaattcccgatattggttaaacagcggcgcaatggcggccgcatctgatgt
ctttgcttggcgaatgttcatcttatttcttcctccctctcaataattttttcattctatccctttctgtaaagtttatttttcagaa
tacttttatcatcatgctttgaaaaaatatcacgataatatccattgttctcacggaagcacacgcaggtcatttgaac
gaatttttcgacaggaatttgccgggactcaggagcatttaacctaaaaaagcatgacatttcagcataatgaac
atttactcatgtctatttcgttcttttctgtatgaaaatagttatttcgagtctctacggaaatagcgagagatgatatacc
taaatagagataaaatcatctcaaaaaaatgggtctactaaaatattattccatctattacaataaattcacagaata
gtcttttaagtaagtctactctgaatttttttaaaaggagagggtaaagagtgtcattaccgttcttaacttctgcaccgg
gaaaggttattattttggtgaacactctgctgtgtacaacaagcctgccgtcgctgctagtgtgtctgcgttgagaac
ctacctgctaataagcgagtcatctgcaccagatactattgaattggacttcccggacattagctttaatcataagtg
gtccatcaatgatttcaatgccatcaccgaggatcaagtaaactcccaaaaattggccaaggctcaacaagcca
ccgatggcttgtctcaggaactcgttagtctttggatccgttgttagctcaactatccgaatccttccactaccatgca
gcgtttgtttcctgtatatgtttgtttgcctatgcccccatgccaagaatattaagtttttctttaaagtctactttacccatcg
gtgctgggttgggctcaagcgcctctatttctgtatcactggccttagctatggcctacttggggggggttaataggatct
aatgacttggaaaagctgtcagaaaacgataagcatatagtgaatcaatgggccttcataggtgaaaagtgtattc
acggtaccccttcaggaatagataacgctgtggccacttatggtaatgccctgctatttgaaaaagactcacataat
ggaacaataaacacaaacaattttaagttcttagatgatttcccagccattccaatgatcctaacctatactagaatt
ccaaggtctacaaaagatcttgttgctcgcgttcgtgtgttggtcaccgagaaatttcctgaagttatgaagccaattc
tagatgccatgggtgaatgtgccctacaaggcttagagatcatgactaagttaagtaaatgtaaaggcaccgatg
acgaggctgtagaaactaataatgaactgtatgaacaactattggaattgataagaataaatcatggactgcttgt
ctcaatcggtgtttctcatcctggattagaacttattaaaaaatctgagcgatgatttgagaattggctccacaaaactt
accggtgctggtggcggcggttgctctttgactttgttacgaagagacattactcaagagcaaattgacagcttcaa
aaagaaattgcaagatgattttagt

Figure 29B

```
tacgagacatttgaaacagacttgggtgggactggctgctgtttgttaagcgcaaaaaatttgaataaagatcttaa
aatcaaatccctagtattccaattatttgaaaataaaactaccacaaagcaacaaattgacgatctattattgccag
gaaacacgaatttaccatggacttcataaaaggagagggtgtcagagttgagagccttcagtgccccagggaa
agcgttactagctggtggatatttagttttagatacaaaatatgaagcatttgtagtcggattatcggcaagaatgcat
gctgtagcccatccttacggttcattgcaagggtctgataagtttgaagtgcgtgtgaaaagtaaacaatttaaagat
ggggagtggctgtaccatataagtcctaaaagtggcttcattcctgtttcgataggcggatctaagaaccctttcattg
aaaaagttatcgctaacgtatttagctactttaaacctaacatggacgactactgcaatagaaacttgttcgttattga
tattttctctgatgatgcctaccattctcaggaggatagcgttaccgaacatcgtggcaacagaagattgagttttcatt
cgcacagaattgaagaagttcccaaaacagggctgggctcctcggcaggtttagtcacagttttaactacagcttt
ggcctccttttttgtatcggacctggaaaataatgtagacaaatatagagaagttattcataatttagcacaagttgct
cattgtcaagctcagggtaaaattggaagcgggtttgatgtagcggcggcagcatatggatctatcagatatagaa
gattcccacccgcattaatctctaatttgccagatattggaagtgctacttacggcagtaaactggcgcatttggttga
tgaagaagactggaatattacgattaaaagtaaccatttaccttcgggattaactttatggatgggcgatattaaga
atggttcagaaacagtaaaactggtccagaaggtaaaaaattggtatgattcgcatatgccagaaagcttgaaaa
tatatacagaactcgatcatgcaaattctagatttatggatggactatctaaactagatcgcttacacgagactcatg
acgattacagcgatcagatatttgagtctcttgagaggaatgactgtacctgtcaaaagtatcctgaaatcacaga
agttagagatgcagttgccacaattagacgttcctttagaaaaataactaaagaatctggtgccgatatcgaacct
cccgtacaaactagcttattggatgattgccagaccttaaaaggagttcttacttgcttaatacctggtgctggtggtta
tgacgccattgcagtgattactaagcaagatgttgatcttagggctcaaaccgctaatgacaaaagatttctaagg
ttcaatggctggatgtaactcaggctgactggggtgttaggaaagaaaaagatccggaaacttatcttgataaata
aaaggagagggtgaccgtttacacagcatccgttaccgcacccgtcaacatcgcaacccttaagtattggggga
aaagggacacgaagttgaatctgcccaccaattcgtccatatcagtgactttatcgcaagatgacctcagaacgtt
gacctctgcggctactgcacctgagtttgaacgcgacactttgtggttaaatggagaaccacacagcatcgacaa
tgaaagaactcaaaattgtctgcgcgacctacgccaattaagaaaggaaatggaatcgaaggacgcctcattgc
ccacattatctcaatggaaactccacattgtctccgaaaataactttcctacagcagctggtttagcttcctccgctgc
tggctttgctgcattggtctctgcaattgctaagttataccaattaccacagtcaacttcagaaatatctagaatagca
agaaaggggtctggttcagcttgtagatcgttgtttggcggatacgtggcctgggaaatgggaaaagctgaagat
ggtcatgattccatggcagtacaaatcgcagacagctctgactggcctcagatgaaagcttgtgtcctagttgtcag
cgatattaaaaaggatgtgagttccactcagggtatgcaattgaccgtggcaacctccgaactatttaaagaaag
aattgaacatgtcgtaccaagagatttgaagtcatgcgtaaagccattgttgaaaaagatttcgccacctttgcaa
aggaaacaatgatggattccaactctttccatgccacatgtttggactctttccctccaatattctacatgaatgacac
ttccaagcgtatcatcagttggtgccacaccattaatcagttttacggagaaacaatcgttgcatacacgtttgatgc
aggtccaaatgctgtgttgtactacttagctgaaaatgagtcgaaactctttgcatttatctataaattgtttggctctgtt
cctggatgggacaagaaatttactactgagcagcttgaggctttcaaccatcaatttgaatcatctaacttttactgca
cgtgaattggatcttgagttgcaaaaggatgttgccagagtgattttaactcaagtcggttcaggcccacaagaaa
caaacgaatctttgattgacgcaaagactggtctaccaaaggaataaaaggagagggtgactgccgacaaca
atagtatgccccatggtgcagtatctagttacgccaaattagt
```

Figure 29C gcaaaaccaaacacctgaagacattttggaagagtttcctgaaattattccattacaacaaagacctaatacccg
atctagtgagacgtcaaatgacgaaagcggagaaacatgtttttctggtcatgatgaggagcaaattaagttaatg
aatgaaaattgtattgttttggattgggacgataatgctattggtgccggtaccaagaaagtttgtcatttaatggaaa
atattgaaaagggtttactacatcgtgcattctccgtctttattttcaatgaacaaggtgaattacttttacaacaaaga
gccactgaaaaaataactttccctgatctttggactaacacatgctgctctcatccactatgtattgatgacgaattag
gtttgaagggtaagctagacgataagattaagggcgctattactgcggcggtgagaaaactagatcatgaattag
gtattccagaagatgaaactaagacaaggggtaagtttcactttttaaacagaatccattacatggcaccaagca
atgaaccatggggtgaacatgaaattgattacatcctattttataagatcaacgctaaagaaaacttgactgtcaac
ccaaacgtcaatgaagttagagacttcaaatgggtttcaccaaatgatttgaaaactatgtttgctgacccaagtta
caagtttacgccttggtttaagattatttgcgagaattacttattcaactggtgggagcaattagatgacctttctgaagt
ggaaaatgacaggcaaattcatagaatgctataaaaaaaaccggccttggccccgccggttttttattattttttcttcc
tccgcatgttcaatccgctccataatcgacggatggctccctctgaaaattttaacgagaaacggcgggttgaccc
ggctcagtcccgtaacggccaagtcctgaaacgtctcaatcgccgcttccggtttccggtcagctcaatgccgta
acggtcggcggcgttttcctgataccgggagacggcattcgtaatttgaatacatacgaacaaattaataaagtga
aaaaaatacttcggaaacatttaaaaaataaccttattggtacttacatgtttggatcaggagttgagagtggacta
aaaccaaatagtgatcttgacttttagtcgtcgtatctgaaccattgacagatcaaagtaaagaaatacttatacaa
aaaattagacctatttcaaaaaaaataggagataaaagcaacttacgatatattgaattaacaattattattcagca
agaaatggtaccgtggaatcatcctcccaaacaagaatttatttatggagaatggttacaagagctttatgaacaa
ggatacattcctcagaaggaattaaattcagatttaaccataatgctttaccaagcaaaacgaaaaaataaaaga
atatacggaaattatgacttagaggaattactacctgatattccattttctgatgtgagaagagccattatggattcgtc
agaggaattaatagataattatcaggatgatgaaaccaactctatattaactttatgccgtatgatttaactatggac
acgggtaaaatcataccaaaagatattgcgggaaatgcagtggctgaatcttctccattagaacatagggagag
aatttgttagcagttcgtagttatcttggagagaatattgaatggactaatgaaaatgtaaatttaactataaactattt
aaataacagattaaaaaaattataatgtaacctttgctttcaaatgagtagaaataatgcacatccatgtttgtatcgt
gcaaataaagtgtttcatccgtaggaaaaaatgactttagtatctgttccgcttttctgatgaaatgtgctccccgaca
aaattgaatgaatcatggacatttgctggcttgatacagcgaaagcagccgttcctatgttatatatcggatttaaca
gcaggacaaaaaacaccatgacagccatcgtcacccacttattcacacgcacataaaccttcctgacttttgga
acagatgatagctcatcaaaaatcccgccattgccaaataaatcgtatatggcattactgcaccataatcttttgag
atttgattgggatatggcgcaagcagcaagacaagcagtccgataatcagcgtataaaataagcctagtaagat
cttatccgttctccaatacagcttgaaaaacactacattcaacgcaatgggaagagtgatgatgaaaaacagaaa
cacgaatgcaatcggctccatcccatccgggtattccttccaatacgaaaagaaactaaaaatcatttgtacgatc
ggcaaactgacaacagcaaggtcgaacgtataaaacttacccttccgccatgatcacgcggcatcagcatata
gtgaaaagccgtcagcagcacatatccgtataacaaaaaatgcagcagcggcagcagttcttttccgtcctctctt
aagtaagcgctggtgaagtttgttgattgcacctggtgaataagttcaacagacactcccgccagcagcacaatc
cgcaatataacacccgccaagaacattgtgcgctgccggtttattttgggatgatgcaccaaaagatataagccc
gccagaacaacaattgaccattgaatcagcagggtgctttgtctgcttaatataaaataacgttcgaaatgcaata
cataatgactgaataactccaacacgaacaacaaaagtgcgcatttt

Figure 29D

Ataaaagctaatgattcagtccacataattgatagacgaattctgctacaggtcacgtggctatgtgaaggatcgc
gcgtccagttaagagcaaaaacattgacaaaaaaatttatttatgctaaaatttactattaatatatttgtatgtataat
aagattctcctggccaggggaatcttattttttgtggaggatcatttcatgaggaaaaatgagtccagcttaacgtctc
taatttcagcttttgcccgtgcatatcacagccgatatgacacacctcttattttgatgattttatcgcaaaagatctcat
taacgaaaaagagtttatcgacatcagtaaaaatatgattcaagaaatatcgtttttcaacaaagagatcgccgaa
cgtcttcaaaatgatcctgaaaaaatattaaaatgggttgcacaaatccagctgtctccaacgcccctagcacgtg
cttcttattgtgaaaaagtcttgcacaacgaattaatcctgggggcaaaacagtatgtcattcttggagcgggactg
gatactttctgctttcggcatccagaattagaaaacagcttacaggttttcgaggttgatcatccggccacacagca
attgaaaaaaaataagctgaaggatgcaaatctgacaattccgggtcatcttcattttgttcctatggatttcaccaa
aacgttttcgtatgatcctctctcttagatgaaggatttaaaaacacaaaaacattcttcagccttctcggagtgtcttatt
atgtaacacgggaagaaaatgcaagcttgatcagcaatttattttctcatgtcccgcctggaagctctattgttttgat
tatgcggacgaaacacttttacagcaaaagggacgtcgaatcgagttgaacatatggtgaagatggctgccgc
aagcggggaaccgatgaaatcatgtttcacttatcaagagattgaacatctg (SEQ ID NO:47)

Figure 31A

5'-
tagaaaaactcatcgagcatcaaatgaaactgcaatttattcatatcaggattatcaataccatattttgaaaaagc
cgtttctgtaatgaaggagaaaactcaccgaggcagttccataggatggcaagatcctggtatcggtctgcgattc
cgactcgtccaacatcaatacaacctattaatttcccctcgtcaaaaataaggttatcaagtgagaaatcaccatg
agtgacgactgaatccggtgagaatggcaaaagtttatgcatttctttccagacttgttcaacaggccagccattac
gctcgtcatcaaaatcactcgcatcaaccaaaccgttattcattcgtgattgcgcctgagcgaggcgaaatacgcg
atcgctgttaaaaggacaattacaaacaggaatcgagtgcaaccggcgcaggaacactgccagcgcatcaac
aatattttcacctgaatcaggatattcttctaatacctggaacgctgtttttccggggatcgcagtggtgagtaaccatg
catcatcaggagtacggataaaatgcttgatggtcggaagtggcataaattccgtcagccagtttagtctgaccatc
tcatctgtaacatcattggcaacgctacctttgccatgtttcagaaacaactctggcgcatcgggcttcccatacaag
cgatagattgtcgcacctgattgcccgacattatcgcgagcccatttatacccatataaatcagcatccatgttggaa
tttaatcgcggcctcgacgtttccgttgaatatggctcatattcttcctttttcaatattattgaagcatttatcagggttatt
gtctcatgagcggatacatatttgaatgtatttagaaaaataaacaaatagggggtcagtgttacaaccaattaacca
attctgaacattatcgcgagcccatttatacctgaatatggctcataacaccccttgtttgcctggcggcagtagcgc
ggtggtcccacctgacccccatgccgaactcagaagtgaaacgccgtagcgccgatggtagtgtggggactccc
catgcgagagtagggaactgccaggcatcaaataaaacgaaaggctcagtcgaaagactgggccttcgccc
gggctaattaggggggtgtcgcccttagtcgctgaacatgtgctctgtttctaccgagaacgtttccttcactgagacg
gaaaccgaggcacgtcgtagcgcgaactacgagccgaatagctgggactacgatttcctgctgtcttccgatact
gacgaatctattgaggtgtacaaagacaaagcaaagaaactggaggctgaagtgcgccgcgaaattaacaac
gagaaagctgaattcctgactctgctggagctgatcgataacgtacagcgcctgggtctgggttaccgcttcgaat
ctgatatccgtcgcgcactggatcgtttcgtaagcagcggcggtttcgatggcgtgaccaaaacgagcctgcacg
ctaccgcgctgtccttccgtctgctgcgtcagcacggcttcgaagtttctcaggaagcattctccggtttcaaagatc
aaaacggtaacttcctggaaaacctgaaagaagacactaaggcgatcctgagcctgtatgaggcaagcttctg
gccctggagggtgagaacatcctggatgaggcgcgcgtattcgccatctcccatctgaaagagctgtctgaaga
gaaaatcggtaaggaactggcagagcaggttaatcacgcactggaactgccgctgcatcgtcgtacccagcgtc
tggaggcggtttggtccatcgaagcgtaccgcaaaaaggaggatgctaaccaggttctgctggaactggccatc
ctggactacaacatgatccagtccgtttaccagcgtgatctgcgtgaaacctcccgttggtggcgccgtgtgggcct
ggcgaccaaactgcacttcgctaaggaccgcctgattgagtcttttactgggcagtcggcgttgcgttcgaacctc
agtattctgactgccgtaacagcgttgcgaaaatgttcagcttcgttactattatcgacgacatctacgacgtttacgg
tactctggacgagctggaactgtttaccgacgctgtcgaacgttgggatgttaacgccatcaacgatctgcctgact
acatgaaactgtgcttcctggcactgtataacacgatcaacgaaattgcatacgacaacctgaaagacaaaggt
gaaaacatcctgccgtacctgactaaagcgtgggcggatctgtgtaacgcttttctgcaagaagcgaaatggctgt
ataacaaatccactccgaccttgacgattatttcggcaatgcctggaaatccagctctggcccgctgcaactgatc
ttcgcttatttgcggttgtccaaaacatcaaaaaggaggaaattgaaaacctgcaaaaataccacgatatcatta
gccgtccttctcatatctttcgcctgtgcaacgacctggcaagcgcgtccgcagagatcgcacgtggcgaaaccg
ctaactctgtttcctgctacatgcgcaccaagggcatttccgaagagctggcaaccgagagcgtaatgaatctgat
cgacgaaacctgtaagaaaatgaacaaagaaaaactgggtggctccctgttcgctaaaccgttcgtagagactg
ctattaacct

Figure 31B ggcacgtcagagccactgcacctaccacaatggtgacgcacatactagcccggatgaactgactcgtaaacgt
gtactgtctgttatcaccgaaccgattctgccgttcgaacgttaactgcagcgtcaatcgaaagggcgacacaaa
atttattctaaatgcataataaatactgataacatcttatagtttgtattatattttgtattatcgttgacatgtataattttgat
atcaaaaactgattttcccttattattttcgagatttattttcttaattctctttaacaaactagaaatattgtatatacaaaa
aatcataaataatagatgaatagtttaattataggtgttcatcaatcgaaaaagcaacgtatcttatttaaagtgcgtt
gcttttttctcatttataaggttaaataattctcatatatcaagcaaagtgacaggcgcccttaaatattctgacaaatg
ctctttccctaaactcccccataaaaaaacccgccgaagcgggttttacgttatttgcggattaacgattactcgtt
atcagaaccgcccaggggccccgagcttaagactggccgtcgttttacaacacagaaagagtttgtagaaacg
caaaaaggccatccgtcaggggccttctgcttagtttgatgcctggcagttccctactctcgccttccgcttcctcgct
cactgactcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaaccgtaaa
aaggccgcgttgctggcgtttttccataggctccgcccccctgacgagcatcacaaaaatcgacgctcaagtcag
aggtggcgaaacccgacaggactataaagataccaggcgtttccccctggaagctccctcgtgcgctctcctgtt
ccgaccctgccgcttaccggatacctgtccgcctttctcccttcgggaagcgtggcgctttctcatagctcacgctgt
aggtatctcagttcggtgtaggtcgttcgctccaagctgggctgtgtgcacgaaccccccgttcagcccgaccgct
gcgccttatccggtaactatcgtcttgagtccaacccggtaagacacgacttatcgccactggcagcagccactg
gtaacaggattagcagagcgaggtatgtaggcggtgctacagagttcttgaagtggtgggctaactacggctaca
ctagaagaacagtatttggtatctgcgctctgctgaagccagttaccttcggaaaaagagttggtagctcttgatccg
gcaaacaaaccaccgctggtagcggtggtttttttgtttgcaagcagcagattacgcgcagaaaaaaaggatctc
aagaagatcctttgatcttttctacggggtctgacgctcagtggaacgacgcgcgcgtaactcacgttaagggatttt
ggtcatgagcttgcgccgtcccgtcaagtcagcgtaatgctctgcttt (SEQ ID NO:48)

Figure 33A

5'-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgtttttgcgccg
acatcataacggttctggcaaatattctgaaatgagctgttgacaattaatcatccggctcgtataatgtgtggaatt
gtgagcggataacaatttcacacaggaaacagcgccgctgagaaaaagcgaagcggcactgctctttaaca
atttatcagacaatctgtgtgggcactcgaccggaattatcgattaactttattattaaaaattaaagaggtatatatt
aatgtatcgattaaataaggaggaataaaccatgtgctctgtttctaccgagaacgtttccttcactgagacggaa
accgaggcacgtcgtagcgcgaactacgagccgaatagctgggactacgatttcctgctgtcttccgatactga
cgaatctattgaggtgtacaaagacaaagcaaagaaactggaggctgaagtgcgccgcgaaattaacaacg
agaaagctgaattcctgactctgctggagctgatcgataacgtacagcgcctgggtctgggttaccgcttcgaat
ctgatatccgtcgcgcactggatcgtttcgtaagcagcggcggtttcgatggcgtgaccaaaacgagcctgcac
gctaccgcgctgtccttccgtctgctgcgtcagcacggcttcgaagtttctcaggaagcattctccggtttcaaaga
tcaaaacggtaacttcctggaaaacctgaaagaagacactaaggcgatcctgagcctgtatgaggcaagcttt
ctggccctggagggtgagaacatcctggatgaggcgcgcgtattcgccatctcccatctgaaagagctgtctga
agagaaaatcggtaaggaactggcagagcaggttaatcacgcactggaactgccgctgcatcgtcgtaccca
gcgtctggaggcggtttggtccatcgaagcgtaccgcaaaaaggaggatgctaaccaggttctgctggaactg
gccatcctggactacaacatgatccagtccgtttaccagcgtgatctgcgtgaaacctcccgttggtggcgccgt
gtgggcctggcgaccaaactgcacttcgctaaggaccgcctgattgagtctttttactgggcagtcggcgttgcgtt
cgaacctcagtattctgactgccgtaacagcgttgcgaaaatgttcagcttcgttactattatcgacgacatctacg
acgtttacggtactctggacgagctggaactgttaccgacgctgtcgaacgttgggatgttaacgccatcaacg
atctgcctgactacatgaaactgtgcttcctggcactgtataacacgatcaacgaaattgcatacgacaacctga
agacaaaggtgaaaacatcctgccgtacctgactaaagcgtgggcggatctgtgtaacgcttttctgcaagaa
gcgaaatggctgtataacaaatccactccgacctttgacgattattcggcaatgcctggaaatccagctctggcc
cgctgcaactgatcttcgcttattttgcggttgtccaaaacatcaaaaaggaggaaattgaaaacctgcaaaaat
accacgatatcattagccgtccttctcatatctttcgcctgtgcaacgacctggcaagcgcgtccgcagagatcgc
acgtggcgaaaccgctaactctgtttcctgctacatgcgcaccaagggcatttccgaagagctggcaaccgag
agcgtaatgaatctgatcgacgaaacctgtaagaaaatgaacaaagaaaaactgggtggctccctgttcgcta
aaccgttcgtagagactgctattaacctggcacgtcagagccactgcacctaccacaatggtgacgcacatact
agcccggatgaactgactcgtaaacgtgtactgtctgttatcaccgaaccgattctgccgttcgaacgttaactgc
agctggtaccatatgggaattcgaagctttctagaacaaaaactcatctcagaagaggatctgaatagcgccgt
cgaccatcatcatcatcatcattgagtttaaacggtctccagcttggctgttttggcggatgagagaagattttcagc
ctgatacagattaaatcagaacgcagaagcggtctgataaaacagaatttgcctggcggcagtagcgcggtgg
tcccacctgaccccatgccgaactcagaagtgaaacgccgtagcgccgatggtagtgtggggtctccccatgc
gagagtagggaactgccaggcatcaaataaaacgaaaggctcagtcgaaagactgggcctttcgttttatctgt
tgtttgtcggtgaacgctctcctgagtaggacaaatccgccgggagcggatttgaacgttgcgaagcaacggcc
cggagggtggcgggcaggacgcccgccataaactgccaggcatcaaattaagcagaaggccatcctgacg
gatggcctttttgcgtttctacaaactcttttgtttatttttctaaatacattcaaatatgtatccgctcatgagacaataa
ccctgataaatgcttcaataatattgaaaaaggaagagtatgagtattcaacatttc

Figure 33B cgtgtcgcccttattccctttttgcggcatttgccttcctgtttttgctcacccagaaacgctggtgaaagtaaaagatg
ctgaagatcagttgggtgcacgagtgggttacatcgaactggatctcaacagcggtaagatccttgagagtttcgc
cccgaagaacgttttccaatgatgagcacttttaaagttctgctatgtggcgcggtattatcccgtgttgacgccgggc
aagagcaactcggtcgccgcatacactattctcagaatgacttggttgagtactcaccagtcacagaaaagcatctt
acggatggcatgacagtaagagaattatgcagtgctgccataaccatgagtgataacactgcggccaacttacttct
gacaacgatcggaggaccgaaggagctaaccgcttttttgcacaacatgggggatcatgtaactcgccttgatcgtt
gggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcggat
aaagttgcaggaccacttctgcgctcggcccttccggctggctggtttattgctgataaatctggagccggtgagcgt
gggtctcgcggtatcattgcagcactggggccagatggtaagccctcccgtatcgtagttatctacacgacgggga
gtcaggcaactatggatgaacgaaatagacagatcgctgagataggtgcctcactgattaagcattggtaactgtc
agaccaagtttactcatatatactttagattgatttaaaacttcatttttaatttaaaaggatctaggtgaagatccttttga
taatctcatgaccaaaatcccttaacgtgagttttcgttccactgagcgtcagacccgtagaaaagatcaaggat
cttcttgagatcctttttttctgcgcgtaatctgctgcttgcaaacaaaaaaaccaccgctaccagcggtggtttgtttgc
cggatcaagagctaccaactctttttccgaaggtaactggcttcagcagagcgcagataccaaatactgtccttcta
gtgtagccgtagttaggccaccacttcaagaactctgtagcaccgcctacatacctcgctctgctaatcctgttacca
gtggctgctgccagtggcgataagtcgtgtcttaccggttggactcaagacgatagttaccggataaggcgcagc
ggtcgggctgaacggggggttcgtgcacacagcccagcttggagcgaacgacctacaccgaactgagataccta
cagcgtgagctatgagaaagcgccacgcttcccgaagggagaaaggcggacaggtatccggtaagcggcagg
gtcggaacaggagagcgcacgagggagcttccaggggggaaacgcctggtatctttatagtcctgtcgggtttcgcc
acctctgacttgagcgtcgatttttgtgatgctcgtcaggggggcggagcctatggaaaaacgccagcaacgcggc
ctttttacggttcctggccttttgctggccttttgctcacatgttctttcctgcgttatcccctgattctgtggataaccgtattac
cgcctttgagtgagctgataccgctcgccgcagccgaacgaccgagcgcagcgagtcagtgagcgaggaagcg
gaagagcgcctgatgcggtatttctccttacgcatctgtgcggtatttcacaccgcatatggtgcactctcagtacaat
ctgctctgatgccgcatagttaagccagtatacactccgctatcgctacgtgactgggtcatggctgcgccccgaca
cccgccaacacccgctgacgcgccctgacgggcttgtctgctcccggcatccgcttacagacaagctgtgaccgtc
tccgggagctgcatgtgtcagaggttttcaccgtcatcaccgaaacgcgcgaggcagcagatcaattcgcgcgcg
aaggcgaagcggcatgcatttacgttgacaccatcgaatggtgcaaaaccttcgcggtatggcatgatagcgccc
ggaagagagtcaattcagggtggtgaatgtgaaaccagtaacgttatacgatgtcgcagagtatgccggtgtctctt
atcagaccgtttcccgcgtggtgaaccaggccagccacgtttctgcgaaaacgcgggaaaaagtggaagcggc
gatggcggagctgaattacattcccaaccgcgtggcacaacaactggcgggcaaacagtcgttgctgattggcgtt
gccacctccagtctggccctgcacgcgccgtcgcaaattgtcgcggcgattaaatctcgcgccgatcaactgggtg
ccagcgtggtgtcgatggtagaacgaagcggcgtcgaagcctgtaaagcggcggtgcacaatcttctcgcgc
aacgcgtcagtgggctgatcattaactatccgctggatgaccaggatgccattgctgtggaagctgcctgcactaat
gttccggcgttatttcttgatgtctctgaccagacacccatcaacagtattattttctcccatgaagacggtacgcgact
gggcgtggagcatctggtcgcattgggtcaccagcaaatcgcgctgttagcgggcccattaagttctgtctcggcgc
gtctgcgtctggctggctggcataaatatctcactcgcaatc

Figure 33C aaattcagccgatagcggaacgggaaggcgactggagtgccatgtccggttttcaacaaaccatgcaaatgctgaa
tgagggcatcgttcccactgcgatgctggttgccaacgatcagatggcgctgggcgcaatgcgcgccattaccgagt
ccgggctgcgcgttggtgcggatatctcggtagtgggatacgacgataccgaagacagctcatgttatatcccgccgt
caaccaccatcaaacaggattttcgcctgctggggcaaaccagcgtggaccgcttgctgcaactctctcagggcca
ggcggtgaagggcaatcagctgttgcccgtctcactggtgaaaagaaaaaccaccctggcgcccaatacgcaaac
cgcctctccccgcgcgttggccgattcattaatgcagctggcacgacaggtttcccgactggaaagcgggcagtgag
cgcaacgcaattaatgtgagttagcgcgaattgatctg (SEQ ID NO:49)

Figure 35A

5'-
ttgtctgctcccggcatccgcttacagacaagctgtgaccgtctccgggagctgcatgtgtcagaggttttcaccgtc
atcaccgaaacgcgcgaggcagcagatcaattcgcgcgcgaaggcgaagcggcatgcatttacgttgacacc
atcgaatggtgcaaaaccttcgcggtatggcatgatagcgcccggaagagagtcaattcagggtggtgaatgtg
aaaccagtaacgttatacgatgtcgcagagtatgccggtgtctcttatcagaccgtttcccgcgtggtgaaccagg
ccagccacgtttctgcgaaaacgcgggaaaaagtggaagcggcgatggcggagctgaattacattcccaacc
gcgtggcacaacaactggcgggcaaacagtcgttgctgattggcgttgccacctccagtctggccctgcacgcg
ccgtcgcaaattgtcgcggcgattaaatctcgcgccgatcaactgggtgccagcgtggtggtgtcgatggtagaa
cgaagcggcgtcgaagcctgtaaagcggcggtgcacaatcttctcgcgcaacgcgtcagtgggctgatcattaa
ctatccgctggatgaccaggatgccattgctgtggaagctgcctgcactaatgttccggcgttatttcttgatgtctctg
accagacacccatcaacagtattatttctcccatgaagacggtacgcgactgggcgtggagcatctggtcgcatt
gggtcaccagcaaatcgcgctgttagcgggcccattaagttctgtctcggcgcgtctgcgtctggctggctggcata
aatatctcactcgcaatcaaattcagccgatagcggaacgggaaggcgactggagtgccatgtccggttttcaac
aaaccatgcaaatgctgaatgagggcatcgttcccactgcgatgctggttgccaacgatcagatggcgctgggc
gcaatgcgcgccattaccgagtccgggctgcgcgttggtgcggatatctcggtagtgggatacgacgataccga
agacagctcatgttatatcccgccgtcaaccaccatcaaacaggattttcgcctgctggggcaaaccagcgtgga
ccgcttgctgcaactctctcagggccaggcggtgaagggcaatcagctgttgcccgtctcactggtgaaaagaaa
aaccaccctggcgcccaatacgcaaaccgcctctccccgcgcgttggccgattcattaatgcagctggcacgac
aggtttcccgactggaaagcgggcagtgagcgcaacgcaattaatgtgagttagcgcgaattgatctggtttgac
agcttatcatcgactgcacggtgcaccaatgcttctggcgtcaggcagccatcggaagctgtggtatggctgtgca
ggtcgtaaatcactgcataattcgtgtcgctcaaggcgcactcccgttctggataatgttttttgcgccgacatcataa
cggttctggcaaatattctgaaatgagctgttgacaattaatcatccggctcgtataatgtgtggaattgtgagcggat
aacaatttcacacaggaaacagcgccgctgagaaaaagcgaagcggcactgctctttaacaatttatcagaca
atctgtgtgggcactcgaccggaattatcgattaactttattattaaaaattaaagaggtatatattaatgtatcgatta
aataaggaggaataaaccatgtgtgcgacctcttctcaatttactcagattaccgagcataattcccgtcgttccgc
aaactatcagccaaacctgtggaatttcgaattcctgcaatccctggagaacgacctgaaagtggaaaagctgg
aggagaaagcgaccaaactggaggaagaagttcgctgcatgatcaaccgtgtagacacccagccgctgtccct
gctggagctgatcgacgatgtgcagcgcctgggtctgacctacaaatttgaaaaagacatcattaaagccctgga
aaacatcgtactgctggacgaaaacaaaaagaacaaatctgacctgcacgcaaccgctctgtctttccgtctgct
gcgtcagcacggtttcgaggtttctcaggatgttttgagcgtttcaaggataaagaaggtggtttcagcggtgaact
gaaaggtgacgtccaaggcctgctgagcctgtatgaagcgtcttacctgggtttcgagggtgagaacctgctgga
ggaggcgcgtaccttttccatcacccacctgaagaacaacctgaaagaaggcattaataccaaggttgcagaac
aagtgagccacgccctggaactgccatatcaccagcgtctgcaccgtctggaggcacgttggttcctggataaat
acgaaccgaaagaaccgcatcaccagctgctgctggagctggcgaagctggattttaacatggtacagaccctg
caccagaaagagctgcaagatctgtcccgctggtggaccgagatgggcctggctagcaaactggatttttgtacg
cgaccgcctgatggaagtttatttctgggcactgggtatggcgccagacccgcagtttggtgaatgtcgcaaagct
gttactaaaatgtttggtctggtgacgatcatcgatgacgtgtatgacgt

Figure 35B ttatggcactctggacgaactgcaactgttcaccgatgctgtagagcgctgggacgttaacgctattaacaccct
gccggactatatgaaactgtgtttcctggcactgtacaacaccgttaacgacacgtcctattctattctgaaagag
aaaggtcataacaacctgtcctatctgacgaaaagctggcgtgaactgtgcaaagcctttctgcaagaggcg
aaatggtccaacaacaaaattatcccggctttctccaagtacctggaaaacgccagcgtttcctcctccggtgt
agcgctgctggcgccgtcttactttttccgtatgccagcagcaggaagacatctccgaccacgcgctgcgttccc
tgaccgacttccatggtctggtgcgttctagctgcgttatcttccgcctgtgcaacgatctggccacctctgcggcg
gagctggaacgtggcgagactaccaattctatcattagctacatgcacgaaaacgatggtaccagcgagga
acaggcccgcgaagaactgcgtaaactgatcgacgccgaatggaaaaagatgaatcgtgaacgcgttagc
gactccaccctgctgcctaaagcgttcatggaaatcgcagttaacatggcacgtgtttcccactgcacctacca
gtatggcgatggtctgggtcgcccagactacgcgactgaaaaccgcatcaaactgctgctgattgacccttttcc
cgattaaccagctgatgtatgtctaactgcatcgcccttaggaggtaaaaaaaaaatgactgccgacaacaata
gtatgccccatggtgcagtatctagttacgccaaattagtgcaaaaccaaacacctgaagacatttggaaga
gtttcctgaaattattccattacaacaaagacctaatacccgatcagtgagacgtcaaatgacgaaagcgga
gaaacatgtttttctggtcatgatgaggagcaaattaagttaatgaatgaaaattgtattgttttggattgggacgat
aatgctattggtgccggtaccaagaaagtttgtcatttaatggaaaatattgaaaagggtttactacatcgtgcatt
ctccgtctttatttttcaatgaacaaggtgaattacttttacaacaaagagccactgaaaaaataactttccctgatc
tttggactaacacatgctgctctcatccactatgtattgatgacgaattaggtttgaagggtaagctagacgataa
gattaagggcgctattactgcggcggtgagaaaactagatcatgaattaggtattccagaagatgaaactaag
acaaggggtaagtttcacttttaaacagaatccattacatggcaccaagcaatgaaccatgggtgaacatg
aaattgattacatcctatttataagatcaacgctaaagaaaacttgactgtcaacccaaacgtcaatgaagtta
gagacttcaaatgggtttcaccaaatgatttgaaaactatgtttgctgacccaagttacaagtttacgccttggttta
agattatttgcgagaattacttattcaactggtgggagcaattagatgacctttctgaagtggaaaatgacaggc
aaattcatagaatgctataacaacgcgtcctgcagctggtaccatatgggaattcgaagctttctagaacaaaa
actcatctcagaagaggatctgaatagcgccgtcgaccatcatcatcatcatcattgagtttaaacggtctccag
cttggctgttttggcggatgagagaagattttcagcctgatacagattaaatcagaacgcagaagcggtctgat
aaaacagaatttgcctggcggcagtagcgcggtggtcccacctgaccccatgccgaactcagaagtgaaac
gccgtagcgccgatggtagtgtggggtctccccatgcgagagtagggaactgccaggcatcaaatataaaacg
aaaggctcagtcgaaagactgggcctttcgtttatctgttgtttgtcggtgaacgctctcctgagtaggacaaatc
cgccgggagcggatttgaacgttgcgaagcaacggcccggagggtggcgggcaggacgcccgccataaa
ctgccaggcatcaaattaagcagaaggccatcctgacggatggcctttttgcgtttctacaaactctttttgtttattt
ttctaaatacattcaaatatgtatccgcttaaccggaattgccagctggggcgccctctggtaaggttgggaagc
cctgcaaagtaaactggatggctttctcgccgccaaggatctgatggcgcaggggatcaagctctgatcaag
agacaggatgaggatcgtttcgcatgattgaacaagatggattgcacgcaggttctccggccgcttgggtgga
gaggctattcggctatgactgggcacaacagacaatcggctgctctgatgccgccgtgttccggctgtcagcg
caggggcgcccggttcttttttgtcaagaccgacctgtccggtgccctgaatgaactgcaagacgaggcagcg
cggctatcgtggctggccacgacgggcgttccttgcgcagctgtgctcgacgttgtcactgaagcgggaaggg
actggctgctattgggcgaagtgccggggcaggatctcctgtcatctcaccttgctcctgccgagaaagtatcc
atcatggctgat

Figure 35C gcaatgcggcggctgcatacgcttgatccggctacctgcccattcgaccaccaagcgaaacatcgcatcgagcg
agcacgtactcggatggaagccggtcttgtcgatcaggatgatctggacgaagagcatcaggggctcgcgcca
gccgaactgttcgccaggctcaaggcgagcatgcccgacggcgaggatctcgtcgtgacccatggcgatgcct
gcttgccgaatatcatggtggaaaatggccgcttttctggattcatcgactgtggccggctgggtgtggcggaccgc
tatcaggacatagcgttggctacccgtgatattgctgaagagcttggcggcgaatgggctgaccgcttcctcgtgct
ttacggtatcgccgctcccgattcgcagcgcatcgccttctatcgccttcttgacgagttcttctgacatgaccaaaat
cccttaacgtgagttttcgttccactgagcgtcagaccccgtagaaaagatcaaaggatcttcttgagatccttttttc
tgcgcgtaatctgctgcttgcaaacaaaaaaaccaccgctaccagcggtggtttgtttgccggatcaagagctacc
aactcttttccgaaggtaactggcttcagcagagcgcagataccaaatactgtccttctagtgtagccgtagttagg
ccaccacttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctgaacg
ggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacagg
agagcgcacgagggagcttccaggggggaaacgcctggtatctttatagtcctgtcgggtttcgccacctctgactt
gagcgtcgatttttgtgatgctcgtcaggggggcggagcctatggaaaaacgccagcaacgcggcctttttacggt
tcctggccttttgctggccttttgctcacatgttctttcctgcgttatcccctgattctgtggataaccgtattaccgcctttg
agtgagctgataccgctcgccgcagccgaacgaccgagcgcagcgagtcagtgagcgaggaagcggaaga
gcgcctgatgcggtattttctccttacgcatctgtgcggtatttcacaccgcatatggtgcactctcagtacaatctgct
ctgatgccgcatagttaagccagtatacactccgctatcgctacgtgactgggtcatggctgcgccccgacacccg
ccaacacccgctgacgcgccctgacgggc (SEQ ID NO:50)

Figure 37A

5'-
ttgtctgctcccggcatccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgttgacaccatcg
aatggtgcaaaaccttttcgcggtatggcatgatagcgcccggaagagagtcaattcagggtggtgaatgtgaaacc
agtaacgttatacgatgtcgcagagtatgccggtgtctcttatcagaccgtttcccgcgtggtgaaccaggccagcca
cgtttctgcgaaaacgcgggaaaaagtggaagcggcgatggcggagctgaattacattcccaaccgcgtggcaca
acaactggcgggcaaacagtcgttgctgattggcgttgccacctccagtctggccctgcacgcgccgtcgcaaattgt
cgcggcgattaaatctcgcgccgatcaactgggtgccagcgtggtggtgtcgatggtagaacgaagcggcgtcgaa
gcctgtaaagcggcggtgcacaatcttctcgcgcaacgcgtcagtgggctgatcattaactatccgctggatgacca
ggatgccattgctgtggaagctgcctgcactaatgttccggcgttatttcttgatgtctctgaccagacacccatcaaca
gtattattttctcccatgaagacggtacgcgactgggcgtggagcatctggtcgcattgggtcaccagcaaatcgcgct
gttagcgggcccattaagttctgtctcggcgcgtctgcgtctggctggctggcataaatatctcactcgcaatcaaattc
agccgatagcggaacgggaaggcgactggagtgccatgtccggttttcaacaaaccatgcaaatgctgaatgagg
gcatcgttcccactgcgatgctggttgccaacgatcagatggcgctgggcgcaatgcgcgccattaccgagtccggg
ctgcgcgttggtgcggatatctcggtagtgggatacgacgataccgaagacagctcatgttatatcccgccgtcaacc
accatcaaacaggattttcgcctgctggggcaaaccagcgtggaccgcttgctgcaactctctcagggccaggcggt
gaagggcaatcagctgttgcccgtctcactggtgaaaagaaaaaccaccctggcgcccaatacgcaaaccgcctc
tccccgcgcgttggccgattcattaatgcagctggcacgacaggtttcccgactggaaagcgggcagtgagcgcaa
cgcaattaatgtgagttagcgcgaattgatctggtttgacagcttatcatcgactgcacggtgcaccaatgcttctggcgt
caggcagccatcggaagctgtggtatggctgtgcaggtcgtaaatcactgcataattcgtgtcgctcaaggcgcactc
ccgttctggataatgttttttgcgccgacatcataacggttctggcaaatattctgaaatgagctgttgacaattaatcatc
cggctcgtataatgtgtggaattgtgagcggataacaatttcacacaggaaacagcgccgctgagaaaaagcgaa
gcggcactgctctttaacaatttatcagacaatctgtgtgggcactcgaccggaattatcgattaactttattattaaaaat
taaagaggtatatattaatgtatcgattaaataaggaggaataaaccatgtgtgcgacctcttctcaatttactcagatta
ccgagcataattcccgtcgttccgcaaactatcagccaaacctgtggaatttcgaattcctgcaatccctggagaacg
acctgaaagtggaaaagctggaggagaaagcgaccaaactggaggaagaagttcgctgcatgatcaaccgtgta
gacacccagccgctgtccctgctggagctgatcgacgatgtgcagcgcctgggtctgacctacaaatttgaaaaag
acatcattaaagccctggaaaacatcgtactgctggacgaaaacaaaagaacaaatctgacctgcacgcaacc
gctctgtctttccgtctgctgcgtcagcacggtttcgaggtttctcaggatgtttttgagcgtttcaaggataaagaaggtg
gtttcagcggtgaactgaaaggtgacgtccaaggcctgctgagcctgtatgaagcgtcttacctggggtttcgagggtg
agaacctgctggaggaggcgcgtaccttttccatcacccacctgaagaacaacctgaaagaaggcattaatacca
aggttgcagaacaagtgagccacgccctggaactgccatatcaccagcgtctgcaccgtctggaggcacgttggttc
ctggataaatacgaaccgaaagaaccgcatcaccagctgctgctggagctggcgaagctggattttaacatggtac
agaccctgcaccagaaagagctgcaagatctgtcccgctggtggaccgagatgggcctggctagcaaactggattt
tgtacgcgaccgcctgatggaagtttatttctgggcactgggtatggcgccagacccgcagtttggtgaatgtcgcaaa
gctgttactaaaatgtttggtctggtgacgatcatcgatgacgtgtatgacgtttatggcactctggacgaactgcaactg
ttcaccgatgctgtagagcgctgggacgttaacgct

Figure 37B attaacaccctgccggactatatgaaactgtgtttcctggcactgtacaacaccgttaacgacacgtcctattctattc
tgaaagagaaaggtcataacaacctgtcctatctgacgaaaagctggcgtgaactgtgcaaagcctttctgcaag
aggcgaaatggtccaacaacaaaattatcccggctttctccaagtacctggaaaacgccagcgtttcctcctccg
gtgtagcgctgctggcgccgtcttacttttccgtatgccagcagcaggaagacatctccgaccacgcgctgcgttcc
ctgaccgacttccatggtctggtgcgttctagctgcgttatcttccgcctgtgcaacgatctggccacctctgcggcg
gagctggaacgtggcgagactaccaattctatcattagctacatgcacgaaaacgatggtaccagcgaggaac
aggcccgcgaagaactgcgtaaactgatcgacgccgaatggaaaaagatgaatcgtgaacgcgttagcgact
ccaccctgctgcctaaagcgttcatggaaatcgcagttaacatggcacgtgtttcccactgcacctaccagtatgg
cgatggtctgggtcgcccagactacgcgactgaaaaccgcatcaaactgctgctgattgacccttttcccgattaac
cagctgatgtatgtctaactgcattcgcccttaggaggtaaaaaaacatgagttttgatattgccaaatacccgacc
ctggcactggtcgactccacccaggagttacgactgttgccgaaagagagtttaccgaaactctgcgacgaactg
cgccgctatttactcgacagcgtgagccgttccagcgggcacttcgcctccgggctgggcacggtcgaactgacc
gtggcgctgcactatgtctacaacaccccgtttgaccaattgatttgggatgtggggcatcaggcttatccgcataa
aattttgaccggacgccgcgacaaaatcggcaccatccgtcagaaaggcggtctgcacccgttcccgtggcgc
ggcgaaagcgaatatgacgtattaagcgtcgggcattcatcaacctccatcagtgccggaattggtattgcggttg
ctgccgaaaaagaaggcaaaaatcgccgcaccgtctgtgtcattggcgatggcgcgattaccgcaggcatggc
gtttgaagcgatgaatcacgcgggcgatatccgtcctgatatgctggtgattctcaacgacaatgaaatgtcgattc
cgaaaatgtcggcgcgctcaacaaccatctggcacagctgctttccggtaagctttactcttcactgcgcgaaggc
gggaaaaaagttttctctggcgtgccgccaattaaagagctgctcaaacgcaccgaagaacatattaaaggcat
ggtagtgcctggcacgttgtttgaagagctgggctttaactacatcggcccggtggacggtcacgatgtgctgggg
cttatcaccacgctaaagaacatgcgcgacctgaaaggcccgcagttcctgcatatcatgaccaaaaaaggtcg
tggttatgaaccggcagaaaaagacccgatcactttccacgccgtgcctaaatttgatccctccagcggttgtttgc
cgaaaagtagcggcggtttgccgagctattcaaaaatctttggcgactggttgtgcgaaacggcagcgaaagac
aacaagctgatggcgattactccggcgatgcgtgaaggttccggcatggtcgagttttcacgtaaattcccggatc
gctacttcgacgtggcaattgccgagcaacacgcggtgacctttgctgcgggtctggcgattggtgggtacaaac
ccattgtcgcgatttactccactttcctgcaacgcgcctatgatcaggtgctgcatgacgtggcgattcaaaagcttc
cggtcctgttcgccatcgaccgcgcgggcattgttggtgctgacggtcaaacccatcaggtgctttgatctctctta
cctgcgctgcataccggaaatggtcattatgaccccgagcgatgaaaacgaatgtcgccagatgctctataccgg
ctatcactataacgatggcccgtcagcggtgcgctacccgcgtggcaacgcggtcggcgtggaactgacgccg
ctggaaaaactaccaattggcaaaggcattgtgaagcgtcgtggcgagaaactggcgatccttaactttggtacg
ctgatgccagaagcggcgaaagtcgccgaatcgctgaacgccacgctggtcgatatgcgttttgtgaaaccgctt
gatgaagcgttaattctggaaatggccgccagccatgaagcgctggtcaccgtagaagaaaacgccattatggg
cggcgcaggcagcggcgtgaacgaagtgctgatggcccatcgtaaaccagtacccgtgctgaacattggcctg
ccggacttctttattccgcaaggaactcaggaagaaatgcgcgccgaactcggcctcgatgccgctggtatggaa
gccaaaatcaaggcctggctggcataactgcagctggtaccatatgggaattcgaagctttctagaacaaaaact
catctcagaagaggatctgaatagcgccgtcgaccatcatcatcatcatcattgagtttaaacggtctccagcttgg
ctgttttggcggatgagagaagattttcagcctgatacagattaaatcagaacgcagaagcggtctgataaaaca
gaatttgcctggcggcagtagcgcg

Figure 37C gtggtcccacctgaccccatgccgaactcagaagtgaaacgccgtagcgccgatggtagtgtggggtctcc
ccatgcgagagtagggaactgccaggcatcaaataaaacgaaaggctcagtcgaaagactgggccttttc
gttttatctgttgtttgtcggtgaacgctctcctgagtaggacaaatccgccgggagcggatttgaacgttgcga
agcaacggcccggagggtggcgggcaggacgcccgccataaactgccaggcatcaaattaagcagaa
ggccatcctgacggatggccttttgcgtttctacaaactcttttgtttattttctaaatacattcaaatatgtatccg
cttaaccggaattgccagctggggcgccctctggtaaggttgggaagccctgcaaagtaaactggatggctt
tctcgccgccaaggatctgatggcgcaggggatcaagctctgatcaagagacaggatgaggatcgtttcgc
atgattgaacaagatggattgcacgcaggttctccggccgcttgggtggagaggctattcggctatgactggg
cacaacagacaatcggctgctctgatgccgccgtgttccggctgtcagcgcaggggcgcccggttcttttgtc
aagaccgacctgtccggtgccctgaatgaactgcaagacgaggcagcgcggctatcgtggctggccacg
acgggcgttccttgcgcagctgtgctcgacgttgtcactgaagcgggaagggactggctgctattgggcgaa
gtgccggggcaggatctcctgtcatctcaccttgctcctgccgagaaagtatccatcatggctgatgcaatgc
ggcggctgcatacgcttgatccggctacctgcccattcgaccaccaagcgaaacatcgcatcgagcgagc
acgtactcggatggaagccggtcttgtcgatcaggatgatctggacgaagagcatcaggggctcgcgccag
ccgaactgttcgccaggctcaaggcgagcatgcccgacggcgaggatctcgtcgtgacccatggcgatgc
ctgcttgccgaatatcatggtggaaaatggccgcttttctggattcatcgactgtggccggctgggtgtggcgg
accgctatcaggacatagcgttggctacccgtgatattgctgaagagcttggcggcgaatgggctgaccgctt
cctcgtgctttacggtatcgccgctcccgattcgcagcgcatcgccttctatcgccttcttgacgagttcttctgac
gcatgaccaaaatcccttaacgtgagttttcgttccactgagcgtcagacccctagaaaagatcaaaggat
cttcttgagatcctttttttctgcgcgtaatctgctgcttgcaaacaaaaaaaccaccgctaccagcggtggtttgt
ttgccggatcaagagctaccaactctttttccgaaggtaactggcttcagcagagcgcagataccaaatactg
tccttctagtgtagccgtagttaggccaccacttcaagaactctgtagcaccgcctacatacctcgctctgctaa
tcctgttaccagtggctgctgccagtggcgataagtcgtgtcttaccgggttggactcaagacgatagttaccg
gataaggcgcagcggtcgggctgaacggggggttcgtgcacacagcccagcttggagcgaacgacctac
accgaactgagatacctacagcgtgagctatgagaaagcgccacgcttcccgaagggagaaaggcgga
caggtatccggtaagcggcagggtcggaacaggagagcgcacgagggagcttccaggggaaacgcc
tggtatctttatagtcctgtcgggtttcgccacctctgacttgagcgtcgatttttgtgatgctcgtcaggggggcg
gagcctatggaaaaacgccagcaacgcggcctttttacggttcctggccttttgctggccttttgctcacatgttc
tttcctgcgttatcccctgattctgtggataaccgtattaccgcctttgagtgagctgataccgctcgccgcagcc
gaacgaccgagcgcagcgagtcagtgagcgaggaagcggaagagcgcctgatgcggtattttctccttac
gcatctgtgcggtatttcacaccgcatatggtgcactctcagtacaatctgctctgatgccgcatagttaagcca
gtatacactccgctatcgctacgtgactgggtcatggctgcgccccgacacccgccaacacccgctgacgc
gccctgacgggc (SEQ ID NO:51)

Figure 39A

5'-
ctggcgtaatagcgaagaggcccgcaccgatcgcccttcccaacagttgcgcagcctgaatggcgaatggcgcc
tgatgcggtattttctccttacgcatctgtgcggtatttcacaccgcatatggtgcactctcagtacaatctgctctgatgc
cgcatagttaagccagccccgacacccgccaacacccgctgacgagcttagtaaagccctcgctagattttaatgc
ggatgttgcgattacttcgccaactattgcgataacaagaaaaagccagcctttcatgatatatctcccaatttgtgtag
ggcttattatgcacgcttaaaaataataaaagcagacttgacctgatagtttggctgtgagcaattatgtgcttagtgca
tctaacgcttgagttaagccgcgccgcgaagcggcgtcggcttgaacgaattgttagacattatttgccgactacctt
ggtgatctcgcctttcacgtagtggacaaattcttccaactgatctcgcgcgcgaggccaagcgatcttcttcttgtccaa
gataagcctgtctagcttcaagtatgacgggctgatactgggccggcaggcgctccattgcccagtcggcagcgac
atccttcggcgcgattttgccggttactgcgctgtaccaaatgcgggacaacgtaagcactacatttcgctcatcgcc
agcccagtcgggcggcgagttccatagcgttaaggtttcatttagcgcctcaaatagatcctgttcaggaaccggat
caaagagttcctccgccgctggacctaccaaggcaacgctatgttctcttgcttttgtcagcaagatagccagatcaa
tgtcgatcgtggctggctcgaagatacctgcaagaatgtcattgcgctgccattctccaaattgcagttcgcgcttagc
tggataacgccacggaatgatgtcgtcgtgcacaacaatggtgacttctacagcgcggagaatctcgctctctcca
ggggaagccgaagtttccaaaaggtcgttgatcaaagctcgccgcgttgtttcatcaagccttacggtcaccgtaac
cagcaaatcaatatcactgtgtggcttcaggccgccatccactgcggagccgtacaaatgtacggccagcaacgt
cggttcgagatggcgctcgatgacgccaactacctctgatagttgagtcgatacttcggcgatcaccgcttccctcat
gatgtttaactttgtttagggcgactgccctgctgcgtaacatcgttgctgctccataacatcaaacatcgacccacgg
cgtaacgcgcttgctgcttggatgcccgaggcatagactgtacccaaaaaaaacagtcataacaagccatgaaa
accgccactgcgccgttaccaccgctgcgttcggtcaaggttctggaccagttgcgtgagcgcatacgctacttgca
ttacagcttacgaaccgaacaggcttatgtccactggttcgtgccttcatccgtttccacggtgtgcgtcacccggca
accttgggcagcagcgaagtcgaggcatttctgtcctggctggcgaacgagcgcaaggtttcggtctccacgcatc
gtcaggcattggcggccttgctgttcttctacggcaaggtgctgtgcacggatctgccctggcttcaggagatcggaa
gacctcggccgtcgcggcgcttgccggtggtgctgaccccggatgaagtggttcgcatcctcggttttctggaaggc
gagcatcgtttgttcgcccagcttctgtatggaacgggcatgcggatcagtgagggtttgcaactgcgggtcaagga
tctggatttcgatcacggcacgatcatcgtgcgggagggcaagggctccaaggatcgggccttgatgttacccgag
agcttggcacccagcctgcgcgagcaggggaattaattcccacgggttttgctgcccgcaaacgggctgttctggtg
ttgctagtttgttatcagaatcgcagatccggcttcagccggtttgccggctgaaagcgctatttcttccagaattgccat
gattttttccccacgggaggcgtcactggctcccgtgttgtcggcagctttgattcgataagcagcatcgcctgtttcag
gctgtctatgtgtgactgttgagctgtaacaagttgtctcaggtgttcaatttcatgttctagttgctttgtttactggtttcac
ctgttctattaggtgttacatgctgttcatctgttacattgtcgatctgttcatggtgaacagctttgaatgcaccaaaaact
cgtaaaagctctgatgtatctatcttttttacaccgttttcatctgtgcatatggacagttttcctttgatatgtaacggtga
acagttgttctactttgtttgttagtcttgatgcttcactgatagatacaagagccataagaacctcagatccttccgtatt
tagccagtatgttctctagtgtggttcgttgtttttgcgtgagccatgagaacgaaccattgagatcatacttacttgcat
gtcactcaaaaattttgcctcaaaactggtgagctgaattttgcagttaaagcatcgtgtagtgttttcttagtccgttat
gtaggtaggaatctgatgtaatggttgttggtattttgtcaccattcattttatctggttgttctcaagttcgg

Figure 39B ttacgagatccatttgtctatctagttcaacttggaaaatcaacgtatcagtcgggcggcctcgcttatcaaccaccaatt
tcatattgctgtaagtgtttaaatctttacttattggtttcaaaacccattggttaagcctttaaactcatggtagttattttcaa
gcattaacatgaacttaaattcatcaaggctaatctctatatttgccttgtgagttttcttttgtgttagttcttttaataaccact
cataaatcctcatagagtatttgttttcaaaagacttaacatgttccagattatattttatgaattttttaactggaaaagata
aggcaatatctcttcactaaaaactaattctaatttttcgcttgagaacttggcatagtttgtccactggaaaatctcaaag
cctttaaccaaaggattcctgatttccacagttctcgtcatcagctctctggttgctttagctaatacaccataagcattttcc
ctactgatgttcatcatctgagcgtattggttataagtgaacgataccgtccgttctttccttgtagggttttcaatcgtgggg
ttgagtagtgccacacagcataaaattagcttggtttcatgctccgttaagtcatagcgactaatcgctagttcatttgcttt
gaaaacaactaattcagacatacatctcaattggtctaggtgattttaatcactataccaattgagatgggctagtcaat
gataattactagtccttttcctttgagttgtgggtatctgtaaattctgctagacctttgctggaaaacttgtaaattctgctag
acccctctgtaaattccgctagacctttgtgtgtttttttgtttatattcaagtggttataatttatagaataaagaaagaataa
aaaaagataaaaagaatagatcccagccctgtgtataactcactactttagtcagttccgcagtattacaaaaggatg
tcgcaaacgctgtttgctcctctacaaaacagaccttaaaaccctaaaggcttaagtagcaccctcgcaagctcggg
caaatcgctgaatattccttttgtctccgaccatcaggcacctgagtcgctgtcttttcgtgacattcagttcgctgcgctc
acggctctggcagtgaatgggggtaaatggcactacaggcgccttttatggattcatgcaaggaaactacccataat
acaagaaaagcccgtcacgggcttctcagggcgttttatggcgggtctgctatgtggtgctatctgactttttgctgttcag
cagttcctgccctctgattttccagtctgaccacttcggattatcccgtgacaggtcattcagactggctaatgcacccag
taaggcagcggtatcatcaacaggcttaccgtctactgtcgggaattcgcgttggccgattcattaatgcagattctg
aaatgagctgttgacaattaatcatccggctcgtataatgtgtggaattgtgagcggataacaatttcacacaggaaac
agcgccgctgagaaaaagcgaagcggcactgctctttaacaatttatcagacaatctgtgtgggcactcgaccgga
attatcgattaactttattattaaaaattaaagaggtatatattaatgtatcgattaaataaggaggaataaaccatgtgtg
cgacctcttctcaatttactcagattaccgagcataattcccgtcgttccgcaaactatcagccaaacctgtggaatttcg
aattcctgcaatccctggagaacgacctgaaagtggaaaagctggaggagaaagcgaccaaactggaggaaga
agttcgctgcatgatcaaccgtgtagacacccagccgctgtccctgctggagctgatcgacgatgtgcagcgcctgg
gtctgacctacaaatttgaaaagacatcattaaagccctggaaaacatcgtactgctggacgaaaacaaaaaga
acaaatctgacctgcacgcaaccgctctgtctttccgtctgctgcgtcagcacggtttcgaggtttctcaggatgttttga
gcgtttcaaggataaagaaggtggtttcagcggtgaactgaaaggtgacgtccaaggcctgctgagcctgtatgaag
cgtcttacctgggtttcgagggtgagaacctgctggaggaggcgcgtaccttttccatcacccacctgaagaacaacc
tgaaagaaggcattaataccaaggttgcagaacaagtgagccacgccctggaactgccatatcaccagcgtctgc
accgtctggaggcacgttggttcctggataaatacgaaccgaaagaaccgcatcaccagctgctgctggagctggc
gaagctggattttaacatggtacagaccctgcaccagaaagagctgcaagatctgtcccgctggtggaccgagatg
ggcctggctagcaaactggatttgtacgcgaccgcctgatggaagtttattctgggcactgggtatggcgccagacc
cgcagtttggtgaatgtcgcaaagctgttactaaaatgtttggtctggtgacgatcatcgatgacgtgtatgacgtttatg
gcactctggacgaactgcaactgttcaccgatgctgtagagcgctgggacgttaacgctattaacacctgccggact
atatgaaactgtgtttcctggcactgtacaacaccgttaacgacacgtcctattctattctgaaagagaaaggtcataac
aacctgtcct

Figure 39C atctgacgaaaagctggcgtgaactgtgcaaagcctttctgcaagaggcgaaatggtccaacaacaaaatta
tcccggctttctccaagtacctggaaaacgccagcgtttcctcctccggtgtagcgctgctggcgccgtcttactt
tccgtatgccagcagcaggaagacatctccgaccacgcgctgcgttccctgaccgacttccatggtctggtgc
gttctagctgcgttatcttccgcctgtgcaacgatctggccacctctgcggcggagctggaacgtggcgagact
accaattctatcattagctacatgcacgaaaacgatggtaccagcgaggaacaggcccgcgaagaactgcg
taaactgatcgacgccgaatggaaaaagatgaatcgtgaacgcgttagcgactccaccctgctgcctaaagc
gttcatggaaatcgcagttaacatggcacgtgtttcccactgcacctaccagtatggcgatggtctgggtcgccc
agactacgcgactgaaaaccgcatcaaactgctgctgattgacccttttcccgattaaccagctgatgtatgtcta
actgcagctggtaccatatgggaattcgaagctttctagaacaaaaactcatctcagaagaggatctgaatag
cgccgtcgaccatcatcatcatcatcattgagtttaaacggtctccagcttggctgttttggcggatgagagaag
attttcagcctgatacagattaaatcagaacgcagaagcggtctgataaaacagaatttgcctggcggcagta
gcgcggtggtcccacctgaccccatgccgaactcagaagtgaaacgccgtagcgccgatggtagtgtgggg
tctccccatgcgagagtagggaactgccaggcatcaaataaaacgaaaggctcagtcgaaagactgggcct
ttcgttttatctgttgtttgtcggtgaacgctctcctgagtaggacaaatccgccgggagcggatttgaacgttgcg
aagcaacggcccggagggtggcgggcaggacgcccgccataaactgccaggcatcaaattaagcagaa
ggccatcctgacggatggcctttttgcgtttctacaaactcttttgtttatttttctaaatacattcaaatatgtatccgc
tcatgagacaataaccctgataaatgcttcaataat (SEQ ID NO:52)

Figure 41A

5'- cccgtcttactgtcgggaattcgcgttggccgattcattaatgcagattattgaagcatttatcagggttattgtctcatg
agcggatacatatttgaatgtatttagaaaaataaacaaaaagagtttgtagaaacgcaaaaaggccatccgtca
ggatggccttctgcttaatttgatgcctggcagtttatggcgggcgtcctgcccgccaccctccgggccgttgcttcg
caacgttcaaatccgctcccggcggatttgtcctactcaggagagcgttcaccgacaaacaacagataaaacga
aaggcccagtcttcgactgagcctttcgttttatttgatgcctggcagttccctactctcgcatggggagaccccaca
ctaccatcggcgctacggcgtttcacttctgagttcggcatggggtcaggtgggaccaccgcgctactgccgcca
ggcaaattctgttttatcagaccgcttctgcgttctgatttaatctgtatcaggctgaaaatcttctctcatccgccaaaa
cagccaagctggagaccgtttaaactcaatgatgatgatgatggtcgacggcgctattcagatcctcttctgag
atgagtttttgttctagaaagcttcgaattcccatatggtaccagctgcagttagacatacatcagctggttaatcggg
aaagggtcaatcagcagcagtttgatgcggttttcagtcgcgtagtctgggcgacccagaccatcgccatactggt
aggtgcagtgggaaacacgtgccatgttaactgcgatttccatgaacgctttaggcagcagggtggagtcgctaa
cgcgttcacgattcatcttttccattcggcgtcgatcagtttacgcagttcttcgcgggcctgttcctcgctggtaccat
cgttttcgtgcatgtagctaatgatagaattggtagtctcgccacgttccagctccgccgcagaggtggccagatcg
ttgcacaggcggaagataacgcagctagaacgcaccagaccatggaagtcggtcagggaacgcagcgcgtg
gtcggagatgtcttcctgctgctggcatacggaaaagtaagacggcgccagcagcgctacaccggaggagga
aacgctggcgttttccaggtacttggagaaagccgggataattttgttgttggaccatttcgcctcttgcagaaaggct
ttgcacagttcacgccagcttttcgtcagataggacaggttgttatgacctttctctttcagaatagaataggacgtgtc
gttaacggtgttgtacagtgccaggaaacacagtttcatatagtccggcagggtgttaatagcgttaacgtcccagc
gctctacagcatcggtgaacagttgcagttcgtccagagtgccataaacgtcatacacgtcatcgatgatcgtcac
cagaccaaacattttagtaacagctttgcgacattcaccaaactgcgggtctggcgccatacccagtgcccagaa
ataaacttccatcaggcggtcgcgtacaaaatccagtttgctagccaggcccatctcggtccaccagcgggaca
gatcttgcagctctttctggtgcagggtctgtaccatgttaaaatccagcttcgccagctccagcagcagctggtgat
gcggttcttccggttcgtatttatccaggaaccaacgtgcctccagacggtgcagacgctggtgatatggcagttcc
agggcgtggctcacttgttctgcaaccttggtattaatgccttctttcaggttgttcttcaggtgggtgatggaaaaggt
acgcgcctcctccagcaggttctcaccctcgaaacccaggtaagacgcttcatacaggctcagcaggccttgga
cgtcacctttcagttcaccgctgaaaccaccttctttatccttgaaacgctcaaaaacatcctgagaaacctcgaaa
ccgtgctgacgcagcagacggaaagacagagcggttgcgtgcaggtcagatttgttctttttgttttcgtccagcagt
acgatgttttccagggctttaatgatgtctttttcaaatttgtaggtcagacccaggcgctgcacatcgtcgatcagctc
cagcagggacagcggctgggtgtctacacggttgatcatgcagcgaacttcttcctccagtttggtcgctttctcctc
cagcttttccactttcaggtcgttctccagggattgcaggaattcgaaattccacaggtttggctgatagtttgcggaa
cgacgggaattatgctcggtaatctgagtaaattgagaagaggtcgcacacatggtttattcctccttatttaatcgat
acattaatatatacctcttttaattttaataataaagttaatcgataattccggtcgagtgcccacacagattgtctgata
aattgttaaagagcagtgccgcttcgctttttctcagcggcgctgtttcctgtgtgaaattgttatccgctcacaattcca
cacattatacgagccggatgattaattgtcaacagctcatttcagaatctggcgtaatagcgaagaggcccgcac
cgatcgcccttcccaacagttgcgcagcctgaatggcgaatggcgcctgatgcggtattttctccttacgcatctgtg
cggtatttcacaccgcatatggtgcactctcagtacaatctgctc

Figure 41B tgatgccgcatagttaagccagccccgacacccgccaacacccgctgacgagcttagtaaagccctcgctagat
tttaatgcggatgttgcgattacttcgccaactattgcgataacaagaaaaagccagcctttcatgatatatctccca
atttgtgtagggcttattatgcacgcttaaaaataataaaaagcagacttgacctgatagtttggctgtgagcaattatg
tgcttagtgcatctaacgcttgagttaagccgcgccgcgaagcggcgtcggcttgaacgaattgttagacattatttg
ccgactaccttggtgatctcgcctttcacgtagtggacaaattcttccaactgatctgcgcgcgaggccaagcgatc
ttcttcttgtccaagataagcctgtctagcttcaagtatgacgggctgatactgggccggcaggcgctccattgccca
gtcggcagcgacatccttcggcgcgattttgccggttactgcgctgtaccaaatgcgggacaacgtaagcactac
atttcgctcatcgccagcccagtcgggcggcgagttccatagcgttaaggtttcatttagcgcctcaaatagatcctg
ttcaggaaccggatcaaagagttcctccgccgctggacctaccaaggcaacgctatgttctcttgcttttgtcagca
agatagccagatcaatgtcgatcgtggctggctcgaagatacctgcaagaatgtcattgcgctgccattctccaaa
ttgcagttcgcgcttagctggataacgccacggaatgatgtcgtcgtgcacaacaatggtgacttctacagcgcgg
agaatctcgctctctccaggggaagccgaagtttccaaaaggtcgttgatcaaagctcgccgcgttgtttcatcaa
gccttacggtcaccgtaaccagcaaatcaatatcactgtgtggcttcaggccgccatccactgcggagccgtaca
aatgtacggccagcaacgtcggttcgagatggcgctcgatgacgccaactacctctgatagttgagtcgatacttc
ggcgatcaccgcttccctcatgatgtttaactttgttttagggcgactgccctgctgcgtaacatcgttgctgctccata
acatcaaacatcgacccacggcgtaacgcgcttgctgcttggatgcccgaggcatagactgtaccccaaaaaa
acagtcataacaagccatgaaaaccgccactgcgccgttaccaccgctgcgttcggtcaaggttctggaccagtt
gcgtgagcgcatacgctacttgcattacagcttacgaaccgaacaggcttatgtccactgggttcgtgccttcatcc
gtttccacggtgtgcgtcacccggcaaccttgggcagcagcgaagtcgaggcatttctgtcctggctggcgaacg
agcgcaaggtttcggtctccacgcatcgtcaggcattggcggccttgctgttcttctacggcaaggtgctgtgcacg
gatctgccctggcttcaggagatcggaagacctcggccgtcgcggcgcttgccggtggtgctgaccccggatga
agtggttcgcatcctcggttttctggaaggcgagcatcgtttgttcgcccagcttctgtatggaacgggcatgcggat
cagtgagggtttgcaactgcgggtcaaggatctggatttcgatcacggcacgatcatcgtgcgggagggcaagg
gctccaaggatcgggccttgatgttacccgagagcttggcacccagcctgcgcgagcaggggaattaattccca
cgggttttgctgcccgcaaacgggctgttctggtgttgctagtttgttatcagaatcgcagatccggcttcagccggtt
gccggctgaaagcgctatttcttccagaattgccatgatttttccccacgggaggcgtcactggctcccgtgttgtcg
gcagctttgattcgataagcagcatcgcctgtttcaggctgtctatgtgtgactgttgagctgtaacaagttgtctcagg
tgttcaatttcatgttctagttgctttgttttactggtttcacctgttctattaggtgttacatgctgttcatctgttacattgtcga
tctgttcatggtgaacagctttgaatgcaccaaaaactcgtaaaagctctgatgtatctatctttttacaccgttttcatc
tgtgcatatggacagttttcccttgatatgtaacggtgaacagttgttctacttttgtttgttagtcttgatgcttcactgata
gatacaagagccataagaacctcagatccttccgtatttagccagtatgttctctagtgtggttcgttgttttgcgtga
gccatgagaacgaaccattgagatcatacttactttgcatgtcactcaaaaatttttgcctcaaaactggtgagctga
attttttgcagttaaagcatcgtgtagtgtttttcttagtccgttatgtaggtaggaatctgatgtaatggttgttggtattttgt
caccattcatttttatctggttgttctcaagttcggttacgagatccatttgtctatctagttcaacttggaaaatcaacgta
tcagtcgggcggcctcgcttatcaaccaccaatttcatattgctgtaagtgtttaaatctttacttattggtttcaaaacc
cattggttaagccttttaaaactcatggtagttattttcaagcattaacatgaacttaaattcatcaaggctaatctctatat
ttgc

Figure 41C cttgtgagttttcttttgtgttagttcttttaataaccactcataaatcctcatagagtatttgttttcaaaagacttaacatgttc
cagattatattttatgaatttttttaactggaaaagataaggcaatatctcttcactaaaaactaattctaatttttcgcttga
gaacttggcatagtttgtccactggaaaatctcaaagcctttaaccaaaggattcctgatttccacagttctcgtcatca
gctctctggttgctttagctaatacaccataagcattttccctactgatgttcatcatctgagcgtattggttataagtgaac
gataccgtccgttctttccttgtagggttttcaatcgtggggttgagtagtgccacacagcataaaattagcttggtttcat
gctccgttaagtcatagcgactaatcgctagttcatttgctttgaaaacaactaattcagacatacatctcaattggtcta
ggtgattttaatcactataccaattgagatgggctagtcaatgataattactagtccttttcctttgagttgtgggtatctgt
aaattctgctagacctttgctggaaaacttgtaaattctgctagaccctctgtaaattccgctagacctttgtgtgtttttttt
gtttatattcaagtggttataatttatagaataaagaaagaataaaaaaagataaaaagaatagatcccagccctgt
gtataactcactactttagtcagttccgcagtattacaaaaggatgtcgcaaacgctgtttgctcctctacaaaacaga
ccttaaaaccctaaaggcttaagtagcaccctcgcaagctcgggcaaatcgctgaatattccttttgtctccgaccat
caggcacctgagtcgctgtcttttcgtgacattcagttcgctgcgctcacggctctggcagtgaatgggggtaaatgg
cactacaggcgcctttatggattcatgcaaggaaactacccataatacaagaaaagcccgtcacgggcttctcag
ggcgtttatggcgggtctgctatgtggtgctatctgacttttgctgttcagcagttcctgccctctgattttccagtctgac
cacttcggattatcccgtgacaggtcattcagactggctaatgcacccagtaaggcagcggtatcatcaacaggctt
a (SEQ ID NO:53)

Figure 43A

5'- ctggcgtaatagcgaagaggcccgcaccgatcgcccttcccaacagttgcgcagcctgaatggcgaatggcg
cctgatgcggtattttctccttacgcatctgtgcggtatttcacaccgcatatggtgcactctcagtacaatctgctctg
atgccgcatagttaagccagccccgacacccgccaacacccgctgacgagcttagtaaagccctcgctagatt
ttaatgcggatgttgcgattacttcgccaactattgcgataacaagaaaaagccagcctttcatgatatatctccca
atttgtgtagggcttattatgcacgcttaaaaataataaaagcagacttgacctgatagtttggctgtgagcaattat
gtgcttagtgcatctaacgcttgagttaagccgcgccgcgaagcggcgtcggcttgaacgaattgttagacattat
ttgccgactaccttggtgatctcgcctttcacgtagtggacaaattcttccaactgatctgcgcgcgaggccaagc
gatcttcttcttgtccaagataagcctgtctagcttcaagtatgacgggctgatactgggccggcaggcgctccatt
gcccagtcggcagcgacatccttcggcgcgattttgccggttactgcgctgtaccaaatgcgggacaacgtaag
cactacatttcgctcatcgccagcccagtcgggcggcgagttccatagcgttaaggtttcatttagcgcctcaaat
agatcctgttcaggaaccggatcaaagagttcctccgccgctggacctaccaaggcaacgctatgttctcttgctt
ttgtcagcaagatagccagatcaatgtcgatcgtggctggctcgaagatacctgcaagaatgtcattgcgctgcc
attctccaaattgcagttcgcgcttagctggataacgccacggaatgatgtcgtcgtgcacaacaatggtgacttc
tacagcgcggagaatctcgctctctccaggggaagccgaagtttccaaaaggtcgttgatcaaagctcgccgc
gttgtttcatcaagccttacggtcaccgtaaccagcaaatcaatatcactgtgtggcttcaggccgccatccactg
cggagccgtacaaatgtacggccagcaacgtcggttcgagatggcgctcgatgacgccaactacctctgatag
ttgagtcgatacttcggcgatcaccgcttccctcatgatgtttaactttgttttagggcgactgccctgctgcgtaacat
cgttgctgctccataacatcaaacatcgacccacggcgtaacgcgcttgctgcttggatgcccgaggcatagac
tgtaccccaaaaaaacagtcataacaagccatgaaaaccgccactgcgccgttaccaccgctgcgttcggtca
aggttctggaccagttgcgtgagcgcatacgctacttgcattacagcttacgaaccgaacaggcttatgtccactg
ggtcgtgccttcatccgtttccacggtgtgcgtcacccggcaaccttgggcagcagcgaagtcgaggcatttctg
tcctggctggcgaacgagcgcaaggtttcggtctccacgcatcgtcaggcattggcggccttgctgttcttctacg
gcaaggtgctgtgcacggatctgccctggcttcaggagatcggaagacctcggccgtcgcggcgcttgccggt
ggtgctgaccccggatgaagtggttcgcatcctcggttttctggaaggcgagcatcgtttgttcgcccagcttctgta
tggaacgggcatgcggatcagtgagggtttgcaactgcgggtcaaggatctggatttcgatcacggcacgatca
tcgtgcgggagggcaagggctccaaggatcgggccttgatgttacccgagagcttggcacccagcctgcgcg
agcaggggaattaattcccacgggttttgctgcccgcaaacgggctgttctggtgttgctagtttgttatcagaatcg
cagatccggcttcagccggtttgccggctgaaagcgctatttcttccagaattgccatgattttttccccacgggag
gcgtcactggctcccgtgttgtcggcagctttgattcgataagcagcatcgcctgtttcaggctgtctatgtgtgact
gttgagctgtaacaagttgtctcaggtgttcaatttcatgttctagttgctttgttttactggtttcacctgttctattaggtgt
tacatgctgttcatctgttacattgtcgatcgttcatggtgaacagctttgaatgcaccaaaaactcgtaaaagctct
gatgtatctatcttttttacaccgttttcatctgtgcatatggacagttttcccttgatatgtaacggtgaacagttgttct
acttttgtttgttagtcttgatgcttcactgatagatacaagagccataagaacctcagatccttccgtatttagccagt
atgttctctagtgtggttcgttgttttgcgtgagccatgagaacgaaccattgagatcatacttactttgcatgtcactc
aaaaattttgcctcaaaactggtgagctgaattttgcagttaaagcatcgtgtagtgttttcttagtccgttatgtagg
taggaatctgatgtaatggttgttggtattttgtcaccattcattttatctggttgttctcaagttcgg

Figure 43B ttacgagatccatttgtctatctagttcaacttggaaaatcaacgtatcagtcgggcggcctcgcttatcaaccacc
aatttcatattgctgtaagtgtttaaatctttacttattggtttcaaaacccattggttaagccttttaaactcatggtagtt
attttcaagcattaacatgaacttaaattcatcaaggctaatctctatatttgccttgtgagttttcttttgtgttagttctttt
aataaccactcataaatcctcatagagtatttgttttcaaaagacttaacatgttccagattatattttatgaatttttta
actggaaaagataaggcaatatctcttcactaaaaactaattctaattttttcgcttgagaacttggcatagtttgtcc
actggaaaatctcaaagcctttaaccaaaggattcctgatttccacagttctcgtcatcagctctctggttgctttagc
taatacaccataagcattttccctactgatgttcatcatctgagcgtattggttataagtgaacgataccgtccgttctt
tccttgtagggttttcaatcgtggggttgagtagtgccacacagcataaaattagcttggtttcatgctccgttaagtc
atagcgactaatcgctagttcatttgctttgaaaacaactaattcagacatacatctcaattggtctaggtgattttaa
tcactataccaattgagatgggctagtcaatgataattactagtccttttcctttgagttgtgggtatctgtaaattctgc
tagacctttgctggaaaacttgtaaattctgctagaccctctgtaaattccgctagacctttgtgtgtttttttgtttatatt
caagtggttataatttatagaataaagaaagaataaaaaaagataaaaagaatagatcccagccctgtgtata
actcactactttagtcagttccgcagtattacaaaaggatgtcgcaaacgctgtttgctcctctacaaaacagacct
taaaaccctaaaggcttaagtagcaccctcgcaagctcgggcaaatcgctgaatattccttttgtctccgaccatc
aggcacctgagtcgctgtcttttcgtgacattcagttcgctgcgctcacggctctggcagtgaatgggggtaaatg
gcactacaggcgccttttatggattcatgcaaggaaactacccataatacaagaaaagcccgtcacgggcttct
cagggcgttttatggcgggtctgctatgtggtgctatctgacttttgtcgttcagcagttcctgccctctgattttccagt
ctgaccacttcggattatcccgtgacaggtcattcagactggctaatgcacccagtaaggcagcggtatcatcaa
caggcttacccgtcttactgtcgggaattcgcgttggccgattcattaatgcagattctgaaatgagctgttgacaat
taatcatccggctcgtataatgtgtggaattgtgagcggataacaatttcacacaggaaacagcgccgctgaga
aaaagcgaagcggcactgctctttaacaatttatcagacaatctgtgtgggcactcgaccggaattatcgattaa
ctttattattaaaaattaaagaggtatatattaatgtatcgattaaataaggaggaataaaccatgtgtgcgacctct
tctcaatttactcagattaccgagcataattcccgtcgttccgcaaactatcagccaaacctgtggaatttcgaattc
ctgcaatccctggagaacgacctgaaagtggaaaagctggaggagaaagcgaccaaactggaggaagaa
gttcgctgcatgatcaaccgtgtagacacccagccgctgtccctgctggagctgatcgacgatgtgcagcgcct
gggtctgacctacaaatttgaaaagagacatcattaaagccctggaaaacatcgtactgctggacgaaaacaaa
aagaacaaatctgacctgcacgcaaccgctctgtctttccgtctgctgcgtcagcacggtttcgaggtttctcagg
atgtttttgagcgtttcaaggataaagaaggtggtttcagcggtgaactgaaaggtgacgtccaaggcctgctga
gcctgtatgaagcgtcttacctgggtttcgagggtgagaacctgctggaggaggcgcgtaccttttccatcaccca
cctgaagaacaacctgaaagaaggcattaataccaaggttgcagaacaagtgagccacgccctggaactgc
catatcaccagcgtctgcaccgtctggaggcacgttggttcctggataaatacgaaccgaaagaaccgcatca
ccagctgctgctggagctggcgaagctggattttaacatggtacagaccctgcaccagaaagagctgcaagat
ctgtcccgctggtggaccgagatgggcctggctagcaaactggattttgtacgcgaccgcctgatggaagtttatt
tctgggcactgggtatggcgccagacccgcagtttggtgaatgtcgcaaagctgttactaaaatgtttggtctggtg
acgatcatcgatgacgtgtatgacgtttatggcactctggacgaactgcaactgttcaccgatgctgtagagcgct
gggacgttaacgctattaacaccctgccggactatatgaaactgtgtttcctggcactgtacaacaccgttaacga
cacgtcctattctattctgaaagagaaaggtcataacaacctgtcct

Figure 43C atctgacgaaaagctggcgtgaactgtgcaaagcctttctgcaagaggcgaaatggtccaacaacaaaatt
atcccggctttctccaagtacctggaaaacgccagcgtttcctcctccggtgtagcgctgctggcgccgtctta
cttttccgtatgccagcagcaggaagacatctccgaccacgcgctgcgttccctgaccgacttccatggtctg
gtgcgttctagctgcgttatcttccgcctgtgcaacgatctggccacctctgcggcggagctggaacgtggcg
agactaccaattctatcattagctacatgcacgaaaacgatggtaccagcgaggaacaggcccgcgaaga
actgcgtaaactgatcgacgccgaatggaaaaagatgaatcgtgaacgcgttagcgactccaccctgctgc
ctaaagcgttcatggaaatcgcagttaacatggcacgtgtttcccactgcacctaccagtatggcgatggtctg
ggtcgcccagactacgcgactgaaaaccgcatcaaactgctgctgattgacccttttcccgattaaccagctg
atgtatgtctaactgcatcgcccttaggaggtaaaaaaaaatgactgccgacaacaatagtatgccccatgg
tgcagtatctagttacgccaaattagtgcaaaaccaaacacctgaagacattttggaagagtttcctgaaatta
ttccattacaacaaagacctaatacccgatctagtgagacgtcaaatgacgaaagcggagaaacatgttttt
ctggtcatgatgaggagcaaattaagttaatgaatgaaaattgtattgttttggattgggacgataatgctattgg
tgccggtaccaagaaagtttgtcatttaatggaaaatattgaaaaggggtttactacatcgtgcattctccgtcttta
ttttcaatgaacaaggtgaattacttttacaacaaagagccactgaaaaaataactttccctgatctttggacta
acacatgctgctctcatccactatgtattgatgacgaattaggtttgaagggtaagctagacgataagattaag
ggcgctattactgcggcggtgagaaaactagatcatgaattaggtattccagaagatgaaactaagacaag
gggtaagtttcacttttttaaacagaatccattacatggcaccaagcaatgaaccatgggtgaacatgaaatt
gattacatcctatttataagatcaacgctaaagaaaacttgactgtcaacccaaacgtcaatgaagttagag
acttcaaatggggtttcaccaaatgatttgaaaactatgtttgctgacccaagttacaagtttacgccttggtttaag
attatttgcgagaattacttattcaactggtgggagcaattagatgaccttctgaagtggaaaatgacaggca
aattcatagaatgctataacgacgcgtcctgcagctggtaccatatgggaattcgaagctttctagaacgaaa
actcatctcagaagaggatctgaatagcgccgtcgaccatcatcatcatcatcattgagtttaaacggtctcca
gcttggctgttttggcggatgagagaagattttcagcctgatacagattaaatcagaacgcagaagcggtctg
ataaaacagaatttgcctggcggcagtagcgcggtggtcccacctgaccccatgccgaactcagaagtga
aacgccgtagcgccgatggtagtgtggggtctccccatgcgagagtagggaactgccaggcatcaaataa
aacgaaaggctcagtcgaaagactgggcctttcgttttatctgttgtttgtcggtgaacgctctcctgagtagga
caaatccgccgggagcggatttgaacgttgcgaagcaacggcccggagggtggcgggcaggacgcccg
ccataaactgccaggcatcaaattaagcagaaggccatcctgacggatggcctttttgcgtttctacaaactct
ttttgtttattttctaaatacattcaaatatgtatccgctcatgagacaataaccctgataaatgcttcaataat (SEQ ID NO:54)

Figure 45A

5'-
cccgtcttactgtcgggaattcgcgttggccgattcattaatgcagattattgaagcatttatcagggttattgtctcatg
agcggatacatatttgaatgtatttagaaaaataaacaaaaagagtttgtagaaacgcaaaaaggccatccgtca
ggatggccttctgcttaatttgatgcctggcagtttatggcgggcgtcctgcccgccaccctccgggccgttgcttcg
caacgttcaaatccgctcccggcggatttgtcctactcaggagagcgttcaccgacaaacaacagataaaacga
aaggcccagtctttcgactgagccttttcgttttatttgatgcctggcagttccctactctcgcatggggagaccccaca
ctaccatcggcgctacggcgtttcacttctgagttcggcatggggtcaggtgggaccaccgcgctactgccgcca
ggcaaattctgttttatcagaccgcttctgcgttctgatttaatctgtatcaggctgaaaatcttctctcatccgccaaaa
cagccaagctggagaccgtttaaactcaatgatgatgatgatggtcgacggcgctattcagatcctcttctgag
atgagttttttgttctagaaagcttcgaattcccatatggtaccagctgcagttatgccagccaggccttgattttggcttc
cataccagcggcatcgaggccgagttcggcgcgcatttcttcctgagttccttgcggaataaagaagtccggcag
gccaatgttcagcacgggtactggtttacgatgggccatcagcacttcgttcacgccgctgcctgcgccgcccata
atggcgttttcttctacggtgaccagcgcttcatggctggcggccatttccagaattaacgcttcatcaagcggtttca
caaaacgcatatcgaccagcgtggcgttcagcgattcggcgactttcgccgcttctggcatcagcgtaccaaagtt
aaggatcgccagtttctcgccacgacgcttcacaatgcctttgccaattggtagttttccagcggcgtcagttccac
gccgaccgcgttgccacgcgggtagcgcaccgctgacgggccatcgttatagtgatagccggtatagagcatct
ggcgacattcgttttcatcgctcggggtcataatgaccatttccggtatgcagcgcaggtaagagagatcaaaagc
accctgatgggtttgaccgtcagcaccaacaatgcccgcgcggtcgatggcgaacaggaccggaagcttttgaa
tcgccacgtcatgcagcacctgatcataggcgcgttgcaggaaagtggagtaaatcgcgacaatgggtttgtacc
caccaatcgccagacccgcagcaaaggtcaccgcgtgttgctcggcaattgccacgtcgaagtagcgatccgg
gaatttacgtgaaaactcgaccatgccggaaccttcacgcatcgccggagtaatcgccatcagcttgttgtctttcg
ctgccgtttcgcacaaccagtcgccaaagattttttgaatagctcggcaaaccgccgctacttttcggcaaacaacc
gctggagggatcaaatttaggcacggcgtggaaagtgatcgggtcttttctctgccggttcataaccacgacctttttg
gtcatgatatgcaggaactgcgggccttttcaggtcgcgcatgttctttagcgtggtgataagccccagcacatcgtg
accgtccaccgggccgatgtagttaaagcccagctcttcaaacaacgtgccaggcactaccatgcctttaatatgt
tcttcggtgcgtttgagcagctcttttaattggcggcacgccagagaaaacttttttcccgccttcgcgcagtgaagag
taaagcttaccggaaagcagctgtgccagatggttgttgagcgcgccgacattttcggaaatcgacatttcattgtc
gttgagaatcaccagcatatcaggacggatatcgcccgcgtgattcatcgcttcaaacgccatgcctgcggtaatc
gcgccatcgccaatgacacagacggtgcggcgattttttgccttcttttcggcagcaaccgcaataccaattccgg
cactgatggaggttgatgaatgcccgacgcttaatacgtcatattcgctttcgccgcgccacgggaacgggtgca
gaccgcctttctgacggatggtgccgattttgtcgcggcgtccggtcaaaattttatgcggataagcctgatgcccca
catcccaaatcaattggtcaaacggggtgttgtagacatagtgcagcgccacggtcagttcgaccgtgcccagcc
cggaggcgaagtgcccgctggaacggctcacgctgtcgagtaaatagcggcgcagttcgtcgcagagtttcggt
aaactctcttcggcaacagtcgtaactcctgggtggagtcgaccagtgccagggtcgggtatttggcaatatcaa
aactcatgttttttacctcctaagggcgaatgcagttagacatacatcagctggttaatcgggaaagggtcaatca
gcagcagtttgatgcggttttcagtcgcgtagtctgggcgacccagaccatcgccatactggtaggtgcagtggga
aacacgtgccatgttaactgcgatttccatgaacgctttaggcagcagggtggagtcgctaacgcgttcacg

Figure 45B attcatcttttccattcggcgtcgatcagtttacgcagttcttcgcgggcctgttcctcgctggtaccatcgttttcgtgca
tgtagctaatgatagaattggtagtctcgccacgttccagctccgccgcagaggtggccagatcgttgcacaggc
ggaagataacgcagctagaacgcaccagaccatggaagtcggtcagggaacgcagcgcgtggtcggagatg
tcttcctgctgctggcatacggaaaagtaagacggcgccagcagcgctacaccggaggaggaaacgctggcgt
tttccaggtacttggagaaagccgggataattttgttgttggaccatttcgcctcttgcagaaaggctttgcacagttca
cgccagcttttcgtcagataggacaggttgttatgacctttctctttcagaatagaataggacgtgtcgttaacggtgtt
gtacagtgccaggaaacacagtttcatatagtccggcagggtgttaatagcgttaacgtcccagcgctctacagc
atcggtgaacagttgcagttcgtccagagtgccataaacgtcatacacgtcatcgatgatcgtcaccagaccaaa
cattttagtaacagctttgcgacattcaccaaactgcgggtctggcgccatacccagtgcccagaaataaacttcc
atcaggcggtcgcgtacaaaatccagtttgctagccaggcccatctcggtccaccagcgggacagatcttgcag
ctctttctggtgcagggtctgtaccatgttaaaatccagcttcgccagctccagcagcagctggtgatgcggttctttc
ggttcgtatttatccaggaaccaacgtgcctccagacggtgcagacgctggtgatatggcagttccagggcgtgg
ctcacttgttctgcaaccttggtattaatgccttctttcaggttgttcttcaggtgggtgatggaaaaggtacgcgcctcc
tccagcaggttctcaccctcgaaacccaggtaagacgcttcatacaggctcagcaggccttggacgtcacctttca
gttcaccgctgaaaccaccttctttatccttgaaacgctcaaaaacatcctgagaaacctcgaaaccgtgctgacg
cagcagacggaaagacagagcggttgcgtcaggtcagatttgttcttttgttttcgtccagcagtacgatgttttcc
agggctttaatgatgtcttttcaaatttgtaggtcagacccaggcgctgcacatcgtcgatcagctccagcaggga
cagcggctgggtgtctacacggttgatcatgcagcgaacttcttcctccagtttggtcgctttctcctccagcttttcca
ctttcaggtcgttctccagggattgcaggaattcgaaattccacaggtttggctgatagtttgcggaacgacgggaa
ttatgctcggtaatctgagtaaattgagaagaggtcgcacacatggtttattcctccttatttaatcgatacattaatata
tacctctttaattttaataataaagttaatcgataattccggtcgagtgcccacacagattgtctgataaattgttaaag
agcagtgccgcttcgcttttctcagcggcgctgtttcctgtgtgaaattgttatccgctcacaattccacacattatacg
agccggatgattaattgtcaacagctcatttcagaatctggcgtaatagcgaagaggcccgcaccgatcgcccttc
ccaacagttgcgcagcctgaatggcgaatggcgcctgatgcggtattttctccttacgcatctgtgcggtatttcaca
ccgcatatggtgcactctcagtacaatctgctctgatgccgcatagttaagccagccccgacacccgccaacacc
cgctgacgagcttagtaaagccctcgctagattttaatgcggatgttgcgattacttcgccaactattgcgataacaa
gaaaaagccagcctttcatgatatatctcccaatttgtgtagggcttattatgcacgcttaaaaataataaaagcag
acttgacctgatagtttggctgtgagcaattatgtgcttagtgcatctaacgcttgagttaagccgcgccgcgaagcg
gcgtcggcttgaacgaattgttagacattatttgccgactaccttggtgatctcgcctttcacgtagtggacaaattctt
ccaactgatctgcgcgcgaggccaagcgatcttcttcttgtccaagataagcctgtctagcttcaagtatgacgggc
tgatactgggccggcaggcgctccattgcccagtcggcagcgacatccttcggcgcgattttgccggttactgcgc
tgtaccaaatgcgggacaacgtaagcactacatttcgctcatcgccagcccagtcgggcggcgagttccatagc
gttaaggtttcatttagcgcctcaaatagatcctgttcaggaaccggatcaaagagttcctccgccgctggacctac
caaggcaacgctatgttctcttgcttttgtcagcaagatagccagatcaatgtcgatcgtggctggctcgaagatac
ctgcaagaatgtcattgcgctgccattctccaaattgcagttcgcgcttagctggataacgccacggaatgatgtcg
tcgtgcacaacaatggtgacttctacagcgcggagaatctcgctctctccaggggaagccgaagtttccaaaag
gtcgttgatcaaagctcgccgcgttgtttcatcaagc

Figure 45C cttacggtcaccgtaaccagcaaatcaatatcactgtgtggcttcaggccgccatccactgcggagccgtaca
aatgtacggccagcaacgtcggttcgagatggcgctcgatgacgccaactacctctgatagttgagtcgatact
tcggcgatcaccgcttccctcatgatgtttaactttgttttagggcgactgccctgctgcgtaacatcgttgctgctc
cataacatcaaacatcgacccacggcgtaacgcgcttgctgcttggatgcccgaggcatagactgtacccca
aaaaaacagtcataacaagccatgaaaaccgccactgcgccgttaccaccgctgcgttcggtcaaggttctg
gaccagttgcgtgagcgcatacgctacttgcattacagcttacgaaccgaacaggcttatgtccactgggttcgt
gccttcatccgtttccacggtgtgcgtcacccggcaaccttgggcagcagcgaagtcgaggcatttctgtcctgg
ctggcgaacgagcgcaaggtttcggtctccacgcatcgtcaggcattggcggccttgctgttcttctacggcaa
ggtgctgtgcacggatctgccctggcttcaggagatcggaagacctcggccgtcgcggcgcttgccggtggtg
ctgaccccggatgaagtggttcgcatcctcggttttctggaaggcgagcatcgtttgttcgcccagcttctgtatgg
aacgggcatgcggatcagtgagggtttgcaactgcgggtcaaggatctggatttcgatcacggcacgatcatc
gtgcgggagggcaagggctccaaggatcgggccttgatgttacccgagagcttggcacccagcctgcgcga
gcaggggaattaattcccacgggttttgctgcccgcaaacgggctgttctggtgttgctagtttgttatcagaatcg
cagatccggcttcagccggtttgccggctgaaagcgctatttcttccagaattgccatgatttttccccacggga
ggcgtcactggctcccgtgttgtcggcagctttgattcgataagcagcatcgcctgtttcaggctgtctatgtgtga
ctgttgagctgtaacaagttgtctcaggtgttcaatttcatgttctagttgctttgttttactggtttcacctgttctattag
gtgttacatgctgttcatctgttacattgtcgatctgttcatggtgaacagctttgaatgcaccaaaaactcgtaaaa
gctctgatgtatctatcttttttacaccgttttcatctgtgcatatggacagttttcccttgatatgtaacggtgaacagt
tgttctactttgtttgttagtcttgatgcttcactgatagatacaagagccataagaacctcagatccttccgtatta
gccagtatgttctctagtgtggttcgttgttttgcgtgagccatgagaacgaaccattgagatcatacttactttgca
tgtcactcaaaaattttgcctcaaaactggtgagctgaattttgcagttaaagcatcgtgtagtgtttttcttagtcc
gttatgtaggtaggaatctgatgtaatggttgttggtattttgtcaccattcatttttatctggttgttctcaagttcggtta
cgagatccatttgtctatctagttcaacttggaaaatcaacgtatcagtcgggcggcctcgcttatcaaccacca
atttcatattgctgtaagtgtttaaatctttacttattggtttcaaaacccattggttaagcctttttaaactcatggtagtt
atttcaagcattaacatgaacttaaattcatcaaggctaatctctatatttgccttgtgagttttctttttgtgttagttcttt
taataaccactcataaatcctcatagagtatttgttttcaaaagacttaacatgttccagattatattttatgaatttttt
aactggaaaagataaggcaatatctcttcactaaaaactaattctaattttcgcttgagaacttggcatagtttgt
ccactggaaaatctcaaagcctttaaccaaaggattcctgatttccacagttctcgtcatcagctctctggttgcttt
agctaatacaccataagcatttccctactgatgttcatcatctgagcgtattggtataagtgaacgataccgtcc
gttctttccttgtagggttttcaatcgtggggttgagtagtgccacacagcataaaattagcttggtttcatgctccgtt
aagtcatagcgactaatcgctagttcatttgctttgaaaacaactaattcagacatacatctcaattggtctaggtg
attttaatcactataccaattgagatgggctagtcaatgataattactagtccttttcctttgagttgtgggtatctgta
aattctgctagacctttgctggaaaacttgtaaattctgctagaccctctgtaaattccgctagacctttgtgtgtttttt
ttgtttatattcaagtggttataatttatagaataaagaaagaataaaaaaagataaaaagaatagatcccagc
cctgtgtataactcactactttagtcagttccgcagtattacaaaaggatgtcgcaaacgctgtttgctcctctaca
aaacagaccttaaaacccctaaaggcttaagtagcaccctcgcaagctcgggcaaatcgctgaatattcctttg
tctccgaccatcaggcacctgagtcgctgtcttttc

Figure 45D

Gtgacattcagttcgctgcgctcacggctctggcagtgaatgggggtaaatggcactacaggcgccttttatggatt
catgcaaggaaactacccataatacaagaaaagcccgtcacgggcttctcagggcgttttatggcgggtctgcta
tgtggtgctatctgacttttgctgttcagcagttcctgccctctgattttccagtctgaccacttcggattatcccgtgaca
ggtcattcagactggctaatgcacccagtaaggcagcggtatcatcaacaggctta (SEQ ID NO:55)

Figure 51A

5'- tcgctgcgctcggtcgttcggctgcggcgagcggtatcagctcactcaaaggcggtaatacggttatccacaga
atcaggggataacgcaggaaagaacatgtgagcaaaaggccagcaaaaggccaggaaccgtaaaaagg
ccgcgttgctggcgtttttccataggctccgcccccctgacgagcatcacaaaaatcgacgctcaagtcagaggt
ggcgaaacccgacaggactataaagataccaggcgtttccccctggaagctccctcgtgcgctctcctgttccg
accctgccgcttaccggatacctgtccgcctttctcccttcgggaagcgtggcgctttctcatagctcacgctgtag
gtatctcagttcggtgtaggtcgttcgctccaagctgggctgtgtgcacgaaccccccgttcagcccgaccgctgc
gccttatccggtaactatcgtcttgagtccaacccggtaagacacgacttatcgccactggcagcagccactggt
aacaggattagcagagcgaggtatgtaggcggtgctacagagttcttgaagtggtggcctaactacggctacac
tagaagaacagtatttggtatctgcgctctgctgaagccagttaccttcggaaaaagagttggtagctcttgatccg
gcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcat
gagattatcaaaaaggatcttcacctagatccttttaaattaaaaatgaagttttaaatcaatctaaagtatatatga
gtaaacttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaatgata
ccgcgagacccacgctcaccggctccagatttatcagcaataaaccagccagccggaagggccgagcga
gaagtggtcctgcaactttatccgcctccatccagtctattaattgttgccgggaagctagagtaagtagttcgcca
gttaatagtttgcgcaacgttgttgccattgctacaggcatcgtggtgtcacgctcgtcgtttggtatggcttcattcag
ctccggttcccaacgatcaaggcgagttacatgatcccccatgttgtgcaaaaaagcggttagctccttcggtcct
ccgatcgttgtcagaagtaagttggccgcagtgttatcactcatggttatggcagcactgcataattctcttactgtc
atgccatccgtaagatgcttttctgtgactggtgagtactcaaccaagtcattctgagaatagtgtatgcggcgacc
gagttgctcttgcccggcgtcaatacgggataataccgcgccacatagcagaactttaaaagtgctcatcattgg
aaaacgttcttcggggcgaaaactctcaaggatcttaccgctgttgagatccagttcgatgtaacccactcgtgca
cccaactgatcttcagcatcttttactttcaccagcgtttctgggtgagcaaaaacaggaaggcaaaatgccgca
aaaaagggaataagggcgacacggaaatgttgaatactcatactcttcctttttcaatattattgaagcatttatca
gggttattgtctcatgagcggatacatatttgaatgtatttagaaaaataaacaaataggggttccgcgcacatttc
cccgaaaagtgccacctgacgtctaagaaaccattattatcatgacattaacctataaaaataggcgtatcacg
aggccctttcgtctcgcgcgtttcggtgatgacggtgaaaacctctgacacatgcagctcccggagacggtcac
agcttgtctgtaagcggatgccgggagcagacaagcccgtcagggcgcgtcagcgggtgttggcgggtgtcg
gggctggcttaactatgcggcatcagagcagattgtactgagagtgcaccatagatctggagctgtaatataaa
aaccttcttcaactaacggggcaggttagtgacattagaaaaccgactgtaaaagtacagtcggcattatctca
tattataaaagccagtcattaggcctatctgacaattcctgaatagagttcataaacaatcctgcatgataaccatc
acaaacagaatgatgtacctgtaaagatagcggtaaatatattgaattaccttattaatgaatttcctgctgtaata
atgggtagaaggtaattactattattattgatatttaagttaaacccagtaaatgaagtccatggaataatagaaag
agaaaaagcattttcaggtataggtgtttgggaaacaatttccccgaaccattatatttctctacatcagaaaggt
ataaatcataaaactctttgaagtcattctttacaggagtccaaataccagagaatgttttagatacaccatcaaa
aattgtataaagtggctctaacttatcccaataacctaactctccgtcgctattgtaaccagttctaaaagctgtattt
gagtttatcacccttgtcactaagaaaataaatgcagggtaaaatttatatccttcttgttttatgtttc

Figure 51B ggtataaaacactaatatcaatttctgtggttatactaaaagtcgtttgttggttcaaataatgattaaatatctc
ttttctcttccaattgtctaaatcaatttattaaagttcatttgatatgcctcctaaattttatctaaagtgaattta
ggaggcttacttgtctgctttcttcattagaatcaatccttttttaaaagtcaatattactgtaacataaatatatat
tttaaaaatatcccactttatccaattttcgtttgttgaactaatgggtgcttttagttgaagaataaaagacctat
gcggtgtgaaataccgcacagatgcgtaaggagaaaataccgcatcaggcgccattcgccattcaggc
tgcgcaactgttgggaagggcgatcggtgcgggcctcttcgctattacgccagctggcgaaaggggat
gtgctgcaaggcgattaagttgggtaacgccagggttttcccagtcacgacgttgtaaaacgacggccag
tgccaagcttgcatgcctgcactccatttcttctgctatcaaaataacagactcgtgattttccaaacgagct
ttcaaaaaagcctctgccccttgcaaatcggatgcctgtctataaaattcccgatattggttaaacagcggc
gcaatggcggccgcatctgatgtctttgcttggcgaatgttcatcttatttcttcctccctctcaataattttttcatt
ctatccctttctgtaaagtttattttcagaatactttatcatcatgctttgaaaaaatatcacgataatatccatt
gttctcacggaagcacacgcaggtcatttgaacgaattttttcgacaggaatttgccgggactcaggagca
tttaacctaaaaaagcatgacatttcagcataatgaacatttactcatgtctatttcgttctttctgtatgaaaa
tagttatttcgagtctctacgaaatagcgagagatgatatacctaaatagagataaaatcatctcaaaaa
aatgggtctactaaaatattattccatctattacaataaattcacagaatagtcttttaagtaagtctactctga
attttttaaaaggagagggtaaagagtgaaaacagtagttattattgatgcattacgaacaccaattggaa
aatataaaggcagcttaagtcaagtaagtgccgtagacttaggaacacatgttacaacacaacttttaaa
aagacattccactatttctgaagaaattgatcaagtaatctttggaaatgttttacaagctggaaatggccaa
aatcccgcacgacaaatagcaataaacagcggtttgtctcatgaaattcccgcaatgacggttaatgagg
tctgcggatcaggaatgaaggccgttatttggcgaaacaattgattcaattaggagaagcggaagttta
attgctggcgggattgagaatatgtcccaagcacctaaattacaacgttttaattacgaaacagaaagcta
cgatgcgcctttttctagtatgatgtatgatggattaacggatgcctttagtggtcaggcaatgggcttaactg
ctgaaaatgtggccgaaaagtatcatgtaactagagaagagcaagatcaatttctgtacattcacaatta
aaagcagctcaagcacaagcagaagggatattcgctgacgaaatagccccattagaagtatcaggaa
cgcttgtggagaaagatgaagggattcgccctaattcgagcgttgagaagctaggaacgcttaaaacag
tttttaaagaagacggtactgtaacagcagggaatgcatcaaccattaatgatggggcttctgctttgattatt
gcttcacaagaatatgccgaagcacacggtcttccttatttagctattattcgagacagtgtggaagtcggt
attgatccagcctatatgggaatttcgccgattaaagccattcaaaaaactgttagcgcgcaatcaacttact
acggaagaaattgatctgtatgaaatcaacgaagcatttgcagcaacttcaatcgtggtccaaagagaa
ctggctttaccagaggaaaaggtcaacatttatggtggcggtatttcattaggtcatgcgattggtgccaca
ggtgctcgtttattaacgagtttaagttatcaattaaatcaaaagaaaagaaatatggagtggcttctttatg
tatcggcggtggcttaggactcgctatgctactagagagacctcagcaaaaaaaaacagccgattttat
caaatgagtcctgaggaacgcctggcttctcttcttaatgaaggccagatttctgctgatacaaaaaaaga
atttgaaaatacggctttatcttcgcagattgccaatcatatgattgaaaatcaaatcagtgaaacagaagt
gccgatgggcgttggcttacatttaacagtggacgaaactgattatttggtaccaatggcgacagaagag
ccctcagttattgcggctttgagtaatggtgcaaaaatagcacaaggatttaaaacagtgaatcaacaac
gcttaatgcgtggacaaatcgtttttacgatgttgcagatcccgagtcattgattgataaactacaagtaag
agaagcggaagttttcaacaagcagagttaagttatccatctatcgttaaacggggcggcggcttaaga
gatttgcaatatcgtactttgatgaatcatttgtatctgtcgacttttagtagatgttaaggatgcaatggggg
caaatatcgttaacgctatgttggaaggtgtg

Figure 51C gccgagttgttccgtgaatggtttgcggagcaaaagatttattcagtattttaagtaattatgccacggagtcggttg
ttacgatgaaaacggctattccagtttcacgtttaagtaaggggagcaatggccgggaaattgctgaaaaaattg
ttttagcttcacgctatgcttcattagatccttatcgggcagtcacgcataacaaaggaatcatgaatggcattgaa
gctgtagttttagctacaggaaatgatacacgcgctgttagcgcttcttgtcatgcttttgcggtgaaggaaggtcgc
taccaaggcttgactagttggacgctggatggcgaacaactaattggtgaaatttcagttccgcttgctttagccac
ggttggcggtgccacaaaagtcttacctaaatctcaagcagctgctgatttgttagcagtgacggatgcaaaaga
actaagtcgagtagtagcggctgttggtttggcacaaaatttagcggcgttacgggccttagtctctgaaggaatt
caaaaaggacacatggctctacaagcacgttctttagcgatgacggtcggagctactggtaaagaagttgagg
cagtcgctcaacaattaaaacgtcaaaaaacgatgaaccaagaccgagccatggctattttaaatgatttaaga
aaacaataaaaggagagggtgacaattgggattgataaaattagttttttttgtgcccccttattatattgatatgacg
gcactggctgaagccagaaatgtagaccctggaaaatttcatattggtattgggcaagaccaaatggcggtga
acccaatcagccaagatattgtgacatttgcagccaatgccgcagaagcgatcttgaccaaagaagataaag
aggccattgatatggtgattgtcgggactgagtccagtatcgatgagtcaaaagcggccgcagttgtcttacatcg
tttaatggggattcaacctttcgctcgctctttcgaaatcaaggaagcttgttacggagcaacagcaggcttacagt
tagctaagaatcacgtagccttacatccagataaaaaagtcttggtcgtagcggcagatattgcaaaatatggct
taaattctggcggtgagcctacacaaggagctggggcggttgcaatgttagttgctagtgaaccgcgcattttggc
tttaaaagaggataatgtgatgctgacgcaagatatctatgactttggcgtccaacaggccacccgtatcctatg
gtcgatggtcctttgtcaaacgaaacctacatccaatcttttgcccaagtctgggatgaacataaaaaacgaacc
ggtcttgattttgcagattatgatgctttagcgttccatattccttacacaaaaatgggcaaaaaagccttattagca
aaaatctccgaccaaactgaagcagaacaggaacgaattttagcccgttatgaagaaagtatcgtctatagtcg
tcgcgtaggaaacttgtatacgggttcactttatctgggactcatttcccttttagaaaatgcaacgactttaaccgc
aggcaatcaaattggtttattcagttatggttctggtgctgtcgctgaattttcactggtgaattagtagctggttatca
aaatcatttacaaaaagaaactcatttagcactgctggataatcggacagaactttctatcgctgaatatgaagcc
atgtttgcagaaactttagacacagacattgatcaaacgttagaagatgaattaaaatatagtatttctgctattaat
aataccgttcgttcttatcgaaactaaaaaaaaccggccttggccccgccggttttttattattttcttcctccgcatgt
tcaatccgctccataatcgacggatggctccctctgaaaattttaacgagaaacggcgggttgacccggctcagt
cccgtaacggccaagtcctgaaacgtctcaatcgccgcttcccggtttccggtcagctcaatgccgtaacggtcg
gcggcgttttcctgataccgggagacggcattcgtaatcgggatccccgggtaccgagctcgaattcgtaatcat
gtcatagctgtttcctgtgtgaaattgttatccgctcacaattccacacaacatacgagccggaagcataaagtgt
aaagcctggggtgcctaatgagtgagctaactcacattaattgcgttgcgctcactgcccgctttccagtcgggaa
acctgtcgtgccagctgcattaatgaatcggccaacgcgcggggagaggcggtttgcgtattgggcgctcttccg
cttcctcgctcactgac (SEQ ID NO:56)

Figure 75A

| Concentration at Deflagration | | | | | | | | | | | | | | | |
|---|---|---|---|---|---|---|---|---|---|---|---|---|---|---|---|
| Fuel Makeup | Oxidizer Makeup | | | Molar Concentration based on 100g of sample | | | | | Volumetric Concentrations based on ideal gas law | | | | | |
| Fuel Conc. (wt.%) | Oxidizer Conc. (wt.%) | Isoprene (wt. %) | H$_2$O (wt. %) | O$_2$ (wt. %) | N$_2$ (wt. %) | Isoprene (mole) | H$_2$O (mole) | O$_2$ (mole) | N$_2$ (mole) | Total (mole) | Isoprene (vol. %) | O$_2$ (vol. %) | N$_2$ (vol. %) | H$_2$O (vol. %) |
| 3.10 | 96.90 | 100 | 0 | 12 | 88 | 4.56 | 0.00 | 36.34 | 304.54 | 345.44 | 1.32 | 10.52 | 88.16 | 0.00 |
| 3.10 | 96.90 | 100 | 0 | 13 | 87 | 4.56 | 0.00 | 39.37 | 301.08 | 345.01 | 1.32 | 11.41 | 87.27 | 0.00 |
| 3.10 | 96.90 | 100 | 0 | 14 | 86 | 4.56 | 0.00 | 42.39 | 297.62 | 344.57 | 1.32 | 12.30 | 86.37 | 0.00 |
| 3.10 | 96.90 | 100 | 0 | 15 | 85 | 4.56 | 0.00 | 45.42 | 294.16 | 344.14 | 1.32 | 13.20 | 85.48 | 0.00 |
| 3.10 | 96.90 | 100 | 0 | 16 | 84 | 4.56 | 0.00 | 48.45 | 290.70 | 343.71 | 1.32 | 14.10 | 84.58 | 0.00 |
| 3.10 | 96.90 | 100 | 0 | 17 | 83 | 4.55 | 0.00 | 51.48 | 287.24 | 343.28 | 1.33 | 15.00 | 83.68 | 0.00 |
| 3.10 | 96.90 | 100 | 0 | 21 | 79 | 4.55 | 0.00 | 63.59 | 273.40 | 341.55 | 1.33 | 18.62 | 80.05 | 0.00 |
| 3.50 | 96.50 | 100 | 0 | 11.1 | 88.9 | 5.15 | 0.00 | 33.47 | 306.39 | 345.01 | 1.49 | 9.70 | 88.81 | 0.00 |
| 4.40 | 95.60 | 100 | 0 | 12 | 88 | 6.47 | 0.00 | 35.85 | 300.46 | 342.78 | 1.89 | 10.46 | 87.65 | 0.00 |
| 5.50 | 94.50 | 100 | 0 | 13 | 87 | 8.09 | 0.00 | 38.39 | 293.63 | 340.10 | 2.38 | 11.29 | 86.33 | 0.00 |
| 6.60 | 93.40 | 100 | 0 | 14 | 86 | 9.71 | 0.00 | 40.86 | 286.87 | 337.44 | 2.88 | 12.11 | 85.01 | 0.00 |
| 7.60 | 92.40 | 100 | 0 | 15 | 85 | 11.18 | 0.00 | 43.31 | 280.50 | 334.99 | 3.34 | 12.93 | 83.73 | 0.00 |
| 8.50 | 91.50 | 100 | 0 | 16 | 84 | 12.50 | 0.00 | 45.75 | 274.50 | 332.75 | 3.76 | 13.75 | 82.49 | 0.00 |
| 9.60 | 90.40 | 100 | 0 | 17 | 83 | 14.12 | 0.00 | 48.03 | 267.97 | 330.11 | 4.28 | 14.55 | 81.18 | 0.00 |
| 10.50 | 86.50 | 100 | 0 | 21 | 79 | 19.85 | 0.00 | 56.77 | 244.05 | 320.67 | 6.19 | 17.70 | 76.11 | 0.00 |

Figure 76A

| Fuel Conc. (wt %) | Oxidizer Conc. (wt %) | Fuel Makeup | Oxidizer Makeup | | | Concentration at Deflagration | | | | | | | |
|---|---|---|---|---|---|---|---|---|---|---|---|---|---|
| | | | | | | Molar Concentration based on 100g of sample | | | | | Volumetric Concentrations based on ideal gas law | | |
| | | Isoprene (wt %) | H₂O (wt %) | O₂ (wt %) | N₂ (wt %) | Isoprene (mole) | H₂O (mole) | O₂ (mole) | N₂ (mole) | Total (mole) | Isoprene (vol %) | O₂ (vol %) | N₂ (vol %) | H₂O (vol %) |
| 3.252 | 96.748 | 100 | 4 | 12 | 84 | 4.78 | 21.50 | 36.26 | 290.24 | 352.81 | 1.36 | 10.28 | 82.27 | 6.09 |
| 3.274 | 96.726 | 100 | 4 | 13 | 83 | 4.81 | 21.49 | 39.29 | 286.72 | 352.33 | 1.37 | 11.15 | 81.38 | 6.10 |
| 3.290 | 96.710 | 100 | 4 | 14 | 82 | 4.84 | 21.49 | 42.31 | 283.22 | 351.86 | 1.38 | 12.02 | 80.49 | 6.11 |
| 3.288 | 96.712 | 100 | 4 | 15 | 81 | 4.84 | 21.49 | 45.33 | 279.77 | 351.43 | 1.38 | 12.90 | 79.61 | 6.12 |
| 3.286 | 96.714 | 100 | 4 | 16 | 80 | 4.83 | 21.49 | 48.36 | 276.33 | 351.01 | 1.38 | 13.78 | 78.72 | 6.12 |
| 3.284 | 96.716 | 100 | 4 | 17 | 79 | 4.83 | 21.49 | 51.38 | 272.88 | 350.58 | 1.38 | 14.66 | 77.84 | 6.13 |
| 3.276 | 96.724 | 100 | 4 | 21 | 75 | 4.82 | 21.49 | 63.48 | 259.08 | 348.87 | 1.38 | 18.19 | 74.28 | 6.16 |
| 3.500 | 96.500 | 100 | 4 | 11.5 | 84.5 | 5.15 | 21.44 | 34.68 | 291.22 | 352.49 | 1.46 | 9.84 | 82.62 | 6.08 |
| 4.200 | 95.800 | 100 | 4 | 12 | 84 | 6.18 | 21.29 | 35.93 | 287.40 | 350.79 | 1.76 | 10.24 | 81.93 | 6.07 |
| 5.300 | 94.700 | 100 | 4 | 13 | 83 | 7.79 | 21.04 | 38.47 | 280.72 | 348.03 | 2.24 | 11.05 | 80.66 | 6.05 |
| 6.400 | 93.600 | 100 | 4 | 14 | 82 | 9.41 | 20.80 | 40.95 | 274.11 | 345.28 | 2.73 | 11.86 | 79.39 | 6.02 |
| 7.400 | 92.600 | 100 | 4 | 15 | 81 | 10.88 | 20.58 | 43.41 | 267.88 | 342.74 | 3.18 | 12.66 | 78.16 | 6.00 |
| 8.500 | 91.500 | 100 | 4 | 16 | 80 | 12.50 | 20.33 | 45.75 | 261.43 | 340.01 | 3.68 | 13.46 | 76.89 | 5.96 |
| 9.400 | 90.600 | 100 | 4 | 17 | 79 | 13.82 | 20.13 | 48.13 | 255.62 | 337.71 | 4.09 | 14.25 | 75.69 | 5.98 |
| 13.300 | 86.700 | 100 | 4 | 21 | 75 | 19.56 | 19.27 | 56.80 | 232.23 | 327.95 | 5.96 | 17.35 | 70.81 | 5.87 |

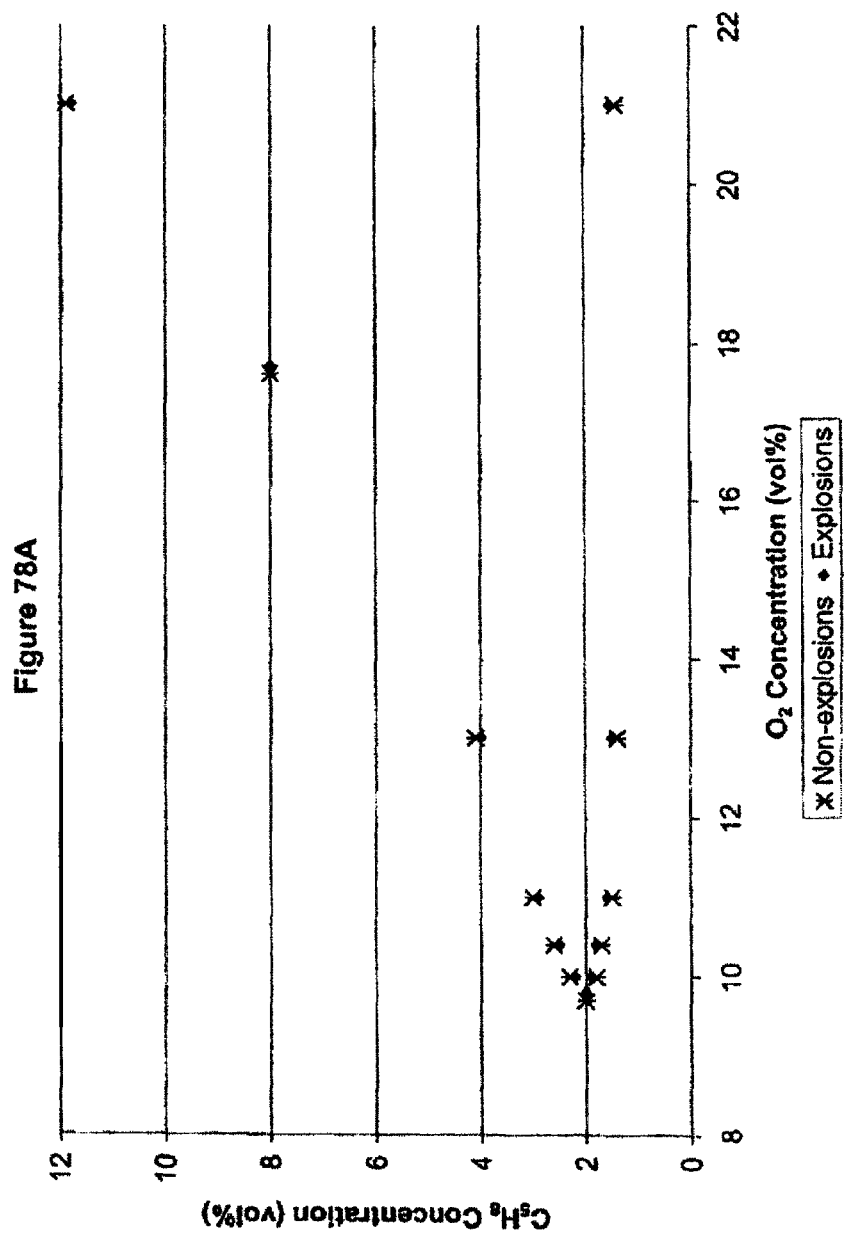

Figure 78B

| Explosions | | Non-explosions | |
|---|---|---|---|
| O$_2$ Concentration | C$_5$H$_8$ Concentration | O$_2$ Concentration | C$_5$H$_8$ Concentration |
| (vol. %) | (vol. %) | (vol. %) | (vol. %) |
| 21.0 | 1.5 | 21.0 | 1.4 |
| 13.0 | 1.5 | 13.0 | 1.4 |
| 11.0 | 1.6 | 11.0 | 1.5 |
| 10.4 | 1.8 | 10.4 | 1.7 |
| 10.0 | 1.9 | 10.0 | 1.8 |
| 9.8 | 2 | 9.7 | 2 |
| 10.0 | 2.2 | 10.0 | 2.3 |
| 10.4 | 2.5 | 10.4 | 2.6 |
| 11.0 | 2.9 | 11.0 | 3.0 |
| 13.0 | 4.0 | 13.0 | 4.1 |
| 17.7 | 8.0 | 17.6 | 8.0 |
| 21.0 | 11.8 | 21.0 | 11.9 |

Figure 79B

| Explosions | | Non-explosions | |
|---|---|---|---|
| $O_2$ Concentration | $C_5H_8$ Concentration | $O_2$ Concentration | $C_5H_8$ Concentration |
| (vol. %) | (vol. %) | (vol. %) | (vol. %) |
| 21.0 | 11.7 | 21.0 | 11.9 |
| 21.0 | 11.8 | 21.0 | 11.9 |
| 21.0 | 11.8 | 21.0 | 11.9 |
| 21.0 | 1.5 | 21.0 | 1.4 |
| 21.0 | 1.5 | 21.0 | 1.4 |
| 10.2 | 2.0 | 21.0 | 1.4 |
| 10.1 | 2.0 | 9.8 | 2.0 |
| 10.0 | 2.0 | 9.8 | 2.0 |
| 9.9 | 2.0 | 9.8 | 2.0 |

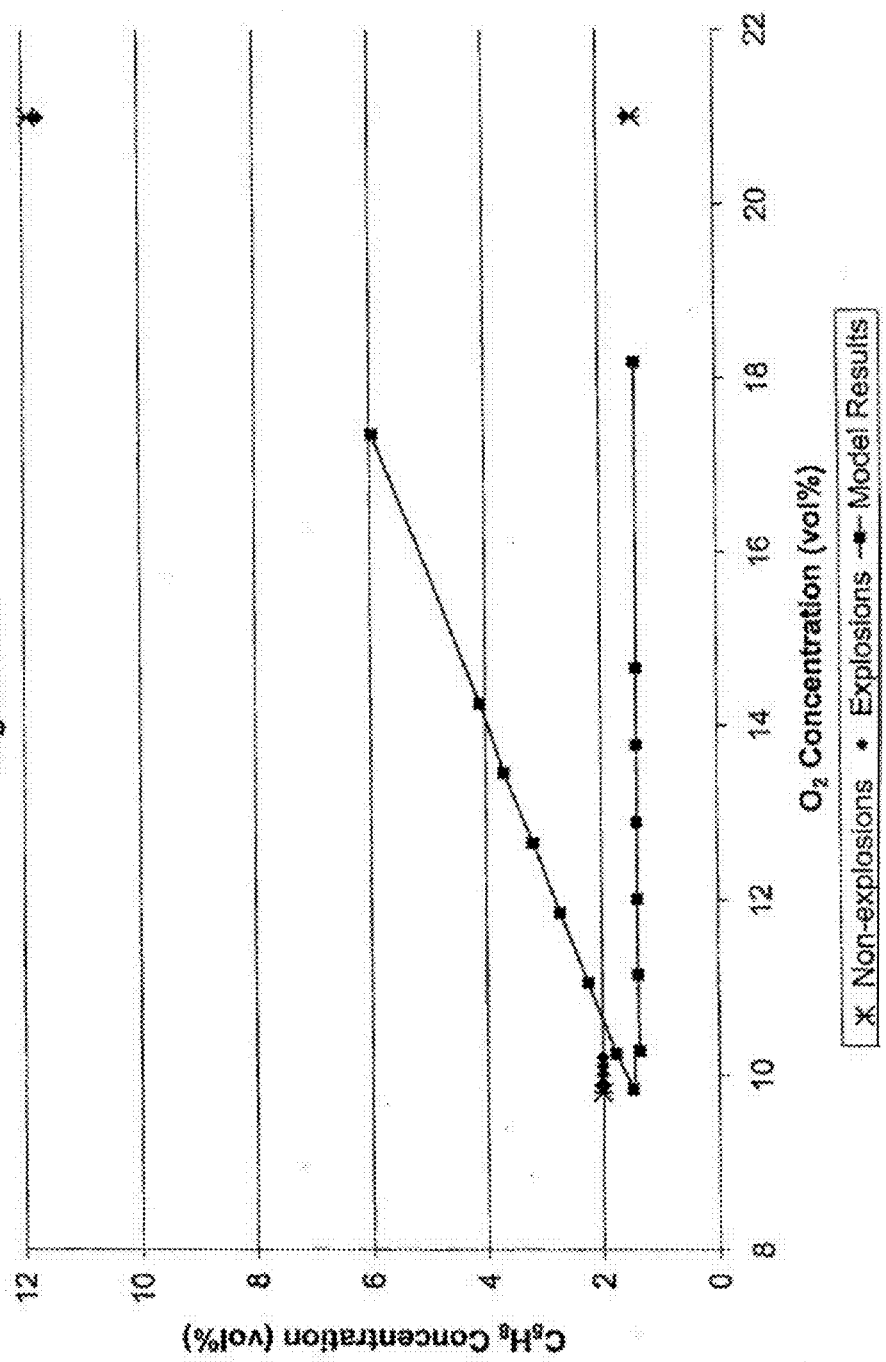

Figure 80A

TEST SERIES 1

| Test | Data File Name | Temp °C | Initial Pressure bara | Partial Pressures C$_5$H$_8$ mbar | N$_2$ mbar | O$_2$ mbar | Concentrations C$_5$H$_8$ vol.% | N$_2$ vol.% | O$_2$ vol.% | Result | Pex bara |
|---|---|---|---|---|---|---|---|---|---|---|---|
| 1 | T11120700 | 40 | 1.012 | 12 | 787 | 213 | 1.2 | 77.8 | 21.0 | Non-Explosion | 1.05 |
| 2 | T11120701 | 40 | 1.016 | 16 | 787 | 213 | 1.6 | 77.5 | 21.0 | Explosion | 5.5 |
| 3 | T11120702 | 40 | 1.015 | 14 | 788 | 213 | 1.4 | 77.6 | 21.0 | Non-Explosion | <1.02 |
| 4 | T11120703 | 40 | 1.014 | 15 | 786 | 213 | 1.5 | 77.5 | 21.0 | Non-Explosion | <1.02 |
| 5 | T11120704 | 40 | 1.014 | 15 | 786 | 213 | 1.5 | 77.5 | 21.0 | Explosion | 4.81 |
| 6 | T11120705 | 40 | 1.017 | 18 | 785 | 214 | 1.8 | 77.2 | 21.0 | Explosion | 5.47 |
| 7 | T11120706 | 40 | 1.014 | 15 | 786 | 213 | 1.5 | 77.5 | 21.0 | Explosion | 4.51 |
| 8 | T11120707 | 40 | 1.014 | 14 | 787 | 213 | 1.4 | 77.6 | 21.0 | Non-Explosion | <1.02 |
| 9 | T11120708 | 40 | 1.014 | 14 | 787 | 213 | 1.4 | 77.6 | 21.0 | Non-Explosion | 1.05 |
| 10 | T11120709 | 40 | 1.015 | 102 | 700 | 213 | 10.0 | 69.0 | 21.0 | Explosion | 1.45 |
| 11 | T11120710 | 40 | 1.014 | 102 | 699 | 213 | 10.1 | 68.9 | 21.0 | Explosion | 1.39 |
| 12 | T11120711 | 40 | 1.014 | 106 | 695 | 213 | 10.5 | 68.5 | 21.0 | Explosion | 1.34 |
| 13 | T11120712 | 40 | 1.014 | 113 | 688 | 213 | 11.1 | 67.9 | 21.0 | Explosion | 1.29 |
| 14 | T11120713 | 40 | 1.014 | 122 | 679 | 213 | 12.0 | 67.0 | 21.0 | Non-Explosion | <1.02 |
| 15 | T11120714 | 40 | 1.014 | 117 | 684 | 213 | 11.5 | 67.5 | 21.0 | Explosion | 1.32 |
| 16 | T11120715 | 40 | 1.014 | 120 | 681 | 213 | 11.8 | 67.2 | 21.0 | Non-Explosion | 1.08 |
| 17 | T11130700 | 40 | 1.014 | 120 | 681 | 213 | 11.8 | 67.2 | 21.0 | Explosion | 1.09 |
| 18 | T11130701 | 40 | 1.014 | 121 | 680 | 213 | 11.9 | 67.1 | 21.0 | Non-Explosion | 1.07 |
| 19 | T11130702 | 40 | 1.015 | 121 | 681 | 213 | 11.9 | 67.1 | 21.0 | Non-Explosion | 1.06 |
| 20 | T11130703 | 40 | 1.015 | 121 | 681 | 213 | 11.9 | 67.1 | 21.0 | Non-Explosion | 1.07 |
| 21 | T11130704 | 40 | 1.015 | 30 | 853 | 132 | 3.0 | 84.0 | 13.0 | Explosion | 1.61 |
| 22 | T11130705 | 40 | 1.014 | 36 | 846 | 132 | 3.6 | 83.4 | 13.0 | Explosion | 1.28 |
| 23 | T11130706 | 40 | 1.014 | 39 | 843 | 132 | 3.8 | 83.1 | 13.0 | Explosion | 1.12 |
| 24 | T11130707 | 40 | 1.015 | 41 | 842 | 132 | 4.0 | 83.0 | 13.0 | Explosion | 1.09 |
| 25 | T11130708 | 40 | 1.014 | 42 | 840 | 132 | 4.1 | 82.8 | 13.0 | Non-Explosion | 1.06 |
| 26 | T11130709 | 40 | 1.015 | 42 | 841 | 132 | 4.1 | 82.9 | 13.0 | Non-Explosion | 1.06 |
| 27 | T11130710 | 40 | 1.014 | 42 | 840 | 132 | 4.1 | 82.8 | 13.0 | Non-Explosion | 1.05 |
| 28 | T11130711 | 40 | 1.014 | 15 | 867 | 132 | 1.5 | 85.5 | 13.0 | Non-Explosion | 1.03 |
| 29 | T11130712 | 40 | 1.014 | 16 | 866 | 132 | 1.6 | 85.4 | 13.0 | Explosion | 4.81 |
| 30 | T11130713 | 40 | 1.014 | 15 | 867 | 132 | 1.5 | 85.5 | 13.0 | Explosion | 4 |
| 31 | T11130714 | 40 | 1.014 | 14 | 868 | 132 | 1.4 | 85.6 | 13.0 | Non-Explosion | 1.03 |
| 32 | T11130715 | 40 | 1.014 | 14 | 868 | 132 | 1.4 | 85.6 | 13.0 | Non-Explosion | <1.02 |
| 33 | T11130716 | 40 | 1.014 | 14 | 868 | 132 | 1.4 | 85.6 | 13.0 | Non-Explosion | 1.03 |
| 34 | T11130717 | 40 | 1.015 | 20 | 883 | 112 | 2.0 | 87.0 | 11.0 | Explosion | 1.7 |
| 35 | T11130718 | 40 | 1.014 | 28 | 874 | 112 | 2.8 | 86.2 | 11.0 | Non-Explosion | 1.08 |
| 36 | T11130719 | 40 | 1.014 | 28 | 874 | 112 | 2.8 | 86.2 | 11.0 | Non-Explosion | 1.08 |
| 37 | T11130720 | 40 | 1.014 | 28 | 874 | 112 | 2.8 | 86.2 | 11.0 | Explosion | 1.13 |
| 38 | T11130721 | 40 | 1.015 | 28 | 874 | 112 | 2.9 | 86.1 | 11.0 | Non-Explosion | 1.08 |
| 39 | T11130722 | 40 | 1.014 | 29 | 873 | 112 | 2.9 | 86.1 | 11.0 | Explosion | 1.1 |

Figure 80B

| Test | Data File Name | Temp °C | Initial Pressure bara | Partial Pressures | | | Concentrations | | | Result | Pex bara |
|---|---|---|---|---|---|---|---|---|---|---|---|
| | | | | $C_3H_8$ mbar | $N_2$ mbar | $O_2$ mbar | $C_3H_8$ vol. % | $N_2$ vol. % | $O_2$ vol. % | | |
| 40 | T11130723 | 40 | 1.014 | 30 | 872 | 112 | 3.0 | 86.0 | 11.0 | Non-Explosion | 1.06 |
| 41 | T11130724 | 40 | 1.014 | 30 | 872 | 112 | 3.0 | 86.0 | 11.0 | Non-Explosion | 1.05 |
| 42 | T11130725 | 40 | 1.014 | 30 | 872 | 112 | 3.0 | 86.0 | 11.0 | Non-Explosion | 1.05 |
| 43 | T11130726 | 40 | 1.014 | 15 | 887 | 112 | 1.5 | 87.5 | 11.0 | Non-Explosion | <1.02 |
| 44 | T11130727 | 40 | 1.014 | 15 | 887 | 112 | 1.5 | 87.5 | 11.0 | Non-Explosion | <1.02 |
| 45 | T11140700 | 40 | 1.014 | 16 | 886 | 112 | 1.6 | 87.4 | 11.0 | Non-Explosion | <1.02 |
| 46 | T11140701 | 40 | 1.014 | 17 | 885 | 112 | 1.7 | 87.3 | 11.0 | Explosion | 1.81 |
| 47 | T11140702 | 40 | 1.014 | 16 | 886 | 112 | 1.6 | 87.4 | 11.0 | Explosion | 1.54 |
| 48 | T11140703 | 40 | 1.014 | 15 | 887 | 112 | 1.5 | 87.5 | 11.0 | Non-Explosion | <1.02 |
| 49 | T11140704 | 40 | 1.015 | 20 | 899 | 96 | 2.0 | 88.6 | 9.5 | Non-Explosion | 1.05 |
| 50 | T11140705 | 40 | 1.014 | 20 | 898 | 96 | 2.0 | 88.6 | 9.5 | Non-Explosion | 1.05 |
| 51 | T11140706 | 40 | 1.014 | 23 | 890 | 101 | 2.3 | 87.8 | 10.0 | Non-Explosion | 1.05 |
| 52 | T11140707 | 40 | 1.015 | 23 | 886 | 106 | 2.3 | 87.3 | 10.4 | Explosion | 1.19 |
| 53 | T11140708 | 40 | 1.014 | 25 | 884 | 105 | 2.5 | 87.2 | 10.4 | Explosion | 1.09 |
| 54 | T11140709 | 40 | 1.014 | 26 | 883 | 105 | 2.6 | 87.1 | 10.4 | Non-Explosion | 1.05 |
| 55 | T11140710 | 40 | 1.014 | 26 | 883 | 105 | 2.6 | 87.1 | 10.4 | Non-Explosion | 1.06 |
| 56 | T11140711 | 40 | 1.014 | 26 | 883 | 105 | 2.6 | 87.1 | 10.4 | Non-Explosion | 1.07 |
| 57 | T11140712 | 40 | 1.014 | 20 | 889 | 105 | 2.0 | 87.7 | 10.4 | Explosion | 1.21 |
| 58 | T11140713 | 40 | 1.014 | 17 | 892 | 105 | 1.7 | 88.0 | 10.4 | Non-Explosion | 1.04 |
| 59 | T11140714 | 40 | 1.014 | 18 | 891 | 105 | 1.8 | 87.9 | 10.4 | Explosion | 1.21 |
| 60 | T11140715 | 40 | 1.014 | 17 | 892 | 105 | 1.7 | 88.0 | 10.4 | Non-Explosion | 1.03 |
| 61 | T11140716 | 40 | 1.014 | 17 | 892 | 105 | 1.7 | 88.0 | 10.4 | Non-Explosion | 1.03 |
| 62 | T11140717 | 40 | 1.014 | 21 | 890 | 103 | 2.1 | 87.8 | 10.2 | Explosion | 1.1 |
| 63 | T11140718 | 40 | 1.014 | 21 | 891 | 102 | 2.1 | 87.9 | 10.1 | Explosion | 1.09 |
| 64 | T11140719 | 40 | 1.014 | 21 | 892 | 101 | 2.1 | 88.0 | 10.0 | Explosion | 1.09 |
| 65 | T11140720 | 40 | 1.014 | 22 | 891 | 101 | 2.2 | 87.9 | 10.0 | Explosion | 1.1 |
| 66 | T11140721 | 40 | 1.014 | 23 | 890 | 101 | 2.3 | 87.8 | 10.0 | Non-Explosion | 1.08 |
| 67 | T11140722 | 40 | 1.014 | 23 | 890 | 101 | 2.3 | 87.8 | 10.0 | Non-Explosion | 1.08 |
| 68 | T11140723 | 40 | 1.014 | 19 | 894 | 101 | 1.9 | 88.2 | 10.0 | Explosion | 1.12 |
| 69 | T11140724 | 40 | 1.014 | 18 | 895 | 101 | 1.8 | 88.3 | 10.0 | Non-Explosion | 1.06 |
| 70 | T11140725 | 40 | 1.014 | 18 | 895 | 101 | 1.8 | 88.3 | 10.0 | Non-Explosion | 1.03 |
| 71 | T11140726 | 40 | 1.014 | 18 | 895 | 101 | 1.8 | 88.3 | 10.0 | Non-Explosion | 1.04 |
| 72 | T11140727 | 40 | 1.014 | 20 | 895 | 99 | 2.0 | 88.3 | 9.8 | Non-Explosion | 1.08 |
| 73 | T11140728 | 40 | 1.014 | 20 | 895 | 99 | 2.0 | 88.3 | 9.8 | Explosion | 1.1 |
| 74 | T11140729 | 40 | 1.014 | 20 | 896 | 98 | 2.0 | 88.4 | 9.7 | Non-Explosion | 1.06 |
| 75 | T11140730 | 40 | 1.014 | 20 | 896 | 98 | 2.0 | 88.4 | 9.7 | Non-Explosion | 1.06 |
| 76 | T11140731 | 40 | 1.014 | 20 | 896 | 98 | 2.0 | 88.4 | 9.7 | Non-Explosion | 1.07 |
| 77 | T11140732 | 40 | 1.014 | 81 | 761 | 172 | 8.0 | 75.0 | 17.0 | Non-Explosion | 1.04 |
| 78 | T11140733 | 40 | 1.014 | 81 | 750 | 183 | 8.0 | 74.0 | 18.0 | Explosion | 1.3 |
| 79 | T11140734 | 40 | 1.014 | 81 | 754 | 179 | 8.0 | 74.4 | 17.7 | Explosion | 1.24 |
| 80 | T11140735 | 40 | 1.014 | 81 | 757 | 176 | 8.0 | 74.7 | 17.4 | Non-Explosion | 1.03 |
| 81 | T11140736 | 40 | 1.014 | 81 | 755 | 178 | 8.0 | 74.5 | 17.6 | Non-Explosion | 1.05 |
| 82 | T11140737 | 40 | 1.014 | 81 | 755 | 178 | 8.0 | 74.5 | 17.6 | Non-Explosion | 1.03 |
| 83 | T11140738 | 40 | 1.014 | 81 | 755 | 178 | 8.0 | 74.5 | 17.6 | Non-Explosion | 1.03 |

Figure 81

TEST SERIES 2

| Test | Data File Name | Temp °C | Initial Pressure bara | Partial Pressures | | | | Concentrations | | | | Result | Pex bara |
|---|---|---|---|---|---|---|---|---|---|---|---|---|---|
| | | | | H₂O mbar | C₃H₈ mbar | N₂ mbar | O₂ mbar | H₂O vol.% | C₃H₈ vol.% | N₂ vol.% | O₂ vol.% | | |
| 1 | T11150700 | 40 | 1.014 | 41 | 119 | 641 | 213 | 4.0 | 11.7 | 63.2 | 21.0 | Explosion | 1.33 |
| 2 | T11150701 | 40 | 1.014 | 40 | 121 | 640 | 213 | 3.9 | 11.9 | 63.1 | 21.0 | Non-explosion | 1.07 |
| 3 | T11150702 | 40 | 1.014 | 41 | 120 | 640 | 213 | 4.0 | 11.8 | 63.1 | 21.0 | Explosion | 1.09 |
| 4 | T11150703 | 40 | 1.014 | 40 | 121 | 640 | 213 | 3.9 | 11.9 | 63.1 | 21.0 | Non-explosion | 1.06 |
| 5 | T11150704 | 40 | 1.014 | 40 | 120 | 641 | 213 | 3.9 | 11.8 | 63.2 | 21.0 | Explosion | 1.09 |
| 6 | T11150705 | 40 | 1.014 | 40 | 121 | 640 | 213 | 3.9 | 11.9 | 63.1 | 21.0 | Non-explosion | 1.08 |
| 7 | T11150706 | 40 | 1.014 | 40 | 15 | 746 | 213 | 3.9 | 1.5 | 73.6 | 21.0 | Explosion | 4.68 |
| 8 | T11150707 | 40 | 1.014 | 41 | 15 | 745 | 213 | 4.0 | 1.5 | 73.5 | 21.0 | Explosion | 5.27 |
| 9 | T11150708 | 40 | 1.014 | 41 | 14 | 746 | 213 | 4.0 | 1.4 | 73.6 | 21.0 | Non-explosion | 1.03 |
| 10 | T11150709 | 40 | 1.014 | 42 | 14 | 745 | 213 | 4.1 | 1.4 | 73.5 | 21.0 | Non-explosion | 1.03 |
| 11 | T11160700 | 40 | 1.014 | 41 | 14 | 746 | 213 | 4.0 | 1.4 | 73.6 | 21.0 | Non-explosion | 1.03 |
| 12 | T11160701 | 40 | 1.014 | 41 | 20 | 850 | 103 | 4.0 | 2.0 | 83.8 | 10.2 | Explosion | 1.11 |
| 13 | T11160702 | 40 | 1.014 | 41 | 20 | 851 | 102 | 4.0 | 2.0 | 83.9 | 10.1 | Explosion | 1.11 |
| 14 | T11160703 | 40 | 1.014 | 41 | 20 | 852 | 101 | 4.0 | 2.0 | 84.0 | 10.0 | Explosion | 1.09 |
| 15 | T11160704 | 40 | 1.014 | 41 | 20 | 853 | 100 | 4.0 | 2.0 | 84.1 | 9.9 | Explosion | 1.09 |
| 16 | T11160705 | 40 | 1.014 | 41 | 20 | 854 | 99 | 4.0 | 2.0 | 84.2 | 9.8 | Non-explosion | 1.07 |
| 17 | T11160706 | 40 | 1.014 | 40 | 20 | 855 | 99 | 3.9 | 2.0 | 84.3 | 9.8 | Non-explosion | 1.06 |
| 18 | T11160707 | 40 | 1.014 | 41 | 20 | 854 | 99 | 4.0 | 2.0 | 84.2 | 9.8 | Non-explosion | 1.08 |

2-methyl-1,3-butadiene standard.

2-methyl-1,3-butadiene from recombinant E. coli

Figure 90
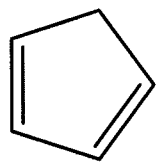
cyclopentadiene
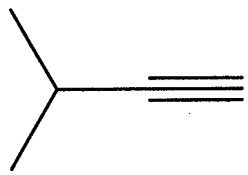
"isopryne" = 3-Me-1-butyne
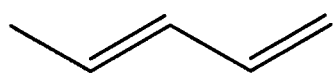
trans-piperylene
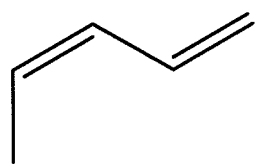
cis-piperylene
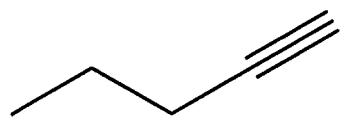
1-pentyne
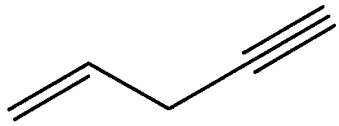
pent-4-ene-1-yne
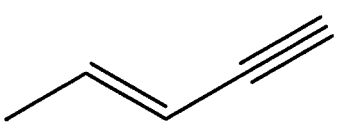
trans-pent-3-ene-1-yne
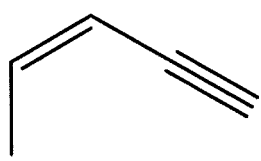
cis-pent-3-ene-1-yne

Figure 92A 1-
gtttgacagcttatcatcgactgcacggtgcaccaatgcttctggcgtcaggcagccatcggaagctgtggtatggctgtgcaggtc
gtaaatcactgcataattcgtgtcgctcaaggcgcactcccgttctggataatgttttttgcgccgacatcataacggttctggcaaata
ttctgaaatgagctgttgacaattaatcatccggctcgtataatgtgtggaattgtgagcggataacaatttcacacaggaaacagcg
ccgctgagaaaaagcgaagcggcactgctctttaacaatttatcagacaatctgtgtgggcactcgaccggaattatcgattaacttt
attattaaaaattaaagaggtatatattaatgtatcgattaaataaggaggaataaaccatggatccgagctcaggaggtaaaaaa
acatgaaaacagtagttattattgatgcattacgaacaccaattggaaaatataaaggcagcttaagtcaagtaagtgccgtagact
taggaacacatgttacaacacaacttttaaaaagacattccactatttctgaagaaattgatcaagtaatctttggaaatgttttacaag
ctggaaatggccaaaatcccgcacgacaaatagcaataaacagcggtttgtctcatgaaattcccgcaatgacggttaatgaggt
ctgcggatcaggaatgaaggccgttattttggcgaaacaattgattcaattaggagaagcggaagttttaattgctggcgggattga
gaatatgtcccaagcacctaaattacaacgttttaattacgaaacagaaagctacgatgcgcctttttctagtatgatgtatgatggatt
aacggatgcctttagtggtcaggcaatgggcttaactgctgaaaatgtggccgaaaagtatcatgtaactagagaagagcaagat
caattttctgtacattcacaattaaaagcagctcaagcacaagcagaagggatattcgctgacgaaatagcccattagaagtatc
aggaacgcttgtggagaaagatgaagggattcgccctaattcgagcgttgagaagctaggaacgcttaaaacagttttaaagaa
gacggtactgtaacagcagggaatgcatcaaccattaatgatggggcttctgctttgattattgcttcacaagaatatgccgaagca
cacggtcttcctatttagctattattcgagacagtgtggaagtcggtattgatccagcctatatgggaatttcgccgattaaagccattc
aaaaactgttagcgcgcaatcaacttactacggaagaaattgatctgtatgaaatcaacgaagcatttgcagcaacttcaatcgtg
gtccaaagagaactggctttaccagaggaaaaggtcaacatttatggtggcggtatttcattaggtcatgcgattggtgccacaggt
gctcgtttattaacgagtttaagttatcaattaaatcaaaaagaaaagaaatatggagtggcttctttatgtatcggcggtggcttagga
ctcgctatgctactagagagacctcagcaaaaaaaaacagccgatttatcaaatgagtcctgaggaacgcctggcttctcttctt
aatgaaggccagatttctgctgatacaaaaaaagaatttgaaaatacggctttatcttcgcagattgccaatcatatgattgaaaatc
aaatcagtgaaacagaagtgccgatgggcgttggcttacatttaacagtggacgaaactgattatttggtaccaatggcgacagaa
gagccctcagttattgcggctttgagtaatggtgcaaaaatagcacaaggatttaaaacagtgaatcaacaacgcttaatgcgtgg
acaaatcgttttttacgatgttgcagatcccgagtcattgattgataaactacaagtaagagaagcggaagtttttcaacaagcagag
ttaagttatccatctatcgttaaacggggcggcggcttaagagatttgcaatatcgtacttttgatgaatcatttgtatctgtcgactttttag
tagatgttaaggatgcaatgggggcaaatatcgttaacgctatgttggaaggtgtggccgagttgttccgtgaatggtttgcggagca
aaagattttattcagtattttaagtaattatgccacggagtcggttgttacgatgaaaacggctattccagtttcacgtttaagtaagggg
agcaatggccgggaaattgctgaaaaaattgtttagcttcacgctatgcttcattagatccttatcgggcagtcacgcataacaaag
gaatcatgaatggcattgaagctgtagttttagctacaggaaatgatacacgcgctgttagcgcttcttgtcatgcttttgcggtgaagg
aaggtcgctaccaaggcttgactagttggacgctggatggcgaacaactaattggtgaaatttcagttccgcttgctttagccacggtt
ggcggtgccacaaaagtcttacctaaatctcaagcagctgctgatttgttagcagtgacggatgcaaaagaactaagtcgagtagt
agcggctgttggtttggcacaaaatttagcggcgttacgggccttagtctctgaaggaattcaaaaaggacacatggctctacaag
cacgttctttagcgatgacggtcggagctactggtaaagaagttgaggcagtcgctcaacaattaaaacgtcaaaaaacgatgaa
ccaagaccgagccatggctatttaaatgatttaagaaaacaataaggaggtaaaaaaacatgacaattgggattgataaaatt
agtttttttgtgccccttattatattgatatgacggcactggctgaagccagaaatgtagaccctggaaaatttcatattggtattgggc
aagaccaaatggcggtgaacccaatcagccaagatattgtgacatttgcagccaatgccgcagaagcgatcttgaccaaagaa
gataaagaggccattgatatggtgattgtcgggactgagtccagtatcgatgagtcaaaagcggccgcagttgtcttacatcgtttaa
tggggattcaaccttcgctcgctctttcgaaatcaaggaagcttgttacggagcaacagcaggcttacagttagctaagaatcacgt
agcttacatccagataaaaaagtcttggtcgtagcggcagatattgcaaaatatggcttaaattctggcggtgagcctacacaag
gagctggggcggttgcaatgttagttgctagtgaaccgcgcatttggctttaaaagaggataatgtgatgctgacgcaagatatctat
gacttttggcgtccaacaggccacccgtatcctatggtcgatggtcctttgtcaaacgaaacctacatccaatcttttgcccaagtctg
ggatgaacataaaaaacgaaccggtcttgattttgcagattatgatgcttagcgttccatattccttacacaaaaatgggcaaaaaa
gccttattagcaaaaatctccgaccaaactgaagcagaacaggaacgaattttagcccgttatgaagaaagtatcgtctatagtcg
tcgcgtaggaaacttgtatacgggttcactttatctgggactcatttcccttttagaaaatgcaacgactttaaccgcaggcaatcaaat
tggtttattcagttatggttctggtgctgtcgctgaatttttcactggtgaattag

Figure 92B tagctggttatcaaaatcatttacaaaaagaaactcatttagcactgctggataatcggacagaactttctatcgctgaatatga
agccatgtttgcagaaactttagacacagacattgatcaaacgttagaagatgaattaaaatatagtatttctgctattaataata
ccgttcgttcttatcgaaactaagagatctgcagctggtaccatatgggaattcgaagcttgggcccgaacaaaaactcatct
cagaagaggatctgaatagcgccgtcgaccatcatcatcatcatcattgagtttaaacggtctccagcttggctgtttggcgg
atgagagaagattttcagcctgatacagattaaatcagaacgcagaagcggtctgataaaacagaatttgcctggcggcag
tagcgcggtggtcccacctgaccccatgccgaactcagaagtgaaacgccgtagcgccgatggtagtgtggggtctcccc
atgcgagagtagggaactgccaggcatcaaataaaacgaaaggctcagtcgaaagactgggccttcgtttatctgttgttt
gtcggtgaacgctctcctgagtaggacaaatccgccgggagcggatttgaacgttgcgaagcaacggcccggagggtgg
cgggcaggacgcccgccataaactgccaggcatcaaattaagcagaaggccatcctgacggatggccttttgcgtttctac
aaactcttttgtttattttctaaatacattcaaatatgtatccgctcatgagacaataaccctgataaatgcttcaataatattgaa
aaaggaagagtatgagtattcaacatttccgtgtcgcccttattccttttttgcggcattttgccttcctgttttgctcacccagaaa
cgctggtgaaagtaaaagatgctgaagatcagttgggtgcacgagtgggttacatcgaactggatctcaacagcggtaaga
tccttgagagttttcgccccgaagaacgttttccaatgatgagcacttttaaagttctgctatgtggcgcggtattatcccgtgttga
cgccgggcaagagcaactcggtcgccgcatacactattctcagaatgacttggttgagtactcaccagtcacagaaaagca
tcttacgatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaacc
ggagctgaatgaagccataccaaacgacgagcgtgacaccacgatgcctgtagcaatggcaacaacgttgcgcaaact
attaactggcgaactacttactctagcttcccggcaacaattaatagactggatggaggcggataaagttgcaggaccacttc
tgcgctcggcccttccggctggctggtttattgctgataaatctggagccggtgagcgtgggtctcgcggtatcattgcagcact
ggggccagatggtaagccctcccgtatcgtagttatctacacgacggggagtcaggcaactatggatgaacgaaatagac
agatcgctgagataggtgcctcactgattaagcattggtaactgtcagaccaagtttactcatatatactttagattgatttaaaa
cttcattttaatttaaaaggatctaggtgaagatcctttttgataatctcatgaccaaaatcccttaacgtgagttttcgttccactga
gcgtcagacccccgtagaaaagatcaaaggatcttcttgagatcctttttttctgcgcgtaatctgctgcttgcaaacaaaaaaa
ccaccgctaccagcggtggtttgtttgccggatcaagagctaccaactctttttccgaaggtaactggcttcagcagagcgca
gataccaaatactgtccttctagtgtagccgtagttaggccaccacttcaagaactctgtagcaccgcctacatacctcgctctg
ctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatac
ctacagcgtgagctatgagaaagcgccacgcttcccgaagggagaaaggcggacaggtatccggtaagcggcagggtc
ggaacaggagagcgcacgagggagcttccagggggaaacgcctggtatctttatagtcctgtcgggtttcgccacctctga
cttgagcgtcgatttttgtgatgctcgtcaggggggcggagcctatggaaaaacgccagcaacgcggcctttttacggttcctg
gccttttgctggccttttgctcacatgttctttcctgcgttatccctgattctgtggataaccgtattaccgcctttgagtgagctgata
ccgctcgccgcagccgaacgaccgagcgcagcgagtcagtgagcgaggaagcggaagagcgcctgatgcggtattttct
ccttacgcatctgtgcggtatttcacaccgcatatggtgcactctcagtacaatctgctctgatgccgcatagttaagccagtata
cactccgctatcgctacgtgactgggtcatggctgcgccccgacacccgccaacacccgctgacgcgccctgacgggcttg
tctgctcccggcatccgcttacagacaagctgtgaccgtctccgggagctgcatgtgtcagaggttttcaccgtcatcaccgaa
acgcgcgaggcagcagatcaattcgcgcgcgaaggcgaagcggcatgcatttacgttgacaccatcgaatggtgcaaaa
cctttcgcggtatggcatgatagcgcccggaagagagtcaattcagggtggtgaatgtgaaaccagtaacgttatacgatgtc
gcagagtatgccggtgtctcttatcagaccgtttcccgcgtggtgaaccaggccagccacgtttctgcgaaaacgcgggaaa
aagtggaagcggcgatggcggagctgaattacattcccaaccgcgtggcacaacaactggcgggcaaacagtcgttgct
gattggcgttgccacctccagtctggccctgcacgcgccgtcgcaaattgtcgcggcgattaaatctcgcgccgatcaactgg
gtgccagcgtggtggtgtcgatggtagaacgaagcggcgtcgaagcctgtaaagcggcggtgcacaatcttctcgcgcaa
cgcgtcagtggctgatcattaactatccgctggatgaccaggatgccattgctgtggaagctgcctgcactaatgttccggcg
ttatttcttgatgtctctgaccagacacccatcaacagtattattttctcccatgaagacggtacgcgactgggcgtggagcatct
ggtcgcattgggtcaccagcaaatcgcgctgttagcgggcccattaagttctgtctcggcgcgtctgcgtctggctggctggca
taaatatctcactcgcaatcaaattcagccgatagcggaacggaaggcgactggagtgccatgtccggttttcaacaaac
catgcaaatgctgaatgagggcatcg

Figure 92C ttcccactgcgatgctggttgccaacgatcagatggcgctgggcgcaatgcgcgccattaccgagtccgggctgcgcgttg
gtgcggatatctcggtagtgggatacgacgataccgaagacagctcatgttatatcccgccgtcaaccaccatcaaacag
gattttcgcctgctggggcaaaccagcgtggaccgcttgctgcaactctctcagggccaggcggtgaagggcaatcagct
gttgcccgtctcactggtgaaaagaaaaaccaccctggcgcccaatacgcaaaccgcctctccccgcgcgttggccgatt
cattaatgcagctggcacgacaggtttcccgactggaaagcgggcagtgagcgcaacgcaattaatgtgagttagcgcg
aattgatctg (SEQ ID NO:86)

Figure 103A cccgtcttactgtcgggaattcgcgttggccgattcattaatgcagattctgaaatgagctgttgacaattaatcatccggctcgt
ataatgtgtggaattgtgagcggataacaatttcacacaggaaacagcgccgctgagaaaaagcgaagcggcactgctctt
taacaatttatcagacaatctgtgtgggcactcgaccggaattatcgattaactttattattaaaaattaaagaggtatatattaat
gtatcgattaaataaggaggaataaaccatggatccgagctcaggaggtaaaaaaacatgaaaacagtagttattattgat
gcattacgaacaccaattggaaaatataaaggcagcttaagtcaagtaagtgccgtagacttaggaacacatgttacaaca
caacttttaaaaagacattccactatttctgaagaaattgatcaagtaatctttggaaatgttttacaagctggaaatggccaaa
atcccgcacgacaaatagcaataaacagcggtttgtctcatgaaattcccgcaatgacggttaatgaggtctgcggatcagg
aatgaaggccgttattttggcgaaacaattgattcaattaggagaagcggaagttttaattgctggcgggattgagaatatgtc
ccaagcacctaaattacaacgttttaattacgaaacagaaagctacgatgcgccttttctagtatgatgtatgatggattaacg
gatgcctttagtggtcaggcaatgggcttaactgctgaaaatgtggccgaaaagtatcatgtaactagagaagagcaagatc
aattttctgtacattcacaattaaaagcagctcaagcacaagcagaagggatattcgctgacgaaatagccccattagaagt
atcaggaacgcttgtggagaaagatgaagggattcgccctaattcgagcgttgagaagctaggaacgcttaaaacagttttt
aaagaagacggtactgtaacagcagggaatgcatcaaccattaatgatggggcttctgctttgattattgcttcacaagaatat
gccgaagcacacggtcttccttatttagctattattcgagacagtgtggaagtcggtattgatccagcctatatgggaatttcgcc
gattaaagccattcaaaaaactgttagcgcgcaatcaacttactacggaagaaattgatctgtatgaaatcaacgaagcatttg
cagcaacttcaatcgtggtccaaagagaactggctttaccagaggaaaaggtcaacatttatggtggcggtatttcattaggtc
atgcgattggtgccacaggtgctcgtttattaacgagtttaagttatcaattaaatcaaaaagaaaagaaatatggagtggcttc
tttatgtatcggcggtggcttaggactcgctatgctactagagagacctcagcaaaaaaaaaacagccgattttatcaaatga
gtcctgaggaacgcctggcttctcttcttaatgaaggccagatttctgctgatacaaaaaaagaatttgaaaatacggctttatct
tcgcagattgccaatcatatgattgaaaatcaaatcagtgaaacagaagtgccgatgggcgttggcttacatttaacagtgga
cgaaactgattatttggtaccaatggcgacagaagagccctcagttattgcggctttgagtaatggtgcaaaaatagcacaa
ggatttaaaacagtgaatcaacaacgcttaatgcgtggacaaatcgtttttacgatgttgcagatcccgagtcattgattgata
aactacaagtaagagaagcggaagttttttcaacaagcagagttaagttatccatctatcgttaaacggggcggcggcttaag
agatttgcaatatcgtactttgatgaatcatttgtatctgtcgactttttagtagatgttaaggatgcaatgggggcaaatatcgtta
acgctatgttggaaggtgtggccgagttgttccgtgaatggtttgcggagcaaaaagattttattcagtattttaagtaattatgcca
cggagtcggttgttacgatgaaaacggctattccagtttcacgtttaagtaaggggagcaatggccgggaaattgctgaaaa
aattgttttagcttcacgctatgcttcattagatcctatcgggcagtcacgcataacaaaggaatcatgaatggcattgaagctg
tagttttagctacaggaaatgatacacgcgctgttagcgcttcttgtcatgcttttgcggtgaaggaaggtcgctaccaaggcttg
actagttggacgctggatggcgaacaactaattggtgaaatttcagttccgcttgcttagccacggttggcggtgccacaaaa
gtcttacctaaatctcaagcagctgctgatttgttagcagtgacggatgcaaaagaactaagtcgagtagtagcggctgttggt
ttggcacaaaatttagcggcgttacgggccttagtctctgaaggaattcaadaaggacacatggctctacaagcacgttcttta
gcgatgacggtcggagctactggtaaagaagttgaggcagtcgctcaacaattaaaacgtcaaaaaacgatgaaccaag
accgagccatggctatttaaatgatttaagaaaacaataaaggaggtaaaaaaacatgacaattgggattgataaaattag
ttttttttgtgccccccttattatattgatatgacggcactggctgaagccagaaatgtagaccctggaaaatttcatattggtattggg
caagaccaaatggcggtgaacccaatcagccaagatattgtgacatttgcagccaatgccgcagaagcgatcttgaccaa
agaagataaagaggccattgatatggtgattgtcgggactgagtccagtatcgatgagtcaaaagcggccgcagttgtctta
catcgtttaatggggattcaacctttcgctcgctctttcgaaatcaaggaagcttgttacggagcaacagcaggcttacagttag
ctaagaatacgctagccttacatccagataaaaaagtcttggtcgtagcggcagatattgcaaaatatggcttaaattctggcg
gtgagcctacacaaggagctggggcggttgcaatgttagttgctagtgaaccgcgcattttggctttaaaagaggataatgtg
atgctgacgcaagatatctatgactttggcgtccaacaggccacccgtatcctatggtcgatggtcctttgtcaaacgaaacct
acatccaatcttttgcccaagtctgggatgaacataaaaaacgaaccggtcttgattttgcagattatgatgctttagcgttccat
attccttacacaaaaatgggcaaaaaagccttattagcaaaaatctccgaccaaactgaagcagaacaggaacgaatttta
gcccgttatgaagaaagtatcgtctatagtcgtcgcgtaggaaacttgtatacggggttcactttatctgggactcatttcccttttag
aaaatgcaacgactttaaccgcaggcaatcaaattggtttattcagttatggttctggtgctgtcgctgaattttcactggtgaatt
agtagctggttatcaaaatcatttacaaaaagaaactcatttagcactgctggataatcggacagaactttctatcgctgaatat
gaagccatgtttgcagaaactttagacacagacattgatcaaacgtta

Figure 103B gaagatgaattaaaatatagtatttctgctattaataataccgttcgttcttatcgaaactaaagatctgcatcctgcattcgccct
taggaggtaaaaaaacatgtgtgcgacctcttctcaatttactcagattaccgagcataattcccgtcgttccgcaaactatc
agccaaacctgtggaatttcgaattcctgcaatccctggagaacgacctgaaagtggaaaagctggaggagaaagcga
ccaaactggaggaagaagttcgctgcatgatcaaccgtgtagacacccagccgctgtccctgctggagctgatcgacgat
gtgcagcgcctgggtctgacctacaaatttgaaaaagacatcattaaagccctggaaaacatcgtactgctggacgaaaa
caaaaagaacaaatctgacctgcacgcaaccgctctgtcttccgtctgctgcgtcagcacggtttcgaggtttctcaggatg
tttttgagcgtttcaaggataaagaaggtggtttcagcggtgaactgaaaggtgacgtccaaggcctgctgagcctgtatga
agcgtcttacctgggtttcgagggtgagaacctgctggaggaggcgcgtaccttttccatcacccacctgaagaacaacct
gaaagaaggcattaataccaaggttgcagaacaagtgagccacgccctggaactgccatatcaccagcgtctgcaccg
tctggaggcacgttggttcctggataaatacgaaccgaaagaaccgcatcaccagctgctgctggagctggcgaagctg
gattttaacatggtacagaccctgcaccagaaagagctgcaagatctgtcccgctggtggaccgagatgggcctggctag
caaactggattttgtacgcgaccgcctgatggaagtttatttctgggcactgggtatggcgccagacccgcagtttggtgaat
gtcgcaaagctgttactaaaatgtttggtctggtgacgatcatcgatgacgtgtatgacgtttatggcactctggacgaactgc
aactgttcaccgatgctgtagagcgctgggacgttaacgctattaacaccctgccggactatatgaaactgtgtttcctggca
ctgtacaacaccgttaacgacacgtcctattctattctgaaagagaaaggtcataacaacctgtcctatctgacgaaaagct
ggcgtgaactgtgcaaagcctttctgcaagaggcgaaatggtccaacaacaaaattatcccggctttctccaagtacctgg
aaaacgccagcgtttcctcctccggtgtagcgctgctggcgccgtcttacttttccgtatgccagcagcaggaagacatctcc
gaccacgcgctgcgttccctgaccgacttccatggtctggtgcgttctagctgcgttatcttccgcctgtgcaacgatctggcc
acctctgcggcggagctggaacgtggcgagactaccaattctatcattagctacatgcacgaaaacgatggtaccagcg
aggaacaggcccgcgaagaactgcgtaaactgatcgacgccgaatggaaaaagatgaatcgtgaacgcgttagcgac
tccaccctgctgcctaaagcgttcatggaaatcgcagttaacatggcacgtgtttcccactgcacctaccagtatggcgatg
gtctgggtcgcccagactacgcgactgaaaaccgcatcaaactgctgctgattgaccctttcccgattaaccagctgatgta
tgtctaactgcagctggtaccatatgggaattcgaagcttgggcccgaacaaaaactcatctcagaagaggatctgaatag
cgccgtcgaccatcatcatcatcatcattgagtttaaacggtctccagcttggctgttttggcggatgagagaagattttcagc
ctgatacagattaaatcagaacgcagaagcggtctgataaaacagaatttgcctggcggcagtagcgcggtggtcccac
ctgaccccatgccgaactcagaagtgaaacgccgtagcgccgatggtagtgtggggtctccccatgcgagagtaggga
actgccaggcatcaaataaaacgaaaggctcagtcgaaagactgggcctttcgttttatctgttgtttgtcggtgaacgctctc
ctgagtaggacaaatccgccgggagcggatttgaacgttgcgaagcaacggcccggagggtggcgggcaggacgcc
cgccataaactgccaggcatcaaattaagcagaaggccatcctgacggatggcctttttgcgtttctacaaactctttttgttta
ttttctaaatacattcaaatatgtatccgctcatgagacaataaccctgataaatgcttcaataatctggcgtaatagcgaag
aggcccgcaccgatcgcccttcccaacagttgcgcagcctgaatggcgaatggcgcctgatgcggtattttctccttacgca
tctgtgcggtatttcacaccgcatatggtgcactctcagtacaatctgctctgatgccgcatagttaagccagccccgacacc
cgccaacacccgctgacgagcttagtaaagccctcgctagattttaatgcggatgttgcgattacttcgccaactattgcgat
aacaagaaaaagccagcctttcatgatatatctcccaatttgtgtagggcttattatgcacgcttaaaaataataaaagcag
acttgacctgatagtttggctgtgagcaattatgtgcttagtgcatctaacgcttgagttaagccgcgccgcgaagcggcgtc
ggcttaacgaattgttagacattatttgccgactaccttggtgatctcgcctttcacgtagtggacaaattcttccaactgatct
gcgcgcgaggccaagcgatcttcttcttgtccaagataagcctgtctagcttcaagtatgacgggctgatactgggccggc
aggcgctccattgcccagtcggcagcgacatccttcggcgcgattttgccggttactgcgctgtaccaaatgcgggacaac
gtaagcactacatttcgctcatcgccagcccagtcgggcggcgagttccatagcgttaaggtttcatttagcgcctcaaatag
atcctgttcaggaaccggatcaaagagttcctccgccgctggacctaccaaggcaacgctatgttctcttgcttttgtcagca
agatagccagatcaatgtcgatcgtggctggctcgaagatacctgcaagaatgtcattgcgctgccattctccaaattgcag
ttcgcgcttagctggataacgccacggaatgatgtcgtcgtgcacaacaatggtgacttctacagcgcggagaatctcgct
ctctccaggggaagccgaagtttccaaaaggtcgttgatcaaagctcgccgcgttgtttcatcaagccttacggtcaccgta
accagcaaatcaatatcactgtgtggcttcaggccgccatccactgcggagccgtacaaatgtacggccagcaacgtcg
gttcgagatggcgctcgatgacgccaactacctctgatagttgagtcgatacttcggcgatcaccgcttccctcatgatgttta
actttgtttagggcgactgccctgctgcgtaacatcgttgctgctccataacatcaaacatcgacccacggcgtaacgcgct
tgctgcttggat

Figure 103C gcccgaggcatagactgtaccccaaaaaaacagtcataacaagccatgaaaaccgccactgcgccgttacca
ccgctgcgttcggtcaaggttctggaccagttgcgtgagcgcatacgctacttgcattacagcttacgaaccgaaca
ggcttatgtccactgggttcgtgccttcatccgtttccacggtgtgcgtcacccggcaaccttgggcagcagcgaagt
cgaggcatttctgtcctggctggcgaacgagcgcaaggtttcggtctccacgcatcgtcaggcattggcggccttgc
tgttcttctacggcaaggtgctgtgcacggatctgccctggcttcaggagatcggaagacctcggccgtcgcggcg
cttgccggtggtgctgaccccggatgaagtggttcgcatcctcggttttctggaaggcgagcatcgtttgttcgcccag
cttctgtatggaacgggcatgcggatcagtgagggtttgcaactgcgggtcaaggatctggatttcgatcacggcac
gatcatcgtgcgggagggcaagggctccaaggatcgggccttgatgttacccgagagcttggcacccagcctgc
gcgagcaggggaattaattcccacgggttttgctgcccgcaaacgggctgttctggtgttgctagtttgttatcagaat
cgcagatccggcttcagccggtttgccggctgaaagcgctatttcttccagaattgccatgatttttccccacgggag
gcgtcactggctcccgtgttgtcggcagctttgattcgataagcagcatcgcctgtttcaggctgtctatgtgtgactgtt
gagctgtaacaagttgtctcaggtgttcaatttcatgttctagttgctttgttttactggtttcacctgttctattaggtgttaca
tgctgttcatctgttacattgtcgatctgttcatggtgaacagctttgaatgcaccaaaaactcgtaaaagctctgatgta
tctatctttttacaccgttttcatctgtgcatatggacagttttccctttgatatgtaacggtgaacagttgttctactttgtttg
ttagtcttgatgcttcactgatagatacaagagccataagaacctcagatccttccgtatttagccagtatgttctctagt
gtggttcgttgttttttgcgtgagccatgagaacgaaccattgagatcatacttactttgcatgtcactcaaaaattttgcct
caaaactggtgagctgaattttttgcagttaaagcatcgtgtagtgtttttcttagtccgttatgtaggtaggaatctgatgt
aatggttgttggtattttgtcaccattcattttatctggttgttctcaagttcggttacgagatccatttgtctatctagttcaa
cttggaaaatcaacgtatcagtcgggcggcctcgcttatcaaccaccaatttcatattgctgtaagtgtttaaatcttta
cttattggtttcaaaacccattggttaagccttttaaactcatggtagttatttcaagcattaacatgaacttaaattcatc
aaggctaatctctatatttgccttgtgagttttcttttgtgttagttcttttaataaccactcataaatcctcatagagtatttgtt
ttcaaaagacttaacatgttccagattatatttttatgaattttttttaactggaaaagataaggcaatatctcttcactaaaa
actaattctaattttttcgcttgagaacttggcatagtttgtccactggaaaatctcaaagcctttaaccaaaggattcctg
atttccacagttctcgtcatcagctctctggttgctttagctaatacaccataagcattttccctactgatgttcatcatctg
agcgtattggtataagtgaacgataccgtccgttctttccttgtagggttttcaatcgtgggggttgagtagtgccacac
agcataaaattagcttggtttcatgctccgttaagtcatagcgactaatcgctagttcatttgctttgaaaacaactaatt
cagacatacatctcaattggtctaggtgattttaatcactataccaattgagatgggctagtcaatgataattactagtc
cttttcctttgagttgtgggtatctgtaaattctgctagacctttgctggaaaacttgtaaattctgctagaccctctgtaaat
tccgctagacctttgtgtgttttttttgtttatattcaagtggttataatttatagaataaagaaagaataaaaaaagataa
aaagaatagatcccagccctgtgtataactcactacttagtcagttccgcagtattacaaaaggatgtcgcaaacg
ctgtttgctcctctacaaaacagaccttaaaaccctaaaggcttaagtagcaccctcgcaagctcgggcaaatcgc
tgaatattccttttgtctccgaccatcaggcacctgagtcgctgtcttttcgtgacattcagttcgctgcgctcacggctc
tggcagtgaatgggggtaaatggcactacaggcgcctttatggattcatgcaaggaaactacccataatacaag
aaaagcccgtcacgggcttctcagggcgttttatggcgggtctgctatgtggtgctatctgacttttgctgttcagcagt
tcctgccctctgattttccagtctgaccacttcggattatcccgtgacaggtcattcagactggctaatgcacccagta
aggcagcggtatcatcaacaggctta (SEQ ID NO:87)

Figure 108A 1-
caagaaaaatgccccgcttacgcagggcatccatttattactcaaccgtaaccgattttgccaggttacgcggctggtcaacg
tcggtgcctttgatcagcgcgacatggtaagccagcagctgcagcggaacggtgtagaagatcggtgcaatcacctcttcca
catgcggcatctcgatgatgtgcatgttatcgctacttacaaaacccgcatcctgatcggcgaagacatacaactgaccgcc
acgcgcgcgaacttcttcaatgttggatttcagtttttccagcaattcgttgttcggtgcaacaacaataaccggcatatcggcat
caattagcgccagcggaccgtgtttcagttcgccagcagcgtaggcttcagcgtgaatgtaagagatctctttcaacttcaatg
cgccttccagcgcgattgggtactgatcgccacggcccaggaacagcgcgtgatgtttgtcagagaaatcttctgccagcgc
ttcaatgcgtttgtcctgagacagcatctgctcaatacggctcggcagcgcctgcagaccatgcacgatgtcatgttcaatgga
ggcatccagaccttcaggcgagacagcttcgccaccagcatcaacagcacagttaactgagtggtgaatgctttagtggat
gccacgccgatttctgtacccgcgttggtcattagcgccagatcggattcgcgcaccagagaagaacccggaacgttacag
attgccagtgaaccaaggtaacccagctctttcgacagacgcaggccagccagggtatccgcggtttcgccagactgtgac
acgatcgcccttcccaacagttgcgcagcctatacgtacggcagtttaaggtttacacctataaaagagagagccgttatcgt
ctgtttgtggatgtacagagtgatattattgacacgccggggcgacggatggtgatcccccctggccagtgcacgtctgctgtca
gataaagtctcccgtgaactttacccggtggtgcatatcggggatgaaagctggcgcatgatgaccaccgatatggccagtg
tgccggtctccgttatcggggaagaagtggctgatctcagccaccgcgaaaatgacatcaaaaacgccattaacctgatgtt
ctggggaatataaatgtcaggcatgagattatcaaaaaggatcttcacctagatcctttcacgtagaaagccagtccgcaga
aacggtgctgaccccggatgaatgtcagctactgggctatctggacaagggaaaacgcaagcgcaaagagaaagcagg
tagcttgcagtgggcttacatggcgatagctagactgggcggttttatggacagcaagcgaaccggaattgccagctgggc
gccctctggtaaggttgggaagccctgcaaagtaaactggatggctttctcgccgccaaggatctgatggcgcaggggatc
aagctctgatcaagagacaggatgaggatcgtttcgcatgattgaacaagatggattgcacgcaggttctccggccgcttgg
gtggagaggctattcggctatgactgggcacaacagacaatcggctgctctgatgccgccgtgttccggctgtcagcgcagg
ggcgcccggttcttttttgtcaagaccgacctgtccggtgccctgaatgaactgcaagacgaggcagcgcggctatcgtggct
ggccacgacgggcgttccttgcgcagctgtgctcgacgttgtcactgaagcgggaagggactggctgctattgggcgaagt
gccggggcaggatctcctgtcatctcaccttgctcctgccgagaaagtatccatcatggctgatgcaatgcggcggctgcata
cgcttgatccggctacctgcccattcgaccaccaagcgaaacatcgcatcgagcgagcacgtactcggatggaagccggt
cttgtcgatcaggatgatctggacgaagagcatcaggggctcgcgccagccgaactgttcgccaggctcaaggcgagcat
gcccgacggcgaggatctcgtcgtgacccatggcgatgcctgcttgccgaatatcatggtggaaaatggccgcttttctggatt
catcgactgtggccggctgggtgtggcggaccgctatcaggacatagcgttggctacccgtgatattgctgaagagcttggc
ggcgaatgggctgaccgcttcctcgtgctttacggtatcgccgctcccgattcgcagcgcatcgccttctatcgccttcttgacg
agttcttctgaattattaacgcttacaatttcctgatgcggtattttctccttacgcatctgtgcggtatttcacaccgcatacaggtg
gcacttttcggggaaatgtgcgcggaaccccctatttgtttatttttctaaatacattcaaatatgtatccgctcatgagacaataac
cctgataaatgcttcaataatagcacgtgaggagggccaccatggccaagttgaccagtgccgttccggtgctcaccgcgc
gcgacgtcgccggagcggtcgagttctggaccgaccggctcgggttctcccctagtaacggccgccagtgtgctggaattc
aggcagttcaacctgttgatagtacgtactaagctctcatgtttcacgtactaagctctcatgtttaacgtactaagctctcatgttt
aacgaactaaaccctcatggctaacgtactaagctctcatggctaacgtactaagctctcatgtttcacgtactaagctctcatg
tttgaacaataaaattaatataaatcagcaacttaaatagcctctaaggttttaagttttataagaaaaaaaagaatatataagg
cttttaaagcttttaaggtttaacggttgtggacaacaagccaggatgtaacgcactgagaagcccttagagcctctcaaag
caattttcagtgacacaggaacacttaacggctgacagcctgaattctgcagatatctgttttccactcttcgttcactttcgcca
ggtagctggtgaagacgaaggaagtcccggagccatctgcgcggcgtactacagcaatgttttgtgaaggcagtttcagac
ccggattcagtttggcgatggcttcatcatcccacttcttgattttgcccaggtagatgtcgccgagggttaccatccagcacc
agttcgccagacttcagccctggaatgttaaccgccagcaccacgccgccaatcacggtcgggaactggaacagaccttc
ctgagccagttttttcgtcagacagcggcgcgtcagaggcaccaaaatcaacggtattagcgataatctgttttacgccaccgg
aagaaccgatacccctggtagttaacttattaccggttctttctggtaagtgtcagcccatttggcatacaccggcgcagggaa
ggttgcacctgcacctgtcaggcttgcttctgcaaacacagagaaagcactcatcgataaggtcgcggcgacaacagttgc
gacggtggtacgcataactttcataatgtctcctgggaggattcataaagcattgttgttggctacgagaagcaaaataggac
aaacaggtgacagttatatgtaaggaatatgacagttttatgacagagagataaagtcttcagtctgatttaaataagcgttgat
attcagtcaattacaaacattaataacg

Figure 108B aagagatgacagaaaaattttcattctgtgacagagaaaaagtagccgaagatgacggtttgtcacatggagttggcagga
tgtttgattaaaagcaattaaccctcactaaagggcggccgcgaagttcctattctctagaaagtataggaacttcattctaccg
ggtaggggaggcgcttttcccaaggcagtctggagcatgcgctttagcagccccgctgggcacttggcgctacacaagtgg
cctctggcctcgcacacattccacatccaccggtaggcgccaaccggctccgttctttggtggcccctttcgcgccaccttccac
tcctcccctagtcaggaagttccccccccgccccgcagctcgcgtcgtgcaggacgtgacaaatggaagtagcacgtctcac
tagtctcgtgcagatggacagcaccgctgagcaatggaagcgggtaggcctttggggcagcggccaatagcagctttgctc
cttcgctttctgggctcagaggctgggaaggggtgggtccgggggcgggctcaggggcgggctcaggggcggggcgggc
gcccgaaggtcctccggaggcccggcattctgcacgcttcaaaagcgcacgtctgccgcgctgttctcctcttcctcatctccg
ggcctttcgacctgcagcagcacgtgttgacaattaatcatcggcatagtatatcggcatagtataatacgacaaggtgagga
actaaaccatggagaaaaaaatcactggatataccaccgttgatatatcccaatggcatcgtaaagaacattttgaggcattt
cagtcagttgctcaatgtacctataaccagaccgttcagctggatattacggccttttaaagaccgtaaagaaaaataagca
caagtttatccggcctttattcacattcttgcccgcctgatgaatgctcatccggaattccgtatggcaatgaaagacggtgagc
tggtgatatgggatagtgttcacccttgttacaccgttttccatgagcaaactgaaacgttttcatcgctctggagtgaataccac
gacgatttccggcagtttctacacatatattcgcaagatgtggcgtgttacggtgaaaacctggcctatttccctaaagggtttatt
gagaatatgttttcgtctcagccaatccctgggtgagtttcaccagttttgatttaaacgtggccaatatggacaacttcttcgcc
cccgttttcaccatgggcaaatattatacgcaaggcgacaaggtgctgatgccgctggcgattcaggttcatcatgccgtttgt
gatggcttccatgtcggcagaatgcttaatgaattacaacagtactgcgatgagtggcagggcggggcgtaagcgggactct
ggggttcgaataaagaccgaccaagcgacgtctgagagctccctggcgaattcggtaccaataaaagagctttatttcatg
atctgtgtgttggttttttgtgtgcggcgcggaagttcctattctctagaaagtataggaacttcctcgagcccctatagtgagtcgtatt
agcccttgacgatgccacatcctgagcaaataattcaaccactaattgtgagcggataacacaaggaggaaacagctatgt
cattaccgttcttaacttctgcaccgggaaaggttattattttttggtgaacactctgctgtgtacaacaagcctgccgtcgctgcta
gtgtgtctgcgttgagaacctacctgctaataagcgagtcatctgcaccagatactattgaattggacttcccggacattagcttt
aatcataagtggtccatcaatgatttcaatgccatcaccgaggatcaagtaaactcccaaaaattggccaaggctcaacaa
gccaccgatggcttgtctcaggaactcgttagtcttttggatccgttgttagctcaactatccgaatccttccactaccatgcagc
gttttgtttcctgtatatgtttgtttgcctatgcccccatgccaagaatattaagttttctttaaagtctactttacccatcggtgctgggtt
gggctcaagcgcctctatttctgtatcactggccttagctatggcctacttgggggggttaataggatctaatgacttggaaaag
ctgtcagaaaacgataagcatatagtgaatcaatgggccttcataggtgaaaagtgtattcacggtacccttcaggaatag
ataacgctgtggccacttatggtaatgccctgctatttgaaaaagactcacataatggaacaataaacacaaacaattttaagt
tcttagatgatttcccagccattccaatgatcctaacctatactagaattccaaggtctacaaaagatcttgttgctcgcgttcgtgt
gttggtcaccgagaaatttcctgaagttatgaagccaattctagatgccatgggtgaatgtgccctacaaggcttagagatcat
gactaagttaagtaaatgtaaaggcaccgatgacgaggctgtagaaactaataatgaactgtatgaacaactattggaattg
ataagaataaatcatggactgcttgtctcaatcggtgtttctcatcctggattagaacttattaaaaatctgagcgatgatttgaga
attggctccacaaaacttaccggtgctggtggcggcggttgctctttgactttgttacgaagagacattactcaagagcaaattg
acagcttcaaaaagaaattgcaagatgattttagttacgagacatttgaaacagacttgggtgggactggctgctgtttgttaag
cgcaaaaaatttgaataaagatcttaaaatcaaatccctagtattccaattatttgaaaataaaactaccacaaagcaacaa
attgacgatctattattgccaggaaacacgaatttaccatggacttcataagctaatttgcgataggcctgcacccttaaggag
gaaaaaaacatgtcagagttgagagccttcagtgccccagggaaagcgttactagctggtggatatttagtttagatacaaa
atatgaagcatttgtagtcggattatcggcaagaatgcatgctgtagcccatccttacggttcattgcaagggtctgataagtttg
aagtgcgtgtgaaaagtaaacaatttaaagatggggagtggctgtaccatataagtcctaaaagtggcttcattcctgtttcgat
aggcggatctaagaaccctttcattgaaaaagttatcgctaacgtatttagctactttaaacctaacatggacgactactgcaat
agaaacttgttcgttattgatattttctctgatgatgcctaccattctcaggaggatagcgttaccgaacatcgtggcaacagaag
attgagttttcattcgcacagaattgaagaagttcccaaaacagggctgggctcctcggcaggtttagtcacagttttaactaca
gctttggcctccttttttgtatcggacctggaaaataatgtagacaaatatagagaagttattcataatttagcacaagttgctcatt
gtcaagctcagggtaaaattggaagcgggtttgatgtagcggcggcagcatatggatctatcagatatagaagattcccacc
cgcattaatctctaatttgccagatattggaagtgctacttacggcagtaaactggcgcatttggttgatgaagaagactggaat
attacgattaaaagtaaccatttaccttc

Figure 108C gggattaactttatggatgggcgatattaagaatggttcagaaacagtaaaactggtccagaaggtaaaaaattggtatgatt
cgcatatgccagaaagcttgaaaatatatacagaactcgatcatgcaaattctagatttatggatggactatctaaactagatc
gcttacacgagactcatgacgattacagcgatcagatatttgagtctcttgagaggaatgactgtacctgtcaaaagtatcctg
aaatcacagaagttagagatgcagttgccacaattagacgttcctttagaaaaataactaaagaatctggtgccgatatcga
acctcccgtacaaactagcttattggatgattgccagaccttaaaaggagttcttacttgcttaatacctggtgctggtggttatga
cgccattgcagtgattactaagcaagatgttgatcttagggctcaaaccgctaatgacaaaagattttctaaggttcaatggctg
gatgtaactcaggctgactggggtgttaggaaagaaaaagatccggaaacttatcttgataaataacttaaggtagctgcatg
cagaattcgcccttaaggaggaaaaaaaaatgaccgtttacacagcatccgttaccgcacccgtcaacatcgcaaccctta
agtattggggggaaaagggacacgaagttgaatctgcccaccaattcgtccatatcagtgactttatcgcaagatgacctcag
aacgttgacctctgcggctactgcacctgagtttgaacgcgacactttgtggttaaatggagaaccacacagcatcgacaat
gaaagaactcaaaattgtctgcgcgacctacgccaattaagaaaggaaatggaatcgaaggacgcctcattgcccacatt
atctcaatggaaactccacattgtctccgaaataactttcctacagcagctggtttagcttcctccgctgctggctttgctgcatt
ggtctctgcaattgctaagttataccaattaccacagtcaacttcagaaatatctagaatagcaagaaaggggtctggttcagc
ttgtagatcgttgtttggcggatacgtggcctgggaaatgggaaaagctgaagatggtcatgattccatggcagtacaaatcg
cagacagctctgactggcctcagatgaaagcttgtgtcctagttgtcagcgatattaaaaaggatgtgagttccactcagggta
tgcaattgaccgtggcaacctccgaactatttaaagaaagaattgaacatgtcgtaccaaagagatttgaagtcatgcgtaa
agccattgttgaaaaagatttcgccacctttgcaaaggaaacaatgatggattccaactctttccatgccacatgtttggactctt
tccctccaatattctacatgaatgacacttccaagcgtatcatcagttggtgccacaccattaatcagttttacggagaaacaat
cgttgcatacacgtttgatgcaggtccaaatgctgtgttgtactacttagctgaaaatgagtcgaaactctttgcatttatctataaa
ttgtttggctctgttcctggatgggacaagaaatttactactgagcagcttgaggctttcaaccatcaatttgaatcatctaacttta
ctgcacgtgaattggatcttgagttgcaaaaggatgttgccagagtgattttaactcaagtcggttcaggcccacaagaaaca
aacgaatctttgattgacgcaaagactggtctaccaaaggaataagatcaattcgctgcatcgcccttaggaggtaaaaaaa
aatgactgccgacaacaatagtatgccccatggtgcagtatctagttacgccaaattagtgcaaaaccaaacacctgaaga
cattttggaagagtttcctgaaattattccattacaacaaagacctaatacccgatctagtgagacgtcaaatgacgaaagcg
gagaaacatgtttttctggtcatgatgaggagcaaattaagttaatgaatgaaaattgtattgtttggattgggacgataatgcta
ttggtgccggtaccaagaaagtttgtcatttaatggaaaatattgaaaagggtttactacatcgtgcattctccgtctttatttcaat
gaacaaggtgaattacttttacaacaaagagccactgaaaaaataactttccctgatctttggactaacacatgctgctctcat
ccactatgtattgatgacgaattaggtttgaagggtaagctagacgataagattaagggcgctattactgcggcggtgagaaa
actagatcatgaattaggtattccagaagatgaaactaagacaaggggtaagtttcacttttaaacagaatccattacatggc
accaagcaatgaaccatggggtgaacatgaaattgattacatcctattttataagatcaacgctaaagaaaacttgactgtca
acccaaacgtcaatgaagttagagacttcaaatgggtttcaccaaatgatttgaaaactatgtttgctgacccaagttacaagtt
tacgccttggtttaagattatttgcgagaattacttattcaactggtgggagcaattagatgacctttctgaagtggaaaatgaca
ggcaaattcatagaatgctataacaacgcgtctacaaataaaaaaggcacgtcagatgacgtgccttttttcttggggcc (SEQ ID NO:90)

Figure 110A 1-
gtgcggccgcaagcttgtcgacggagctcgaattcggatccctgcagttagacatacatcagctggttaatcgggaaagggtc
aatcagcagcagtttgatgcggttttcagtcgcgtagtctgggcgacccagaccatcgccatactggtaggtgcagtgggaaa
cacgtgccatgttaactgcgatttccatgaacgctttaggcagcagggtggagtcgctaacgcgttcacgattcatcttttccattc
ggcgtcgatcagtttacgcagttcttcgcgggcctgttcctcgctggtaccatcgttttcgtgcatgtagctaatgatagaattggta
gtctcgccacgttccagctccgccgcagaggtggccagatcgttgcacaggcggaagataacgcagctagaacgcaccag
accatggaagtcggtcagggaacgcagcgcgtggtcggagatgtcttcctgctgctggcatacggaaaagtaagacggcgc
cagcagcgctacaccggaggaggaaacgctggcgttttccaggtacttggagaaagccgggataattttgttgttggaccattt
cgcctcttgcagaaaggctttgcacagttcacgccagcttttcgtcagataggacaggttgttatgacctttctctttcagaatagaa
taggacgtgtcgttaacggtgttgtacagtgccaggaaacacagtttcatatagtccggcagggtgttaatagcgttaacgtccc
agcgctctacagcatcggtgaacagttcagttcgtccagagtgccataaacgtcatacacgtcatcgatgatcgtcaccaga
ccaaacattttagtaacagctttgcgacattcaccaaactgcgggtctggcgccatacccagtgcccagaaataaacttccatc
aggcggtcgcgtacaaaatccagtttgctagccaggcccatctcggtccaccagcgggacagatcttgcagctctttctggtgc
agggtctgtaccatgttaaaatccagcttcgccagctccagcagcagctggtgatgcggttctttcggttcgtatttatccaggaac
caacgtgcctccagacggtgcagacgctggtgatatggcagttccagggcgtggctcacttgttctgcaaccttggtattaatgc
cttctttcaggttgttcttcaggtgggtgatggaaaaggtacgcgcctcctccagcaggttctcaccctcgaaacccaggtaaga
cgcttcatacaggctcagcaggccttggacgtcacctttcagttcaccgctgaaaccaccttctttatccttgaaacgctcaaaaa
catcctgagaaacctcgaaaccgtgctgacgcagcagacggaaagacagagcggttgcgtgcaggtcagatttgttcttttgt
tttcgtccagcagtacgatgttttccagggctttaatgatgtcttttttcaaatttgtaggtcagacccaggcgctgcacatcgtcgatc
agctccagcagggacagcggctgggtgtctacacggttgatcatgcagcgaacttcttcctccagtttggtcgctttctcctccag
cttttccactttcaggtcgttctccagggattgcaggaattcgaaattccacaggtttggctgatagtttgcggaacgacgggaatt
atgctcggtaatctgagtaaattgagaagaggtcgcacacatggtatatctccttcttaaagttaaacaaaattatttctagaggg
gaattgttatccgctcacaattcccctatagtgagtcgtattaatttcgcgggatcgagatctcgatcctctacgccggacgcatcg
tggccggcatcaccggcgccacaggtgcggttgctggcgcctatatcgccgacatcaccgatggggaagatcgggctcgcc
acttcgggctcatgagcgcttgtttcggcgtgggtatggtggcaggccccgtggccgggggactgttgggcgccatctccttgca
tgcaccattccttgcggcggcggtgctcaacggcctcaacctactactgggctgcttcctaatgcaggagtcgcataagggag
agcgtcgagatcccggacaccatcgaatggcgcaaaaccttcgcggtatggcatgatagcgcccggaagagagtcaattc
agggtggtgaatgtgaaaccagtaacgttatacgatgtcgcagagtatgccggtgtctcttatcagaccgtttcccgcgtggtga
accaggccagccacgtttctgcgaaaacgcgggaaaaagtggaagcggcgatggcggagctgaattacattcccaaccgc
gtggcacaacaactggcgggcaaacagtcgttgctgattggcgttgccacctccagtctggccctgcacgcgccgtcgcaaat
tgtcgcggcgattaaatctcgcgccgatcaactgggtgccagcgtggtggtgtcgatggtagaacgaagcggcgtcgaagcc
tgtaaagcggcggtgcacaatcttctcgcgcaacgcgtcagtgggctgatcattaactatccgctggatgaccaggatgccatt
gctgtggaagctgcctgcactaatgttccggcgttatttcttgatgtctctgaccagacacccatcaacagtattatttctcccatga
agacggtacgcgactgggcgtggagcatctggtcgcattgggtcaccagcaaatcgcgctgttagcgggcccattaagttctgt
ctcggcgcgtctgcgtctggctggctggcataaatatctcactcgcaatcaaattcagccgatagcggaacgggaaggcgact
ggagtgccatgtccggttttcaacaaaccatgcaaatgctgaatgagggcatcgttcccactgcgatgctggttgccaacgatc
agatggcgctgggcgcaatgcgcgccattaccgagtccgggctgcgcgttggtgcggatatctcggtagtgggatacgacga
taccgaagacagctcatgttatatcccgccgttaaccaccatcaaacaggattttcgcctgctggggcaaaccagcgtggacc
gcttgctgcaactctctcagggccaggcggtgaagggcaatcagctgttgcccgtctcactggtgaaaagaaaaaccaccct
ggcgcccaatacgcaaaccgcctctccccgcgcgttggccgattcattaatgcagctggcacgacaggtttcccgactggaa
agcgggcagtgagcgcaacgcaattaatgtaagttagctcactcattaggcacccgggatctcgaccgatgcccttgagagcct
tcaacccagtcagctccttccggtgggcgcggggcatgactatcgtcgccgcacttatgactgtcttctttatcatgcaactcgtag
gacaggtgccggcagcgctctgggtcattttcggcgaggaccgctttcgctggagcgcgacgatgatcggcctgtcgcttgcg
gtattcggaatcttgcacgccctcgctcaagccttcgtcactggtcccgccaccaaacgtttcggcgagaagcaggccattatc
gccggcatggcggccccacgggtgcgcatgatcgtgctcctg

Figure 110B tcgttgaggacccggctaggctggcggggttgccttactggttagcagaatgaatcaccgatacgcgagcgaacgtgaagcgact
gctgctgcaaaacgtctgcgacctgagcaacaacatgaatggtcttcggtttccgtgtttcgtaaagtctggaaacgcggaagtcag
cgccctgcaccattatgttccggatctgcatcgcaggatgctgctggctaccctgtggaacacctacatctgtattaacgaagcgctg
gcattgaccctgagtgattttctctggtcccgccgcatccataccgccagttgtttaccctcacaacgttccagtaaccgggcatgttc
atcatcagtaacccgtatcgtgagcatcctctctcgtttcatcggtatcattaccccatgaacagaaatcccccttacacggaggca
tcagtgaccaaacaggaaaaaaccgcccttaacatggcccgctttatcagaagccagacattaacgcttctggagaaactcaac
gagctggacgcggatgaacaggcagacatctgtgaatcgcttcacgaccacgctgatgagctttaccgcagctgcctcgcgcgttt
cggtgatgacggtgaaaacctctgacacatgcagctcccggagacggtcacagcttgtctgtaagcggatgccgggagcagac
aagcccgtcagggcgcgtcagcgggtgttggcgggtgtcggggcgcagccatgacccagtcacgtagcgatagcggagtgtat
actggcttaactatgcggcatcagagcagattgtactgagagtgcaccatatatgcggtgtgaaataccgcacagatgcgtaagg
agaaaataccgcatcaggcgctcttccgcttcctcgctcactgactcgctgcgctcggtcgttcggctgcggcgagcggtatcagct
cactcaaaggcggtaatacggttatccacagaatcaggggataacgcaggaaagaacatgtgagcaaaaggccagcaaaag
gccaggaaccgtaaaaaggccgcgttgctggcgtttttccataggctccgcccccctgacgagcatcacaaaaatcgacgctca
agtcagaggtggcgaaacccgacaggactataaagataccaggcgtttccccctggaagctccctcgtgcgctctcctgttccga
ccctgccgcttaccggatacctgtccgcctttctcccttcgggaagcgtggcgctttctcatagctcacgctgtaggtatctcagttcggt
gtaggtcgttcgctccaagctgggctgtgtgcacgaaccccccgttcagcccgaccgctgcgccttatccggtaactatcgtcttgag
tccaacccggtaagacacgacttatcgccactggcagcagccactggtaacaggattagcagagcgaggtatgtaggcggtgct
acagagttcttgaagtggtggcctaactacggctacactagaaggacagtatttggtatctgcgctctgctgaagccagttaccttcg
gaaaaagagttggtagctcttgatccggcaaacaaaccaccgctggtagcggtggtttttttgtttgcaagcagcagattacgcgca
gaaaaaaaggatctcaagaagatcctttgatcttttctacggggtctgacgctcagtggaacgaaaactcacgttaagggattttggt
catgaacaataaaactgtctgcttacataaacagtaatacaagggggtgttatgagccatattcaacgggaaacgtcttgctctaggc
cgcgattaaattccaacatggatgctgatttatatgggtataaatgggctcgcgataatgtcgggcaatcaggtgcgacaatctatcg
attgtatgggaagcccgatgcgccagagttgtttctgaaacatggcaaaggtagcgttgccaatgatgttacagatgagatggtcag
actaaactggctgacggaatttatgcctcttccgaccatcaagcattttatccgtactcctgatgatgcatggttactcaccactgcgat
ccccgggaaaacagcattccaggtattagaagaatatcctgattcaggtgaaaatattgttgatgcgctggcagtgttcctgcgccg
gttgcattcgattcctgtttgtaattgtccttttaacagcgatcgcgtatttcgtctcgctcaggcgcaatcacgaatgaataacggttggt
tgatgcgagtgattttgatgacgagcgtaatggctggcctgttgaacaagtctggaaagaaatgcataaacttttgccattctcaccg
gattcagtcgtcactcatggtgatttctcacttgataaccttatttttgacgaggggaaattaataggttgtattgatgttggacgagtcgg
aatcgcagaccgataccaggatcttgccatcctatggaactgcctcggtgagttttctccttcattacagaaacggcttttcaaaaat
atggtattgataatcctgatatgaataaattgcagtttcatttgatgctcgatgagttttctaagaattaattcatgagcggatacatatttg
aatgtatttagaaaaataaacaaataggggttccgcgcacatttccccgaaaagtgccacctgaaattgtaaacgttaatattttgtta
aaattcgcgttaaattttgttaaatcagctcatttttaaccaataggccgaaatcggcaaaatcccttataaatcaaaagaatagac
cgagatagggttgagtgttgttccagtttggaacaagagtccactattaaagaacgtggactccaacgtcaaagggcgaaaaacc
gtctatcagggcgatggcccactacgtgaaccatcaccctaatcaagttttttggggtcgaggtgccgtaaagcactaaatcggaa
ccctaaagggagcccccgatttagagcttgacggggaaagccggcgaacgtggcgagaaaggaagggaagaaagcgaaa
ggagcgggcgctagggcgctggcaagtgtagcggtcacgctgcgcgtaaccaccacacccgccgcgcttaatgcgccgctac
agggcgcgtcccattcgccaatccggatatagttcctcctttcagcaaaaaacccctcaagacccgtttagaggccccaagggggtt
atgctagttattgctcagcggtggcagcagccaactcagcttcctttcgggctttgttagcagccggatctcagtggtggtggtggtggt
gctcga (SEQ ID NO:101)

Figure 112B gcggccgcgcccttgacgatgccacatcctgagcaaataattcaaccactaattgtgagcggataacacaaggaggaaacag
ccatggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcacccttatgtgtctgcggtaattgagaaaatgcgcaaatcattcctattaacggtgttttcttgaccgtcgattccgacatccc
ggtgggctccggtctgggtagcagcgcagccgttactatcgcgtctattggtgcgctgaacgagctgttcggctttggcctcagcct
gcaagaaatcgctaaactgggccacgaaatcgaaattaaagtacagggtgccgcgtccccaaccgatacgtatgtttctaccttc
ggcggcgtggttaccatcccggaacgtcgcaaactgaaaactccggactgcggcattgtgattggcgataccggcgttttctcct
ccaccaaagagttagtagctaacgtacgtcagctgcgcgaaagctacccggatttgatcgaaccgctgatgacctctattggca
aaatctctcgtatcggcgaacaactggttctgtctggcgactacgcatccatcggccgcctgatgaacgtcaaccagggtctcctg
gacgccctgggcgttaacatcttagaactgagccagctgatctattccgctcgtgcggcaggtgcgtttggcgctaaaatcacgg
gcgctggcggcggtggctgtatggttgcgctgaccgctccggaaaaatgcaaccaagtggcagaagcggtagcaggcgctgg
cggtaaagtgactatcactaaaccgaccgagcaaggtctgaaagtagattaagccttgacttaatagctgcttatttcgcccttatg
gtacctagtaggaggaaaaaaacatggaaatgcgtcaaccggctgtcgcaggtcaattctacccactgcgttgcgagaacctg
gaaaacgaactgaaacgctgcttcgaaggcctggagatccgcgaacaagaagtgctgggcgcagtctgtccgcacgccggtt
atatgtactctggcaaagttgcggcgcacgtctatgccactctgccggaagctgataccacgtaatcttcggcccgaaccacac
cggctacggtagccctgtctctgtgagccgtgaaacttggaagacccccgttgggcaatatcgatgttgacctggaactggcggac
ggcttcctgggttccatcgtagatgcggatgaactcggtcacaaatacgaacactctatcgaagttcagctgccgtttctgcaatac
cgttttgaacgcgatttcaaaattctgccaatctgcatgggtatgcaagacgaagaaaccgcggtcgaagtaggtaacctgctgg
cggatctgatcagcgagtccggtaaacgtgctgtgatcatcgcaagctctgatttcacccactatgagacggctgaacgtgccaa
agaaatcgattccgaagttattgattctatcctgaactttgacatctctggcatgtacgatcgcctgtatcgccgtaacgcctctgtttg
cggttacggcccgatcaccgctatgctgacggcaagcaaaaagctgggcggctcgtgcgactttgctgaaatacgcaaaca
gcggtgacgtgtccggtgataaagacgctgtggtgggctacgccgccatcatcgttgagtaagctgattaaaggttgaacagata
ggatttcgtcatggatcctacaaggaggaaaaaaaacatgaatgcttctaatgaaccggtgattctgaaactgggtggctctgctatt
accgacaaaggtgcctacgaaggcgtagttaaggaagctgatttgctgcgcatcgcacaggaagttagcggttccgtggcaa
gatgatcgtggttcatggtgctggtagcttcggccatacgtacgcgaagaaatacggcctggaccgtaccttcgacccagaggg
cgcaattgttactcatgaatctgttaaaaagctcgcctccaaagttgtaggtgctctgaatagcttcggcgtgcgtgctatcgcggtg
catcctatggactgcgcagtatgccgtaacggtcgtatcgaaacgatgtatctggactccatcaagttaatgctggaaaaaggtct
ggtgccggttctgcacggcgacgtcgcaatggatattgaactgggcacttgtatcctgtccggtgatcaaatcgttccttacctggc
caaagaactgggtatctcccgcctcggcctgggcagcgcagaggatggtgtgctggatatggagggcaaacctgtaccggaa
atcaccccagaaactttcgaagagttccgccactgcatcggtggttctggttctactgatgtaaccggtggcatgctgggcaaagt
gctggaacttctggaattgagcaaaaattcttccattactagctacattttcaacgctggtaaagcagacaacatctaccgcttctg
aatggtgagtccatcggcactcgcatcagcccggacaagcgtgtttaagctagttattaacctaaatgctctaaaccagttatgag
ctctacaaggaggaaaaaaacatgattaacactaccagccgccgcaaaattgaacacctgaaactctgcgcagaatccccg
gttgaagcgcgtcaggtatctgccggctttgaagacgttactctgatccaccgcgctttaccggagctgaacatggatgaactgga
cctcagcgttgatttcctgggtaaacgcatcaaagcgccgttcctgattgcgtctatcacgggtggtcacccagataccatcccggt
taacgctgcgctggcagctgctgctgaggagctgggtgttggcatcggcgttggctctcagcgcgcggccattgatgatccgagc
caggaagacagcttccgtgtagtgcgtgatgaagcccagatgcgtttgtttatggcaacgtcggcgcagcacagatccgtcagt
atggtgttgaaggtgttgaaaaactgatcgaaatgattgacgcagatgccttggcaatccacctgaactttctgcaagaagcggtc
caaccggaaggtgaccgcgacgcgaccggttgcctggacatgattaccgaaatttgctctcagattaaaactccggtaatcgtg
aaagaaaccggtgcaggcattagccgtgaagatgcgattctgttccagaaagctggcgtgagcgcaatcgacgttggcggcg
cgggcggcacctcctgggctggcgtcgaggtctaccgtgctaaagaaagccgtgactctgttagcgagcgtttaggtgagctgttt
tgggatttcggcattccgacggtagcttctctgattgaatcccgcgtttccttgccgctgatcgcaaccggcggtatccgtaacggtct
ggacattgctaaaagcattgctctcggcgcaagcgctgccagcgccgctctgccgttcgttggtccgtccctggagggcaaaga
atccgttgtacgtgtgctgagctgcatgctggaagaatttaaagcagcaatgttttgtgcggttgcggcaacatcaaaga

Figure 112C cctgcacaactctccagtagtggtaactggttggacccgcgaatacctggagcagcgcggttttaacgttaaggacct
ctccctgccgggcaacgctctgtaagcttcaacgcgtctacaaataaaaaaggcacgtcagatgacgtgccttttttct
tgtctaga (SEQ ID NO:102)

Figure 113B gtttgacagcttatcatcgactgcacggtgcaccaatgcttctggcgtcaggcagccatcggaagctgtggtatggctgtgca
ggtcgtaaatcactgcataattcgtgtcgctcaaggcgcactcccgttctggataatgtttttgcgccgacatcataacggttctg
gcaaatattctgaaatgagctgttgacaattaatcatccggctcgtataatgtgtggaattgtgagcggataacaatttcacaca
ggaaacagcgccgctgagaaaaagcgaagcggcactgctctttaacaatttatcagacaatctgtgtgggcactcgaccg
gaattatcgattaactttattattaaaaattaaagaggtatatattaatgtatcgattaaataaggaggaataaaccatgtgtgcg
acctcttctcaatttactcagattaccgagcataattcccgtcgttccgcaaactatcagccaaacctgtggaatttcgaattcct
gcaatccctggagaacgacctgaaagtggaaaagctggaggagaaagcgaccaaactggaggaagaagttcgctgca
tgatcaaccgtgtagacacccagccgctgtccctgctggagctgatcgacgatgtgcagcgcctgggtctgacctacaaattt
gaaaaagacatcattaaagccctggaaaacatcgtactgctggacgaaaacaaaaagaacaaatctgacctgcacgca
accgctctgtctttccgtctgctgcgtcagcacggtttcgaggtttctcaggatgtttttgagcgtttcaaggataaagaaggtggtt
tcagcggtgaactgaaaggtgacgtccaaggcctgctgagcctgtatgaagcgtcttacctgggtttcgagggtgagaacct
gctggaggaggcgcgtaccttttccatcacccacctgaagaacaacctgaaagaaggcattaataccaaggttgcagaac
aagtgagccacgccctggaactgccatatcaccagcgtctgcaccgtctggaggcacgttggttcctggataaatacgaac
cgaaagaaccgcatcaccagctgctgctggagctggcgaagctggattttaacatggtacagaccctgcaccagaaaga
gctgcaagatctgtcccgctggtggaccgagatgggcctggctagcaaactggattttgtacgcgaccgcctgatggaagttt
atttctgggcactgggtatggcgccagacccgcagtttggtgaatgtcgcaaagctgttactaaaatgtttggtctggtgacgat
catcgatgacgtgtatgacgtttatggcactctggacgaactgcaactgttcaccgatgctgtagagcgctgggacgttaacg
ctattaacaccctgccggactatatgaaactgtgtttcctggcactgtacaacaccgttaacgacacgtcctattctattctgaaa
gagaaaggtcataacaacctgtcctatctgacgaaaagctggcgtgaactgtgcaaagcctttctgcaagaggcgaaatgg
tccaacaacaaaattatcccggctttctccaagtacctggaaaacgccagcgtttcctcctccggtgtagcgctgctggcgcc
gtcttacttttccgtatgccagcagcaggaagacatctccgaccacgcgctgcgttccctgaccgacttccatggtctggtgcgt
tctagctgcgttatcttccgcctgtgcaacgatctggccacctctgcggcggagctggaacgtggcgagactaccaattctatc
attagctacatgcacgaaaacgatggtaccagcgaggaacaggcccgcgaagaactgcgtaaactgatcgacgccgaa
tggaaaaagatgaatcgtgaacgcgttagcgactccaccctgctgcctaaagcgttcatggaaatcgcagttaacatggca
cgtgtttcccactgcacctaccagtatggcgatggtctgggtcgcccagactacgcgactgaaaaccgcatcaaactgctgct
gattgacccttcccgattaaccagctgatgtatgtctaactgcataaaggaggtaaaaaaacatggtatcctgttctgcgccg
ggtaagatttacctgttcggtgaacacgccgtagtttatggcgaaactgcaattgcgtgtgcggtggaactgcgtacccgtgttc
gcgcggaactcaatgactctatcactattcagagccagatcggccgcaccggtctggatttcgaaaagcacccttatgtgtct
gcggtaattgagaaaatgcgcaaatctattcctattaacggtgttttcttgaccgtcgattccgacatcccggtgggctccggtct
gggtagcagcgcagccgttactatcgcgtcattggtgcgctgaacgagctgttcggcttttggcctcagcctgcaagaaatcg
ctaaactgggccacgaaatcgaaattaaagtacagggtgccgcgtccccaaccgatacgtatgtttctaccttcggcggcgt
ggttaccatcccggaacgtcgcaaactgaaaactccggactgcggcattgtgattggcgataccggcgttttctcctccacca
aagagttagtagctaacgtacgtcagctgcgcgaaagctacccggatttgatcgaaccgctgatgacctctattggcaaaat
ctctcgtatcggcgaacaactggttctgtctggcgactacgcatccatcggccgcctgatgaacgtcaaccagggtctcctgg
acgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagaagcggtagcaggcg
ctggcggtaaagtgactatcactaaaccgaccgagcaaggtctgaaagtagattaaagtctagttaaagtttaaacggtctcc
agcttggctgttttggcggatgagagaagattttcagcctgatacagattaaatcagaacgcagaagcggtctgataaaaca
gaatttgcctggcggcagtagcgcggtggtcccacctgaccccatgccgaactcagaagtgaaacgccgtagcgccgatg
gtagtgtggggtctcccatgcgagagtagggaactgccaggcatcaaataaaacgaaaggctcagtcgaaagactggg
cctttcgttttatctgttgtttgtcggtgaacgctctcctgagtaggacaaatccgccgggagcggatttgaacgttgcgaagcaa
cggcccggagggtggcgggcaggacgcccgccataaactgccaggcatcaaattaagcagaaggccatcctgacggat
ggcctttttgcgtttctacaaactcttttgttttattttctaaatacattcaaatatgtatccgcttaaccggaattgccagctggggcg
ccctctggtaaggttgggaagccctgcaaagtaaactggatggctttctcgccgccaaggatctgatggcgcaggggatca
agctctgatcaagagacaggatgaggatcgtttcgcatgattgaacaagatggattgcacgcaggttctccggccgcttgggt
ggagaggctattcggctatgactgggcacaa

Figure 113C cagacaatcggctgctctgatgccgccgtgttccggctgtcagcgcaggggcgcccggttcttttgtcaagaccgacctgtccgg
tgccctgaatgaactgcaagacgaggcagcgcggctatcgtggctggccacgacgggcgttccttgcgcagctgtgctcgacgt
tgtcactgaagcgggaagggactggctgctattgggcgaagtgccggggcaggatctcctgtcatctcaccttgctcctgccgag
aaagtatccatcatggctgatgcaatgcggcggctgcatacgcttgatccggctacctgcccattcgaccaccaagcgaaacat
cgcatcgagcgagcacgtactcggatggaagccggtcttgtcgatcaggatgatctggacgaagagcatcaggggctcgcgc
cagccgaactgttcgccaggctcaaggcgagcatgcccgacggcgaggatctcgtcgtgacccatggcgatgcctgcttgccg
aatatcatggtggaaaatggccgcttttctggattcatcgactgtggccggctgggtgtggcggaccgctatcaggacatagcgtt
ggctacccgtgatattgctgaagagcttggcggcgaatgggctgaccgcttcctcgtgctttacggtatcgccgctcccgattcgca
gcgcatcgccttctatcgccttcttgacgagttcttctgacgcatgaccaaaatcccttaacgtgagttttcgttccactgagcgtcag
accccgtagaaaagatcaaaggatcttcttgagatcctttttttctgcgcgtaatctgctgcttgcaaacaaaaaaaccaccgctac
cagcggtggtttgtttgccggatcaagagctaccaactcttttccgaaggtaactggcttcagcagagcgcagataccaaatact
gtccttctagtgtagccgtagttaggccaccacttcaagaactctgtagcaccgcctacatacctcgctctgctaatcctgttaccag
tggctgctgccagtggcgataagtcgtgtcttaccgggttggactcaagacgatagttaccggataaggcgcagcggtcgggct
gaacggggggttcgtgcacacagcccagcttggagcgaacgacctacaccgaactgagatacctacagcgtgagctatgag
aaagcgccacgcttcccgaagggagaaaggcggacaggtatccggtaagcggcagggtcggaacaggagagcgcacga
gggagcttccaggggaaacgcctggtatctttatagtcctgtcgggtttcgccacctctgacttgagcgtcgatttttgtgatgctcgt
caggggggcggagcctatggaaaaacgccagcaacgcggcctttttacggttcctggccttttgctggccttttgctcacatgttctt
tcctgcgttatcccctgattctgtggataaccgtattaccgcctttgagtgagctgataccgctcgccgcagccgaacgaccgagc
gcagcgagtcagtgagcgaggaagcggaagagcgcctgatgcggtattttctccttacgcatctgtgcggtatttcacaccgcat
atggtgcactctcagtacaatctgctctgatgccgcatagttaagccagtatacactccgctatcgctacgtgactgggtcatggct
gcgccccgacacccgccaacacccgctgacgcgccctgacgggcttgtctgctcccggcatccgcttacagacaagctgtgac
cgtctccgggagctgcatgtgtcagaggttttcaccgtcatcaccgaaacgcgcgaggcagcagatcaattcgcgcgcgaagg
cgaagcggcatgcatttacgttgacaccatcgaatggtgcaaaacctttcgcggtatggcatgatagcgcccggaagagagtca
attcagggtggtgaatgtgaaaccagtaacgttatacgatgtcgcagagtatgccggtgtctcttatcagaccgtttcccgcgtggt
gaaccaggccagccacgtttctgcgaaaacgcgggaaaaagtggaagcggcgatggcggagctgaattacattcccaaccg
cgtggcacaacaactggcgggcaaacagtcgttgctgattggcgttgccacctccagtctggccctgcacgcgccgtcgcaaat
tgtcgcggcgattaaatctcgcgccgatcaactgggtgccagcgtggtggtgtcgatggtagaacgaagcggcgtcgaagcctg
taaagcggcggtgcacaatcttctcgcgcaacgcgtcagtgggctgatcattaactatccgctggatgaccaggatgccattgct
gtggaagctgcctgcactaatgttccggcgttatttcttgatgtctctgaccagacacccatcaacagtattatttctcccatgaaga
cggtacgcgactgggcgtggagcatcggtcgcattgggtcaccagcaaatcgcgctgttagcgggcccattaagttctgtctcg
gcgcgtctgcgtctggctggctggcataaatatctcactcgcaatcaaattcagccgatagcggaacgggaaggcgactggagt
gccatgtccggttttcaacaaaccatgcaaatgctgaatgagggcatcgttcccactgcgatgctggttgccaacgatcagatgg
cgctgggcgcaatgcgcgccattaccgagtccgggctgcgcgttggtgcggatatctcggtagtgggatacgacgataccgaa
gacagctcatgttatatcccgccgtcaaccaccatcaaacaggattttcgcctgctggggcaaaccagcgtggaccgcttgctgc
aactctctcagggccaggcggtgaagggcaatcagctgttgcccgtctcactggtgaaaagaaaaaccaccctggcgcccaat
acgcaaaccgcctctccccgcgcgttggccgattcattaatgcagctggcacgacaggtttcccgactggaaagcgggcagtg
agcgcaacgcaattaatgtgagttagcgcgaattgatctg (SEQ ID NO:103)

MCM376 - MVK from M. mazei archeal Lower in pET200D
6647 bp

Figure 114B aagggcgagctcaacgatccggctgctaacaaagcccgaaaggaagctgagttggctgctgccaccgctgagcaataact
agcataaccccttggggcctctaaacgggtcttgaggagttttttgctgaaaggaggaactatatccggatatcccgcaagagg
cccggcagtaccggcataaccaagcctatgcctacagcatccagggtgacggtgccgaggatgacgatgagcgcattgtta
gatttcatacacggtgcctgactgcgttagcaatttaactgtgataaactaccgcattaaagcttatcgatgataagctgtcaaac
atgagaattaattcttgaagacgaaagggcctcgtgatacgcctattttataggttaatgtcatgataataatggtttcttagacgtc
aggtggcacttttcggggaaatgtgcgcggaaccccctatttgtttattttctaaatacattcaaatatgtatccgctcatgagacaat
aaccctgataaatgcttcaataatattgaaaaaggaagagtatgattgaacaagatggattgcacgcaggttctccggccgctt
gggtggagaggctattcggctatgactgggcacaactgacaatcggctgctctgatgccgccgtgttccggctgtcagcgcag
gggcgcccggttcttttgtcaagaccgacctgtccggtgccctgaatgaactgcaggacgaggcagcgcggctatcgtggct
ggccacgacgggcgttcttgcgcagctgtgctcgacgttgtcactgaagcgggaagggactggctgctattgggcgaagtgc
cggggcaggatctcctgtcatctcaccttgctcctgccgagaaagtatccatcatggctgatgcaatgcggcggctgcatacgct
tgatccggctacctgcccattcgaccaccaagcgaaacatcgcatcgagcgggcacgtactcggatggaagccggtcttgtc
gatcaggatgatctggacgaagagcatcaggggctcgcgccagccgaactgttcgccaggctcaaggcgcgcatgcccga
cggcgaggatctcgtcgtgacacatggcgatgcctgcttgccgaatatcatggtggaaaatggccgcttttctggattcatcgact
gtggccggctgggtgtggcggaccgctatcaggacatagcgttggctacccgtgatattgctgaagagcttggcggcgaatgg
gctgaccgcttcctcgtgctttacggtatcgccgctcccgattcgcagcgcatcgccttctatcgccttcttgacgagttcttctgagc
gggactctggggttcgaaatgaccgaccaagcgacgcctaactgtcagaccaagtttactcatatatactttagattgatttaaa
acttcattttaatttaaaaggatctaggtgaagatcctttttgataatctcatgaccaaaatcccttaacgtgagttttcgttccactga
gcgtcagaccccgtagaaaagatcaaaggatcttcttgagatcctttttttctgcgcgtaatctgctgcttgcaaacaaaaaaacc
accgctaccagcggtggtttgtttgccggatcaagagctaccaactctttttccgaaggtaactggcttcagcagagcgcagata
ccaaatactgtccttcagtgtagccgtagttaggccaccacttcaagaactctgtagcaccgcctacatacctcgctctgctaat
cctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagc
gtgagctatgagaaagcgccacgcttcccgaagggagaaaggcggacaggtatccggtaagcggcagggtcggaacag
gagagcgcacgagggagcttccaggggggaaacgcctggtatctttatagtcctgtcgggtttcgccacctctgacttgagcgtc
gatttttgtgatgctcgtcaggggggcggagcctatggaaaaacgccagcaacgcggcctttttacggttcctggccttttgctgg
ccttttgctcacatgttctttcctgcgttatcccctgattctgtggataaccgtattaccgcctttgagtgagctgataccgctcgccgc
agccgaacgaccgagcgcagcgagtcagtgagcgaggaagcggaagagcgcctgatgcggtattttctccttacgcatctgt
gcggtatttcacaccgcaatggtgcactctcagtacaatctgctctgatgccgcatagttaagccagtatacactccgctatcgct
acgtgactgggtcatggctgcgccccgacacccgccaacacccgctgacgcgccctgacgggcttgtctgctcccggcatcc
gcttacagacaagctgtgaccgtctccgggagctgcatgtgtcagaggttttcaccgtcatcaccgaaacgcgcgaggcagct
gcggtaaagctcatcagcgtggtcgtgaagcgattcacagatgtctgcctgttcatccgcgtccagctcgttgagttctccagaa
gcgttaatgtctggcttctgataaagcgggccatgttaagggcggttttttcctgtttggtcactgatgcctccgtgtaaggggattt
ctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttc
gttaatacagatgtaggtgttccacagggtagccagcagcatcctgcgatgcagatccggaacataatggtgcagggcgctg
acttccgcgtttccagactttacgaaacacggaaaccgaagaccattcatgttgttgctcaggtcgcagacgttttgcagcagca
gtcgcttcacgttcgctcgcgtatcggtgattcattctgctaaccagtaaggcaacccccgccagcctagccgggtcctcaacga
caggagcacgatcatgcgcacccgtggccaggacccaacgctgcccgagatgcgccgcgtgcggctgctggagatggcg
gacgcgatggatatgttctgccaagggttggtttgcgcattcacagttctccgcaagaattgattggctccaattcttggagtggtg
aatccgttagcgaggtgccgccggcttccattcaggtcgaggtggcccggctccatgcaccgcgacgcaacgcggggaggc
agacaaggtataggcggcgcctacaatccatgccaacccgttccatgtgctcgccgaggcggcataaatcgccgtgacga
tcagcggtccaatgatcgaagttaggctggtaagagccgcgagcgatcttgaagctgtccctgatggtcgtcatctacctgcct
ggacagcatggcctgcaacgcgggcatcccgatgccgccggaagcgagaagaatcataatggggaaggccatccagcct
cgcgtcgcgaacgccagcaagacgtagcccagcgcgt

Figure 114C cggccgccatgccggcgataatggcctgcttctcgccgaaacgtttggtggcgggaccagtgacgaaggctt
gagcgagggcgtgcaagattccgaataccgcaagcgacaggccgatcatcgtcgcgctccagcgaaagc
ggtcctcgccgaaaatgacccagagcgctgccggcacctgtcctacgagttgcatgataaagaagacagtc
ataagtgcggcgacgatagtcatgccccgcgcccaccggaaggagctgactggttgaaggctctcaaggg
catcggtcgagatcccggtgcctaatgagtgagctaacttacattaattgcgttgcgctcactgcccgctttccag
tcgggaaacctgtcgtgccagctgcattaatgaatcggccaacgcgcggggagaggcggtttgcgtattggg
cgccagggtggttttcttttcaccagtgagacgggcaacagctgattgcccttcaccgcctggccctgagaga
gttgcagcaagcggtccacgctggtttgccccagcaggcgaaaatcctgtttgatggtggttaacggcgggat
ataacatgagctgtcttcggtatcgtcgtatcccactaccgagatatccgcaccaacgcgcagcccggactcg
gtaatggcgcgcattgcgcccagcgccatctgatcgttggcaaccagcatcgcagtgggaacgatgccctcat
tcagcatttgcatggtttgttgaaaaccggacatggcactccagtcgccttcccgttccgctatcggctgaatttga
ttgcgagtgagatatttatgccagccagccagacgcagacgcgccgagacagaacttaatgggcccgctaa
cagcgcgatttgctggtgacccaatgcgaccagatgctccacgcccagtcgcgtaccgtcttcatgggagaaa
ataatactgttgatgggtgtctggtcagagacatcaagaaataacgccggaacattagtgcaggcagcttcca
cagcaatggcatcctggtcatccagcggatagttaatgatcagcccactgacgcgttgcgcgagaagattgtg
caccgccgctttacaggcttcgacgccgcttcgttctaccatcgacaccaccacgctggcacccagttgatcgg
cgcgagatttaatcgccgcgacaatttgcgacggcgcgtgcagggccagactggaggtggcaacgccaatc
agcaacgactgtttgcccgccagttgttgtgccacgcggttgggaatgtaattcagctccgccatcgccgcttcc
acttttcccgcgttttcgcagaaacgtggctggcctggttcaccacgcgggaaacggtctgataagagacacc
ggcatactctgcgacatcgtataacgttactggtttcacattcacccctgaattgactctcttccgggcgctatc
atgccataccgcgaaaggttttgcgccattcgatggtgtccgggatctcgacgctctcccttatgcgactcctgca
ttaggaagcagcccagtagtaggttgaggccgttgagcaccgccgccgcaaggaatggtgcatgcaagga
gatggcgcccaacagtcccccggccacggggcctgccaccatacccacgccgaaacaagcgctcatgag
cccgaagtggcgagcccgatcttccccatcggtgatgtcggcgatataggcgccagcaaccgcacctgtggc
gccggtgatgccggccacgatgcgtccggcgtagaggatcgagatctcgatcccgcgaaattaatacgactc
actatagggaattgtgagcggataacaattcccctctagaaataattttgtttaactttaagaaggagatataca
tatgcggggttctcatcatcatcatcatcatggtatggctagcatgactggtggacagcaaatgggtcgggatct
gtacgacgatgacgataaggatcatcccttcaccatgtatcctgttctgcgccgggtaagatttacctgttcggt
gaacacgccgtagtttatggcgaaactgcaattgcgtgtgcggtggaactgcgtacccgtgttcgcgcggaact
caatgactctatcactattcagagccagatcggccgcaccggtctggatttcgaaaagcacccttatgtgtctgc
ggtaattgagaaaatgcgcaaatctattcctattaacggtgttttcttgaccgtcgattccgacatcccggtgggct
ccggtctgggtagcagcgcagccgttactatcgcgtctattggtgcgctgaacgagctgttcggctttggcctca
gcctgcaagaaatcgctaaactgggccacgaaatcgaattaaagtacagggtgccgcgtcccaaccgat
acgtatgtttctaccttcggcggcgtggttaccatcccggaacgtcgcaaactgaaaactccggactgcggcat
tgtgattggcgataccggcgttttctcctccaccaaagagttagtagctaacgtacgtcagctgcgcgaaagcta
cccggatttgatcgaaccgctgatgacctctattggcaaaatctctcgtatcggcgaacaactggttctgtctggc
gactacgcatccatcggccgcctgatgaacgtcaaccagggtctcctggacgccctgggcgttaacatcttag
aactgagccagctgatctattccgctcgtgcggcaggtgcgtttggcgctaaaatcacgggcgctggcggcgg
tggctgtatggttgcgctgaccgctccggaaaaatgcaaccaagtggcagaagcggtagcaggcgctggcg
gtaaagtgactatcactaaaccgaccgagcaaggtctgaaagtagattaa (SEQ ID NO:108)

Figure 137A tggcgaatgggacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcgggggctcccttta
gggttccgatttagtgctttacggcacctcgaccccaaaaaacttgattagggtgatggttcacgtagtgggccatcgccctgatagac
ggtttttcgcccttttgacgttggagtccacgttctttaatagtggactcttgttccaaactggaacaacactcaaccctatctcggtctattctt
ttgatttataagggattttgccgatttcggcctattggttaaaaaatgagctgatttaacaaaaatttaacgcgaattttaacaaaatattaa
cgtttacaatttcaggtggcacttttcggggaaatgtgcgcggaacccctatttgtttatttttctaaatacattcaaatatgtatccgctcatg
aattaattcttagaaaaactcatcgagcatcaaatgaaactgcaatttattcatatcaggattatcaataccatattttgaaaaagccgtt
tctgtaatgaaggagaaaactcaccgaggcagttccataggatggcaagatcctggtatcggtctgcgattccgactcgtccaacat
caatacaacctattaatttcccctcgtcaaaaataaggttatcaagtgagaaatcaccatgagtgacgactgaatccggtgagaatgg
caaaagtttatgcatttctttccagacttgttcaacaggccagccattacgctcgtcatcaaaatcactcgcatcaaccaaaccgttatc
attcgtgattgcgcctgagcgagacgaaatacgcgatcgctgttaaaaggacaattacaaacaggaatcgaatgcaaccggcgca
ggaacactgccagcgcatcaacaatattttcacctgaatcaggatattcttctaatacctggaatgctgtttccggggatcgcagtgg
tgagtaaccatgcatcatcaggagtacggataaaatgcttgatggtcggaagaggcataaattccgtcagccagtttagtctgaccat
ctcatctgtaacatcattggcaacgctacctttgccatgtttcagaaacaactctggcgcatcgggcttcccatacaatcgatagattgtc
gcacctgattgcccgacattatcgcgagcccatttatacccatataaatcagcatccatgttggaatttaatcgcggcctagagcaaga
cgtttcccgttgaatatggctcataacaccccttgtattactgtttatgtaagcagacagttttattgttcatgaccaaaatcccttaacgtga
gttttcgttccactgagcgtcagaccccgtagaaaagatcaaaggatcttcttgagatcctttttttctgcgcgtaatctgctgcttgcaaac
aaaaaaaccaccgctaccagcggtggtttgtttgccggatcaagagctaccaactctttttccgaaggtaactggcttcagcagagcg
cagataccaaatactgtccttctagtgtagccgtagttaggccaccacttcaagaactctgtagcaccgcctacatacctcgctctgcta
atcctgttaccagtggctgctgccagtggcgataagtcgtgtcttaccgggttggactcaagacgatagttaccggataaggcgcagc
ggtcgggctgaacggggggttcgtgcacacagcccagcttggagcgaacgacctacaccgaactgagatacctacagcgtgagc
tatgagaaagcgccacgcttcccgaagggagaaaggcggacaggtatccggtaagcggcagggtcggaacaggagagcgca
cgagggagcttccaggggggaaacgcctggtatctttatagtcctgtcgggtttcgccacctctgacttgagcgtcgatttttgtgatgctc
gtcaggggggcggagcctatggaaaaacgccagcaacgcggcctttttacggttcctggccttttgctggccttttgctcacatgttcttt
cctgcgttatcccctgattctgtggataaccgtattaccgcctttgagtgagctgataccgctcgccgcagccgaacgaccgagcgca
gcgagtcagtgagcgaggaagcggaagagcgcctgatgcggtattttctccttacgcatctgtgcggtatttcacaccgcatatatggt
gcactctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctccggg
agctgcatgtgtcagaggttttcaccgtcatcaccgaaacgcgcgaggcagctgcggtaaagctcatcagcgtggtcgtgaagcga
ttcacagatgtctgcctgttcatccgcgtccagctcgttgagtttctccagaagcgttaatgtctggcttctgataaagcgggccatgttaa
gggcggttttttcctgtttggtcactgatgcctccgtgtaagggggatttctgttcatgggggtaatgataccgatgaaacgagagaggat
gctcacgatacgggttactgatgatgaacatgcccggttactggaacgttgtgagggtaaacaactggcggtatggatgcggcggg
accagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgtt
gttgctcaggtcgcagacgttttgcagcagcagtcgcttcacgttcgctcgcgtatcggtgattcattctgctaaccagtaaggcaaccc
cgccagcctagccgggtcctcaacgacaggagcacgatcatgcgcacccgtggggccgccatgccggcgataatggcctgcttct
cgccgaaacgtttggtggcgggaccagtgacgaaggcttgagcgagggcgtgcaagattccgaataccgcaagcgacaggccg
atcatcgtcgcgctccagcgaaagcggtcctcgccgaaaatgacccagagcgctgccggcacctgtcctacgagttgcatgataa
agaagacagtcataagtgcggcgacgatagtcatgccccgcgcccaccggaaggagctgactgggttgaaggctctcaagggc
atcggtcgagatcccggtgcctaatgagtgagctaacttacattaattgcgttgcgctcactgcccgctttccagtcgggaaacctgtcg
tgccagctgcattaatgaatcggccaacgcgcggggagaggcggtttgcgtattgggcgccagggtggtttttcttttcaccagtgaga
cgggcaacagctgattgcccttcaccgcctggccctgagagagttgcagcaagcggtccacgctggtttgccccagcaggcgaaa
atcctgtttgatggtggttaacggcgggatataacatgagctgtcttcggtatc

Figure 137B gtcgtatcccactaccgagatatccgcaccaacgcgcagcccggactcggtaatggcgcgcattgcgcccagcgccatct
gatcgttggcaaccagcatcgcagtgggaacgatgccctcattcagcatttgcatggtttgttgaaaaccggacatggcactc
cagtcgccttcccgttccgctatcggctgaatttgattgcgagtgagatatttatgccagccagccagacgcagacgcgccga
gacagaacttaatgggcccgctaacagcgcgatttgctggtgacccaatgcgaccagatgctccacgcccagtcgcgtacc
gtcttcatgggagaaaataatactgttgatgggtgtctggtcagagacatcaagaaataacgccggaacattagtgcaggca
gcttccacagcaatggcatcctggtcatccagcggatagttaatgatcagcccactgacgcgttgcgcgagaagattgtgca
ccgccgctttacaggcttcgacgccgcttcgttctaccatcgacaccaccacgctggcacccagttgatcggcgcgagattta
atcgccgcgacaatttgcgacggcgcgtgcagggccagactggaggtggcaacgccaatcagcaacgactgtttgcccg
ccagttgttgtgccacgcggttgggaatgtaattcagctccgccatcgccgcttccacttttcccgcgttttcgcagaaacgtgg
ctggcctggttcaccacgcgggaaacggtctgataagagacaccggcatactctgcgacatcgtataacgttactggtttcac
attcaccaccctgaattgactctcttccgggcgctatcatgccataccgcgaaaggttttgcgccattcgatggtgtccgggatc
tcgacgctctcccttatgcgactcctgcattaggaagcagcccagtagtaggttgaggccgttgagcaccgccgccgcaag
gaatggtgcatgcaaggagatggcgcccaacagtcccccggccacggggcctgccaccatacccacgccgaaacaag
cgctcatgagcccgaagtggcgagcccgatcttccccatcggtgatgtcggcgatataggcgccagcaaccgcacctgtgg
cgccggtgatgccggccacgatgcgtccggcgtagaggatcgagatctcgatcccgcgaaattaatacgactcactatagg
ggaattgtgagcggataacaattcccctctagaaataattttgtttaactttaagaaggagatatacatatgcgttgtagcgtgtc
caccgaaaatgtgtctttcaccgaaactgaaaccgaagctcgtcgttctgcgaactacgaacctaacagctgggactatgatt
acctgctgtcctccgacacggacgagtccatcgaagtatacaaagacaaagcgaaaaagctggaagccgaagttcgtcg
cgagattaataacgaaaaagcagaatttctgaccctgctggaactgattgacaacgtccagcgcctgggcctgggttaccgt
ttcgagtctgatatccgtggtgcgctggatcgcttcgttcctccggcggcttcgatgcggtaaccaagacttccctgcacggta
cggcactgtctttccgtctgctgcgtcaacacggttttgaggtttctcaggaagcgttcagcggcttcaaagaccaaaacggca
acttcctggagaacctgaaggaagatatcaaagctatcctgagcctgtacgaggccagcttcctggctctggaaggcgaaa
acatcctggacgaggcgaaggttttcgcaatctctcatctgaaagaactgtctgaagaaaagatcggtaaagagctggcag
aacaggtgaaccatgcactggaactgccactgcatcgccgtactcagcgtctggaagcagtatggtctatcgaggcctacc
gtaaaaaggaggacgcgaatcaggttctgctggagctggcaattctggattacaacatgatccagtctgtataccagcgtgat
ctgcgtgaaacgtcccgttggtggcgtcgtgtgggtctggcgaccaaactgcactttgctcgtgaccgcctgattgagagcttct
actgggccgtgggtgtagcattcgaaccgcaatactccgactgccgtaactccgtcgcaaaaatgttttctttcgtaaccattat
cgacgatatctacgatgtatacggcaccctggacgaactggagctgtttactgatgcagttgagcgttgggacgtaaacgcc
atcaacgacctgccggattacatgaaactgtgctttctggctctgtataacactattaacgaaatcgcctacgacaacctgaaa
gataaaggtgagaacatcctgccgtatctgaccaaagcctgggctgacctgtgcaacgctttcctgcaagaagccaagtgg
ctgtacaacaaatctactccgacctttgacgactacttcggcaacgcatggaaatcctcttctggcccgctgcaactggtgttcg
cttacttcgctgtcgtgcagaacattaaaaaggaagagatcgaaacctgcaaaaataccatgacaccatctctcgtccttcc
catatcttccgtctgtgcaatgacctggctagcgcgtctgcggaaattgcgcgtggtgaaaccgcaaatagcgtttcttgttaca
tgcgcactaaaggtatctccgaagaactggctaccgaaagcgtgatgaatctgatcgatgaaacctggaaaaagatgaac
aaggaaaaactgggtggtagcctgttcgcgaaaccgttcgtggaaaccgcgatcaacctggcacgtcaatctcactgcactt
atcataacggcgacgcgcataccctccggatgagctgacccgcaaacgcgttctgtctgtaatcactgaaccgattctgccg
tttgaacgctaaggatccgaattcgagctccgtcgacaagcttgcggccgcactcgagcaccaccaccaccaccactgag
atccggctgctaacaaagcccgaaaggaagctgagttggctgctgccaccgctgagcaataactagcataaccccttggg
gcctctaaacgggtcttgaggggttttttgctgaaaggaggaactatatccggat (SEQ ID NO:109)

Figure 137C tggcgaatgggacgcgccctgtagcggcgcattaagcgcggcgggtgtggtggttacgcgcagcgtgaccgctacacttgc
cagcgccctagcgcccgctcctttcgctttcttcccttccttctcgccacgttcgccggctttccccgtcaagctctaaatcgggg
gctcccttlagggttccgatttagtgctttacggcacctcgaccccaaaaaacttgattagggtgatggttcacgtagtgggccat
cgccctgatagacggtttttcgcccttgacgttggagtccacgttctttaatagtggactcttgttccaaactggaacaacactca
accctatctcggtctattcttttgatttataagggattttgccgatttcggcctattggttaaaaaatgagctgatttaacaaaaattta
acgcgaattttaacaaaatattaacgtttacaatttcaggtggcacttttcggggaaatgtgcgcggaacccctatttgtttattttc
taaatacattcaaatatgtatccgctcatgaattaattcttagaaaaactcatcgagcatcaaatgaaactgcaatttattcatatc
aggattatcaataccatatttttgaaaaagccgtttctgtaatgaaggagaaaactcaccgaggcagttccataggatggcaa
gatcctggtatcggtctgcgattccgactcgtccaacatcaatacaacctattaatttcccctcgtcaaaaataaggttatcaagt
gagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgc
gatcgctgttaaaaggacaattacaaacaggaatcgaatgcaaccggcgcaggaacactgccagcgcatcaacaatattt
tcacctgaatcaggatattcttctaatacctggaatgctgttttcccggggatcgcagtggtgagtaaccatgcatcatcaggag
tacggataaaatgcttgatggtcggaagaggcataaattccgtcagccagtttagtctgaccatctcatctgtaacatcattggc
aacgctacctttgccatgtttcagaaacaactctggcgcatcgggcttcccatacaatcgatagattgtcgcacctgattgccc
gacattatcgcgagcccatttatacccatataaatcagcatccatgttggaatttaatcgcggcctagagcaagacgtttcccgt
tgaatatggctcataacaccccttgtattactgtttatgtaagcagacagttttattgttcatgaccaaaatcccttaacgtgagtttt
cgttccactgagcgtcagaccccgtagaaaagatcaaaggatcttcttgagatccttttttctgcgcgtaatctgctgcttgcaa
acaaaaaaaccaccgctaccagcggtggtttgtttgccggatcaagagctaccaactcttttccgaaggtaactggcttcag
cagagcgcagataccaaatactgtccttctagtgtagccgtagttaggccaccacttcaagaactctgtagcaccgcctacat
acctcgctctgctaatcctgttaccagtggctgctgccagtggcgataagtcgtgtcttaccgggttggactcaagacgatagtt
accggataaggcgcagcggtcgggctgaacggggggttcgtgcacacagcccagcttggagcgaacgacctacaccga
actgagatacctacagcgtgagctatgagaaagcgccacgcttcccgaagggagaaaggcggacaggtatccggtaag
cggcagggtcggaacaggagagcgcacgagggagcttccaggggggaaacgcctggtatctttatagtcctgtcgggtttcg
ccacctctgacttgagcgtcgattttttgtgatgctcgtcaggggggcggagccctatggaaaaacgccagcaacgcggccttttt
acggttcctggccttttgctggccttttgctcacatgttcttcctgcgttatcccctgattctgtggataaccgtattaccgcctttgagt
gagctgataccgctcgccgcagccgaacgaccgagcgcagcgagtcagtgagcgaggaagcggaagagcgcctgat
gcggtattttctccttacgcatctgtgcggtatttcacaccgcatatatggtgcactctcagtacaatctgctctgatgccgcatagt
taagccagtatacactccgctatcgctacgtgactgggtcatggctgcgccccgacacccgccaacacccgctgacgcgcc
ctgacgggcttgtctgctcccggcatccgcttacagacaagctgtgaccgtctccgggagctgcatgtgtcagaggttttcacc
gtcatcaccgaaacgcgcgaggcagctgcggtaaagctcatcagcgtggtcgtgaagcgattcacagatgtctgcctgttca
tccgcgtccagctcgttgagtttctccagaagcgttaatgtctggcttctgataaagcgggccatgttaagggcggttttttcctgtt
tggtcactgatgcctccgtgtaagggggatttctgttcatgggggtaatgataccgatgaaacgagagaggatgctcacgata
cgggttactgatgatgaacatgcccggttactggaacgttgtgagggtaaacaactggcggtatggatgcggcgggaccag
agaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccatt
catgttgttgctcaggtcgcagacgttttgcagcagcagtcgcttcacgttcgctcgcgtatcggtgattcattctgctaaccagta
aggcaaccccgccagcctagccgggtcctcaacgacaggagcacgatcatgcgcacccgtggggccgccatgccggc
gataatggcctgcttctcgccgaaacgtttggtggcgggaccagtgacgaaggcttgagcgagggcgtgcaagattccgaa
taccgcaagcgacaggccgatcatcgtcgcgctccagcgaaagcggtcctcgccgaaaatgacccagagcgctgccgg
cacctgtcctacgagttgcatgataaagaagacagtcataagtgcggcgacgatagtcatgccccgcgcccaccggaagg
agctgactgggttgaaggctctcaagggcatcggtcgagatcccggtgcctaatgagtgagctaacttacattaattgcgttgc
gctcactgcccgctttccagtcgggaaacctgtcgtgccagctgcattaatgaatcggccaacgcgcggggagaggcggttt
gcgtattgggcgccagggtggtttttcttttcaccagtgagacgggcaacagctgattgcccttcaccgcctggccctgagaga
gttgcagcaagcggtccacgctggtttgccccagcaggcgaaaatcctgtttgatggtggttaacggcgggatataacatga
gctgtcttcggtatc

Figure 137D gtcgtatcccactaccgagatatccgcaccaacgcgcagcccggactcggtaatggcgcgcattgcgcccagcgccat
ctgatcgttggcaaccagcatcgcagtgggaacgatgccctcattcagcatttgcatggtttgttgaaaaccggacatggc
actccagtcgccttcccgttccgctatcggctgaatttgattgcgagtgagatatttatgccagccagccagacgcagacg
cgccgagacagaacttaatgggcccgctaacagcgcgatttgctggtgacccaatgcgaccagatgctccacgccca
gtcgcgtaccgtcttcatgggagaaaataatactgttgatgggtgtctggtcagagacatcaagaaataacgccggaac
attagtgcaggcagcttccacagcaatggcatcctggtcatccagcggatagttaatgatcagcccactgacgcgttgcg
cgagaagattgtgcaccgccgctttacaggcttcgacgccgcttcgttctaccatcgacaccaccacgctggcacccagt
tgatcggcgcgagatttaatcgccgcgacaatttgcgacggcgcgtgcagggccagactggaggtggcaacgccaat
cagcaacgactgtttgcccgccagttgttgtgccacgcggttgggaatgtaattcagctccgccatcgccgcttccactttt
cccgcgttttcgcagaaacgtggctggcctggttcaccacgcgggaaacggtctgataagagacaccggcatactctgc
gacatcgtataacgttactggtttcacattcaccaccctgaattgactctcttccgggcgctatcatgccataccgcgaaag
gttttgcgccattcgatggtgtccgggatctcgacgctctcccttatgcgactcctgcattaggaagcagcccagtagtagg
ttgaggccgttgagcaccgccgccgcaaggaatggtgcatgcaaggagatggcgcccaacagtcccccggccacgg
ggcctgccaccataccacgccgaaacaagcgctcatgagcccgaagtggcgagcccgatcttcccatcggtgatgt
cggcgatataggcgccagcaaccgcacctgtggcgccggtgatgccggccacgatcgtccggcgtagaggatcga
gatctcgatcccgcgaaattaatacgactcactatagggaattgtgagcggataacaattcccctctagaaataattttgt
ttaactttaagaaggagatatacatatgcgttgtagcgtgtccaccgaaaatgtgtctttcaccgaaactgaaaccgaaac
gcgtcgttctgcgaactacgaacctaacagctgggactatgattacctgctgtcctccgacacggacgagtccatcgaag
tatacaaagacaaagcgaaaaagctggaagccgaagttcgtcgcgagattaataacgaaaaagcagaatttctgacc
ctgccggaactgattgacaacgtccagcgcctgggcctgggttaccgtttcgagtctgatatccgtcgtgcgctggatcgct
tcgtttcctccggcggcttcgatgcggtaaccaagacttccctgcacgcgacggcactgtctttccgtctgctgcgtcaaca
cggttttgaggtttctcaggaagcgttcagcggcttcaaagaccaaaacggcaacttcctgaaaaacctgaaggaagat
atcaaagctatcctgagcctgtacgaggccagcttcctggctctggaaggcgaaaacatcctggacgaggcgaaggttt
tcgcaatctctcatctgaaagaactgtctgaagaaaagatcggtaaagatctggcagaacaggtgaaccatgcactgg
aactgccactgcatcgccgtactcagcgtctggaagcagtatggtctatcgaggcctaccgtaaaaaggaggacgcgg
atcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggt
gtagcattcgaaccgcaatactccgactgccgtaactccgtcgcaaaaatgttttctttcgtaaccattatcgacgatatcta
cgatgtatacggcacccctggacgaactgagctgtttactgacgcagttgagcgttgggacgtaaacgccatcgacgat
ctgccggattacatgaaactgtgctttctggctctgtataacactattaacgaaatcgcctacgacaacctgaaagataaa
ggtgagaacatcctgccgtatctgaccaaagcctgggctgacctgtgcaacgctttcctgcaagaagccaagtggctgt
acaacaaatctactccgaccttgacgaatacttcggcaacgcatggaaatcctcttctggcccgctgcaactggtgttcg
cttacttcgctgtcgtcagaacattaaaaaggaagagatcgataacctgcaaaaataccatgacatcatctctcgtcctt
cccatatcttccgtctgtgcaatgacctggctagcgcgtctgcggaaattgcgcgtggtgaaaccgcaaatagcgtttcttg
ttacatgcgcactaaaggtatctccgaagaactggctaccgaaagcgtgatgaatctgatcgatgaaacctggaaaaa
gatgaacaaggaaaaactgggtggtagcctgttcgcgaaaccgttcgtggaaaccgcgatcaacctggcacgtcaatc
tcactgcacttatcataacggcgacgcgcatacctctccggatgagctgacccgcaaacgcgttctgtctgtaatcactga
accgattctgccgtttgaacgctaaggatccgaattcgagctccgtcgacaagcttgcggccgcactcgagcaccacca
ccaccaccactgagatccggctgctaacaaagcccgaaaggaagctgagttggctgctgccaccgctgagcaataac
tagcataacccccttggggcctctaaacgggtcttgaggggttttttgctgaaaggaggaactatatccggat (SEQ ID NO:110)

Figure 137E

```
tggcgaatgggacgcgccctgtagcggcgcattaagcgcggcgggtgtggtggttacgcgcagcgtgaccgctacacttgc
cagcgccctagcgcccgctcctttcgctttcttcccttcctttctcgccacgttcgccggctttccccgtcaagctctaaatcgggg
gctcccttagggttccgatttagtgctttacggcacctcgaccccaaaaaacttgattagggtgatggttcacgtagtgggcca
tcgccctgatagacggttttcgcccttgacgttggagtccacgttcttaatagtggactcttgttccaaactggaacaacactc
aaccctatctcggtctattcttttgatttataagggattttgccgatttcggcctattggttaaaaaatgagctgatttaacaaaaattt
aacgcgaattttaacaaaatattaacgtttacaatttcaggtggcacttttcggggaaatgtgcgcggaaccccctatttgtttatttt
tctaaatacattcaaatatgtatccgctcatgaattaattcttagaaaaactcatcgagcatcaaatgaaactgcaatttattcata
tcaggattatcaataccatatttttgaaaaagccgtttctgtaatgaaggagaaaactcaccgaggcagttccataggatggc
aagatcctggtatcggtctgcgattccgactcgtccaacatcaatacaacctattaatttcccctcgtcaaaaataaggttatca
agtgagaaatcaccatgagtgacgactgaatccggtgagaatggcaaaagtttatgcatttctttccagacttgttcaacaggc
cagccattacgctcgtcatcaaaatcactcgcatcaaccaaaccgttattcattcgtgattgcgcctgagcgagacgaaatac
gcgatcgctgttaaaaggacaattacaaacaggaatcgaatgcaaccggcgcaggaacactgccagcgcatcaacaat
attttcacctgaatcaggatattcttctaatacctggaatgctgttttcccggggatcgcagtggtgagtaaccatgcatcatcag
gagtacggataaaatgcttgatggtcggaagaggcataaattccgtcagccagtttagtctgaccatctcatctgtaacatcatt
ggcaacgctacctttgccatgtttcagaaacaactctggcgcatcgggcttcccatacaatcgatagattgtcgcacctgattg
cccgacattatcgcgagcccatttatacccatataaatcagcatccatgttggaatttaatcgcggcctagagcaagacgttc
ccgttgaatatggctcataacaccccttgtattactgtttatgtaagcagacagttttattgttcatgaccaaaatcccttaacgtga
gttttcgttccactgagcgtcagaccccgtagaaaagatcaaaggatcttcttgagatccttttttctgcgcgtaatctgctgcttg
caaacaaaaaaaccaccgctaccagcggtggtttgtttgccggatcaagagctaccaactcttttccgaaggtaactggctt
cagcagagcgcagataccaaatactgtccttctagtgtagccgtagttaggccaccacttcaagaactctgtagcaccgcct
acatacctcgctctgctaatcctgttaccagtggctgctgccagtggcgataagtcgtgtcttaccgggttggactcaagacgat
agttaccggataaggcgcagcggtcgggctgaacggggggttcgtgcacacagcccagcttggagcgaacgacctacac
cgaactgagatacctacagcgtgagctatgagaaagcgccacgcttcccgaagggagaaaggcggacaggtatccggt
aagcggcagggtcggaacaggagagcgcacgagggagcttccaggggaaacgcctggtatctttatagtcctgtcgggt
ttcgccacctctgacttgagcgtcgatttttgtgatgctcgtcagggggcggagcctatggaaaaacgccagcaacgcggc
cttttacggttcctggccttttgctggccttttgctcacatgttcttcctgcgttatcccctgattctgtggataaccgtattaccgccttt
gagtgagctgataccgctcgccgcagccgaacgaccgagcgcagcgagtcagtgagcgaggaagcggaagagcgcct
gatgcggtattttctccttacgcatctgtgcggtatttcacaccgcatatatggtgcactctcagtacaatctgctctgatgccgcat
agttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttc
accgtcatcaccgaaacgcgcgaggcagctgcggtaaagctcatcagcgtggtcgtgaagcgattcacagatgtctgcctg
ttcatccgcgtccagctcgttgagtttctccagaagcgttaatgtctggcttctgataaagcgggccatgttaagggcggttttttc
ctgtttggtcactgatgcctccgtgtaagggggatttctgttcatgggggtaatgataccgatgaaacgagagaggatgctcac
gatacgggttactgatgatgaacatgcccggttactggaacgttgtgagggtaaacaactggcggtatggatgcggcggga
ccagagaaaaatcactcagggtcaatgccagcgcttcgttaatacagatgtaggtgttccacagggtagccagcagcatcc
tgcgatgcagatccggaacataatggtgcagggcgctgacttccgcgtttccagactttacgaaacacggaaaccgaaga
ccattcatgttgttgctcaggtcgcagacgttttgcagcagcagtcgcttcacgttcgctcgcgtatcggtgattcattctgctaac
cagtaaggcaacccgccagcctagccgggtcctcaacgacaggagcacgatcatgcgcacccgtggggccgccatgc
cggcgataatggcctgcttctcgccgaaacgtttggtggcgggaccagtgacgaaggcttgagcgagggcgtgcaagattc
cgaataccgcaagcgacaggccgatcatcgtcgcgctccagcgaaagcggtcctcgccgaaaatgacccagagcgctg
ccggcacctgtcctacgagttgcatgataaagaagacagtcataagtgcggcgacgatagtcatgccccgcgcccaccgg
aaggagctgactgggttgaaggctctcaagggcatcggtcgagatcccggtgcctaatgagtgagctaacttacattaattgc
gttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctg
agagagttgcagcaagcggtccacgctggtttgccccagcaggcgaaaatcctgtttgatggtggttaacggcgggatataa
catgagctgtcttcggtatc
```

Figure 137F gtcgtatcccactaccgagatatccgcaccaacgcgcagcccggactcggtaatggcgcgcattgcgcccagcgccatctgat
cgttggcaaccagcatcgcagtgggaacgatgccctcattcagcatttgcatggtttgttgaaaaccggacatggcactccagtc
gccttcccgttccgctatcggctgaatttgattgcgagtgagatatttatgccagccagccagacgcagacgcgccgagacaga
acttaatgggcccgctaacagcgcgatttgctggtgacccaatgcgaccagatgctccacgcccagtcgcgtaccgtcttcatgg
gagaaaataatactgttgatgggtgtctggtcagagacatcaagaaataacgccggaacattagtgcaggcagcttccacagc
aatggcatcctggtcatccagcggatagttaatgatcagcccactgacgcgttgcgcgagaagattgtgcaccgccgctttacag
gcttcgacgccgcttcgttctaccatcgacaccaccacgctggcacccagttgatcggcgcgagatttaatcgccgcgacaattt
gcgacggcgcgtgcagggccagactggaggtggcaacgccaatcagcaacgactgtttgcccgccagttgttgtgccacgcg
gttgggaatgtaattcagctccgccatcgccgcttccacttttccccgcgttttcgcagaaacgtggctggcctggttcaccacgcgg
gaaacggtctgataagagacaccggcatactctgcgacatcgtataacgttactggtttcacattcaccaccctgaattgactctct
tccgggcgctatcatgccataccgcgaaaggttttgcgccattcgatggtgtccgggatctcgacgctctcccttatgcgactcctg
cattaggaagcagcccagtagtaggttgaggccgttgagcaccgccgccgcaaggaatggtgcatgcaaggagatggcgcc
caacagtcccccggccacggggcctgccaccatacccacgccgaaacaagcgctcatgagcccgaagtggcgagcccgat
cttccccatcggtgatgtcggcgatataggcgccagcaaccgcacctgtggcgccggtgatgccggccacgatgcgtccggcg
tagaggatcgagatctcgatcccgcgaaattaatacgactcactataggggaattgtgagcggataacaattcccctctagaaat
aattttgtttaactttaagaaggagatatacatatgcgttgtagcgtgtccaccgaaaatgtgtctttctctgaaactgaaaccgaaac
gcgtcgttctgcgaactacgaacctaacagctgggactatgattacctgctgtcctccgacacggacgagtccatcgaagtacac
aaagacaaagcgaaaaagctggaagccgaagttcgtcgcgagattaataacgaaaaagcagaatttctgaccctgctggaa
ctgattgacaacgtccagcgcctgggcctgggttaccgtttcgagtctgatatccgtcgtgcgctggatcgcttcgtttcctccggcg
gcttcgatggcgtaaccaagacttccctgcacggtacggcactgtctttccgtctgctgcgtcaacacggttttgaggtttctcagga
agcgttcagcggcttcaaagaccaaaacggcaacttcctggagaacctgaaggaagatatcaaagctatcctgagcctgtacg
aggccagcttcctggctctggaaggcgaaaacatcctggacgaggcgaaggttttcgcaatctctcatctgaaagaactgtctga
agaaaagatcggtaaagagctggcagaacaggtgtcccatgcactggaactgccactgcatcgccgtactcagcgtctggaa
gcagtatggtctatcgaggcctaccgtaaaaaggaggacgcgaaccaggttctgctggagctggcaattctggattacaacatg
atccagtctgtataccagcgtgatctgcgtgaaacgtcccgttggtggcgtcgtgtgggtctggcgaccaaactgcactttgctcgt
gaccgcctgattgagagcttctactgggccgtgggtgtagcattcgaaccgcaatactccgactgccgtaactccgtcgcaaaaa
tgtttctttcgtaaccattatcgacgatatctacgatgtatacggcaccctggacgaactggagctgtttactgatgcagttgagcgtt
gggacgtaaacgccatcaacgacctgccggattacatgaaactgtgctttctggctctgtataacactattaacgaaatcgcctac
gacaacctgaaagataaaggtgagaacatcctgccgtatctgaccaaagcctgggctgacctgtgcaacgcttcctgcaaga
agccaagtggctgtacaacaaatctactccgacctttgacgactacttcggcaacgcatggaaatcctcttctggcccgctgcaa
ctgatcttcgcttacttcgctgtcgtgcagaacattaaaaaggaagagatcgaaaacctgcaaaaataccatgacatcatctctcg
tccttcccatatcttccgtctgtgcaatgacctggctagcgcgtctgcggaaattgcgcgtggtgaaaccgcaaatagcgtttcttgtt
acatgcgcactaaaggtatctccgaagaactggctaccgaaagcgtgatgaatctgatcgatgaaacctggaaaaagatgaa
caaggaaaaactgggtggtagcctgttcgcgaaaccgttcgtggaaaccgcgatcaacctggcacgtcaatctcactgcactta
tcataacggcgacgcgcatacctctccggatgagctgacccgcaaacgcgttctgtctgtaatcactgaaccgattctgccgtttg
aacgctaaggatccgaattcgagctccgtcgacaagcttgcggccgcactcgagcaccaccaccaccactgagatccgg
ctgctaacaaagcccgaaaggaagctgagttggctgctgccaccgctgagcaataactagcataaccccttggggcctctaaa
cgggtcttgaggggttttttgctgaaaggaggaactatatccggat (SEQ ID NO:123)

Figure 137G

MRCSVSTENVSFSETETETRRSANYEPNSWDYDYLLSSDTDESIEVHKDKAKKL
EAEVRREINNEKAEFLTLLELIDNVQRLGLGYRFESDIRRALDRFVSSGGFDGVT
KTSLHGTALSFRLLRQHGFEVSQEAFSGFKDQNGNFLENLKEDIKAILSLYEASFL
ALEGENILDEAKVFAISHLKELSEEKIGKELAEQVSHALELPLHRRTQRLEAVWSIE
AYRKKEDANQVLLELAILDYNMIQSVYQRDLRETSRWWRRVGLATKLHFARDRL
IESFYWAVGVAFEPQYSDCRNSVAKMFSFVTIIDDIYDVYGTLDELELFTDAVER
WDVNAINDLPDYMKLCFLALYNTINEIAYDNLKDKGENILPYLTKAWADLCNAFLQ
EAKWLYNKSTPTFDDYFGNAWKSSSGPLQLIFAYFAVVQNIKKEEIENLQKYHDII
SRPSHIFRLCNDLASASAEIARGETANSVSCYMRTKGISEELATESVMNLIDETW
KKMNKEKLGGSLFAKPFVETAINLARQSHCTYHNGDAHTSPDELTRKRVLSVITE
PILPFER (SEQ ID NO: 124)

Figure 137H

```
tggcgaatgggacgcgccctgtagcggcgcattaagcgcggcgggtgtggtggttacgcgcagcgtgaccgctacactt
gccagcgccctagcgcccgctcctttcgctttcttcccttccttctcgccacgttcgccggctttccccgtcaagctctaaatcg
ggggctcccttttagggttccgatttagtgctttacggcacctcgaccccaaaaaacttgattagggtgatggttcacgtagtgg
gccatcgccctgatagacggttttcgcccctttgacgttggagtccacgttctttaatagtggactcttgttccaaactggaaca
acactcaaccctatctcggtctattcttttgatttataagggatttgccgatttcggcctattggttaaaaaatgagctgatttaac
aaaaatttaacgcgaattttaacaaaatattaacgtttacaatttcaggtggcacttttcggggaaatgtgcgcggaacccct
atttgtttattttctaaatacattcaaatatgtatccgctcatgaattaattcttagaaaaactcatcgagcatcaaatgaaactg
caatttattcatatcaggattatcaataccatattttgaaaaagccgtttctgtaatgaaggagaaaactcaccgaggcagtt
ccataggatggcaagatcctggtatcggtctgcgattccgactcgtccaacatcaatacaacctattaatttcccctcgtcaa
aaataaggttatcaagtgagaaatcaccatgagtgacgactgaatccggtgagaatggcaaaagtttatgcatttctttcca
gacttgttcaacaggccagccattacgctcgtcatcaaaatcactcgcatcaaccaaaccgttattcattcgtgattgcgcct
gagcgagacgaaatacgcgatcgctgttaaaaggacaattacaaacaggaatcgaatgcaaccggcgcaggaacact
gccagcgcatcaacaatattttcacctgaatcaggatattcttctaatacctggaatgctgttttcccggggatcgcagtggtg
agtaaccatgcatcatcaggagtacggataaaatgcttgatggtcggaagaggcataaaattccgtcagccagtttagtctg
accatctcatctgtaacatcattggcaacgctaccttttgccatgtttcagaaacaactctggcgcatcgggcttccatacaat
cgatagattgtcgcacctgattgcccgacattatcgcgagcccatttatacccatataaatcagcatccatgttggaatttaat
cgcggcctagagcaagacgtttcccgttgaatatggctcataacaccccttgtattactgtttatgtaagcagacagttttattgt
tcatgaccaaaatcccttaacgtgagttttcgttccactgagcgtcagaccccgtagaaaagatcaaaggatcttcttgagat
ccttttttctgcgcgtaatctgctgcttgcaaacaaaaaaaccaccgctaccagcggtggtttgtttgccggatcaagagcta
ccaactcttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggcgataagt
cgtgtcttaccgggttggactcaagacgatagttaccggataaggcgcagcggtcgggctgaacggggggttcgtgcaca
cagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccagg
gggaaacgcctggtatctttatagtcctgtcgggtttcgccacctctgacttgagcgtcgatttttgtgatgctcgtcaggggg
cggagcctatggaaaaacgccagcaacgcggcctttttacggttcctggccttttgctggccttttgctcacatgttctttcctgc
gttatcccctgattctgtggataaccgtattaccgcctttgagtgagctgataccgctcgccgcagccgaacgaccgagcgc
agcgagtcagtgagcgaggaagcggaagagcgcctgatgcggtattttctccttacgcatctgtgcggtatttcacaccgc
atatatggtgcactctcagtacaatctgctctgatgccgcatagttaagccagtatacactccgctatcgctacgtgactgggt
catggctgcgccccgacaccgccaacacccgctgacgcgccctgacgggcttgtctgctcccggcatccgcttacaga
caagctgtgaccgtctccgggagctgcatgtgtcagaggttttcaccgtcatcaccgaaacgcgcgaggcagctgcggta
aagctcatcagcgtggtcgtgaagcgattcacagatgtctgcctgttcatccgcgtccagctcgttgagtttctccagaagcgt
taatgtctggcttctgataaagcgggccatgttaagggcggttttttcctgtttggtcactgatgcctccgtgtaagggggatttct
gttcatggggtaatgataccgatgaaacgagagaggatgctcacgatacgggttactgatgatgaacatgcccggttact
ggaacgttgtgagggtaaacaactggcggtatggatgcggcgggaccagagaaaaatcactcagggtcaatgccagc
gcttcgttaatacagatgtaggtgttccacagggtagccagcagcatcctgcgatgcagatccggaacataatggtgcagg
gcgctgacttccgcgtttccagactttacgaaacacggaaaccgaagaccattcatgttgttgctcaggtcgcagacgttttg
cagcagcagtcgcttcacgttcgctcgcgtatcggtgattcattctgctaaccagtaaggcaaccccgccagcctagccgg
gtcctcaacgacaggagcacgatcatgcgcacccgtggggccgccatgccggcgataatggcctgcttctcgccgaaac
gtttggtggcgggaccagtgacgaaggcttgagcgagggcgtgcaagattccgaataccgcaagcgacaggccgatca
tcgtcgcgctccagcgaaagcggtcctcgccgaaaatgacccagagcgctgccggcacctgtcctacgagttgcatgat
aaagaagacagtcataagtgcggcgacgatagtcatgccccgcgcccaccggaaggagctgactgggttgaaggctct
caagggcatcggtcgagatcccggtgcctaatgagtgagctaacttacattaattgcgttgcgctcactgcccgctttccagt
cgggaaacctgtcgtgccagctgcattaatgaatcggccaacgcgcggggagaggcggtttgcgtattgggcgccaggg
tggtttttcttttcaccagtgagacgggcaacagctgattgcccttcaccgcctggccctgagagagttgcagcaagcggtcc
acgctggtttgccccagcaggcgaaaatcctgtttgatggtggttaacggcgggatataacatgagctgtcttcggtatc
```

Figure 137I gtcgtatcccactaccgagatatccgcaccaacgcgcagcccggactcggtaatggcgcgcattgcgcccagcgccatc
tgatcgttggcaaccagcatcgcagtgggaacgatgccctcattcagcatttgcatggtttgttgaaaaccggacatggcac
tccagtcgccttcccgttccgctatcggctgaatttgattgcgagtgagatatttatgccagccagccagacgcagacgcgc
cgagacagaacttaatgggcccgctaacagcgcgatttgctggtgacccaatgcgaccagatgctccacgcccagtcgc
gtaccgtcttcatgggagaaaataatactgttgatgggtgtctggtcagagacatcaagaaataacgccggaacattagtg
caggcagcttccacagcaatggcatcctggtcatccagcggatagttaatgatcagcccactgacgcgttgcgcgagaag
attgtgcaccgccgctttacaggcttcgacgccgcttcgttctaccatcgacaccaccacgctggcacccagttgatcggcg
cgagatttaatcgccgcgacaatttgcgacggcgcgtgcagggccagactggaggtggcaacgccaatcagcaacga
ctgtttgcccgccagttgttgtgccacgcggttgggaatgtaattcagctccgccatcgccgcttccacttttcccgcgttttcgc
agaaacgtggctggcctggttcaccacgcgggaaacggtctgataagagacaccggcatactctgcgacatcgtataac
gttactggtttcacattcaccaccctgaattgactctcttccgggcgctatcatgccataccgcgaaaggttttgcgccattcga
tggtgtccgggatctcgacgctctcccttatgcgactcctgcattaggaagcagcccagtagtaggttgaggccgttgagca
ccgccgccgcaaggaatggtgcatgcaaggagatggcgcccaacagtcccccggccacggggcctgccaccatacc
cacgccgaaacaagcgctcatgagcccgaagtggcgagcccgatcttcccatcggtgatgtcggcgatataggcgcc
agcaaccgcacctgtggcgccggtgatgccggccacgatgcgtccggcgtagaggatcgagatctcgatcccgcgaaa
ttaatacgactcactatagggaattgtgagcggataacaattcccctctagaaataattttgtttaactttaagaaggagatat
acatatgcatatgcgttgtagcgtgtccaccgaaaatgtgtctttcaccgaaactgaaaccgaaacgcgtcgttctgcgaac
tacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattga
caacgtccagcgcctgggcctgggttaccgtttcgagtctgatatccgtcgtgcgctggatcgcttcgtttcctccggcggcttc
gatgcggtaaccaagacttccctgcacgcgacggcactgtctttccgtctgctgcgtcaacacggttttgaggtttctcagga
agcgttcagcggcttcaaagaccaaaacggcaacttcctggagaacctgaaggaagatatcaaagctatcctgagcctg
tacgaggccagcttcctggctctggaaggcgaaaacatcctggacgaggcgaaggttttcgcaatctctcatctgaaaga
actgtctgaagaaaagatcggtaaagatctggcagaacaggtgaaccatgcactggaactgccactgcatcgccgtact
cagcgtctggaagcagtactgtctatcgaggcctaccgtaaaaaggaggacgcggatcaggttctgctggagctggcaat
tctggattacaacatgatccagtctgtataccagcgtgatctgcgtgaaacgtcccgttggtggcgtcgtgtgggtctggcga
ccaaactgcactttgctcgtgaccgcctgattgagagcttctactgggccgtgggtgtagcattcgaaccgcaatactccga
ctgccgtaactccgtcgcaaaaatgttttctttcgtaaccattatcgacgatatctacgatgtatacggcaccctggacgaact
ggagctgtttactaacgcagttgagcgttgggacgtaaacgccatcgacgatctgccggattacatgaaactgtgctttctgg
ctctgtataacactattaacgaaatcgcctacgacaacctgaaagaaaaggtgagaacatcctgccgtatctgaccaaa
gcctgggctgacctgtgcaacgctttcctgcaagaagccaagtggctgtacaacaaatctactccgaccttgacgaatact
tcggcaacgcatggaaatcctcttctggcccgctgcaactggtgttcgcttacttcgctgtcgtgcagaacattaaaaagga
agagatcgaaacctgcaaaaataccatgacatcatctctcgtccttcccatatcttccgtctgtgcaatgacctggctagcg
cgtctgcggaaattgcgcgtggtgaaaccgcaaatagcgtttcttgttacatgcgcactaaaggtatctccgaagaactggc
taccgaaagcgtgatgaatctgatcgatgaaacctggaaaaagatgaacaaggaaaaactgggtggtagcctgttcgcg
aaaccgttcgtggaaaccgcgatcaacctggcacgtcaatctcactgcacttatcataacggcgacgcgcatacctctccg
gatgagctgacccgcaaacgcgttctgtctgtaatcactgaaccgattctgccgtttgaacgctaaggatccgaattcgagc
tccgtcgacaagcttgcggccgcactcgagcaccaccaccaccaccactgagatccggctgctaacaaagcccgaaa
ggaagctgagttggctgctgccaccgctgagcaataactagcataacccctggggcctctaaacgggtcttgaggggtttt
ttgctgaaaggaggaactatatccggat (SEQ ID NO:111)

Figure 137J

```
tggcgaatgggacgcgccctgtagcggcgcattaagcgcggcgggtgtggtggttacgcgcagcgtgaccgctacactt
gccagcgccctagcgcccgctcctttcgctttcttcccttcctttctcgccacgttcgccggcttttccccgtcaagctctaaatcg
ggggctcccttlagggttccgatttagtgctttacggcacctcgaccccaaaaaacttgattagggtgatggttcacgtagtgg
gccatcgccctgatagacggttttcgccctttgacgttggagtccacgttcttlaatagtggactcttgttccaaactggaaca
acactcaaccctatctcggtctattcttttgatttataagggattttgccgatttcggcctattggttaaaaaatgagctgatttaac
aaaaatttaacgcgaattttaacaaaatattaacgtttacaatttcaggtggcacttttcggggaaatgtgcgcggaaccccct
atttgtttattttctaaatacattcaaatatgtatccgctcatgaattaattcttagaaaaactcatcgagcatcaaatgaaactg
caatttattcatatcaggattatcaataccatatttttgaaaaagccgtttctgtaatgaaggagaaaactcaccgaggcagtt
ccataggatggcaagatcctggtatcggtctgcgattccgactcgtccaacatcaatacaacctattaatttccctcgtcaa
aaataaggttatcaagtgagaaatcaccatgagtgacgactgaatccggtgagaatggcaaaagtttatgcatttctttcca
gacttgttcaacaggccagccattacgctcgtcatcaaaatcactcgcatcaaccaaaccgttattcattcgtgattgcgcct
gagcgagacgaaatacgcgatcgctgttaaaaggacaattacaaacaggaatcgaatgcaaccggcgcaggaacact
gccagcgcatcaacaatattttcacctgaatcaggatattcttctaatacctggaatgctgttttcccggggatcgcagtggtg
agtaaccatgcatcatcaggagtacggataaaatgcttgatggtcggaagaggcataaattccgtcagccagtttagtctg
accatctcatctgtaacatcattggcaacgctacctttgccatgtttcagaaacaactctggcgcatcgggcttcccatacaat
cgatagattgtcgcacctgattgcccgacattatcgcgagcccatttatacccatataaatcagcatccatgttggaatttaat
cgcggcctagagcaagacgtttcccgttgaatatggctcataacaccccttgtattactgtttatgtaagcagacagttttattgt
tcatgaccaaaatcccttaacgtgagttttcgttccactgagcgtcagacccgtagaaaagatcaaaggatcttcttgagat
ccttttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggcgataagt
cgtgtcttaccgggttggactcaagacgatagttaccggataaggcgcagcggtcgggctgaacggggggttcgtgcaca
cagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccagg
gggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctgc
gttatcccctgattctgtggataaccgtattaccgcctttgagtgagctgataccgctcgccgcagccgaacgaccgagcgc
agcgagtcagtgagcgaggaagcggaagagcgcctgatgcggtattttctccttacgcatctgtgcggtatttcacaccgc
atatatggtgcactctcagtacaatctgctctgatgccgcatagttaagccagtatacactccgctatcgctacgtgactgggt
catggctgcgccccgacacccgccaacacccgctgacgcgccctgacgggcttgtctgctcccggcatccgcttacaga
caagctgtgaccgtctccgggagctgcatgtgtcagaggttttcaccgtcatcaccgaaacgcgcgaggcagctgcggta
aagctcatcagcgtggtcgtgaagcgattcacagatgtctgcctgttcatccgcgtccagctcgttgagtttctccagaagcgt
taatgtctggcttctgataaagcgggccatgttaagggcggttttttcctgtttggtcactgatgcctccgtgtaaggggggattct
gttcatgggggtaatgataccgatgaaacgagagaggatgctcacgatacgggttactgatgatgaacatgcccggttact
ggaacgttgtgagggtaaacaactggcggtatggatgcggcgggaccagagaaaaatcactcagggtcaatgccagc
gcttcgttaatacagatgtaggtgttccacagggtagccagcagcatcctgcgatgcagatccggaacataatggtgcagg
gcgctgacttccgcgtttccagactttacgaaacacggaaaccgaagaccattcatgttgttgctcaggtcgcagacgttttg
cagcagcagtcgcttcacgttcgctcgcgtatcggtgattcattctgctaaccagtaaggcaaccccgccagcctagccgg
gtcctcaacgacaggagcacgatcatgcgcacccgtggggccgccatgccggcgataatggcctgcttctcgccgaaac
gtttggtggcgggaccagtgacgaaggcttgagcgagggcgtgcaagattccgaataccgcaagcgacaggccgatca
tcgtcgcgctccagcgaaagcggtcctcgccgaaaatgacccagagcgctgccggcacctgtcctacgagttgcatgat
aaagaagacagtcataagtgcggcgacgatagtcatgccccgcgcccaccggaaggagctgactgggttgaaggctct
caagggcatcggtcgagatcccggtgcctaatgagtgagctaacttacattaattgcgttgcgctcactgcccgctttccagt
cgggaaacctgtcgtgccagctgcattaatgaatcggccaacgcgcggggagaggcggtttgcgtattgggcgccaggg
tggttttcttttcaccagtgagacgggcaacagctgattgcccttcaccgcctggccctgagagagttgcagcaagcggtcc
acgctggtttgccccagcaggcgaaaatcctgtttgatggtggttaacggcgggatataacatgagctgtcttcggtatc
```

Figure 137K gtcgtatcccactaccgagatatccgcaccaacgcgcagcccggactcggtaatggcgcgcattgcgcccagcgccatctg
atcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagac
agaacttaatgggcccgctaacagcgcgatttgctggtgacccaatgcgaccagatgctccacgcccagtcgcgtaccgtctt
catgggagaaaataatactgttgatgggtgtctggtcagagacatcaagaaataacgccggaacattagtgcaggcagcttcc
acagcaatggcatcctggtcatccagcggatagttaatgatcagcccactgacgcgttgcgcgagaagattgtgcaccgccg
ctttacaggcttcgacgccgcttcgttctaccatcgacaccaccacgctggcacccagttgatcggcgcgagatttaatcgccg
cgacaatttgcgacggcgcgtgcagggccagactggaggtggcaacgccaatcagcaacgactgtttgcccgccagttgttg
tgccacgcggttgggaatgtaattcagctccgccatcgccgcttccacttttttcccgcgttttcgcagaaacgtggctggcctggtt
caccacgcgggaaacggtctgataagagacaccggcatactctgcgacatcgtataacgttactggtttcacattcaccaccct
gaattgactctcttccgggcgctatcatgccataccgcgaaaggttttgcgccattcgatggtgtccgggatctcgacgctctccct
tatgcgactcctgcattaggaagcagcccagtagtaggttgaggccgttgagcaccgccgccgcaaggaatggtgcatgcaa
ggagatggcgcccaacagtcccccggccacggggcctgccaccatacccacgccgaaacaagcgctcatgagcccgaa
gtggcgagcccgatcttccccatcggtgatgtcggcgatataggcgccagcaaccgcacctgtggcgccggtgatgccggcc
acgatgcgtccggcgtagaggatcgagatctcgatcccgcgaaattaatacgactcactatagggggaattgtgagcggataa
caattcccctctagaaataattttgtttaactttaagaaggagatatacatatgtgctctgtttctaccgagaacgtttccttcactgag
acggaaaccgaggcacgtcgtagcgcgaactacgagccgaatagctgggactacgatttcctgctgtcttccgatactgacg
aatctattgaggtgtacaaagacaaagcaaagaaactggaggctgaagtgcgccgcgaaattaacaacgagaaagctga
attcctgactctgctggagctgatcgataacgtacagcgcctgggtctgggttaccgcttcgaatctgatatccgtcgcgcactgg
atcgtttcgtaagcagcggcggtttcgatggcgtgaccaaaacgagcctgcacgctaccgcgctgtccttccgtctgctgcgtca
gcacggcttcgaagtttctcaggaagcattctccggtttcaaagatcaaaacggtaacttcctggaaaacctgaaagaagaca
ctaaggcgatcctgagcctgtatgaggcaagctttctggccctggagggtgagaacatcctggatgaggcgcgcgtattctcca
tctcccatctgaaagagctgtctgaagagaaaatcggtaaggaactggcagagcaggttaatacgcactggaactgccgct
gcatcgtcgtacccagcgtctggaggcggtttggtccatcgaagcgtaccgcaaaaaggaggatgctaaccaggttctgctgg
aactggccatcctggactacaacatgatccagtccgtttaccagcgtgatctgcgtgaaacctcccgttggtggcgccgtgtgg
gcctggcgaccaaaactgcacttcgctaaggaccgcctgattgagtcttttttactgggcagtcggcgttgcgttcgaacctcagtat
tctgactgccgtaacagcgttgcgaaaatgttcagcttcgttactattatcgacgacatctacgacgtttacggtactctggacgag
ctggaactgtttaccgacgctgtcgaacgttgggatgttaacgccatcaacgatctgcctgactacatgaaactgtgcttcctggc
actgtataacacgatcaacgaaattgcatacgacaacctgaaagacaaaggtgaaaacatcctgccgtacctgactaaagc
gtgggcggatctgtgtaacgcttttctgcaagaagcgaaatggctgtataacaaatccactccgacctttgacgattatttcggca
atgcctggaaatccagctctggcccgctgcaactgatcttcgcttattttgcggttgtccaaaacatcaaaaaggaggaaattga
aaacctgcaaaaataccacgatatcattagccgtccttctcatatctttcgcctgtgcaacgacctggcaagcgcgtccgcaga
gatcgcacgtggcgaaaccgctaactctgtttcctgctacatgcgcaccaagggcatttccgaagagctggcaaccgagagc
gtaatgaatctgatcgacgaaacctgtaagaaaatgaacaaagaaaaactgggtggctccctgttcgctaaaccgttcgtaga
gactgctattaacctggcacgtcagagccactgcacctaccacaatggtgacgcacatactagcccggatgaactgactcgta
aacgtgtactgtctgttataccgaaccgattctgccgttcgaacgttaactgcagctggtaggatccgaattcgagctccgtcga
caagcttgcggccgcactcgagcaccaccaccaccaccactgagatccggctgctaacaaagcccgaaaggaagctgag
ttggctgctgccaccgctgagcaataactagcataaccccttggggcctctaaacgggtcttgaggggttttttgctgaaaggag
gaactatatccggat (SEQ ID NO:112)

Figure 137M aagggcgaatactgcagatatccatcacactggcggccgctcgagcatgcatctagagggcccaattcgccctatagtgagtcgt
attacaattcactggccgtcgttttacaacgtcgtgactgggaaaaccctggcgttacccaacttaatcgccttgcagcacatccccc
tttcgccagctggcgtaatagcgaagaggcccgcaccgatcgcccttcccaacagttgcgcagcctgaatggcgaatggacgcg
ccctgtagcggcgcattaagcgcggcgggtgtggtggttacgcgcagcgtgaccgctacacttgccagcgccctagcgcccgctc
ctttcgctttcttcccttccttttctcgccacgttcgccggctttccccgtcaagctctaaatcgggggctcccttttagggttccgatttagtgc
tttacggcacctcgaccccaaaaaacttgattagggtgatggttcacgtagtgggccatcgccctgatagacggtttttcgccctttga
cgttggagtccacgttctttaatagtggactcttgttccaaactggaacaacactcaaccctatctcggtctattcttttgatttataaggg
attttgccgatttcggcctattggttaaaaaatgagctgatttaacaaaaatttaacgcgaattttaacaaaattcagggcgcaagggc
tgctaaaggaagcggaacacgtagaaagccagtccgcagaaacggtgctgaccccggatgaatgtcagctactgggctatctg
gacaagggaaaacgcaagcgcaaagagaaagcaggtagcttgcagtgggcttacatggcgatagctagactgggcggttttat
ggacagcaagcgaaccggaattgccagctggggcgccctctggtaaggttgggaagccctgcaaagtaaactggatggctttctt
gccgccaaggatctgatggcgcaggggatcaagatctgatcaagagacaggatgaggatcgtttcgcatgattgaacaagatgg
attgcacgcaggttctccggccgcttgggtggagaggctattcggctatgactgggcacaacagacaatcggctgctctgatgccg
ccgtgttccggctgtcagcgcaggggcgcccggttcttttgtcaagaccgacctgtccggtgccctgaatgaactgcaggacgag
gcagcgcggctatcgtggctggccacgacgggcgttccttgcgcagctgtgctcgacgttgtcactgaagcgggaagggactggc
tgctattgggcgaagtgccggggcaggatcCcctgtcatcccaccttgctcctgccgagaaagtatccatcatggctgatgcaatg
cggcggctgcatacgcttgatccggctacctgcccattcgaccaccaagcgaaacatcgcatcgagcgagcacgtactcggatg
gaagccggtcttgtcgatcaggatgatctggacgaagagcatcaggggctcgcgccagccgaactgttcgccaggctcaaggc
gcgcatgcccgacggcgaggatctcgtcgtgacccatggcgatgcctgcttgccgaatatcatggtggaaaatggccgcttttctgg
attcatcgactgtggccggctgggtgtggcggaccgctatcaggacatagcgttggctacccgtgatattgctgaagagcttggcgg
cgaatgggctgaccgcttcctcgtgctttacggtatcgccgctcccgattcgcagcgcatcgccttctatcgccttcttgacgagttcttc
tgaattgaaaaaggaagagtatgagtattcaacatttccgtgtcgcccttattccctttttgcggcattttgccttcctgttttgctcaccc
agaaacgctggtgaaagtaaaagatgctgaagatcagttgggtgcacgagtgggttacatcgaactggatctcaacagcggtaa
gatccttgagagttttcgccccgaagaacgttttccaatgatgagcacttttaaagttctgctatgtggcgcggtattatcccgtattgac
gccgggcaagagcaactcggtcgccgcatacactattctcagaatgacttggttgagtactcaccagtcacagaaaagcatcttac
ggatggcatgacagtaagagaattatgcagtgctgccataaccatgagtgataacactgcggccaacttacttctgacaacgatcg
gaggaccgaaggagctaaccgcttttttgcacaacatgggggatcatgtaactcgccttgatcgttgggaaccggagctgaatga
agccataccaaacgacgagcgtgacaccacgatgcctgtagcaatggcaacaacgttgcgcaaactattaactggcgaactact
tactctagcttcccggcaacaattaatagactggatggaggcggataaagttgcaggaccacttctgcgctcggcccttccggctgg
ctggtttattgctgataaatctggagccggtgagcgtgggtctcgcggtatcattgcagcactggggccagatggtaagccctcccgt
atcgtagttatctacacgacggggagtcaggcaactatggatgaacgaaatagacagatcgctgagataggtgcctcactgatta
agcattggtaactgtcagaccaagtttactcatatatactttagattgatttaaaacttcattttttaatttaaaaggatctaggtgaagatcc
ttttgataatctcatgaccaaaatcccttaacgtgagttttcgttccactgagcgtcagaccccgtagaaaagatcaaaggatcttctt
gagatcctttttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgttcttctagtgtagccgtagttaggccaccactt
caagaactctgtagcaccgcctacatacctcgctctgctaatcctgttaccagtggctgctgccagtggcgataagtcgtgtcttacc
gggttggactcaagacgatagttaccggataaggcgcagcggtcgggctgaacggggggttcgtgcacacagcccagcttgga
gcgaacgacctacaccgaactgagatacctacagcgtgagctatgagaaagcgccacgcttcccgaagggagaaaggcgga
caggtatccggtaagcggcagggtcggaacaggagagcgcacgagggagcttccaggggaaacgcctggtatctttatagtc
ctgtcgggtttcgccacctctgacttgagcgtcgatttttgtgatgctcgtcaggggggcggagcctatggaaaaacgccagcaacg
cggcctttttacggttcctggccttttgctggccttttgctcacatgttctttcctgcgttatcccctgattctgtggataaccgtattaccgcct
ttgagtgagctgataccgctcgccgcagccgaacgaccgagcgcagcgagtcagtgagcgaggaagcggaagagcgccca
atacgcaaaccgcctctccccgcgcgttggccgattcattaatgcagctggcacgacaggtttcccgactggaaagcgggcagtg
agcgcaacgcaattaatgtgagttagctcactcattaggcaccccaggctttacactttatgcttccggctcgtatgttgtgtggaattgt
gagcggataacaatttcacacaggaaacagctatgaccatgattacgccaagcttggtaccgagctcggatccactagtaacgg
ccgccagtgtgctggaattcgcccttgatcatgcattcgcccttaggaggtaaaaaaacatgtgtgcgacctcttctcaatttactcag
attaccgagcataattcccgtcgttccgcaaactatcagccaaacctgtggaatttcgaattcctgcaatccctggagaacgacctg

Figure 137N

```
aaagtggaaaagctggaggagaaagcgaccaaactggaggaagaagttcgctgcatgatcaaccgtgtagacaccca
gccgctgtccctgctggagctgatcgacgatgtgcagcgcctgggtctgacctacaaatttgaaaaagacatcatta
aagccctggaaaacatcgtactgctggacgaaaacaaaaagaacaaatctgacctgcacgcaaccgctctgtctttc
cgtctgctgcgtcagcacggtttcgaggtttctcaggatgtttttgagcgtttcaaggataaagaaggtggtttcag
cggtgaactgaaaggtgacgtccaaggcctgctgagcctgtatgaagcgtcttacctgggtttcgagggtgagaacc
tgctggaggaggcgcgtaccttttccatcacccacctgaagaacaacctgaaagaaggcattaataccaaggttgca
gaacaagtgagccacgccctggaactgccatatcaccagcgtctgcaccgtctggaggcacgttggttcctggataa
atacgaaccgaaagaaccgcatcaccagctgctgctggagctggcgaagctggattttaacatggtacagaccctgc
accagaaagagctgcaagatctgtcccgctggtggaccgagatgggcctggctagcaaactggattttgtacgcgac
cgcctgatggaagtttatttctgggcactgggtatggcgccagacccgcagtttggtgaatgtcgcaaagctgttac
taaaatgtttggtctggtgacgatcatcgatgacgtgtatgacgtttatggcactctggacgaactgcaactgttca
ccgatgctgtagagcgctgggacgttaacgctattaacaccctgccggactatatgaaactgtgtttcctggcactg
tacaacaccgttaacgacacgtcctattctattctgaaagagaaaggtcataacaacctgtcctatctgacgaaaag
ctggcgtgaactgtgcaaagccttctctgcaagaggcgaaatggtccaacaacaaaattatcccggctttctccaagt
acctggaaaacgccagcgtttcctcctccggtgtagcgctgctggcgccgtcttacttttccgtatgccagcagcag
gaagacatctccgaccacgcgctgcgttccctgaccgacttccatggtctggtgcgttctagctgcgttatcttccg
cctgtgcaacgatctggccacctctgcggcggagctggaacgtggcgagactaccaattctatcattagctacatgc
acgaaaacgatggtaccagcgaggaacaggcccgcgaagaactgcgtaaactgatcgacgccgaatggaaaaagatg
aatcgtgaacgcgttagcgactccaccctgctgcctaaagcgttcatggaaatcgcagttaacatggcacgtgtttc
ccactgcacctaccagtatggcgatggtctgggtcgcccagactacgcgactgaaaaccgcatcaaactgctgctga
ttgaccctttcccgattaaccagctgatgtatgtctaactgcagggatccgtcgaccg
```

(SEQ ID NO:113)

Figure 137P

```
pET24D-Kudzu                Kudzu IspS ORF 48-1742 (complementary)
gtgcggccgcaagcttgtcgacggagctcgaattcggatccctgcagttagacatacatcagctggttaatcgggaa
agggtcaatcagcagcagtttgatgcggttttcagtcgcgtagtctgggcgacccagaccatcgccatactggtagg
tgcagtgggaaacacgtgccatgttaactgcgatttccatgaacgctttaggcagcagggtggagtcgctaacgcgt
tcacgattcatcttttccattcggcgtcgatcagtttacgcagttcttcgcgggcctgttcctcgctggtaccatc
gttttcgtgcatgtagctaatgatagaattggtagtctcgccacgttccagctccgccgcagaggtggccagatcgt
tgcacaggcggaagataacgcagctagaacgcaccagaccatggaagtcggtcagggaacgcagcgcgtggtcggag
atgtcttcctgctgctggcatacggaaaagtaagacggcgccagcagcgctacaccggaggaggaaacgctggcgtt
ttccaggtacttggagaaagccgggataattttgttgttggaccatttcgcctcttgcagaaaggctttgcacagtt
cacgccagcttttcgtcagataggacaggttgttatgacctttctctttcagaatagaataggacgtgtcgttaacg
gtgttgtacagtgccaggaaacacagtttcatatagtccggcagggtgttaatagcgttaacgtcccagcgctctac
agcatcggtgaacagttgcagttcgtccagagtgccataaacgtcatacacgtcatcgatgatcgtcaccagaccaa
acatttagtaacagctttgcgacattcaccaaactgcgggtctggcgccataccccagtgcccagaaataaacttcc
atcaggcggtcgcgtacaaaatccagtttgctagccaggcccatctcggtccaccagcgggacagatcttgcagctc
tttctggtgcagggtctgtaccatgttaaaaatccagcttcgccagctccagcagcagctggtgatgcggttctttcg
gttcgtatttatccaggaaccaacgtgcctccagacggtgcagacgctggtgatatggcagttccagggcgtggctc
acttgttctgcaaccttggtattaatgccttcttttcaggttgttcttcaggtgggtgatggaaaaggtacgcgcctc
ctccagcaggttctcaccctcgaaacccaggtaagacgcttcatacaggctcagcaggccttggacgtcaccttca
gttcacgctgaaaccaccttctttatccttgaaacgctcaaaaacatcctgagaaacctcgaaaccgtgctgacgc
agcagacggaaagacagagcggttgcgtgcaggtcagatttgttcttttttgttttcgtccagcagtacgatgttttc
cagggctttaatgatgtcttttcaaatttgtaggtcagacccaggcgctgcacatcgtcgatcagctccagcaggg
acagcggctgggtgtctacacggttgatcatgcagcgaacttcttcctccagtttggtcgctttctcctccagctt
tccactttcaggtcgttctccaggattgcaggaattcgaaattccacaggtttggctgatagtttgcggaacgacg
ggaattatgctcggtaatctgagtaaattgagaagaggtcgcacacatggtatatctccttcttaaagttaaacaaa
attatttctagaggggaattgttatccgctcacaattcccctatagtgagtcgtattaatttcgcgggatcgagatc
tcgatcctctacgccggacgcatcgtggccggcatcaccggcgccacaggtgcggttgctggcgcctatatcgccga
catcaccgatggggaagatcgggctcgccacttcgggctcatgagcgcttgttcggcgtgggtatggtggcaggcc
ccgtggccgggggactgttgggcgccatctccttgcatgcaccattccttgcggcggcggtgctcaacggcctcaac
ctactactgggctgcttcctaatgcaggagtcgcataagggagagcgtcgagatcccggacaccatcgaatggcgca
aaacctttcgcggtatggcatgatagcgcccgaagagagtcaattcagggtggtgaatgtgaaaccagtaacgtta
tacgatgtcgcagagtatgccggtgtctcttatcagaccgtttcccgcgtggtgaaccaggccagccacgtttctgc
gaaaacgcgggaaaaagtggaagcggcgatggcggagctgaattacattcccaaccgcgtggcacaacaactggcgg
gcaaacagtcgttgctgattggcgttgccacctccagtctggccctgcacgcgcgtcgcaaattgtcgcggcgatt
aaatctcgcgccgatcaactgggtgccagcgtggtggtgtcgatggtagaacgaagcggcgtcgaagcctgtaaagc
ggcggtgcacaatcttctcgcgcaacgcgtcagtgggctgatcattaactatccgctggatgaccaggatgccattg
ctgtggaagctgcctgcactaatgttccggcgttatttcttgatgtctctgaccagacacccatcaacagtattatt
ttctcccatgaagacggtacgcgactgggcgtggagcatctggtcgcattgggtcaccagcaaatcgcgctgttagc
gggcccattaagttctgtctcggcgcgtctgcgtctggctggctggcataaatatctcactcgcaatcaaattcagc
cgatagcggaacgggaaggcgactggagtgccatgtccggttttcaacaaaccatgcaaatgctgaatgagggcatc
gttccactgcgatgctggttgcaacgatcagatggcgctgggcgcaatgcgcgccattaccgagtccgggctgcg
cgttggtgcggatatctcggtagtgggatacgacgataccgaagacagctcatgttatatcccgccgttaaccacca
tcaaacaggattttcgcctgctggggcaaaccagcgtggaccgcttgctgcaactctctcagggccaggcggtgaag
ggcaatcagctgttgcccgtctcactggtgaaaagaaaaaccaccctggcgcccaatacgcaaaccgcctctcccg
cgcgttggccgattcattaatgcagctggcacgacaggtttcccgactggaaagcgggcagtgagcgcaacgcaatt
aatgtaagttagctcactcattaggcaccgggatctcgaccgatgcccttgagagccttcaacccagtcagctcctt
ccggtgggcgcggggcatgactatcgtcgccgcacttatgactgtcttctttatcatgcaactcgtaggacaggtgc
cggcagcgctctgggtcattttcggcgaggaccgctttcgctggagcgcgacgatgatcggcctgtcgcttgcggta
ttcggaatcttgcacgccctcgctcaagccttcgtcactggtcccgccaccaaacgtttcggcgagaagcaggccat
tatcgccggcatggcggccccacgggtgcgcatgatcgtgctcctgtcgttgaggacccggctaggctggcggggtt
gccttactggttagcagaatgaatcaccgatacgcgagcgaacgtgaagcgactgctgctgcaaaacgtctgcgacc
tgagcaacaacatgaatggcttcggtttccgtgtttcgtaaagtctgaaacgcggaagtcagcgccctgcaccat
tatgttccggatctgcatcgcaggatgctgctggctaccctgtggaacacctacatctgtattaacgaagcgctggc
attgaccctgagtgattttctctggtcccgccgcatccataccgccagttgtttaccctcacaacgttccagtaac
cgggcatgttcatcatcagtaacccgtatcgtgagcatcctctctcgtttcatcggtatcattaccccatgaacag
```

Figure 137Q

```
aaatcccccttacacggaggcatcagtgaccaaacaggaaaaaaccgcccttaacatggcccgctttatcagaagcc
agacattaacgcttctggagaaactcaacgagctggacgcggatgaacaggcagacatctgtgaatcgcttcacgac
cacgctgatgagctttaccgcagctgcctcgcgcgtttcggtgatgacggtgaaaacctctgacacatgcagctccc
ggagacggtcacagcttgtctgtaagcggatgccgggagcagacaagcccgtcagggcgcgtcagcgggtgttggcg
ggtgtcggggcgcagccatgacccagtcacgtagcgatagcggagtgtatactggcttaactatgcggcatcagagc
agattgtactgagagtgcaccatatatgcggtgtgaaataccgcacagatgcgtaaggagaaaataccgcatcaggc
gctcttccgcttcctcgctcactgactcgctgcgctcggtcgttcggctgcggcgagcggtatcagctcactcaaag
gcggtaatacggttatccacagaatcaggggataacgcaggaaagaacatgtgagcaaaaggccagcaaaaggccag
gaaccgtaaaaaggccgcgttgctggcgtttttccataggctccgcccccctgacgagcatcacaaaaatcgacgct
caagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctc
acgctgtaggtatctcagttcggtgtaggtcgttcgctccaagctgggctgtgtgcacgaaccccccgttcagcccg
accgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggcta
cactagaaggacagtatttggtatctgcgctctgctgaagccagttaccttcggaaaaagagttggtagctcttgat
ccggcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcat
gaacaataaaactgtctgcttacataaacagtaatacaaggggtgttatgagccatattcaacgggaaacgtcttgc
tctaggccgcgattaaattccaacatggatgctgatttatatgggtataaatgggctcgcgataatgtcgggcaatc
aggtgcgacaatctatcgattgtatgggaagcccgatgcgccagagttgtttctgaaacatggcaaaggtagcgttg
ccaatgatgttacagatgagatggtcagactaaactggctgacggaatttatgcctcttccgaccatcaagcatttt
atccgtactcctgatgatgcatggttactcaccactgcgatccccgggaaaacagcattccaggtattagaagaata
tcctgattcaggtgaaaatattgttgatgcgctggcagtgttcctgcgccggttgcattcgattcctgtttgtaatt
gtccttttaacagcgatcgcgtatttcgtctcgctcaggcgcaatcacgaatgaataacggtttggttgatgcgagt
gattttgatgacgagcgtaatggctggcctgttgaacaagtctggaaagaaatgcataaacttttgccattctcacc
ggattcagtcgtcactcatggtgatttctcacttgataaccttatttttgacgaggggaaattaataggttgtattg
atgttggacgagtcggaatcgcagaccgataccaggatcttgccatcctatggaactgcctcggtgagttttctcct
tcattacagaaacggctttttcaaaaatatggtattgataatcctgatatgaataaattgcagtttcatttgatgct
cgatgagttttttctaagaattaattcatgagcggatacatatttgaatgtatttagaaaaataaacaaatagggt
ccgcgcacatttcccccgaaaagtgccacctgaaattgtaaacgttaatattttgttaaaattcgcgttaaatttttg
ttaaatcagctcattttttaaccaataggccgaaatcggcaaaatcccttataaatcaaaagaatagaccgagatag
ggttgagtgttgttccagtttggaacaagagtccactattaagaacgtggactccaacgtcaagggcgaaaaacc
gtctatcagggcgatggcccactacgtgaaccatcaccctaatcaagttttttggggtcgaggtgccgtaaagcact
aaatcggaaccctaaagggagccccgatttagagcttgacggggaaagccggcgaacgtggcgagaaaggaaggga
agaaagcgaaaggagcgggcgctagggcgctggcaagtgtagcggtcacgctgcgcgtaaccaccacaccgccgcg
cttaatgcgccgctacagggcgcgtcccattcgccaatccggatatagttcctcctttcagcaaaaaaccctcaag
acccgtttagaggccccaaggggttatgctagttattgctcagcggtggcagcagccaactcagcttcctttcgggc
tttgttagcagccggatctcagtggtggtggtggtggtgctcga
```

(SEQ ID NO:114)

Figure 141 gaattcaaaatgtgtgcaacttcatcccaattcactcaaatcacagagcataattctagacgttcagctaactaccaaccaa
atctgtggaattttgaatttcttcaatcccttgaaaatgatttgaaagtggaaaagttggaggaaaaagccacaaaactaga
ggaagaagttagatgtatgataaacagagtagatacacaacctctgtcactactagaattgattgacgatgtccagaggct
gggtttaacatataagttcgaaaaggatataatcaaagccttagaaaacatagtccttctagatgaaaacaagaagaata
agtctgacttgcacgcaaccgctctgagttttagattgctgagacaacatggttttgaagtaagtcaagatgtgtttgaaaggtt
caaagacaaagagggaggattctcaggagaattaaagggagatgtgcagggtctgttgtcattgtacgaggccagttattt
ggggtttgaaggggaaaatctactagaggaggccagaaccttctctataacccatctgaagaataacttgaaagaaggc
atcaatacaaaagtggctgaacaagtttcacatgcattggaattgccctaccaccaaagacttcatagacttgaagccaga
tggttttggacaagtatgaaccaaaggagcctcaccatcaactttattggaattagcaaaactggattttaacatggttcag
acattacaccagaaagaattgcaggacctatcaagatggtggacggagatgggtttagccagcaagttagatttcgttaga
gatagattgatggaagtttacttttgggcactgggaatggcaccagatcctcaatttggtgaatgtagaaaggcagttacaa
agatgtttggtctagtaacaatcattgatgatgtttatgatgtgtacggaactttggatgaattacaactattcaccgacgcagtt
gaacgttgggatgtaaacgcaataaacacgttgcctgattatatgaagctgtgttttctggcattgtacaacacagtcaatga
cacttcttactccatttaaaggagaaagggcataacaatctatcctatttgacaaaatcatggagggagttatgcaaagcat
tccttcaagaagctaagtggtctaacaataagataatcccagcattctccaagtatcttgaaaacgcttccgtatcctcctccg
gtgtggccctactagcaccatcatattttccgtctgccagcagcaggaagatatctctgatcatgctttgagatccttaacag
attttcatggtctagtcagatcctcttgcgtgattttcagattgtgcaatgatttggctacttcagccgcagagttagagaggggt
gaaaccacgaactcaattattagttatatgcacgagaatgatggaacatccgaagaacaagcccgtgaagaattaagaa
aactgatcgatgctgaatggaagaagatgaatagagaaagagtttccgacagcactttgctgcctaaggcattcatggag
atagctgttaacatggctagggtttcacactgtacataccaatacggggacggtcttggaaggcccgactacgccactgaa
aatagaattaaactgctactgattgatcctttccccattaaccagttaatgtacgtgtaatagggatccgaattc (SEQ ID NO:115)

Figure 142B acggattagaagccgccgagcgggtgacagccctccgaaggaagactctcctccgtgcgtcctcgtcttcaccggtcgcg
ttcctgaaacgcagatgtgcctcgcgccgcactgctccgaacaataaagattctacaatactagctttatggttatgaagag
gaaaaattggcagtaacctggccccacaaaccttcaaatgaacgaatcaaattaacaaccataggatgataatgcgatta
gtttttagccttatttctggggtaattaatcagcgaagcgatgattttgatctattaacagatatataaatgcaaaaactgcata
accactttaactaatactttcaacattttcggtttgtattacttcttattcaaatgtaataaaagtatcaacaaaaaattgttaatata
cctctatactttaacgtcaaggagaaaaaaccccggatcggactactagcagctgtaatacgactcactatagggaatatt
aagctatcaaacaagtttgtacaaaaaagcaggctgaatt<u>caaaatgtgtgcaacttcatcccaattcactcaaatcacag</u>
<u>agcataattctagacgttcagctaactaccaaccaaatctgtggaattttgaatttcttcaatcccttgaaaatgatttgaaagt</u>
<u>ggaaaagttggaggaaaaagccacaaaactagaggaagaagttagatgtatgataaacagagtagatacacaacctc</u>
<u>tgtcactactagaattgattgacgatgtccagaggctggtttaacatataagttcgaaaaggatataatcaaagccttagaa</u>
<u>aacatagtccttctagatgaaaacaagaagaataagtctgacttgcacgcaaccgctctgagttttagattgctgagacaac</u>
<u>atggttttgaagtaagtcaagatgtgtttgaaaggttcaaagacaaagagggaggattctcaggagaattaaagggagat</u>
<u>gtgcagggtctgttgtcattgtacgaggccagttatttggggtttgaaggggaaaatctactagaggaggccagaaccttctc</u>
<u>tataacccatctgaagaataacttgaaagaaggcatcaatacaaaagtggctgaacaagtttcacatgcattggaattgcc</u>
<u>ctaccaccaaagacttcatagacttgaagccagatggttttggacaagtatgaaccaaaggagcctcaccatcaactttta</u>
<u>ttggaattagcaaaactggatttaacatggttcagacattacaccagaaagaattgcaggacctatcaagatggtggacg</u>
<u>gagatgggtttagccagcaagttagatttcgttagagatagattgatggaagtttactttttgggcactgggaatggcaccaga</u>
<u>tcctcaatttggtgaatgtagaaaggcagttacaaagatgtttggtcagtaacaatcattgatgatgtttatgatgtgtacgga</u>
<u>actttggatgaattacaactattcaccgacgcagttgaacgttgggatgtaaacgcaataaacacgttgcctgattatatgaa</u>
<u>gctgtgttttctggcattgtacaacacagtcaatgacacttcttactccattttaaaggagaaagggcataacaatctatcctatt</u>
<u>tgacaaaatcatggaggggagttatgcaaagcattccttcaagaagctaagtggtctaacaataagataatcccagcattct</u>
<u>ccaagtatcttgaaaacgcttccgtatcctcctccggtgtggccctactagcaccatcatatttttccgtctgccagcagcagg</u>
<u>aagatatctctgatcatgctttgagatccttaacagattttcatggtctagtcagatcctcttgcgtgattttcagattgtgcaatga</u>
<u>tttggctacttcagccgcagagttagagaggggtgaaaccacgaactcaattattagttatatgcacgagaatgatggaac</u>
<u>atccgaagaacaagcccgtgaagaattaagaaaactgatcgatgctgaatggaagaagatgaatagagaaagagtttc</u>
<u>cgacagcactttgctgcctaaagcattcatggagatagctgttaacatggctagggtttcacactgtacataccaatacggg</u>
<u>gacggtcttggaaggcccgactacgccactgaaaatagaattaaactgctactgattgatcctttccccattaaccagttaat</u>
<u>gtacgtgtaataggg</u>atccgaattcacccagctttcttgtacaaagtggttcgatctagagggcccttcgaaggtaagcctat
ccctaaccctctcctcggtctcgattctacgcgtaccggtcatcatcaccatcaccattgagtttaaacccgctgatcctagag
ggccgcatcatgtaattagttatgtcacgcttacattcacgccctccccccacatccgctctaaccgaaaaggaaggagtta
gacaacctgaagtctaggtccctatttatttttttatagttatgttagtattaagaacgttatttatatttcaaattttttcttttttctgtac
agacgcgtgtacgcatgtaacattatactgaaaaccttgcttgagaaggttttgggacgctcgaaggctttaatttgcaagct
gcggccctgcattaatgaatcggccaacgcgcggggagaggcggtttgcgtattgggcgctcttccgcttcctcgctcactg
actcgctgcgctcggtcgttcggctgcggcgagcggtatcagctcactcaaaggcggtaatacggttatccacagaatcag
gggataacgcaggaaagaacatgtgagcaaaaggccagcaaaagcccaggaaccgtaaaaaggccgcgttgctgg
cgttttccataggctccgcccccctgacgagcatcacaaaaatcgacgctcaagtcagaggtggcgaaacccgacagg
actataaagataccaggcgtttccccctggaagctccctcgtgcgctctcctgttccgaccctgccgcttaccggatacctgt
ccgcctttctcccttcgggaagcgtggcgctttctcatagctcacgctgtaggtatctcagttcggtgtaggtcgttcgctccaa
gctgggctgtgtgcacgaaccccccgttcagcccgaccgctgcgccttatccggtaactatcgtcttgagtccaacccggta
agacacgacttatcgccactggcagcagccactggtaacaggattagcagagcgaggtatgtaggcggtgctacagagt
tcttgaagtggtggcctaactacggctacactagaaggacagtatttggtatctgcgctctgctgaagccagttaccttcgga
aaaagagttggtagctcttgatccggcaaacaaaccaccgctggtagcggtggtttttttgtttgcaagcagcagattacgcg
cagaaaaaaaggatctcaagaagatcctttgatcttttctacggggtctgacgctcagtggaacgaaaactcacgttaagg
gattttggtcatgagattatcaaaaaggatcttcacctagatccttttaaattaaaaatgaagttttaaatcaatctaaagtatat
atgagtaaacttggtctgacagttaccaatgcttaatcagtgaggcacctatctcagcgatctgtctatttcgttcatccatagtt
gcctgactccccgtcgtgtagataactacgatacgggagcgcttaccatcggccccagtgctgcaatgataccgcgaga
cccacgctcaccggctccagatt

Figure 142C tatcagcaataaaccagccagccggaagggccgagcgcagaagtggtcctgcaactttatccgcctccatccagtctattaattg
ttgccgggaagctagagtaagtagttcgccagttaatagtttgcgcaacgttgttggcattgctacaggcatcgtggtgtcactctcg
tcgtttggtatggcttcattcagctccggttcccaacgatcaaggcgagttacatgatcccccatgttgtgcaaaaaagcggttagct
ccttcggtcctccgatcgttgtcagaagtaagttggccgcagtgttatcactcatggttatggcagcactgcataattctcttactgtca
tgccatccgtaagatgcttttctgtgactggtgagtactcaaccaagtcattctgagaatagtgtatgcggcgaccgagttgctcttgc
ccggcgtcaatacgggataatagtgtatcacatagcagaactttaaaagtgctcatcattggaaaacgttcttcggggcgaaaac
tctcaaggatcttaccgctgttgagatccagttcgatgtaacccactcgtgcacccaactgatcttcagcatcttttactttcaccagc
gtttctgggtgagcaaaaacaggaaggcaaaatgccgcaaaaagggaataagggcgacacggaaatgttgaatactcata
ctcttccttttcaatgggtaataactgatataattaaattgaagctctaatttgtgagtttagtatacatgcatttacttataatacagtttttt
agttttgctggccgcatcttctcaaatatgcttcccagcctgcttttctgtaacgttcaccctctaccttagcatcccttcccttttgcaaata
gtcctcttccaacaataataatgtcagatcctgtagagaccacatcatccacggttctatactgttgacccaatgcgtctcccttgtca
tctaaacccacaccgggtgtcataatcaaccaatcgtaaccttcatctcttcacccatgtctctttgagcaataaagccgataaca
aaatctttgtcgctcttcgcaatgtcaacagtacccttagtatattctccagtagatagggagcccttgcatgacaattctgctaacat
caaaaggcctctaggttcctttgttacttcttctgccgcctgcttcaaaccgctaacaatacctgggcccaccacaccgtgtgcattc
gtaatgtctgcccattctgctattctgtatacacccgcagagtactgcaatttgactgtattaccaatgtcagcaaattttctgtcttcga
agagtaaaaaattgtacttggcggataatgcctttagcggcttaactgtgccctccatggaaaaatcagtcaagatatccacatgt
gttttagtaaacaaattttgggacctaatgcttcaactaactccagtaattccttggtggtacgaacatccaatgaagcacacaagt
ttgtttgcttttcgtgcatgatattaaatagcttggcagcaacaggactaggatgagtagcagcacgttccttatatgtagctttcgaca
tgatttatcttcgtttcctgcaggttttgttctgtgcagttgggttaagaatactgggcaatttcatgtttcttcaacactacatatgcgtata
tataccaatctaagtctgtgctccttccttcgttcttccttctgttcggagattaccgaatcaaaaaaatttcaaagaaaccgaaatca
aaaaaaagaataaaaaaaaaatgatgaattgaattgaaaagctagcttatcgatgataagctgtcaaagatgagaattaattcc
acggactatagactatactagatactccgtctactgtacgatacacttccgctcaggtccttgtcctttaacgaggccttaccactcttt
tgttactctattgatccagctcagcaaaggcagtgtgatctaagattctatcttcgcgatgtagtaaaactagctagaccgagaaag
agactagaaatgcaaaaggcacttctacaatggctgccatcattattatccgatgtgacgctgcagcttctcaatgatattcgaata
cgctttgaggagatacagcctaatatccgacaaactgttttacagatttacgatcgtacttgttacccatcattgaatttgaacatccg
aacctgggagttttccctgaaacagatagtatatttgaacctgtataataatatatagtctagcgctttacggaagacaatgtatgtat
ttcggttcctggagaaactattgcatctattgcataggtaatcttgcacgtcgcatccccggttcatttctgcgtttccatcttgcacttca
atagcatatctttgttaacgaagcatctgtgcttcattttgtagaacaaaaatgcaacgcgagagcgctaattttcaaacaaagaat
ctgagctgcattttacagaacagaaatgcaacgcgaaagcgctatttaccaacgaagaatctgtgcttcattttgtaaaacaaa
aatgcaacgcgacgagagcgctaattttcaaacaaagaatctgagctgcattttacagaacagaaatgcaacgcgagagcg
ctattttaccaacaaagaatctatacttcttttttgttctacaaaaatgcatcccgagagcgctattttctaacaaagcatcttagattac
ttttttctccttgtgcgctctataatgcagtctcttgataacttttgcactgtaggtccgttaaggttagaagaaggctactttggtgtcta
ttttctcttccataaaaaaagcctgactccacttcccgcgttactgattactagcgaagctgcgggtgcattttttcaagataaaggc
atccccgattatattctataccgatgtggattgcgcatactttgtgaacagaaagtgatagcgttgatgattcttcattggtcagaaaat
tatgaacggtttcttctattttgtctctatatactacgtataggaaatgtttacattttcgtattgttttcgattcactctatgaatagttcttacta
caatttttttgtctaaagagtaatactagagataaacataaaaaatgtagaggtcgagtttagatgcaagttcaaggagcgaaag
gtggatgggtaggttatataggatatagcacagagatatatagcaaagagatacttttgagcaatgtttgtggaagcggtattcg
caatgggaagctccaccccggttgataatcagaaaagccccaaaaacaggaagattgtataagcaaatatttaaattgtaaac
gttaatattttgttaaaattcgcgttaaattttgttaaatcagctcattttttaacgaatagcccgaaatcggcaaaatcccttataaatc
aaaagaatagaccgagatagggttgagtgttgttccagtttccaacaagagtccactattaaagaacgtggactccaacgtcaa
agggcgaaaaggtctatcagggcgatggcccactacgtgaaccatcaccctaatcaagttttttggggtcgaggtgccgtaa
agcagtaaatcggaagggtaaacggatgcccccatttagagcttgacggggaaagccggcgaacgtggcgagaaaggaag
ggaagaaagcgaaaggagcgggggctagggcggtgggaagtgtaggggtcacgctgggcgtaaccaccacacccgccg
cgcttaatggggcgctacagggcgcgtggggatgatccactagt (SEQ ID NO:119)

Figure 144
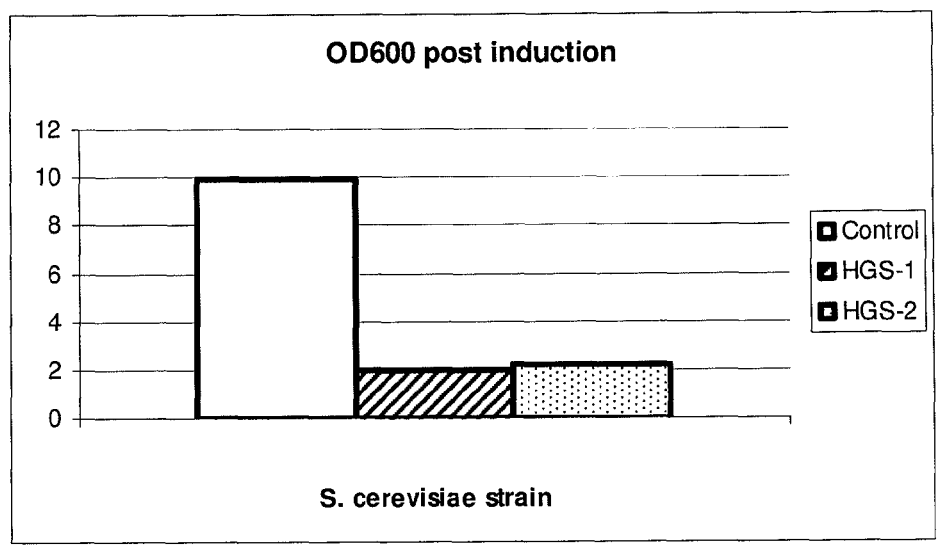
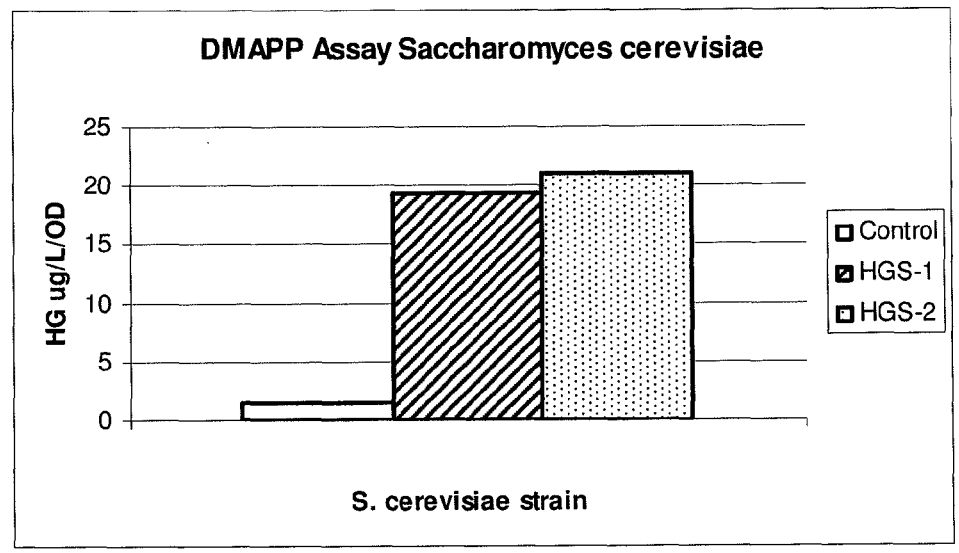

HGS opt Pseudo fluo2-2 with Rest sites
1746 bp

Figure 145B catcttaagcttgtttaactttaagaaggagatatacatatgtgcgccaccagcagccagttcacccagatcaccgagcat
aatagccgtcggtccgcgaactaccagcccaacctgtggaacttcgagttcctgcagagcctggaaaacgacctgaag
gtggagaagctcgaagagaaggccaccaagctggaggaggaggtgcgttgcatgatcaaccgggtggacacccag
cccctgagcctgctggagctcatcgacgacgtgcagcgcctgggcctgacctacaagtttgagaaagatatcatcaag
gcgctggagaacatcgtcctgctggacgagaataagaagaacaaaagcgatctgcacgcgaccgccctgagcttcc
gcctgctgcggcagcatggctttgaggtgagccaggacgtgttcgagcgcttcaaggacaaagaagggggcttctccg
gggaactgaagggtgacgtgcagggcctgctgagcctgtacgaggccagctatctcggtttcgaaggcgaaaatctgct
ggaggaggcccgtaccttcagcatcacccatctgaagaacaacctcaaggaggggatcaacacgaaggtggccga
gcaggtgtcccacgcgctggagctgccgtatcatcaacgcctgcaccgcctggaggcgcggtggttctggacaagtac
gaacccaaggagccgcatcaccagctgctgctggaactggccaaactcgatttcaacatggtccagaccctgcacca
aaaagagctgcaggacctgagccggtggtggaccgagatgggcctcgccagcaagctggatttcgtgcgggaccgc
ctgatggaagtgtacttctgggcgctgggcatggcgccggacccgcagttcggcgaatgccgcaaggccgtcaccaa
gatgttcggtctggtcaccattatcgatgacgtctatgacgtgtacggtaccctggacgaactgcagctcttcaccgacgc
ggtggaacgctgggacgtgaacgccatcaacacgctgcccgactatatgaagctgtgcttcctggccctgtacaacacc
gtgaacgacacgtcctactccatcctgaaggagaagggccacaataacctgagctatctgaccaaaagctggcgcga
actgtgcaaggccttcctgcaagaagccaagtggagcaataacaagatcatccccgccttcagcaagtacctggaga
acgccagcgtgtcctccagcggggtcgcgctgctggcgccgagctacttctcggtctgccagcagcaggaagatatctc
ggaccacgccctccgctccctgaccgacttccacggcctggtgcgctcgtcctgcgtgatctttcggctgtgcaacgatct
ggcgacctcggcggcggaactcgaacgcggcgaaaccaccaacagcatcatcagctacatgcacgagaacgacg
gcacgagcgaggaacaggcccgcgaagagctgcgcaagctgatcgacgccgagtggaagaaaatgaaccgcga
gcgcgtgtcggacagcaccctgctgccgaaggcgttcatggagatcgccgtgaacatggcccgcgtgagccactgca
cctaccaatatggggacgggctggccgcccggattacgccaccgagaaccgcatcaagctgctgctcatcgacccg
ttccccatcaaccagctgatgtacgtgtgaggatcccgtaac (SEQ ID NO:120)

Figure 146B ctcgggccgtctcttgggcttgatcggccttcttgcgcatctcacgcgctcctgcggcggcctgtagggcaggctcataccccctgcc
gaaccgcttttgtcagccggtcggccacggcttccggcgtctcaacgcgctttgagattcccagcttttcggccaatccctgcggtg
cataggcgcgtggctcgaccgcttgcgggctgatggtgacgtggcccactggtggccgctccagggcctcgtagaacgcctga
atgcgcgtgtgacgtgccttgctgccctcgatgccccgttgcagccctagatcggccacagcggccgcaaacgtggtctggtcg
cgggtcatctgcgctttgttgccgatgaactccttggccgacagcctgccgtcctgcgtcagcggcaccacgaacgcggtcatgt
gcgggctggtttcgtcacggtggatgctggccgtcacgatgcgatccgccccgtacttgtccgccagccacttgtgcgccttctcg
aagaacgccgcctgctgttcttggctggccgacttccaccattccgggctggccgtcatgacgtactcgaccgccaacacagcgt
ccttgcgccgcttctctggcagcaactcgcgcagtcggcccatcgcttcatcggtgctgctggccgcccagtgctcgttctctggcg
tcctgctggcgtcagcgttgggcgtctcgcgctcgcggtaggcgtgcttgagactggccgccacgttgcccattttcgccagcttctt
gcatcgcatgatcgcgtatgccgccatgcctgccccctcccttttggtgtccaaccggctcgacgggggcagcgcaaggcggtgc
ctccggcgggccactcaatgcttgagtatactcactagactttgcttcgcaaagtcgtgaccgcctacggcggctgcggcgccct
acggggcttgctctccgggcttcgccctgcgcggtcgctgcgctcccttgccagcccgtggatatgtggacgatggccgcgagcg
gccaccggctggctcgcttcgctcggcccgtggacaaccctgctggacaagctgatggacaggctgcgcctgcccacgagctt
gaccacagggattgcccaccggctacccagccttcgaccacatacccaccggctccaactgcgcggcctgcggccttgcccc
atcaatttttttaattttctctggggaaaagcctccggcctgcggcctgcgcgcttcgcttgccggttggacaccaagtggaaggcg
ggtcaaggctcgcgcagcgaccgcgcagcggcttggccttgacgcgcctggaacgacccaagcctatgcgagtgggggcag
tcgaaggcgaagcccgcccgcctgcccccccgagcctcacggcggcgagtgcggggggttccaagggggcagcgccaccttg
ggcaaggccgaaggccgcgcagtcgatcaacaagcccggaggggccacttttttgccggaggggggagccgcgccgaagg
cgtgggggaaccccgcaggggtgcccttctttgggcaccaaagaactagatatagggcgaaatgcgaaagacttaaaaatca
acaacttaaaaaagggggggtacgcaacagctcattgcggcacccccccgcaatagctcattgcgtaggttaaagaaaatctgta
attgactgccacttttacgcaacgcataattgttgtcgcgctgccgaaaagttgcagctgattgcgcatggtgqcgcaaccgtgcg
gcaccctaccgcatggagataagcatggccacgcagtccagagaaatcggcattcaagccaagaacaagcccggtcactgg
gtgcaaacggaacgcaaagcgcatgaggcgtgggccgggcttattgcgaggaaacccacggcggcaatgctgctgcatcac
ctcgtggcgcagatgggccaccagaacgccgtggtggtcagccagaagacacttccaagctcatcggacgttctttgcggacg
gtccaatacgcagtcaaggacttggtggccgagcgctggatctccgtcgtgaagctcaacggccccggcaccgtgtcggccta
cgtggtcaatgaccgcgtggcgtggggccagccccgcgaccagttgcgcctgtcggtgttcagtgccgccgtggtggttgatcac
gacgaccaggacgaatcgctgttggggcatggcgacctgcgccgcatcccgaccctgtatccgggcgagcagcaactaccg
accggccccggcgaggagccgcccagccagcccggcattccgggcatggaaccagacctgccagccttgaccgaaacgg
aggaatgggaacggcgcgggcagcagcgcctgccgatgcccgatgagccgtgttttctggacgatggcgagccgttggagcc
gccgacacgggtcacgctgccgcgccggtagcacttgggttgcgcagcaacccgtaagtgcgctgttccagactatcggctgta
gccgcctcgccgccctataccttgtctgcctccccgcgttcgtcgcggtcatggagccgggccacctcgacctgaatggaag
ccggcggcacctcgctaacggattcaccgtttttatcaggctctggaggcagaataaatgatcatatcgtcaattattacctccac
ggggagagcctgagcaaactggcctcaggcatttgagaagcacacggtcacactgcttccggtagtcaataaaccggtaaac
cagcaatagacataagcggctatttaacgaccctgccctgaaccgacgaccgggtcgaatttgctttcgaatttctgccattcatcc
gcttattatcacttattcaggcgtagcaccaggcgtttaagggcaccaataactgccttaaaaaaattacgccccgccctgccact
catcgcagtcggcctattggttaaaaaatgagctgatttaacaaaaatttaacgcgaattttaacaaaatattaacgcttacaatttc
cattcgccattcaggctgcgcaactgttgggaagggcgatcggtgcgggcctcttcgctattacgccagctggcgaaaggggga
tgtgctgcaaggcgattaagttgggtaacgccagggttttcccagtcacgacgttgtaaaacgacggccagtgagcgcgcgtaa
tacgactcactatagggcgaattggagctccaccgcggtggcggccgctctagaactagtggatccccgggctgcaggaattc
gatatcaagcttatcgataccgtcgacctcgagggggggcccggtacccagcttttgttcccttagtgagggttaattgcgcgcttg
gcgtaatcatggtcatagctgtttcctgtgtgaaattgttatccgctcacaattccacacaacatacgagccggaagcataaagtgt
aaagcctggggtgcctaatgagtgagctaactcacattaattgcgttgcgctcactgcccgctttccagtcgggaaacctgtcgtg
ccagctgcattaatgaatcggccaacgcgcggggagaggcggtttgcgtattgggcgcatgcataaaaactgttgtaattcatta
agcattctgccgacatggaagccatcacaaacggcatgatgaacctgaatcgccagcggcatcagcac

Figure 146C cttgtcgccttgcgtataatatttgcccatggacgcacaccgtggaaacggatgaaggcacgaacccagttgacataa
gcctgttcggttcgtaaactgtaatgcaagtagcgtatgcgctcacgcaactggtccagaaccttgaccgaacgcagc
ggtggtaacggcgcagtggcggttttcatggcttgttatgactgttttttgtacagtctatgcctcgggcatccaagcagca
agcgcgttacgccgtgggtcgatgtttgatgttatggagcagcaacgatgttacgcagcagcaacgatgttacgcagc
agggcagtcgccctaaaacaaagttaggtggctcaagtatgggcatcattcgcacatgtaggctcggccctgaccaa
gtcaaatccatgcgggctgctcttgatcttttcggtcgtgagttcggagacgtagccacctactcccaacatcagccgga
ctccgattacctcgggaacttgctccgtagtaagacattcatcgcgcttgctgccttcgaccaagaagcggttgttggcg
ctctcgcggcttacgttctgcccaggtttgagcagccgcgtagtgagatctatatctatgatctcgcagtctccggcgagc
accggaggcagggcattgccaccgcgctcatcaatctcctcaagcatgaggccaacgcgcttggtgcttatgtgatct
acgtgcaagcagattacggtgacgatcccgcagtggctctctatacaaagttgggcatacgggaagaagtgatgcac
tttgatatcgacccaagtaccgccacctaacaattcgttcaagccgagatcggcttcccggccgcggagttgttcggta
aattgtcacaacgccgccaggtggcacttttcgggaaatgtgcgcgcccgcgttcctgctggcgctgggcctgtttctg
gcgctggacttcccgctgttccgtcagcagcttttcgcccacggccttgatgatcgcggcggccttggcctgcatatcccg
attcaacggccccagggcgtccagaacgggcttcaggcgctcccgaaggt (SEQ ID NO:121)

Figure 147B ctcgggccgtctcttgggcttgatcggccttcttgcgcatctcacgcgctcctgcggcggcctgtagggcaggctcataccct
gccgaaccgcttttgtcagccggtcggccacggcttccggcgtctcaacgcgctttgagattccagcttttcggccaatccct
gcggtgcataggcgcgtggctcgaccgcttgcgggctgatggtgacgtggcccactggtggccgctccagggcctcgtaga
acgcctgaatgcgcgtgtgacgtgccttgctgccctcgatgccccgttgcagccctagatcggccacagcggccgcaaacg
tggtctggtcgcgggtcatctgcgctttgttgccgatgaactccttggccgacagcctgccgtcctgcgtcagcggcaccacga
acgcggtcatgtgcgggctggtttcgtcacggtggatgctggccgtcacgatgcgatccgccccgtacttgtccgccagccac
ttgtgcgccttctcgaagaacgccgcctgctgttcttggctggccgacttccaccattccgggctggccgtcatgacgtactcga
ccgccaacacagcgtccttgcgccgcttctctggcagcaactcgcgcagtcggcccatcgcttcatcggtgctgctggccgc
ccagtgctcgttctctggcgtcctgctggcgtcagcgttgggcgtctcgcgctcgcggtaggcgtgcttgagactggccgccac
gttgcccattttcgccagcttcttgcatcgcatgatcgcgtatgccgccatgcctgcccctcccttttggtgtccaaccggctcgac
ggggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctcccttgccagcccgt
ggatatgtggacgatggccgcgagcggccaccggctggctcgcttcgctcggcccgtggacaaccctgctggacaagctg
atggacaggctgcgcctgcccacgagcttgaccacagggattgcccaccggctacccagccttcgaccacataccaccg
gctccaactgcgcggcctgcggccttgccccatcaatttttttaattttctctggggaaaagcctccggcctgcggcctgcgcgc
ttcgcttgccggttggacaccaagtggaaggcgggtcaaggctcgcgcagcgaccgcgcagcggcttggccttgacgcgc
ctggaacgacccaagcctatgcgagtgggggcagtcgaaggcgaagcccgcccgcctgccccccgagcctcacggcg
gcgagtgcggggggttccaaggggggcagcgccaccttgggcaaggccgaaggccgcgcagtcgatcaacaagcccgg
agggggccacttttttgccggaggggggagccgcgccgaaggcgtgggggaaccccgcaggggtgcccttctttgggcacca
aagaactagatatagggcgaaatgcgaaagacttaaaaatcaacaacttaaaaaaggggggtacgcaacagctcattgc
ggcacccccccgcaatagctcattgcgtaggttaaagaaaatctgtaattgactgccacttttacgcaacgcataattgttgtcgc
gctgccgaaaagttgcagctgattgcgcatggtgccgcaaccgtgcggcaccctaccgcatggagataagcatggccacg
cagtccagagaaatcggcattcaagccaagaacaagcccggtcactgggtgcaaacggaacgcaaagcgcatgaggc
gtgggccgggcttattgcgaggaaacccacggcggcaatgctgctgcatcacctcgtggcgcagatgggccaccagaac
gccgtggtggtcagccagaagacactttccaagctcatcggacgttctttgcggacggtccaatacgcagtcaaggacttggt
ggccgagcgctggatctccgtcgtgaagctcaacggccccggcaccgtgtcggcctacgtggtcaatgaccgcgtggcgtg
gggccagccccgcgaccagttgcgcctgtcggtgttcagtgccgccgtggtggttgatcacgacgaccaggacgaatcgct
gttggggcatggcgacctgcgccgcatcccgaccctgtatccgggcgagcagcaactaccgaccggccccggcgagga
gccgcccagccagcccggcattccgggcatggaaccagacctgccagccttgaccgaaacggaggaatgggaacggc
gcgggcagcagcgcctgccgatgcccgatgagccgtgttttctggacgatggcgagccgttggagccgccgacacgggtc
acgctgccgcgccggtagcacttgggttgcgcagcaacccgtaagtgcgctgttccagactatcggctgtagccgcctcgcc
gccctataccttgtctgcctccccgcgttgcgtcgcggtgcatggagccgggccacctcgacctgaatggaagccggcggc
acctcgctaacggattcaccgtttttatcaggctctgggaggcagaataaatgatcatatcgtcaattattacctccacgggga
gagcctgagcaaactggccctcaggcatttgagaagcacacggtcacactgcttccggtagtcaataaaccggtaaaccag
caatagacataagcggctatttaacgaccctgccctgaaccgacgacccgggtcgaatttgctttcgaatttctgccattcatcc
gcttattatcacttattcaggcgtagcaccaggcgtttaagggcaccaataactgccttaaaaaaattacgccccgccctgcc
actcatcgcagtcggcctattggttaaaaaatgagctgatttaacaaaaatttaacgcgaattttaacaaaatattaacgcttac
aatttccattcgccattcaggctgcgcaactgttgggaagggcgatcggtgcgggcctcttcgctattacgccagctggcgaa
aggggggatgtgctgcaaggcgattaagttgggtaacgccagggttttcccagtcacgacgttgtaaaacgacggccagtga
gcgcgcgtaatacgactcactatagggcgaattggagctccaccgcggtggcggccgctctagaactagtggatcctcaca
cgtacatcagctggttgatggggaacgggtcgatgagcagcagcttgatgcggttctcggtggcgtaatccgggcggccca
gcccgtcccatattggtaggtgcagtggctcacgcgggccatgttcacggcgatctccatgaacgccttcggcagcagggt
gctgtccgacacgcgctcgcggttcattttcttccactcggcgtcgatcagcttgcgcagctcttcgcgggcctgttcctcgctcg
tgccgtcgttctcgtcatgtagctgatgatgctgttggtggtttcgccgcgttcgagttccgccgccgaggtcgccagatcgttg
cacagccgaaagatcacgcaggacgagcgcaccaggccgtggaagtcggtcagggagcggagggcgtggtccgaga
tatcttcctg

Figure 147C ctgctggcagaccgagaagtagctcggcgccagcagcgcgaccccgctggaggacacgctggcgttctccaggtacttgct
gaaggcggggatgatcttgttattgctccacttggcttcttgcaggaaggccttgcacagttcgcgccagcttttggtcagatagct
caggttattgtggcccttctccttcaggatggagtaggacgtgtcgttcacggtgttgtacagggccaggaagcacagcttcatat
agtcgggcagcgtgttgatggcgttcacgtccagcgttccaccgcgtcggtgaagagctgcagttcgtccagggtaccgtac
acgtcatagacgtcatcgataatggtgaccagaccgaacatcttggtgacggccttgcggcattcgccgaactgcgggtccgg
cgccatgcccagcgcccagaagtacacttccatcaggcggtcccgcacgaaatccagcttgctggcgaggcccatctcggtc
caccaccggctcaggtcctgcagctcttttggtgcagggtctggaccatgttgaaatcgagtttggccagttccagcagcagct
ggtgatgcggctccttgggttcgtacttgtccagaaaccaccgcgcctccaggcggtgcaggcgttgatgatacggcagctcc
agcgcgtgggacacctgctcggccaccttcgtgttgatccctccttgaggttgttcttcagatgggtgatgctgaaggtacgggc
ctcctccagcagattttcgccttcgaaaccgagatagctggcctcgtacaggctcagcaggccctgcacgtcaccttcagttcc
ccggagaagccccctctttgtccttgaagcgctcgaacacgtcctggctcacctcaaagccatgctgccgcagcaggcgga
agctcagggcggtcgcgtgcagatcgcttttgttcttcttattctcgtccagcaggacgatgttctccagcgccttgatgatatctttct
caaacttgtaggtcaggcccaggcgctgcacgtcgtcgatgagctccagcaggctcaggggctgggtgtccacccggttgat
catgcaacgcacctcctcctccagcttggtggccttctcttcgagcttctccaccttcaggtcgtttccaggctctgcaggaactcg
aagttccacaggttgggctggtagttcgcggaccgacggctattatgctcggtgatctgggtgaactggctgctggtggcgcac
atatgtatatctccttcttaaagttaaacaagcttatcgataccgtcgacctcgagggggggcccggtacccagcttttgttcccttt
agtgagggttaattgcgcgcttggcgtaatcatggtcatagctgtttcctgtgtgaaattgttatccgctcacaattccacacaacat
acgagccggaagcataaagtgtaaagcctggggtgcctaatgagtgagctaactcacattaattgcgttgcgctcactgcccg
ctttccagtcgggaaacctgtcgtgccagctgcattaatgaatcggccaacgcgcggggagaggcggtttgcgtattgggcgc
atgcataaaaactgttgtaattcattaagcattctgccgacatggaagccatcacaaacggcatgatgaacctgaatcgccag
cggcatcagcaccttgtcgccttgcgtataatatttgcccatggacgcacaccgtggaaacggatgaaggcacgaacccagtt
gacataagcctgttcggttcgtaaactgtaatgcaagtagcgtatgcgctcacgcaactggtccagaaccttgaccgaacgca
gcggtggtaacggcgcagtggcggttttcatggcttgttatgactgtttttttgtacagtctatgcctcgggcatccaagcagcaag
cgcgttacgccgtgggtcgatgtttgatgttatggagcagcaacgatgttacgcagcagcaacgatgttacgcagcagggcag
tcgccctaaaacaaagttaggtggctcaagtatgggcatcattcgcacatgtaggctcggccctgaccaagtcaaatccatgc
gggctgctcttgatcttttcggtcgtgagttcggagacgtagccacctactcccaacatcagccggactccgattacctcgggaa
cttgctccgtagtaagacattcatcgcgcttgctgccttcgaccaagaagcggttgttggcgctctcgcggcttacgttctgcccag
gtttgagcagccgcgtagtgagatctatatctatgatctcgcagtctccggcgagcaccggaggcagggcattgccaccgcgc
tcatcaatctcctcaagcatgaggccaacgcgcttggtgcttatgtgatctacgtgcaagcagattacggtgacgatcccgcagt
ggctctctatacaaagttgggcatacgggaagaagtgatgcactttgatatcgacccaagtaccgccacctaacaattcgttca
agccgagatcggcttcccggccgcggagttgttcggtaaattgtcacaacgccgccaggtggcacttttcggggaaatgtgcg
cgcccgcgttcctgctggcgctgggcctgtttctggcgctggacttcccgctgttccgtcagcagctttcgcccacggccttgatg
atcgcggcggccttggcctgcatatcccgattcaacggccccagggcgtccagaacgggcttcaggcgctcccgaaggt (SEQ ID NO:122)

Figure 152B

```
AGCGCCCAATACGCAAACCGCCTCTCCCCGCGCGTTGGCCGATTCATTAATGCAGCTGGCA
CGACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTGTGA
GCGGATAACAATTTCACACAGGAAACAGCTATGACCATGATTACGCCAAGCTATTTAGGTGAC
GCGTTAGAATACTCAAGCTATGCATCAAGCTTGGTACCGAGCTCGGATCCACTAGTAACGGC
CGCCAGTGTGCTGGAATTCAGGCGGTCCGGAAAGAGAAGCAGTATAGCGTCAGGTGAACGC
TGCTCCAACCGTTGCATAACAACAAAGACGCCTTCATGTTATACTGCGGCAAAATACTGATGA
TGTGTCGCGATTGCGGCCAACCGTTTCCACCCCAGGCGAGAGACAATGACCAACCTACAGA
CTTTCGAGTTACCTACCGAGGTAACCGGCTGCGCCGCCGATATCTCATTGGGAAGGGCGCT
GATCCAAGCCTGGCAAAAAGATGGCATTTTTCAGATCAAGACCGATAGTGAGCAGGATCGCA
AAACGCAGGAAGCAATGGCTGCTAGCAAGCAGTTTTGCAAGGAACCGCTGACTTTTAAGAGT
AGCTGCGTTAGCGATCTGACCTACAGCGGCTATGTTGCGTCAGGCGAGGAAGTCACAGCTG
GTAAACCTGATTTCCCTGAAATCTTCACTGTCTGCAAGGACTTGTCGGTAGGCGATCAGCGT
GTAAAAGCCGGCTGGCCTTGCCATGGTCCGGTGCCATGGCCAAATAACACCTATCAGAAAAG
CATGAAGACCTTCATGGAAGAGCTGGGTTTAGCGGGCGAACGGTTGCTCAAACTGACAGCG
CTCGGCTTTGAACTACCCATCAACACGTTCACCGACTTAACTCGCGATGGTTGGCACCACAT
GCGTGTATTACGCTTCCCGCCCCAAACATCCACGCTGTCCCGTGGAATTGGTGCGCACACTG
ACTATGGGTTGTTGGTAATTGCCGCTCAGGACGATGTTGGTGGCTTATATATTCGCCCTCCAG
TCGAGGGAGAGAAGCGTAATCGTAACTGGTTGCCTGGTGAGAGCTCAGCAGGCATGTTTGA
GCACGATGAACCTTGGACCTTCGTGACGCCCACCCCAGGCGTGTGGACAGTTTTCCCAGGT
GATATCTTGCAGTTCATGACCGGCGGCCAGCTGCTTTCCACTCCGCACAAGGTTAAGCTCAA
TACCCGCGAACGTTTCGCCTGCGCTTATTTTCATGAGCCTAATTTTGAAGCATCCGCCTATCC
GTTGTTCGAGCCCAGCGCCAATGAGCGTATTCATTATGGTGAGCACTTTACCAACATGTTTAT
GCGTTGCTATCCAGATCGGATCACCACCCAGAGCATCAACAAGGAGAATCGCCTGGCGCACT
TGGAGGACTTGAAGAAGTATTCGGACACCCGCGCGACAGGCTCATGACGGTCCGCCTGAAT
TCTGCAGATATCCATCACACTGGCGGCCGCTCGAGCATGCATCTAGAGGGCCCAATTCGCCC
TATAGTGAGTCGTATTACAATTCACTGGCCGTCGTTTTACAACGTCGTGACTGGGAAAACCCT
GGCGTTACCCAACTTAATCGCCTTGCAGCACATCCCCCTTTCGCCAGCTGGCGTAATAGCGA
AGAGGCCCGCACCGATCGCCCTTCCCAACAGTTGCGCAGCCTATACGTACGGCAGTTTAAG
GTTTACACCTATAAAAGAGAGAGCCGTTATCGTCTGTTTGTGGATGTACAGAGTGATATTATT
GACACGCCGGGGCGACGGATGGTGATCCCCCTGGCCAGTGCACGTCTGCTGTCAGATAAAG
TCTCCCGTGAACTTTACCCGGTGGTGCATATCGGGGATGAAAGCTGGCGCATGATGACCACC
GATATGGCCAGTGTGCCGGTCTCCGTTATCGGGGAAGAAGTGGCTGATCTCAGCCACCGCG
AAAATGACATCAAAAACGCCATTAACCTGATGTTCTGGGGAATATAAATGTCAGGCATGAGAT
TATCAAAAAGGATCTTCACCTAGATCCTTTTCACGTAGAAAGCCAGTCCGCAGAAACGGTGCT
GACCCCGGATGAATGTCAGCTACTGGGCTATCTGGACAAGGGAAAACGCAAGCGCAAAGAG
AAAGCAGGTAGCTTGCAGTGGGCTTACATGGCGATAGCTAGACTGGGCGGTTTTATGGACAG
CAAGCGAACCGGAATTGCCAGCTGGGGCGCCCTCTGGTAAGGTTGGGAAGCCCTGCAAAGT
AAACTGGATGGCTTTCTTGCCGCCAAGGATCTGATGGCGCAGGGGATCAAGCTCTGATCAAG
AGACAGGATGAGGATCGTTTCGCATGATTGAACAAGATGGATTGCACGCAGGTTCTCCGGCC
GCTTGGGTGGAGAGGCTATTCGGCTATGACTGGGCACAACAGACAATCGGCTGCTCTGATG
CCGCCGTGTTCCGGCTGTCAGCGCAGGGGCGCCCGGTTCTTTTTGTCAAGACCGACCTGTC
CGGTGCCCTGAATGAACTGCAAGACGAGGCAGCGCGGCTATCGTGGCTGGCCACGACGGG
CGTTCCTTGCGCAGCTGTGCTCGACGTTGTCACTGAAGCGGGAAGGGACTGGCTGCTATTG
GGCGAAGTGCCGGGGCAGGATCTCCTGTCATCTCACCTTGCTCCTGCCGAGAAAGTATCCAT
CATGGCTGATGCAATGCGGCGGCTGCATACGCTTGATCCGGCTACCTGCCCATTCGACCAC
CAAGCGAAACATCGCATCGAGCGAGCACGTACTCGGATGGAAGCCGGTCTTGTCGATCAGG
ATGATCTGGACGAAGAGCATCAGGGGCTCGCGCCAGCCGAACTGTTCGCCAGGCTCAAGGC
GAGCATGCCCGACGGCGAGGATCTCGTCGTGACCCATGGCGATGCCTGCTTGCCGAATATC
```

Figure 152B (continued)

```
ATGGTGGAAAATGGCCGCTTTTCTGGATTCATCGACTGTGGCCGGCTGGGTGTGGCG
GACCGCTATCAGGACATAGCGTTGGCTACCCGTGATATTGCTGAAGAGCTTGGCGGC
GAATGGGCTGACCGCTTCCTCGTGCTTTACGGTATCGCCGCTCCCGATTCGCAGCGC
ATCGCCTTCTATCGCCTTCTTGACGAGTTCTTCTGAATTATTAACGCTTACAATTTCCTG
ATGCGGTATTTTCTCCTTACGCATCTGTGCGGTATTTCACACCGCATCAGGTGGCACTT
TTCGGGGAAATGTGCGCGGAACCCCTATTTGTTTATTTTTCTAAATACATTCAAATATGT
ATCCGCTCATGAGACAATAACCCTGATAAATGCTTCAATAATAGCACGTGAGGAGGGC
CACCATGGCCAAGTTGACCAGTGCCGTTCCGGTGCTCACCGCGCGCGACGTCGCCG
GAGCGGTCGAGTTCTGGACCGACCGGCTCGGGTTCTCCCGGGACTTCGTGGAGGAC
GACTTCGCCGGTGTGGTCCGGGACGACGTGACCCTGTTCATCAGCGCGGTCCAGGA
CCAGGTGGTGCCGGACAACACCCTGGCCTGGGTGTGGGTGCGCGGCCTGGACGAGC
TGTACGCCGAGTGGTCGGAGGTCGTGTCCACGAACTTCCGGGACGCCTCCGGGCCG
GCCATGACCGAGATCGGCGAGCAGCCGTGGGGCGGGAGTTCGCCCTGCGCGACC
CGGCCGGCAACTGCGTGCACTTCGTGGCCGAGGAGCAGGACTGACACGTGCTAAAA
CTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTTTCCGAAGG
TAACTGGCTTCAGCAGAGCGCAGATACCAAATACTGTTCTTCTAGTGTAGCCGTAGTTA
GGCCACCACTTCAAGAACTCTGTAGCACCGCCTACATACCTCGCTCTGCTAATCCTGT
TACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAG
CCCAGCTTGGAGCGAACGACCTACACCGAACTGAGATACCTACAGCGTGAGCTATGA
GAAAGCGCCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCG
CAGCGAGTCAGTGAGCGAGGAAGCGGAAG
```

US 8,569,026 B2

SYSTEMS USING CELL CULTURE FOR PRODUCTION OF ISOPRENE

CROSS-REFERENCE TO RELATED APPLICATIONS

This applications claims the benefit of U.S. Provisional patent application 61/097,163, filed on Sep. 15, 2008, and U.S. Provisional patent application 61/187,832, filed on Jun. 17, 2009, the contents of both are hereby incorporated by reference in its entirety.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIGS. 19A and 19B). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

The invention provided herein addresses these needs and provides additional benefits as well.

BRIEF SUMMARY OF THE INVENTION

The invention provides for, inter alia, compositions, systems, cells and methods for producing a compound having one or both of the following characteristics: (a) a Henry's law coefficient of less than about 250 M/atm and/or (b) a solubility in water of less than about 100 g/L. In one embodiment, the compound is isoprene. In another embodiment, the compound is ethylene. The invention also provides for methods of producing isoprene comprising: a) culturing cells under suitable conditions for production of isoprene; and b) producing isoprene, wherein cells produce greater than about 400 nmole/$g_{wcm}$/hour of isoprene, and the carbon dioxide evolution rate of the cells is greater than about $1\times10^{-18}$ mmol/L/hour. In some embodiments, the methods further comprise recovering the compound, such as isoprene. In one embodiment, the cells further comprise one or more heterologous nucleic acids or one or more additional copies of an endogenous nucleic acid encoding an isoprene synthase polypeptide. In another embodiment, the cells further comprise one or more heterologous nucleic acids or one or more additional copies of an endogenous nucleic acid encoding an IDI polypeptide, an MVA pathway enzyme, or a DXP pathway enzyme. In another embodiment, the MVA pathway enzyme is mevalonate kinase.

Further provided herein are methods of producing isoprene comprising: a) culturing cells under suitable conditions for production of isoprene; and b) producing isoprene, wherein the cumulative total productivity of the isoprene produced by the cells in culture is greater than about 0.2 mg/$L_{broth}$/hour and the carbon dioxide evolution rate of the cells is greater than about $1\times10^{-18}$ mmol/L/hour. In some embodiments, the methods further comprise recovering the isoprene. In one embodiment, the cells further comprise one or more heterologous nucleic acids or one or more additional copies of an endogenous nucleic acid encoding an isoprene synthase polypeptide. In another embodiment, the cells further comprise one or more heterologous nucleic acids or one or more additional copies of an endogenous nucleic acid encoding an IDI polypeptide, an MVA pathway enzyme, or a DXP pathway enzyme. In another embodiment, the MVA pathway enzyme is mevalonate kinase.

Methods of producing isoprene are also provided herein comprising: a) culturing cells under suitable conditions for production of isoprene; and b) producing isoprene, wherein the peak concentration of the isoprene produced by the cells in culture is greater than about 10 ng/$L_{broth}$ and the carbon dioxide evolution rate of the cells is greater than about $1\times10^{-18}$ mmol/L/hour. In some embodiments of any of these methods, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about 50 mmol/L/hour or about 500 mmol/L/hour. In some embodiments, the methods further comprise recovering the isoprene. In one embodiment, the cells further comprise one or more heterologous nucleic acids or one or more additional copies of an endogenous nucleic acid encoding an isoprene synthase polypeptide. In another embodiment, the cells further comprise one or more heterologous nucleic acids or one or more additional copies of an endogenous nucleic acid encoding an IDI polypeptide, an MVA pathway enzyme, or a DXP pathway enzyme. In another embodiment, the MVA pathway enzyme is mevalonate kinase.

Further provided herein are cells in culture comprising a nucleic acid encoding an isoprene synthase polypeptide, wherein the cells produce greater than about 400 nmole/$g_{wcm}$/hour of isoprene and carbon dioxide evolution rate of the cells is greater than about $1\times10^{-18}$ mmol/L/hour. Provided herein are also cells in culture comprising a nucleic acid encoding an isoprene synthase polypeptide, wherein cumulative total productivity of the isoprene produced by the cells in culture is greater than about 0.2 mg/$L_{broth}$/hour and carbon dioxide evolution rate of the cells is greater than about $1\times10^{-18}$ mmol/L/hour. In addition, provided herein are cells in culture comprising a nucleic acid encoding an isoprene synthase polypeptide, wherein peak concentration of the isoprene produced by the cells in culture is greater than about 10 ng/$L_{broth}$ and carbon dioxide evolution rate of the cells is greater than about $1\times10^{-18}$ mmol/L/hour. In some embodiments of any of these cells in culture, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about 50 mmol/L/hour or about 500 mmol/L/hour. The invention also provides for composition and/or systems comprising one or more of any of the cells disclosed herein.

Provided herein are also methods of producing isoprene comprising a) culturing cells under suitable conditions for production of isoprene; and b) producing isoprene, wherein the liquid phase concentration of isoprene is less than about 2 g/L and the cells produce greater than about 400 nmole/$g_{wcm}$/hour of isoprene. In some embodiments, the liquid phase concentration of isoprene in the culture is less than about 1 g/L. In some embodiments, the liquid phase concentration of isoprene in the culture is less than about 200 mg/L. In some embodiments, the liquid phase concentration of isoprene in the culture is less than any of about 1.9 g/L, 1.8 g/L, 1.7 g/L, 1.6 g/L, 1.5 g/L, 1.4 g/L, 1.3 g/L, 1.2 g/L, or 1.1 g/L. In some embodiments, the liquid phase concentration of isoprene in the culture is less than any of about 900 mg/L, 800 mg/L, 700 mg/L, 600 mg/L, 500 mg/L, 400 mg/L, or 300 mg/L. In some embodiments, the liquid phase concentration of isoprene in the culture is less than about any of 175 mg/L, 150 mg/L, 125 mg/L, 100 mg/L, 75 mg/L, 50 mg/L, 25 mg/L, 20 mg/L, 15 mg/L, 10 mg/L, 5 mg/L, or 2.5 mg/L. In some embodiments, the liquid phase concentration of isoprene in culture is between about any of 0.1 mg/L to 200 mg/L, 1 mg/L to 200 mg/L, 1 mg/L to 150 mg/L, 1 mg/L to 100 mg/L, 1 mg/L to 50 mg/L, 1 mg/L to 25 mg/L, 1 mg/L to 20 mg/L, or 10 mg/L to 20 mg/L, 1 mg/L to 1 g/L, 0.1 mg/L to 2 g/L, 1 g/L to 2 g/L, 10 mg/L to 1 g/L, or 100 mg/L to 1 g/L. In some embodiments, the liquid phase concentration is below the solubility limit of isoprene. In some embodiments, the liquid phase in the culture is saturated with isoprene, and isoprene is additionally present in a second liquid phase. In some embodiments, the second liquid phase comprises at least about 50, 60, 70, 80, 85, 90, 95, or 98% isoprene. In some embodiments, the methods further comprise recovering the isoprene. In one embodiment, the cells further comprise one or more heterologous nucleic acids or one or more additional copies of an endogenous nucleic acid encoding an isoprene synthase polypeptide. In another embodiment, the cells further comprise one or more heterologous nucleic acids or one or more additional copies of an endogenous nucleic acid encoding an IDI polypeptide, an MVA pathway enzyme, or a DXP pathway enzyme. In another embodiment, the MVA pathway enzyme is mevalonate kinase.

Also provided herein are methods of producing a compound, wherein the compound has one or more characteristics selected from the group consisting of (a) a Henry's law coefficient of less than about 250 M/atm and (b) a solubility in water of less than about 100 g/L. In some embodiments, the method comprises: a) culturing cells under suitable conditions for production of the compound, wherein gas is added (such as the addition of gas to a system such as a fermentation system) at a gas sparging rate between about 0.01 vvm to about 2 vvm; and b) producing the compound. In one embodiment, anaerobic conditions are used. In another embodiment, the gas sparging rate is 0 vvm. In another embodiment, the gas sparging rate is 0 vvm-0.01 vvm. In other embodiments, the method comprises: a) culturing cells under suitable conditions for production of the compound; b) producing the compound; and c) recovering the compound in the gas phase. In some embodiments, the method comprises: a) culturing cells under suitable conditions for production of the compound; b) producing the compound; and c) recovering the compound from the gas phase. In one embodiment, the compound produced is ethylene. In some embodiments, the Henry's law coefficient of the compound is less than about any of 200 M/atm, 150 M/atm, 100 M/atm, 75 M/atm, 50 M/atm, 25 M/atm, 10 M/atm, 5 M/atm, or 1 M/atm. In some embodiments, the solubility in water of the compound is less than about any of 75 g/L, 50 g/L, 25 g/L, 10 g/L, 5 g/L, or 1 g/L. In some embodiments, the compound is selected from a group consisting of isoprene, an aldehyde (e.g., acetaldehyde), a ketone (e.g., acetone, methyl ethyl ketone or 2-butanone), an alcohol (e.g., methanol, ethanol, 1-butanol, or C5 alcohols such as 3-methyl-3-buten-1-ol or 3-methyl-2-buten-1-ol), an ester of an alcohol (e.g., ethyl acetate, esters of 3-methyl-2-buten-1-ol, or acetyl esters of C5 alcohols), a hemiterpene, a monoterpene, a sesquiterpene, and C1 to C5 hydrocarbons (e.g., methane, ethane, ethylene, or propylene). In some embodiments, the C1 to C5 hydrocarbons are saturated, unsaturated, or branched. In some embodiments, the C1 to C5 hydrocarbon is an unsaturated aliphatic hydrocarbon (e.g. ethylene, propene, butylene, or isobutylene). In some embodiments the C1 to C5 hydrocarbon is a diolefin. In particular embodiments, the compound is isoprene. In other particular embodiments, the compound is ethylene. In some embodiments of the methods of producing any of the compounds described above, the gas sparing rate is between about any of 0 vvm to 0.1 vvm, 0.1 vvm to 1 vvm, 0.2 vvm to 1 vvm, or 0.5 vvm to 1 vvm. In some embodiments of the methods of producing any of the compounds described above, the gas sparging rate is 0.0 vvm.

In one aspect, the invention features methods of producing ethylene. In some embodiments, the method comprises: a) culturing cells under suitable conditions for production of ethylene, wherein gas is added (such as the addition of gas to a system such as a fermentation system) at a gas sparging rate between about 0.01 vvm to about 2 vvm; b) producing ethylene. In other embodiments, the method comprises: a) culturing cells under suitable conditions for production of ethylene; and b) producing ethylene; and c) recovering the ethylene in the gas phase. In some embodiments of the methods of producing ethylene, the gas sparging rate is between about any of 0 vvm to 0.1 vvm, 0.1 vvm to 1 vvm, 0.2 vvm to 1 vvm, or 0.5 vvm to 1 vvm. In some embodiments of the methods of producing ethylene, the gas sparging rate is 0.0 vvm.

In any of the embodiments, the methods further comprise recovering the isoprene and/or ethylene. In some embodiments, ethylene is recovered by adsorption. In a particular embodiment, ethylene is adsorbed on a silver-modified clay. In other embodiments, ethylene is recovered by cryogenic separation or absorption/stripping.

In one aspect, the invention features cells in culture that produce isoprene. In some embodiments, the invention provides cells in culture that produce greater than about 400 nmole of isoprene/gram of cells for the wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In one aspect, the invention features cells in culture that produce a compound, wherein the compound has one or more characteristics selected from the group consisting of (a) a Henry's law coefficient of less than about 250 M/atm and (b) a solubility in water of less than about 100 g/L. In some embodiments, the cells have a heterologous nucleic acid that (i) encodes a synthase polypeptide capable of producing the compound and (ii) is operably linked to a promoter. In some embodiments, the compound produced is ethylene and the synthase polypeptide is ethylene-forming enzyme (efe). In some embodiments, the cells are cultured in a culture medium that includes one or more carbon source(s), such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract. In some embodiments, the cells are cultured under limited glucose conditions.

In one aspect, the invention features methods of producing isoprene, such as methods of using any of the cells described herein to produce isoprene. In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the gas phase comprises greater than or about 9.5% (volume) oxygen, and the concentration of isoprene in the gas phase is less than the lower flammability limit or greater than the upper flammability limit. In particular embodiments, (i) the concentration of isoprene in the gas phase is less than the lower flammability limit or greater than the upper flammability limit, and (ii) the cells produce greater than about 400 nmole/$g_{wcm}$/hr of isoprene.

In some embodiments, the method includes culturing cells under conditions sufficient to convert more than about 0.002% of the carbon (mol/mol) in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time.

In one aspect, the invention features methods of producing a compound, wherein the compound has one or more characteristics selected from the group consisting of (a) a Henry's law coefficient of less than about 250 M/atm and (b) a solubility in water of less than about 100 g/L, such as methods of using any of the cells described herein to produce the compound. In some embodiments, the compound produced is ethylene. In some embodiments, the method also includes recovering the compound produced by the cells. In some embodiments, the method includes purifying the compound produced by the cells. In some embodiments, the method includes polymerizing the compound. In some embodiments, the cells have a heterologous nucleic acid that (i) encodes a synthase polypeptide capable of producing the compound and (ii) is operably linked to a promoter. In a particular embodiment, the heterologous nucleic acid encodes efe. In some embodiments, the cells are cultured in a culture medium that includes one or more carbon source(s), such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract. In some embodiments, the cells are cultured under limited glucose conditions. In various embodiments, the amount of the compound produced (such as the total amount of the compound produced or the amount of the compound produced per liter of broth per hour per $OD_{600}$) during stationary phase is greater than or about 2 or more times the amount of the compound produced during the growth phase for the same length of time. In some embodiments, the gas phase comprises greater than or about 9.5% (volume) oxygen, and the concentration of the compound in the gas phase is less than the lower flammability limit or greater than the upper flammability limit.

In some embodiments, the compound is only produced in stationary phase. In some embodiments, the compound is produced in both the growth phase and stationary phase. In various embodiments, the amount of the compound produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of the compound produced during the growth phase for the same length of time.

In one aspect, the invention features compositions and systems that comprise isoprene. In some embodiments, the composition comprises greater than or about 2, 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene (w/w) of the volatile organic fraction of the composition is isoprene.

In some embodiments, the composition comprises greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition.

In some embodiments, the composition has less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In particular embodiments, the composition also has greater than about 2 mg of isoprene.

In some embodiments, the composition has one or more compounds selected from the group consisting of ethanol, acetone, C5 prenyl alcohols, and isoprenoid compounds with 10 or more carbon atoms. In some embodiments, the composition has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the composition has greater than about 2 mg of isoprene and has one or more compounds selected from the group consisting of ethanol, acetone, C5 prenyl alcohols, and isoprenoid compounds with 10 or more carbon atoms.

In some embodiments, the composition includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to the amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w).

In some embodiments, the composition comprises (i) a gas phase that comprises isoprene and (ii) cells in culture that produce greater than about 400 nmole/$g_{wcm}$/hr of isoprene. In some embodiments, the composition comprises a closed system, and the gas phase comprises greater than or about 5, 10, 20, 30, 40, 50, 60, 70, 80, 90, 100 ug/L of isoprene when normalized to 1 mL of 1 $OD_{600}$ cultured for 1 hour. In some embodiments, the composition comprises an open system, and the gas phase comprises greater than or about 5, 10, 20, 30, 40, 50, 60, 70, 80, 90, 100 ug/L of isoprene when sparged at a rate of 1 vvm. In some embodiments, the volatile organic fraction of the gas phase comprises greater than or about 99.90, 99.92, 99.94, 99.96, 99.98, or 100% isoprene by weight compared to the total weight of all C5 hydrocarbons in the volatile organic fraction. In some embodiments, the volatile organic fraction of the gas phase comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)) by weight compared to the total weight of all C5 hydrocarbons in the volatile organic fraction. In some embodiments, the volatile organic fraction of the gas phase has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) by weight compared to the total weight of all C5 hydrocarbons in the volatile organic fraction. In particular embodiments, the volatile organic fraction of the gas phase has greater than about 2 mg of isoprene and has greater than or about 99.90, 99.92, 99.94, 99.96, 99.98, or 100% isoprene by weight compared to the total weight of all C5 hydrocarbons in the volatile organic fraction.

In some embodiments, the volatile organic fraction of the gas phase has less than or about 50, 40, 30, 20, 10, 5, 1, 0.5, 0.1, 0.05, 0.01, or 0.005 ug/L of a compound that inhibits the polymerization of isoprene for any compound in the volatile organic fraction of the gas phase that inhibits the polymerization of isoprene. In particular embodiments, the volatile organic fraction of the gas phase also has greater than about 2 mg of isoprene.

In some embodiments, the volatile organic fraction of the gas phase has one or more compounds selected from the group consisting of ethanol, acetone, C5 prenyl alcohols, and isoprenoid compounds with 10 or more carbon atoms. In some embodiments, the volatile organic fraction of the gas phase has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the volatile organic fraction of the gas phase has greater than about 2 mg of isoprene and has one or more compounds selected from the group consisting of ethanol, acetone, C5 prenyl alcohols, and isoprenoid compounds with 10 or more carbon atoms.

In some embodiments, the volatile organic fraction of the gas phase has includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w) in the volatile organic fraction of the gas phase.

In some embodiments of any of the compositions of the invention, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon. In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments, the composition includes between about 4 to about 15% by weight of isoprene, such as between about 4 to about 8%, about 8 to about 12%, or about 12 to about 15% by weight of isoprene.

In some embodiments, the invention also features systems that include any of the cells and/or compositions described herein. In some embodiments, the system includes a reactor that chamber comprises cells in culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene. In another aspect, the invention provides methods of manufacturing a tire wherein the improvement comprises using any one or more the compositions, cells, systems and/or methods described herein to produce isoprene for the manufacture of the tire.

In some embodiments of any of the compositions, systems, and methods of the invention, a nonflammable concentration of isoprene in the gas phase is produced. In some embodiments, the gas phase comprises less than about 9.5% (volume) oxygen. In some embodiments, the gas phase comprises greater than or about 9.5% (volume) oxygen, and the concentration of isoprene in the gas phase is less than the lower flammability limit or greater than the upper flammability limit. In some embodiments, the portion of the gas phase other than isoprene comprises between about 0% to about 100% (volume) oxygen, such as between about 10% to about 100% (volume) oxygen. In some embodiments, the portion of the gas phase other than isoprene comprises between about 0% to about 99% (volume) nitrogen. In some embodiments, the portion of the gas phase other than isoprene comprises between about 1% to about 50% (volume) $CO_2$.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an isopentenyl-diphosphate delta-isomerase (IDI) polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a 1-Deoxyxylulose-5-phosphate synthase (DXS) polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid and/or the heterologous efe nucleic acid is operably linked to a T7 promoter, such as a T7 promoter contained in a medium or high copy plasmid. In some embodiments of any of the aspects of the invention, the heterologous isoprene synthase nucleic acid or the heterologous efe nucleic acid is operably linked to a Trc promoter, such as a Trc promoter contained in a medium or high copy plasmid. In some embodiments of any of the aspects of the invention, the heterologous isoprene synthase nucleic acid or the heterologous efe nucleic acid is operably linked to a Lac promoter, such as a Lac promoter contained in a low copy plasmid. In some embodiments of any of the aspects of the invention, the heterologous isoprene synthase nucleic acid or the heterologous efe nucleic acid is operably linked to an endogenous promoter, such as an endogenous alkaline serine protease promoter. In some embodiments, the heterologous isoprene synthase nucleic acid or the heterologous efe nucleic acid integrates into a chromosome of the cells without a selective marker.

In some embodiments, one or more MVA pathway, IDI, DXP pathway, efe or isoprene synthase nucleic acids are placed under the control of a promoter or factor that is more active in stationary phase than in the growth phase. For example, one or more MVA pathway, IDI, DXP pathway, efe or isoprene synthase nucleic acids may be placed under control of a stationary phase sigma factor, such as RpoS. In some embodiments, one or more MVA pathway, IDI, DXP pathway, efe or isoprene synthase nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase nucleic acid or efe nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, efe, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisiae* or *Enterococcus faecalis*). In one embodiment, MVA pathway polypeptide is mevalonate kinase. In some embodiments of any of the aspects of the invention, the cells further comprise an insertion of a copy of an endogenous nucleic acid encoding an MVA pathway polypeptide (such as an MVA pathway polypeptide from *Saccharomyces cerevisiae* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a polypeptide from a plant such as *Pueraria* (e.g., *Pueraria montana* or *Pueraria lobata*) or *Populus* (e.g., *Populus tremuloides*, *Populus alba*, *Populus nigra*, *Populus trichocarpa*, or the hybrid, *Populus alba*×*Populus tremula*). In some embodiments of any of the aspects of the invention, the efe is a polypeptide from a bacteria such as *Pseudomonas* (e.g., *Pseudomonas syringae*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans*, *Streptomyces coelicolor*, or *Streptomyces griseus* cells). In some embodiments of any of the aspects of the invention, the cells are gram-negative bacterial cells (e.g., *Escherichia* cells such as *Escherichia coli* cells, *Rhodopseudomonas* sp. such as *Rhodopseudomonas palustris* cells, *Pseudomonas* sp. such as *Pseudomonas fluorescens* cells or *Pseudomonas putida* cells, or *Pantoea* cells such as *Pantoea citrea* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells or *Saccharomyces* cells such as *Saccharomyces cerevisiae*).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention features a product produced by any of the compositions or methods of the invention. It is to be understood that one, some, or all of the properties of the various embodiments described herein may be combined to form other embodiments of the present invention. The headings provided herein are not limitations of the various aspects or embodiments of the invention which can be had by reference to the specification as a whole.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIGS. 3A-C are the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIGS. 5A-C are the nucleotide sequence of pET-NHisKudzu (SEQ ID NO:5).

FIGS. 7A-C are the nucleotide sequence of pCL-lac-Kudzu (SEQ ID NO:7).

FIGS. 12A-C are the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

FIGS. 15A-C are the nucleotide sequence of vector pSPZ1 (MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba*×*Populus tremula*) isoprene synthase gene (SEQ ID NO:13). The ATG start codon is in bold and the stop codon is underlined.

FIG. 18A shows a schematic outlining construction of vectors pYLA 1, pYL1 and pYL2 (SEQ ID NO:79, 77, 76, 75, 74, and 73).

FIG. 18D shows a schematic outlining construction of the vector pYLI(KZ1) (SEQ ID NO: 70 and 71).

FIG. 18E shows a schematic outlining construction of the vector pYLI(MAP29).

FIGS. 22A-D are the nucleotide sequence of pTrcKudzu yIDI DXS Kan (SEQ ID NO:20).

FIGS. 25A-D are a nucleotide sequence of pTrcKKDyIkIS kan (SEQ ID NO:33).

FIGS. 27A-27D is a nucleotide sequence of pCL PtrcUpperPathway (SEQ ID NO:46).

FIGS. 29A-D are a nucleotide sequence of cassette containing the lower MVA pathway and yeast IDI for integration into the *B. subtilis* chromosome at the nprE locus (SEQ ID NO:47).

FIGS. 31A and B are a nucleotide sequence of p9796-poplar (SEQ ID NO:48).

FIGS. 33A-C are a nucleotide sequence of pTrcPoplar (SEQ ID NO:49).

FIGS. 35A-C are a nucleotide sequence of pTrcKudzu yIDI Kan (SEQ ID NO:50).

FIGS. 37A-C are a nucleotide sequence of pTrcKudzuDXS Kan (SEQ ID NO:51).

FIGS. 39A-C are a nucleotide sequence of pCL PtrcKudzu (SEQ ID NO:52).

FIGS. 41A-C are a nucleotide sequence of pCL PtrcKudzu A3 (SEQ ID NO:53).

FIGS. 43A-C are a nucleotide sequence of pCL PtrcKudzu yIDI (SEQ ID NO:54).

FIGS. 45A-D are a nucleotide sequence of pCL PtrcKudzu DXS (SEQ ID NO:55).

FIGS. 51A-C are the nucleotide sequence of pJMupperpathway2 (SEQ ID NO:56).

FIG. 75A is a table of the conversion of the CAFT Model results from weight percent to volume percent for series A.

FIG. 76A is a table of the conversion of the CAFT Model results from weight percent to volume percent for series B.

FIG. 78A is a graph of the flammability Curve for Test Series 1: 0% Steam, 0 psig, and 40° C.

FIG. 78B is a table summarizing the explosion and non-explosion data points for Test Series 1.

FIG. 79B is a table summarizing the explosion and non-explosion data points for Test Series 2.

FIG. 79C is a graph of the flammability curve for Test Series 2 compared with the CAFT Model.

FIGS. 80A and 80B are a table of the detailed experimental conditions and results for Test Series 1.

FIG. 81 is a table of the detailed experimental conditions and results for Test Series 2.

Figure 88A:
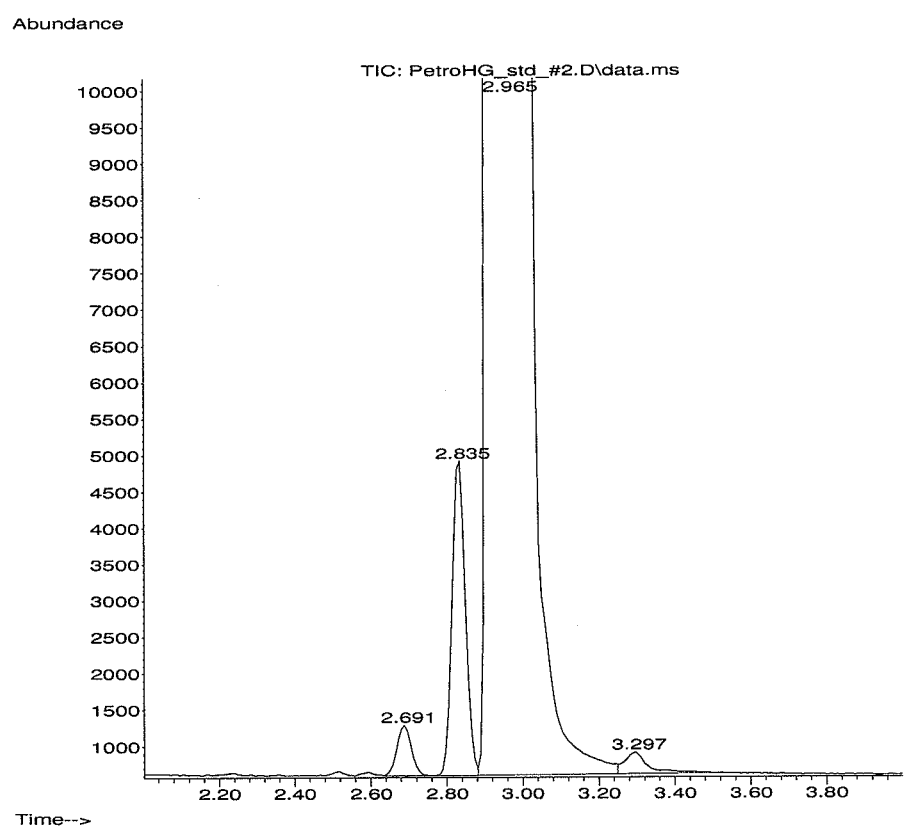
Figure 88B:
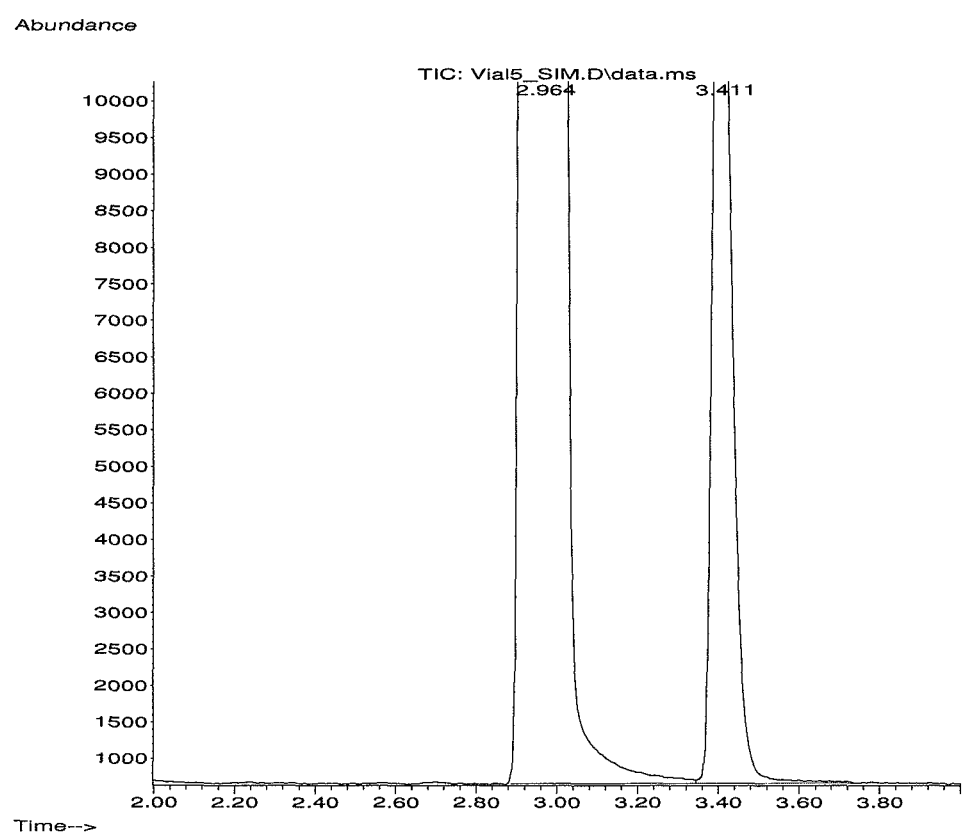

FIGS. 88A and 88B are GC/MS chromatogram comparing C5 hydrocarbons from petroleum-derived isoprene (FIG. 88A) and biologically produced isoprene (FIG. 88B). The standard contains three C5 hydrocarbon impurities eluting around the main isoprene peak (FIG. 88A). In contrast, biologically produced isoprene contains amounts of ethanol and acetone (run time of 3.41 minutes) (FIG. 88A).

Figure 89:
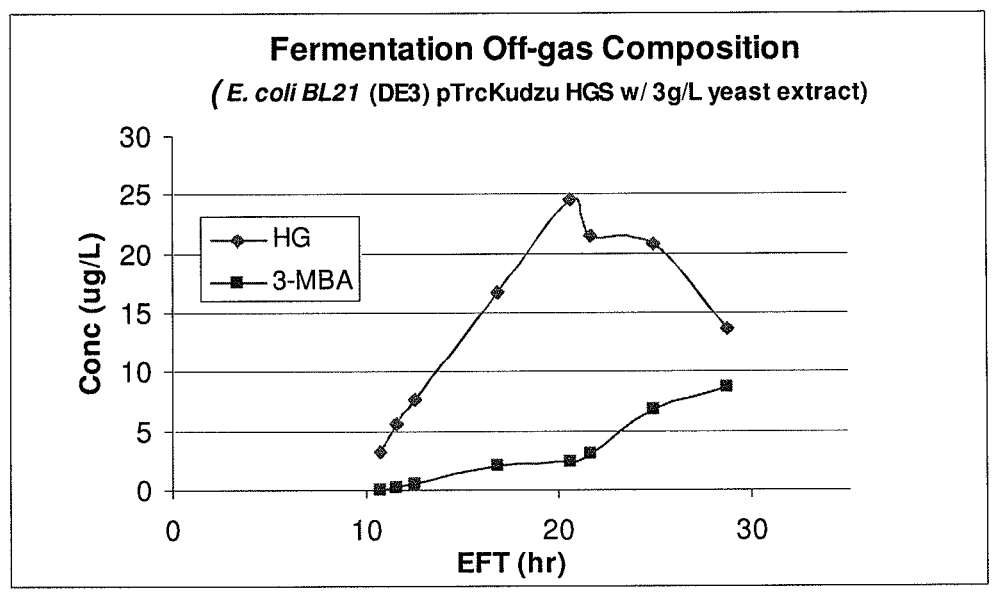

FIG. 89 is a graph of the analysis of fermentation off-gas of an *E. coli* BL21 (DE3) pTrcIS strain expressing a Kudzu isoprene synthase and fed glucose with 3 g/L yeast extract.

FIG. 90 shows the structures of several impurities that are structurally similar to isoprene and may also act as polymerization catalyst poisons.

Figure 91:
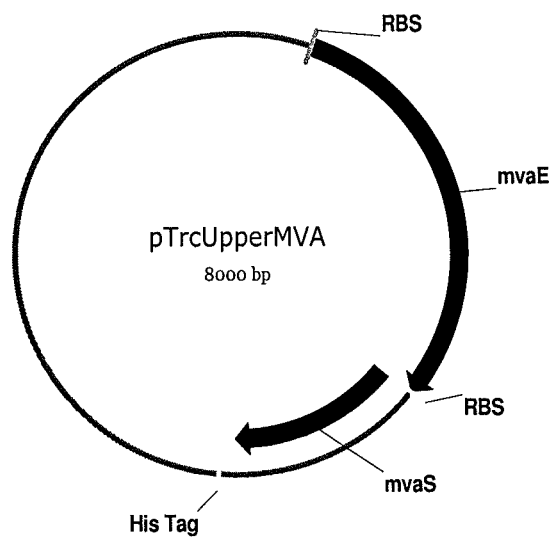

FIG. 91 is a map of pTrcHis2AUpperPathway (also called pTrcUpperMVA).

FIGS. 92A-92C are the nucleotide sequence of pTrcHis2AUpperPathway (also called pTrcUpperMVA) (SEQ ID NO:86).

Figure 93:
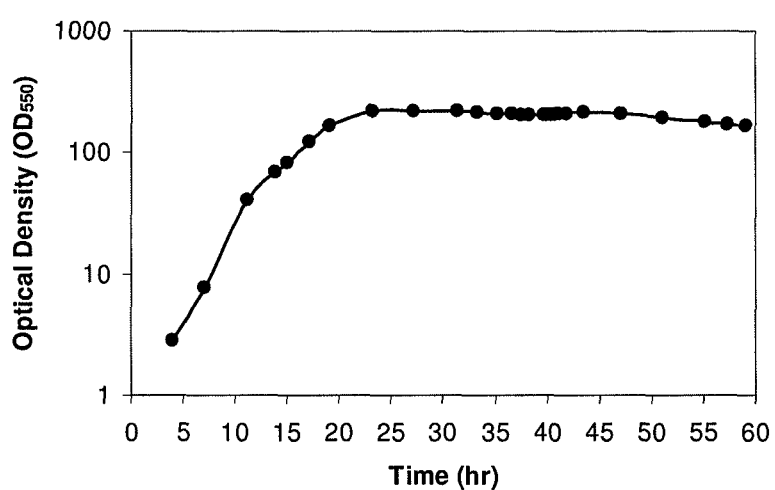

FIG. 93 is a time course of optical density within the 15-L bioreactor fed with glucose.

Figure 94:
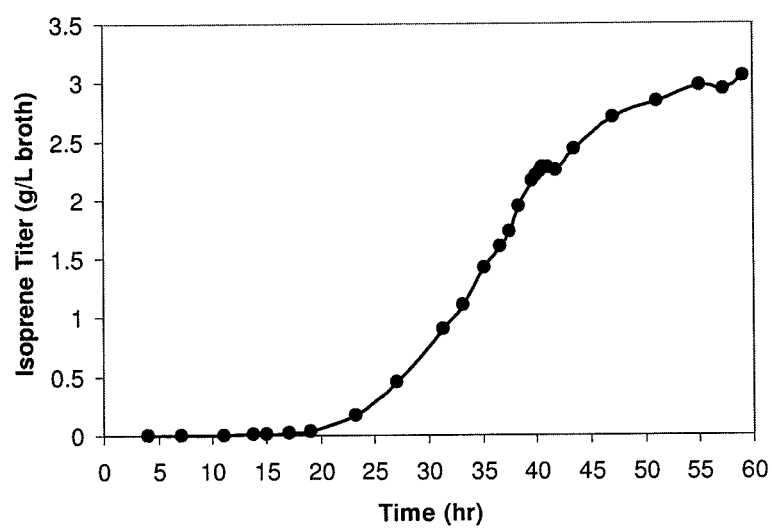

FIG. 94 is a time course of isoprene titer within the 15-L bioreactor fed with glucose. The titer is defined as the amount of isoprene produced per liter of fermentation broth.

Figure 95:
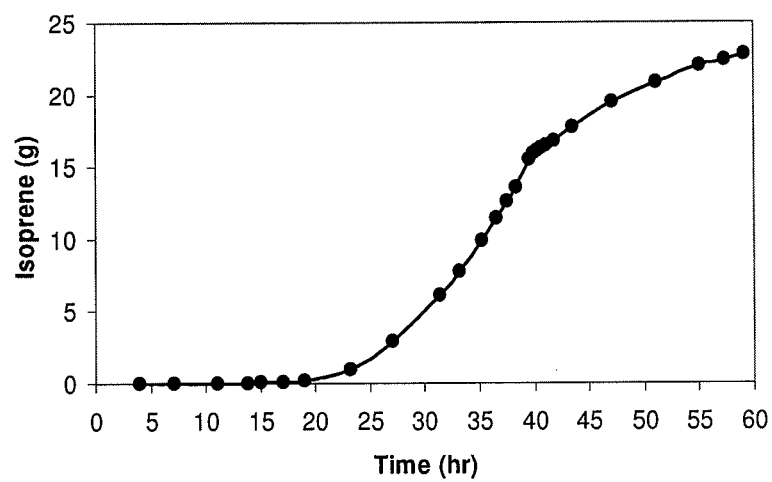

FIG. 95 is a time course of total isoprene produced from the 15-L bioreactor fed with glucose.

Figure 96:
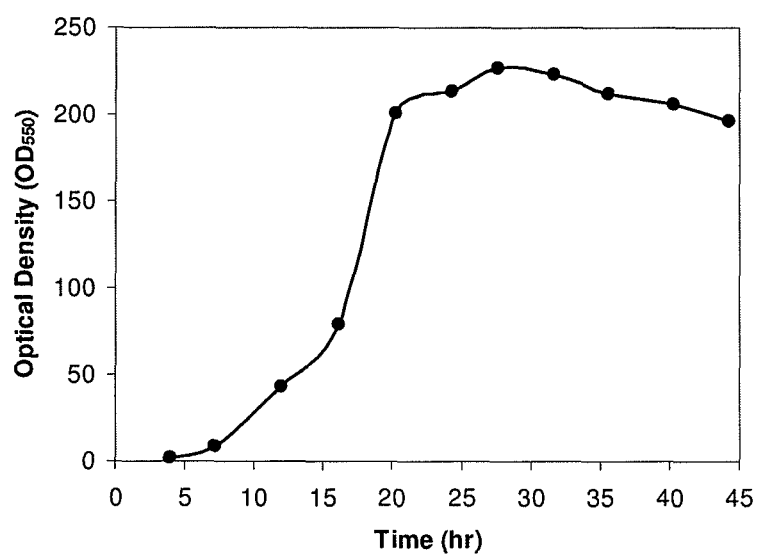

FIG. 96 is a time course of optical density within the 15-L bioreactor fed with invert sugar.

Figure 97:
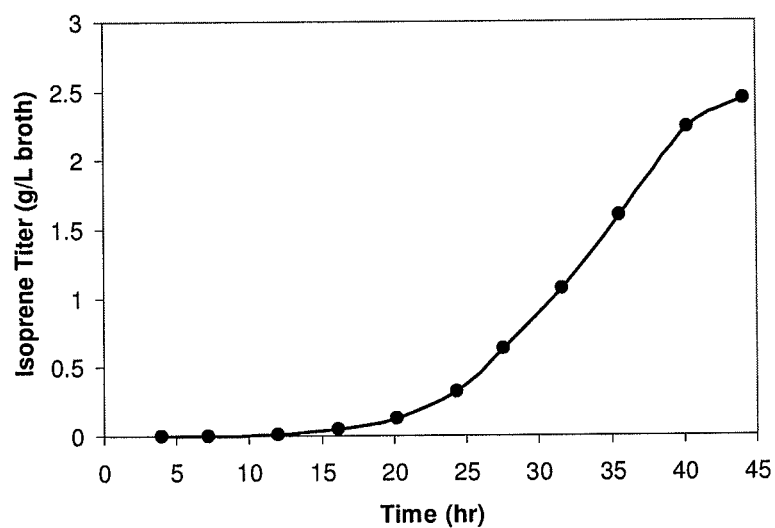

FIG. 97 is a time course of isoprene titer within the 15-L bioreactor fed with invert sugar. The titer is defined as the amount of isoprene produced per liter of fermentation broth.

Figure 98:
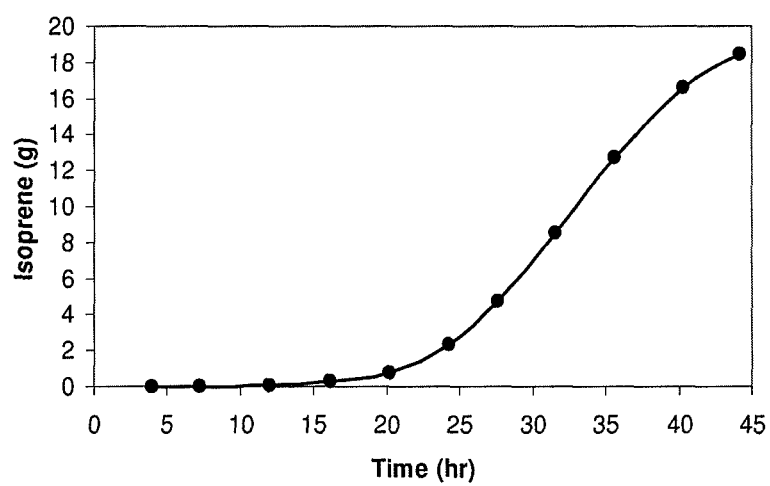

FIG. 98 is a time course of total isoprene produced from the 15-L bioreactor fed with invert sugar.

Figure 99:
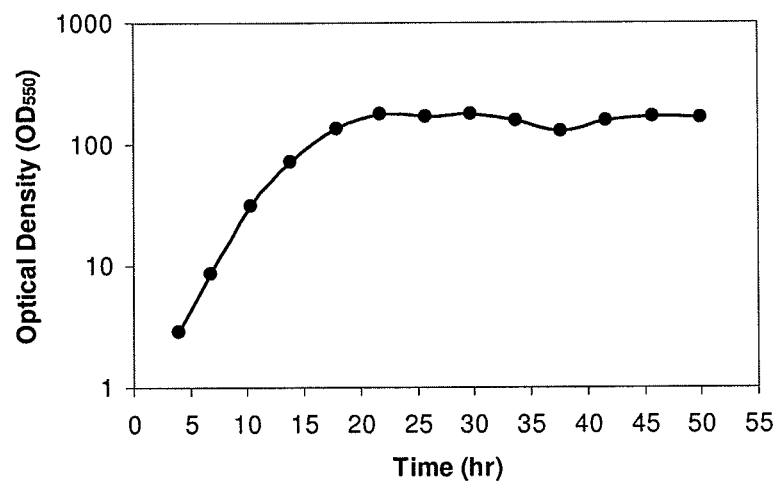

FIG. 99 is a time course of optical density within the 15-L bioreactor fed with glucose.

Figure 100:
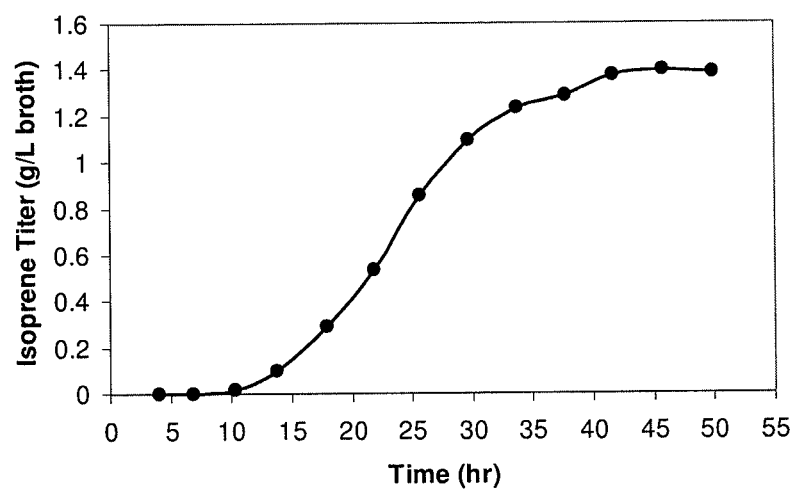

FIG. 100 is a time course of isoprene titer within the 15-L bioreactor fed with glucose. The titer is defined as the amount of isoprene produced per liter of fermentation broth.

Figure 101:
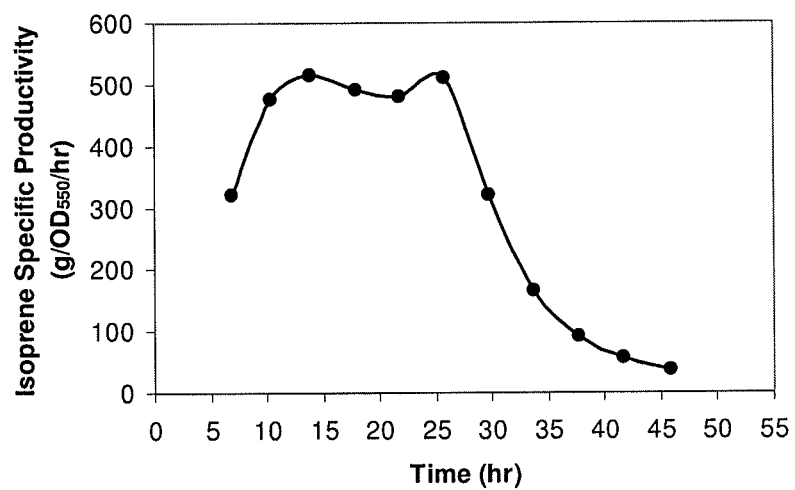

FIG. 101 is a time course of isoprene specific activity from the 15-L bioreactor fed with glucose.

Figure 102:
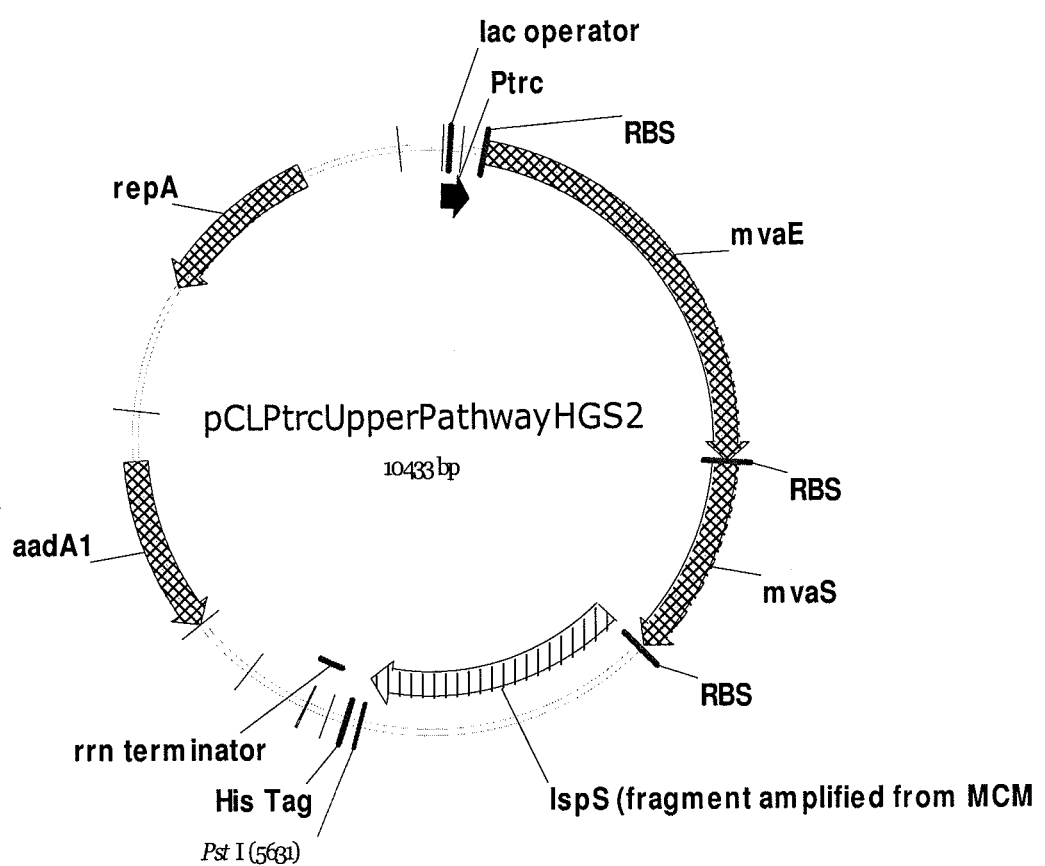

FIG. 102 is a map of pCLptrcUpperPathwayHGS2.

FIGS. 103A-103C are the nucleotide sequence of pCLPtrcUpperPathwayHGS2 (SEQ ID NO:87).

Figure 104:
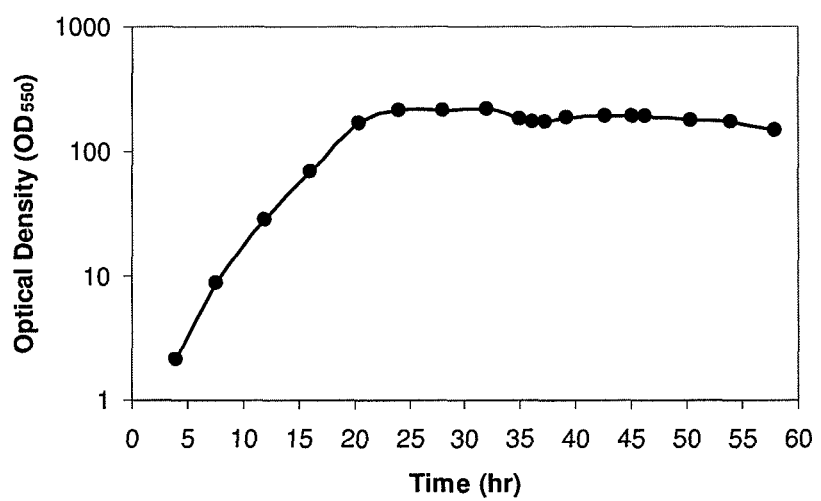

FIG. 104 is a time course of optical density within the 15-L bioreactor fed with glucose.

Figure 105:
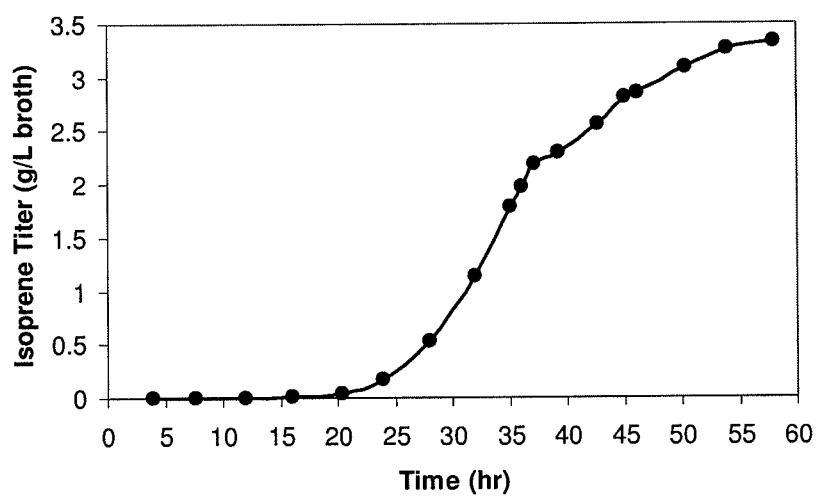

FIG. 105 is a time course of isoprene titer within the 15-L bioreactor fed with glucose. The titer is defined as the amount of isoprene produced per liter of fermentation broth.

Figure 106:
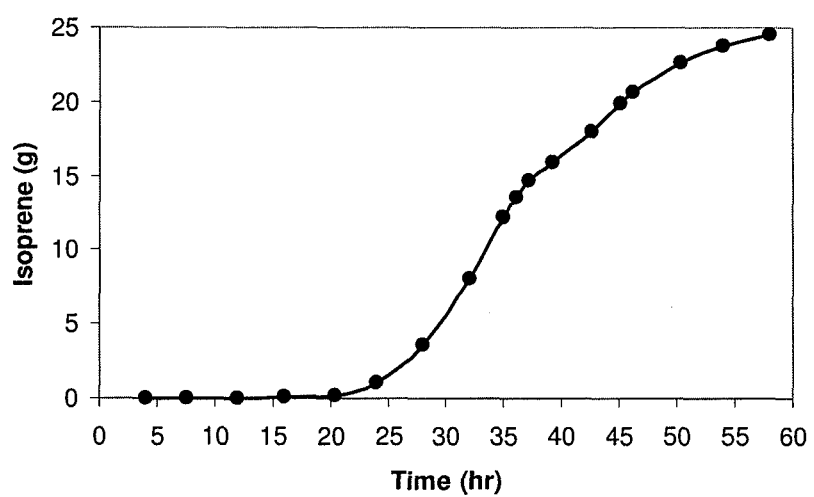

FIG. 106 is a time course of total isoprene produced from the 15-L bioreactor fed with glucose.

Figure 107:
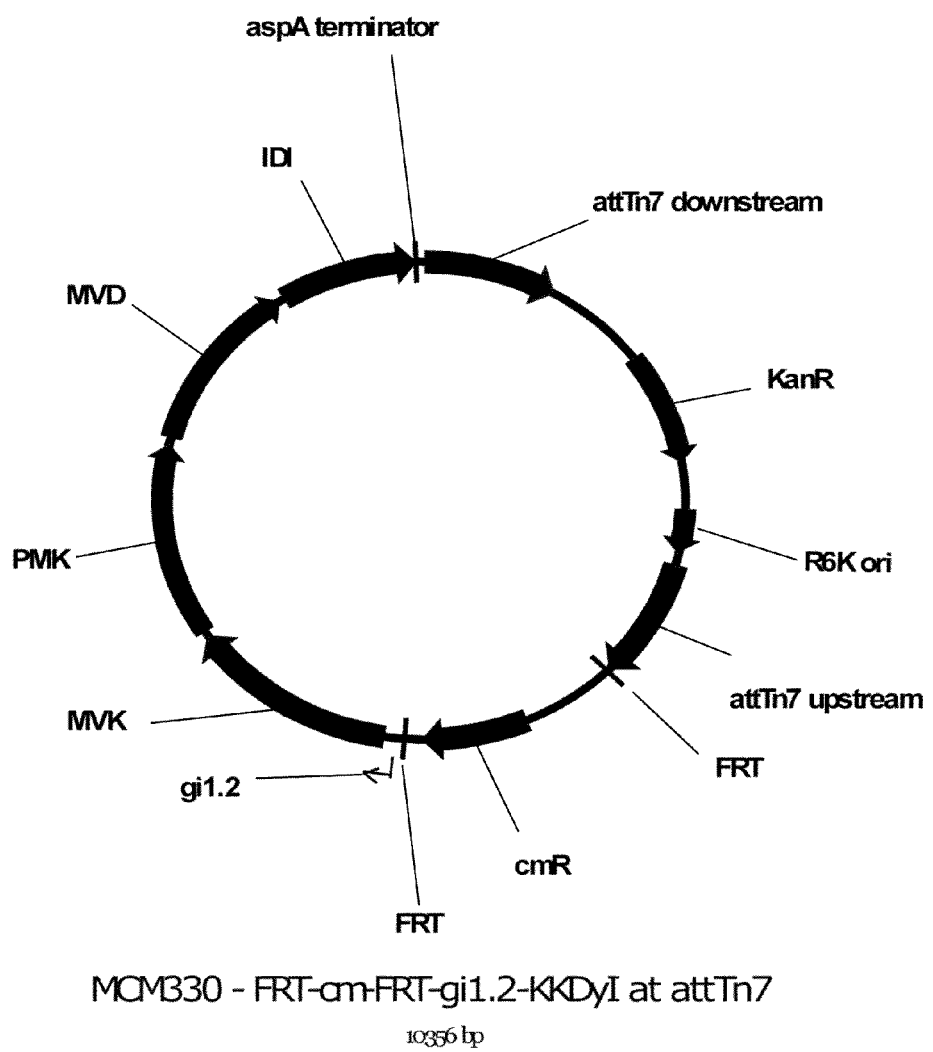

FIG. 107 is a map of plasmid MCM330.

FIGS. 108A-108C are the nucleotide sequence of plasmid MCM330 (SEQ ID NO:90).

Figure 109:
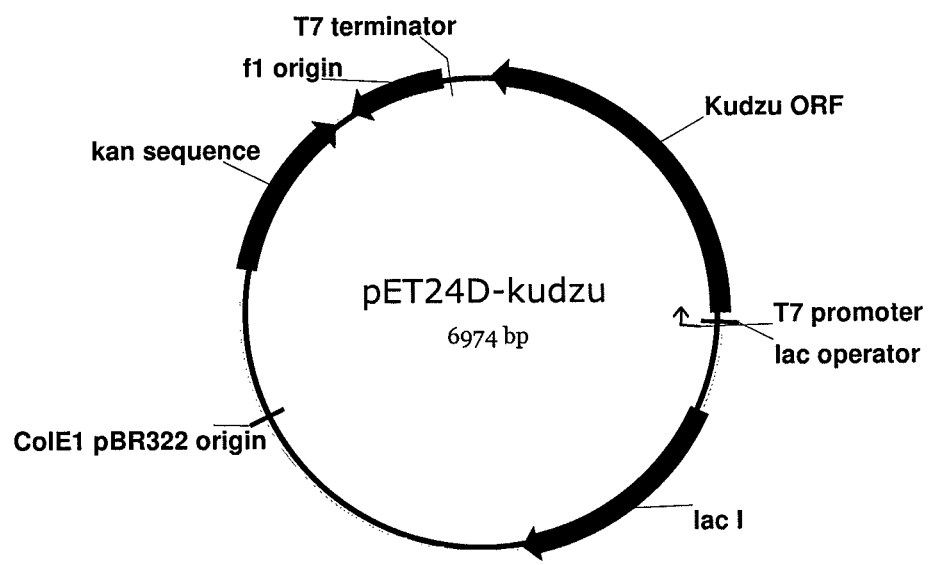

FIG. 109 is a map of pET24D-Kudzu.

FIGS. 110A and 110B are the nucleotide sequence of pET24D-Kudzu (SEQ ID NO:101).

Figure 111A:
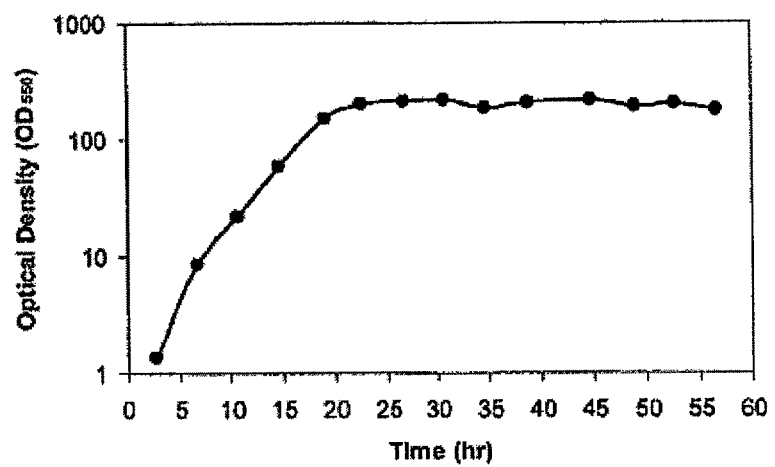

FIG. 111A is a time course of optical density within the 15-L bioreactor fed with glucose.

Figure 111B:
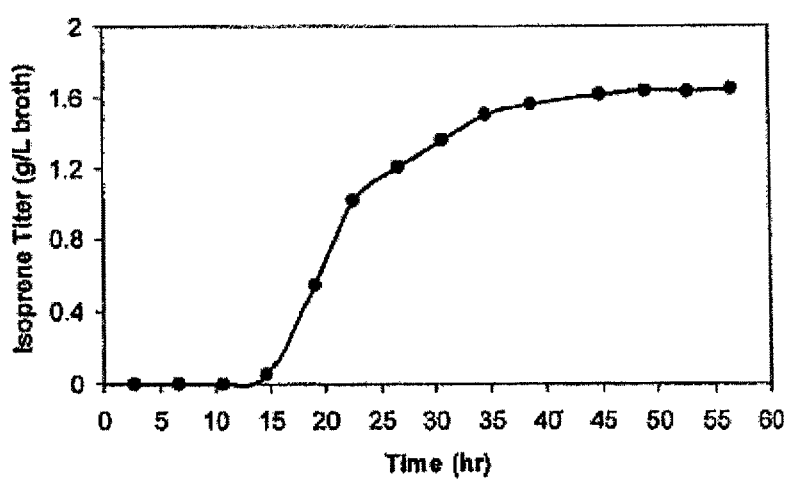

FIG. 111B is a time course of isoprene titer within the 15-L bioreactor fed with glucose. The titer is defined as the amount of isoprene produced per liter of fermentation broth.

Figure 111C:
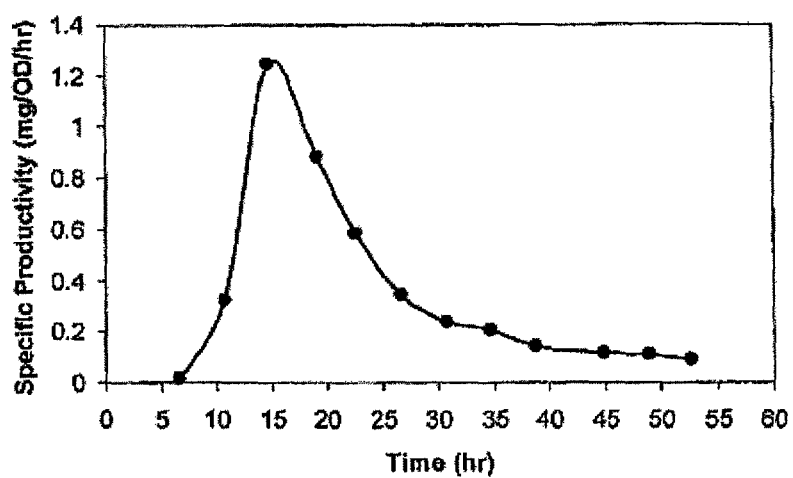

FIG. 111C is a time course of specific productivity of isoprene in the 15-L bioreactor fed with glucose.

Figure 112A:
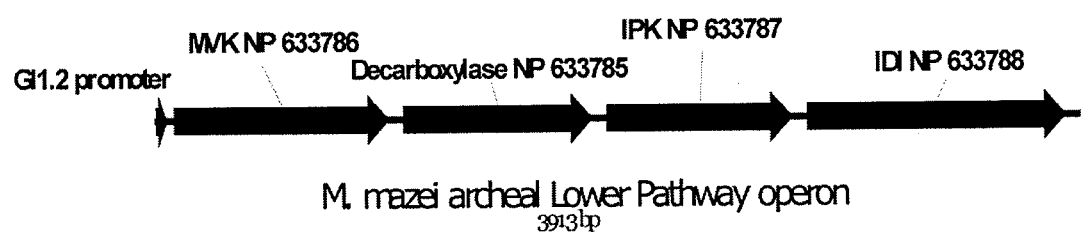

FIG. 112A is a map of the *M. mazei* archeal Lower Pathway operon.

FIGS. 112B and 112C are the nucleotide sequence of the *M. mazei* archeal lower Pathway operon (SEQ ID NO:102).

Figure 113A:
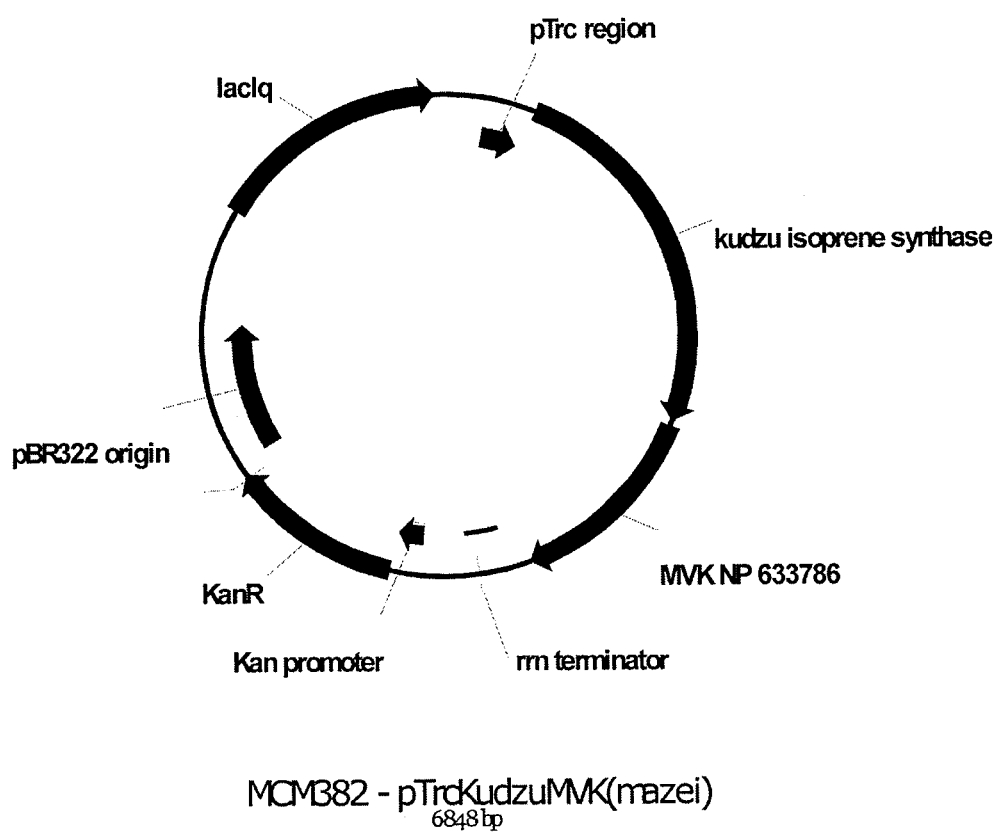

FIG. 113A is a map of MCM382 pTrcKudzuMVK(*mazei*).

FIGS. 113B and 113C are the nucleotide sequence of MCM382 pTrcKudzuMVK(*mazei*) (SEQ ID NO:103).

Figure 114A:
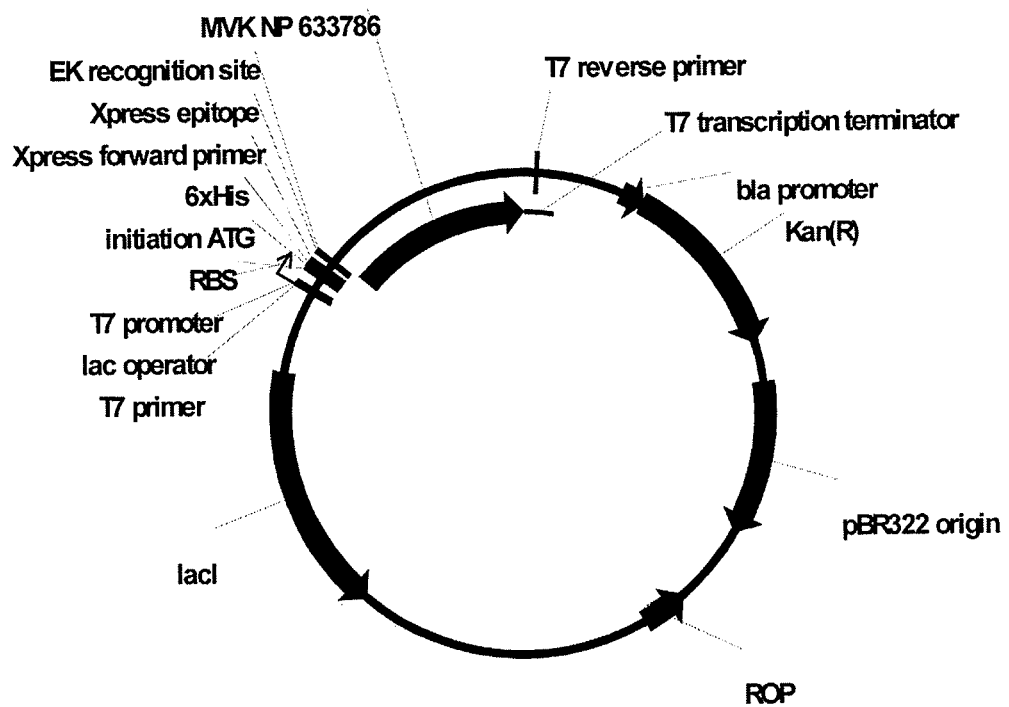

FIG. 114A is a map of MCM376-MVK from *M. mazei* archeal Lower in pET200D.

FIGS. 114B and 114C are the nucleotide sequence of MCM376-MVK from *M. mazei* archeal Lowerin pET200D (SEQ ID NO:108).

Figure 115:
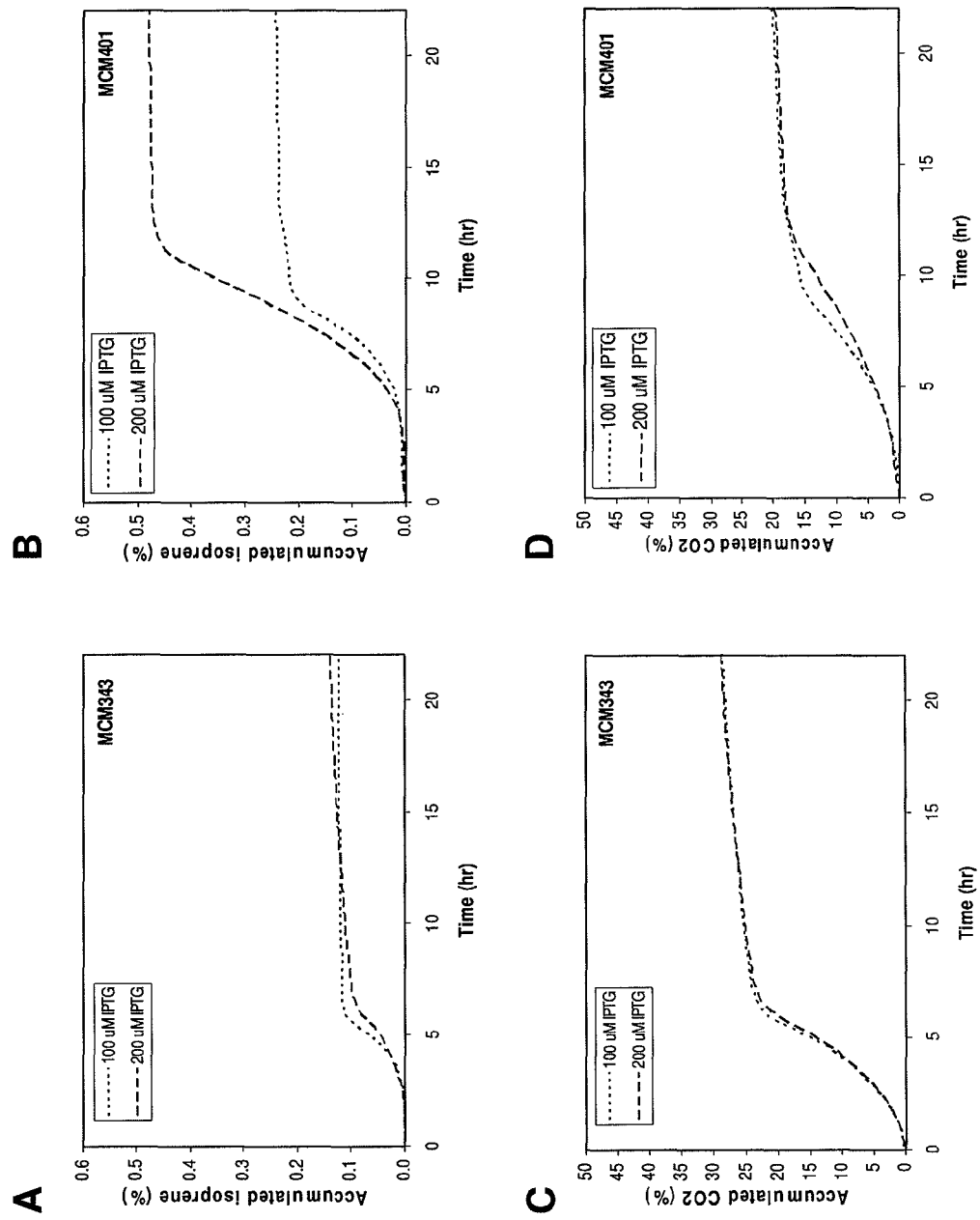

FIGS. 115A-115D demonstrate that over-expression of MVK and isoprene synthase results in increased isoprene production. Accumulated isoprene and $CO_2$ from MCM401 and MCM343 during growth on glucose in 100 mL bioreactors with 100 and 200 uM IPTG induction of isoprene production was measured over a 22 hour time course. FIG. 115A is a graph of the accumulated isoprene (%) from MCM343. FIG. 115B is a graph of the accumulated isoprene (%) from MCM401. FIG. 115C is a graph of the accumulated $CO_2$(%) from MCM343. FIG. 115D is a graph of the accumulated $CO_2$(%) from MCM401.

Figure 116:
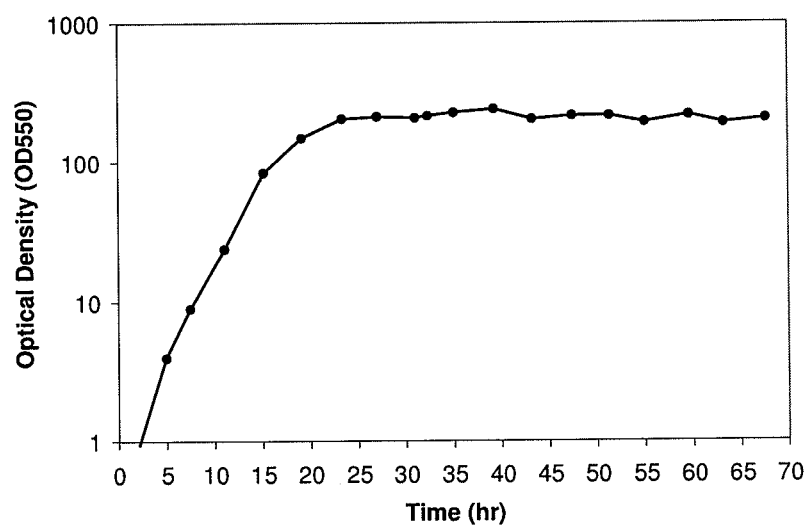

FIG. 116 is a time course of optical density within the 15-L bioreactor fed with glucose.

Figure 117:
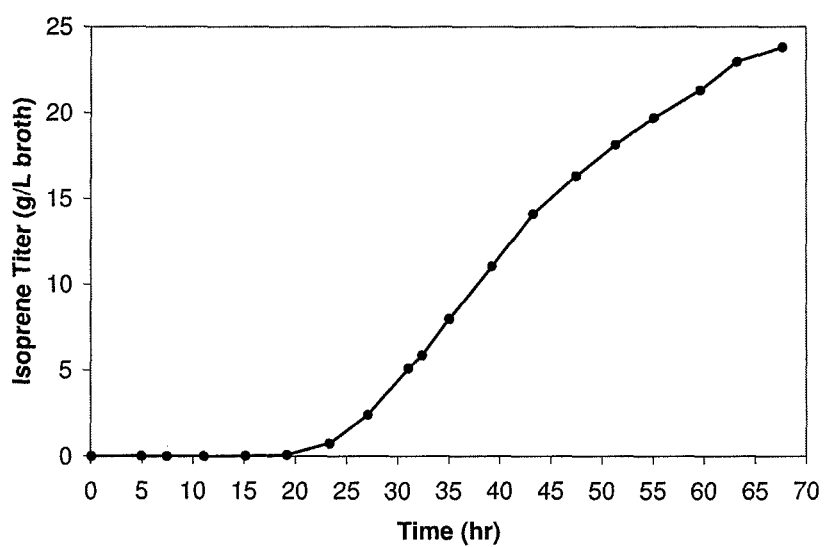

FIG. 117 is a time course of isoprene titer within the 15-L bioreactor fed with glucose. The titer is defined as the amount of isoprene produced per liter of fermentation broth.

Figure 118:
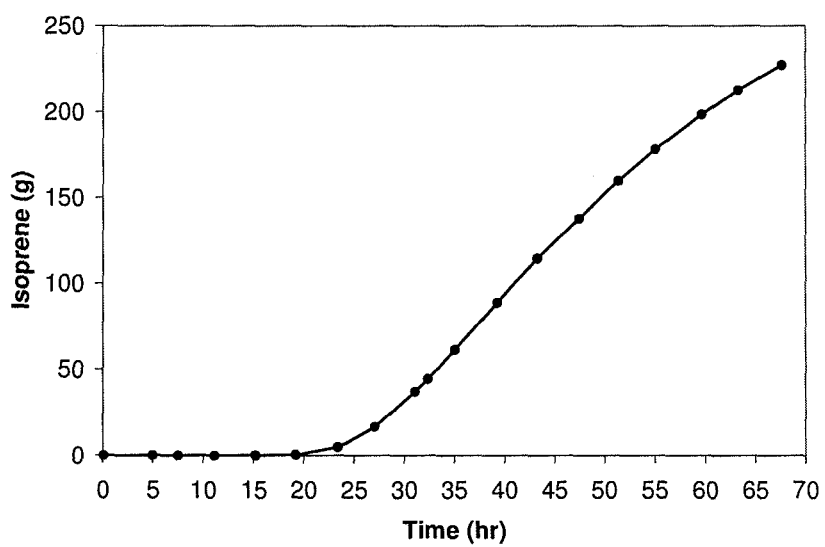

FIG. 118 is a time course of total isoprene produced from the 15-L bioreactor fed with glucose.

Figure 119:
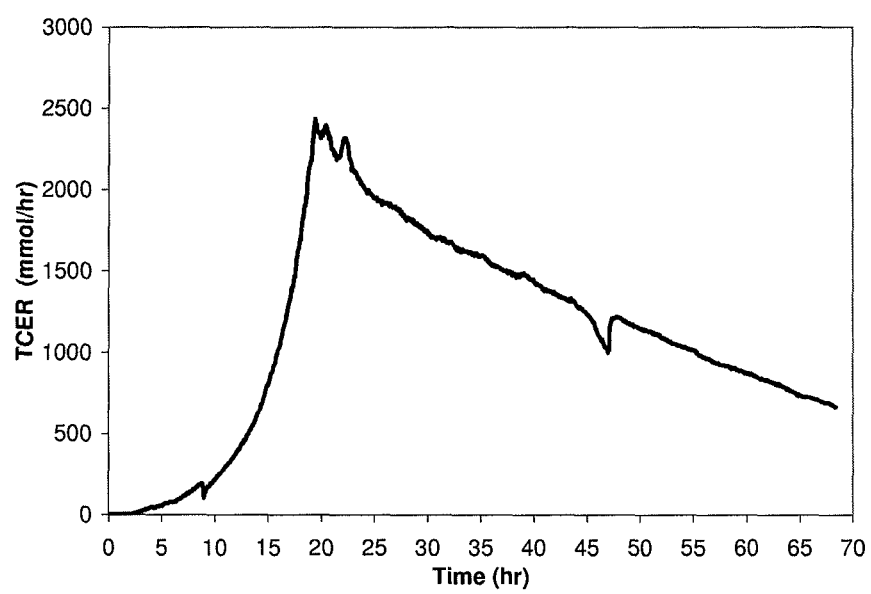

FIG. 119 is a graph of the total carbon dioxide evolution rate (TCER), or metabolic activity profile, within the 15-L bioreactor fed with glucose.

Figure 120:
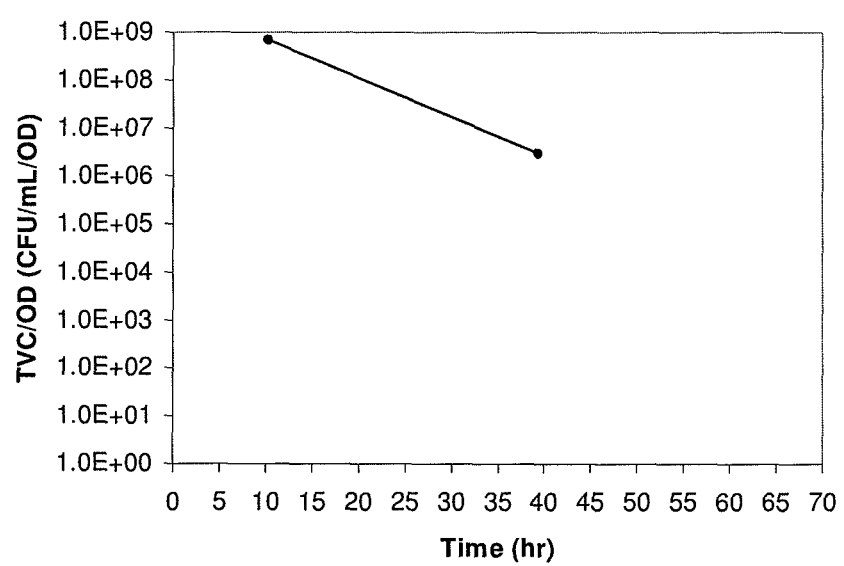

FIG. 120 is a graph of the cell viability during isoprene production within the 15-L bioreactor fed with glucose. TVC/OD is the total viable counts (colony forming units) in 1 mL of broth per optical density unit ($OD_{550}$).

Figure 121:
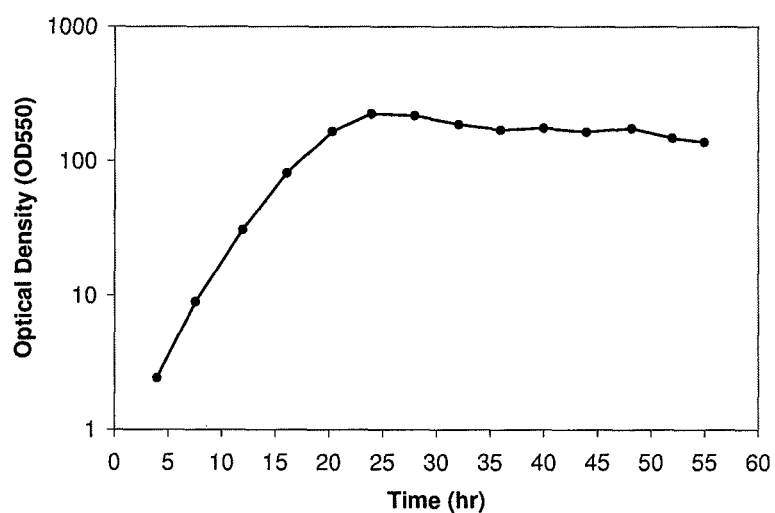

FIG. 121 is a time course of optical density within the 15-L bioreactor fed with glucose.

Figure 122:
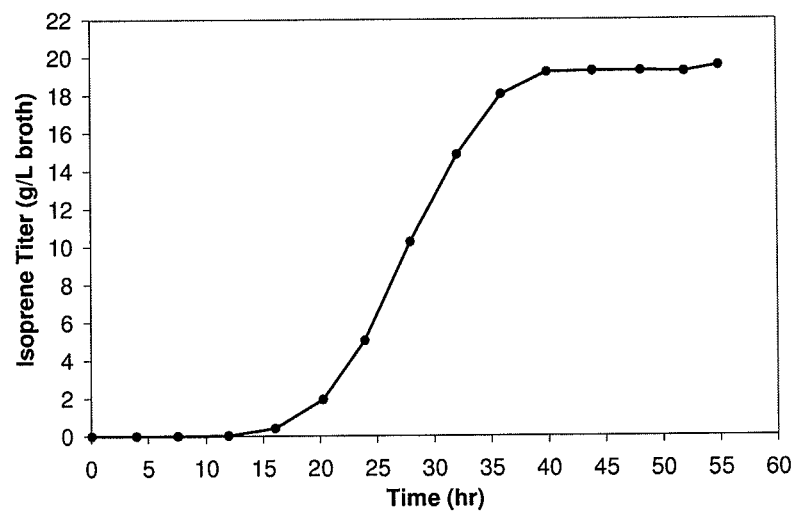

FIG. 122 is a time course of isoprene titer within the 15-L bioreactor fed with glucose. The titer is defined as the amount of isoprene produced per liter of fermentation broth.

Figure 123:
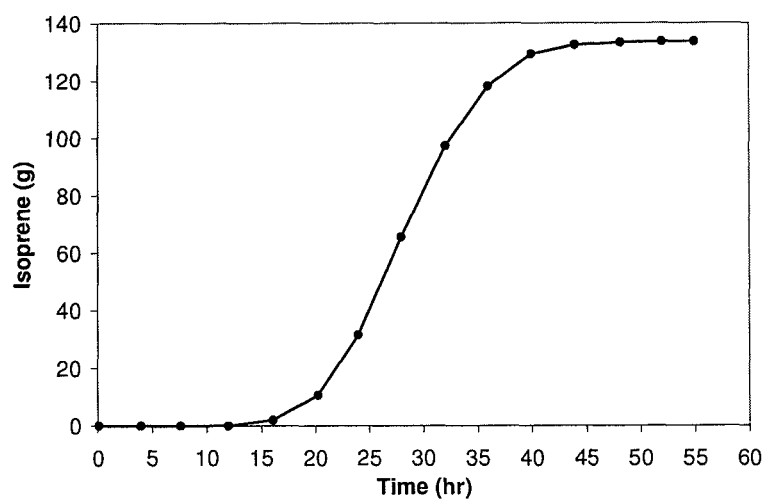

FIG. 123 is a time course of total isoprene produced from the 15-L bioreactor fed with glucose.

Figure 124:
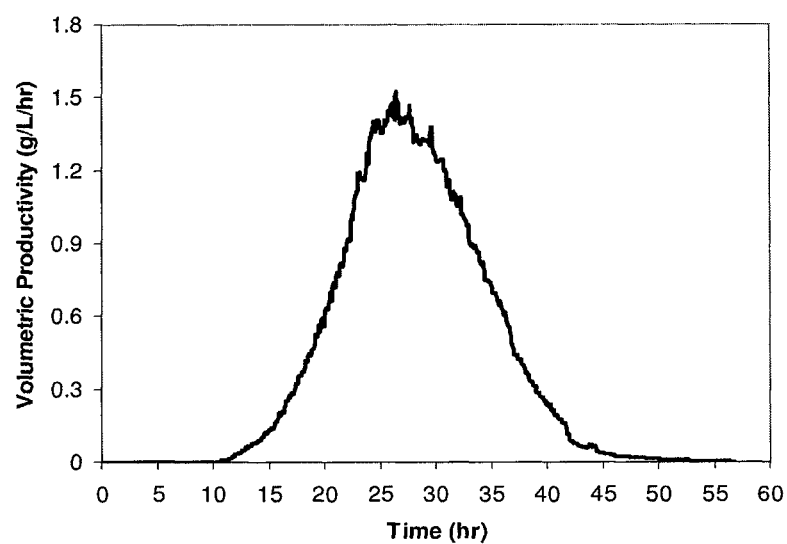

FIG. 124 is a time course of volumetric productivity within the 15-L bioreactor fed with glucose. The volumetric productivity is defined as the amount of isoprene produced per liter of broth per hour.

Figure 125:
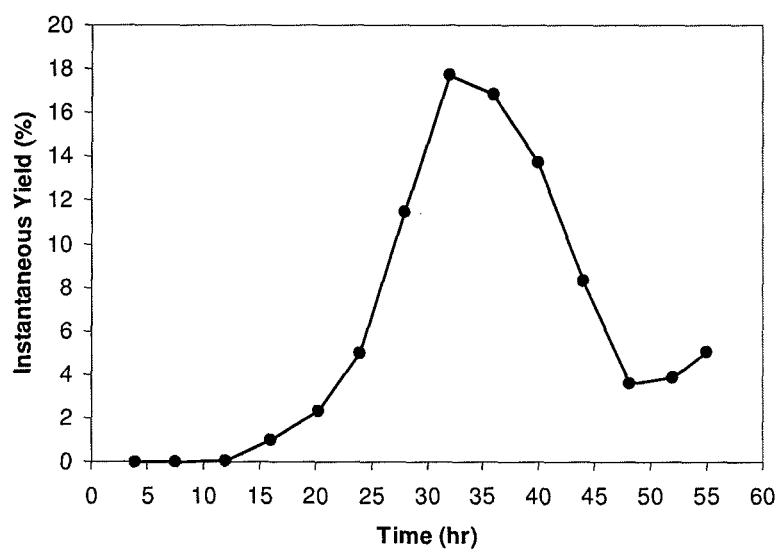

FIG. 125 is a time course of instantaneous yield within the 15-L bioreactor fed with glucose. The instantaneous yield is defined as the amount of isoprene (gram) produced per amount of glucose (gram) fed to the bioreactor (w/w) during the time interval between the data points.

Figure 126:
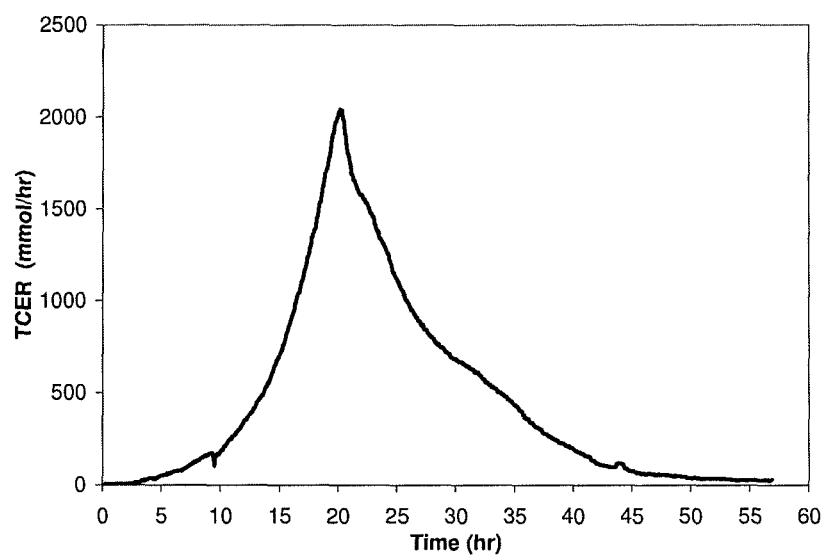

FIG. 126 is a graph of the total carbon dioxide evolution rate (TCER), or metabolic activity profile, within the 15-L bioreactor fed with glucose.

Figure 127:
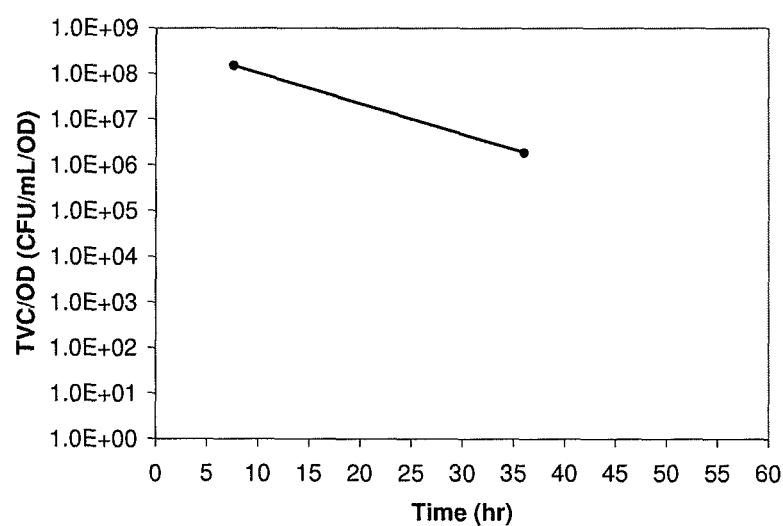

FIG. 127 is cell viability during isoprene production within the 15-L bioreactor fed with glucose. TVC/OD is the total viable counts (colony forming units) in 1 mL of broth per optical density unit ($OD_{550}$).

Figure 128:
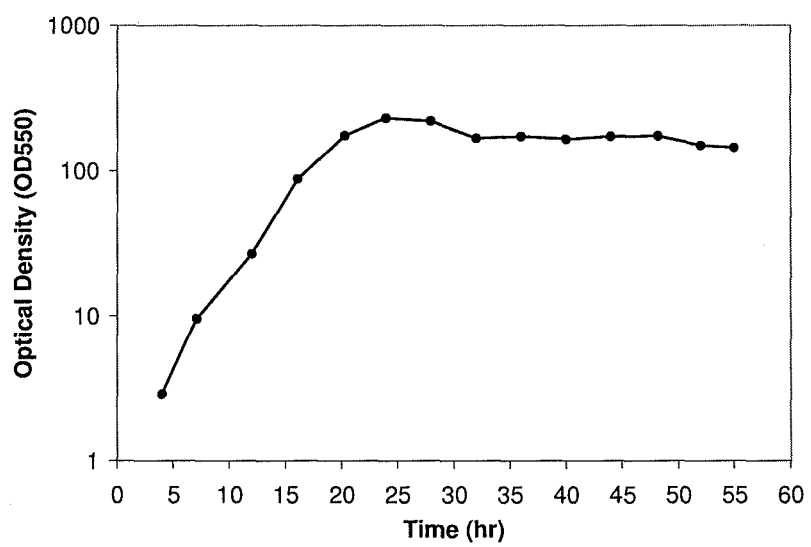

FIG. 128 is a time course of optical density within the 15-L bioreactor fed with glucose.

Figure 129:
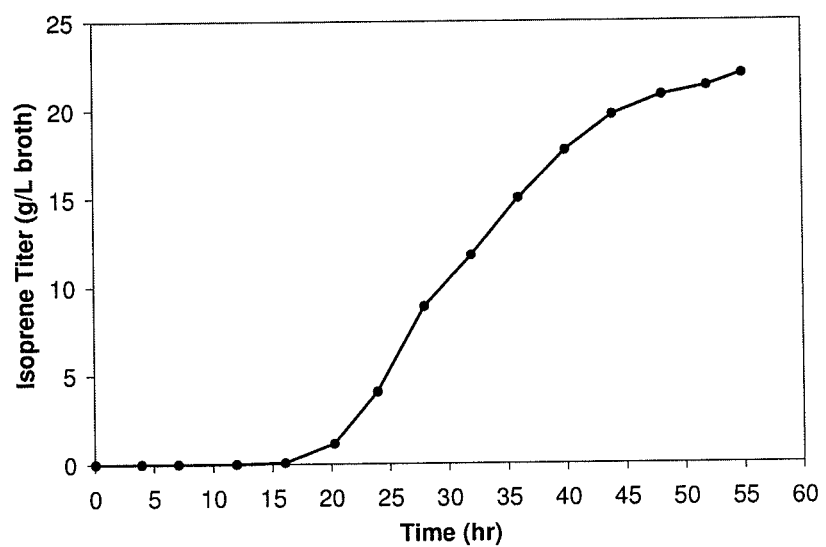

FIG. 129 is a time course of isoprene titer within the 15-L bioreactor fed with glucose. The titer is defined as the amount of isoprene produced per liter of fermentation broth.

Figure 130:
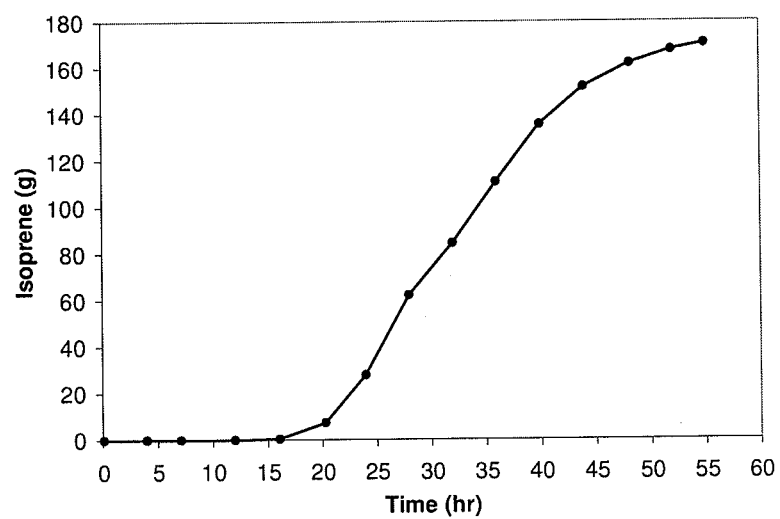

FIG. 130 is a time course of total isoprene produced from the 15-L bioreactor fed with glucose.

Figure 131:
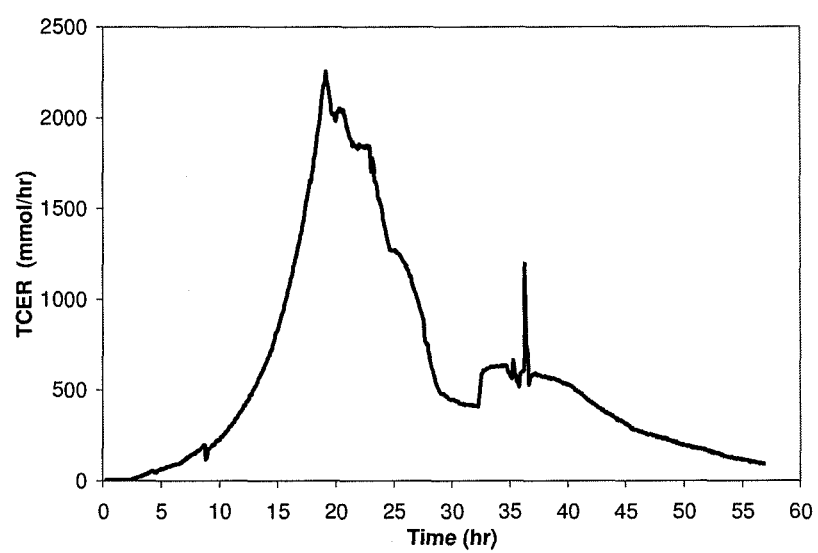

FIG. 131 is a graph of total carbon dioxide evolution rate (TCER), or metabolic activity profile, within the 15-L bioreactor fed with glucose.

Figure 132:
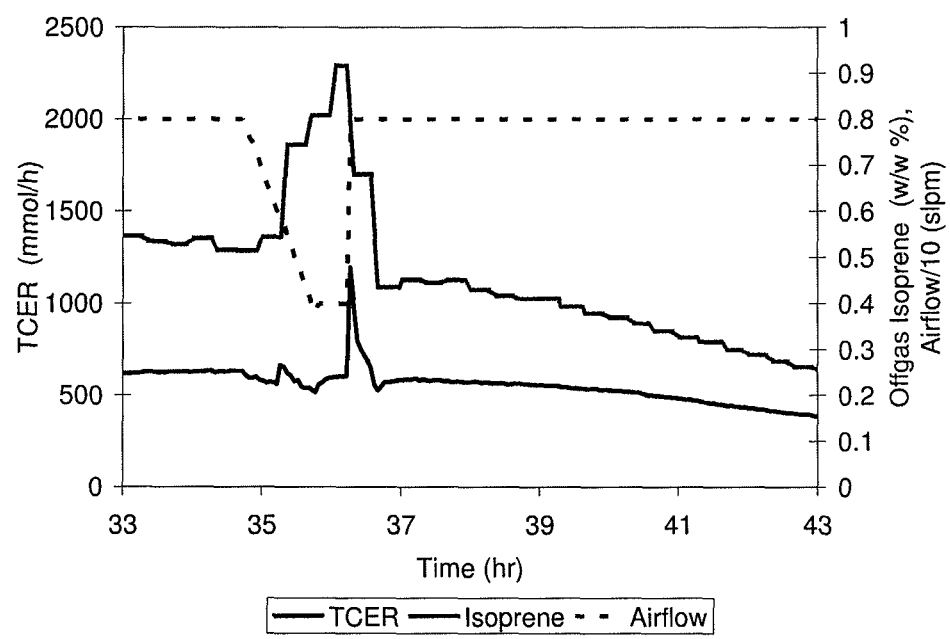

FIG. 132 is a graph showing that a transient decrease in the airflow to the bioreactor caused a spike in the concentration of isoprene in the offgas that did not cause a dramatic decrease in metabolic activity (TCER). TCER, or metabolic activity, is the total carbon dioxide evolution rate.

Figure 133:
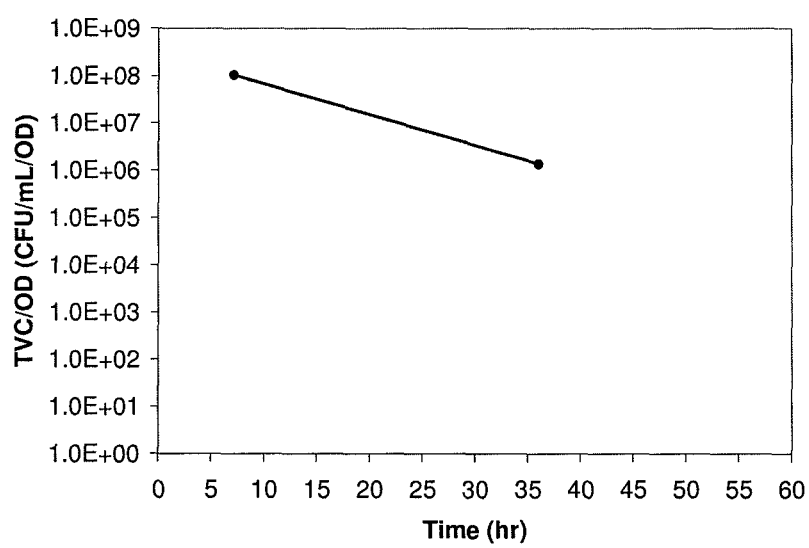

FIG. 133 is a graph of the cell viability during isoprene production within the 15-L bioreactor fed with glucose. TVC/OD is the total viable counts (colony forming units) in 1 mL of broth per optical density unit ($OD_{550}$).

Figure 134:
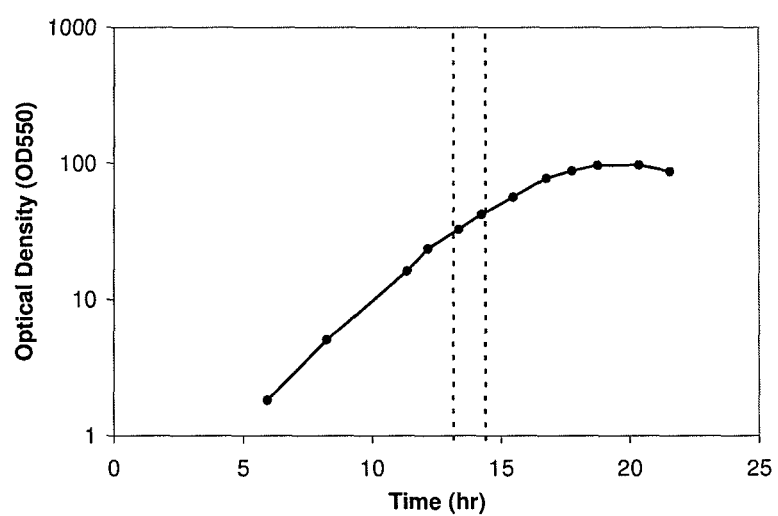

FIG. 134 is a time course of optical density within the 15-L bioreactor fed with glucose. Dotted vertical lines denote the time interval when isoprene was introduced into the bioreactor at a rate of 1 g/L/hr.

Figure 135:
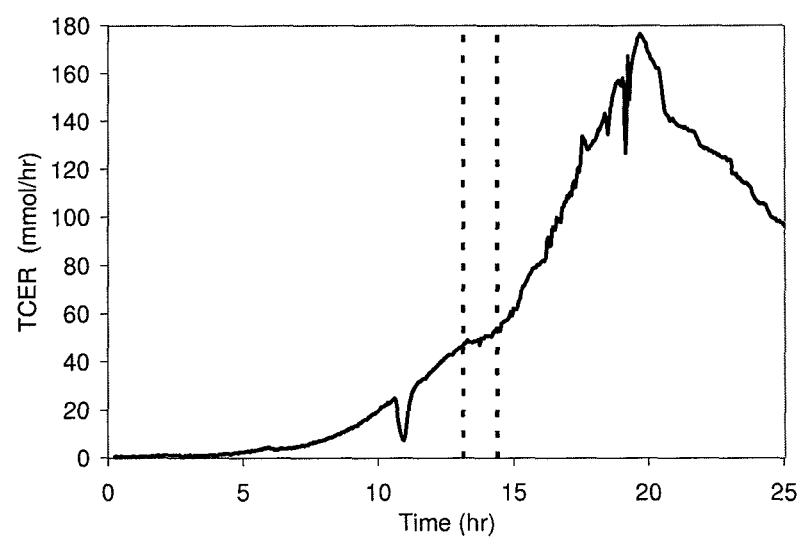

FIG. 135 is total carbon dioxide evolution rate (TCER), or metabolic activity profile, within the 15-L bioreactor fed with glucose. Dotted vertical lines denote the time interval when isoprene was introduced into the bioreactor at a rate of 1 g/L/hr.

Figure 136:
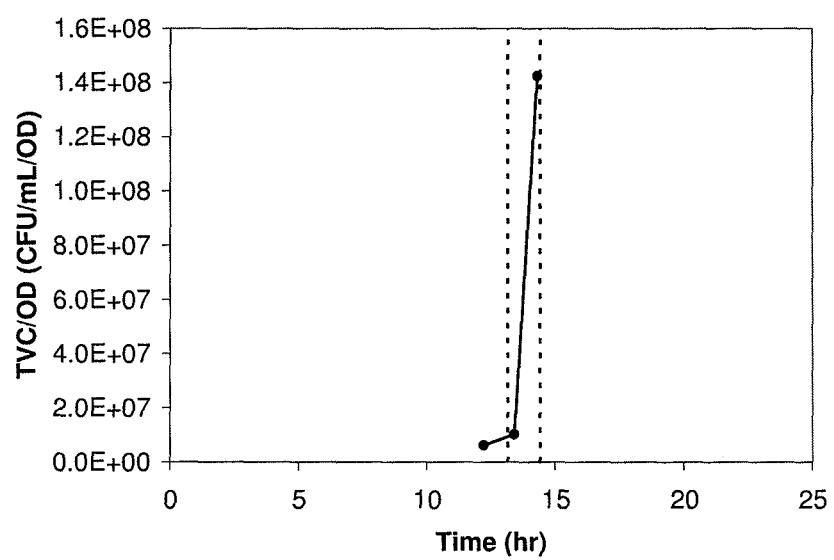

FIG. 136 is cell viability during isoprene production within the 15-L bioreactor fed with glucose. TVC/OD is the total viable counts (colony forming units) in 1 mL of broth per optical density unit ($OD_{550}$). Dotted vertical lines denote the time interval when isoprene was introduced into the bioreactor at a rate of 1 g/L/hr.

FIGS. 137A and B are the sequence of *Populus alba* pET24a: isoprene synthase gene highlighted in bold letters (SEQ ID NO:109).

FIGS. 137C and D are the sequence of *Populus nigra* pET24a: isoprene synthase gene highlighted in bold letters (SEQ ID NO:110).

FIGS. 137E and F are the sequence of *Populus tremuloides* pET24a (SEQ ID NO:123).

FIG. 137G is the amino acid sequence of *Populus tremuloides* isoprene synthase gene (SEQ ID NO:124).

FIGS. 137H and I are the sequence of *Populus trichocarpa* pET24a: isoprene synthase gene highlighted in bold letters (SEQ ID NO:111).

FIGS. 137J and K are the sequence of *Populus tremula×Populus alba* pET24a: isoprene synthase gene highlighted in bold letters (SEQ ID NO:112).

Figure 137L:
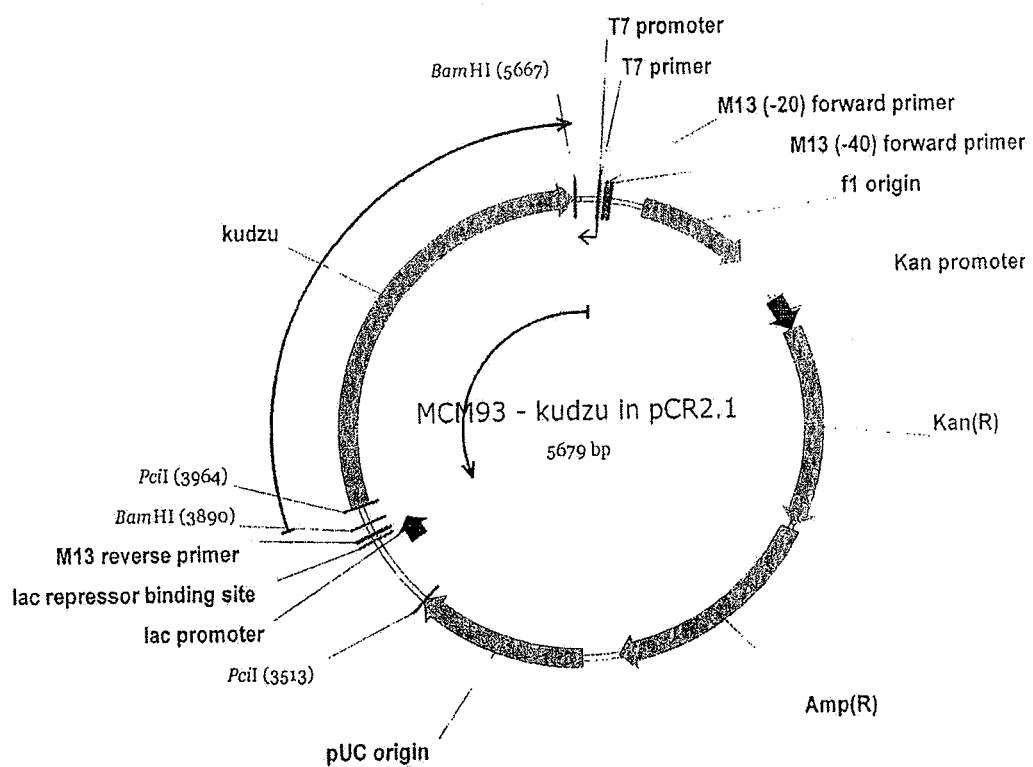

FIG. 137L is a map of MCM93 which contains the kudzu IspS coding sequence in a pCR2.1 backbone.

FIGS. 137M and N are the sequence of MCM93 (SEQ ID NO:113).

Figure 137O:
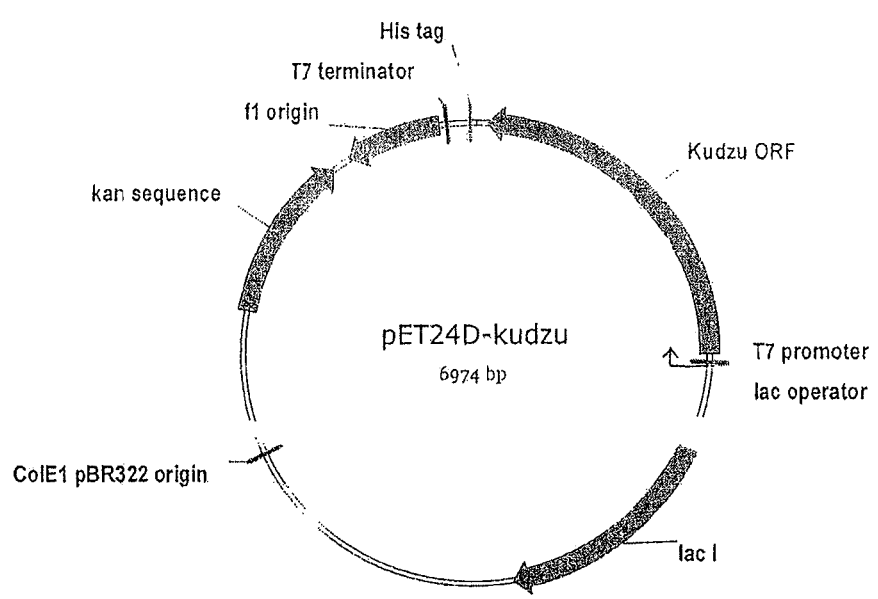

FIG. 137O is a map of pET24D-Kudzu.

FIGS. 137P and Q are the sequence of pET24D-Kudzu (SEQ ID NO:114).

Figure 138:
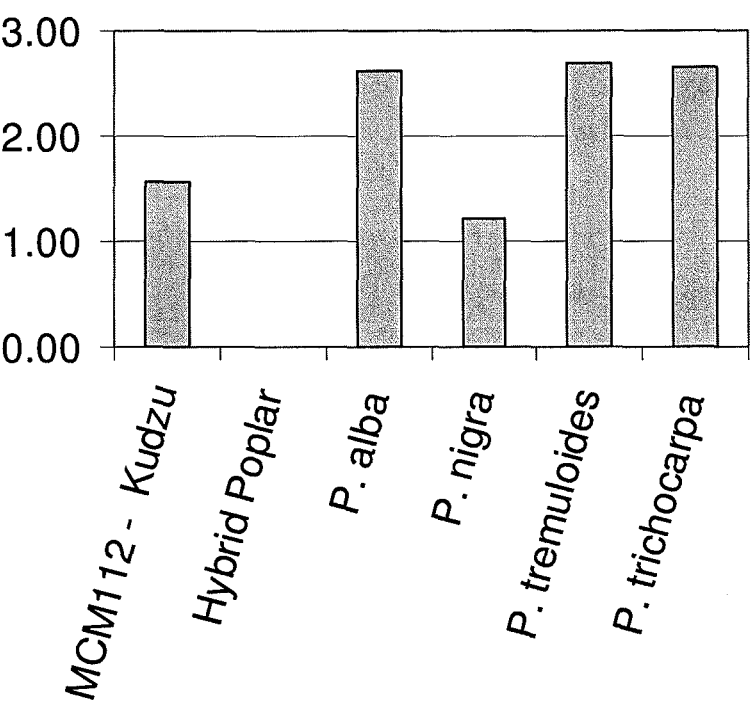

FIG. 138 is isoprene synthase expression data for various poplar species as measured in the whole cell head space assay. Y-axis is ug/L/OD of isoprene produced by 0.2 mL of a culture induced with IPTG.

Figure 139:
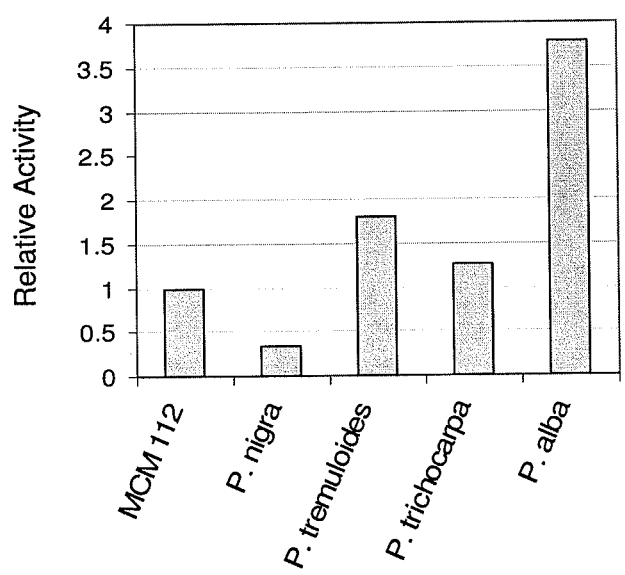

FIG. 139 is relative activity of Poplar isoprene synthase enzymes as measured by DMAPP assay. Poplar enzymes have significantly higher activity than the isoprene synthase from Kudzu. Poplar [*alba×tremula*] only had traces (<1%) of activity and is not shown in the plot.

Figure 140:
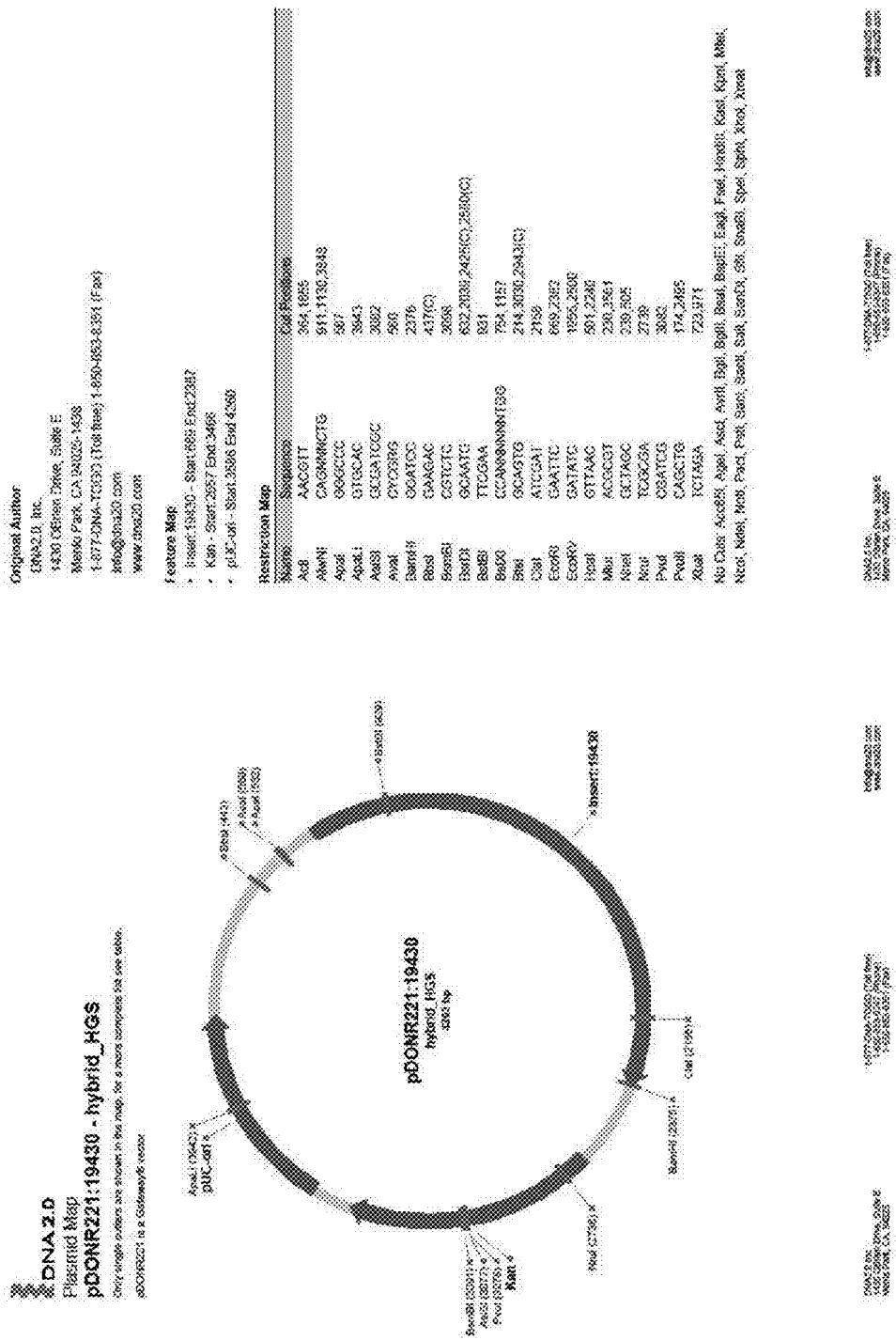

FIG. 140 is a map of pDONR221:19430—hybrid_HGS (Bstx1=SEQ ID NO:131).

FIG. 141 is the nucleotide sequence of pDONR221:19430-hybrid_HGS, the sequence of Kudzu isoprene synthase codon-optimized for yeast (SEQ ID NO:115).

Figure 142A:
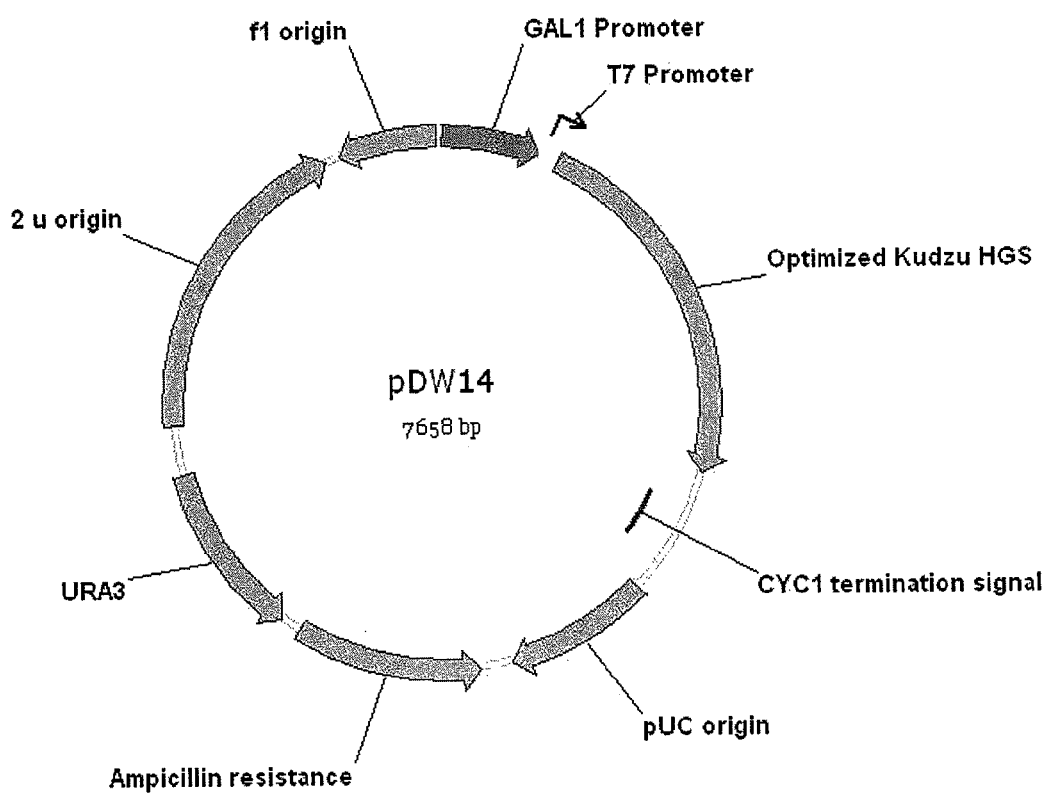

FIG. 142A is a map of pDW14.

FIGS. 142B and C are the complete nucleotide sequence of pDW14 (SEQ ID NO:119).

Figure 143:
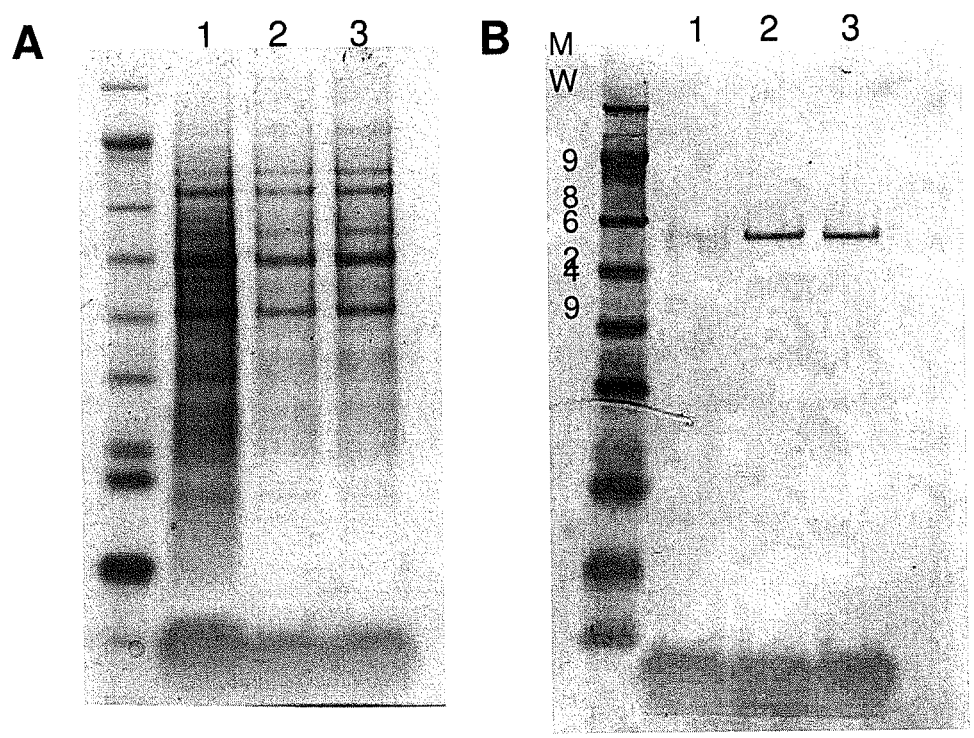

FIG. 143 shows induced INVSc-1 strains harboring pDW14 or pYES-DEST52. FIG. 143A. A 4-12% bis tris gel (Novex, Invitrogen) of lysates generated from INVSc-1 strains induced with galactose and stained with SimplyBlue SafeStain (Invitrogen). FIG. 143B. Western blot analysis of the same strains using the WesternBreeze kit (Invitrogen). Lanes are as follows: 1, INVSc-1+pYES-DEST52; 2, INVSc-1+pDW14 (isolate 1); 3, INVSc-1+pDW14 (isolate 2). MW (in kDa) is indicated (using the See Blue Plus2 molecular weight standard).

FIG. 144 shows induced INVSc-1 strains harboring pDW14 or pYES-DEST52. FIG. 144A. $OD_{600}$ of galactose-induced strains prior to lysis. The y-axis is $OD_{600}$. FIG. 144B. DMAPP assay of isoprene synthase headspace in control and isoprene synthase-harboring strains. Specific activity was calculated as μg HG/L/OD. Samples are as follows: Control, INVSc-1+pYES-DEST52; HGS-1, INVSc-1+pDW14 (isolate 1); HGS-2, INVSc-1+pDW14 (isolate 2).

Figure 145A:
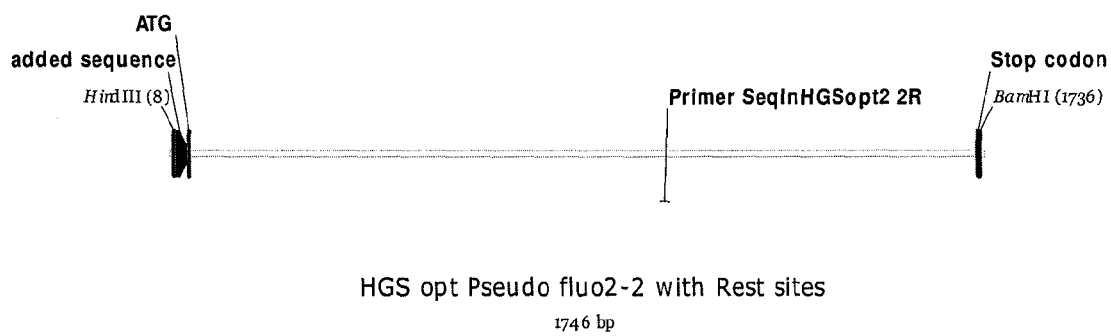

FIG. 145A is a map of codon optimized isoprene synthase fluo-opt2v2.

FIG. 145B is the nucleotide sequence of codon optimized isoprene synthase fluo-opt2v2 (SEQ ID NO:120).

Figure 146A:
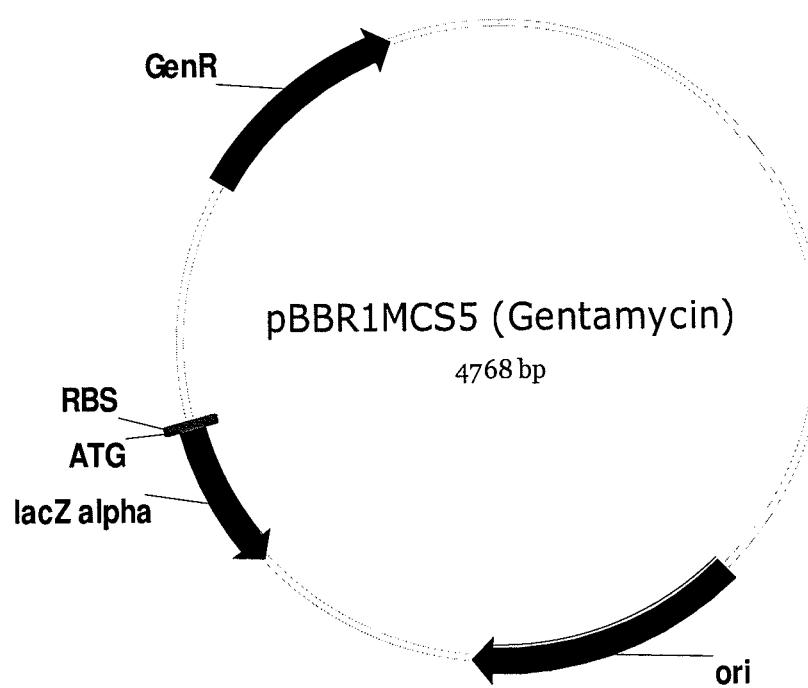

FIG. 146A is a map of pBBR1MCS5.

FIGS. 146B and C are the nucleotide sequence of pBBR1MCS5 (SEQ ID NO:121).

Figure 147A:
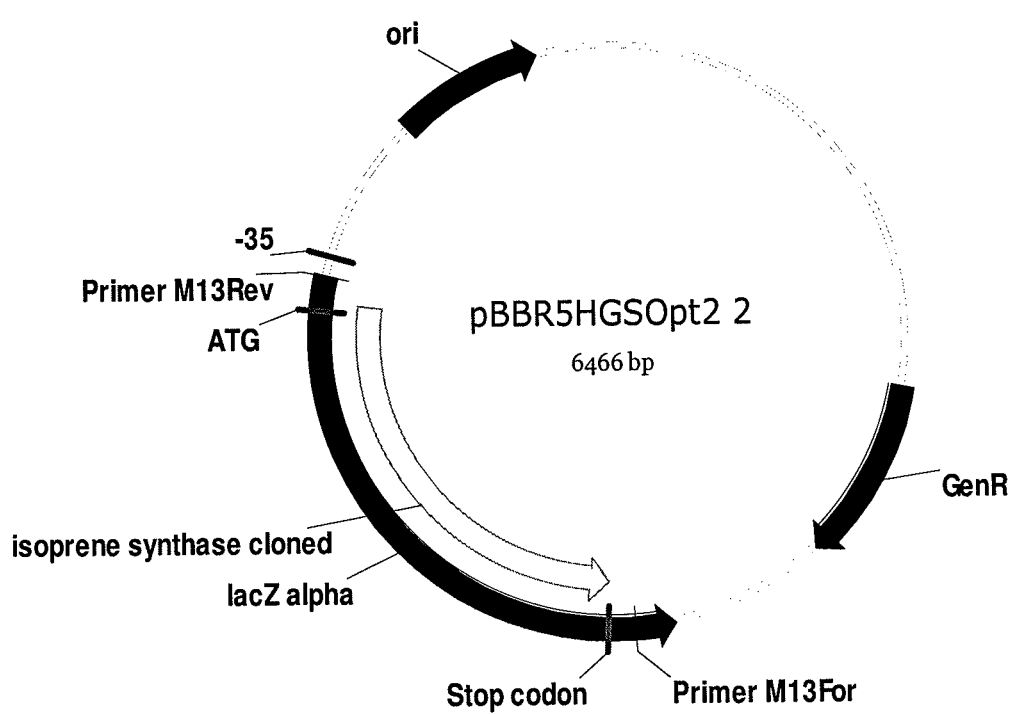

FIG. 147A is a map of pBBR5HGSOpt2_2.

FIGS. 147B and C are the nucleotide sequence of pBBR5HGSOpt2_2 (SEQ ID NO:122).

Figure 148:
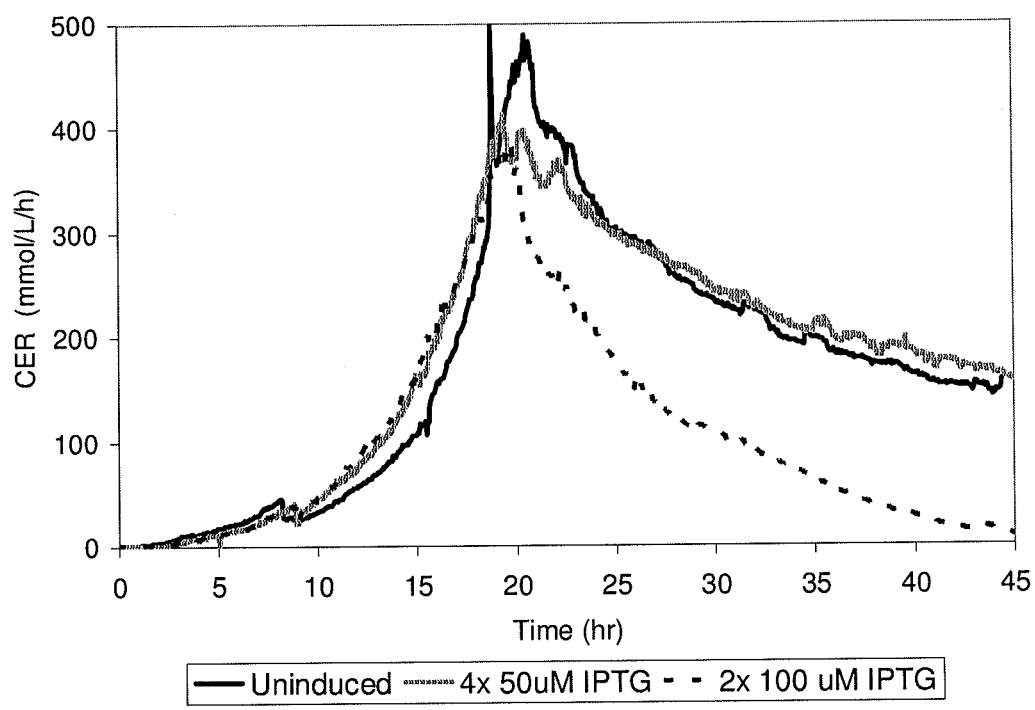

FIG. 148 is a graph of CER versus fermentation time for strain MCM401, uninduced, induced with IPTG (4×50 mmol) or IPTG (2×100 mmol).

Figure 149:
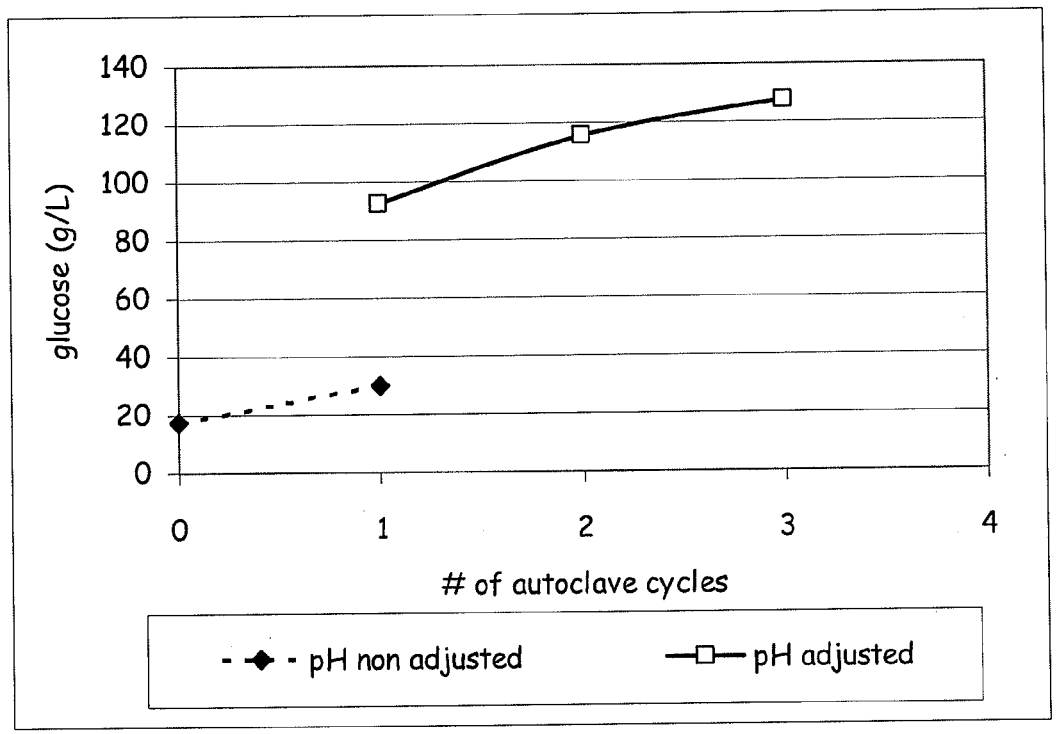

FIG. 149 shows concentration of glucose in sugar cane solutions, pH adjusted or not, as a function of the number of autoclaving cycles (one cycle=30 min).

Figure 150:
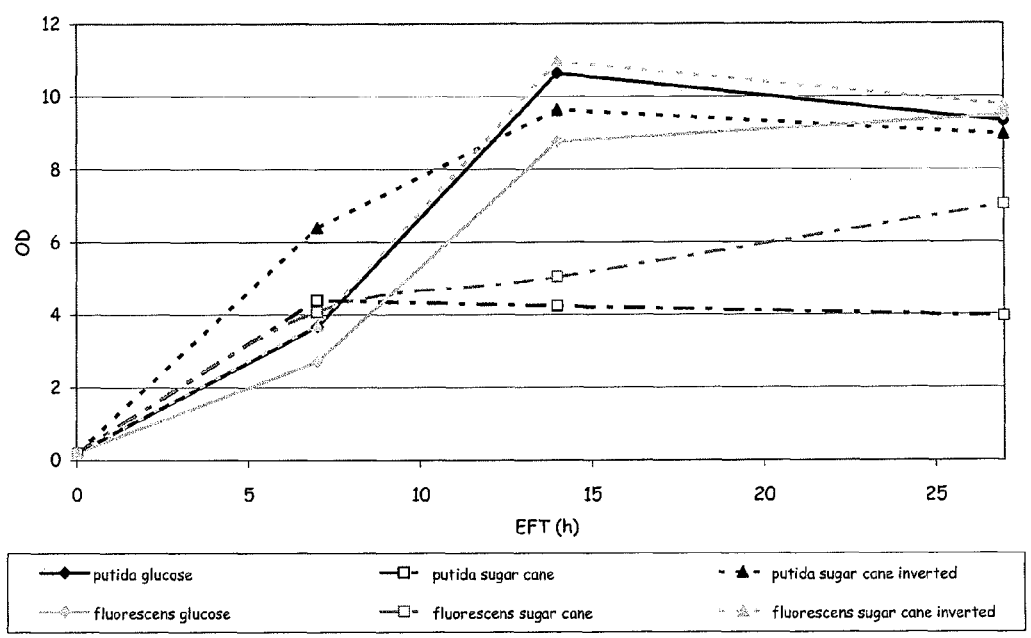

FIG. 150 shows growth curves ($OD_{600}$ as a function of time) of *Pseudomonas putida* F1 and *Pseudomonas fluorescens* ATCC13525 on glucose, sugar cane, and inverted sugar cane.

Figure 151:
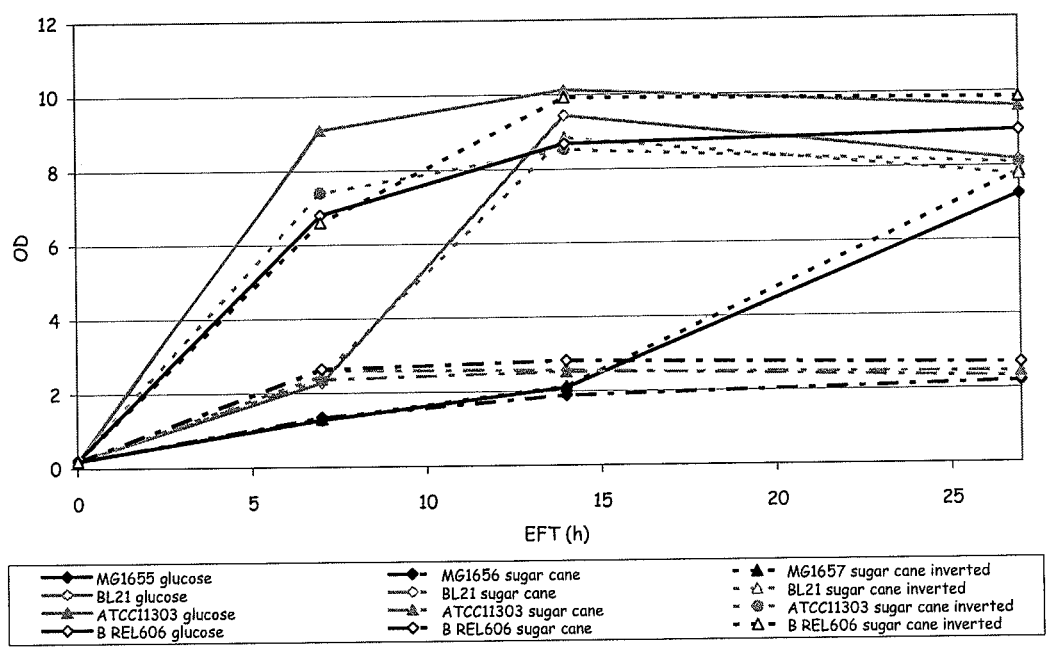

FIG. 151 shows growth curves ($OD_{600}$ as a function of time) of *E. coli* BL21(DE3), MG1655, ATCC11303 and B REL 606 on glucose, sugar cane, and inverted sugar cane.

Figure 152A:
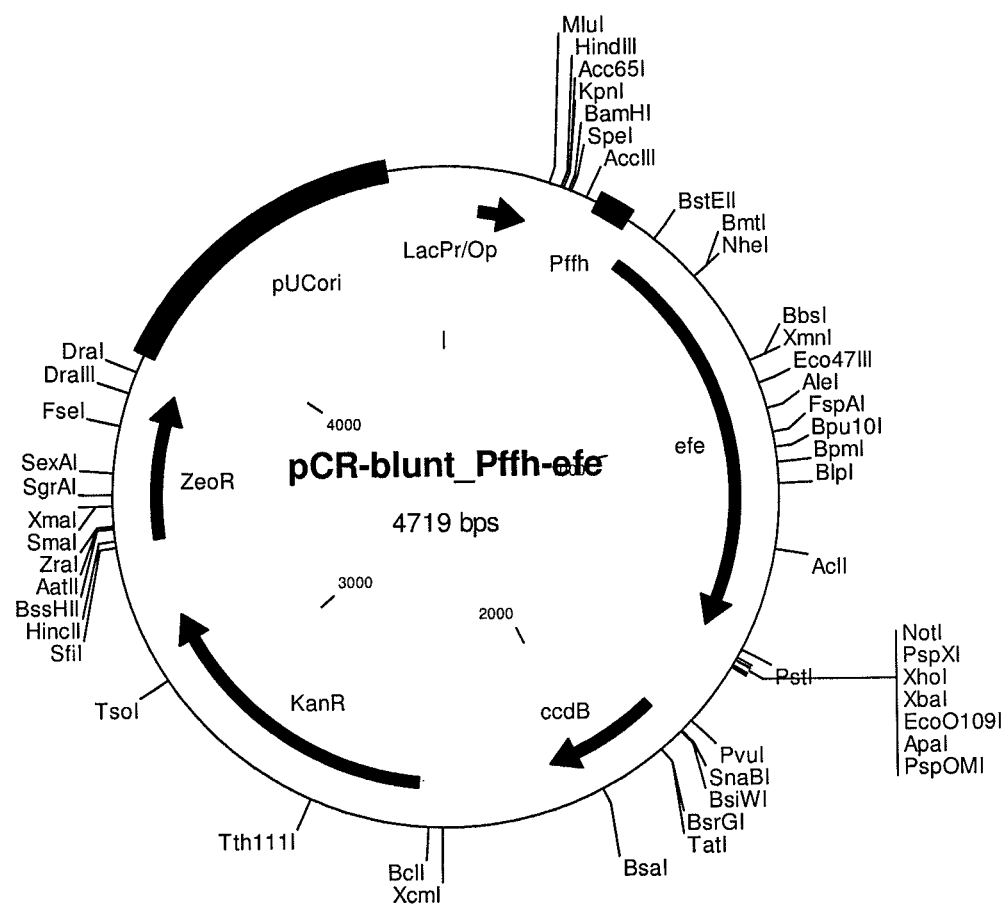

FIG. 152A shows the plasmid map of pCR-blunt_Pffe-efe.

FIG. 152B shows the nucleic acid sequence of pCR-blunt_Pffe-efe (SEQ ID NO:125).

Figure 153:
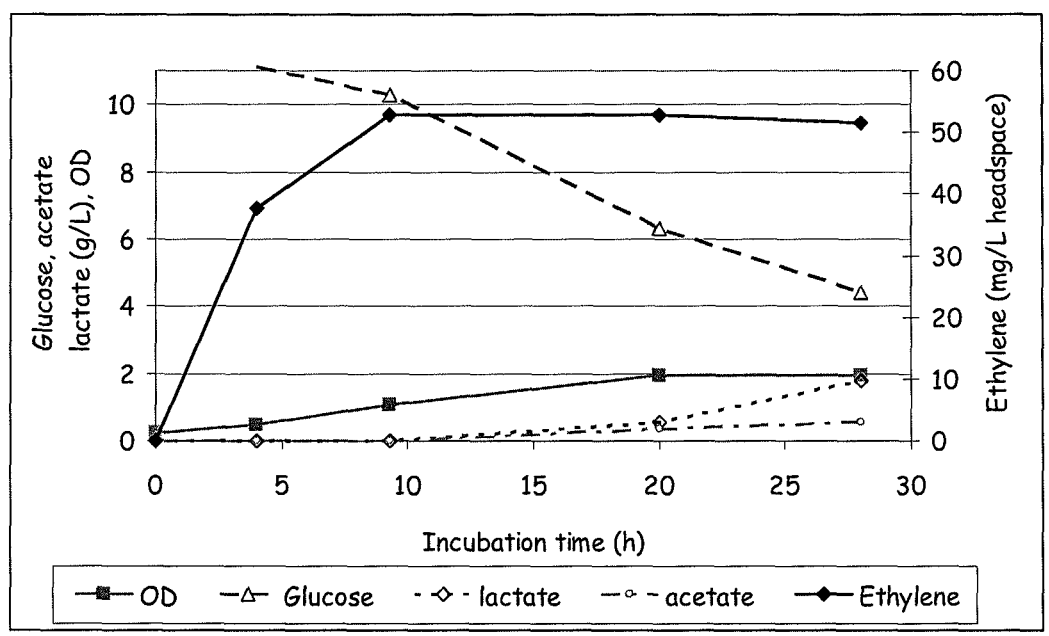

FIG. 153 shows production of ethylene by *E. coli* DH5α, pCRblunt-Pffh-efe, 5 mL broth at OD 0.23 incubated in a 20 mL headspace vial.

Figure 154:
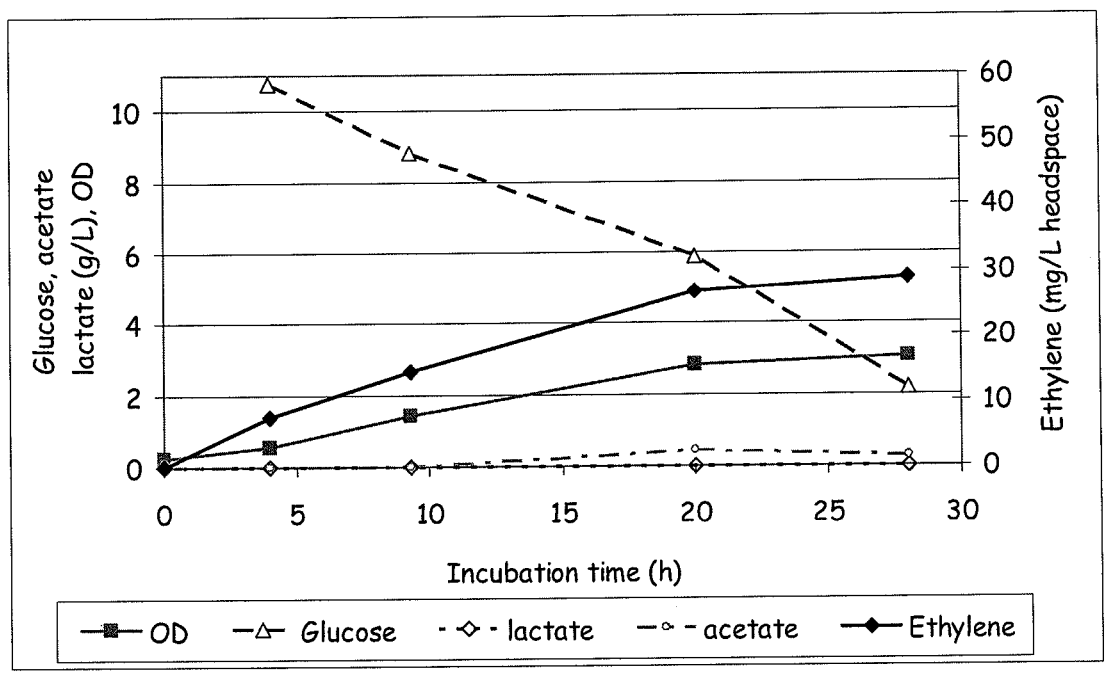

FIG. 154 shows production of ethylene by *E. coli* DH5α, pCRblunt-Pffh-efe, 1 mL broth at OD 0.23 incubated in a 20 mL headspace vial.

Figure 155:
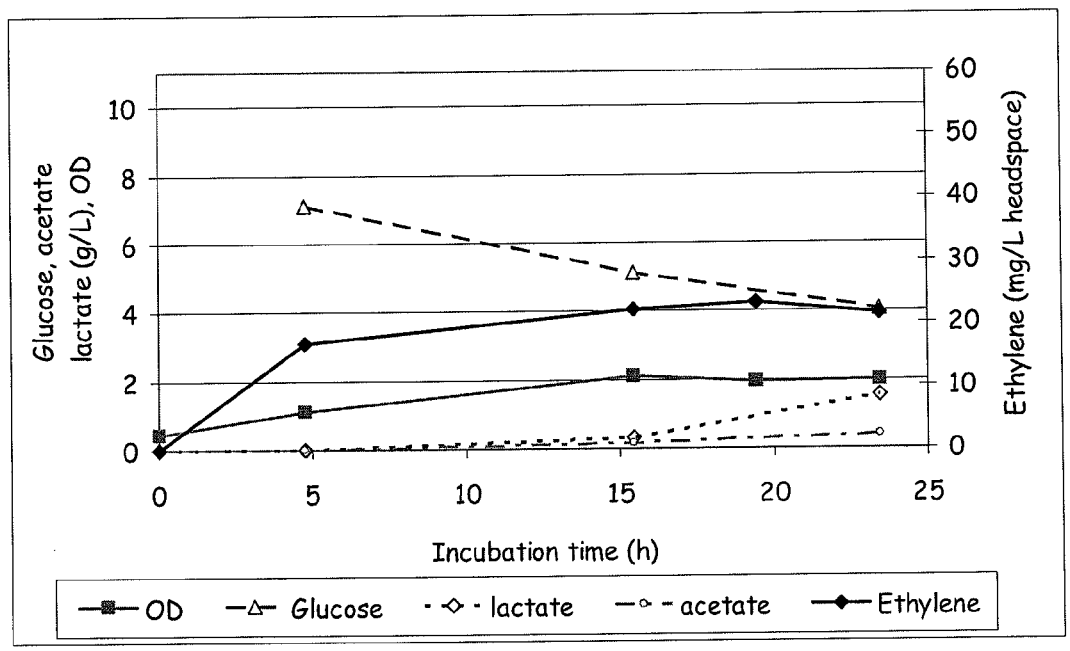

FIG. 155 shows production of ethylene by *E. coli* DH5α, pCRblunt-Pffh-efe, 5 mL broth at OD 0.45 incubated in a 20 mL headspace vial.

DETAILED DESCRIPTION OF THE INVENTION

The invention provides for, inter alia, compositions and methods for producing a compound having one or both of the following characteristics: (a) a Henry's law coefficient of less than about 250 M/atm and/or (b) a solubility in water of less than about 100 g/L. In one embodiment, the compound is isoprene. In another embodiment, the compound is ethylene. The invention features methods of producing isoprene by culturing cells under conditions suitable for isoprene production while maintaining cell viability and/or metabolic activity as indicated by carbon dioxide evolution rate or total carbon dioxide evolution rate. Carbon dioxide evolution rate (CER) and total carbon dioxide evolution rate (total CER) are terms well-known to one of skill in the art of fermentation and commonly refers to the carbon dioxide evolved by the culture (e.g., mmol/L/hr).

Further, in some aspects, the invention features methods of producing isoprene by culturing cells under suitable conditions for production of isoprene with concentrated isoprene in the gas phase using reduced gas sparging rates or no gas sparging. In some aspects, the invention also features methods of producing a compound with a Henry's law coefficient of less than about 250 M/atm and/or low water solubility (high water insolubility). In some aspects, the invention also features method of producing ethylene.

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

Cell Viability at High Isoprene Titer

Isoprene is a hydrophobic molecule secreted by many plants, animals, and microbes. Bacteria, such as *Bacillus*, produce isoprene at fairly low levels. While there is some evidence that plants secrete isoprene to help with thermoprotection, it has been hypothesized that isoprene may act antagonistically to cyanobacteria or fungi, or as an antimicrobial agent. See, e.g., Ladygina et al., *Process Biochemistry* 41:1001-1014 (2006), which is incorporated by reference in its entirety, particularly with respect to isoprene acting antagonistically. Since the very low production levels happening in nature are sufficient to be anti-microbial, it was of great concern that the titers and productivity levels of isoprene necessary for commercialization of isoprene would kill the host microbe.

We have found methods for producing titers and productivity levels of isoprene for commercialization of isoprene while maintaining cell viability and/or metabolic activity as indicated by carbon dioxide evolution rate or total carbon dioxide evolution rate.

Provided herein are methods of producing isoprene comprising: a) culturing cells under suitable conditions for production of isoprene; and b) producing isoprene, wherein cells produce greater than about 400 nmole/$g_{wcm}$/hour of isoprene, and the carbon dioxide evolution rate of the cells is greater than about $1 \times 10^{-18}$ mmol/L/hour. In some embodiments, the isoprene produced is any concentration or amount disclosed in the section entitled "Exemplary Production of Isoprene." In some embodiments, the amount of isoprene is between about any of 400 nmole/$g_{wcm}$/hour to 1 mole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour. In some embodiments, the carbon dioxide evolution rate is between about any of $1 \times 10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

Provided herein are also methods of producing isoprene comprising: a) culturing cells under suitable conditions for production of isoprene; and b) producing isoprene, wherein cells produce greater than about 400 nmole/$g_{wcm}$/hour of isoprene, and cell viability is reduced by less than about two-fold. In some embodiments, the isoprene produced is any concentration or amount disclosed in the section entitled "Exemplary Production of Isoprene." In some embodiments, the amount of isoprene is between about any of 400 nmole/$g_{wcm}$/hour to 1 mole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour. In some embodiments, cell viability is reduced by less than about any of 1.75-fold, 1.5-fold, 1.25-fold, 1-fold, 0.75-fold, 0.5-fold, or 0.25-fold. In some embodiments, cell viability is reduced by about 2-fold.

Further provided herein are methods of producing isoprene comprising: a) culturing cells under suitable conditions for production of isoprene; and b) producing isoprene, wherein the cumulative total productivity of the isoprene produced by the cells in culture is greater than about 0.2 mg/$L_{broth}$/hour and the carbon dioxide evolution rate of the cells is greater than about $1\times10^{-18}$ mmol/L/hour. In some embodiments, the cumulative total productivity of isoprene is any concentration or amount disclosed in the section entitled "Exemplary Production of Isoprene." In some embodiments, the cumulative total productivity of the isoprene is between about any of 0.2 mg/$L_{broth}$/hour to 5 g/$L_{broth}$/hour, 0.2 mg/$L_{broth}$/hour to 1 g/$L_{broth}$/hour, 1 g/$L_{broth}$/hour to 2.5 g/$L_{broth}$/hour, 2.5 g/$L_{broth}$/hour to 5 g/$L_{broth}$/hour. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

Provided herein are methods of producing isoprene comprising: a) culturing cells under suitable conditions for production of isoprene; and b) producing isoprene, wherein the cumulative total productivity of the isoprene produced by the cells in culture is greater than about 0.2 mg/$L_{broth}$/hour and cell viability is reduced by less than about two-fold. In some embodiments, the cumulative total productivity of isoprene is any concentration or amount disclosed in the section entitled "Exemplary Production of Isoprene." In some embodiments, the cumulative total productivity of the isoprene is between about any of 0.2 mg/$L_{broth}$/hour to 5 g/$L_{broth}$/hour, 0.2 mg/$L_{broth}$/hour to 1 g/$L_{broth}$/hour, 1 g/$L_{broth}$/hour to 2.5 g/$L_{broth}$/hour, 2.5 g/$L_{broth}$/hour to 5 g/$L_{broth}$/hour. In some embodiments, cell viability is reduced by less than about any of 1.75-fold, 1.5-fold, 1.25-fold, 1-fold, 0.75-fold, 0.5-fold, or 0.25-fold.

Methods of producing isoprene are also provided herein comprising: a) culturing cells under suitable conditions for production of isoprene; and b) producing isoprene, wherein the peak concentration of the isoprene produced by the cells in culture is greater than about 10 ng/$L_{broth}$ and the carbon dioxide evolution rate of the cells is greater than about $1\times10^{-18}$ mmol/L/hour. In some embodiments, the peak concentration of isoprene is any concentration or amount disclosed in the section entitled "Exemplary Production of Isoprene." In some embodiments, the peak concentration of isoprene is between about any of 10 ng/$L_{broth}$ to 500 ng/$L_{broth}$, 500 ng/$L_{broth}$ to 1 µg/$L_{broth}$, 1 µg/$L_{broth}$ to 5 µg/$L_{broth}$, 5 µg/$L_{broth}$ to 50 µg/$L_{broth}$, 5 µg/$L_{broth}$ to 100 µg/$L_{broth}$, 5 µg/$L_{broth}$ to 250 µg/$L_{broth}$, 250 µg/$L_{broth}$ to 500 µg/$L_{broth}$, 500 µg/$L_{broth}$ to 1 mg/$L_{broth}$, 1 mg/$L_{broth}$ to 50 mg/$L_{broth}$, 1 mg/$L_{broth}$ to 100 µg/$L_{broth}$, 1 mg/$L_{broth}$ to 200 mg/$L_{broth}$, 10 ng/$L_{broth}$ to 200 mg/$L_{broth}$, 5 µg/$L_{broth}$ to 100 mg/$L_{broth}$, or 5 µg/$L_{broth}$ to 200 mg/$L_{broth}$. In some embodiments, the peak concentration is any of about 10 ng/$L_{broth}$, 100 ng/$L_{broth}$, 1 µg/$L_{broth}$, 5 µg/$L_{broth}$, 1 mg/$L_{broth}$, 30 mg/$L_{broth}$, 100 mg/$L_{broth}$, or 200 mg/$L_{broth}$. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

In addition, methods of producing isoprene are also provided herein comprising: a) culturing cells under suitable conditions for production of isoprene; and b) producing isoprene, wherein the peak concentration of the isoprene produced by the cells in culture is greater than about 10 ng/$L_{broth}$ and cell viability is reduced by less than about two-fold. In some embodiments, the peak concentration of isoprene is any concentration or amount disclosed in the section entitled "Exemplary Production of Isoprene." In some embodiments, the peak concentration of isoprene is between about any of 10 ng/$L_{broth}$ to 500 ng/$L_{broth}$, 500 ng/$L_{broth}$ to 1 µg/$L_{broth}$, 1 µg/$L_{broth}$ to 5 µg/$L_{broth}$, 5 µg/$L_{broth}$ to 50 µg/$L_{broth}$, 5 µg/$L_{broth}$ to 100 µg/$L_{broth}$, 5 µg/$L_{broth}$ to 250 µg/$L_{broth}$, 250 µg/$L_{broth}$ to 500 µg/$L_{broth}$, 500 µg/$L_{broth}$ to 1 mg/$L_{broth}$, 1 mg/$L_{broth}$ to 50 mg/$L_{broth}$, 1 mg/$L_{broth}$ to 100 µg/$L_{broth}$, 1 mg/$L_{broth}$ to 200 mg/$L_{broth}$, 10 ng/$L_{broth}$ to 200 mg/$L_{broth}$, 5 µg/$L_{broth}$ to 100 mg/$L_{broth}$, or 5 µg/$L_{broth}$ to 200 mg/$L_{broth}$. In some embodiments, the peak concentration is any of about 10 ng/$L_{broth}$, 100 ng/$L_{broth}$, 1 µg/$L_{broth}$, 5 µg/$L_{broth}$, 1 mg/$L_{broth}$, 30 mg/$L_{broth}$, 100 mg/$L_{broth}$, or 200 mg/$L_{broth}$. In some embodiments, cell viability is reduced by less than about any of 1.75-fold, 1.5-fold, 1.25-fold, 1-fold, 0.75-fold, 0.5-fold, or 0.25-fold. In some embodiments, cell viability is reduced by about 2-fold.

Cells in culture are also provided herein comprising a nucleic acid encoding an isoprene synthase polypeptide, wherein the cells produce greater than about 400 nmole/$g_{wcm}$/hour of isoprene and carbon dioxide evolution rate of the cells is greater than about $1\times10^{-18}$ mmol/L/hour. In some embodiments, the isoprene produced is any concentration or amount disclosed in the section entitled "Exemplary Production of Isoprene." In some embodiments, the amount of isoprene is between about any of 400 nmole/$g_{wcm}$/hour to 1 mole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

Provided herein are also cells in culture comprising a nucleic acid encoding an isoprene synthase polypeptide, wherein cumulative total productivity of the isoprene produced by the cells in culture is greater than about 0.2 mg/$L_{broth}$/hour and carbon dioxide evolution rate of the cells is greater than about $1\times10^{-18}$ mmol/L/hour. In some embodiments, the cumulative total productivity of isoprene is any concentration or amount disclosed in the section entitled "Exemplary Production of Isoprene." In some embodiments, the cumulative total productivity of the isoprene is between about any of 0.2 mg/$L_{broth}$/hour to 5 g/$L_{broth}$/hour, 0.2 mg/$L_{broth}$/hour to 1 g/$L_{broth}$/hour, 1 g/$L_{broth}$/hour to 2.5 g/$L_{broth}$/hour, 2.5 g/$L_{broth}$/hour to 5 g/$L_{broth}$/hour. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

In addition, provided herein are cells in culture comprising a nucleic acid encoding an isoprene synthase polypeptide, wherein peak concentration of the isoprene produced by the cells in culture is greater than about 10 $ng/L_{broth}$ and carbon dioxide evolution rate of the cells is greater than about $1\times10^{-18}$ mmol/L/hour. In some embodiments, the peak concentration of isoprene is any concentration or amount disclosed in the section entitled "Exemplary Production of Isoprene." In some embodiments, the peak concentration of isoprene is between about any of 10 $ng/L_{broth}$ to 500 $ng/L_{broth}$, 500 $ng/L_{broth}$ to 1 $\mu g/L_{broth}$, 1 $\mu g/L_{broth}$ to 5 $\mu g/L_{broth}$, 5 $\mu g/L_{broth}$ to 50 $\mu g/L_{broth}$, 5 $\mu g/L_{broth}$ to 100 $\mu g/L_{broth}$, 5 $\mu g/L_{broth}$ to 250 $\mu g/L_{broth}$, 250 $\mu g/L_{broth}$ to 500 $\mu g/L_{broth}$, 500 $\mu g/L_{broth}$ to 1 $mg/L_{broth}$, 1 $mg/L_{broth}$ to 50 $mg/L_{broth}$, 1 $mg/L_{broth}$ to 100 $mg/L_{broth}$, 1 $mg/L_{broth}$ to 200 $mg/L_{broth}$, 10 $ng/L_{broth}$ to 200 $mg/L_{broth}$, 5 $\mu g/L_{broth}$ to 100 $mg/L_{broth}$, or 5 $\mu g/L_{broth}$ to 200 $mg/L_{broth}$. In some embodiments, the peak concentration is any of about 10 $ng/L_{broth}$, 100 $ng/L_{broth}$, 1 $\mu g/L_{broth}$, 5 $\mu g/L_{broth}$, 1 $mg/L_{broth}$, 30 $mg/L_{broth}$, 100 $mg/L_{broth}$, or 200 $mg/L_{broth}$. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

In some embodiments of any of the methods and cells described herein, carbon dioxide evolution rate and/or cell viability of a cell expressing a MVA pathway and/or DXP pathway RNA and/or protein from one or more of a heterologous and/or duplicate copy of a MVA pathway and/or DXP pathway nucleic acid is compared to a control cell lacking one or more of a heterologous and/or duplicate copy of a MVA pathway and/or DXP pathway nucleic acid. In some embodiments, carbon dioxide evolution rate and/or cell viability of a cell expressing a MVA pathway and/or DXP pathway RNA and/or protein from one or more of a heterologous and/or duplicate copy of a MVA pathway and/or DXP pathway nucleic acid under the control of an inducible promoter, wherein the promoter is induced, is compared to a control cell containing one or more of a heterologous and/or duplicate copy of a MVA pathway and/or DXP pathway nucleic acid under the control of an inducible promoter, wherein the promoter is not induced (uninduced). In some embodiments, the inducible promoter is a beta-galactosidase promoter.

Isoprene

The invention features compositions and methods for the production of isoprene in increased amounts and/or purity. As used herein, the term "isoprene" or "2-methyl-1,3-butadiene" (CAS#78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules.

The vast majority of isoprene is derived from petrochemical sources as an impure C5 hydrocarbon fraction which requires extensive purification before the material is suitable for polymerization. Several impurities are particularly problematic given their structural similarity to isoprene and the fact that they can act as polymerization catalyst poisons. Such compounds include 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) (FIG. 90). In other embodiments, the impurities can be 3-hexen-1-ol, 3-hexen-1-yl acetate, limonene, geraniol (trans-3,7-dimethyl-2,6-octadien-1-ol) and citronellol (3,7-dimethyl-6-octen-1-ol). In some embodiments, the isoprene composition of the invention is substantially free of any contaminating unsaturated C5 hydrocarbons. As described further in Example 10, no detectable amount of unsaturated C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)) was found in isoprene compositions produced using the methods described herein. Some isoprene compositions produced using the methods described herein contain ethanol, acetone, and C5 prenyl alcohols as determined by GC/MS analysis. All of these components are far more readily removed from the isoprene stream than the isomeric C5 hydrocarbon fractions that are present in isoprene compositions derived from petrochemical sources. Accordingly, in some embodiments, the isoprene compositions of the invention require minimal treatment in order to be of polymerization grade.

In one aspect, compositions and methods of the invention increase the rate of isoprene production and increase the total amount of isoprene that is produced. For example, cell culture systems that generate $4.8\times10^4$ $nmole/g_{wcm}/hr$ of isoprene have been produced (Table 1). The efficiency of these systems is demonstrated by the conversion of about 2.2% of the carbon that the cells consume from a cell culture medium into isoprene. As shown in the Examples and Table 2, approximately 3 g of isoprene per liter of broth was generated. If desired, even greater amounts of isoprene can be obtained using other conditions, such as those described herein. In some embodiments, a renewable carbon source is used for the production of isoprene. In some embodiments, the production of isoprene is decoupled from the growth of the cells. In some embodiments, the concentrations of isoprene and any oxidants are within the nonflammable ranges to reduce or eliminate the risk that a fire may occur during production or recovery of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) isoprene synthase polypeptide was expressed in a variety of host cells, such as *Escherichia coli, Pantoea citrea, Bacillus subtilis, Yarrowia lipolytica*, and *Trichoderma reesei*. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 300 mg of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention. The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| Strain | Isoprene Production in a Headspace vial* | |
|---|---|---|
| | Headspace concentration $\mu g/L_{gas}$ | Specific Rate $\mu g/L_{broth}$/hr/OD (nmol/$g_{wcm}$/hr) |
| *E. coli* BL21/pTrcKudzu IS | 1.40 | 53.2 (781.2) |
| *E. coli* BL21/pCL DXS yidi Kudzu IS | 7.61 | 289.1 (4.25 × 10$^3$) |
| *E. coli* BL21/MCM127 with kudzu IS and entire MVA pathway | 23.0 | 874.1 (12.8 × 10$^3$) |
| *E. coli* BL21/pET N-HisKudzu IS | 1.49 | 56.6 (831.1) |
| *Pantoea citrea*/pTrcKudzu IS | 0.66 | 25.1 (368.6) |
| *E. coli* w/ Poplar IS [Miller (2001)] | — | 5.6 (82.2) |
| *Bacillus licheniformis* Fall U.S. Pat. No. 5,849,970 | — | 4.2 (61.4) |
| *Yarrowia lipolytica* with kudzu isoprene synthase | ~0.05 µg/L | ~2 (~30) |
| *Trichoderma reesei* with kudzu isoprene synthase | ~0.05 µg/L | ~2 (~30) |
| *E. coli* BL21/pTrcKKD$_y$I$_k$IS with kudzu IS and lower MVA pathway | 85.9 | 3.2 × 10$^3$ (4.8 × 10$^4$) |

*Normalized to 1 mL of 1 OD$_{600}$, cultured for 1 hour in a sealed headspace vial with a liquid to headspace volume ratio of 1:19.

TABLE 2

Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| Strain | Isoprene Production in Fermentors | | |
|---|---|---|---|
| | Peak Headspace concentration** ($\mu g/L_{gas}$) | Titer (mg/$L_{broth}$) | Peak Specific rate $\mu g/L_{broth}$/hr/OD (nmol/$g_{wcm}$/hr) |
| *E. coli* BL21/pTrcKudzu with Kudzu IS | 52 | 41.2 | 37 (543.3) |
| *E. coli* FM5/pTrcKudzu IS | 3 | 3.5 | 21.4 (308.1) |
| *E. coli* BL21/triple strain (DXS, yidi, IS) | 285 | 300 | 240 (3.52 × 10$^3$) |
| *E. coli* FM5/triple strain (DXS, yidi, IS) | 50.8 | 29 | 180.8 (2.65 × 10$^3$) |
| *E. coli*/MCM127 with Kudzu IS and entire MVA pathway | 3815 | 3044 | 992.5 (1.46 × 10$^4$) |
| *E. coli* BL21/pCLPtrc UpperPathway gi1.2 integrated lower pathway pTrcKudzu | 2418 | 1640 | 1248 (1.83 × 10$^4$) |
| *E. coli* BL21/MCM401 with 4 × 50 µM IPTG | 13991 | 23805 | 3733 (5.49 × 10$^4$) |
| *E. coli* BL21/MCM401 with 2 × 1000 µM IPTG | 22375 | 19541 | 5839.5 (8.59 × 10$^4$) |
| *E. coli* BL21/pCLPtrc UpperPathwayHGS2-pTrcKKDyIkIS | 3500 | 3300 | 1088 (1.60 × 10$^4$) |
| *Bacillus subtilis* wild-type | 1.5 | 2.5 | 0.8 (11.7) |
| *Bacillus* pBS Kudzu IS | 16.6 | ~30 (over 100 hrs) | 5 (73.4) |
| *Bacillus* Marburg 6051 [Wagner and Fall (1999)] | 2.04 | 0.61 | 24.5 (359.8) |
| *Bacillus* Marburg 6051 Fall U.S. Pat. No. 5,849,970 | 0.7 | 0.15 | 6.8 (100) |

**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
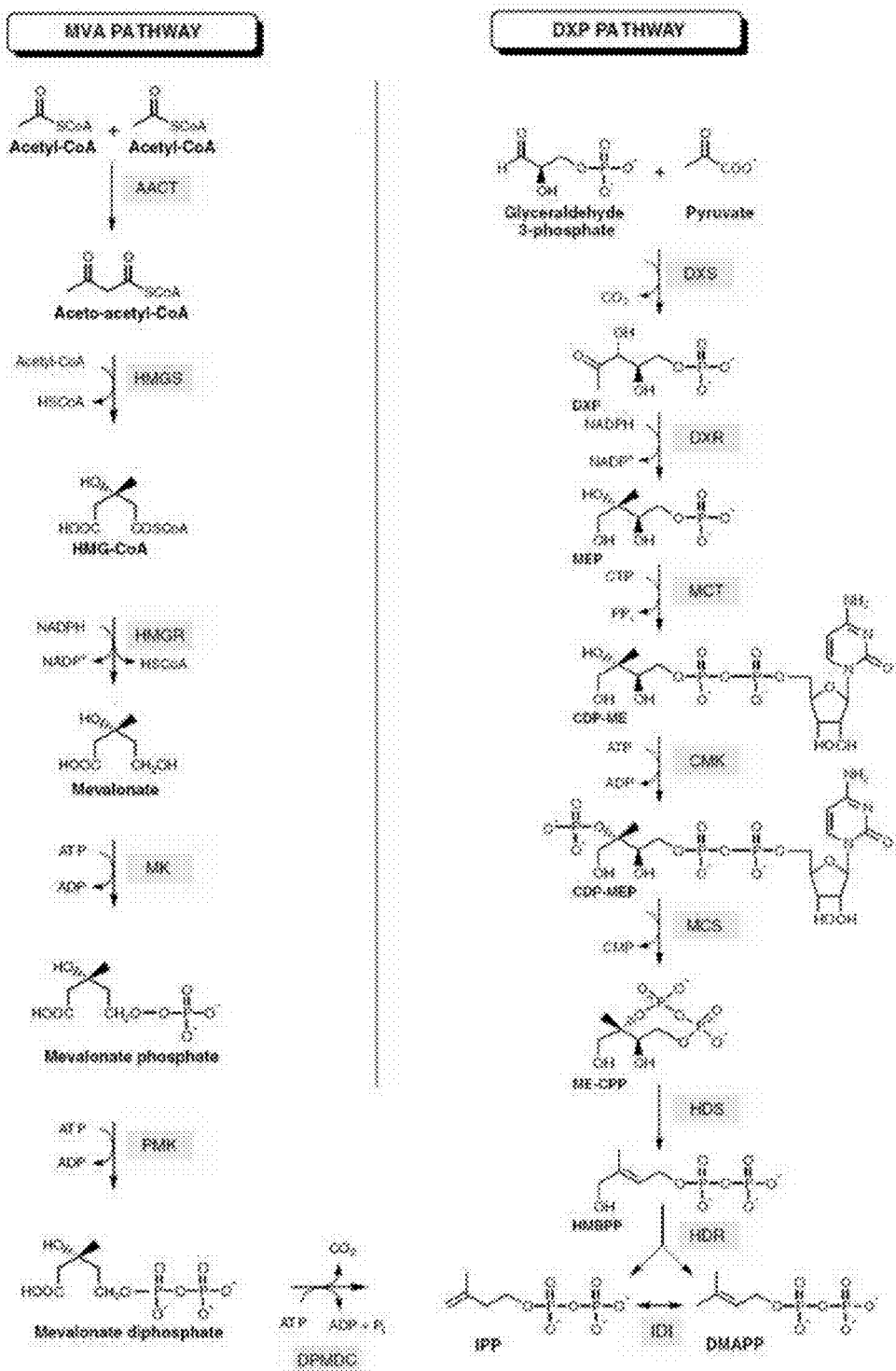
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The encoded DXS and IDI polypeptides are part of the DXP pathway for the biosynthesis of isoprene (FIG. 19A).

DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount (and conversion rate) of IPP that is converted into DMAPP, which in turn is converted into isoprene.

For example, fermentation of E. coli cells with a kudzu isoprene synthase, S. cerevisiae IDI, and E. coli DXS nucleic acids was used to produce isoprene. The levels of isoprene varied from 50 to 300 µg/L over a time period of 15 hours (Example 7, part VII).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by E. coli cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
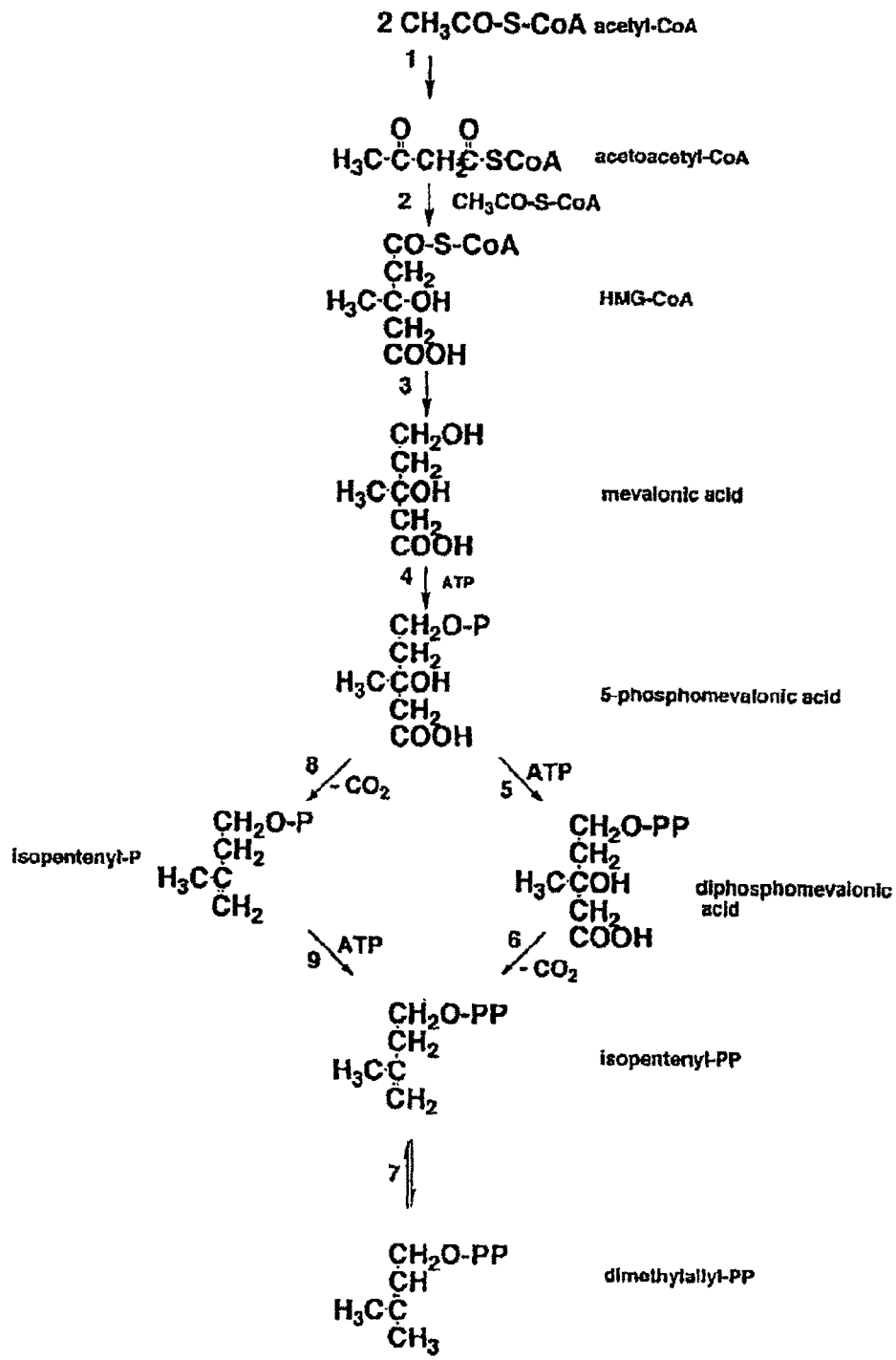
FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology. Reviews*, 71:97-120, 2007, which is incorporated by reference in its entirety, particular with respect to nucleic acids and polypeptides of the modified MVA pathway. The modified MVA pathway is present, for example, in some archaeal organisms, such as *Methanosarcina mazei*.

In some embodiments, the production of isoprene by cells by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain an entire MVA pathway that includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, E. coli cells containing a nucleic acid encoding a kudzu isoprene synthase polypeptide and nucleic acids encoding Saccharomyces cerevisiae MVK, PMK, MVD, and IDI polypeptides generated isoprene at a rate of $6.67 \times 10^{-4}$ mol/$L_{broth}$/$OD_{600}$/hr (see Example 8). Additionally, a 14 liter fermentation of E. coli cells with nucleic acids encoding Enterococcus faecalis AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in E. coli. E. coli cells that contain nucleic acids for both the upper MVA pathway and the lower MVA pathway as well as a kudzu isoprene synthase (strain MCM 127) produced significantly more isoprene (874 ug/L) compared to E. coli cells with nucleic acids for only the lower MVA pathway and the kudzu isoprene synthase (strain MCM 131) (see Table 3 and Example 8, part VIII).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
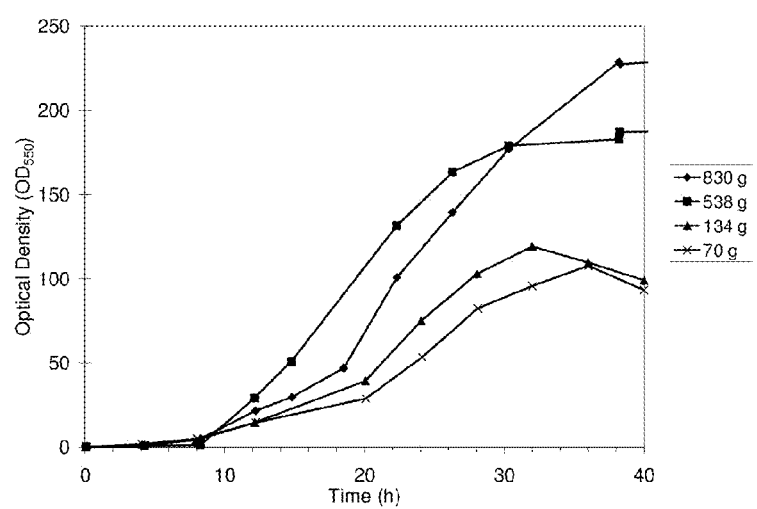
FIGS. 48A-C show graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in *E. coli* grown in fed-batch culture.
Figure 48B:
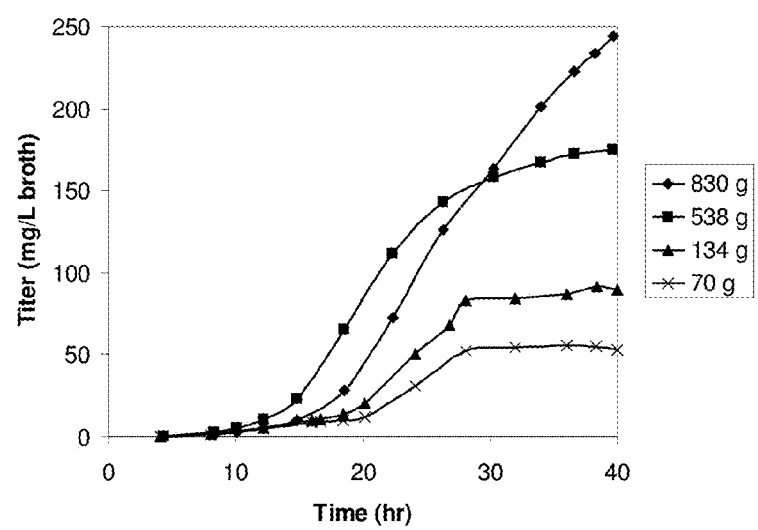
Figure 48C:
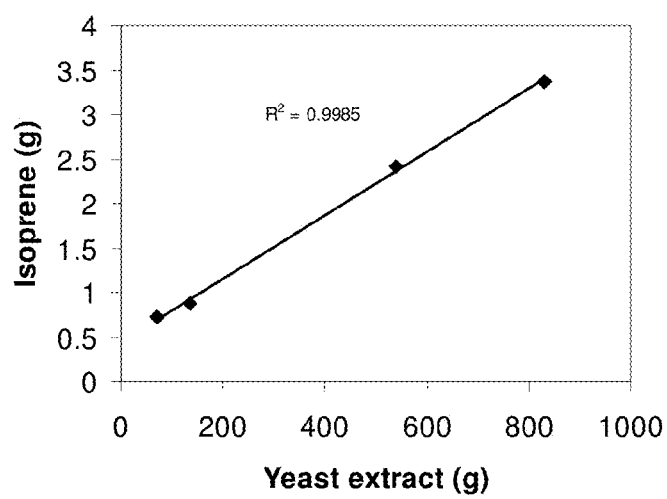

As indicated in Example 7, part VI, the amount of isoprene produced can be further increased by adding yeast extract to the cell culture medium. In this example, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Both of these experiments used E. coli cells with kudzu isoprene synthase, S. cerevisiae IDI, and E. coli DXS nucleic acids to produce isoprene. Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 46A:
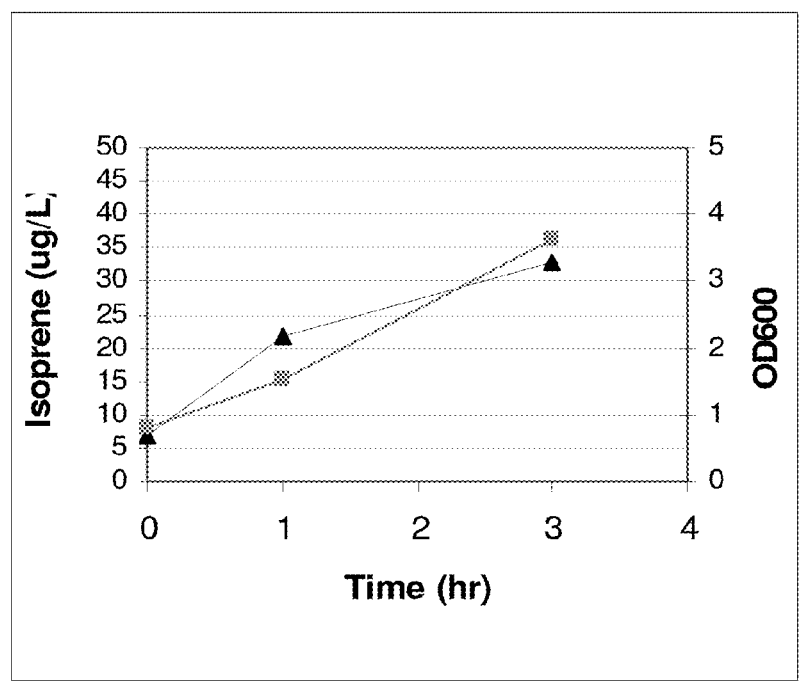
FIGS. 46A-E show graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent OD$_{600}$ measurements of the cultures at the indicated times post-inoculation and black triangles represent isoprene production at the indicated times post-inoculation.
Figure 46B:
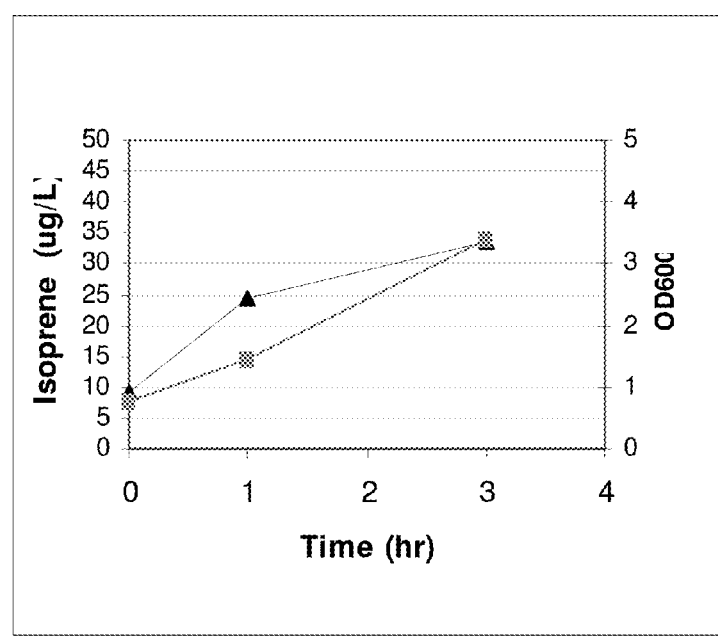
Figure 46C:
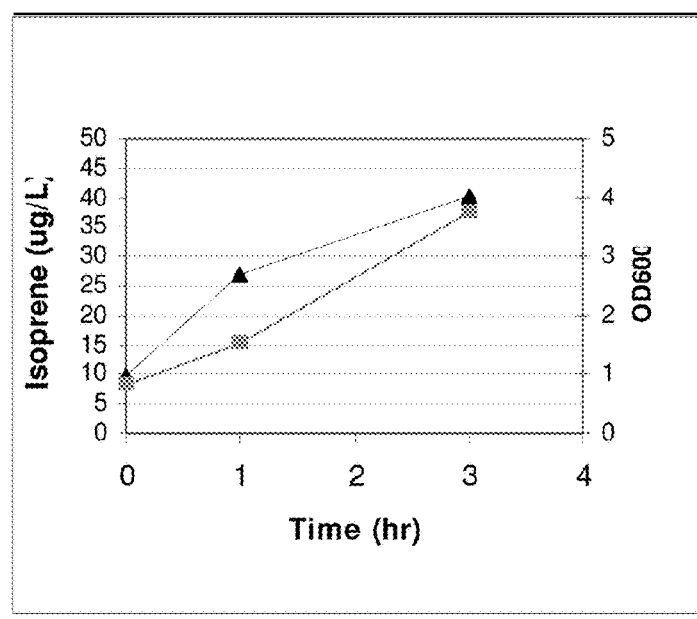
Figure 46D:
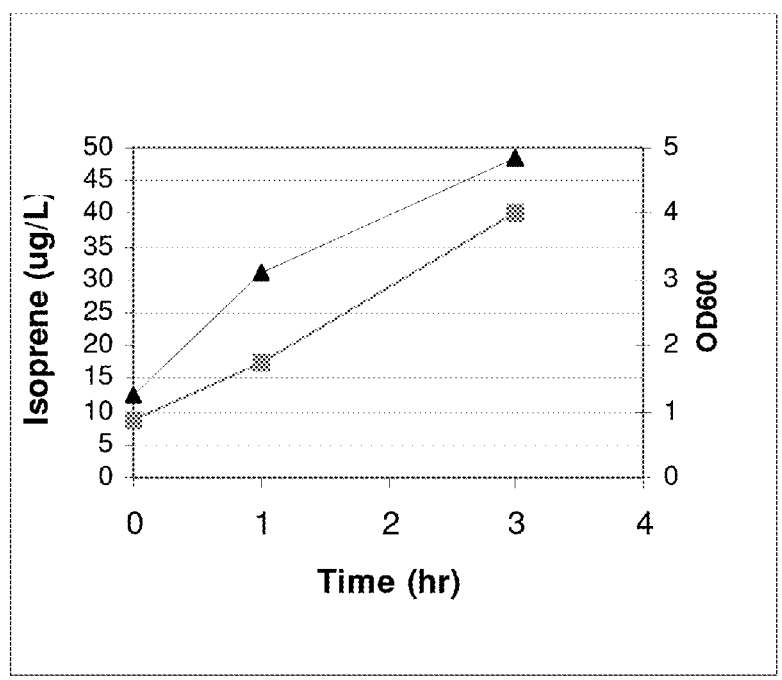
Figure 46E:
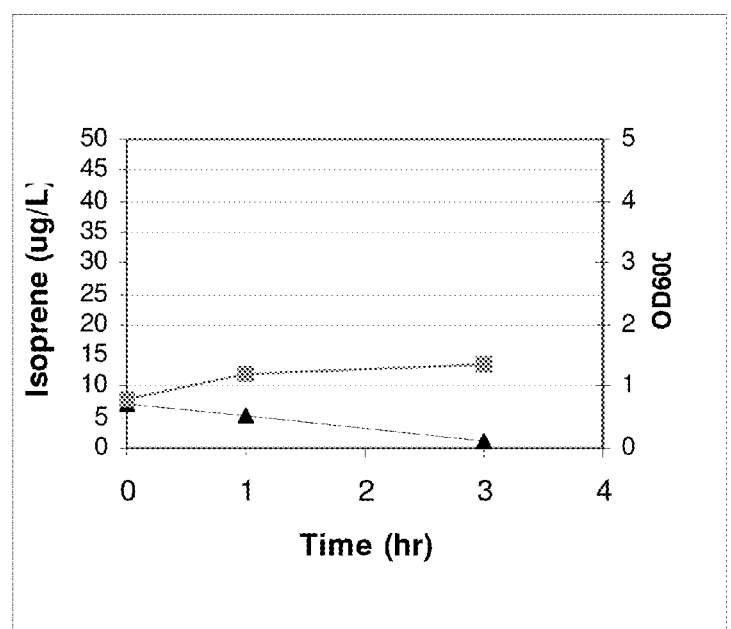
Figure 47A:
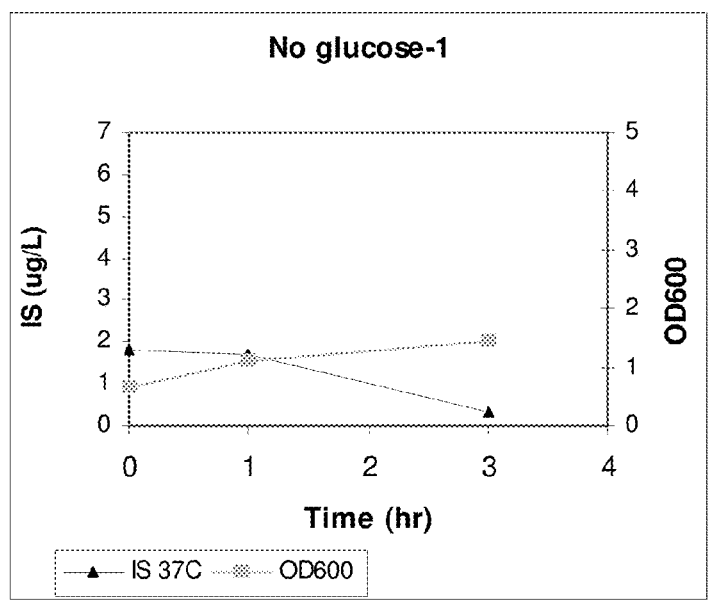
FIG. 47A shows a graph representing isoprene production by BL21 (λDE3) pTrcKudzu yIDI DXS (kan) in a culture with no glucose added. Squares represent OD$_{600}$, and triangles represent isoprene produced (μg/ml).
Figure 47B:
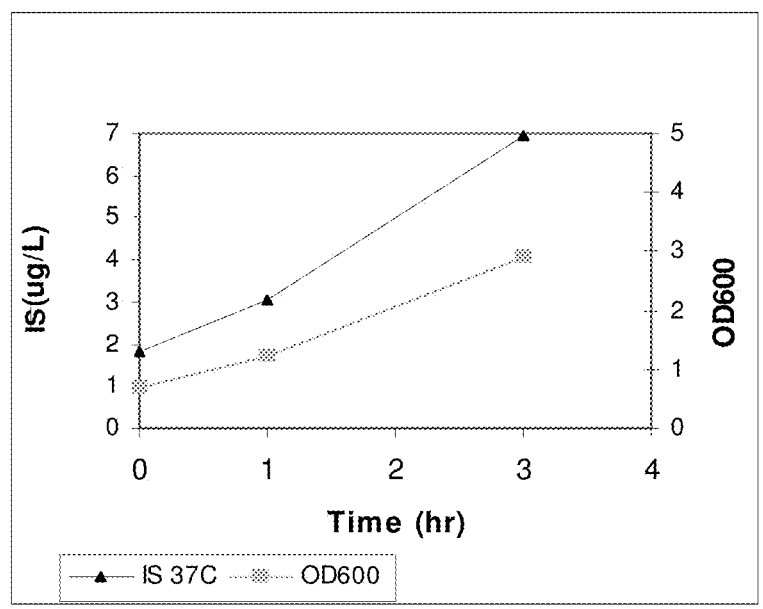
FIG. 47B shows a graph representing isoprene production from 1% glucose feedstock invert sugar by BL21 (λDE3) pTrcKudzu yIDI DXS (kan). Squares represent OD$_{600}$, and triangles represent isoprene produced (μg/ml).
Figure 47C:
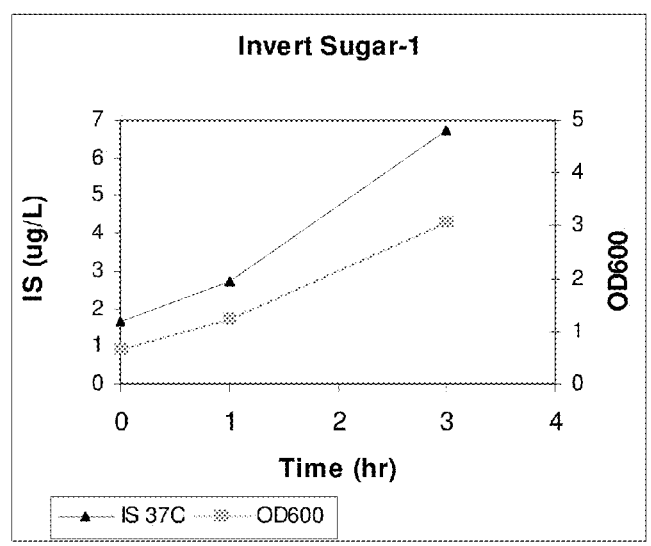
FIG. 47C shows a graph representing isoprene production from 1% invert sugar feedstock by BL21 (λDE3) pTrcKudzu yIDI DXS (kan). Squares represent OD$_{600}$, and triangles represent isoprene produced (μg/ml).
Figure 47D:
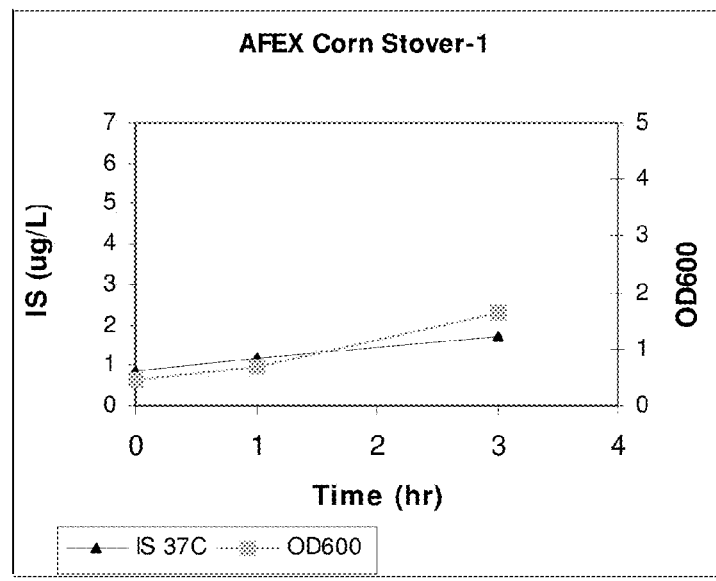
FIG. 47D shows a graph representing isoprene production from 1% AFEX corn stover feedstock by BL21 (λDE3) pTrcKudzu yIDI DXS (kan). Squares represent OD$_{600}$, and triangles represent isoprene produced (μg/ml).

Isoprene production was also demonstrated using three types of hydrolyzed biomass (bagasse, corn stover, and soft wood pulp) as the carbon source (FIGS. 46A-C). E. coli cells with kudzu isoprene synthase, S. cerevisiae IDI, and E. coli DXS nucleic acids produced as much isoprene from these hydrolyzed biomass carbon sources as from the equivalent amount of glucose (e.g., 1% glucose, w/v). If desired, any other biomass carbon source can be used in the compositions and methods of the invention. Biomass carbon sources are desirable because they are cheaper than many conventional cell mediums, thereby facilitating the economical production of isoprene.

Additionally, invert sugar was shown to function as a carbon source for the generation of isoprene (FIGS. 47C and 96-98). For example, 2.4 g/L of isoprene was produced from cells expressing MVA pathway polypeptides and a Kudzu isoprene synthase (Example 8, part XV). Glycerol was as also used as a carbon source for the generation of 2.2 mg/L of isoprene from cells expressing a Kudzu isoprene synthase (Example 8, part XIV). Expressing a DXS nucleic acid, an IDI nucleic acid, and/or one or more MVA pathway nucleic acids (such as nucleic acids encoding the entire MVA pathway) in addition to an isoprene synthase nucleic acid may increase the production of isoprene from glycerol.

In some embodiments, an oil is included in the cell medium. For example, B. subtilis cells containing a kudzu isoprene synthase nucleic acid produced isoprene when cultured in a cell medium containing an oil and a source of glucose (Example 4, part III). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

One of the major hurdles to commercial production of small molecules such as isoprene in cells (e.g., bacteria) is the decoupling of production of the molecule from growth of the cells. In some embodiments for the commercially viable production of isoprene, a significant amount of the carbon from the feedstock is converted to isoprene, rather than to the growth and maintenance of the cells ("carbon efficiency"). In various embodiments, the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In particular embodiments, a significant portion of the carbon from the feedstock that is converted to downstream products is converted to isoprene. As described further in Example 11, E. coli cells expressing MVA pathway and kudzu isoprene synthase nucleic acids exhibited decoupling of the production of isoprene or the intermediate mevalonic acid from growth, resulting in high carbon efficiency. In particular, mevalonic acid was formed from cells expressing the upper MVA pathway from Enterococcus faecalis. Isoprene was formed from cells expressing the upper MVA pathway from Enterococcus faecalis, the lower MVA pathway from Saccharomyces cerevisiae, and the isoprene synthase from Pueraria montana (Kudzu). This decoupling of isoprene or mevalonic acid production from growth was demonstrated in four different strains of E. coli: BL21(LDE3), BL21(LDE3) Tuner, FM5, and MG1655. The first two E. coli strains are B strains, and the latter two are K12 strains. Decoupling of production from growth was also demonstrated in a variant of MG1655 with ack and pta genes deleted. This variant also demonstrated less production of acetate.

Production of Ethylene

The invention features methods for the production of ethylene (CAS#74-85-1) using cell culture. In some embodiments, ethylene refers to the final volatile C2 hydrocarbon product from the conversion of 2-oxoglutarate, an intermediate of the tricarboxylic acid (TCA) cycle by the ethylene-forming enzyme (efe). Ethylene is used in the manufacture of polymers such as polyethylene, polyester, polyvinyl chloride, and polystyrene, as well as fibers and other organic chemicals.

Provided herein are methods of producing a compound, wherein the compound has one or more characteristics selected from the group consisting of (a) a Henry's law coefficient of less than about 250 M/atm and (b) a solubility in water of less than about 100 g/L. In some embodiments, the method comprises: a) culturing cells under suitable conditions for production of the compound, wherein gas is added (such as the addition of gas to a system such as a fermentation system) at a gas sparging rate between about 0 vvm to about 2 vvm; and b) producing the compound. In other embodiments, the method comprises: a) culturing cells under suitable conditions for production of the compound; b) producing the compound; and c) recovering the compound in the gas phase. In some embodiments, the method comprises: a) culturing cells under suitable conditions for production of the compound; b) producing the compound; and c) recovering the compound from the gas phase. In some embodiments, the Henry's law coefficient of the compound is less than about any of 200 M/atm, 150 M/atm, 100 M/atm, 75 M/atm, 50 M/atm, 25 M/atm, 10 M/atm, 5 M/atm, or 1 M/atm. In some embodiments, the solubility in water of the compound is less than about any of 75 g/L, 50 g/L, 25 g/L, 10 g/L, 5 g/L, or 1 g/L. In some embodiments, the compound is selected from a group consisting of isoprene, an aldehyde (e.g., acetaldehyde), a ketone (e.g., acetone, methyl ethyl ketone or 2-butanone), an alcohol (e.g., methanol, ethanol, 1-butanol, or C5 alcohols such as 3-methyl-3-buten-1-ol or 3-methyl-2-buten-1-ol), an ester of an alcohol (e.g., ethyl acetate, esters of 3-methyl-2-buten-1-ol or acetyl esters of C5 alcohols), a hemiterpene, a monoterpene, a sesquiterpene, and C1 to C5 hydrocarbons (e.g., methane, ethane, ethylene, or propylene). In some embodiments, the C1 to C5 hydrocarbons are saturated, unsaturated, or branched. In some embodiments, the C1 to C5 hydrocarbon is an unsaturated aliphatic hydrocarbon (e.g. ethylene, propene, butylene, or isobutylene). In some embodiments, the C1 to C5 hydrocarbon is a diolefin. In particular embodiments, the compound is isoprene. In other particular embodiments, the compound is ethylene. In some embodiments, isoprene and ethylene are co-produced. In some embodiments of the methods of producing any of the compounds described above, the gas sparing rate is between about any of 0 vvm to 0.1 vvm, 0.1 vvm to 1 vvm, 0.2 vvm to 1 vvm, or 0.5 vvm to 1 vvm. In some embodiments of the methods of producing any of the compounds described above, the gas sparging rate is 0.0 vvm.

In one aspect, the invention features methods of producing ethylene. In some embodiments, the method comprises: a) culturing cells under suitable conditions for production of ethylene, wherein gas is added (such as the addition of gas to a system such as a fermentation system) at a gas sparging rate between about 0.01 vvm to about 2 vvm; b) producing ethylene. In other embodiments, the method comprises: a) culturing cells under suitable conditions for production of ethylene; and b) producing ethylene; and c) recovering the ethylene in the gas phase. In some embodiments of the methods of producing ethylene, the gas sparing rate is between about any of 0.0 vvm to 0.1 vvm, 0.1 vvm to 1 vvm, 0.2 vvm to 1 vvm, or 0.5 vvm to 1 vvm. In some embodiments of the methods of producing ethylene, the gas sparging rate is 0.0 vvm.

In one aspect, the invention features cells in culture that produce a compound, wherein the compound has one or more characteristics selected from the group consisting of (a) a Henry's law coefficient of less than about 250 M/atm and (b) a solubility in water of less than about 100 g/L. In some embodiments, the cells have a heterologous nucleic acid that (i) encodes a synthase polypeptide capable of producing the compound and (ii) is operably linked to a promoter. In some embodiments, the compound produced is ethylene and the synthase polypeptide is ethylene-forming enzyme (efe). In some embodiments, the promoter is the promoter region of the ffh gene of $E.$ $coli$, wherein the ffh promoter drives constitutive expression of efe. In some embodiments, the cells are cultured in a culture medium that includes one or more carbon source(s), such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract. In some embodiments, the cells are cultured under limited glucose conditions.

If isoprene and ethylene are co-produced, then they can be separated during recovery as described herein or by other means known to one of skill in the art. In one aspect of the invention, ethylene is recovered by adsorption. In some embodiments, ethylene is adsorbed on a silver-modified clay. In some embodiments, fermentation off-gas is dehumidified and run into a silver-modified clay filter in order to remove ethylene from the off-gas stream, followed by desorption of the ethylene from the silver-clay filter using a pressure swing cycle. In some embodiments, the fermentation off-gas is further treated before introduction into the silver-clay filter by sparging through an aqueous sodium hydroxide solution in order to remove carbon dioxide. In another aspect of the invention, ethylene is recovered by cryogenic separation or absorption/stripping.

Exemplary Polypeptides and Nucleic Acids

Various isoprene synthase, efe, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides. In some embodiments, the fusion polypeptide includes part or all of a first polypeptide (e.g., an isoprene synthase, efe, DXS, IDI, or MVA pathway polypeptide or catalytically active fragment thereof) and may optionally include part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, efe, DXS, IDI, or MVA pathway polypeptide. In some embodiments, the polypeptide has one or more mutations compared to the sequence of a wild-type (i.e., a sequence occurring in nature) isoprene synthase, efe, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type nucleic acid that is found in the same host cell in nature.

As used herein, a "nucleic acid" refers to one or two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In various embodiments, a nucleic acid is a recombinant nucleic acid. In some embodiments, an isoprene synthase, efe, DXS, IDI, or MVA pathway nucleic acid is operably linked to another nucleic acid encoding all or a portion of another polypeptide such that the recombinant nucleic acid encodes a fusion polypeptide that includes an isoprene synthase, efe, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized. It is to be understood that mutations, including single nucleotide mutations, can occur within a nucleic acid as defined herein.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments, the nucleic acid includes a segment of or the entire nucleic acid sequence of any naturally-occurring isoprene synthase, efe, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid, efe nucleic acid, DXS, IDI, or MVA pathway nucleic acid. In some embodiments, the nucleic acid has one or more mutations compared to the sequence of a wild-type (i.e., a sequence occurring in nature) isoprene synthase, efe, DXS, IDI, or MVA pathway nucleic acid. In some embodiments, the nucleic acid has one or more mutations (e.g., a silent mutation) that increase the transcription or translation of isoprene synthase, efe, DXS, IDI, or MVA pathway nucleic acid. In some embodiments, the nucleic acid is a degenerate variant of any nucleic acid encoding an isoprene synthase, efe, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the worldwide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Sep. 14, 2008 such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., *J. Biol. Chem.* 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) is added to 25 μL of cell extract in a 20 ml Headspace vial with a metal screw cap and teflon coated silicon septum (Agilent Technologies) and cultured at 37° C. for 15 minutes with shaking. The reaction is quenched by adding 200 μL of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa*, or *Populus alba×tremula* (CAC35696) Miller et al., *Planta* 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary efe Polypeptides and Nucleic Acids

As noted above, ethylene-forming enzyme (efe) polypeptides convert 2-oxoglutarate into ethylene. Exemplary efe polypeptides include polypeptides, fragments of polypeptides, peptides, and fusions polypeptides that have at least one activity of an efe polypeptide. A suitable ethylene-forming enzyme includes, but is not limited to, that identified by Genbank Accession No. EF175870, which is hereby incorporated by reference in its entirety, particularly with respect to the sequences of efe nucleic acids and polypeptides. Standard methods (such as those described herein) can be used to determine whether a polypeptide has efe polypeptide activity by measuring the ability of the polypeptide to convert 2-oxoglutarate into ethylene in vitro, in a cell extract, or in vivo. Exemplary efe nucleic acids include nucleic acids that encode a polypeptide, fragment of a polypeptide, peptide, or fusion polypeptide that has at least one activity of an efe polypeptide. Exemplary efe polypeptides and nucleic acids include naturally-occurring polypeptides and nucleic acids from any of the source organisms described herein as well as mutant polypeptides and nucleic acids derived from any of the source organisms described herein.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. In one embodiment, a diphosphomevalonate decarboxylase-IDI fusion from *Coxiella burnetti* is made. In another embodiment, an IDI-IspS (isoprene synthase) fusion is made. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonate decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, efe, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, efe, DXS, IDI, and/or MVA pathway nucleic acids (such as any isoprene synthase, efe, DXS, IDI, and/or MVA pathway nucleic acids with a known nucleic acid sequence) can be chemically synthesized using standard methods.

Additional isoprene synthase, efe, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as E. coli, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as E. coli. Once injected into the cell, the heterologous DNA circularizes under the influence of the cos sticky ends. In this manner, large segments of heterologous DNA can be introduced and expressed in host cells.

Additional methods for obtaining isoprene synthase, efe, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, efe, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., Applied. Microbiol. Biotechnol. 75: 1377-84, 2007; Withers et al., Appl Environ Microbiol. 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (worldwide web at "expasy.org", Swiss Institute of Bioinformatics Swiss-Prot group CMU-1 rue Michel Servet CH-1211 Geneva 4, Switzerland) can also be used to identify isoprene synthase, efe, DXS, IDI, or MVA pathway polypeptides and nucleic acids. The secondary and/or tertiary structure of an isoprene synthase, efe, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, efe, DXS, IDI, or MVA pathway polypeptide can be determined using standard methods. Additional isoprene synthase, efe, DXS, IDI, or MVA pathway nucleic acids can also be identified by hybridization to probes generated from known isoprene synthase, efe, DXS, IDI, or MVA pathway nucleic acids.

Exemplary Promoters and Vectors

Any of the isoprene synthase, efe, DXS, IDI, or MVA pathway nucleic acid described herein can be included in one or more vectors. Accordingly, the invention also features vectors with one more nucleic acids encoding any of the isoprene synthase, efe, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., *EMBO J.* 4:475-479, 1985 and Penttila et al., *Gene* 61:155-164, 1987 (which are each hereby incorporated by reference in their entireties, particularly with respect to selective markers). In some embodiments, an isoprene synthase, efe, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, efe, DXS, IDI, or MVA pathway nucleic acid in the host cell. Initiation control regions or promoters, which are useful to drive expression of isoprene synthase, efe, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and ffh, lac, trp, $\lambda P_L$, $\lambda P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an isoprene synthase, efe, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, efe, DXS, IDI, or MVA pathway nucleic acid is operably linked to a T7 promoter. In some embodiments, the heterologous or extra endogenous isoprene synthase, efe, DXS, IDI, or MVA pathway nucleic acid operably linked to a T7 promoter is contained in a medium or high copy plasmid. In some embodiments, the heterologous or extra endogenous isoprene synthase, efe, DXS, IDI, or MVA pathway nucleic acid is operably linked to a Trc promoter. In some embodiments, the heterologous or extra endogenous isoprene synthase, efe, DXS, IDI, or MVA pathway nucleic acid operably linked to a Trc promoter is contained in a medium or high copy plasmid. In some embodiments, the heterologous or extra endogenous isoprene synthase, efe, DXS, IDI, or MVA pathway nucleic acid is operably linked to a Lac promoter. In some embodiments, the heterologous or extra endogenous isoprene synthase, efe, DXS, IDI, or MVA pathway nucleic acid operably linked to a Lac promoter is contained in a low copy plasmid. In some embodiments, the heterologous or extra endogenous isoprene synthase, efe, DXS, IDI, or MVA pathway nucleic acid is operably linked to an endogenous promoter, such as an endogenous *Escherichia, Pantoea, Bacillus, Yarrowia, Streptomyces,* or *Trichoderma* promoter or an endogenous alkaline serine protease, isoprene synthase, efe, DXS, IDI, or MVA pathway promoter. In some embodiments, the heterologous or extra endogenous isoprene synthase, efe, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, efe, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell. Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei cellobiohydrolase* 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell. Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, efe, DXS, IDI, or MVA pathway nucleic acid to be expressed. In some embodiments, the coding region for an isoprene synthase, efe, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, efe, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, efe, DXS, IDI, or MVA pathway nucleic acid), a promoter, a terminator, and other sequences and to insert them into a suitable vector are well known in the art. For example, restriction enzymes can be used to cleave the isoprene synthase, efe, DXS, IDI, or MVA pathway nucleic acid and the vector. Then, the compatible ends of the cleaved isoprene synthase, efe, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, efe, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, efe, DXS, IDI, or MVA pathway nucleic acids (and their encoded polypeptides) can be obtained from any organism that naturally contains isoprene synthase, efe, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIGS. 19A and 19B). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, efe, DXS, IDI, or MVA pathway nucleic is identical to the sequence of a nucleic acid that is produced by any of the following organisms in nature. In some embodiments, the amino acid sequence of the isoprene synthase, efe, DXS, IDI, or MVA pathway polypeptide is identical to the sequence of a polypeptide that is produced by any of the following organisms in nature. In some embodiments, the isoprene synthase, efe, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens*, *H. lanuginose*, or *H. grisea*); *Chrysosporium* sp. (e.g., *C. lucknowense*), *Gliocladium* sp., *Aspergillus* sp. (e.g., *A. oryzae*, *A. niger*, *A sojae*, *A. japonicus*, *A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum*, *F. graminum F. cerealis*, *F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., *Sci.* 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans*, *A. awamori*, *A. oryzae*, *A. aculeatus*, *A. niger*, *A. japonicus*, *T. reesei*, *T. viride*, *F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei*.

In some embodiments, the source organism is a yeast, such as *Saccharomyces* sp., *Schizosaccharomyces* sp., *Pichia* sp., or *Candida* sp. In some embodiments, the *Saccharomyces* sp. is *Saccharomyces cerevisiae*.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, *P. putida*, *P. syringae*, or *P. fluorescens*, strains of *Streptomyces* such as *S. lividans* or *S. rubiginosus*, strains of *Corynebacterium* sp. such as *Corynebacterium glutamicum*, strains of *Rhodopseudomonas* sp. such as *Rhodopseudomonas palustris*, or strains of *Escherichia* such as *E. coli*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

In some embodiments, the source organism is a gram-positive bacterium. Non-limiting examples include strains of *Streptomyces* (e.g., *S. lividans*, *S. coelicolor*, or *S. griseus*) and *Bacillus*. In some embodiments, the source organism is a gram-negative bacterium, such as *E. coli.*, *Rhodopseudomonas* sp. such as *Rhodopseudomonas palustris*, or *Pseudomonas* sp., such as *P. alcaligenes*, *P. putida*, *P. syringae*, or *P. fluorescens*.

In some embodiments, the source organism is a plant, such as a plant from the family Fabaceae, such as the Faboideae subfamily. In some embodiments, the source organism is kudzu, poplar (such as *Populus alba*×*tremula* CAC35696), aspen (such as *Populus tremuloides*), or *Quercus robur*.

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: *Chroococcales*, *Pleurocapsales*, *Oscillatoriales*, *Nostocales*, or *Stigonematales*.

Exemplary Host Cells

A variety of host cells can be used to express isoprene synthase, efe, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or ethylene or a cell that does not naturally produce isoprene or ethylene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways. In some embodiments, the host cell naturally produces ethylene, and an efe nucleic acid is added to enhance production of ethylene.

Exemplary Transformation Methods

Isoprene synthase, efe, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, efe, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, 2$^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., *Molecular Cloning: A Laboratory Manual*, Cold Spring Harbor, 1982, which is hereby incorporated by reference in its entirety, particularly with respect to transformation methods.

Exemplary Cell Culture Media

The invention also includes a cell or a population of cells in culture that produce isoprene or ethylene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], 7th ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell medias). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in Manual of *Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, efe, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene. In some embodiments, cells in log phase are responsible for the bulk of the ethylene production. In some embodiments, cells in stationary phase produce ethylene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene or ethylene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, efe, DXS, IDI, or MVA pathway nucleic acid(s) operably linked to the promoter. In some embodiments, a compound (such as IPTG) is added to induce expression of the isoprene synthase, efe, DXS, IDI, or MVA pathway nucleic acid(s) operably linked to the promoter.

Exemplary Methods for Decoupling Isoprene Production from Cell Growth

Desirably, carbon from the feedstock is converted to isoprene rather than to the growth and maintenance of the cells. In some embodiments, the cells are grown to a low to medium $OD_{600}$, then production of isoprene is started or increased. This strategy permits a large portion of the carbon to be converted to isoprene.

In some embodiments, cells reach an optical density such that they no longer divide or divide extremely slowly, but continue to make isoprene for several hours (such as about 2, 4, 6, 8, 10, 15, 20, 25, 30, or more hours). For example, FIGS. 60A-67C illustrate that cells may continue to produce a substantial amount of mevalonic acid or isoprene after the cells reach an optical density such that they no longer divide or divide extremely slowly. In some cases, the optical density at 550 nm decreases over time (such as a decrease in the optical density after the cells are no longer in an exponential growth phase due to cell lysis), and the cells continue to produce a substantial amount of mevalonic acid or isoprene. In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr) during this time period. In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium) during this time period. In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene during this time period. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells are in stationary phase. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells divide slowly or not at all such that the optical density at 550 nm of the cells increases by less than or about 50% (such as by less than or about 40, 30, 20, 10, 5, or 0%). In some embodiments, isoprene is only produced in the growth phase.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

Production of Isoprene within Safe Operating Ranges

The production of isoprene within safe operating levels according to its flammability characteristics simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene).

Thus, computer modeling and experimental testing were used to determine the flammability limits of isoprene (such as isoprene in the presence of $O_2$, $N_2$, $CO_2$, or any combination of two or more of the foregoing gases) in order to ensure process safety. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment.

The following conditions were tested using computer simulation and mathematical analysis and experimental testing. If desired, other conditions (such as other temperature, pressure, and permanent gas compositions) may be tested using the methods described herein to determine the LFL, UFL, and LOC concentrations.

(1) Computer Simulation and Mathematical Analysis
Test Suite 1:
isoprene: 0 wt %-14 wt %
$O_2$: 6 wt %-21 wt %
$N_2$: 79 wt %-94 wt %
Test Suite 2:
isoprene: 0 wt %-14 wt %
$O_2$: 6 wt %-21 wt %
$N_2$: 79 wt %-94 wt %
Saturated with $H_2O$
Test Suite 3:
isoprene: 0 wt %-14 wt %
$O_2$: 6 wt %-21 wt %
$N_2$: 79 wt %-94 wt %
$CO_2$: 5 wt %-30 wt %

(2) Experimental Testing for Final Determination of Flammability Limits
Test Suite 1:
isoprene: 0 wt %-14 wt %
$O_2$: 6 wt %-21 wt %
$N_2$: 79 wt %-94 wt %
Test Suite 2:
isoprene: 0 wt %-14 wt %
$O_2$: 6 wt %-21 wt %
$N_2$: 79 wt %-94 wt %
Saturated with $H_2O$ Simulation software was used to give an estimate of the flammability characteristics of the system for several different testing conditions. $CO_2$ showed no significant affect on the system's flammability limits. Test suites 1 and 2 were confirmed by experimental testing. The modeling results were in-line with the experimental test results. Only slight variations were found with the addition of water.

The LOC was determined to be 9.5 vol % for an isoprene, $O_2$, $N_2$, and $CO_2$ mixture at 40° C. and 1 atmosphere. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol. % to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 Standard on Explosion Prevention Systems, 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7% vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

High Efficiency Production and Recovery of Isoprene, a Volatile Hydrocarbon, by Fermentation Further, provided herein are methods for the high efficiency production and recovery of volatives such as isoprene using reduced gas-sparging rates. The use of reduced gas-sparging rates facilitates the recovery of isoprene and other volatiles (such as ethylene) by increasing the concentration of the volatile in the fermentation off-gas, which can facilitate downstream recovery of the volatile from permanent gases and other impurities. Another advantage of volatile production and recovery at reduced gas-sparging rates is that the amount of oxygen present in the off-gas is reduced as a greater percentage of the initial oxygen is consumed by the cells in the fermentor. Low oxygen concentrations are advantageous as the reaction of oxygen with isoprene to form undesirable polymers and oxidized compounds is reduced. In addition, the use of reduced gas-sparging rates maximizes the amount of volatile in the off-gas, while minimizing permanent gases, in particular oxygen. The maximization of the amount of the volatile is also important in maintaining safe operating conditions in view of the extremely volatile nature of isoprene and other unsaturated hydrocarbons in the process as discussed above.

The continuous removal of volatile organic compounds (VOCs) from fermentation broth by gas stripping is most effective for substances whose physical properties favor partitioning into the gas phase at ambient temperatures and pressures. In general, a compound can be recovered by gas stripping if it possesses a high vapor pressure at fermentation temperatures, combined with low water solubility. The Henry's law coefficient is also used to estimate the effectiveness of gas stripping for removal of organic compounds from aqueous solution. At equilibrium, the relation between the concentrations of a volatile compound in the liquid and gaseous phases is given by Henry's gas law (eq. 1).

$$P = kC \qquad \text{(eq. 1)}$$

Where P is the partial pressure, C the aqueous concentration and k is Henry's law coefficient. Under dynamic conditions, such as the case of a gas-sparged fermentator producing a volatile organic compound, the concentration of a volatile in the liquid phase is dependant on several additional factors, summarized below;

i) Rate of volatile production (g/L/hr)
ii) Gas sparging rate (vvm)
iii) Bubble surface area ($m^{-2}$)
iv) Agitation rate Thus at a constant rate of volatile production, higher gas-sparging rates will tend to reduce the steady-state aqueous concentration of the volatile. The rate of volatile mass transfer from the liquid to the gaseous phase (or vice versa) is a function of the difference between the aqueous volatile concentration and the expected concentration at equilibrium, multiplied by a mass transfer coefficient.

$$F = K_L[C - (P/k)] \quad \text{(eq. 2)}$$

Where F is flux (mol $s^{-1}$), $K_L$ the gas transfer velocity (m $s^{-1}$), C the aqueous volatile concentration, P is partial pressure and k representing Henry's gas law coefficient for the volatile. When the aqueous concentration is greater than the equilibrium concentration, gas efflux will occur from the liquid to the gaseous phase. The gas transfer velocity, $K_L$, will also be influenced by the total gas/liquid surface area, which will change as a function of the degree of agitation of the fermentation broth. For a well stirred fermentor, it can be assumed that the bulk gas and liquid phases are at equilibrium, and thus the aqueous concentration of a volatile is predominantly a function of the partial pressure in the gas phase above the liquid, in accordance with Henry's law (eq. 1). It should be understood that the value of Henry's coefficient varies with temperature and the composition of the aqueous phase of the system. Thus, the actual amount of isoprene present in aqueous fermentation broth at a give time may vary from the theoretical amount in an ideal system.

For isoprene at 298K, the Henry's Law coefficient is 0.029 M/atm. See Weitz and Loser in *Ullmann's Encyclopedia of Industrial Chemistry*, 7th edn., Electronic release, Wiley-VCH Verlag GMBH, Weinheim (2005); see also Karl et al. (2003) *Int. J. Mass Spec.*, 223-224, 383-395, which are incorporated by reference in their entirety, particularly with respect to Henry's Law coefficient calculations. Therefore, if the off-gas exiting the fermentor has an isoprene partial pressure of 0.01 atm (1% v/v) at 0.5 vvm, then the steady state liquid concentration in the fermentation broth will be 0.29 mM, or about 20 mg/L. Doubling the airflow to 1 vvm will halve the partial pressure of isoprene above the fermentor to 0.05%, and therefore the liquid phase concentration will be reduced to around 10 mg/L.

Methods are provided herein of producing isoprene comprising a) culturing cells under suitable conditions for production of isoprene; and b) producing isoprene, wherein the liquid phase concentration of isoprene is less than about 2 g/L. In some embodiments, the liquid phase concentration of isoprene in the culture is less than about 1 g/L. In some embodiments, the liquid phase concentration of isoprene in the culture is less than about 200 mg/L. In some embodiments, the liquid phase concentration of isoprene in the culture is less than any of about 1.9 g/L, 1.8 g/L, 1.7 g/L, 1.6 g/L, 1.5 g/L, 1.4 g/L, 1.3 g/L, 1.2 g/L, or 1.1 g/L. In some embodiments, the liquid phase concentration of isoprene in the culture is less than any of about 900 mg/L, 800 mg/L, 700 mg/L, 600 mg/L, 500 mg/L, 400 mg/L, or 300 mg/L. In some embodiments, the liquid phase concentration of isoprene in the culture is less than about any of 175 mg/L, 150 mg/L, 125 mg/L, 100 mg/L, 75 mg/L, 50 mg/L, 25 mg/L, 20 mg/L, 15 mg/L, 10 mg/L, 5 mg/L, or 2.5 mg/L. In some embodiments, the liquid phase concentration of isoprene in culture is between about any of 0.1 mg/L to 200 mg/L, 1 mg/L to 200 mg/L, 1 mg/L to 150 mg/L, 1 mg/L to 100 mg/L, 1 mg/L to 50 mg/L, 1 mg/L to 25 mg/L, 1 mg/L to 20 mg/L, or 10 mg/L to 20 mg/L, 1 mg/L to 1 g/L, 0.1 mg/L to 2 g/L, 1 g/L to 2 g/L, 10 mg/L to 1 g/L, or 100 mg/L to 1 g/L. In some embodiments, the isoprene produced is any concentration or amount disclosed in the section entitled "Exemplary Production of Isoprene." In some embodiments, the liquid phase concentration is below the solubility limit of isoprene. In some embodiments, the liquid phase in the culture is saturated with isoprene, and isoprene is additionally present in a second liquid phase. In some embodiments, the second liquid phase comprises at least about 50, 60, 70, 80, 85, 90, 95, or 98% isoprene.

In some embodiments of the methods, the cells produce greater than about 400 nmole/gwcm/hour of isoprene. In some embodiments, the amount of isoprene is between about any of 400 nmole/$g_{wcm}$/hour to 1 mole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour.

The low value for Henry's coefficient means that isoprene can be recovered from fermentation broth by gas stripping at low sparging rates, for example 0.01 vvm to 2 vvm. In some embodiments, the gas sparging rate is between about any of 0 vvm to 0.01 vvm, 0.01 vvm to 0.1 vvm, 0.1 vvm to 1 vvm, 0.01 vvm to 0.5 vvm, 0.2 vvm to 1 vvm, or 0.5 vvm to 1 vvm. In some embodiments, the gas sparging rate is about any of 0.1 vvm, 0.25 vvm, 0.5 vvm, 0.75 vvm, 1 vvm, 1.25 vvm, 1.5 vvm, 1.75 vvm, or 2 vvm. In one embodiment, gas sparging is not used. In some embodiments, the low sparging rates are maintained for the entire course of the fermentation run, during growth phase, or during stationary phase. In some embodiments, the low sparging rates are maintained for between about any of 1 hour to 5 hours, 5 hours to 10 hours, 10 hours to 20 hours, 20 hours to 30 hours, 30 hours to 40 hours, 40 hours to 50 hours, or 50 hours to 60 hours. The lower desirable gas sparge limit is defined by the point at which the aqueous phase becomes saturated with isoprene and a liquid organic phase forms. This can only occur below the boiling point of isoprene (34.1° C. at 1 atm), above which a liquid isoprene phase will never form. At temperatures below the boiling point of isoprene, the formation of a liquid phase is determined by the aqueous solubility of isoprene, which is approximately 650 mg/L at 25° C. While it is highly desirable to avoid the formation of a liquid isoprene phase, it is not absolutely required provided that the cells can tolerate the presence of liquid isoprene without toxic effects.

In some embodiments, the oxygen, $CO_2$, and isoprene are any of the amounts or concentrations discussed in the section entitled "Production of Isoprene with Safe Operating Ranges." In some embodiments, all the oxygen is consumed by the cells while maintaining fully aerobic metabolism. In some embodiments, an excess of oxygen is used in order to satisfy the oxygen demands of the cells. Desirable ranges of oxygen in the off-gas are less than 20%, or less than 15% or less than 10% (v/v). Levels of oxygen below the limiting oxygen concentration required for combustion of isoprene (9.5% v/v at 1 atm) are particularly desirable. In some embodiments, oxygen-enriched air is utilized with the purpose of allowing minimal gas sweep rates while satisfying the cellular oxygen demand. In some embodiments, the portion of the gas phase of the gas sweep comprises between about 0.1% to about 10%, about 10% to about 20%, or about 20% to about 30% (volume) oxygen. In some embodiments, isoprene fermentations are performed under high pressure in order minimize the amount of excess oxygen required to maintain the required dissolved oxygen levels in the liquid phase.

In some embodiments, the reduction of the gas sweep rate through the fermentor is advantageous for an integrated isoprene production process in that such conditions enrich the off-gas isoprene levels up to about 30,000 ug/L (about 1% v/v) without adversely affecting the physiology of the cells.

In some embodiments, reduced gas-sparge rates do not significantly adversely affect the physiology of the cells. In some embodiments, the carbon dioxide evolution rate of cells in culture with reduced gas-sparge rates is between about any of $1 \times 10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour. In some embodiments, cell viability with reduced gas-sparge rates is reduced by less than about any of 1.75-fold, 1.5-fold, 1.25-fold, 1-fold, 0.75-fold, 0.5-fold, or 0.25-fold. In some embodiments, cell viability with reduced gas-sparge rates is reduced by about 2-fold. In some embodiments, cell viability with reduced gas-sparge rates of a cell expressing a MVA pathway and/or DXP pathway RNA and/or protein from one or more of a heterologous and/or duplicate copy of a MVA pathway and/or DXP pathway nucleic acid is compared to a control cell lacking one or more of a heterologous and/or duplicate copy of a MVA pathway and/or DXP pathway nucleic acid with reduced gas-sparge rates. In some embodiments, cell viability with reduced gas-sparge rates of a cell expressing a MVA pathway and/or DXP pathway RNA and/or protein from one or more of a heterologous and/or duplicate copy of a MVA pathway and/or DXP pathway nucleic acid under the control of an inducible promoter, wherein the promoter is induced, is compared to a control cell containing one or more of a heterologous and/or duplicate copy of a MVA pathway and/or DXP pathway nucleic acid under the control of an inducible promoter, wherein the promoter is not induced (uninduced) with reduced gas-sparge rates. In some embodiments, the inducible promoter is a beta-galactosidase promoter.

In some embodiments, the fermentation of a genetically modified host organism that converts at least 5% of the total carbon consumed by the organism into a volatile, unsaturated hydrocarbon. In some embodiments, the production of an unsaturated hydrocarbon at such a rate as to be present in the fermentation off-gas at a level of at least about any of 100 ug/L, 500 ug/L, 1000 ug/L, 2, 500 ug/L, 5,000 ug/L, 7,500 ug/L, or 10,000 ug/L.

In some embodiments, the unsaturated hydrocarbon is recovered from the off-gas stream in a manner that is suited to high-rates of production, which correspond to concentrations in the offgas of at least about any of 100 ug/L, 500 ug/L, 1000 ug/L, 2,500 ug/L, 5,000 ug/L, 7,500 ug/L, or 10,000 ug/L. In some embodiments, the continuous extraction and recovery of an unsaturated hydrocarbon from the fermentation off-gas in particular at low gas sweep rates such that the resulting off-gas is enriched in the volatile component of interest. In some embodiments, recovery of the volatile hydrocarbon by methods that depend on elevated concentrations of the volatile. For example, efficient capture of isoprene in fermentation off-gas through the use of compression/condensation or extractive distillation technologies. Also contemplated is the use of activated carbon cartridges in addition to silica gel adsorbants, desorption and concentration of isoprene from carbon cartridges, and/or construction and fermentation of host organisms such as E. coli strains that can convert about 5% or more of the glucose substrate to isoprene and result in off-gas concentrations of greater than about 15,000 ug/L isoprene. Recovery methods include any of the methods described herein.

Also provided herein are methods of producing a compound, wherein the compound has one or more characteristics selected from the group consisting of (a) a Henry's law coefficient of less than about 250 M/atm and (b) a solubility in water of less than about 100 g/L. In some embodiments, the method comprises: a) culturing cells under suitable conditions for production of the compound, wherein gas is added (such as the addition of gas to a system such as a fermentation system) at a gas sparging rate between about 0.01 vvm to about 2 vvm; and b) producing the compound. In one embodiment, the gas sparging rate is 0 vvm. In another embodiment, the gas sparging rate is 0 to 0.01 vvm.

In some embodiments, the amount of the compound that partitions into the cell mass is not included in the liquid phase solubility values. In some embodiments, the liquid phase concentration is below the solubility limit of compound.

In some embodiments, the compounds can be continuously recovered from fermentation broth by gas stripping at moderate to low gas sparging rates, in particular those compounds with Henry's law coefficients of about any of less than 250 M/atm, 200 M/atm, 150 M/atm, 100 M/atm, 75 M/atm, 50 M/atm, 25 M/atm, 10 M/atm, 5 M/atm, or 1 M/atm. Examples include aldehydes such as acetaldehyde (15 M/atm), ketones such as acetone (30 M/atm), methyl ethyl ketone (100 M/atm), or 2-butanone (20 M/atm), or alcohols including methanol (220 M/atm), ethanol (200 M/atm), 1-butanol (120 m/atm) or C5 alcohols including 3-methyl-3-buten-1-ol, and 3-methyl-2-buten-1-ol (50-100 M/atm). Esters of alcohols generally have lower Henry's constants than the respective alcohols, for example ethyl acetate (6-9 M/atm) or the acetyl esters of C5 alcohols (<5 M/atm). Compounds with Henry's law coefficients of less than 1M/atm are particularly desirable. Examples include hemiterpenes, monoterpenes, or sesquiterpenes, in addition to other hydrocarbons such as C1 to C5 hydrocarbons (e.g., methane, ethane, ethylene, or propylene). In some embodiments, the hydrocarbons such as C1 to C5 hydrocarbons are saturated, unsaturated, or branched. In some embodiments, the C1 to C5 hydrocarbon is an unsaturated aliphatic hydrocarbon (e.g. ethylene, propylene, butylene, or isobutylene). In some embodiments, the C1 to C5 hydrocarbon is a diolefin.

In general, there is a correlation between Henry's law coefficient and water solubility in that compounds with very low coefficients are sparingly soluble in water (substantially water insoluble). Although volatiles with infinite solubilities in water (e.g. acetone or ethanol) can be removed by gas stripping, desirable solubility limits are less than about any of 100 g/L, 75 g/L, 50 g/L, 25 g/L, 10 g/L, 5 g/L, or 1 g/L.

In some embodiments of any of the methods of producing any of the compounds described above, the gas sparging rate is between about any of 0 vvm to 0.01 vvm, 0.01 vvm to 0.1 vvm, 0.1 vvm to 1 vvm, 0.2 vvm to 1 vvm, or 0.5 vvm to 1 vvm. In some embodiments, the gas sparging rate is about any of 0.1 vvm, 0.25 vvm, 0.5 vvm, 0.75 vvm, 1 vvm, 1.25 vvm, 1.5 vvm, 1.75 vvm, or 2 vvm. In some embodiments, the low sparging rates are maintained for the entire course of the fermentation run, during growth phase, or during stationary phase. In some embodiments, the low sparging rates are maintained for between about any of 1 hour to 5 hours, 5 hours to 10 hours, 10 hours to 20 hours, 20 hours to 30 hours, 30 hours to 40 hours, 40 hours to 50 hours, or 50 hours to 60 hours.

Any of the systems described herein can be used in the methods of producing a compound described above. Standard method would be used to purify such as those described in the section entitled "Exemplary Purification Methods." Separate can be performed post-recovery for example, by distillation or selective adsorption techniques.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "peak concentration" is meant the maximum amount of isoprene produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprene produced per cell is at a maximum. In some embodiments, the isoprene amount is measured at the peak concentration time point. In some embodiments, the peak concentration for the cells is about any of the isoprene amounts disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

By "relative detector response" refers to the ratio between the detector response (such as the GC/MS area) for one compound (such as isoprene) to the detector response (such as the GC/MS area) of one or more compounds (such as all C5 hydrocarbons). The detector response may be measured as described herein, such as the GC/MS analysis performed with an Agilent 6890 GC/MS system fitted with an Agilent HP-5MS GC/MS column (30 m×250 µm; 0.25 µm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr ($ng/g_{wcm}/h$). In some embodiments, the amount of isoprene is between about 2 to about 5,000 $ng/g_{wcm}/h$, such as between about 2 to about 100 $ng/g_{wcm}/h$, about 100 to about 500 $ng/g_{wcm}/h$, about 500 to about 1,000 $ng/g_{wcm}/h$, about 1,000 to about 2,000 $ng/g_{wcm}/h$, or about 2,000 to about 5,000 $ng/g_{wcm}/h$. In some embodiments, the amount of isoprene is between about 20 to about 5,000 $ng/g_{wcm}/h$, about 100 to about 5,000 $ng/g_{wcm}/h$, about 200 to about 2,000 $ng/g_{wcm}/h$, about 200 to about 1,000 $ng/g_{wcm}/h$, about 300 to about 1,000 $ng/g_{wcm}/h$, or about 400 to about 1,000 $ng/g_{wcm}/h$. The amount of isoprene in $ng/g_{wcm}/h$ can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth/hr}$ can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100    Equation 1

For this calculation, yeast extract can be assumed to contain 50% w/w carbon. As an example, for the 500 liter described in Example 7, part VIII, the percent conversion of carbon into isoprene can be calculated as shown in Equation 2.

Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042%    Equation 2

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein. Example 11, part V describes the 1.53% conversion of carbon to isoprene using the methods described herein.

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate)    Equation 3

1 nmol isoprene/$g_{wcm}$/hr=1 nmol isoprene/$L_{broth}$/hr/$OD_{600}$(This conversion assumes that one liter of broth with an $OD_{600}$ value of 1 has a wet cell weight of 1 gram.)    Equation 4

1 nmol isoprene/$g_{wcm}$/hr=68.1 ng isoprene/$g_{wcm}$/hr (given the molecular weight of isoprene)    Equation 5

1 nmol isoprene/$L_{gas}$ $O_2$/hr=90 nmol isoprene/$L_{broth}$/hr(at an $O_2$ flow rate of 90 L/hr per L of culture broth)    Equation 6

1 ug isoprene/$L_{gas}$ isoprene in off-gas=60 ug isoprene/$L_{broth}$/hr at a flow rate of 60 $L_{gas}$ per $L_{broth}$(1 vvm)    Equation 7

Units for Titer (Total and Specific)

$$1 \text{ nmol isoprene/mg cell protein} = 150 \text{ nmol isoprene/} L_{broth}/OD_{600} \text{(This conversion assumes that one liter of broth with an } OD_{600} \text{ value of 1 has a total cell protein of approximately 150 mg)(specific productivity)} \quad \text{Equation 8}$$

$$1 \text{ g isoprene/} L_{broth} = 14.7 \text{ mmol isoprene/} L_{broth} \text{(total titer)} \quad \text{Equation 9}$$

If desired, Equation 10 can be used to convert any of the units that include the wet weight of the cells into the corresponding units that include the dry weight of the cells.

$$\text{Dry weight of cells} = \text{(wet weight of cells)}/3.3 \quad \text{Equation 10}$$

If desired, Equation 11 can be used to convert between units of ppm and ug/L. In particular, "ppm" means parts per million defined in terms of ug/g (w/w). Concentrations of gases can also be expressed on a volumetric basis using "ppmv" (parts per million by volume), defined in terms of uL/L (vol/vol). Conversion of ug/L to ppm (e.g., ug of analyte per g of gas) can be performed by determining the mass per L of off-gas (i.e., the density of the gas). For example, a liter of air at standard temperature and pressure (STP; 101.3 kPa (1 bar) and 273.15K) has a density of approximately 1.29 g/L. Thus, a concentration of 1 ppm (ug/g) equals 1.29 ug/L at STP (equation 11). The conversion of ppm (ug/g) to ug/L is a function of both pressure, temperature, and overall composition of the off-gas.

$$1 \text{ ppm(ug/g)equals } 1.29 \text{ ug/L at standard temperature and pressure(STP;101.3 kPa(1 bar)and 273.15K).} \quad \text{Equation 11}$$

Conversion of ug/L to ppmv (e.g., uL of analyte per L of gas) can be performed using the Universal Gas Law (equation 12). For example, an off-gas concentration of 1000 ug/$L_{gas}$ corresponds to 14.7 umol/$L_{gas}$. The universal gas constant is 0.082057 L·atm $K^{-1}$mol$^{-1}$, so using equation 12, the volume occupied by 14.7 umol of HG at STP is equal to 0.329 mL. Therefore, the concentration of 1000 ug/L HG is equal to 329 ppmv or 0.0329% (v/v) at STP.

$$PV=nRT, \text{where "}P\text{" is pressure,"}V\text{" is volume,"}n\text{" is moles of gas,"}R\text{" is the Universal gas constant, and "}T\text{" is temperature in Kelvin.} \quad \text{Equation 12}$$

The amount of impurities in isoprene compositions are typically measured herein on a weight per volume (w/v) basis in units such as ug/L. If desired, measurements in units of ug/L can be converted to units of mg/m³ using equation 13.

$$1 \text{ ug/L}=1 \text{ mg/m}^3 \quad \text{Equation 13}$$

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

In some embodiments, the isoprene composition comprises greater than or about 99.90, 99.92, 99.94, 99.96, 99.98, or 100% isoprene by weight compared to the total weight of all C5 hydrocarbons in the composition. In some embodiments, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some embodiments, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some embodiments, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)) by weight compared to the total weight of all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) compared to the detector response for all C5 hydrocarbons in the composition. In some embodiments, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)) by weight compared to the total weight of all C5 hydrocarbons in the composition.

In some embodiments, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some embodiments, the isoprene composition comprises less than or about 50, 40, 30, 20, 10, 5, 1, 0.5, 0.1, 0.05, 0.01, or 0.005 ug/L of a hydrocarbon other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1- yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)). In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some embodiments, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some embodiments, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the isoprene composition comprises less than or about 5, 1, 0.5, 0.1, 0.05, 0.01, or 0.005 ppm of sulfur or allenes. In some embodiments, the isoprene composition comprises less than or about 30, 20, 15, 10, 5, 1, 0.5, 0.1, 0.05, 0.01, or 0.005 ppm of all acetylenes (such as pentyne-1, butyne-2, 2 MB1-3yne, and 1-pentyne-4-yne). In some embodiments, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimmers (e.g., cyclic C10 compounds derived from the dimerization of two isoprene units).

In some embodiments, the isoprene composition includes ethanol, acetone, a C5 prenyl alcohol (such as 3-methyl-3-buten-1-ol or 3-methyl-2-buten-1-ol), or any two or more of the foregoing. In particular embodiments, the isoprene composition comprises greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In some embodiments, the isoprene composition comprises between about 0.005 to about 120, such as about 0.01 to about 80, about 0.01 to about 60, about 0.01 to about 40, about 0.01 to about 30, about 0.01 to about 20, about 0.01 to about 10, about 0.1 to about 80, about 0.1 to about 60, about 0.1 to about 40, about 5 to about 80, about 5 to about 60, or about 5 to about 40 ug/L of ethanol, acetone, a C5 prenyl alcohol, or any two or more of the foregoing.

In some embodiments, the isoprene composition includes one or more of the following components: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenopyridine, or a linear isoprene polymer (such as a linear isoprene dimer or a linear isoprene trimer derived from the polymerization of multiple isoprene units). In various embodiments, the amount of one of these components relative to amount of isoprene in units of percentage by weight (i.e., weight of the component divided by the weight of isoprene times 100) is greater than or about 0.01, 0.02, 0.05, 0.1, 0.5, 1, 5, 10, 20, 30, 40, 50, 60, 70, 80, 90, 100, or 110% (w/w). In some embodiments, the relative detector response for the second compound compared to the detector response for isoprene is greater than or about 0.01, 0.02, 0.05, 0.1, 0.5, 1, 5, 10, 20, 30, 40, 50, 60, 70, 80, 90, 100, or 110%. In various embodiments, the amount of one of these components relative to amount of isoprene in units of percentage by weight (i.e., weight of the component divided by the weight of isoprene times 100) is between about 0.01 to about 105% (w/w), such as about 0.01 to about 90, about 0.01 to about 80, about 0.01 to about 50, about 0.01 to about 20, about 0.01 to about 10, about 0.02 to about 50, about 0.05 to about 50, about 0.1 to about 50, or 0.1 to about 20% (w/w).

In some embodiments, the isoprene composition includes one or more of the following: an alcohol, an aldehyde, or a ketone (such as any of the alcohols, aldehyes, or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone.

In some embodiments, the isoprene composition contains one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the isoprene composition contains 1 ppm or more of one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the concentration of more of one or more of the following: methanol, acetaldehyde, ethanol, methanethiol, 1-butanol, 3-methyl-1-propanol, acetone, acetic acid, 2-butanone, 2-methyl-1-butanol, or indole, is between about 1 to about 10,000 ppm in an isoprene composition (such as off-gas before it is purified). In some embodiments, the isoprene composition (such as off-gas after it has undergone one or more purification steps) includes one or more of the following: methanol, acetaldehyde, ethanol, methanethiol, 1-butanol, 3-methyl-1-propanol, acetone, acetic acid, 2-butanone, 2-methyl-1-butanol, or indole, at a concentration between about 1 to about 100 ppm, such as about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, or about 90 to about 100 ppm. Volatile organic compounds from cell cultures (such as volatile organic compounds in the headspace of cell cultures) can be analyzed using standard methods such as those described herein or other standard methods such as proton transfer reaction-mass spectrometry (see, for example, Bunge et al., *Applied and Environmental Microbiology*, 74(7):2179-2186, 2008 which is hereby incorporated by reference in its entirety, particular with respect to the analysis of volatile organic compounds).

In some embodiments, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some embodiments, greater than or about 20, 25, 30, 40, 50, 60, 70, 80, 90, or 95% by weight of the volatile organic fraction of the composition is isoprene.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

In some embodiments encompassed by the invention, a cell comprising one or more heterologous nucleic acids encoding an isoprene synthase polypeptide, DXS polypeptide, IDI polypeptide, and/or MVA pathway polypeptide produces an amount of an isoprenoid compound (such as a compound with 10 or more carbon atoms that is formed from the reaction of one or more IPP molecules with one or more DMAPP molecules) that is greater than or about 2-fold, 3-fold, 5-fold, 10-fold, 25-fold, 50-fold, 100-fold, 150-fold, 200-fold, 400-fold, or greater than the amount of the isoprenoid compound produced from a corresponding cell grown under essentially the same conditions without the one or more heterologous nucleic acids. In some embodiments encompassed by the invention, a cell comprising one or more heterologous nucleic acids encoding an isoprene synthase polypeptide, DXS polypeptide, IDI polypeptide, and/or MVA pathway polypeptide produces an amount of a C5 prenyl alcohol (such as 3-methyl-3-buten-1-ol or 3-methyl-2-buten-1-ol) that is greater than or about 2-fold, 3-fold, 5-fold, 10-fold, 25-fold, 50-fold, 100-fold, 150-fold, 200-fold, 400-fold, or greater than the amount of the C5 prenyl alcohol produced from a corresponding cell grown under essentially the same conditions without the one or more heterologous nucleic acids.

Exemplary Purification Methods

In some embodiments, any of the methods described herein further include recovering the compound. In some embodiments, any of the methods described herein further include recovering the isoprene or ethylene. While the exemplary purification methods below refer to isoprene, any compound disclosed herein can be purified by the methods discussed below.

The isoprene produced using the compositions and methods of the invention can be recovered using standard techniques. such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In particular, embodiments, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, at least a portion of the gas phase remaining after one or more recovery steps for the removal of isoprene is recycled by introducing the gas phase into a cell culture system (such as a fermentor) for the production of isoprene.

In some embodiments, any of the methods described herein further include polymerizing the isoprene. For example, standard methods can be used to polymerize the purified isoprene to form cis-polyisoprene or other down stream products using standard methods. Accordingly, the invention also features a tire comprising polyisoprene, such as cis-1,4-polyisoprene and/or trans-1,4-polyisoprene made from any of the isoprene compositions disclosed herein.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Production of Isoprene in *E. Coli* Expressing Recombinant Kudzu Isoprene Synthase I. Construction of Vectors for Expression of the Kudzu Isoprene Synthase in *E. coli*

Figure 2:
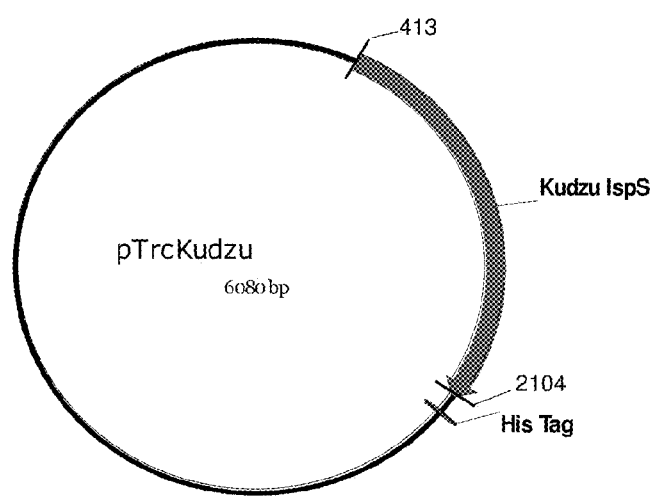
FIG. 2 is a map of pTrcKudzu.

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
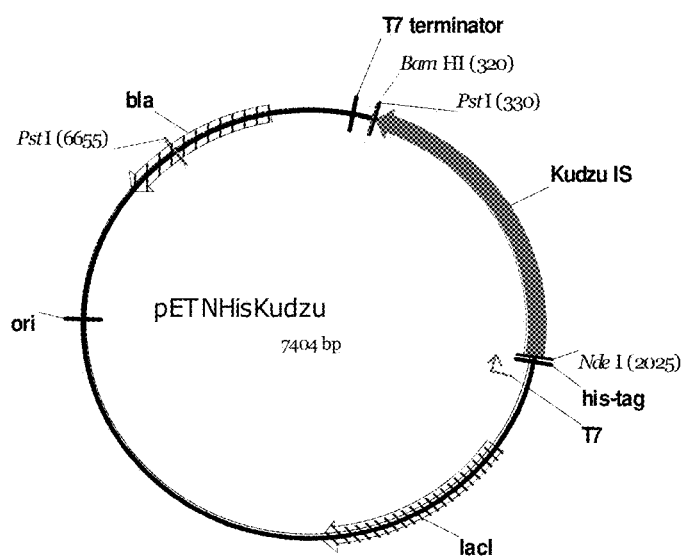
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGAT-CATATGTGTGCGACCTCTTCTCAATTTAC (SEQ ID NO:3) and pET-His-Kudzu-R: 5'-CGGTCGACGGATC-CCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 µl. The PCR product was digested with NdeI/BamH1 and cloned into pET16b digested with the same enzymes. The ligation mix was transformed into E. coli Top10 (Invitrogen) and the correct clone selected by sequencing. The resulting plasmid, in which the kudzu isoprene synthase gene was expressed from the T7 promoter, was designated pET-NHisKudzu (FIGS. 4 and 5).

Figure 6:
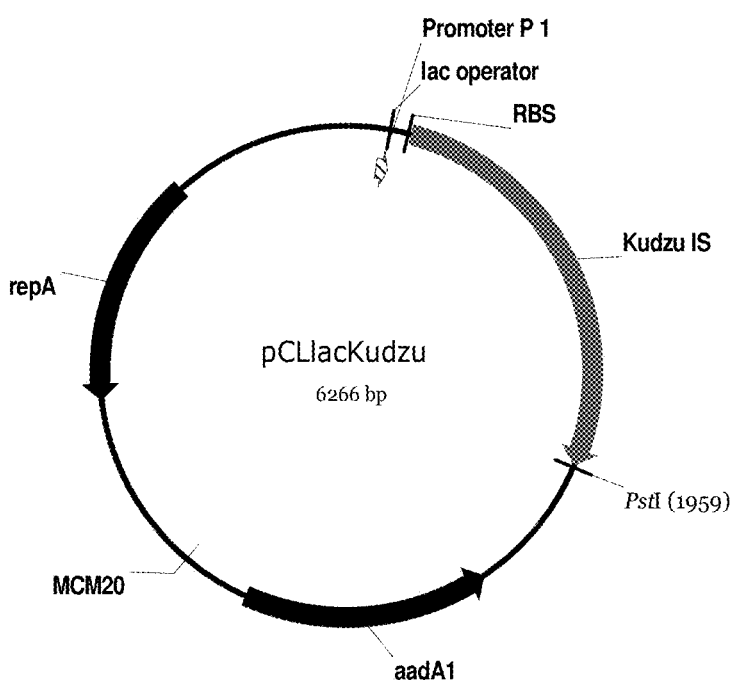
FIG. 6 is a map of pCL-lac-Kudzu.
Figure 8A:
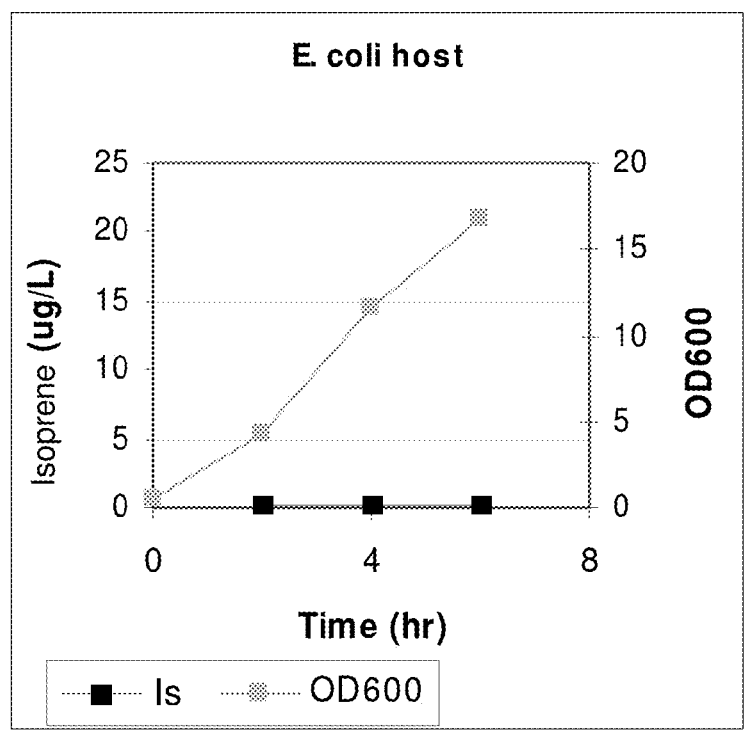
FIG. 8A is a graph showing the production of isoprene in *E. coli* BL21 cells with no vector.
Figure 8B:
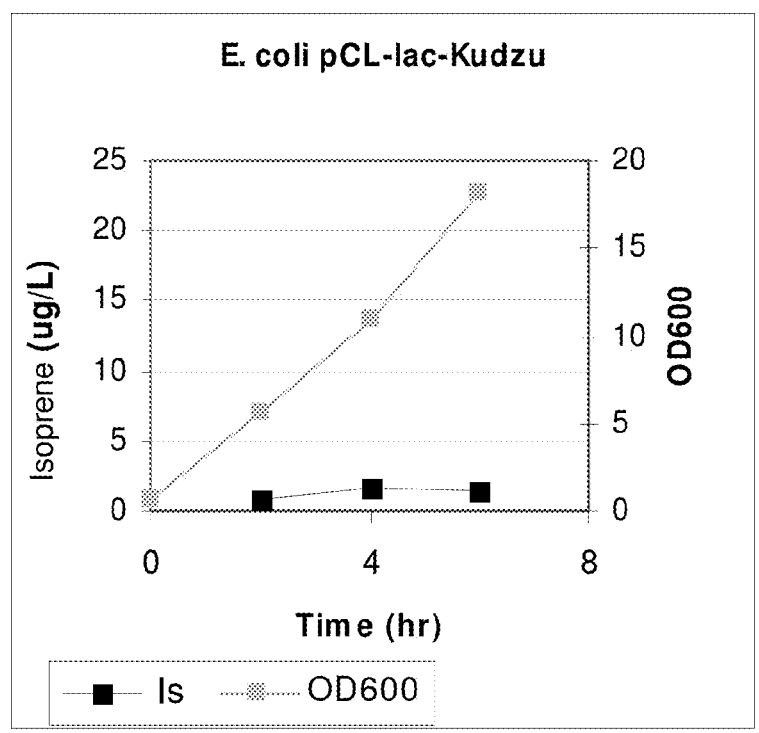
FIG. 8B is a graph showing the production of isoprene in *E. coli* BL21 cells with pCL-lac-Kudzu
Figure 8C:
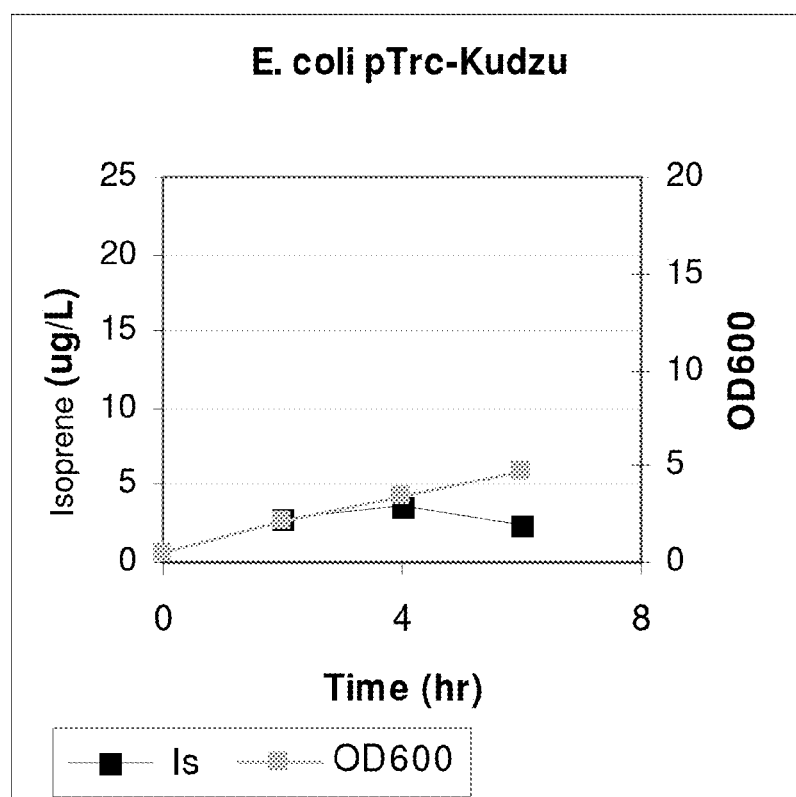
FIG. 8C is a graph showing the production of isoprene in *E. coli* BL21 cells with pTrcKudzu.
Figure 8D:
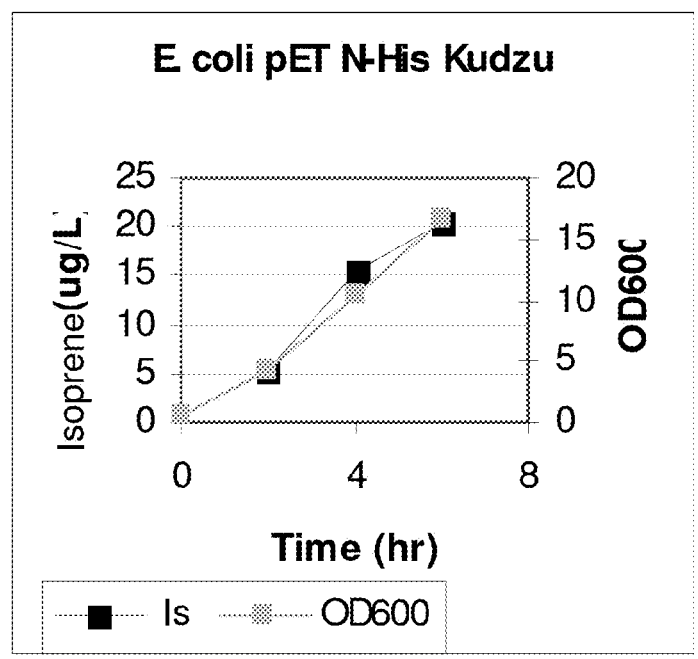
FIG. 8D is a graph showing the production of isoprene in *E. coli* BL21 cells with pETN-HisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an E. coli consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATC-GATTAAATAAGGAGGAATAAACC (SEQ ID NO:6) and BamH1-Kudzu R:

5'-CGGTCGACGGATCCCTGCAGTTAGA-CATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into E. coli Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 2000 µg/L. The limit of detection was estimated to be 50 to 100 ng/L using this method.

III. Production of Isoprene in Shake Flasks Containing E. coli Cells Expressing Recombinant Isoprene Synthase The vectors described above were introduced to E. coli strain BL21 (Novagen) to produce strains BL21/ptrcKudzu, BL21/pCL-lac-Kudzu and BL21/pETHisKudzu. The strains were spread for isolation onto LA (Luria agar)+carbenicillin (50 µg/ml) and incubated overnight at 37° C. Single colonies were inoculated into 250 ml baffled shake flasks containing 20 ml Luria Bertani broth (LB) and carbenicillin (100 µg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen)+carbenicillin (100 µg/ml) to an $OD_{600}$~0.05. The culture was incubated at 30° C. with shaking at 200 rpm. When the $OD_{600}$~0.5-0.8, 400 µM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from E. coli containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and q.s. to volume. The final product was filter sterilized with 0.22µ filter (only, do not autoclave). The recipe for 1000× Modified Trace Metal Solution was as follows: Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, pH to 3.0 with HCl/NaOH, then q.s. to volume and filter sterilized with a 0.22µ filter.

Figure 9A:
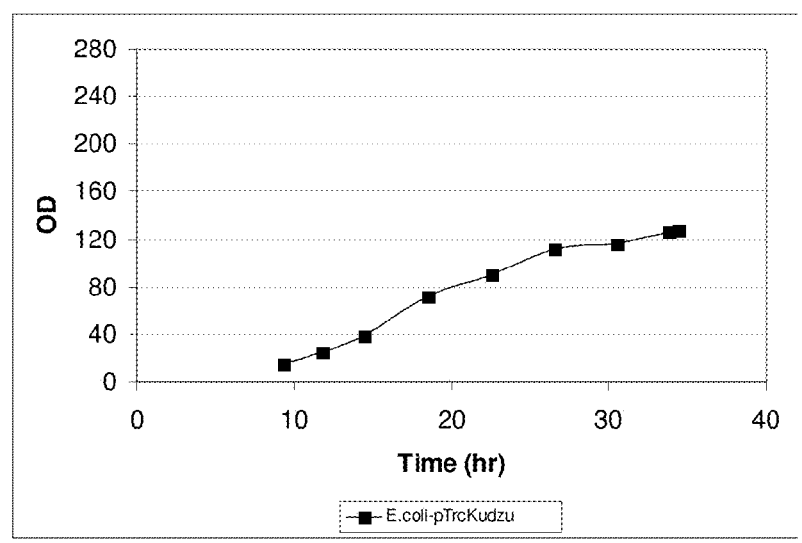
FIG. 9A is a graph showing OD over time of fermentation of *E. coli* BL21/pTrcKudzu in a 14 liter fed batch fermentation.
Figure 9B:
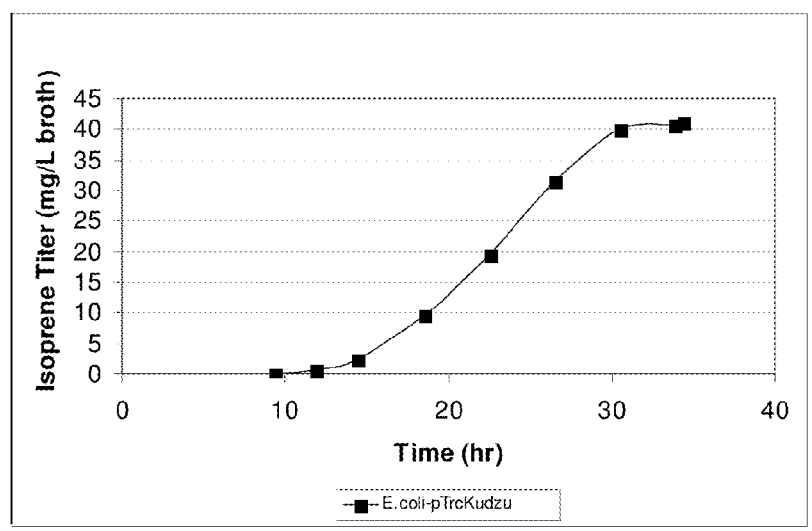
FIG. 9B is a graph showing isoprene production over time of fermentation of *E. coli* BL21/pTrcKudzu in a 14 liter fed batch fermentation.

This experiment was carried out in 14 L bioreactor to monitor isoprene formation from glucose at the desired fermentation, pH 6.7 and temperature 34° C. An inoculum of E. coli strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Example 2

Figure 30:
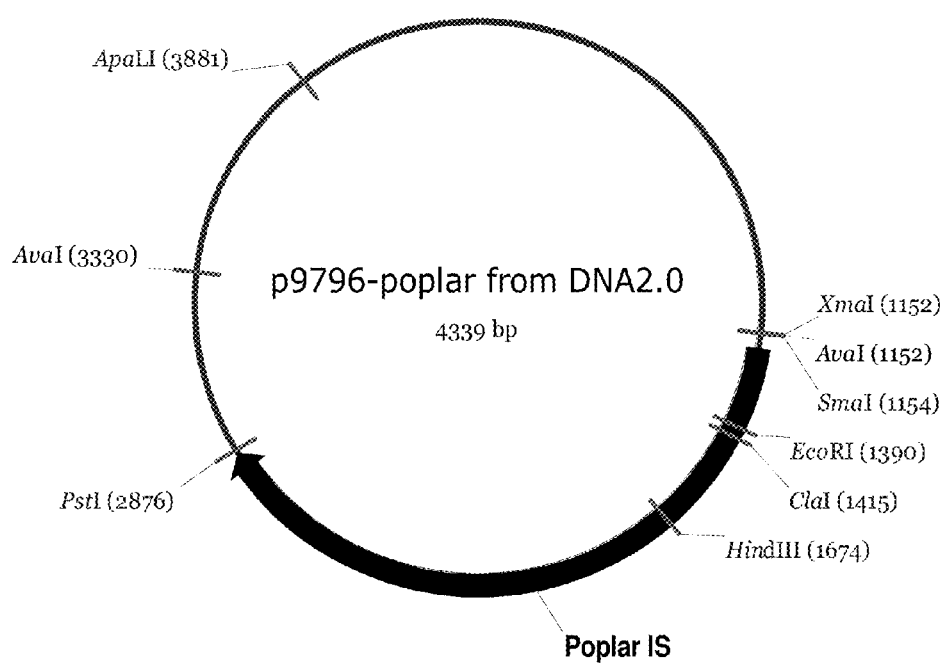
FIG. 30 is a map of p9796-poplar.
Figure 32:
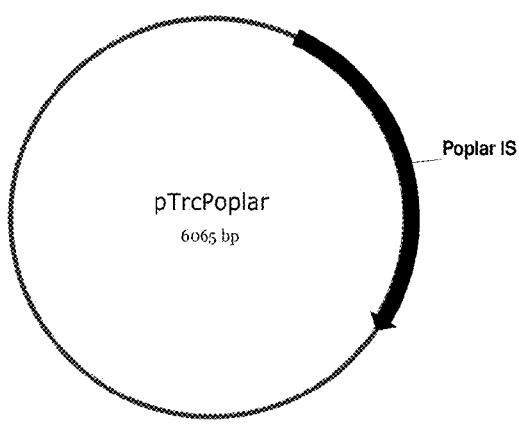
FIG. 32 is a map of pTrcPoplar.

Production of Isoprene in *E. Coli* Expressing Recombinant Poplar Isoprene Synthase The protein sequence for the poplar (*Populus alba*×*Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33), was verified by sequencing.

Example 2B

Demonstration of Isoprene Synthase Activity from Several *Populus* Isoprene Synthases The following isoprene synthases were examined; *Populus alba* (Accession number BAD98243; FIGS. 137A and B; SEQ ID NO:109), *Populus nigra* (Accession number CAL69918; FIGS. 137C and D; SEQ ID NO:110), *Populus tremuloides* (Accession number AAQ16588; FIGS. 137 E, F, and G; SEQ ID NO:123), *Populus trichocarpa* (Accession number ACD70404; FIGS. 137H and I; SEQ ID NO:111), *Populus alba*×*Populus tremula* (Accession number CAJ29303; FIGS. 137J and K; SEQ ID NO:112), and MCM112-Kudzu.

pET24Kudzu (also referred to as MCM112) was constructed as follows: the kudzu isoprene synthase gene was subcloned into the pET24d vector (Novagen) from the pCR2.1 vector (Invitrogen). The kudzu IspS gene was amplified from pTrcKudzu template DNA using primers MCM50 5'-GATCATGCAT TCGCCCTTAG GAGGTAAAAAAA-CATGTGTGCGACCTCTTC TCAATTTACT (SEQ ID NO:31); and MCM53 5'-CGGTCGACGGATCCCTGCAG TTAGACATAC ATCAGCTG (SEQ ID NO:32). PCR reactions were carried out using Taq DNA Polymerase (Invitrogen), and the resulting PCR product was cloned into pCR2.1-TOPO TA cloning vector (Invitrogen), and transformed into *E. coli* Top10 chemically competent cells (Invitrogen). Transformants were plated on L-agar containing carbenicillin (50 μg/ml) and incubated overnight at 37° C. Five ml Luria Broth cultures containing carbenicillin 50 μg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu IspS coding sequence in a pCR2.1 backbone (FIG. 137L). The sequence of MCM93 (SEQ ID NO:113) is shown in FIGS. 137M and N.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu IspS fragment was ligated to the NcoI/BamH1 digested pET24d using the Rapid DNA Ligation Kit (Roche) at a 5:1 fragment to vector ratio in a total volume of 20 μl. A portion of the ligation mixture (5 μl) was transformed into *E. coli* Top 10 chemically competent cells and plated on L agar containing kanamycin (50 μg/ml). The correct transformant was confirmed by sequencing and transformed into chemically competent BL21(λDE3)pLysS cells (Novagen). A single colony was selected after overnight growth at 37° C. on L agar containing kanamycin (50 μg/ml). A map of the resulting plasmid designated as pET24D-Kudzu is shown in FIG. 137O. The sequence of pET24D-Kudzu (SEQ ID NO:114) is shown in FIGS. 137P and Q.

*Escherichia coli* optimized isoprene synthase genes cloned into the pET24a expression vector (Novagen) were purchased from DNA2.0 (Menlo Park, Calif.) for *Populus tremuloides, Populus alba, Populus nigra* and *Populus trichocarpa*. Genes were synthesized with the chloroplast transit peptide sequence removed, resulting in expression of mature proteins.

The construct for the Kudzu isoprene synthase was used as control in this example. The plasmids were transformed into the *E. coli* expression host BL21(DE3)plysS and transformants were grown in 0.6 ml TM3 medium. The recipe for TM3 medium is as follows: $K_2HPO_4$ (13.6 g/l) $KH_2PO_4$ (13.6 g/l), $MgSO_4*7H_2O$ (2 g/L) Citric Acid Monohydrate (2 g/L) Ferric Ammonium Citrate (0.3 g/L) $(NH_4)_2SO_4$ (3.2 g/L) yeast extract (0.2 g/L) 1 ml of 1000× Trace Elements solution, pH adjusted to 6.8 with ammonium hydroxide qs to volume with sterile DI $H_2O$ and filter sterilized with a 0.22 micron filter. The recipe for 1000× Trace Elements solution is as follows: Citric Acids*$H_2O$ (40 g/L), $MnSO_4*H_2O$ (30 g/L), NaCl (10 g/L), $FeSO_4*7H_2O$ (1 g/L), $CoCl_2*6H_2O$ (1 g/L), $ZnSO_4*7H_2O$ (1 g/L), $CuSO_4*5H_2O$ (100 mg/L), $H_3BO_3$ (100 mg/L), $NaMoO_4*2H_2O$ (100 mg/L). Each component was dissolved one at a time in DI $H_2O$, pH adjusted to 3.0 with HCl/NaOH, qs to volume and filter sterilized with a 0.22 micron filter.

The cultures were induced with 400 uM IPTG and growth was continued to $OD_{600}$ of about 5. Aliquots of culture were transferred to a deep well glass plate and wells were sealed with aluminum plate sealer. The plate was incubated at 25° C. for 30 minutes with shaking at 450 rpm. The reactions were heat inactivated by raising the temperature to 70° C. for 5 minutes. Whole cell head space was measured by the GCMS method as described in Example 1, Part II.

$K_m$ values were obtained from cultures grown in similar manner but cells were harvested and lysed by a freeze/thaw lysozyme protocol. A volume of 400 μL of culture was transferred into a new 96-well plate (Perkin Elmer, Catalog No. 6008290) and cells were harvested by centrifugation in a Beckman Coulter Allegra 6R centrifuge at 2500×g. The pellet was resuspended in 200 mL of hypotonic buffer (5 mM $MgCL_2$, 5 mM Tris HCl, 5 mM DTT pH 8.0) and the plate was frozen at −80° C. for a minimum time of 60 minutes. Cell lysate was prepared by thawing the plate and adding 32 mL of isoprene synthase DMAPP assay buffer (57 mM Tris HCl, 19 mM $MgCl_2$, 74 mg/mL DNase I (Sigma Catalog No. DN-25), $2.63×10^5$ U/mL of ReadyLyse lysozyme solution (Epicentre Catalog No. R1802M), and 5 mg/mL of molecular biology grade BSA. The plate was incubated with shaking at 25° C. for 30 minutes and then placed on ice. DMAPP and lysate were added at desired concentration in a sealed deep well glass block for the whole cell head space assay described above. The reactions were allowed to proceed for 1 hour and then terminated by the heat step described above and head space activity was measured also as described.

In an alternate approach, the activity of the enzymes was measured from cells cultured in 25 mL volume and induced similarly as described above. Cells were harvested by centrifugation and the pellets were lysed by French pressing in buffer consisting of 50% glycerol mixed 1:1 with 20 mM Tris/HCl pH 7.4, 20 mM $MgCl_2$, 200 mM KCl, 1 mM DTT. A lysate volume of 25 uL was assayed for isoprene synthase activity in 2 mL screw cap vials containing 75 uL of assay buffer (66.6 mM Tris/HCl pH 8, 6.66 mM DMAPP, 43 mM, $MgCl_2$). The reaction was incubated for 15 minutes at 30° C. and was quenched by the addition of 100 uL of 250 mM EDTA through the septum of the vial. Isoprene was measured by GC/MS as described in Example 1, Part II.

All methods for the determination of activity showed that the poplar enzyme derived from the pure bred poplars were several-fold higher than the *Populus [alba×tremula]*. FIGS. 138 and 139 showed these results for the whole cell head space assay and the DMAPP assay, respectively, and surprisingly indicate that enzymes from *P. nigra, P. tremuloides, P. trichocarpa,* and *P. alba* all had significantly higher activity than hybrid *[P. alba×P. tremula]*.

The DMAPP assay was performed as follows: a volume of 400 μL of culture was transferred into a new 96-well plate (Perkin Elmer, Catalog No. 6008290) and cells were harvested by centrifugation in a Beckman Coulter Allegra 6R centrifuge at 2500×g. The pellet was resuspended in 200 mL of hypotonic buffer (5 mM $MgCL_2$, 5 mM Tris HCl, 5 mM DTT pH 8.0) and the plate was frozen at −80° C. for a minimum time of 60 minutes. Cell lysate was prepared by thawing the plate and adding 32 mL of isoprene synthase DMAPP assay buffer (57 mM Tris HCl, 19 mM $MgCl_2$, 74 mg/mL DNase I (Sigma Catalog No. DN-25), $2.63×10^5$ U/mL of ReadyLyse lysozyme solution (Epicentre Catalog No. R1802M), and 5 mg/mL of molecular biology grade BSA. The plate was incubated with shaking at 25° C. for 30 minutes and then placed on ice. For isoprene production an 80 mL aliquot of lysate was transferred to a 96-deep well glass plate (Zinsser Catalog No. 3600600) and 20 mL of a 10 mM DMAPP solution in 100 mM $KHPO_4$, pH 8.2 (Cayman Chemical Catalog No. 63180) was added. The plate was sealed with an aluminum plate seal (Beckman Coulter Catalog No. 538619) and incubated with shaking at 30° C. for 60 minutes. The enzymatic reactions were terminated by heating the glass block (70° C. for 5 minutes). The cell head space of each well was quantitatively analyzed as described in Example 1, Part II.

Notably, *P. alba, P. tremuloides, P. trichocarpa* had higher activity than the isoprene synthase from Kudzu. The enzyme from *P. alba* was expressed with the greatest activity of all enzymes tested. The higher activities observed with the cell lysate compared to the whole cell head space assay was likely due to limitations in DMAPP, the substrate for these enzymes, delivered by the endogenous deoxyxylulose 5-phosphate (DXP) pathway of the cell.

$K_m$ kinetic parameter was measured to be about 2 to 3 mM for all enzymes for which the value was determined.

Example 3

Figure 10A:
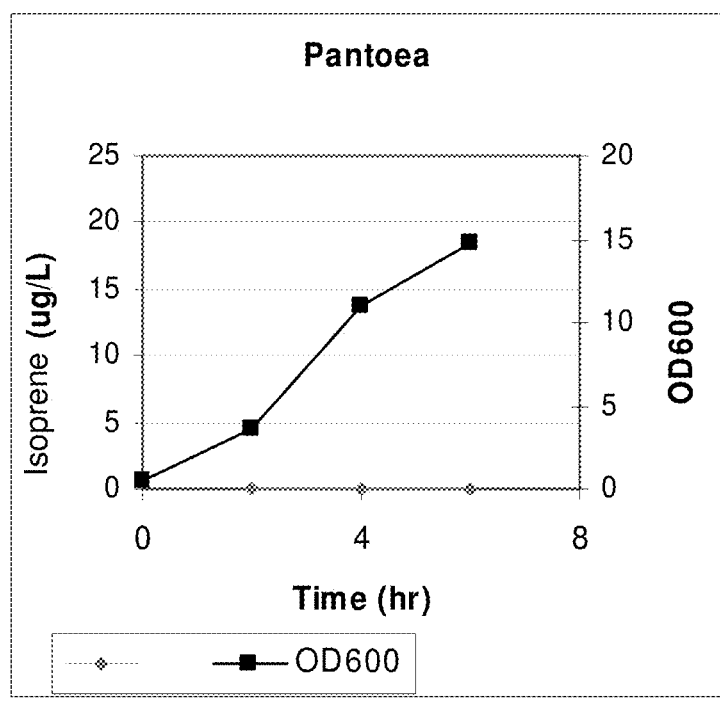
FIG. 10A is a graph showing the production of isoprene in *Pantoea citrea*. Control cells without recombinant kudzu isoprene synthase. Grey diamonds represent isoprene synthesis, black squares represent $OD_{600}$.
Figure 10B:
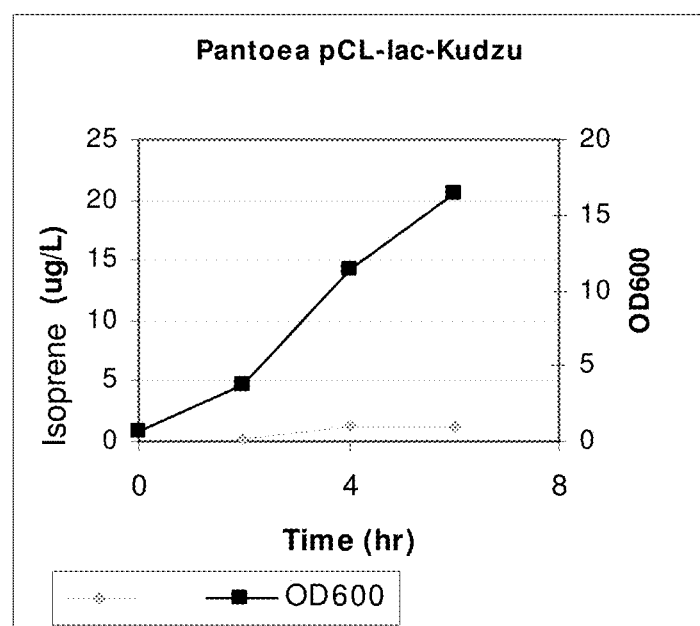
FIG. 10B is a graph showing the production of isoprene in *Pantoea citrea* expressing pCL-lac Kudzu. Grey diamonds represent isoprene synthesis, black squares represent $OD_{600}$.
Figure 10C:
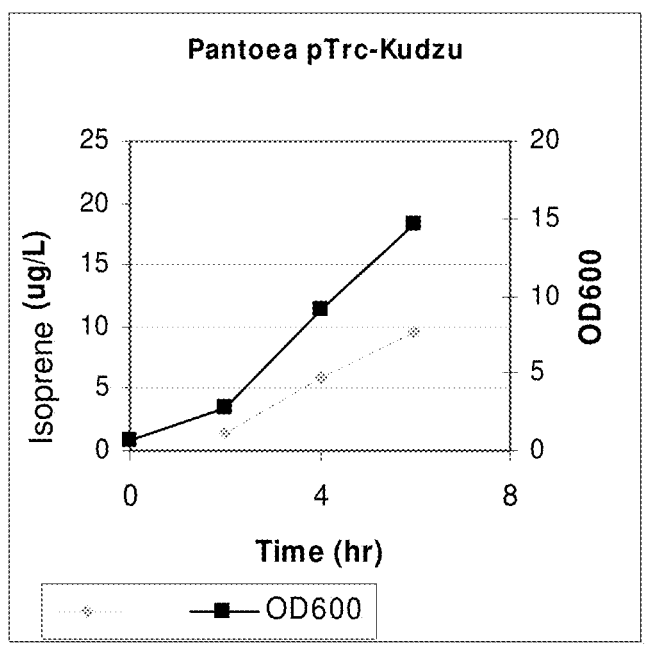
FIG. 10C is a graph showing the production of isoprene in *Pantoea citrea* expressing pTrcKudzu. Grey diamonds represent isoprene synthesis, black squares represent $OD_{600}$.

Production of Isoprene in *Pantoea citrea* Expressing Recombinant Kudzu Isoprene Synthase The pTrcKudzu and pCL-lac Kudzu plasmids described in Example 1 were electroporated into *P. citrea* (U.S. Pat. No. 7,241,587). Transformants were selected on LA containing carbenicillin (200 μg/ml) or spectinomycin (50 μg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4

Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis*.

a) Amplification of the aprE Promoter

The aprE promoter was amplified from chromosomal DNA from *Bacillus subtilis* using the following primers:

```
CF 797 (+) Start aprE promoter MfeI
                                (SEQ ID NO: 58)
5'-GACATCAATTGCTCCATTTTCTTCTGCTATC CF 07-43 (-) Fuse aprE promoter to Kudzu ispS
                                (SEQ ID NO: 59)
5'-ATTGAGAAGAGGTCGCACACACTCTTTACCCTCTCCTTTTA
``` b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+) Fuse the aprE promoter to
kudzu isoprene synthase gene (GTG start codon)
                                (SEQ ID NO: 60)
5'-TAAAAGGAGAGGGTAAAGAGTGTGTGCGACCTCTTCTCAAT CF 07-45 (-) Fuse the 3' end of kudzu
isoprene synthase gene to the terminator
                                (SEQ ID NO: 61)
5'-CCAAGGCCGGTTTTTTTTAGACATACATCAGCTGGTTAATC
``` c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu
isoprene synthase to the terminator
                                (SEQ ID NO: 62)
5'-GATTAACCAGCTGATGTATGTCTAAAAAAAACCGGCCTTGG CF 07-46 (-) End of B. amyliquefaciens
terminator (BamHI)
                                (SEQ ID NO: 63)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                    (SEQ ID NO: 60)
5'-TAAAAGGAGAGGGTAAAGAGTGTGTGCGACCTCTTCTCAAT CF 07-46 (-) End of B. amyliquefaciens
terminator (BamHI)
                                    (SEQ ID NO: 63)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                    (SEQ ID NO: 64)
5'-GACATCAATTGCTCCATTTTCTTCTGCTATC CF 07-46 (-) End of B. amyliquefaciens
terminator (BamHI)
                                    (SEQ ID NO: 63)
5'-GACATGACGGATCCGATTACGAATGCCGTCTC
```

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA+50 carbenicillin plates. A total of six colonies were chosen and grown overnight in LB+50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                    (SEQ ID NO: 65)
5'-GACATGAATTCCTCCATTTTCTTCTGC CF 847 (+) Sequence in pXX 049
(end of aprE promoter)
                                    (SEQ ID NO: 66)
5'-AGGAGAGGGTAAAGAGTGAG CF 07-45 (-) Fuse the 3' end of kudzu
isoprene synthase to the terminator
                                    (SEQ ID NO: 61)
5'-CCAAGGCCGGTTTTTTTTAGACATACATCAGCTGGTTAATC CF 07-48 (+) Sequencing primer for kudzu
isoprene synthase
                                    (SEQ ID NO: 67)
5'-CTTTTCCATCACCCACCTGAAG CF 07-49 (+) Sequencing in kudzu
isoprene synthase
                                    (SEQ ID NO: 68)
5'-GGCGAAATGGTCCAACAACAAAATTATC
```

Figure 52:
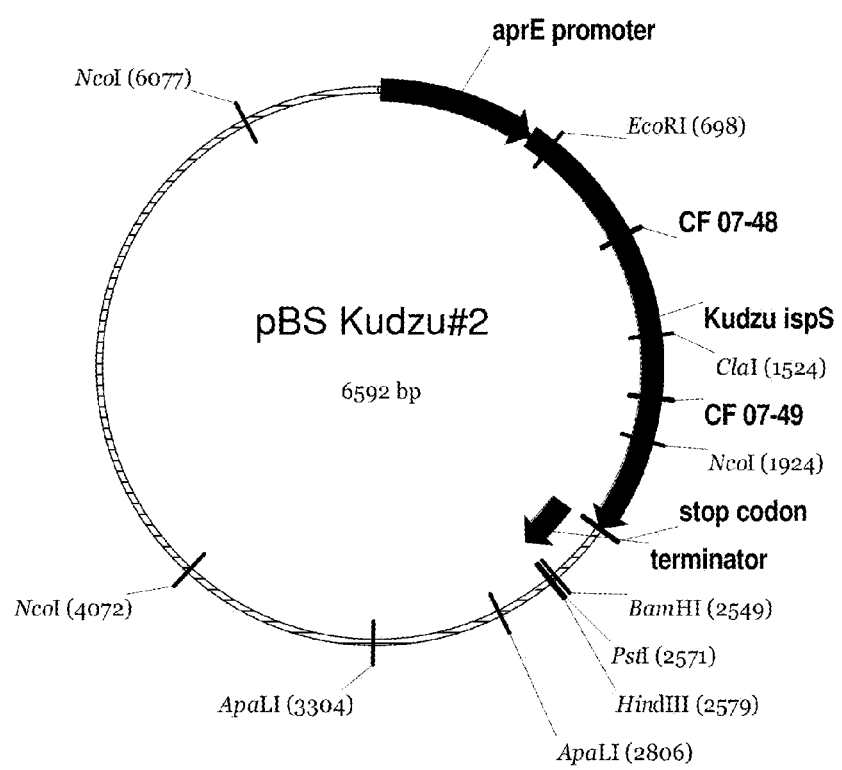
FIG. 52 is a map of pBS Kudzu #2.

The plasmid designated pBS Kudzu #2 (FIGS. 52 and 12) was correct by sequencing and was transformed into BG 3594 comK, a *Bacillus subtilis* host strain. Selection was done on LA+5 chloramphenicol plates. A transformant was chosen and struck to single colonies on LA+5 chloramphenicol, then grown in LB+5 chloramphenicol until it reached an $OD_{600}$ of 1.5. It was stored frozen in a vial at −80° C. in the presence of glycerol. The resulting strain was designated CF 443.

Figure 11:
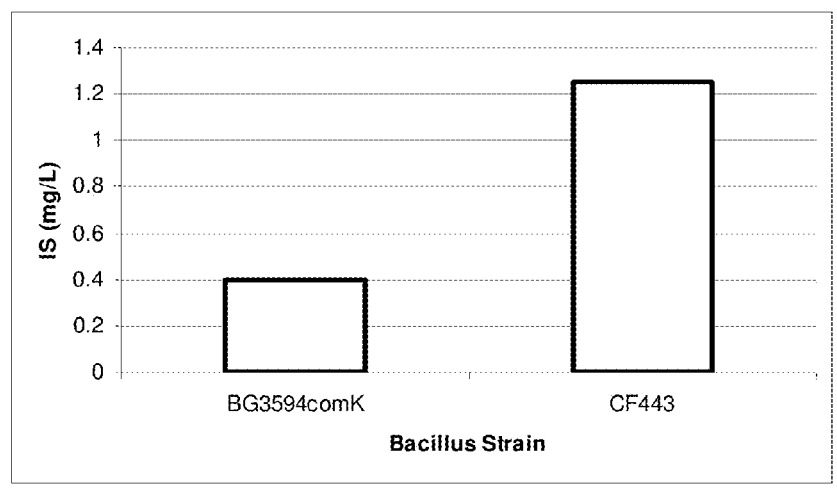
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. subtilis* Cells Expressing Recombinant Isoprene Synthase Overnight cultures were inoculated with a single colony of CF 443 from a LA+Chloramphenicol (Cm, 25 μg/ml). Cultures were grown in LB+Cm at 37° C. with shaking at 200 rpm. These overnight cultures (1 ml) were used to inoculate 250 ml baffled shake flasks containing 25 ml Grants II media and chloramphenicol at a final concentration of 25 μg/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2*2H_2O$, 0.4 g $FeSO_4*7H_2O$, 0.1 g $MnSO_4*H_2O$, 0.1 g $ZnSO_4*H_2O$, 0.05 g $CuCl_2*2H_2O$, 0.1 g $CoCl_2*6H_2O$, 0.1 g $Na_2MoO_4*2H_2O$, q.s. to 1 L with $H_2O$, Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Figure 53A:
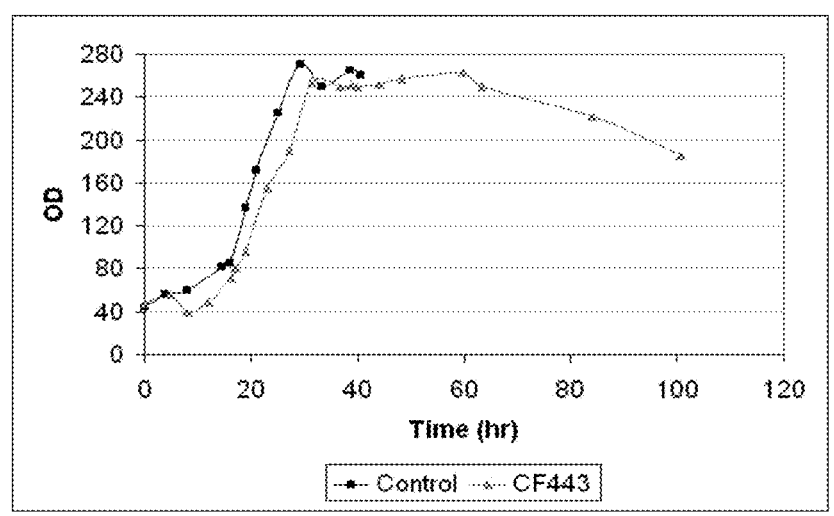
FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 53B:
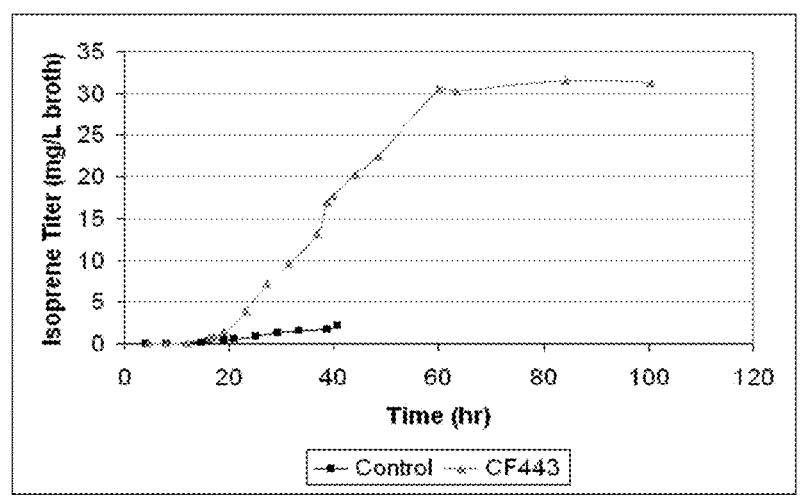
FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO %, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. subtilis*.

The kudzu isoprene synthase gene was cloned in an integrating plasmid (pJH101-cmpR) under the control of the aprE promoter. Under the conditions tested, no isoprene was detected.

Example 5

Production of Isoprene in *Trichoderma*

I. Construction of Vectors for Expression of the Kudzu Isoprene Synthase in *Trichoderma reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 pJ plasmid template (20 ng/ul), 1 μl Primer EL-945 (10 uM) 5'-GCTTATGGATCCTCTAGACTATTA-CACGTACATCAATTGG (SEQ ID NO:9), 1 μl Primer EL-965 (10 uM) 5'-CACCATGTGTGCAACCTCCTC-CCAGTTTAC (SEQ ID NO:10), 1 μl dNTP (10 mM), 5 μl 10×PfuUltra II Fusion HS DNA Polymerase Buffer, 1 μl PfuUltra II Fusion HS DNA Polymerase, 40 μl water in a total reaction volume of 50 μl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 μl PCR reaction, 1 μl Salt solution, 1 μl TOPO pENTR/D-TOPO vector and 3 μl water in a total reaction volume of 6 μl. The reaction was incubated at room temperature for 5 minutes. One microliter of TOPO reaction was transformed into TOP10 chemically competent *E. coli* cells. The transformants were selected on LA+50 μg/ml kanamycin plates. Several colonies were picked and each was inoculated into a 5 ml tube containing LB+50 μg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 μl *Y. lipolytica* codon-optimized kudzu isoprene synthase gene pENTR/D-TOPO donor vector, 1 μl pTrex3g destination vector, 6 μl TE buffer, pH 8.0 in a total reaction volume of 8 μl. The reaction was incubated at room temperature for 1 hour and then 1 μl proteinase K solution was added and the incubation continued at 37° C. for 10 minutes. Then 1 μl of reaction was transformed into TOP10 chemically competent *E. coli* cells. The transformants were selected on LA+50 μg/ml carbenicillin plates. Several colonies were picked and each was inoculated into a 5 ml tube containing LB+50 μg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
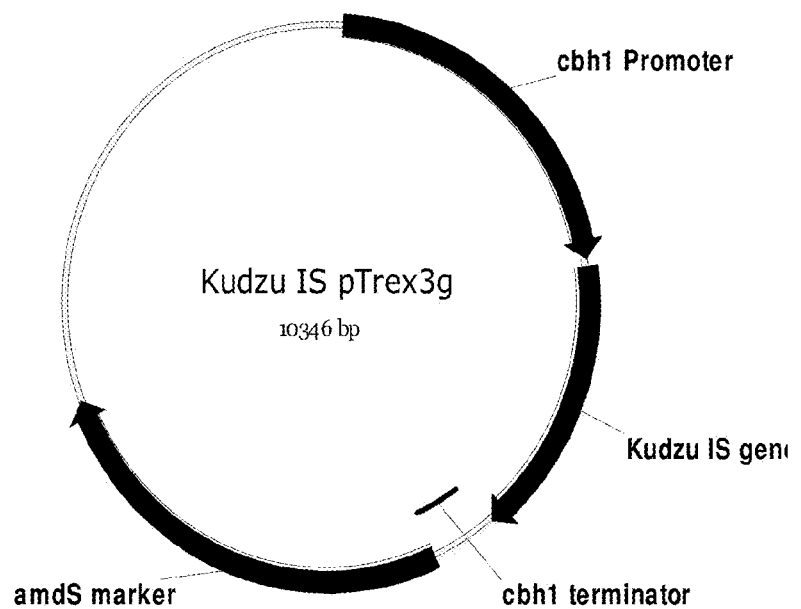
FIG. 14 is a map of pTrex3g comprising a kudzu isoprene synthase gene codon-optimized for expression in *Yarrowia*.

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 μg/L for the 14 hour incubation. The untransformed control showed no detectable levels of isoprene. This experiment shows that *T. reesei* is capable of producing isoprene from endogenous precursor when supplied with an exogenous isoprene synthase.

Example 6

Production of Isoprene in *Yarrowia*

I. Construction of Vectors for Expression of the Kudzu Isoprene Synthase in *Yarrowia lipolytica*.

The starting point for the construction of vectors for the expression of the kudzu isoprene synthase gene in *Yarrowia lipolytica* was the vector pSPZ1(MAP29Spb). The complete sequence of this vector (SEQ ID No:11) is shown in FIG. 15.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

```
ICL1 3
                                       (SEQ ID NO: 69)
5'-GGTGAATTCAGTCTACTGGGGATTCCCAAATCTATATATACTGCAGG

TGAC

ICL1 5
                                       (SEQ ID NO: 70)
5'-GCAGGTGGGAAACTATGCACTCC

XPR 3
                                       (SEQ ID NO: 71)
5'-CCTGAATTCTGTTGGATTGGAGGATTGGATAGTGGG

XPR 5
                                       (SEQ ID NO: 72)
5'-GGTGTCGACGTACGGTCGAGCTTATTGACC

XPRT3
                                       (SEQ ID NO: 73)
5'-GGTGGGCCCGCATTTTGCCACCTACAAGCCAG

XPRT 5
                                       (SEQ ID NO: 74)
5'-GGTGAATTCTAGAGGATCCCAACGCTGTTGCCTACAACGG

Y18S3
                                       (SEQ ID NO: 75)
5'-GGTGCGGCCGCTGTCTGGACCTGGTGAGTTTCCCCG

Y18S 5
                                       (SEQ ID NO: 76)
5'-GGTGGGCCCATTAAATCAGTTATCGTTTATTTGATAG

YURA3
                                       (SEQ ID NO: 77)
5'-GGTGACCAGCAAGTCCATGGGTGGTTTGATCATGG

YURA 50
                                       (SEQ ID NO: 78)
5'-GGTGCGGCCGCCTTTGGAGTACGACTCCAACTATG

YURA 51
                                       (SEQ ID NO: 79)
5'-GCGGCCGCAGACTAAATTTATTTCAGTCTCC
```

For PCR amplification the PfuUltraII polymerase (Stratagene), supplier-provided buffer and dNTPs, 2.5 μM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
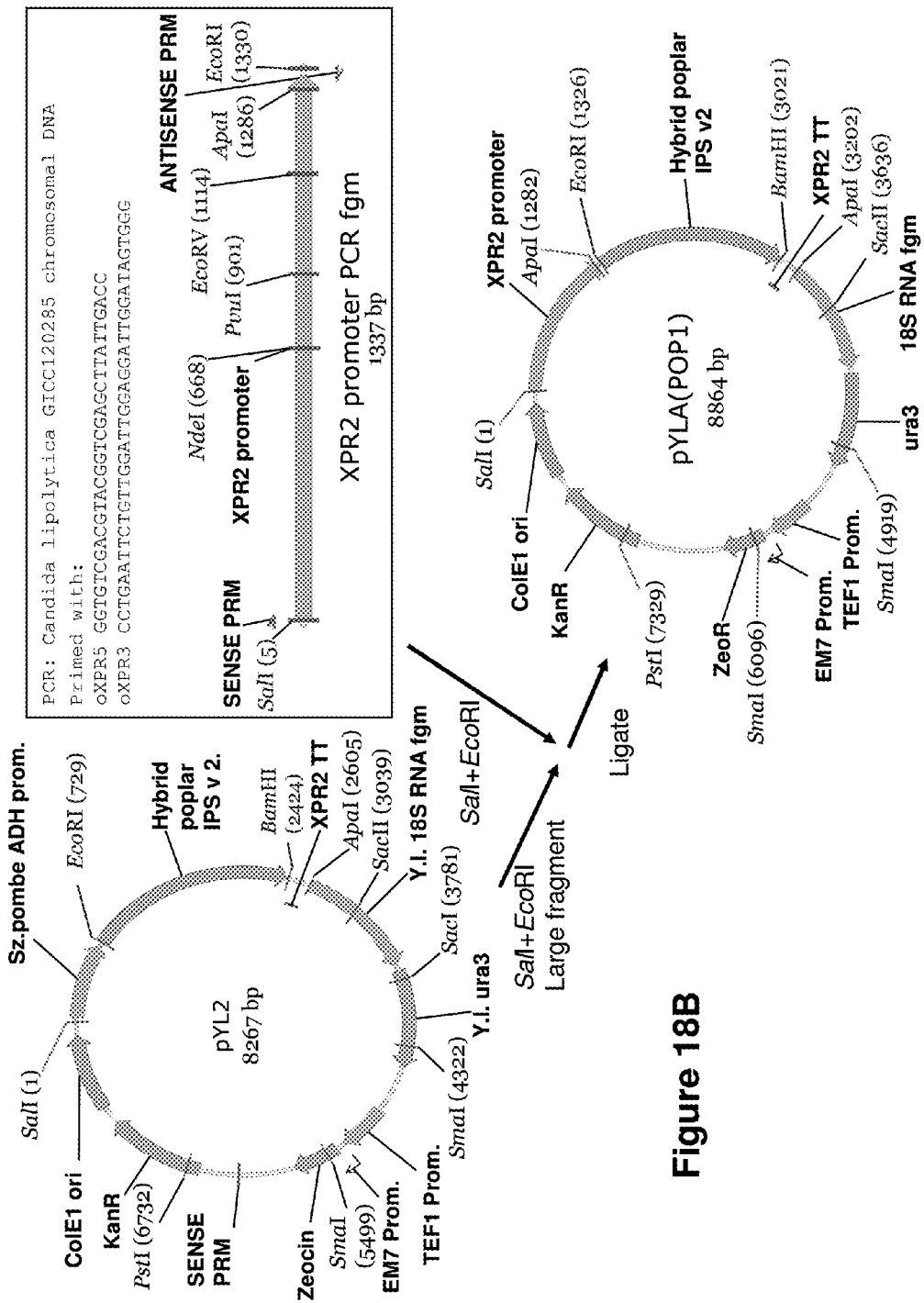
FIG. 18B shows a schematic outlining construction of the vector pYLA(POP1) (SEQ ID NO:72 and 73).
Figure 18C:
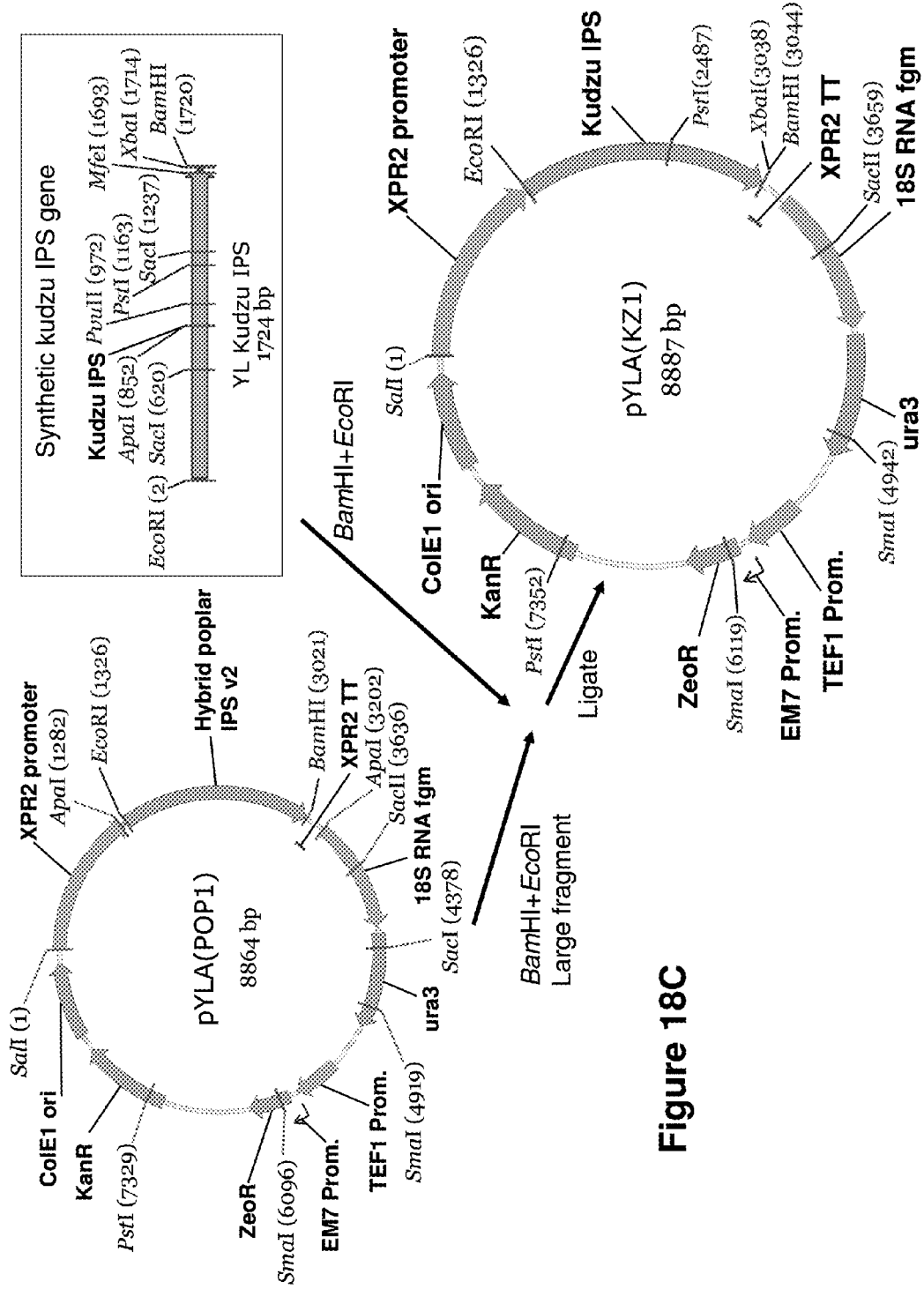
FIG. 18C shows a schematic outlining construction of the vector pYLA(KZ1) (SEQ ID NO:70 and 71).
Figure 18F:
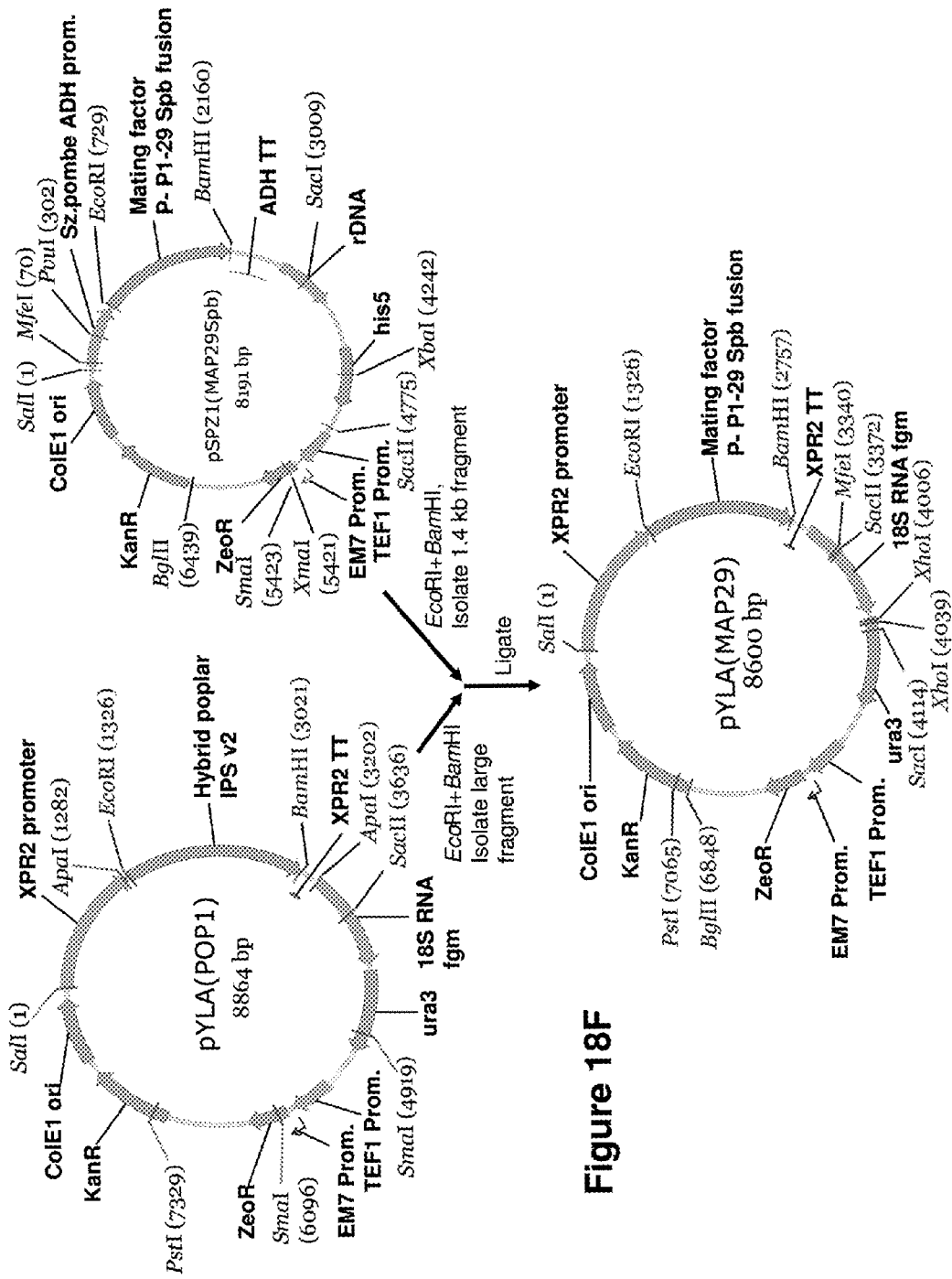
FIG. 18F shows a schematic outlining construction of the vector pYLA(MAP29).

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba×Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. lipolytica*.

Vectors pYLA(KZ1), pYLI(KZ1), pYLA(MAP29) and pYLI (MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred µl aliquots of the cell suspension were mixed with linearized plasmid DNA solution (10-20 µg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Figure 20A:
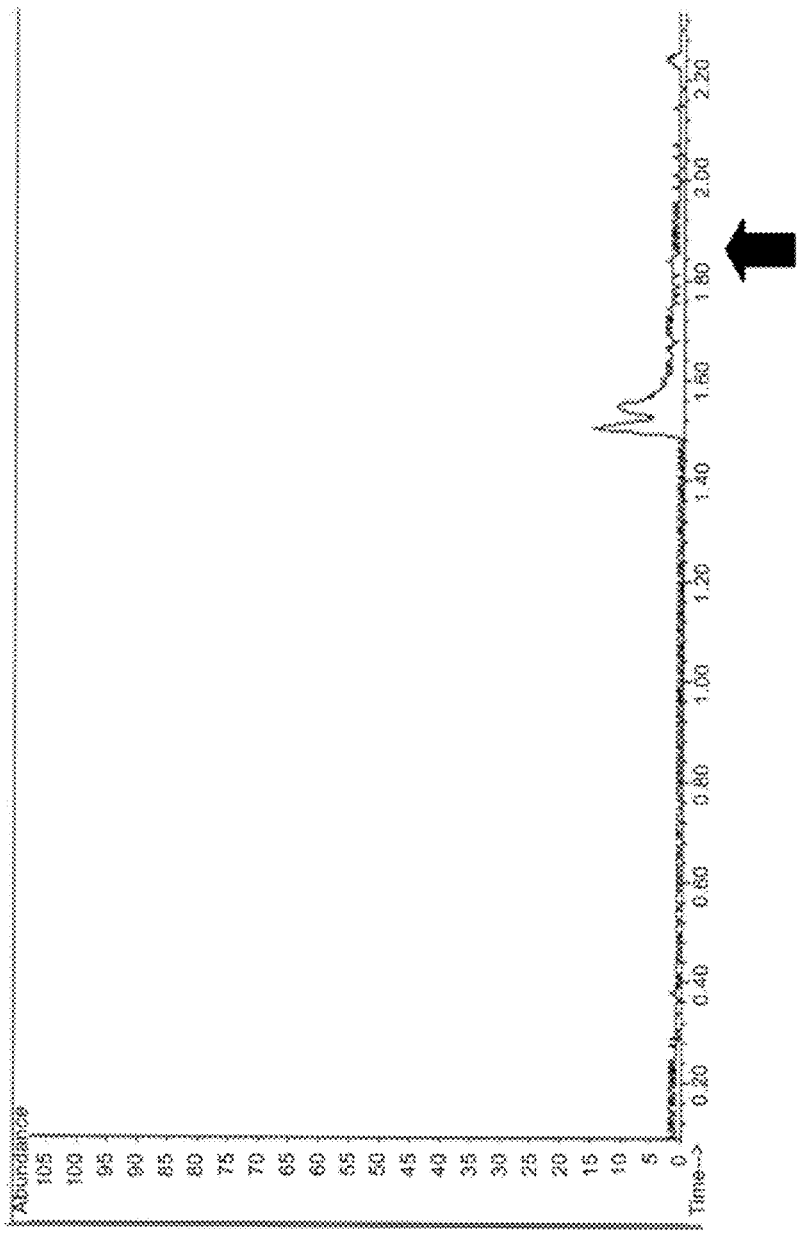
FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.
Figure 20B:
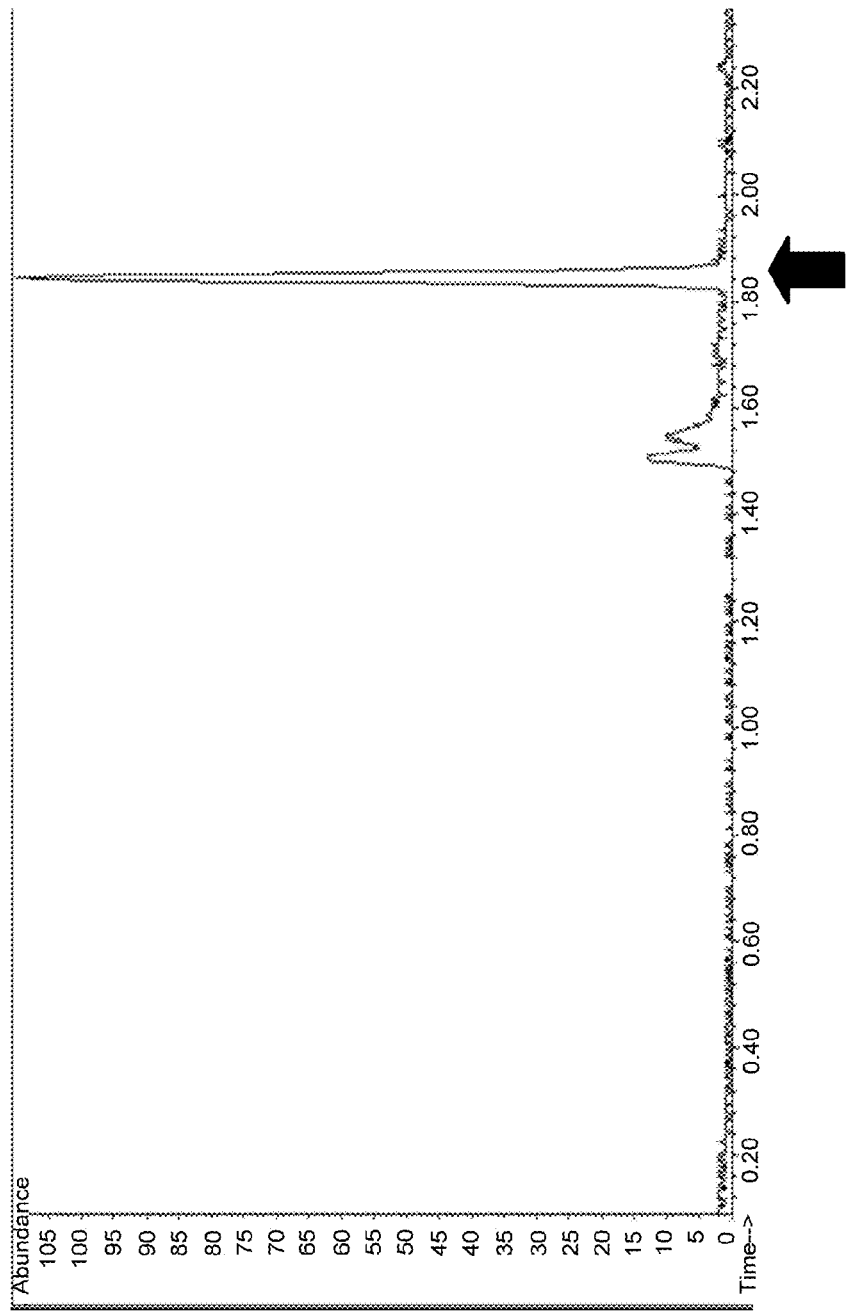

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 µg/L to 1 µg/L, FIG. 20). No isoprene was detected in the headspace of the control strains carrying phytase gene instead of an isoprene synthase gene.

Example 7

Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

Figure 34:
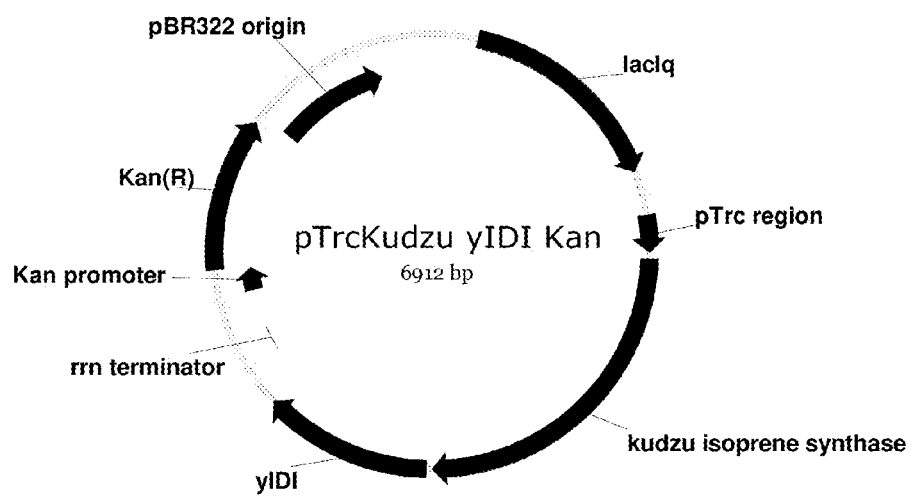
FIG. 34 is a map of pTrcKudzu yIDI Kan.

The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the kan$^r$ gene which had been PCR amplified from pCR-Blunt-II-TOPO using primers MCM22 5'-GATCAAGCTTAACCGGAATTGCCAGCTG (SEQ ID NO:14) and MCM23 5'-GATCCGATCGTCAGAAGAACTCGTCAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 µg/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATGCATCGCCCTTAGGAGGTAAAAAAAAATGAC (SEQ ID NO:16) and PstI-YIDI 1 R 5'-CCTTCTGCAGGACGCGTTGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 µg/ml kanamycin. Several transformants were isolated and sequenced and the resulting plasmid was called pTrcKudzu-yIDI(kan) (FIGS. 34 and 35).

iii) Construction of pTrcKudzu DXS Kan

Figure 21:
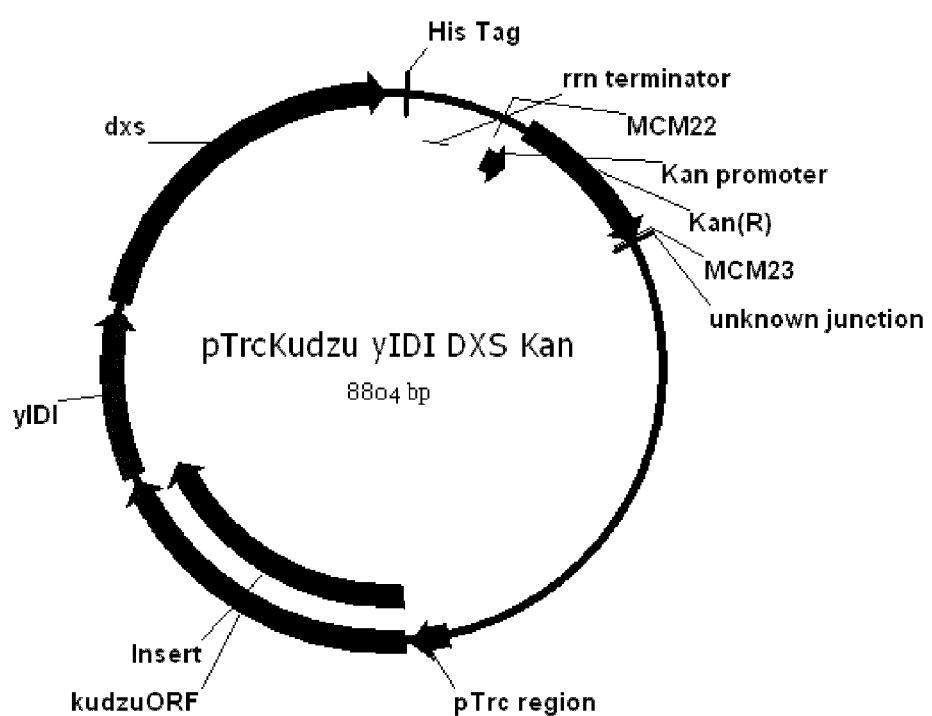
FIG. 21 is a map of pTrcKudzu yIDI DXS Kan.
Figure 36:
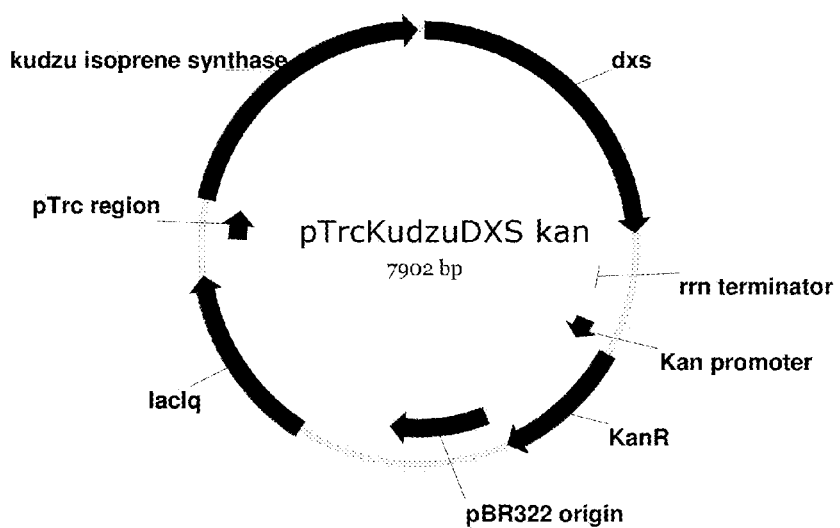
FIG. 36 is a map of pTrcKudzuDXS Kan.
Figure 38:
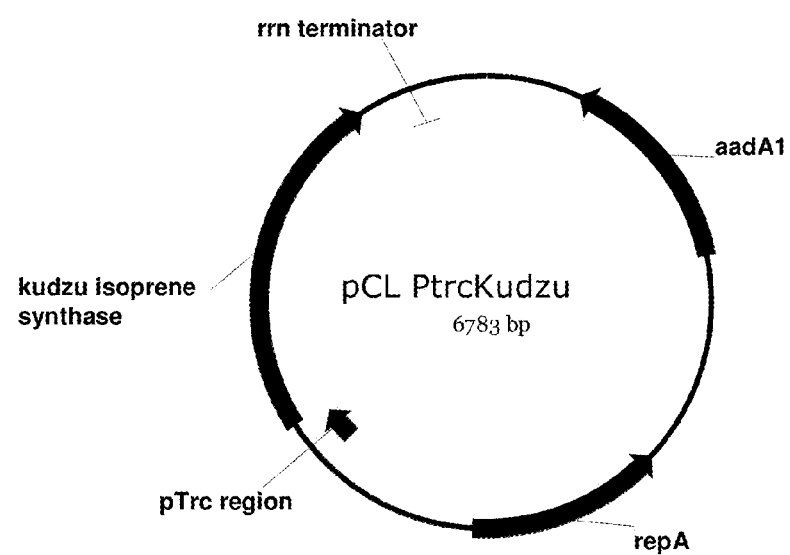
FIG. 38 is a map of pCL PtrcKudzu.
Figure 40:
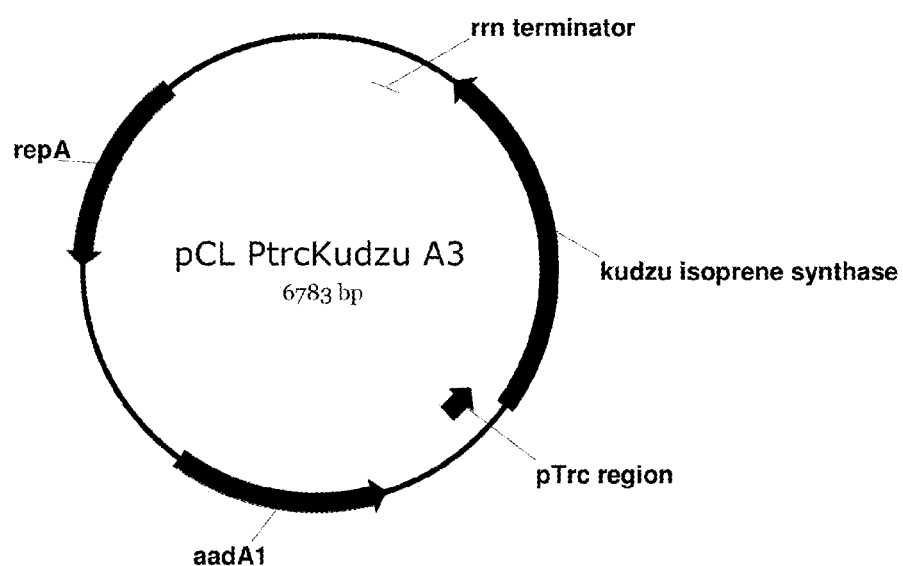
FIG. 40 is a map of pCL PtrcKudzu A3.

Plasmid pTrcKudzuKan was digested with PstI, treated with SAP, heat killed and gel purified. It was ligated to a PCR product encoding dxs from *E. coli* with a synthetic RBS. The primers for PCR were MCM13 5'-GATCATGCATTCGCCCTTAGGAGGTAAAAAAACATGAGTTTTGATATTGCCAAATACCC G (SEQ ID NO:18) and MCM14 5'-CATGCTGCAGTTATGCCAGCCAGGCCTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 µg/ml. Several transformants were isolated and sequenced and the resulting plasmid was called pTrcKudzu-DXS(kan) (FIGS. 36 and 37).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGGTAAAAAAACATGAGTTTTGATATTGCCAAATACCC G (SEQ ID NO:18) and MCM14 5'-CATGCTGCAGTTATGCCAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 µg/ml. Several clones were isolated and sequenced and two were selected. pCL PtrcKudzu and pCL PtrcKudzu (A3) have the insert in opposite orientations (FIGS. 38-41).

vi) Construction of pCL PtrcKudzu yIDI

Figure 42:
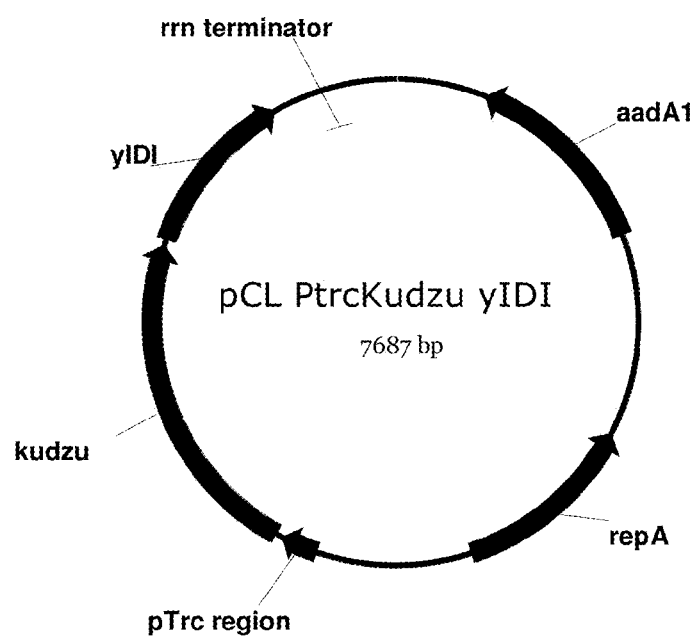
FIG. 42 is a map of pCL PtrcKudzu yIDI.

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu yIDI (FIGS. 42 and 43).

vii) Construction of pCL PtrcKudzu DXS

Figure 44:
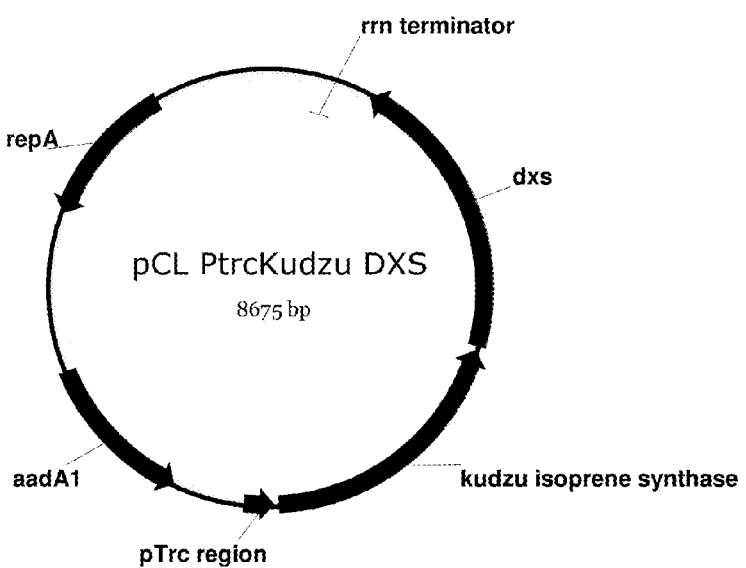
FIG. 44 is a map of pCL PtrcKudzu DXS.

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu DXS (FIGS. 44 and 45).

II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 µg/mL. Cultures of pCL PtrcKudzu (E), pCL PtrcKudzu, pCL PtrcKudzu-yIDI (F) and pCL PtrcKudzu-DXS (G) were grown in LB spectinomycin 50 µg/mL. Cultures were induced with 400 µM IPTG at time 0 ($OD_{600}$ approximately 0.5) and samples taken for isoprene headspace measurement (see Example 1). Results are shown in FIG. 23A-23G.

Figure 23A:
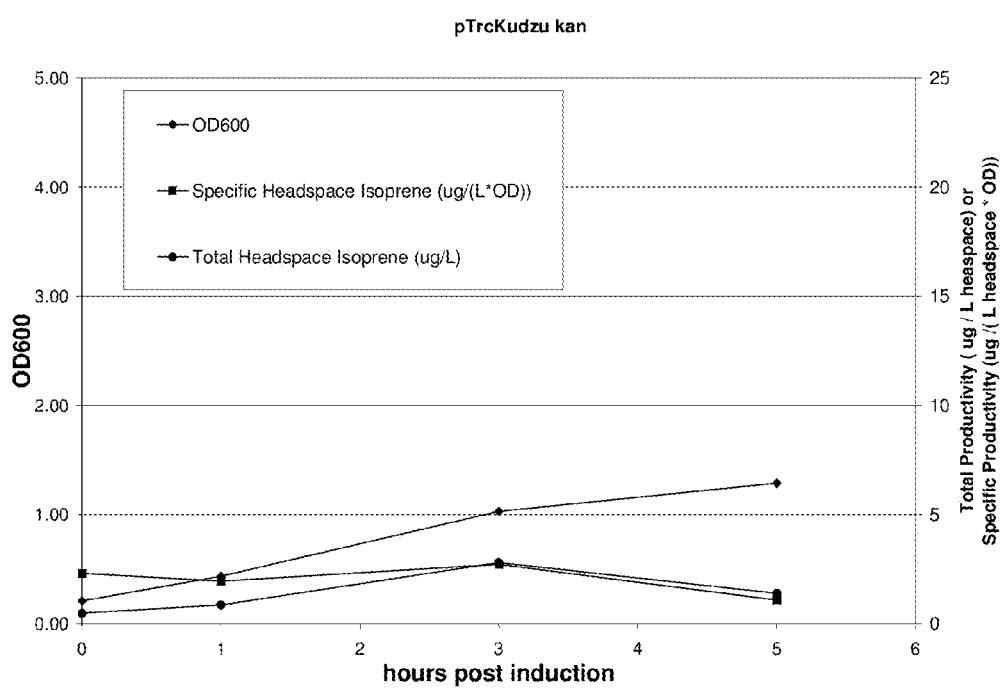
FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23B:
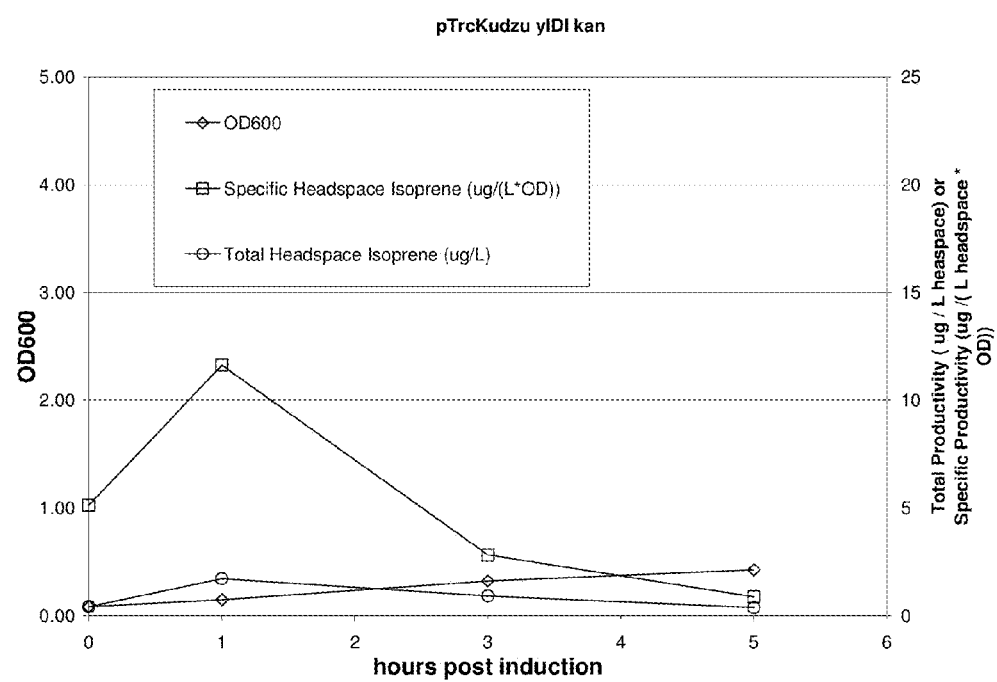
FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23C:
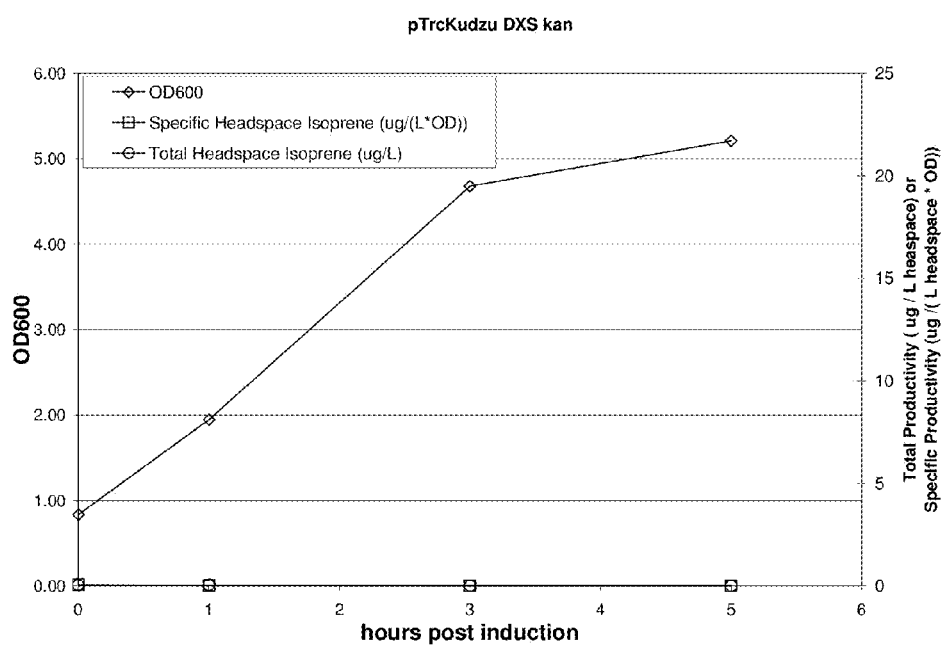
FIG. 23C is a graph showing production of isoprene from glucose in BL21/pTrcKudzu DXS kan. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23D:
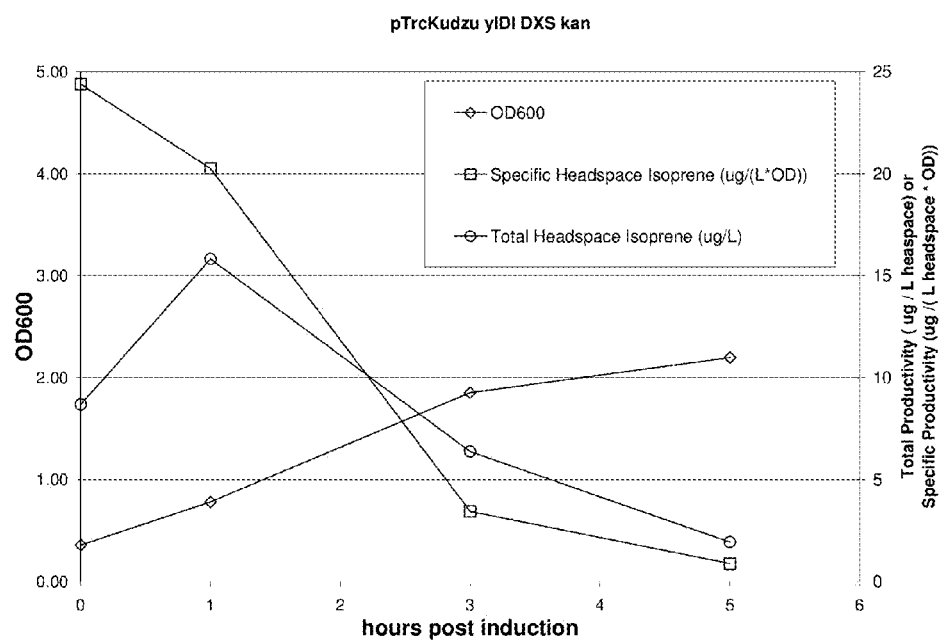
FIG. 23D is a graph showing production of isoprene from glucose in BL21/pTrcKudzu yIDI DXS kan. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23E:
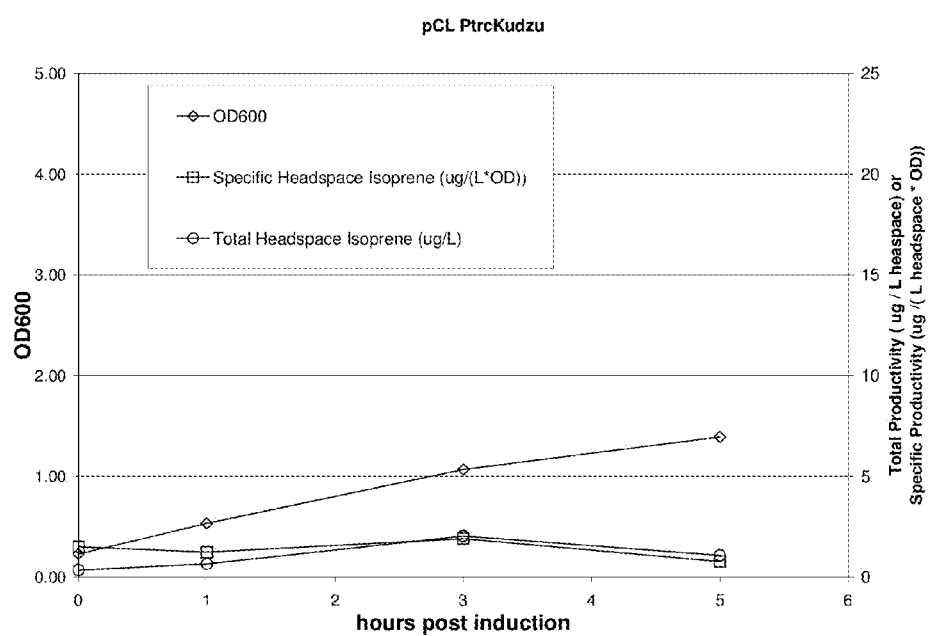
FIG. 23E is a graph showing production of isoprene from glucose in BL21/pCL PtrcKudzu. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23F:
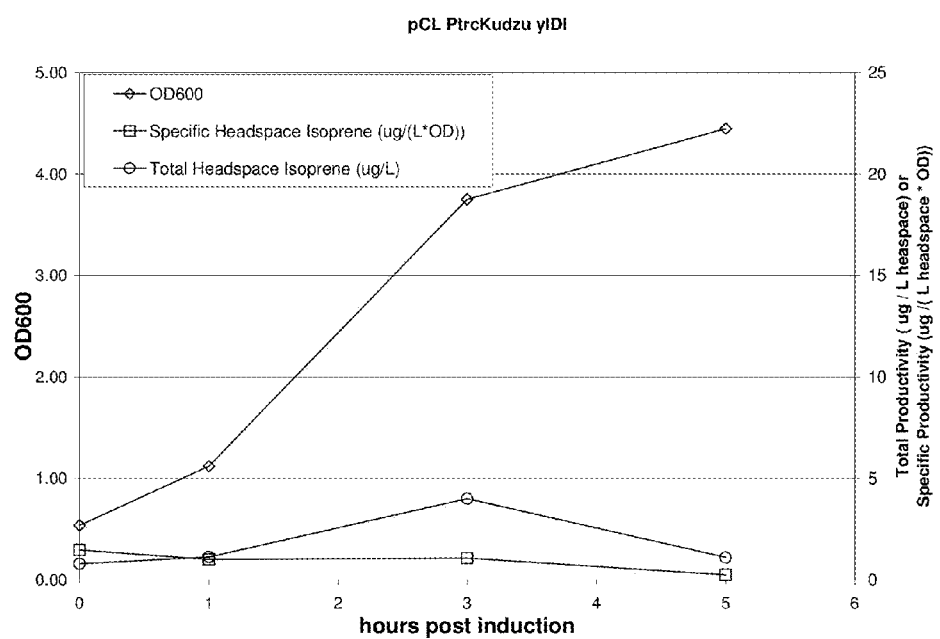
FIG. 23F is a graph showing production of isoprene from glucose in BL21/pCL PtrcKudzu yIDI. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23G:
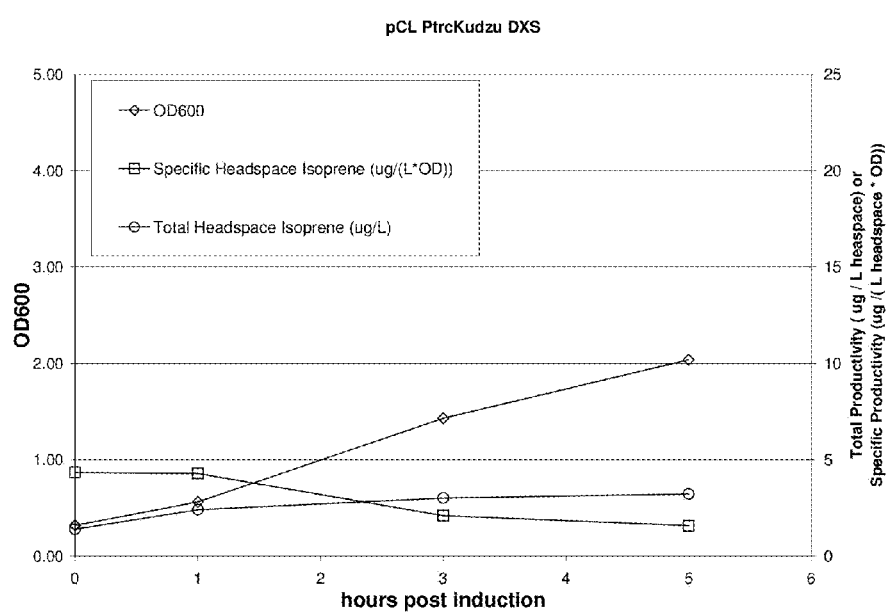
FIG. 23G is a graph showing production of isoprene from glucose in BL21/pCL PtrcKudzu DXS. Time 0 is the time of induction with IPTG (400 μmol). The x-axis is time after induction; the y-axis is OD$_{600}$ and the y2-axis is total productivity of isoprene (μg/L headspace or specific productivity (μg/L headspace/OD). Diamonds represent OD$_{600}$, circles represent total isoprene productivity (μg/L) and squares represent specific productivity of isoprene (μg/L/OD).
Figure 23H:
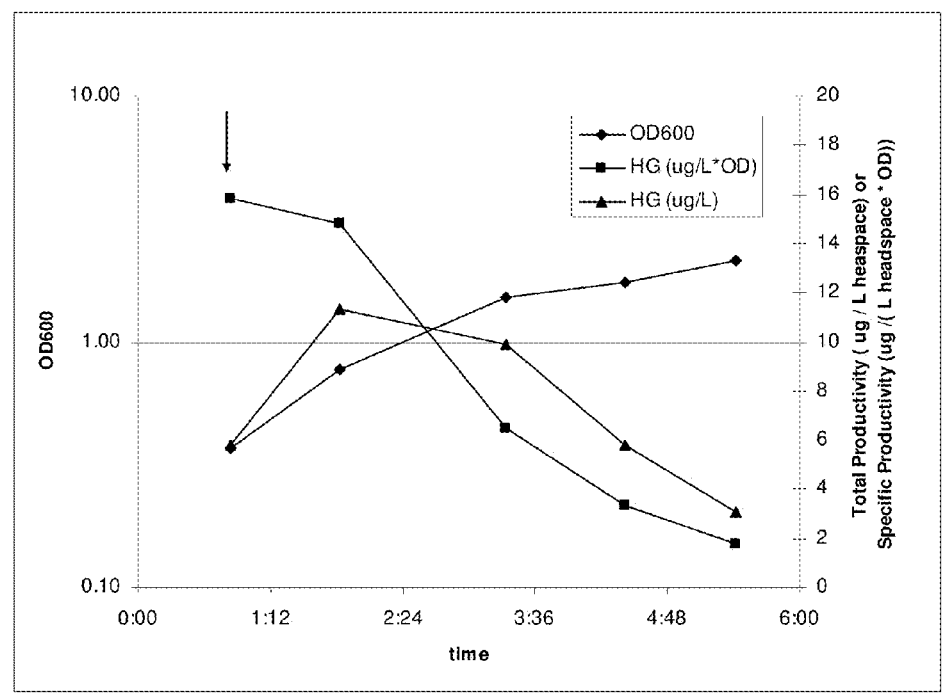
FIG. 23H is a graph showing production of isoprene from glucose in BL21/pTrcKudzuIDIDXSkan. The arrow indicates the time of induction with IPTG (400 μmol). The x-axis is time after inoculation; the y-axis is OD600 and the y2-axis is total productivity of isoprene (μg/L headspace or specific productivity (μg/L headspace/OD). Diamonds represent OD600, triangles represent total isoprene productivity (μg/L) and squares represent specific productivity of isoprene (μg/L/OD).

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 µg/ml) at 20° C. and used to inoculate shake flasks of TM3 (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 µM IPTG. Samples were taken at various times after induction and the amount of isoprene in the head space was measured as described in Example 1. Results are shown in FIG. 23H.

III. Production of Isoprene from Biomass in *E. coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L. and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 µg/ml). The culture was incubated overnight at 25° C. with shaking. The following day the overnight culture was diluted to an $OD_{600}$ of 0.05 in 25 ml of TM3+0.2% YE+1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. coli*/pTrcKudzuIDIDXS

A single colony from a plate freshly transformed cells of BL21 (λDE3)/pTrcKudzu yIDI DXS (kan) was used to inoculate 5 mL of LB+kanamycin (50 µg/ml). The culture was incubated overnight at 25° C. with shaking. The following day the overnight culture was diluted to an $OD_{600}$ of 0.05 in 25 ml of TM3+0.2% YE+1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 µg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. coli* Grown in Fed-Batch Culture Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000×

Modified Trace Metal Solution 1 ml. All of the components were added together and dissolved in diH$_2$O. This solution was autoclaved. The pH was adjusted to 7.0 with ammonium gas (NH$_3$) and q.s. to volume. Glucose 10 g, thiamine*HCl 0.1 g, and antibiotic were added after sterilization and pH adjustment.

1000× Modified Trace Metal Solution:

Citric Acids*H$_2$O 40 g, MnSO$_4$*H$_2$O 30 g, NaCl 10 g, FeSO$_4$*7H$_2$O 1 g, CoCl$_2$*6H$_2$O 1 g, ZnSO*7H$_2$O 1 g, CuSO$_4$*5H$_2$O 100 mg, H$_3$BO$_3$ 100 mg, NaMoO$_4$*2H$_2$O 100 mg. Each component is dissolved one at a time in DI H$_2$O, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
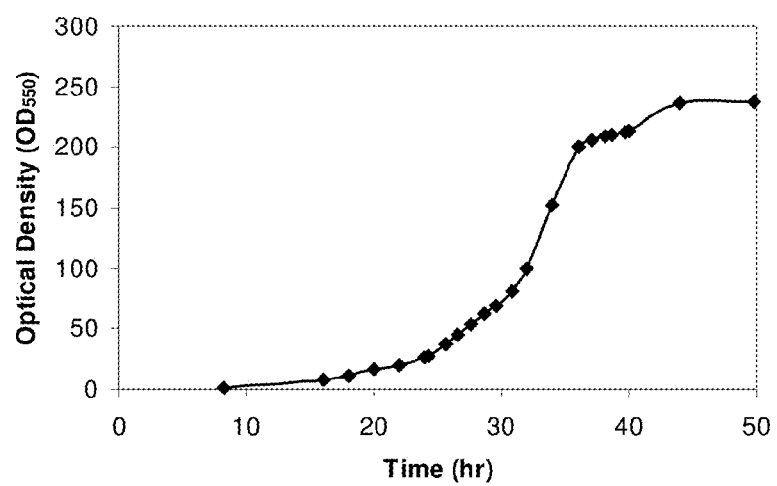
FIGS. 49A-C show graphs demonstrating isoprene production from a 500 L bioreactor with *E. coli* cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.
Figure 49B:
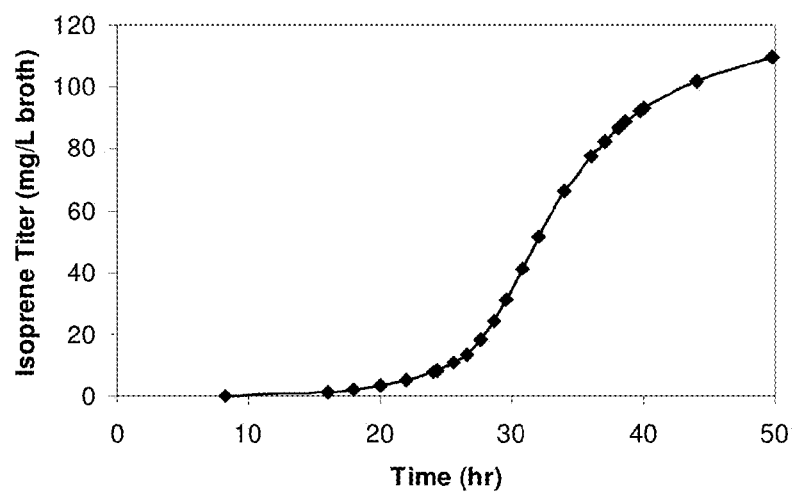
Figure 49C:
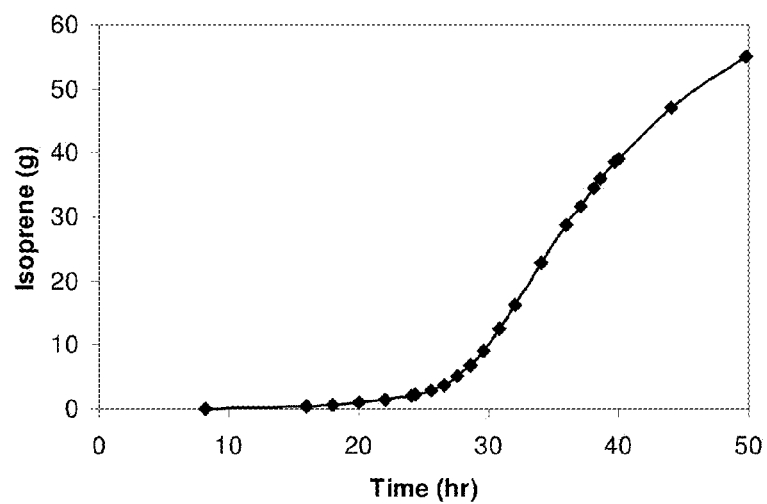

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 8

Production of Isoprene in *E. coli* Expressing Kudzu Isoprene Synthase and Recombinant Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonate decarboxylase (MVD) and isopentenyl diphosphate isomerase genes were amplified by PCR from *S. cerevisiae* chromosomal DNA and cloned individually into the pCR BluntII TOPO plasmid (Invitrogen). In some cases, the idi gene was amplified from *E. coli* chromosomal DNA. The primers were designed such that an *E. coli* consensus RBS (AGGAGGT (SEQ ID NO:80) or AAGGAGG (SEQ ID NO:81)) was inserted at the 5' end, 8 bp upstream of the start codon and a PstI site was added at the 3' end. The genes were then cloned one by one into the pTrcHis2B vector until the entire pathway was assembled.

Chromosomal DNA from *S. cerevisiae* S288C was obtained from ATCC (ATCC 204508D). The MVK gene was amplified from the chromosome of *S. cerevisiae* using primers MVKF (5'-AGGAGGTAAAAAAACATGTCATTAC-CGTTCTTAACTTCTGC, SEQ ID NO:21) and MVK-PstI-R (5'-ATGGCTGCAGGCCTATCGCAAATTAGCTTA TGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZer-oBLUNT TOPO. The resulting plasmid was designated pMVK1. The plasmid pMVK1 was digested with SacI and Taq1 restriction endonucleases and the fragment was gel purified and ligated into pTrcHis2B digested with SacI and BstBI. The resulting plasmid was named pTrcMVK1.

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCAC-CCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTG-GAATTCGCCCTTCTGCAGC, SEQ ID NO:25) and NsiI-MVD 1 F (5'-GTAGATGCATGCAGAATTCGCCCTTAAG-GAGG, SEQ ID NO:26) to amplify the MVD gene and PstI-YIDI 1 R (5'-CCTTCTGCAGGACGCGTTGTTATAGC, SEQ ID NO:27) and NsiI-YIDI 1 F (5'-CATCAATG-CATCGCCCTTAGGAGGTAAAAAAAAATGAC, SEQ ID NO:28) to amplify the yIDI gene. In some cases the IPP isomerase gene, idi from *E. coli* was used. To amplify idi from *E. coli* chromosomal DNA, the following primer set was used: PstI-CIDI 1 R (5'-GTGTGATGGATATCTGCAGAAT-TCG, SEQ ID NO:29) and NsiI-CIDI 1 F (5'-CATCAATG-CATCGCCCTTAGGAGGTAAAAAAACATG, SEQ ID NO:30). Template DNA was chromosomal DNA isolated by standard methods from *E. coli* FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the *E. coli* idi gene. The plasmids were transformed into *E. coli* hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into *E. coli* TOP10 cells and transformants were grown at 37° C. overnight with selection on LA containing kanamycin (50 µg/ml). The transformants were verified by restriction enzyme digestion and one was frozen as a stock. The plasmid was designated pTrcK-anKKDIy.

II. Cloning a Kudzu Isoprene Synthase Gene into pTtrcK-anKKDIy

The kudzu isoprene synthase gene was amplified by PCR from pTrcKudzu, described in Example 1, using primers MCM50 5'-GATCATGCATTCGCCCTTAGGAGG-TAAAAAAACATGTGTGCGACCTCTTCTCAATTTACT (SEQ ID NO:31) and MCM53 5'-CGGTCGACGGATCCCT-GCAGTTAGACATACATCAGCTG (SEQ ID NO:32). The resulting PCR fragment was cloned into pCR2.1 and transformed into E. coli TOP10. This fragment contains the coding sequence for kudzu isoprene synthase and an upstream region containing a RBS from E. coli. Transformants were incubated overnight at 37° C. with selection on LA containing carbenicillin (50 µg/ml). The correct insertion of the fragment was verified by sequencing and this strain was designated MCM93.

Figure 24:
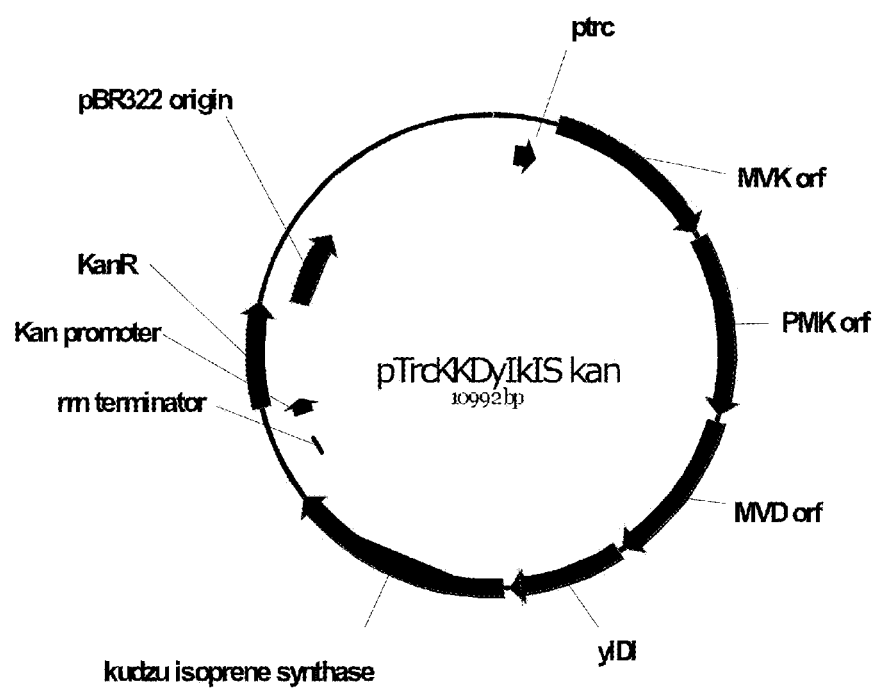
FIG. 24 is a map of pTrcKKDyIkIS kan.
Figure 26:
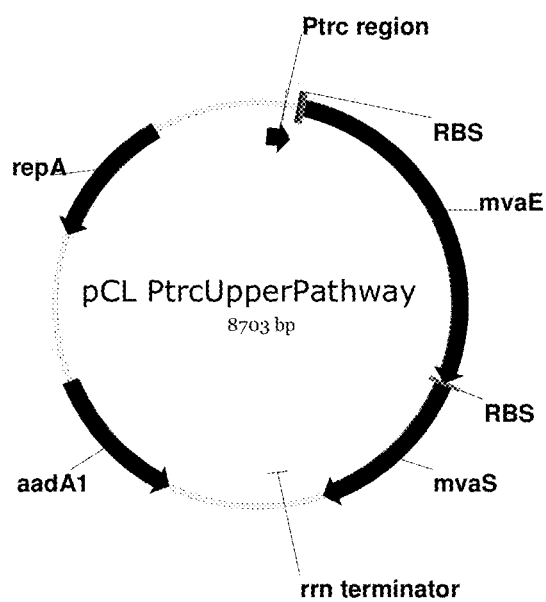
FIG. 26 is a map of pCL PtrcUpperPathway.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into E. coli TOP10 cells and transformants were grown overnight at 37° C. with selection on LA containing Kanamycin at 50 µg/ml. The correct transformant was verified by restriction digestion and the plasmid was designated pTrcKKDyIkISKan (FIGS. 24 and 25). This plasmid was transformed into BL21(λDE3) cells (Invitrogen).

III. Isoprene Production from Mevalonate in E. coli Expressing the Recombinant Lower Mevalonate Pathway and Isoprene Synthase from Kudzu.

Strain BL21/pTrcKKDyIkISKan was cultured in MOPS medium (Neidhardt et al., (1974) J. Bacteriology 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 µM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 1. Maximum production of isoprene was $6.67 \times 10^{-4}$ mol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from Enterococcus faecalis. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from E. faecalis genomic DNA (ATCC 700802D-5) with an E. coli ribosome binding site and a spacer in front using the following primers:

```
CF 07-60 (+) Start of mvaE w/ RBS + ATG
start codon SacI
                                      (SEQ ID NO: 34)
5'-GAGACATGAGCTCAGGAGGTAAAAAAACATGAAAACAGTAGTTATTA

TTG

CF 07-62 (-) Fuse mvaE to mvaS with RBS in between
                                      (SEQ ID NO: 35)
5'-TTTATCAATCCCAATTGTCATGTTTTTTTACCTCCTTTATTGTTTTC

TTAAATC
```

The mvaS gene was amplified from E. faecalis genomic DNA (ATCC 700802D-5) with a RBS and spacer from E. coli in front using the following primers:

```
CF 07-61 (+) Fuse mvaE to mvaS with RBS in between
                                      (SEQ ID NO: 36)
5'-GATTTAAGAAAACAATAAAGGAGGTAAAAAAACATGACAATTGGGAT

TGATAAA

CF 07-102 (-) End of mvaS gene BglII
                                      (SEQ ID NO: 37)
5'-GACATGACATAGATCTTTAGTTTCGATAAGAACGAACGGT
```

The PCR fragments were fused together with PCR using the following primers:

```
CF 07-60 (+) Start of mvaE w/ RBS + ATG
start codon SacI
                                      (SEQ ID NO: 34)
5'-GAGACATGAGCTCAGGAGGTAAAAAAACATGAAAACAGTAGTTATTA

TTG

CF 07-102 (-) End of mvaS gene BglII
                                      (SEQ ID NO: 37)
5'-GACATGACATAGATCTTTAGTTTCGATAAGAACGAACGGT
```

The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into E. coli Top 10 cells and colonies were selected on LA+50 µg/ml carbenicillin plates. A total of six colonies were chosen and grown overnight in LB+50 µg/ml carbenicillin and plasmids were isolated using a Qiagen kit. The plasmids were digested with SacI and BglII to check for inserts and one correct plasmid was sequenced with the following primers:

```
CF 07-58 (+) Start of mvaE gene
                                      (SEQ ID NO: 38)
5'-ATGAAAACAGTAGTTATTATTGATGC CF 07-59 (-) End of mvaE gene
                                      (SEQ ID NO: 39)
5'-ATGTTATTGTTTTCTTAAATCATTTAAAATAGC CF 07-82 (+) Start of mvaS gene
                                      (SEQ ID NO: 40)
5'-ATGACAATTGGGATTGATAAAATTAG CF 07-83 (-) End of mvaS gene
                                      (SEQ ID NO: 41)
5'-TTAGTTTCGATAAGAACGAACGGT CF 07-86 (+) Sequence in mvaE
                                      (SEQ ID NO: 42)
5'-GAAATAGCCCCATTAGAAGTATC CF 07-87 (+) Sequence in mvaE
                                      (SEQ ID NO: 43)
5'-TTGCCAATCATATGATTGAAAATC CF 07-88 (+) Sequence in mvaE
                                      (SEQ ID NO: 44)
5'-GCTATGCTTCATTAGATCCTTATCG CF 07-89 (+) Sequence mvaS
                                      (SEQ ID NO: 45)
5'-GAAACCTACATCCAATCTTTTGCCC
```

The plasmid called pTrcHis2AUpperPathway#1 was correct by sequencing and was transformed into the commercially available *E. coli* strain BL21. Selection was done on LA+50 µg/ml carbenicillin. Two transformants were chosen and grown in LB+50 µg/ml carbenicillin until they reached an $OD_{600}$ of 1.5. Both strains were frozen in a vial at −80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920

The plasmid pTrcHis2AUpperPathway was digested with the restriction endonuclease SspI to release a fragment containing pTrc-mvaE-mvaS-(His tag)-terminator. In this fragment, the his-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 µg/ml). A correct colony was identified by screening for the presence of the insert by PCR. The plasmid was designated pCL PtrcUpperPathway (FIGS. 26 and 27A-27D).

VI. Strains Expressing the Combined Upper and Lower Mevalonic Acid Pathways

To obtain a strain with a complete mevalonic acid pathway plus kudzu isoprene synthase, plasmids pTrcKKDyIkISkan and pCLpTrcUpperPathway were both transformed into BL21(λDE3) competent cells (Invitrogen) and transformants were selected on LA containing kanamycin (50 µg/ml) and Spectinomycin (50 µg/ml). The transformants were checked by plasmid prep to ensure that both plasmids were retained in the host. The strain was designated MCM127.

VII. Production of Mevalonic Acid from Glucose in *E. coli*/pUpperpathway

Single colonies of the BL21/pTrcHis2A-mvaE/mvaS or FM5/p pTrcHis2A-mvaE/mvaS are inoculated into LB+carbenicillin (100 µg/ml) and are grown overnight at 37° C. with shaking at 200 rpm. These cultures were diluted into 50 ml medium in 250 ml baffled flasks to an $OD_{600}$ of 0.1. The medium was TM3+1 or 2% glucose+carbenicillin (100 ug/ml) or TM3+1% glucose+hydrolyzed soy oil+carbenicillin (100 ug/ml) or TM3+biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 µM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli*.

VIII. Production of Isoprene from *E. coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21(λDE3) and the transformations were done by standard methods. Transformants were selected on L agar containing kanamycin (50 µg/ml) or kanamycin plus spectinomycin (both at a concentration of 50 µg/ml). Plates were grown at 37° C. The resulting strains were designated as follows:

Grown on Kanamycin Plus Spectinomycin (50 µg/ml each)
MCM127—pCL Upper MVA+pTrcKKDyIkIS (kan) in BL21(λDE3)
MCM131—pCL1920+pTrcKKDyIkIS (kan) in BL21(λDE3)
MCM125—pCL Upper MVA+pTrcHis2B (kan) in BL21(λDE3)

Grown on Kanamycin (50 µg/ml)
MCM64—pTrcKudzu yIDI DXS (kan) in BL21(λDE3)
MCM50—pTrcKudzu (kan) in BL21(λDE3)
MCM123—pTrcKudzu yIDI DXS DXR (kan) in BL21(λDE3)

The above strains were streaked from freezer stocks to LA+appropriate antibiotic and grown overnight at 37° C. A single colony from each plate was used to inoculate shake flasks (25 ml LB+the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB+the appropriate antibiotic. The cultures were then diluted into 25 ml LB+1% glucose+the appropriate antibiotic to an $OD_{600}$ of 0.1. Two flasks for each strain were set up, one set for induction with IPTG (800 µM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 1. Results are presented in Table 3. The amount of isoprene made is presented as the amount at the peak production for the particular strain.

TABLE 3

| Production of isoprene in *E. coli* strains | |
|---|---|
| Strain | Isoprene (µg/liter/OD/hr) |
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid

Mevalonolactone (1.0 g, 7.7 mmol) (CAS#503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1H$ NMR analysis. Samples for HPLC analysis were prepared by centrifugation at 14,000 rpm for 5 minutes to remove cells, followed by the addition of a 300 µl aliquot of supernatant to 900 µl of H₂O. Perchloric acid (36 µl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (RI) detection. Under these conditions mevalonic acid eluted as the lactone form at 18.5 minutes.

X. Production of Isoprene from *E. coli* BL21 Containing the Upper MVA Pathway Plus Kudzu Isoprene Synthase A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 2.2 g/L of isoprene.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperPathway (FIG. 26) and pTrcKKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into soytone-yeast extract-glucose medium. After the inoculum grew to OD 1.0 when measured at 550 nm, 500 mL was used to inoculate a 5-L bioreactor.

Figure 54:
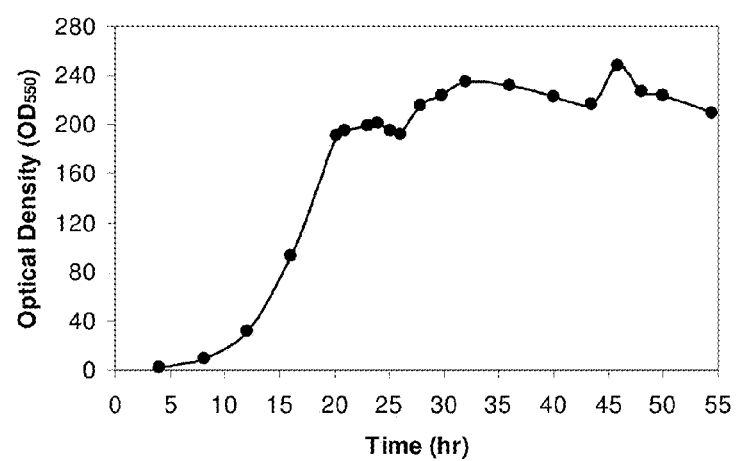
FIG. 54 is a time course of optical density within the 15-L bioreactor fed with glucose.
Figure 55:
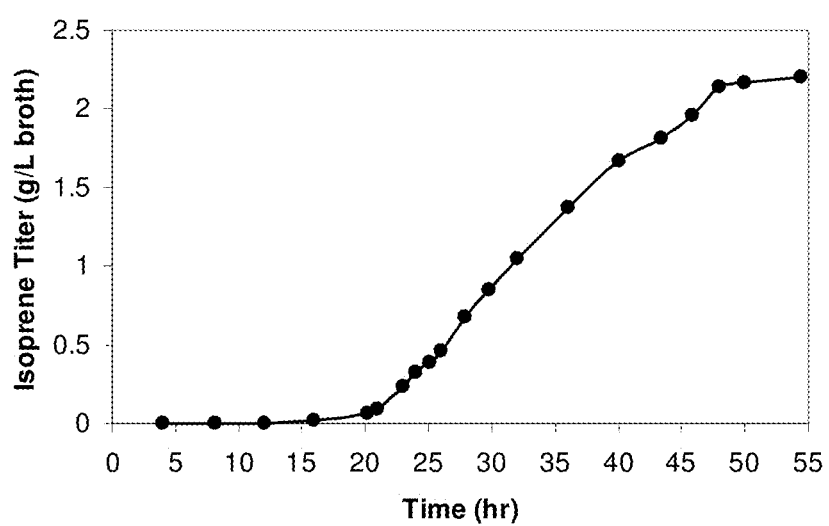
FIG. 55 is a time course of isoprene titer within the 15-L bioreactor fed with glucose. The titer is defined as the amount of isoprene produced per liter of fermentation broth.
Figure 56:
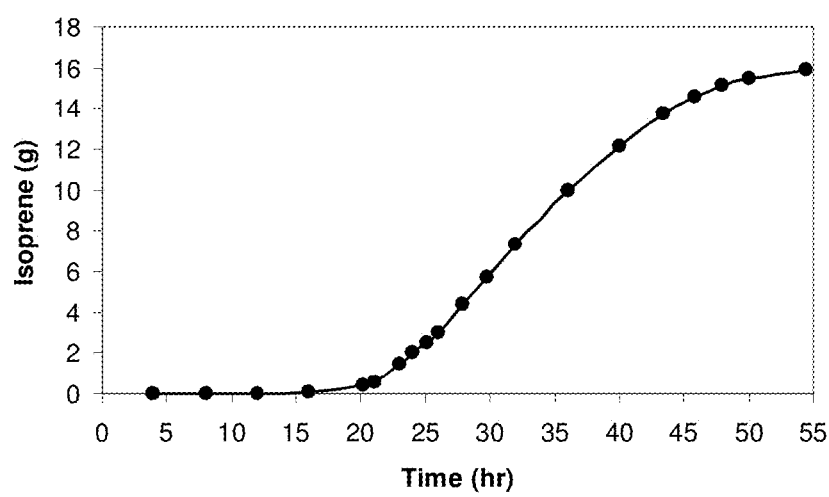
FIG. 56 is a time course of total isoprene produced from the 15-L bioreactor fed with glucose.

Glucose was fed at an exponential rate until cells reached the stationary phase. After this time the glucose feed was decreased to meet metabolic demands. The total amount of glucose delivered to the bioreactor during the 54 hour fermentation was 3.7 kg. Induction was achieved by adding isopropyl-beta-D-1-thiogalactopyranoside (IPTG). The IPTG concentration was brought to 25 uM when the optical density at 550 nm ($OD_{550}$) reached a value of 10. The IPTG concentration was raised to 50 uM when $OD_{550}$ reached 190. IPTG concentration was raised to 100 uM at 38 hours of fermentation. The $OD_{550}$ profile within the bioreactor over time is shown in FIG. 54. The isoprene level in the off gas from the bioreactor was determined as described herein. The isoprene titer increased over the course of the fermentation to a final value of 2.2 g/L (FIG. 55). The total amount of isoprene produced during the 54 hour fermentation was 15.9 g, and the time course of production is shown in FIG. 56.

XI. Isoprene Fermentation from *E. coli* Expressing Genes from the Mevalonic Acid Pathway and Grown in Fed-Batch Culture at the 15-L Scale A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 3.0 g/L of isoprene.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time, the glucose feed was decreased to meet metabolic demands. The total amount of glucose delivered to the bioreactor during the 59 hour fermentation was 2.2 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 93. The isoprene level in the off gas from the bioreactor was determined as described herein. The isoprene titer increased over the course of the fermentation to a final value of 3.0 g/L (FIG. 94). The total amount of isoprene produced during the 59 hour fermentation was 22.8 g, and the time course of production is shown in FIG. 95. The molar yield of utilized carbon that went into producing isoprene during fermentation was 2.2%. The weight percent yield of isoprene from glucose was 1.0%.

XII. Isoprene Fermentation from *E. coli* Expressing Genes from the Mevalonic Acid Pathway and Grown in Fed-Batch Culture at the 15-L Scale A 15-L scale fermentation of *E. coli* expressing mevalonic acid pathway polypeptides, *Pueraria lobata* isoprene synthase, and Kudzu isoprene synthase was used to produce isoprene from cells in fed-batch culture. This experiment demonstrates that growing cells under glucose limiting conditions resulted in the production of 3.3 g/L of isoprene.

i) Construction of pCLPtrcUpperPathwayHGS2

The gene encoding isoprene synthase from *Pueraria lobata* was PCR-amplified using primers NsiI-RBS-HGS F (CTTGATGCATCCTGCATTCGCCCTTAGGAGG, SEQ ID NO:88) and pTrcR(CCAGGCAAATTCTGTTTTATCAG, SEQ ID NO:89), and pTrcKKDyIkIS as a template. The PCR product thus obtained was restriction-digested with NsiI and PstI and gel-purified. The plasmid pCL PtrcUpperPathway was restriction-digested with PstI and dephosphorylated using rAPid alkaline phosphatase (Roche) according to manufacturer's instructions.

These DNA fragments were ligated together and the ligation reaction was transformed into *E. coli* Top10 chemically competent cells (Invitrogen), plated on L agar containing spectinomycin (50 ug/ml) and incubated overnight at 37° C. Plasmid DNA was prepared from 6 clones using the Qiaquick Spin Mini-prep kit. The plasmid DNA was digested with restriction enzymes EcoRV and MluI to identify a clone in which the insert had the right orientation (i.e., the gene oriented in the same way as the pTrc promoter).

The resulting correct plasmid was designated pCLPtrcUpperPathwayHGS2. This plasmid was assayed using the headspace assay described herein and found to produce isoprene in *E. coli* Top10, thus validating the functionality of the gene. The plasmid was transformed into BL21(LDE3) containing pTrcKKDyIkIS to yield the strain BL21/pCLPtrcUpperPathwayHGS2-pTrcKKDyIkIS. This strain has an extra copy of the isoprene synthase compared to the BL21/pCL PtrcUpperMVA and pTrc KKDyIkIS strain (Example 8, part XI). This strain also had increased expression and activity of HMGS compared to the BL21/pCL PtrcUpperMVA and pTrc KKDyIkIS strain used in Example 8, part XI.

ii) Isoprene Fermentation from *E. coli* Expressing pCLPtrcUpperPathwayHGS2-pTrcKKDyIkIS and Grown in Fed-Batch Culture at the 15-L Scale Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in Di $H_2O$, pH to 3.0 with HCl/NaOH, then q.s. to volume and filter sterilized with 0.22 micron filter.

Fermentation was performed in a 15-L bioreactor with BL21 (DE3) *E. coli* cells containing the pCLPtrcUpperPathwayHGS2 and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0 measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 58 hour fermentation was 2.1 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 170. The $OD_{550}$ profile within the bioreactor over time is shown in FIG. 104. The isoprene level in the off gas from the bioreactor was determined as described herein. The isoprene titer increased over the course of the fermentation to a final value of 3.3 g/L (FIG. 105). The total amount of isoprene produced during the 58 hour fermentation was 24.5 g and the time course of production is shown in FIG. 106. The molar yield of utilized carbon that went into producing isoprene during fermentation was 2.5%. The weight percent yield of isoprene from glucose was 1.2%. Analysis showed that the activity of the isoprene synthase was increased by approximately 3-4 times that compared to BL21 expressing CL PtrcUpperMVA and pTrc KKDyIkIS plasmids (data not shown).

XIII. Chromosomal Integration of the Lower Mevalonate Pathway in *E. coli*.

A synthetic operon containing mevalonate kinase, mevalonate phosphate kinase, mevalonate pyrophosphate decarboxylase, and the IPP isomerase was integrated into the chromosome of *E. coli*. If desired, expression may be altered by integrating different promoters 5' of the operon.

Table 9 lists primers used for this experiment.

TABLE 9

| | | Primers |
|---|---|---|
| MCM78 | attTn7 up rev for integration construct | gcatgctcgagcggccgcTTTTAATCAAACATCCTGCCAACTC (SEQ ID NO: 91) |
| MCM79 | attTn7 down rev for integration construct | gatcgaagggcgatcgTGTCACAGTCTGGCGAAACCG (SEQ ID NO: 92) |
| MCM88 | attTn7 up forw for integration construct | ctgaattctgcagatatcTGTTTTTCCACTCTTCGTTCACTTT (SEQ ID NO: 93) |
| MCM89 | attTn7 down forw for integration construct | tctagagggcccAAGAAAAATGCCCCGCTTACG (SEQ ID NO: 94) |
| MCM104 | GI1.2 promoter - MVK | Gatcgcggccgcgcccttgacgatgccacatcctgagcaaataattcaaccactaa ttgtgagcggataacacaaggaggaaacagctatgtcattaccgttcttaacttc (SEQ ID NO: 95) |

TABLE 9-continued

Primers

MCM105 aspA terminator - yIDI   Gatcgggccccaagaaaaaaggcacgtcatctgacgtgccttttttatttgtagacgc
                                gttgttatagcattcta (SEQ ID NO: 96)

MCM120 Forward of attTn7:       aaagtagccgaagatgacggtttgtcacatggagttggcaggatgtttgattaaaagc
       attTn7 homology, GB      AATTAACCCTCACTAAAGGGCGG (SEQ ID NO: 97)
       marker homology MCM127 Rev complement of 1.2    AGAGTGTTCACCAAAAATAATAACCTTTCCCGGTGCAgaag
       GI: GB marker            ttaagaacggtaatgacatagctgtttcctccttgtgttatccgctcacaattagtggttga
       homology (extra long),   attatttgctcaggatgtggcatcgtcaagggcTAATACGACTCACTATAG
       promoter, RBS, ATG       GGCTCG (SEQ ID NO: 98)

i) Target Vector Construction

The attTn7 site was selected for integration. Regions of homology upstream (attTn7 up) (primers MCM78 and MCM79) and downstream (attTn7 down) (primers MCM88 and MCM89) were amplified by PCR from MG1655 cells. A 50 uL reaction with 1 uL 10 uM primers, 3 uL ddH2O, 45 uL Invitrogen Platinum PCR Supermix High Fidelity, and a scraped colony of MG1655 was denatured for 2:00 at 94° C., cycled 25 times (2:00 at 94° C., 0:30 at 50° C., and 1:00 at 68° C.), extended for 7:00 at 72° C., and cooled to 4° C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcK-KDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM120 and MCM127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 uL PCR reactions containing 1 uL~10 ng/uL template, 1 uL each primer, 1.25 uL 10 mM dNTPs, 5 uL 10× buffer, 1 uL enzyme, and 39.75 uL ddH2O. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions were recovered in LB for 3 hr at 30° C. Transformant MCM330 was selected on LA with CMP5, Kan50 (FIGS. 107 and 108A-108C).

iii) Integration into E. coli Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 4° C. ddH2O before electroporation with 2 uL of DNA. Integrants were selected on L agar with containing chloramphenicol (5 ug/ml) and subsequently confirmed to not grow on L agar+Kanamycin (50 ug/ml). BL21 integrant MCM331 and MG1655 integrant MCM333 were frozen.

iv) Construction of pET24D-Kudzu Encoding Kudzu Isoprene Synthase

The kudzu isoprene synthase gene was subcloned into the pET24d vector (Novagen) from the pCR2.1 vector (Invitrogen). In particular, the kudzu isoprene synthase gene was amplified from the pTrcKudzu template DNA using primers MCM50 5'-GATCATGCAT TCGCCCTTAG GAGG-TAAAAA AACATGTGTG CGACCTCTTC TCAATT-TACT (SEQ ID NO:99) and MCM53 5'-CGGTCGACGG ATCCCTGCAG TTAGACATAC ATCAGCTG (SEQ ID NO:100). PCR reactions were carried out using Taq DNA Polymerase (Invitrogen), and the resulting PCR product was cloned into pCR2.1-TOPO TA cloning vector (Invitrogen), and transformed into E. coli Top10 chemically competent cells (Invitrogen). Transformants were plated on L agar containing carbenicillin (50 μg/ml) and incubated overnight at 37° C. Five ml Luria Broth cultures containing carbenicillin 50 μg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu isoprene synthase coding sequence in a pCR2.1 backbone.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu isoprene synthase fragment was ligated to the NcoI/BamH1 digested pET24d using the Rapid DNA Ligation Kit (Roche) at a 5:1 fragment to vector ratio in a total volume of 20 μl. A portion of the ligation mixture (5 μl) was transformed into E. coli Top 10 chemically competent cells and plated on L agar containing kanamycin (50 μg/ml). The correct transformant was confirmed by sequencing and transformed into chemically competent BL21(λDE3)pLysS cells (Novagen). A single colony was selected after overnight growth at 37° C. on L agar containing kanamycin (50 μg/ml). A map of the resulting plasmid designated as pET24D-Kudzu is shown in FIG. 109. The sequence of pET24D-Kudzu (SEQ ID NO:101) is shown in FIGS. 110A and 110B. Isoprene synthase activity was confirmed using a headspace assay.

v) Production Strains

Strains MCM331 and MCM333 were cotransformed with plasmids pCLPtrcupperpathway and either pTrcKudzu or pETKudzu, resulting in the strains shown in Table 10.

TABLE 10

Production Strains

| Background | Integrated Lower | Upper MVA plasmid | Isoprene synthase plasmid | Production Stain |
|---|---|---|---|---|
| BL21(DE3) | MCM331 | pCLPtrcUpper Pathway | pTrcKudzu | MCM343 |
| BL21(DE3) | MCM331 | pCLPtrcUpper Pathway | pET24D-Kudzu | MCM335 |
| MG1655 | MCM333 | pCLPtrcUpper Pathway | pTrcKudzu | MCM345 | vi) Isoprene Fermentation from *E. coli* Expressing Genes from the Mevalonic Acid Pathway and Grown in Fed-Batch Culture at the 15-L Scale.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the gi1.2 integrated lower MVA pathway described above and the pCL PtrcUpperMVA and pTrcKudzu plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time, the glucose feed was decreased to meet metabolic demands. The total amount of glucose delivered to the bioreactor during the 57 hour fermentation was 3.9 kg. Induction was achieved by adding IPTG. The IPTG concentration was brought to 100 uM when the carbon dioxide evolution rate reached 100 mmol/L/hr. The $OD_{550}$ profile within the bioreactor over time is shown in FIG. 111A. The isoprene level in the off gas from the bioreactor was determined as described herein. The isoprene titer increased over the course of the fermentation to a final value of 1.6 g/L (FIG. 111B). The specific productivity of isoprene over the course of the fermentation is shown in FIG. 111C and peaked at 1.2 mg/OD/hr. The total amount of isoprene produced during the 57 hour fermentation was 16.2 g. The molar yield of utilized carbon that went into producing isoprene during fermentation was 0.9%. The weight percent yield of isoprene from glucose was 0.4%.

XIV. Production of Isoprene from *E. coli* BL21 Containing the Kudzu Isoprene Synthase Using Glycerol as a Carbon Source A 15-L scale fermentation of *E. coli* expressing Kudzu isoprene synthase was used to produce isoprene from cells fed glycerol in fed-batch culture. This experiment demonstrates that growing cells in the presence of glycerol (without glucose) resulted in the production of 2.2 mg/L of isoprene.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, and 1000× modified trace metal solution 1 ml. All of the components were added together and dissolved in diH2O. This solution was autoclaved. The pH was adjusted to 7.0 with ammonium hydroxide (30%) and q.s. to volume. Glycerol 5.1 g, thiamine*HCl 0.1 g, and antibiotics were added after sterilization and pH adjustment.

1000× Modified Trace Metal Solution:

The medium was generated using the following components per liter fermentation medium: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in diH2O, pH to 3.0 with HCl/NaOH, then q.s. to volume and filter sterilized with a 0.22 micron filter.

Fermentation was performed in a 15-L bioreactor with BL21 (DE3) *E. coli* cells containing the pTrcKudzu plasmid. This experiment was carried out to monitor isoprene formation from glycerol at the desired fermentation pH 7.0 and temperature 35° C. An inoculum of *E. coli* strain taken from a frozen vial was streaked onto an LA broth agar plate (with antibiotics) and incubated at 37° C. A single colony was inoculated into soytone-yeast extract-glucose medium and grown at 35° C. After the inoculum grew to OD 1.0, measured at 550 nm, 600 mL was used to inoculate a 7.5-L bioreactor.

Figure 57:
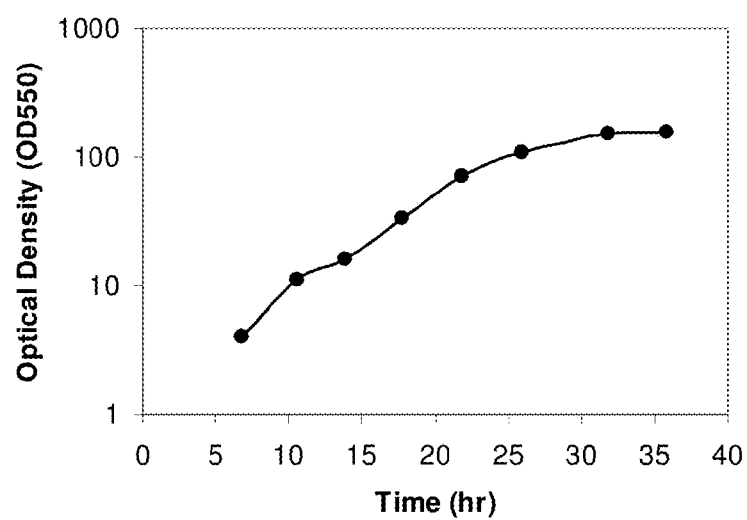
FIG. 57 is a time course of optical density within the 15-L bioreactor fed with glycerol.
Figure 58:
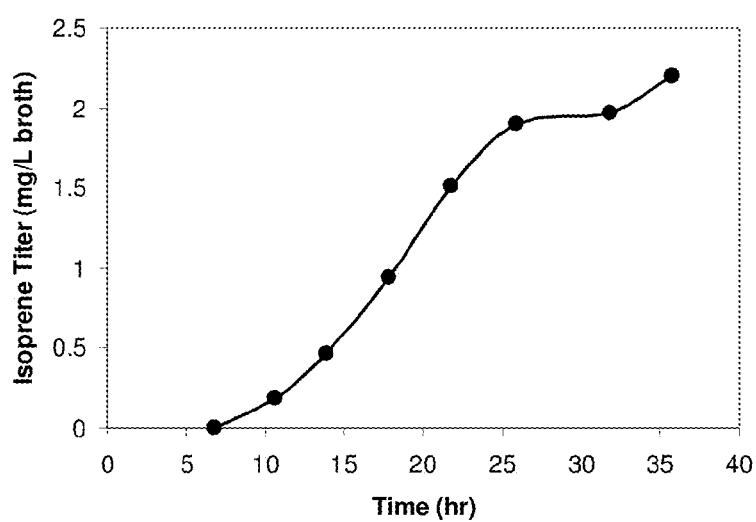
FIG. 58 is a time course of isoprene titer within the 15-L bioreactor fed with glycerol. The titer is defined as the amount of isoprene produced per liter of fermentation broth.
Figure 59:
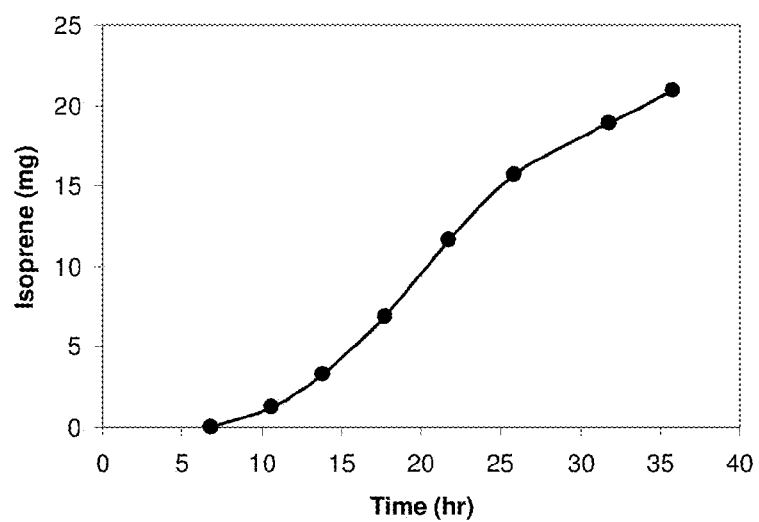
FIG. 59 is a time course of total isoprene produced from the 15-L bioreactor fed with glycerol.

Glycerol was fed at an exponential rate until cells reached an optical density at 550 nm ($OD_{550}$) of 153. The total amount of glycerol delivered to the bioreactor during the 36 hour fermentation was 1.7 kg. Other than the glucose in the inoculum, no glucose was added to the bioreactor. Induction was achieved by adding IPTG. The IPTG concentration was brought to 20 uM when the $OD_{550}$ reached a value of 50. The $OD_{550}$ profile within the bioreactor over time is shown in FIG. 57. The isoprene level in the off gas from the bioreactor was determined as described herein. The isoprene titer increased over the course of the fermentation to a final value of 2.2 mg/L (FIG. 58). The total amount of isoprene produced during the 54 hour fermentation was 20.9 mg, and the time course of production is shown in FIG. 59.

XV. Isoprene Fermentation from *E. coli* Expressing Genes from the Mevalonic Acid Pathway and Grown in Fed-Batch Culture at the 15-L Scale Using Invert Sugar as a Carbon Source A 15-L scale fermentation of *E. coli* expressing mevalonic acid pathway polypeptides and Kudzu isoprene synthase was used to produce isoprene from cells fed invert sugar in fed-batch culture. This experiment demonstrates that growing cells in the presence of invert sugar resulted in the production of 2.4 g/L of isoprene.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in diH$_2$O. This solution was autoclaved. The pH was adjusted to 7.0 with ammonium hydroxide (30%) and q.s. to volume. Invert sugar 10 g, thiamine*HCl 0.1 g, and antibiotics were added after sterilization and pH adjustment.

1000× Modified Trace Metal Solution:

The 1000× modified trace metal solution was generated using the following components: citric acids*H$_2$O 40 g, MnSO$_4$*H$_2$O 30 g, NaCl 10 g, FeSO$_4$*7H$_2$O 1 g, CoCl$_2$*6H$_2$O 1 g, ZnSO*7H$_2$O 1 g, CuSO$_4$*5H$_2$O 100 mg, H$_3$BO$_3$ 100 mg, and NaMoO$_4$*2H$_2$O 100 mg. Each component is dissolved one at a time in Di H2O, pH to 3.0 with HCl/NaOH, then q.s. to volume and filter sterilized with 0.22 micron filter.

Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from invert sugar at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Invert sugar was fed at an exponential rate until cells reached the stationary phase. After this time the invert sugar feed was decreased to meet metabolic demands. The total amount of invert sugar delivered to the bioreactor during the 44 hour fermentation was 2.4 kg. Induction was achieved by adding IPTG. The IPTG concentration was brought to 25 uM when the optical density at 550 nm (OD$_{550}$) reached a value of 9. The IPTG concentration was raised to 50 uM when OD$_{550}$ reached 200. The OD$_{550}$ profile within the bioreactor over time is shown in FIG. 96. The isoprene level in the off gas from the bioreactor was determined as described herein. The isoprene titer increased over the course of the fermentation to a final value of 2.4 g/L (FIG. 97). The total amount of isoprene produced during the 44 hour fermentation was 18.4 g and the time course of production is shown in FIG. 98. The molar yield of utilized carbon that went into producing isoprene during fermentation was 1.7%. The weight percent yield of isoprene from glucose was 0.8%.

Example 9

Construction of the Upper and Lower MVA Pathway for Integration into *Bacillus subtilis*

I. Construction of the Upper MVA Pathway in *Bacillus subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allowed them to be fused together by a PCR reaction. PCR amplifications are carried out using Herculase polymerase according to manufacturer's instructions.

```
1. PaprE
CF 07-134 (+) Start of aprE promoter PstI
                                                    (SEQ ID NO: 82)
5'-GACATCTGCAGCTCCATTTTCTTCTGC CF 07-94 (-) Fuse PaprE to mvaE
                                                    (SEQ ID NO: 83)
5'-CAATAATAACTACTGTTTTCACTCTTTACCCTCTCCTTTTAA
Template: Bacillus subtilis chromosomal DNA 2. mvaE
CF 07-93 (+) fuse mvaE to the aprE promoter (GTG start codon)
                                                    (SEQ ID NO: 84)
5'-TTAAAAGGAGAGGGTAAAGAGTGAAAACAGTAGTTATTATTG CF 07-62 (-) Fuse mvaE to mvaS with RBS in between
                                                    (SEQ ID NO: 35)
5'-TTTATCAATCCCAATTGTCATGTTTTTTTACCTCCTTTATTGTTTTCTTAAATC
Template: Enterococcus faecalis chromosomal DNA (from ATCC)

3. mvaS
CF 07-61 (+) Fuse mvaE to mvaS with RBS in between
                                                    (SEQ ID NO: 36)
5'-GATTTAAGAAAACAATAAAGGAGGTAAAAAAACATGACAATTGGGATTGATAAA CF 07-124 (-) Fuse the end of mvaS to the terminator
                                                    (SEQ ID NO: 85)
5'-CGGGGCCAAGGCCGGTTTTTTTTAGTTTCGATAAGAACGAACGGT
Template: Enterococcus faecalis chromosomal DNA 4. B. amyliquefaciens alkaline serine protease terminator
CF 07-123 (+) Fuse the end of mvaS to the terminator
                                                    (SEQ ID NO: 126)
5'-ACCGTTCGTTCTTATCGAAACTAAAAAAAACCGGCCTTGGCCCCG CF 07-46 (-) End of B. amyliquefaciens terminator BamHI
                                                    (SEQ ID NO: 63)
5'-GACATGACGGATCCGATTACGAATGCCGTCTC
```

-continued
Template: Bacillus amyliquefaciens chromosomal DNA

PCR Fusion Reactions
5. Fuse mvaE to mvaS
CF 07-93 (+) fuse mvaE to the aprE promoter (GTG start codon)
(SEQ ID NO: 84)
5'-TTAAAAGGAGAGGGTAAAGAGTGAAAACAGTAGTTATTATTG CF 07-124 (-) Fuse the end of mvaS to the terminator
(SEQ ID NO: 85)
5'-CGGGGCCAAGGCCGGTTTTTTTAGTTTCGATAAGAACGAACGGT
Template: #2 and 3 from above 6. Fuse mvaE-mvaS to aprE promoter
CF 07-134 (+) Start of aprE promoter PstI
(SEQ ID NO: 82)
5'-GACATCTGCAGCTCCATTTTCTTCTGC CF 07-124 (-) Fuse the end of mvaS to the terminator
(SEQ ID NO: 85)
5'-CGGGGCCAAGGCCGGTTTTTTTAGTTTCGATAAGAACGAACGGT
Template #1 and #4 from above 7. Fuse PaprE-mvaE-mvaS to terminator
CF 07-134 (+) Start of aprE promoter PstI
(SEQ ID NO: 82)
5'-GACATCTGCAGCTCCATTTTCTTCTGC CF 07-46 (-) End of B. amyliquefaciens terminator BamHI
(SEQ ID NO: 63)
5'-GACATGACGGATCCGATTACGAATGCCGTCTC
Template: #4 and #6
```

Figure 50:
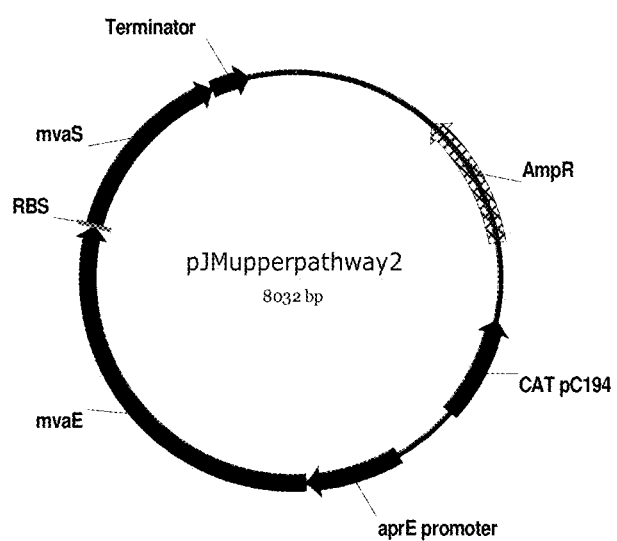
FIG. 50 is a map of pJMupperpathway2.

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 μg/ml). The correct plasmid is identified by sequencing and is designated pJMUpperpathway2 (FIGS. 50 and 51). Purified plasmid DNA is transformed into *Bacillus subtilis* aprEnprE PxylcomK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.

```
Sequencing primers:

CF 07-134 (+) Start of aprE promoter PstI
(SEQ ID NO: 82)
5'-GACATCTGCAGCTCCATTTTCTTCTGC CF 07-58 (+) Start of mvaE gene
(SEQ ID NO: 38)
5'-ATGAAAACAGTAGTTATTATTGATGC
```

```
-continued
Sequencing primers:

CF 07-59 (-) End of mvaE gene
(SEQ ID NO: 39)
5'-ATGTTATTGTTTTCTTAAATCATTTAAAATAGC CF 07-82 (+) Start of mvaS gene
(SEQ ID NO: 40)
5'-ATGACAATTGGGATTGATAAAATTAG CF 07-83 (-) End of mvaS gene
(SEQ ID NO: 41)
5'-TTAGTTTCGATAAGAACGAACGGT CF 07-86 (+) Sequence in mvaE
(SEQ ID NO: 42)
5'-GAAATAGCCCCATTAGAAGTATC CF 07-87 (+) Sequence in mvaE
(SEQ ID NO: 43)
5'-TTGCCAATCATATGATTGAAAATC CF 07-88 (+) Sequence in mvaE
(SEQ ID NO: 44)
5'-GCTATGCTTCATTAGATCCTTATCG CF 07-89 (+) Sequence mvaS
(SEQ ID NO: 45)
5'-GAAACCTACATCCAATCTTTTGCCC
```

Transformants are selected on LA containing chloramphenicol at a concentration of 5 μg/ml. One colony is confirmed to have the correct integration by sequencing and is plated on LA containing increasing concentrations of chloramphenicol over several days, to a final level of 25 μg/ml. This results in amplification of the cassette containing the genes of interest. The resulting strain is designated CF 455: pJMupperpathway#1×*Bacillus subtilis* aprEnprE Pxyl comK (amplified to grow on LA containing chloramphenicol 25 μg/ml).

II. Construction of the Lower MVA Pathway in *Bacillus subtilis*

Figure 28:
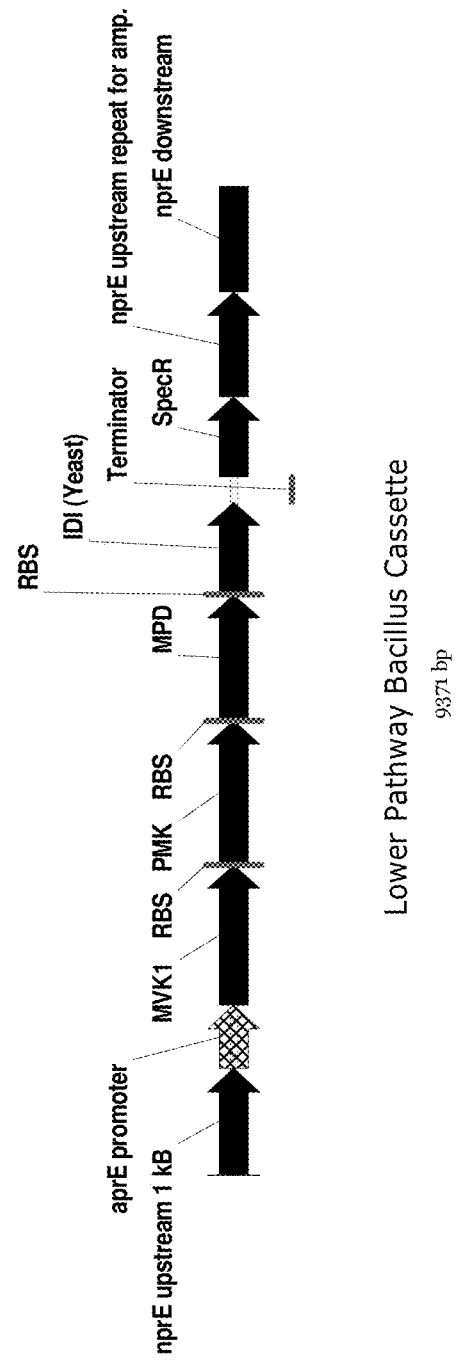
FIG. 28 shows a map of the cassette containing the lower MVA pathway and yeast IDI for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonate kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast IDI gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

The lower MVA pathway, consisting of the genes mvk1, pmk, mpd and idi are combined in a cassette consisting of flanking DNA regions from the nprE region of the *B. subtilis* chromosome (site of integration), the aprE promoter, and the spectinomycin resistance marker (see FIGS. 28 and 29). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 4 and is transformed into the strain with both upper and lower pathways integrated.

Example 10

Exemplary Isoprene Compositions and Methods of Making them

I. Compositional Analysis of Fermentation Off-Gas Containing Isoprene

A 14 L scale fermentation was performed with a recombinant *E. coli* BL21 (DE3) strain containing two plasmids (pCL upperMev; pTrcKKDyIkIS) encoding the full mevalonate pathway for isoprenoid precursor biosynthesis, an isoprenyl pyrophosphate isomerase from yeast, and an isoprene synthase from Kudzu. Fermentation off-gas from the 14 L tank was collected into 20 mL headspace vials at around the time of peak isoprene productivity (27.9 hours elapsed fermentation time, "EFT") and analyzed by headspace GC/MS for volatile components.

Headspace analysis was performed with an Agilent 6890 GC/MS system fitted with an Agilent HP-5MS GC/MS column (30 m×250 μm; 0.25 μm film thickness). A combiPAL autoinjector was used for sampling 500 uL aliquots from 20 mL headspace vials. The GC/MS method utilized helium as the carrier gas at a flow of 1 mL/min. The injection port was held at 250° C. with a split ratio of 50:1. The oven temperature was held at 37° C. for an initial 2 minute period, followed an increase to 237° C. at a rate of 25° C./min for a total method time of 10 minutes. The Agilent 5793N mass selective detector scanned from m/z 29 to m/z 300. The limit of detection of this system is approximately 0.1 ug/$L_{gas}$ or approximately 0.1 ppm. If desired, more sensitive equipment with a lower limit of detection may be used.

Figure 86A:
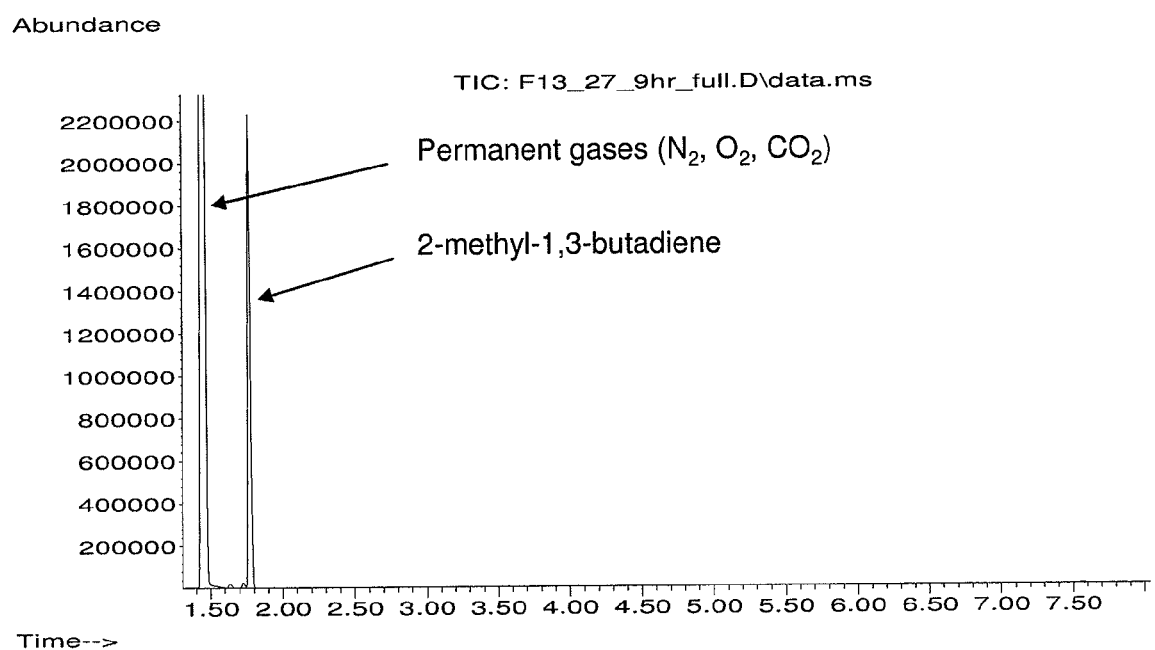
FIG. 86A is a GC/MS chromatogram of fermentation off-gas.
Figure 86B:
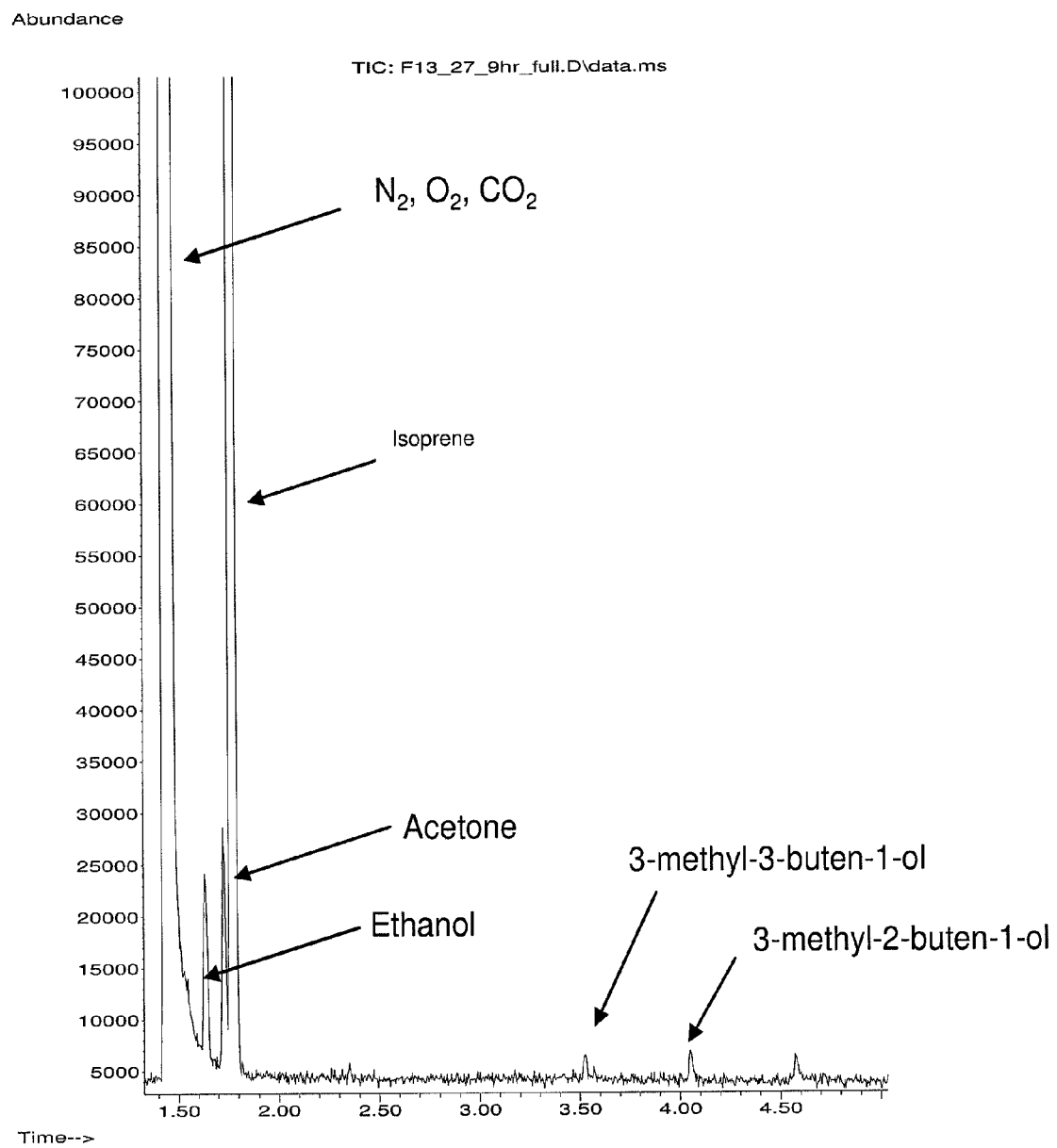
FIG. 86B is an expansion of FIG. 86A to show minor volatiles present in fermentation off-gas.
Figure 87A:
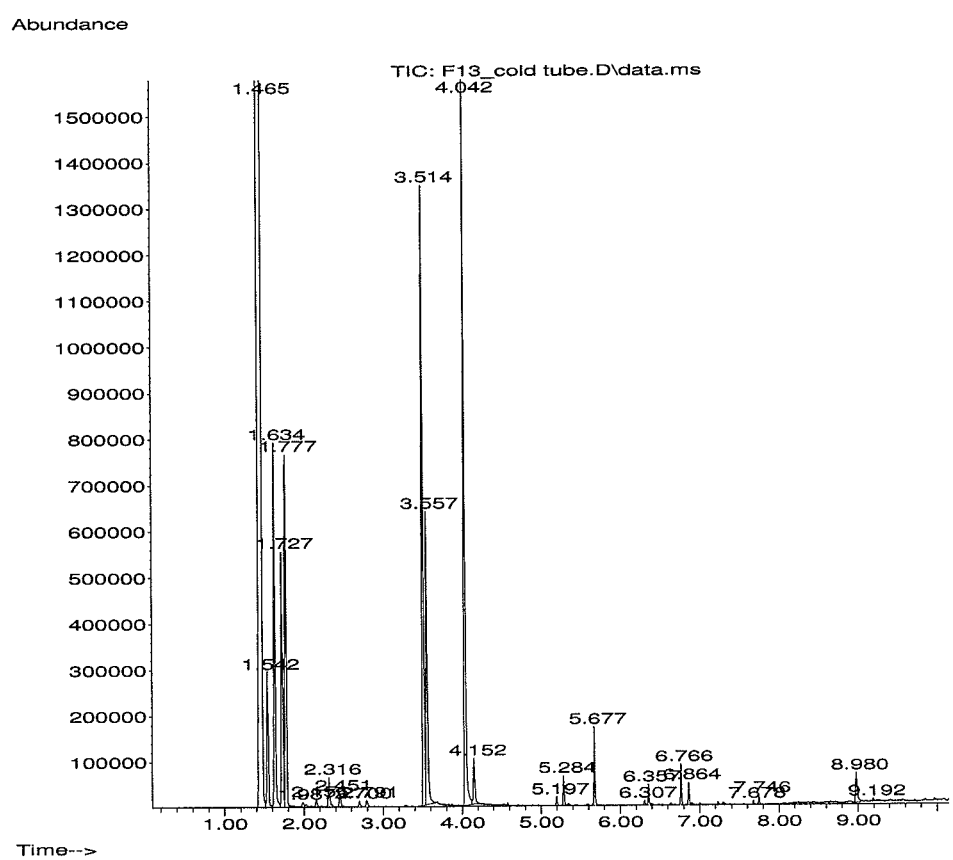
FIG. 87A is a GC/MS chromatogram of trace volatiles present in off-gas following cryo-trapping at −78° C.
Figure 87B:
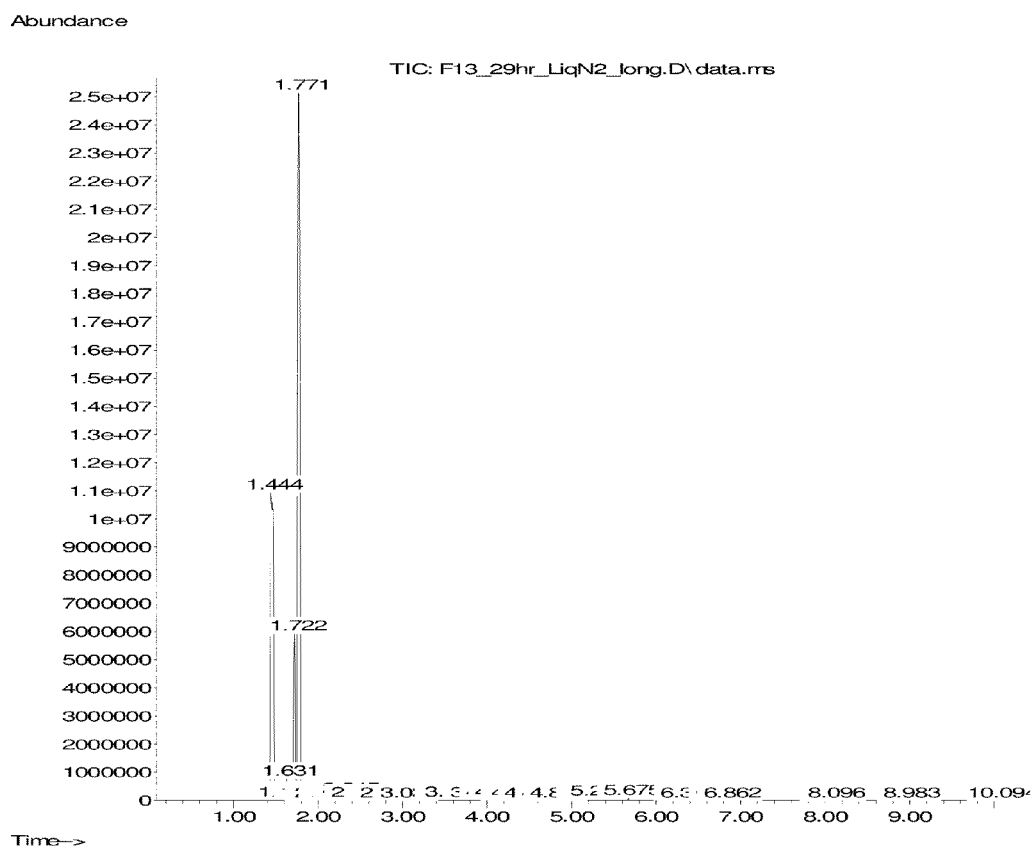
FIG. 87B is a GC/MS chromatogram of trace volatiles present in off-gas following cryo-trapping at −196° C.
Figure 87C:
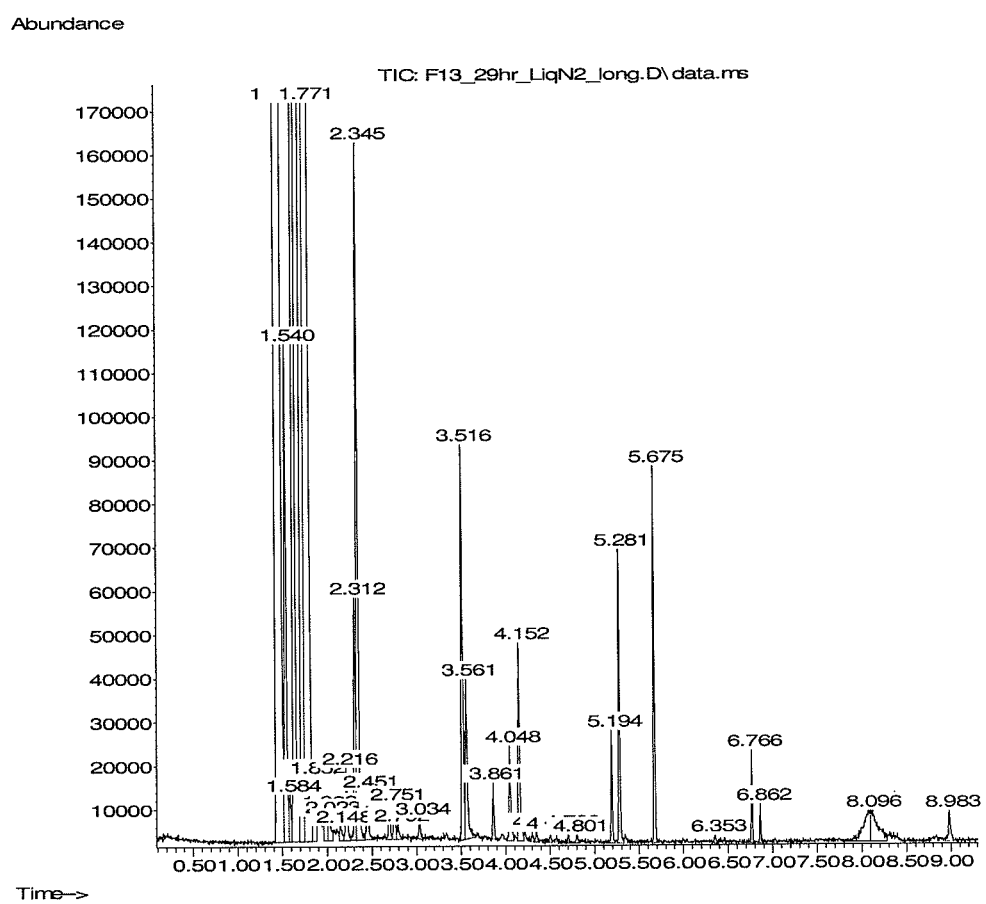
FIG. 87C is an expansion of FIG. 87B.
Figure 87D:
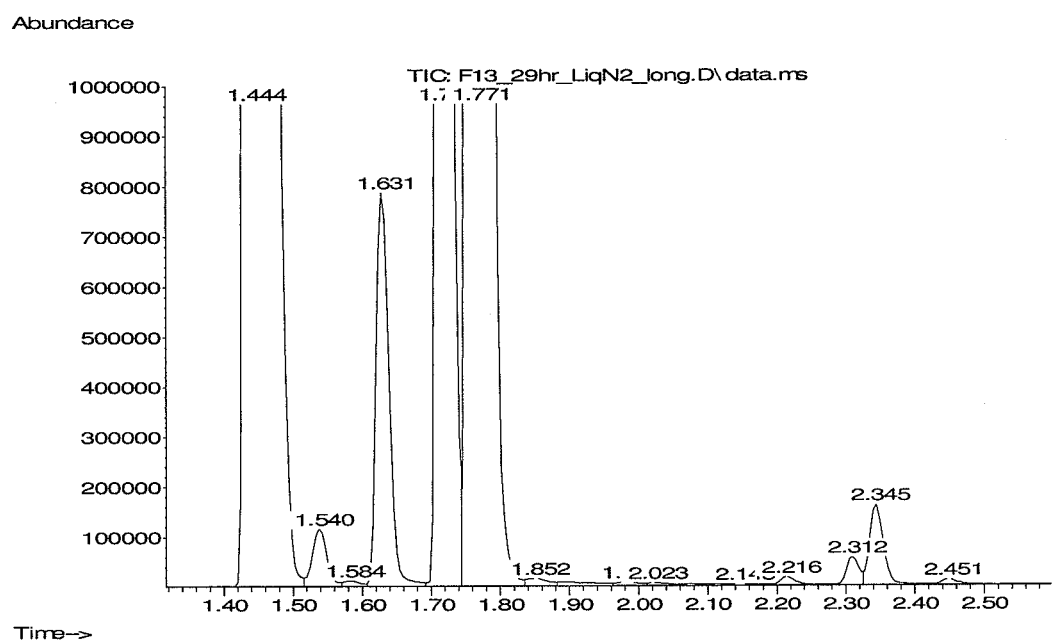
FIG. 87D is an expansion of FIG. 87C.

The off-gas consisted of 99.925% (v/v) permanent gases ($N_2$, $CO_2$ and $O_2$), approximately 0.075% isoprene (2-methyl-1,3-butadiene) (~750 ppmv, 2100 μg/L) and minor amounts (<50 ppmv) of ethanol, acetone, and two C5 prenyl alcohols. The amount of water vapor was not determined but was estimated to be equal to the equilibrium vapor pressure at 0° C. The composition of the volatile organic fraction was determined by integration of the area under the peaks in the GC/MS chromatogram (FIGS. 86A and 86B) and is listed in Table 6. Calibration curves for ethanol and acetone standards enabled the conversion of GC area to gas phase concentration in units of ug/L using standard methods.

TABLE 6

Composition of volatile organic components in fermentation off-gas. The off-gas was analyzed at the 27.9 hour time point of a fermentation using an *E. coli* BL21 (DE3) strain expressing a heterologous mevalonate pathway, an isoprenyl pyrophosphate isomerase from yeast, and an isoprene synthase from Kudzu.

| Compound | RT (min) | GC area | Area % | Conc. (ug/L) |
|---|---|---|---|---|
| Ethanol | 1.669 | 239005 | 0.84 | 62 +/− 6 |
| Acetone | 1.703 | 288352 | 1.02 | 42 +/− 4 |
| Isoprene (2-methyl-1,3-butadiene) | 1.829 | 27764544 | 97.81 | 2000 +/− 200 |
| 3-methyl-3-buten-1-ol | 3.493 | 35060 | 0.12 | <10 |
| 3-methyl-2-buten-1-ol | 4.116 | 58153 | 0.20 | <10 |

II. Measurement of Trace Volatile Organic Compounds (VOCs) Co-Produced with Isoprene During Fermentation of a Recombinant *E. coli* Strain A 14 L scale fermentation was performed with a recombinant *E. coli* BL21 (DE3) strain containing two plasmids (pCL upperMev; pTrcKKDyIkIS) encoding the full mevalonate pathway for isoprenoid precursor biosynthesis, an isoprenyl pyrophosphate isomerase from yeast, and an isoprene synthase from Kudzu.

Fermentation off-gas was passed through cooled headspace vials in order to concentrate and identify trace volatile organic components. The off-gas from this fermentation was sampled at a rate of 1 L/min for 10 minutes through a 20 mL headspace vial packed with quartz wool (2 g) and cooled to −78° C. with dry ice. The vial was recapped with a fresh vial cap and analyzed by headspace GC/MS for trapped VOCs using the conditions described in Example 10, part I. The ratios of compounds observed in FIGS. 87A-87D are a combination of overall level in the fermentation off-gas, the relative vapor pressure at −78° C., and the detector response of the mass spectrometer. For example, the low level of isoprene relative to oxygenated volatiles (e.g., acetone and ethanol) is a function of the high volatility of this material such that it does not accumulate in the headspace vial at −78° C.

The presence of many of these compounds is unique to isoprene compositions derived from biological sources. The results are depicted in FIGS. 87A-87D and summarized in Tables 7A and 7B.

TABLE 7A

Trace volatiles present in off-gas produced by *E. coli* BL21 (DE3) (pCL upperMev; pTrcKKDyIkIS) following cryo-trapping at −78° C.

| Compound | RT (min) | GC Area[1] | Area %[2] | Ratio %[3] |
|---|---|---|---|---|
| Acetaldehyde | 1.542 | 4019861 | 4.841 | 40.14 |
| Ethanol | 1.634 | 10553620 | 12.708 | 105.39 |
| Acetone | 1.727 | 7236323 | 8.714 | 72.26 |
| 2-methyl-1,3-butadiene | 1.777 | 10013714 | 12.058 | 100.00 |
| 1-propanol | 1.987 | 163574 | 0.197 | 1.63 |
| Diacetyl | 2.156 | 221078 | 0.266 | 2.21 |
| 2-methyl-3-buten-2-ol | 2.316 | 902735 | 1.087 | 9.01 |
| 2-methyl-1-propanol | 2.451 | 446387 | 0.538 | 4.46 |
| 3-methyl-1-butanal | 2.7 | 165162 | 0.199 | 1.65 |
| 1-butanol | 2.791 | 231738 | 0.279 | 2.31 |
| 3-methyl-3-buten-1-ol | 3.514 | 14851860 | 17.884 | 148.32 |
| 3-methyl-1-butanol | 3.557 | 8458483 | 10.185 | 84.47 |
| 3-methyl-2-buten-1-ol | 4.042 | 18201341 | 21.917 | 181.76 |
| 3-methyl-2-butenal | 4.153 | 1837273 | 2.212 | 18.35 |
| 3-methylbutyl acetate | 5.197 | 196136 | 0.236 | 1.96 |
| 3-methyl-3-buten-1-yl acetate | 5.284 | 652132 | 0.785 | 6.51 |
| 2-heptanone | 5.348 | 67224 | 0.081 | 0.67 |
| 2,5-dimethylpyrazine | 5.591 | 58029 | 0.070 | 0.58 |

TABLE 7A-continued

Trace volatiles present in off-gas produced by *E. coli* BL21 (DE3)
(pCL upperMev; pTrcKKDyIkIS) following cryo-trapping at −78° C.

| Compound | RT (min) | GC Area[1] | Area %[2] | Ratio %[3] |
|---|---|---|---|---|
| 3-methyl-2-buten-1-yl acetate | 5.676 | 1686507 | 2.031 | 16.84 |
| 6-methyl-5-hepten-2-one | 6.307 | 101797 | 0.123 | 1.02 |
| 2,4,5-trimethylpyridine | 6.39 | 68477 | 0.082 | 0.68 |
| 2,3,5-trimethylpyrazine | 6.485 | 30420 | 0.037 | 0.30 |
| (E)-3,7-dimethyl-1,3,6-octatriene | 6.766 | 848928 | 1.022 | 8.48 |
| (Z)-3,7-dimethyl-1,3,6-octatriene | 6.864 | 448810 | 0.540 | 4.48 |
| 3-methyl-2-buten-1-yl butyrate | 7.294 | 105356 | 0.127 | 1.05 |
| Citronellal | 7.756 | 208092 | 0.251 | 2.08 |
| 2,3-cycloheptenolpyridine | 8.98 | 1119947 | 1.349 | 11.18 |

[1] GC area is the uncorrected area under the peak corresponding to the listed compound.
[2] Area % is the peak area expressed as a % relative to the total peak area of all compounds.
[3] Ratio % is the peak area expressed as a % relative to the peak area of 2-methyl-1,3-butadiene.

TABLE 7B

Trace volatiles present in off-gas produced by *E. coli* BL21 (DE3)
(pCL upperMev; pTrcKKDyIkIS) following cryo-trapping at −196° C.

| Compound | RT (min) | GC Area[1] | Area %[2] | Ratio %[3] |
|---|---|---|---|---|
| Acetaldehyde | 1.54 | 1655710 | 0.276 | 0.33 |
| Methanethiol | 1.584 | 173620 | 0.029 | 0.03 |
| Ethanol | 1.631 | 10259680 | 1.707 | 2.03 |
| Acetone | 1.722 | 73089100 | 12.164 | 14.43 |
| 2-methyl-1,3-butadiene | 1.771 | 506349429 | 84.269 | 100.00 |
| methyl acetate | 1.852 | 320112 | 0.053 | 0.06 |
| 1-propanol | 1.983 | 156752 | 0.026 | 0.03 |
| Diacetyl | 2.148 | 67635 | 0.011 | 0.01 |
| 2-butanone | 2.216 | 254364 | 0.042 | 0.05 |
| 2-methyl-3-buten-2-ol | 2.312 | 684708 | 0.114 | 0.14 |
| ethyl acetate | 2.345 | 2226391 | 0.371 | 0.44 |
| 2-methyl-1-propanol | 2.451 | 187719 | 0.031 | 0.04 |
| 3-methyl-1-butanal | 2.696 | 115723 | 0.019 | 0.02 |
| 3-methyl-2-butanone | 2.751 | 116861 | 0.019 | 0.02 |
| 1-butanol | 2.792 | 54555 | 0.009 | 0.01 |
| 2-pentanone | 3.034 | 66520 | 0.011 | 0.01 |
| 3-methyl-3-buten-1-ol | 3.516 | 1123520 | 0.187 | 0.22 |
| 3-methyl-1-butanol | 3.561 | 572836 | 0.095 | 0.11 |
| ethyl isobutyrate | 3.861 | 142056 | 0.024 | 0.03 |
| 3-methyl-2-buten-1-ol | 4.048 | 302558 | 0.050 | 0.06 |
| 3-methyl-2-butenal | 4.152 | 585690 | 0.097 | 0.12 |
| butyl acetate | 4.502 | 29665 | 0.005 | 0.01 |
| 3-methylbutyl acetate | 5.194 | 271797 | 0.045 | 0.05 |
| 3-methyl-3-buten-1-yl acetate | 5.281 | 705366 | 0.117 | 0.14 |
| 3-methyl-2-buten-1-yl acetate | 5.675 | 815186 | 0.136 | 0.16 |
| (E)-3,7-dimethyl-1,3,6-octatriene | 6.766 | 207061 | 0.034 | 0.04 |
| (Z)-3,7-dimethyl-1,3,6-octatriene | 6.863 | 94294 | 0.016 | 0.02 |
| 2,3-cycloheptenolpyridine | 8.983 | 135104 | 0.022 | 0.03 |

[1] GC area is the uncorrected area under the peak corresponding to the listed compound.
[2] Area % is the peak area expressed as a % relative to the total peak area of all compounds.
[3] Ratio % is the peak area expressed as a % relative to the peak area of 2-methyl-1,3-butadiene.

III. Absence of C5 Hydrocarbon Isomers in Isoprene Derived from Fermentation.

Cryo-trapping of isoprene present in fermentation off-gas was performed using a 2 mL headspace vial cooled in liquid nitrogen. The off-gas (1 L/min) was first passed through a 20 mL vial containing sodium hydroxide pellets in order to minimize the accumulation of ice and solid $CO_2$ in the 2 mL vial (−196° C.). Approximately 10 L of off-gas was passed through the vial, after which it was allowed to warm to −78° C. with venting, followed by resealing with a fresh vial cap and analysis by GC/MS.

GC/MS headspace analysis was performed with an Agilent 6890 GC/MS system using a 100 uL gas tight syringe in headspace mode. A Zebron ZB-624 GC/MS column (30 m×250 µm; 1.40 µm film thickness) was used for separation of analytes. The GC autoinjector was fitted with a gas-tight 100 uL syringe, and the needle height was adjusted to allow the injection of a 50 uL headspace sample from a 2 mL GC vial. The GC/MS method utilized helium as the carrier gas at a flow of 1 mL/min. The injection port was held at 200° C. with a split ratio of 20:1. The oven temperature was held at 37° C. for the 5 minute duration of the analysis. The Agilent 5793N mass selective detector was run in single ion monitoring (SIM) mode on m/z 55, 66, 67 and 70. Under these conditions, isoprene was observed to elute at 2.966 minutes (FIG. 88B). A standard of petroleum derived isoprene (Sigma-Aldrich) was also analyzed using this method and was found to contain additional C5 hydrocarbon isomers, which eluted shortly before or after the main peak and were quantified based on corrected GC area (FIG. 88A).

TABLE 8A

GC/MS analysis of petroleum-derived isoprene

| Compound | RT (min) | GC area | Area % of total C5 hydrocarbons |
|---|---|---|---|
| 2-methyl-1-butene | 2.689 | $18.2 \times 10^3$ | 0.017% |
| (Z)-2-pentene | 2.835 | $10.6 \times 10^4$ | 0.101% |
| Isoprene | 2.966 | $10.4 \times 10^7$ | 99.869% |
| 1,3-cyclopentadiene (CPD) | 3.297 | $12.8 \times 10^3$ | 0.012% |

TABLE 8B

GC/MS analysis of fermentation-derived isoprene (% total C5 hydrocarbons)

| Compound | RT (min) | Corrected GC Area | % of total C5 hydrocarbons |
|---|---|---|---|
| Isoprene | 2.966 | $8.1 \times 10^7$ | 100% |

In a separate experiment, a standard mixture of C5 hydrocarbons was analyzed to determine if the detector response was the same for each of the compounds. The compounds were 2-methyl-1-butene, 2-methyl-1,3-butadiene, (E)-2-pentene, (Z)-2-pentene and (E)-1,3-pentadiene. In this case, the analysis was performed on an Agilent DB-Petro column (100 m×0.25 mm, 0.50 um film thickness) held at 50° C. for 15 minutes. The GC/MS method utilized helium as the carrier gas at a flow of 1 mL/min. The injection port was held at 200° C. with a split ratio of 50:1. The Agilent 5793N mass selective detector was run in full scan mode from m/z 19 to m/z 250. Under these conditions, a 100 ug/L concentration of each standard produced the same detector response within experimental error.

IV. Compositions Comprising Isoprene Adsorbed to a Solid Phase.

Biologically-produced isoprene was adsorbed to activated carbon resulting in a solid phase containing 50 to 99.9% carbon, 0.1% to 50% isoprene, 0.01% to 5% water, and minor amounts (<0.1%) of other volatile organic components.

Fermentation off-gas was run through a copper condensation coil held at 0° C., followed by a granulated silica desiccant filter in order to remove water vapor. The dehumidified off-gas was then run through carbon containing filters (Koby Jr, Koby Filters, Mass.) to the point at which breakthrough of isoprene was detected in the filter exhaust by GC/MS. The amount of isoprene adsorbed to the cartridge can be determined indirectly by calculating the concentration in the offgas, the overall flow rate and the percent breakthrough over the collection period. Alternately the adsorbed isoprene can be recovered from the filters by thermal, vacuum, or solvent-mediated desorption.

V. Collection and Analysis of Condensed Isoprene.

Fermentation off-gas is dehumidified, and the $CO_2$ removed by filtration through a suitable adsorbent (e.g., ascarite). The resulting off-gas stream is then run through a liquid nitrogen-cooled condenser in order to condense the VOCs in the stream. The collection vessel contains t-butyl catechol to inhibit the resulting isoprene condensate. The condensate is analyzed by GC/MS and NMR in order to determine purity using standard methods, such as those described herein.

VI. Production of Prenyl Alcohols by Fermentation

Analysis of off-gas from an *E. coli* BL21 (DE3) strain expressing a Kudzu isoprene synthase revealed the presence of both isoprene and 3-methyl-3-buten-1-ol (isoprenol). The levels of the two compounds in the fermentation off-gas over the fermentation are shown in FIG. 89 as determined by headspace GC/MS. Levels of isoprenol (3-methyl-3-buten-1-ol, 3-MBA) attained was nearly 10 ug/$L_{offgas}$ in this experiment. Additional experiments produced levels of approximately 20 ug/$L_{offgas}$ in the fermentation off-gas.

Example 11

The De-Coupling of Growth and Production of Isoprene in *E. coli* Expressing Genes From the Mevalonic Acid Pathway and Fermented in a Fed-Batch Culture Example 11 illustrates the de-coupling of cell growth from mevalonic acid and isoprene production.

I. Fermentation Conditions

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in Di $H_2O$, pH to 3.0 with HCl/NaOH, then q.s. to volume, and filter sterilized with a 0.22 micron filter.

Fermentation was performed with *E. coli* cells containing the pTrcHis2AUpperPathway (also called pTrcUpperMVA, FIGS. 91 and 92A-92C) (50 µg/ml carbenicillin) or the pCL PtrcUpperMVA (also called pCL PtrcUpperPathway (FIG. 26)) (50 µg/ml spectinomycin) plasmids. For experiments in which isoprene was produced, the *E. coli* cells also contained the pTrc KKDyIkIS (50 µg/ml kanamycin) plasmid. These experiments were carried out to monitor mevalonic acid or isoprene formation from glucose at the desired fermentation pH 7.0 and temperature 30° C. An inoculum of an *E. coli* strain taken from a frozen vial was streaked onto an LA broth agar plate (with antibiotics) and incubated at 37° C. A single colony was inoculated into tryptone-yeast extract medium. After the inoculum grew to optical density 1.0 when measured at 550 nm, it was used to inoculate the bioreactor.

Glucose was fed at an exponential rate until cells reached the stationary phase. After this time the glucose feed was decreased to meet metabolic demands. Induction was achieved by adding IPTG. The mevalonic acid concentration in fermentation broth was determined by applying perchloric acid (Sigma-Aldrich #244252) treated samples (0.3 M incubated at 4° C. for 5 minutes) to an organic acids HPLC column (BioRad #125-0140). The concentration was determined by comparing the broth mevalonic acid peak size to a calibration curve generated from mevalonolacetone (Sigma-Aldrich #M4667) treated with perchloric acid to form D,L-mevalonate. The isoprene level in the off gas from the bioreactor was determined as described herein. The isoprene titer is defined as the amount of isoprene produced per liter of fermentation broth.

Figure 60A:
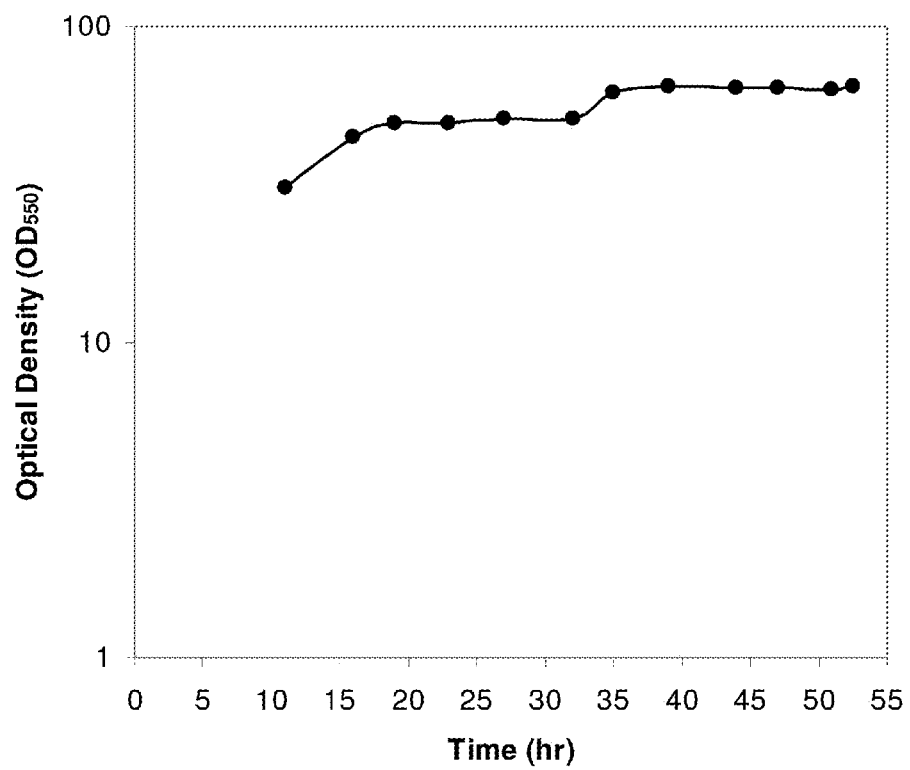
FIGS. 60A-60C are the time courses of optical density, mevalonic acid titer, and specific productivity within the 150-L bioreactor fed with glucose.
Figure 60B:
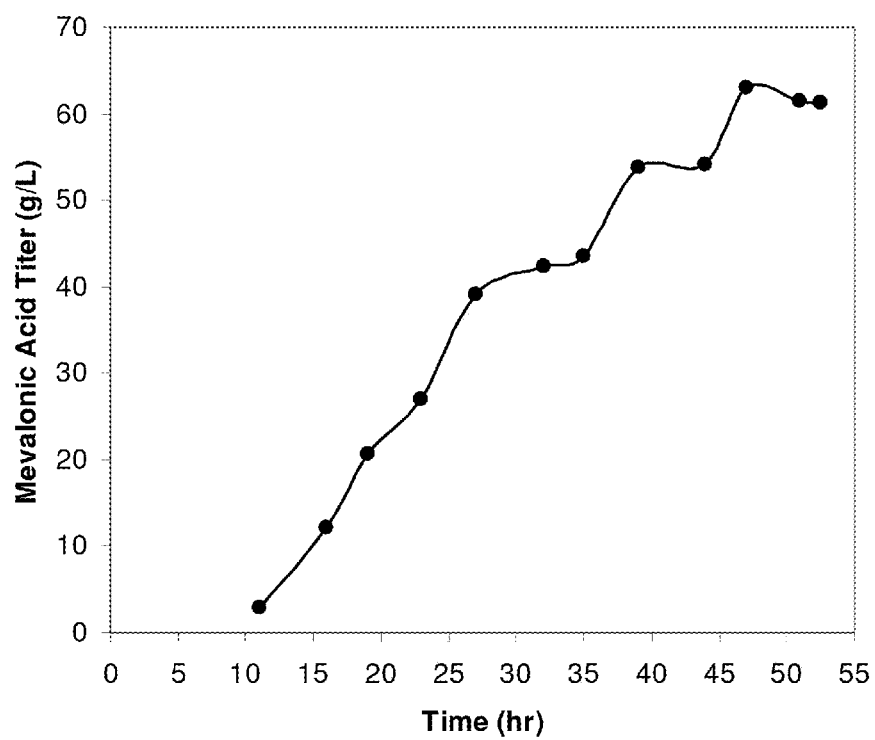
Figure 60C:
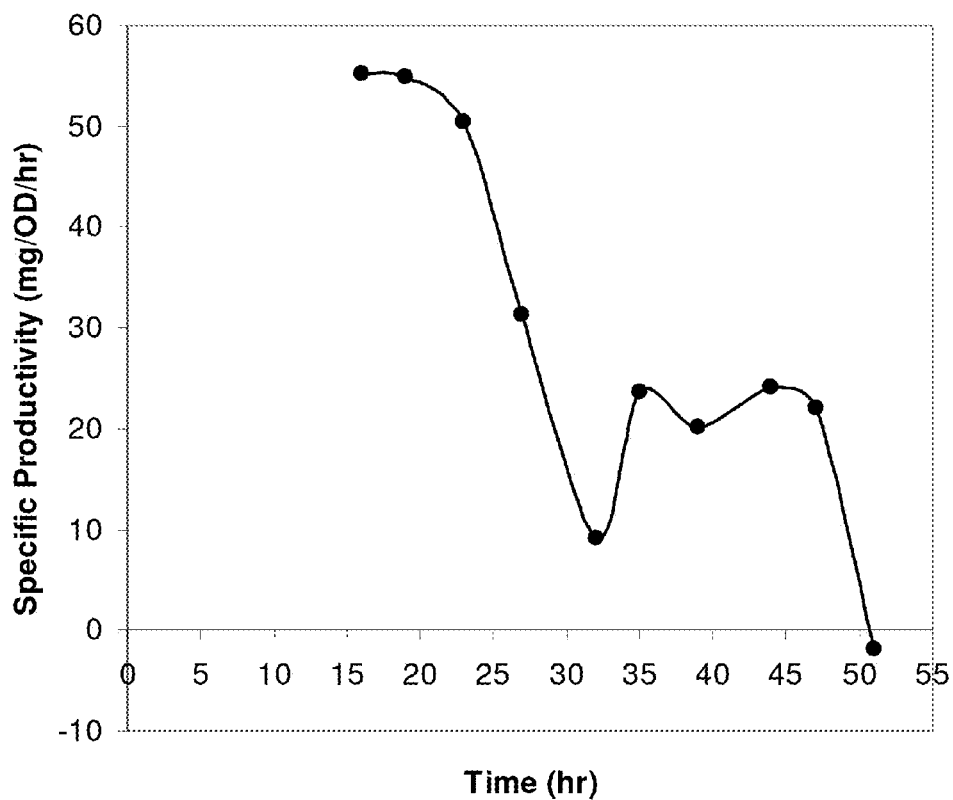

II. Mevalonic Acid Production from *E. coli* BL21 (DE3) Cells Expressing the pTrcUpperMVA Plasmid at a 150-L Scale BL21 (DE3) cells that were grown on a plate as explained above in Example 11, part I were inoculated into a flask containing 45 mL of tryptone-yeast extract medium and incubated at 30° C. with shaking at 170 rpm for 5 hours. This solution was transferred to a 5-L bioreactor of tryptone-yeast extract medium, and the cells were grown at 30° C. and 27.5 rpm until the culture reached an $OD_{550}$ of 1.0. The 5 L of inoculum was seeded into a 150-L bioreactor containing 45-kg of medium. The IPTG concentration was brought to 1.1 mM when the $OD_{550}$ reached a value of 10. The $OD_{550}$ profile within the bioreactor over time is shown in FIG. 60A. The mevalonic acid titer increased over the course of the fermentation to a final value of 61.3 g/L (FIG. 60B). The specific productivity profile throughout the fermentation is shown in FIG. 60C and a comparison to FIG. 60A illustrates the de-coupling of growth and mevalonic acid production. The total amount of mevalonic acid produced during the 52.5 hour fermentation was 4.0 kg from 14.1 kg of utilized glucose. The molar yield of utilized carbon that went into producing mevalonic acid during fermentation was 34.2%.

Figure 61A:
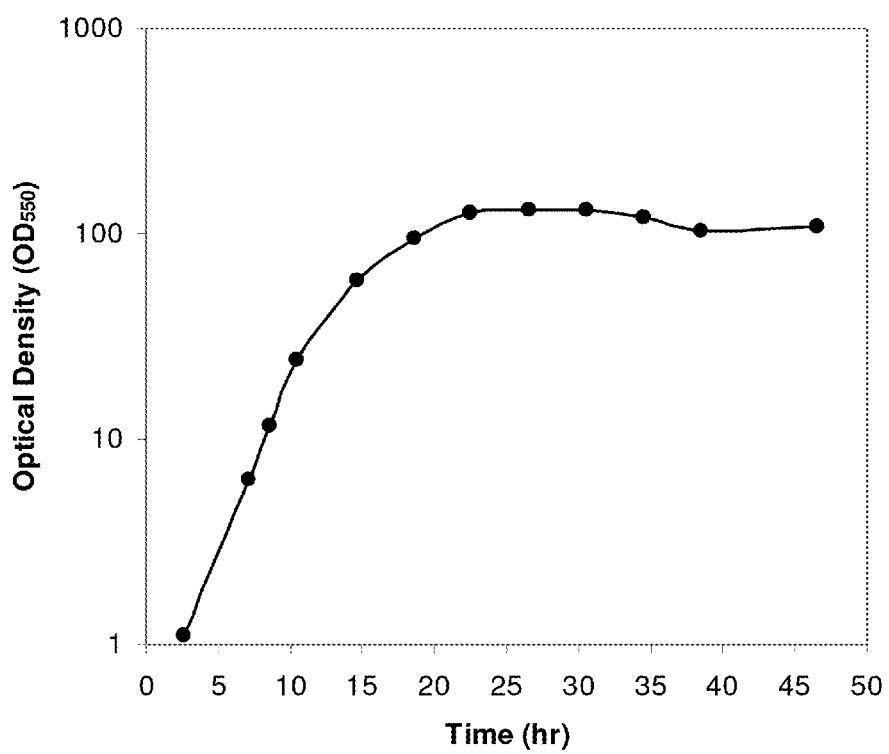
FIGS. 61A-61C are the time courses of optical density, mevalonic acid titer, and specific productivity within the 15-L bioreactor fed with glucose.
Figure 61B:
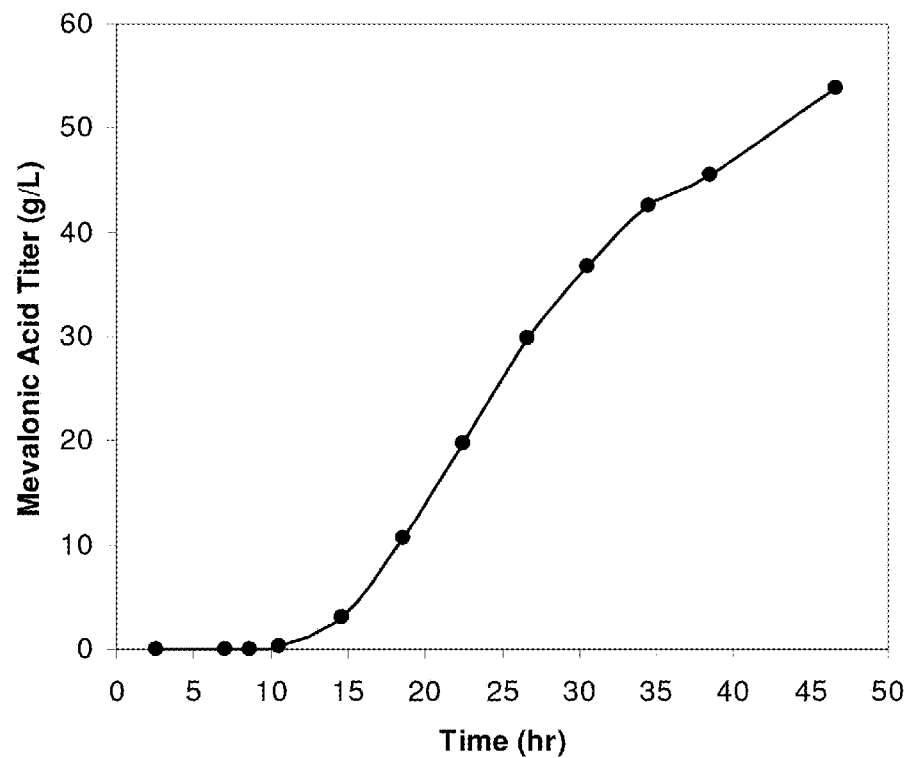
Figure 61C:
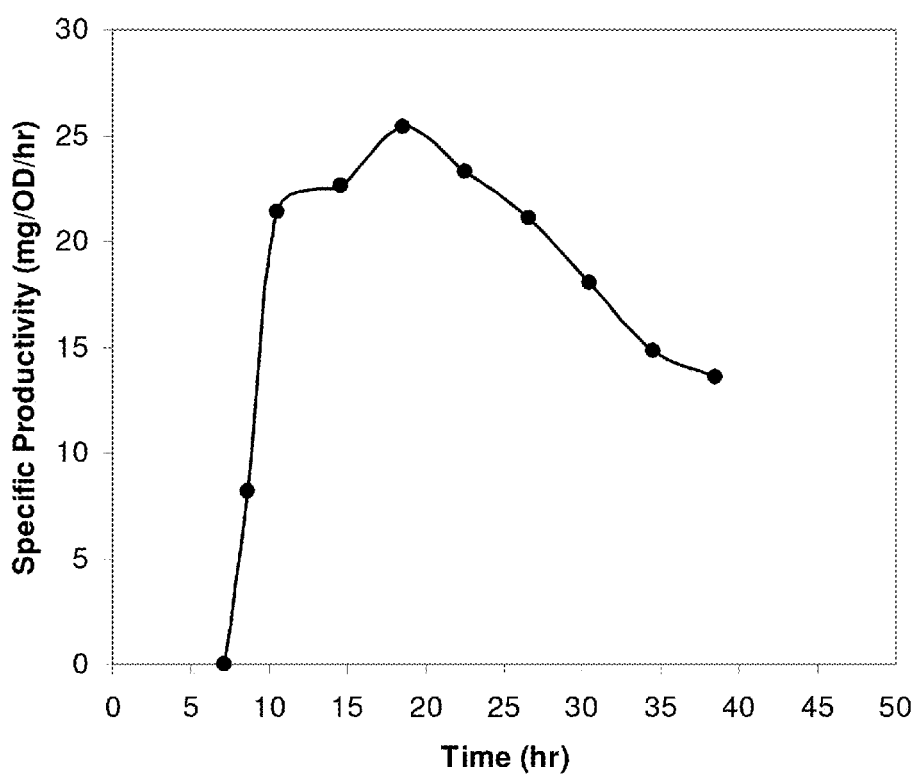

III. Mevalonic Acid Production from *E. coli* BL21 (DE3) Cells Expressing the pTrcUpperMVA Plasmid at a 15-L Scale BL21 (DE3) cells that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 10. The $OD_{550}$ profile within the bioreactor over time is shown in FIG. 61A. The mevalonic acid titer increased over the course of the fermentation to a final value of 53.9 g/L (FIG. 61B). The specific productivity profile throughout the fermentation is shown in FIG. 61C and a comparison to FIG. 61A illustrates the de-coupling of growth and mevalonic acid production. The total amount of mevalonic acid produced during the 46.6 hour fermentation was 491 g from 2.1 kg of utilized glucose. The molar yield of utilized carbon that went into producing mevalonic acid during fermentation was 28.8%.

Figure 62A:
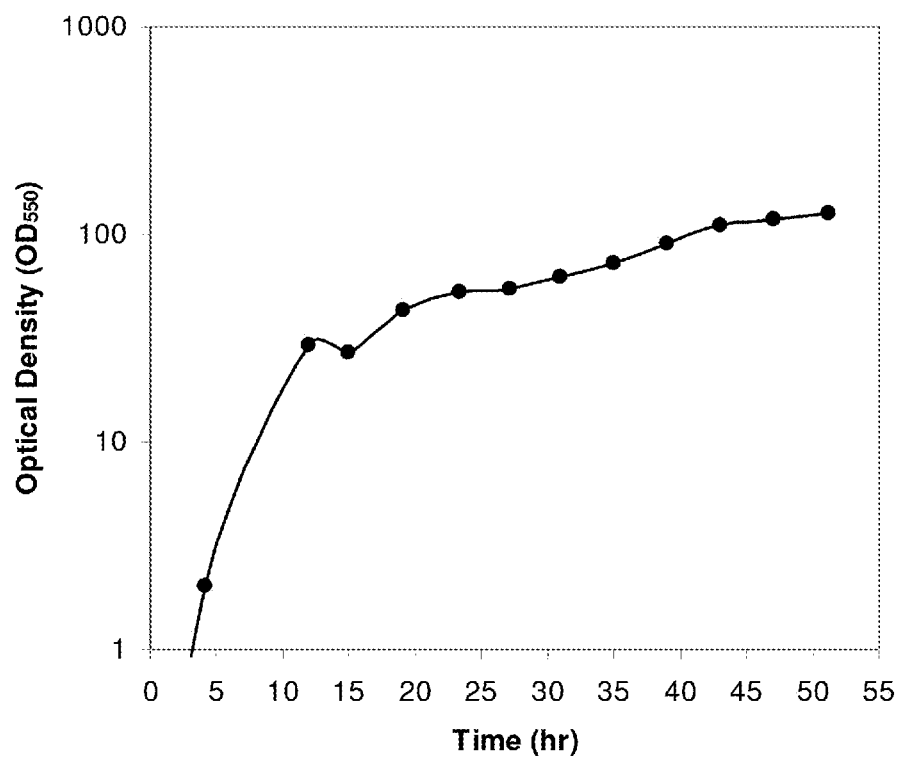
FIGS. 62A-62C are the time courses of optical density, mevalonic acid titer, and specific productivity within the 15-L bioreactor fed with glucose.
Figure 62B:
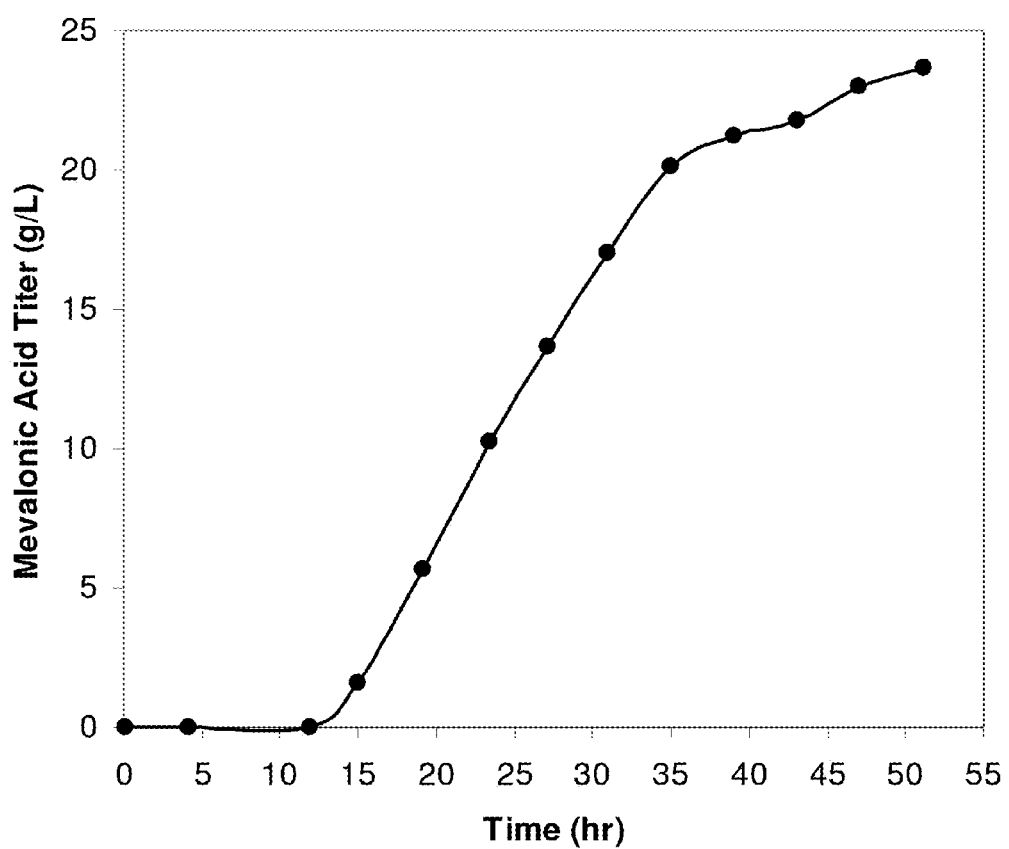
Figure 62C:
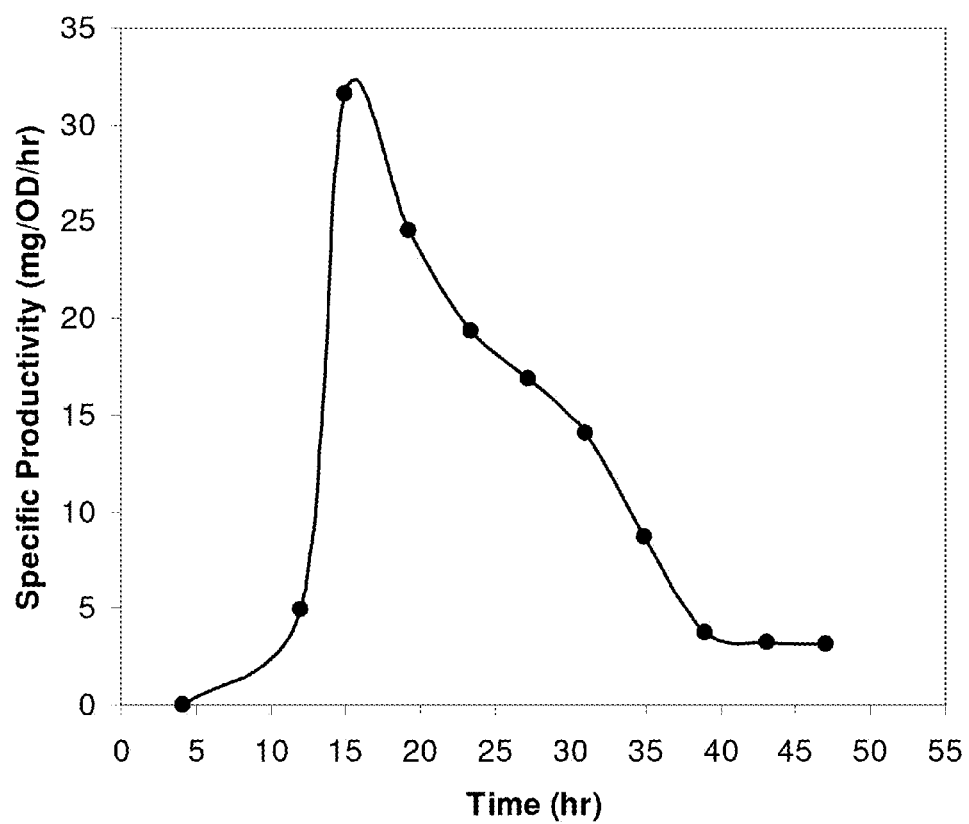

IV. Mevalonic Acid Production from *E. coli* FM5 Cells Expressing the pTrcUpperMVA Plasmid at a 15-L Scale FM5 cells that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 30. The $OD_{550}$ profile within the bioreactor over time is shown in FIG. 62A. The mevalonic acid titer increased over the course of the fermentation to a final value of 23.7 g/L (FIG. 62B). The specific productivity profile throughout the fermentation is shown in FIG. 62C and a comparison to FIG. 62A illustrates the de-coupling of growth and mevalonic acid production. The total amount of mevalonic acid produced during the 51.2 hour fermentation was 140 g from 1.1 kg of utilized glucose. The molar yield of utilized carbon that went into producing mevalonic acid during fermentation was 15.2%.

Figure 63A:
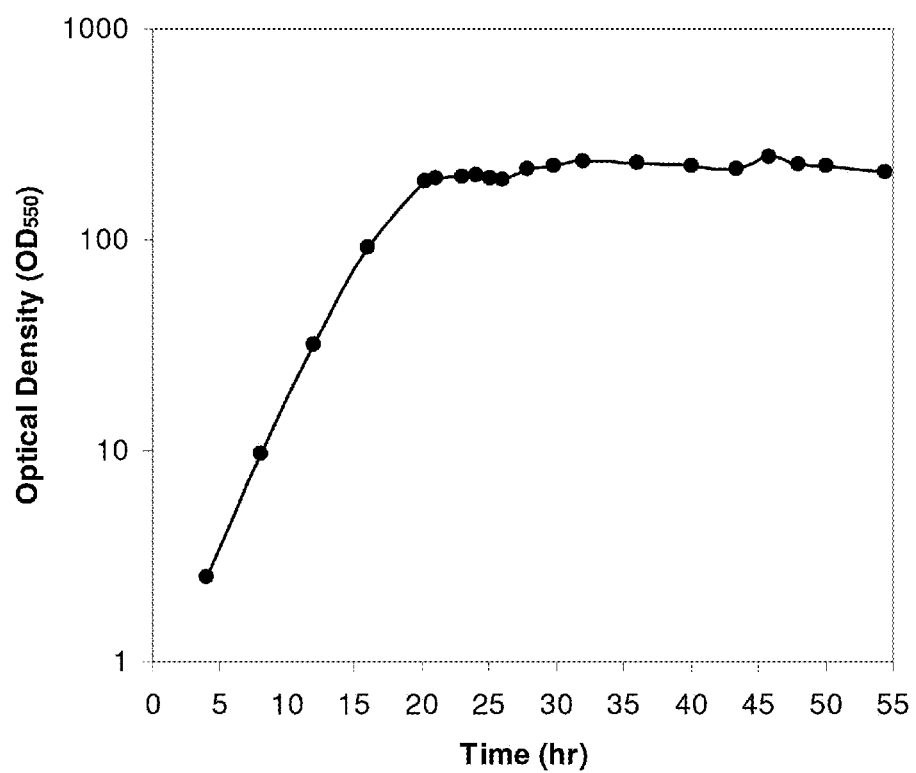
FIG. 63A-63C are the time courses of optical density, isoprene titer, and specific productivity within the 15-L bioreactor fed with glucose.
Figure 63B:
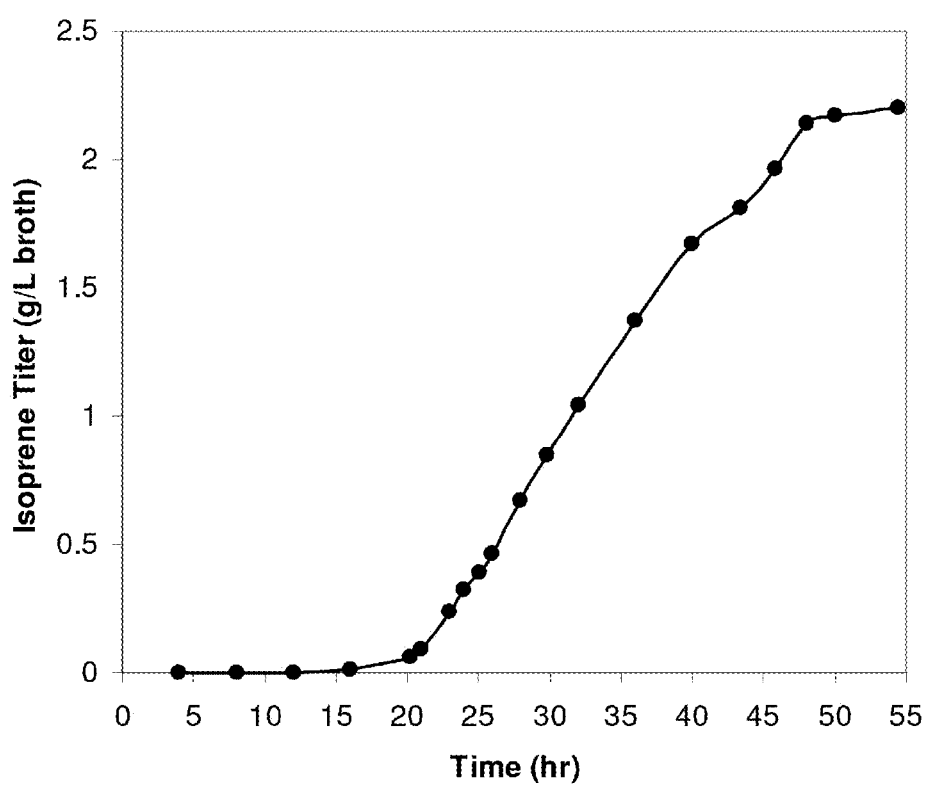
Figure 63C:
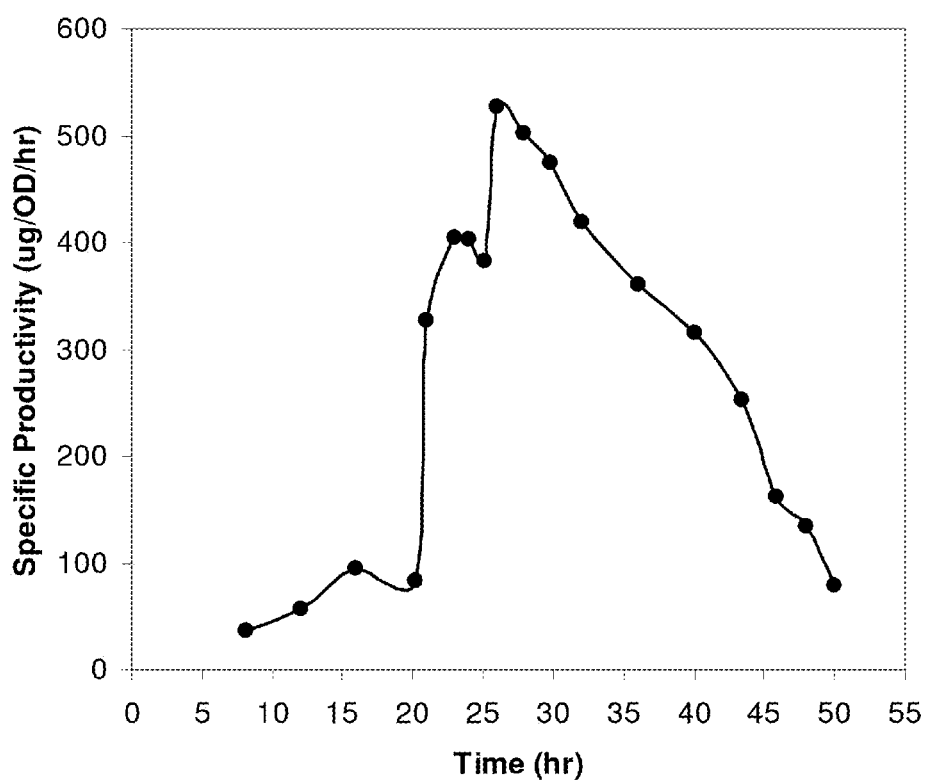

V. Isoprene Production from *E. coli* BL21 (DE3) Cells Expressing the pCL PtrcUpperMVA and pTrc KKDyIkIS Plasmids at a 15-L Scale BL21 (DE3) cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 25 µM when the $OD_{550}$ reached a value of 10. The IPTG concentration was raised to 50 uM when $OD_{550}$ reached 190. The IPTG concentration was raised to 100 uM at 38 hours of fermentation. The $OD_{550}$ profile within the bioreactor over time is shown in FIG. 63A. The isoprene titer increased over the course of the fermentation to a final value of 2.2 g/L broth (FIG. 63B). The specific productivity profile throughout the fermentation is shown in FIG. 63C and a comparison to FIG. 63A illustrates the de-coupling of growth and isoprene production. The total amount of isoprene produced during the 54.4 hour fermentation was 15.9 g from 2.3 kg of utilized glucose. The molar yield of utilized carbon that went into producing isoprene during fermentation was 1.53%.

Figure 64A:
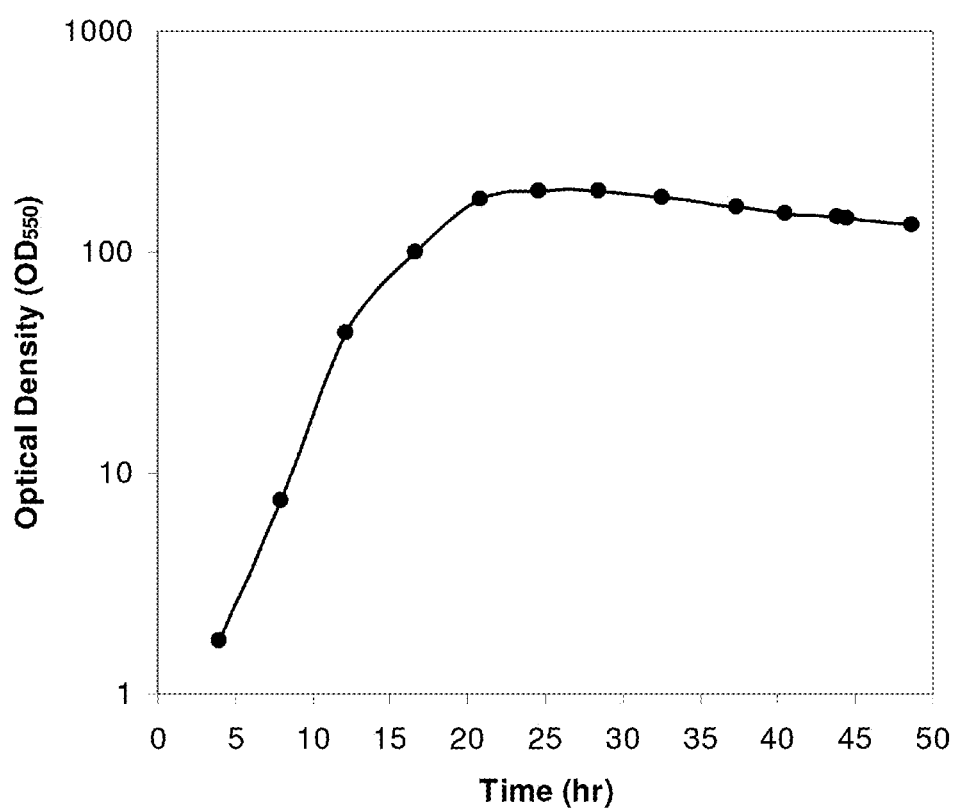
FIGS. 64A-64C are the time courses of optical density, isoprene titer, and specific productivity within the 15-L bioreactor fed with glucose.
Figure 64B:
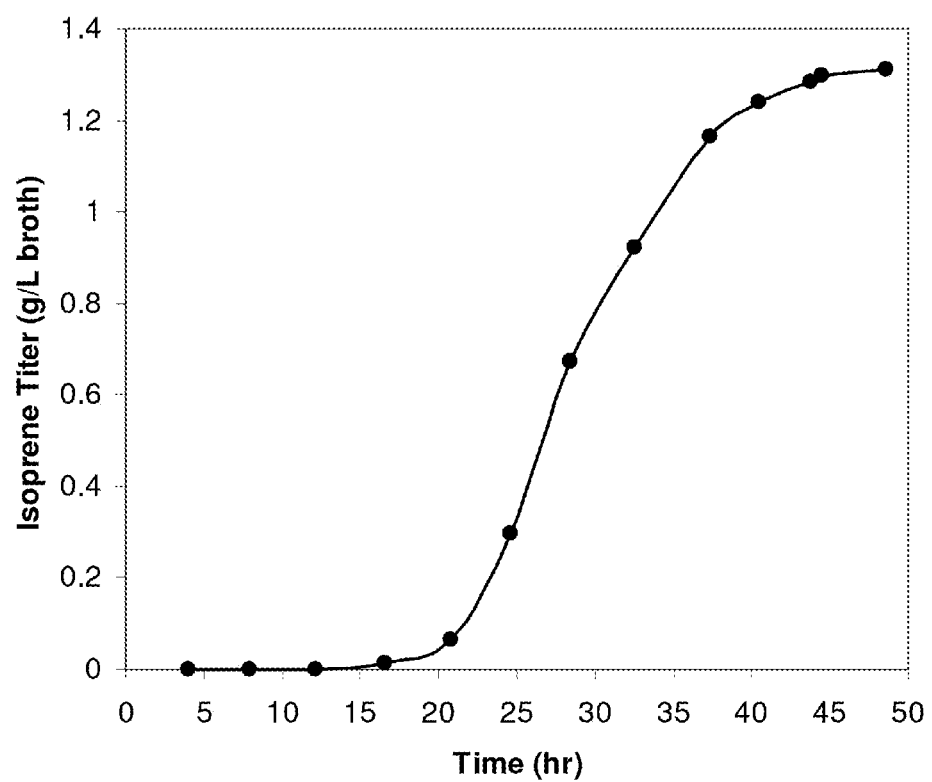
Figure 64C:
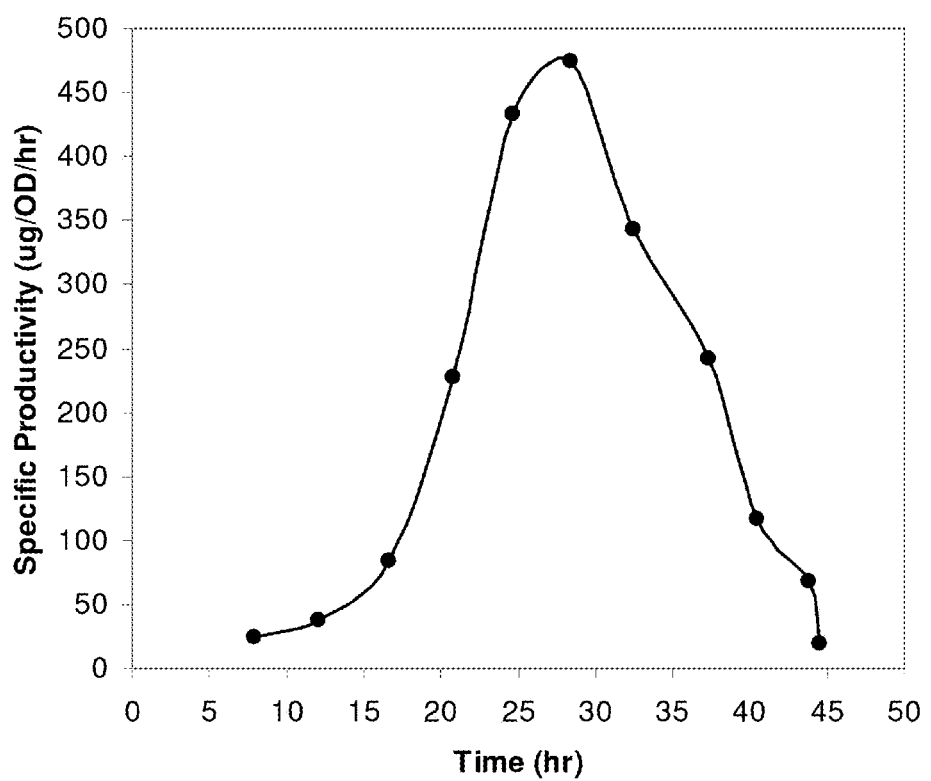

VI. Isoprene Production from *E. coli* BL21 (DE3) Tuner Cells Expressing the pCL PtrcUpperMVA and pTrc KKDyIkIS Plasmids at a 15-L Scale BL21 (DE3) tuner cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 26 µM when the $OD_{550}$ reached a value of 10. The IPTG concentration was raised to 50 uM when $OD_{550}$ reached 175. The $OD_{550}$ profile within the bioreactor over time is shown in FIG. 64A. The isoprene titer increased over the course of the fermentation to a final value of 1.3 g/L broth (FIG. 64B). The specific productivity profile throughout the fermentation is shown in FIG. 64C and a comparison to FIG. 64A illustrates the de-coupling of growth and isoprene production. The total amount of isoprene produced during the 48.6 hour fermentation was 9.9 g from 1.6 kg of utilized glucose. The molar yield of utilized carbon that went into producing isoprene during fermentation was 1.34%.

Figure 65A:
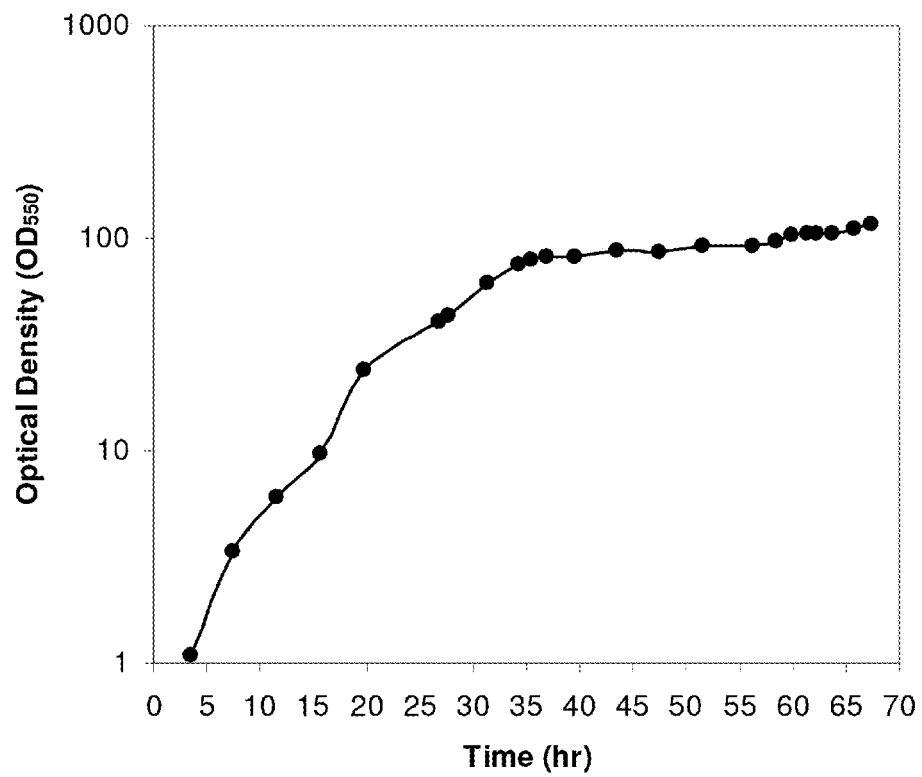
FIGS. 65A-65C are the time courses of optical density, isoprene titer, and specific productivity within the 15-L bioreactor fed with glucose.
Figure 65B:
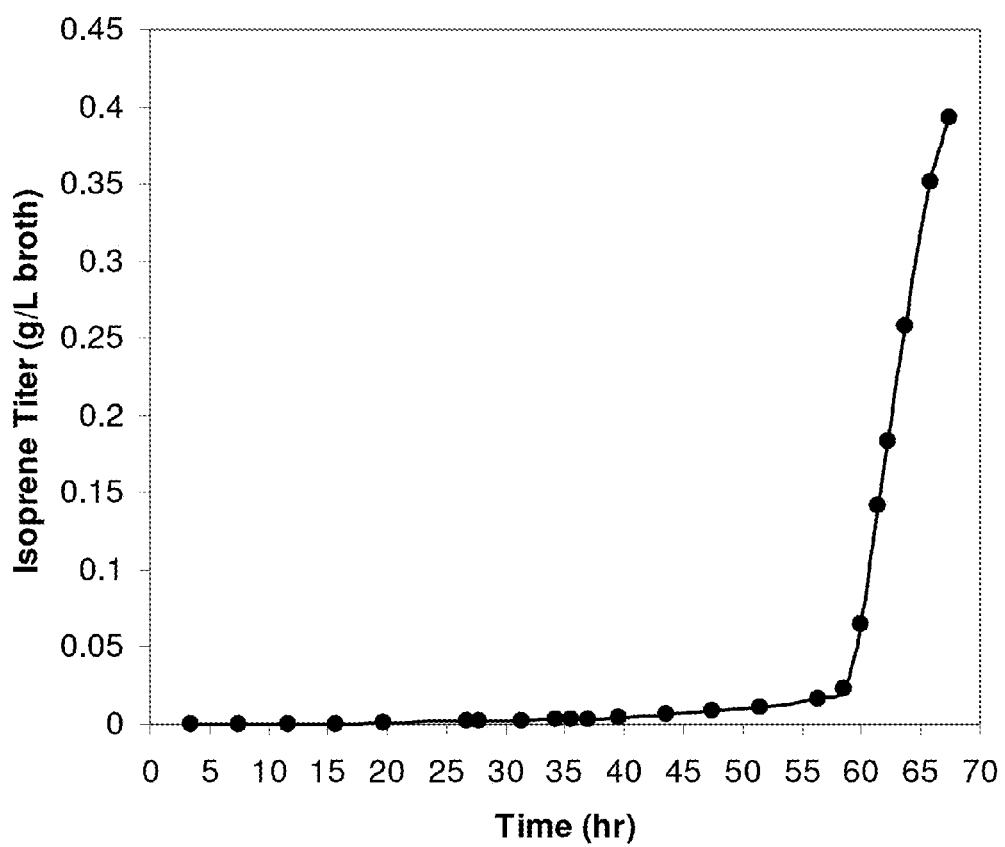
Figure 65C:
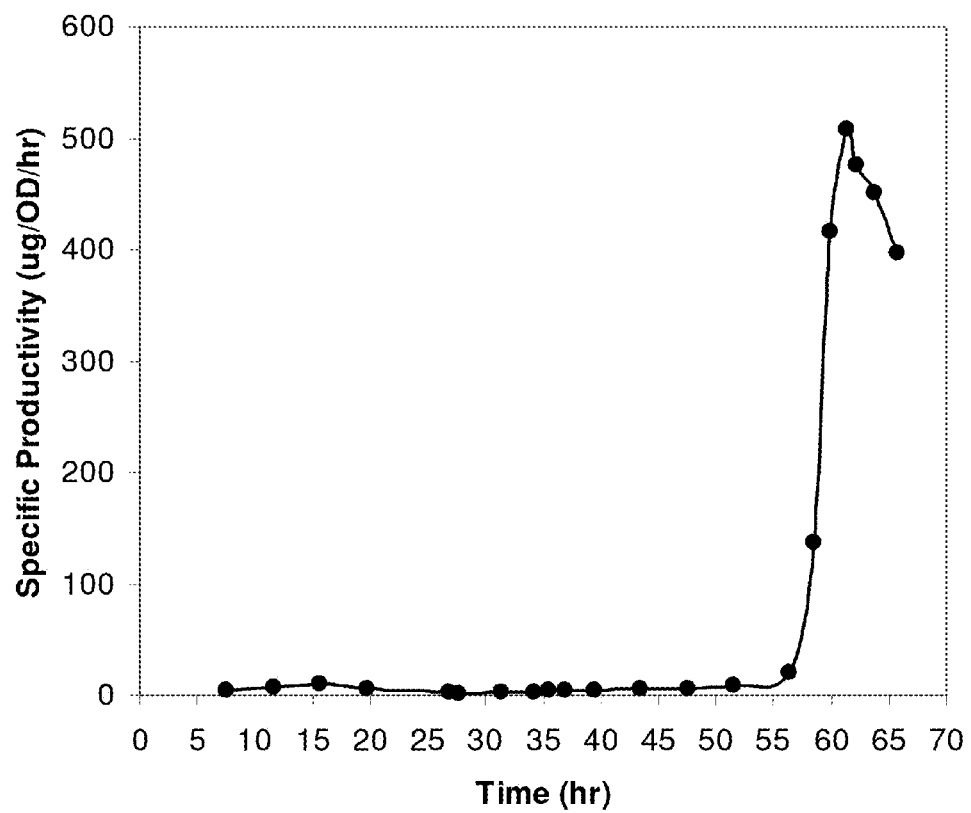

VII. Isoprene Production from *E. coli* MG1655 Cells Expressing the pCL PtrcUpperMVA and pTrc KKDyIkIS Plasmids at a 15-L Scale MG1655 cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 24 µM when the $OD_{550}$ reached a value of 45. The $OD_{550}$ profile within the bioreactor over time is shown in FIG. 65A. The isoprene titer increased over the course of the fermentation to a final value of 393 mg/L broth (FIG. 65B). The specific productivity profile throughout the fermentation is shown in FIG. 65C and a comparison to FIG. 65A illustrates the de-coupling of growth and isoprene production. The total amount of isoprene produced during the 67.4 hour fermentation was 2.2 g from 520 g of utilized glucose. The molar yield of utilized carbon that went into producing isoprene during fermentation was 0.92%.

Figure 66A:
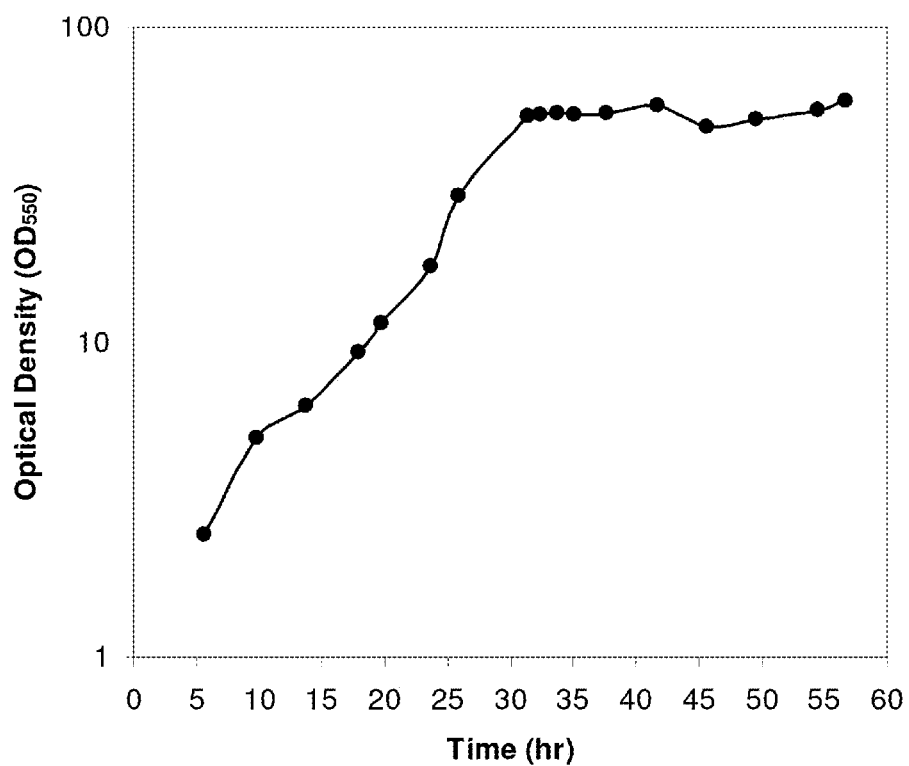
FIGS. 66A-66C are the time courses of optical density, isoprene titer, and specific productivity within the 15-L bioreactor fed with glucose.
Figure 66B:
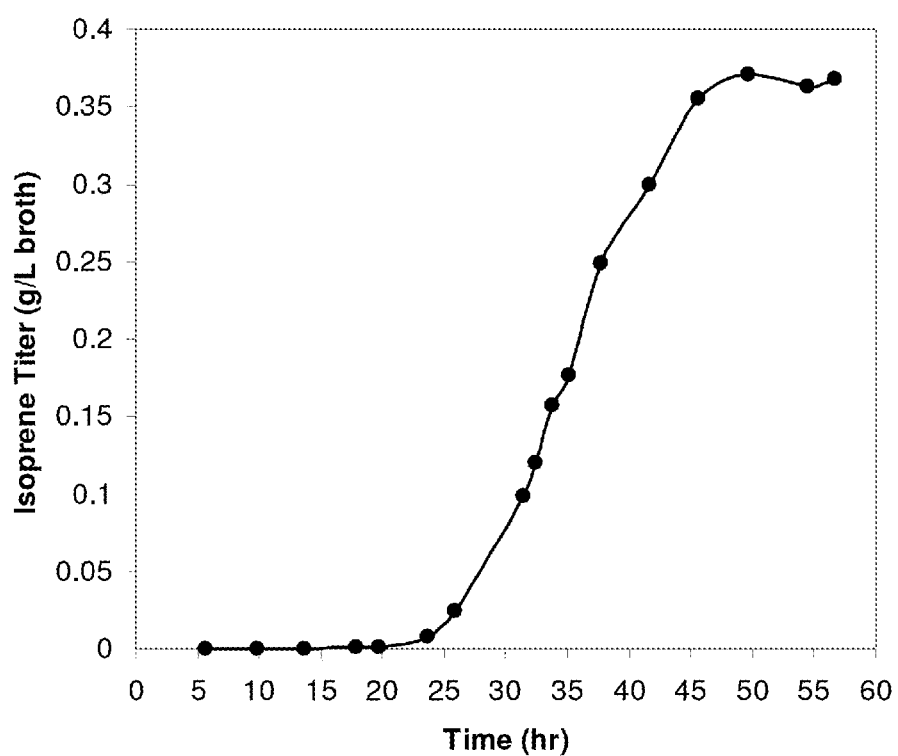
Figure 66C:
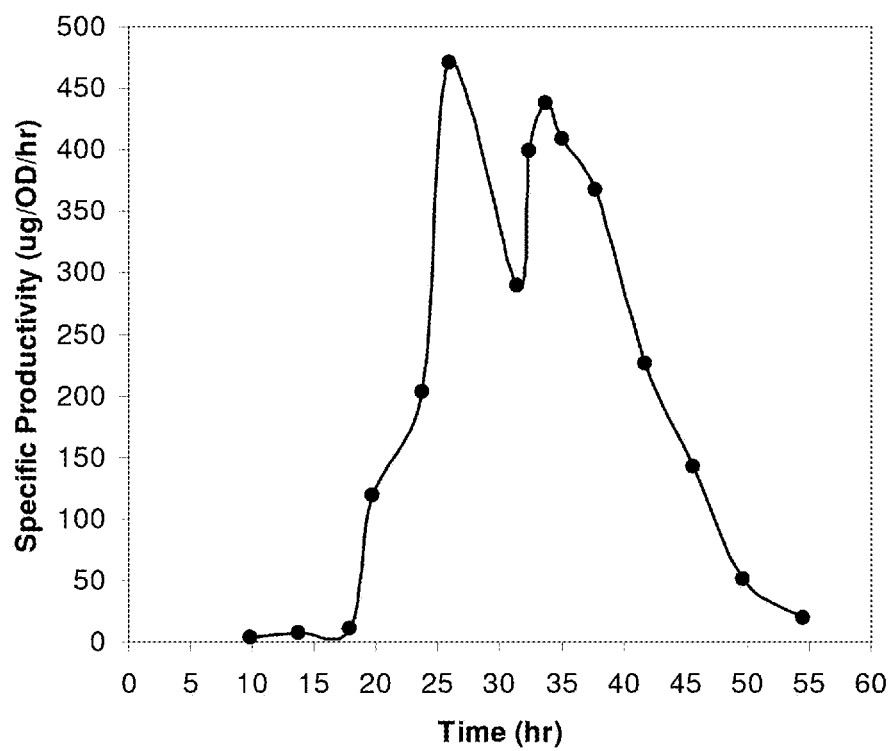

VIII. Isoprene Production from *E. coli* MG1655ack-pta Cells Expressing the pCL PtrcUpperMVA and pTrc KKDyIkIS Plasmids at a 15-L Scale MG1655ack-pta cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 30 µM when the $OD_{550}$ reached a value of 10. The $OD_{550}$ profile within the bioreactor over time is shown in FIG. 66A. The isoprene titer increased over the course of the fermentation to a final value of 368 mg/L broth (FIG. 66B). The specific productivity profile throughout the fermentation is shown in FIG. 66C and a comparison to FIG. 66A illustrates the de-coupling of growth and isoprene production. The total amount of isoprene produced during the 56.7 hour fermentation was 1.8 g from 531 g of utilized glucose. The molar yield of utilized carbon that went into producing isoprene during fermentation was 0.73%.

Figure 67A:
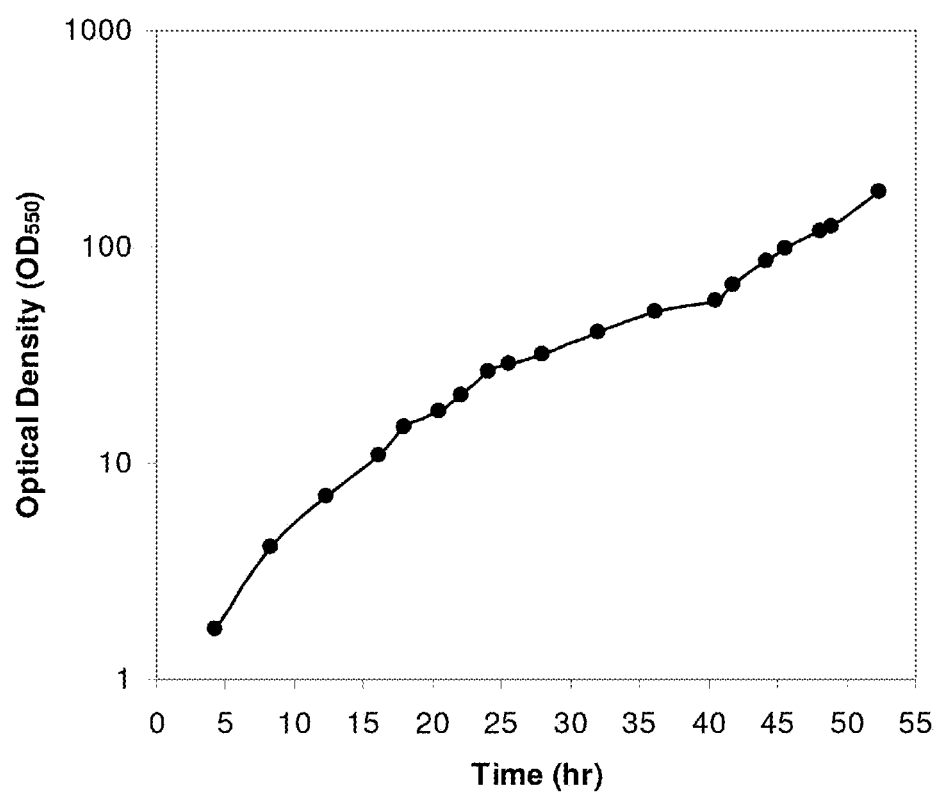
FIG. 67A-67C are the time courses of optical density, isoprene titer, and specific productivity within the 15-L bioreactor fed with glucose.
Figure 67B:
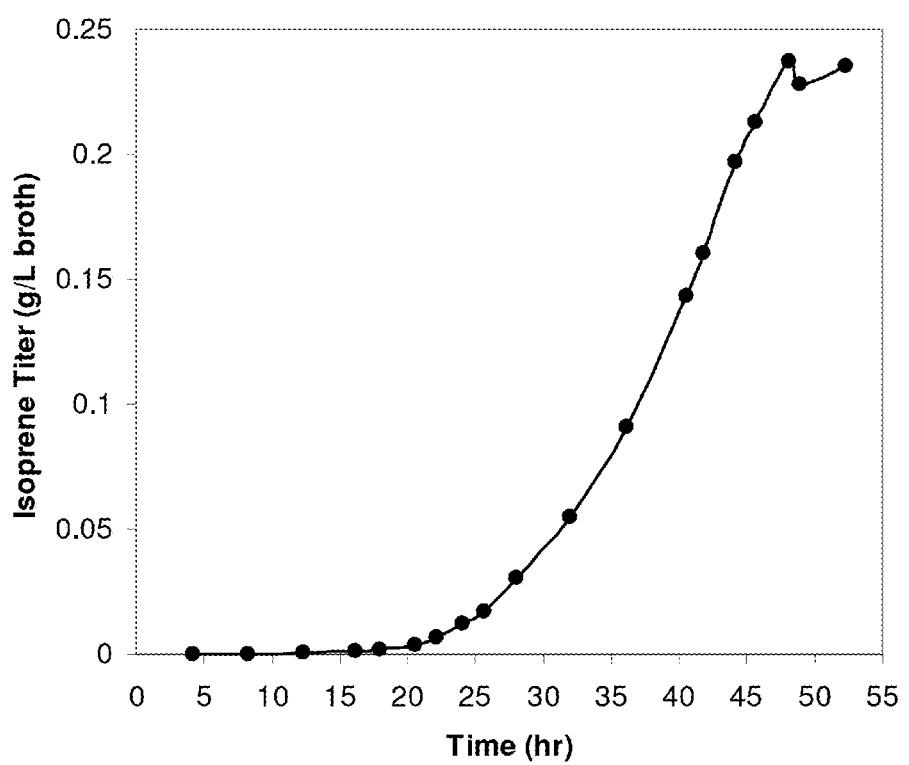
Figure 67C:
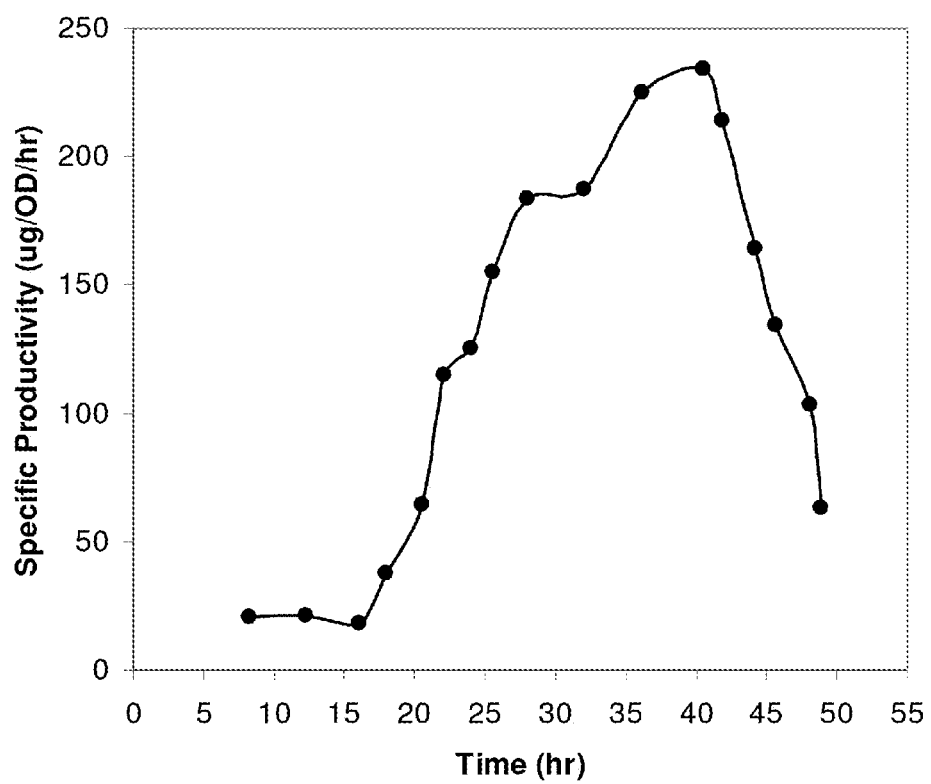

IX. Isoprene Production from *E. coli* FM5 Cells Expressing the pCL PtrcUpperMVA and pTrc KKDyIkIS Plasmids at a 15-L Scale FM5 cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 27 µM when the $OD_{550}$ reached a value of 15. The $OD_{550}$ profile within the bioreactor over time is shown in FIG. 67A. The isoprene titer increased over the course of the fermentation to a final value of 235 mg/L broth (FIG. 67B). The specific productivity profile throughout the fermentation is shown in FIG. 67C and a comparison to FIG. 67A illustrates the de-coupling of growth and isoprene production. The total amount of isoprene produced during the 52.3 hour fermentation was 1.4 g from 948 g of utilized glucose. The molar yield of utilized carbon that went into producing isoprene during fermentation was 0.32%.

Example 12

Production of Isoprene During the Exponential Growth Phase of *E. coli* Expressing Genes from the Mevalonic Acid Pathway and Fermented in a Fed-Batch Culture Example 12 illustrates the production of isoprene during the exponential growth phase of cells.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH$_2$O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*H$_2$O 40 g, MnSO$_4$*H$_2$O 30 g, NaCl 10 g, FeSO$_4$*7H$_2$O 1 g, CoCl$_2$*6H$_2$O 1 g, ZnSO*7H$_2$O 1 g, CuSO$_4$*5H$_2$O 100 mg, H$_3$BO$_3$ 100 mg, and NaMoO$_4$*2H$_2$O 100 mg. Each component is dissolved one at a time in Di H2O, pH to 3.0 with HCl/NaOH, then q.s. to volume and filter sterilized with 0.22 micron filter.

Fermentation was performed in a 15-L bioreactor with ATCC11303 E. coli cells containing the pCL PtrcUpperMVA and pTrc KKDyIkIS plasmids. This experiment was carried out to monitor isoprene formation from glucose at the desired fermentation pH 7.0 and temperature 30° C. An inoculum of E. coli strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 50 hour fermentation was 2.0 kg. Induction was achieved by adding IPTG. The IPTG concentration was brought to 25 uM when the optical density at 550 nm (OD$_{550}$) reached a value of 10. The IPTG concentration was raised to 50 uM when OD$_{550}$ reached 190. The OD$_{550}$ profile within the bioreactor over time is shown in FIG. 99. The isoprene level in the off gas from the bioreactor was determined as described herein. The isoprene titer increased over the course of the fermentation to a final value of 1.4 g/L (FIG. 100). The total amount of isoprene produced during the 50 hour fermentation was 10.0 g. The profile of the isoprene specific productivity over time within the bioreactor is shown in FIG. 101. The molar yield of utilized carbon that contributed to producing isoprene during fermentation was 1.1%. The weight percent yield of isoprene from glucose was 0.5%.

Example 13

Flammability Modeling and Testing of Isoprene

I. Summary of Flammability Modeling and Testing of Isoprene

Flammability modeling and experiments were performed for various hydrocarbon/oxygen/nitrogen/water/carbon dioxide mixtures. This modeling and experimental tested was aimed at defining isoprene and oxygen/nitrogen flammability curves under specified steam and carbon monoxide concentrations at a fixed pressure and temperature. A matrix of the model conditions is shown in Table 4, and a matrix of the experiments performed is shown in Table 5.

TABLE 4

Summary of Modeled Isoprene Flammability

| Series | Temperature (° C.) | Pressure (psig) | Steam Concentration (wt %) | Carbon Dioxide Concentration (wt. %) | Isoprene Concentration (vol. %) | Oxygen Concentration (vol. %) |
|---|---|---|---|---|---|---|
| A | 40 | 0 | 0 | 0 | Varying | Varying |
| B | 40 | 0 | 4 | 0 | Varying | Varying |
| C | 40 | 0 | 0 | 5 | Varying | Varying |
| D | 40 | 0 | 0 | 10 | Varying | Varying |
| E | 40 | 0 | 0 | 15 | Varying | Varying |
| F | 40 | 0 | 0 | 20 | Varying | Varying |
| G | 40 | 0 | 0 | 30 | Varying | Varying |

TABLE 5

Summary of Isoprene Flammability Tests

| Series Number | Temperature (° C.) | Pressure (psig) | Steam Concentration (vol. %) | Isoprene Concentration (vol. %) | Oxygen Concentration (vol. %) |
|---|---|---|---|---|---|
| 1 | 40 | 0 | 0 | Varying | Varying |
| 2 | 40 | 0 | 4 | Varying | Varying |

II. Description of Calculated Adiabatic Flame Temperature (CAFT) Model

Calculated adiabatic flame temperatures (CAFT) along with a selected limit flame temperature for combustion propagation were used to determine the flammability envelope for isoprene. The computer program used in this study to calculate the flame temperatures is the NASA Glenn Research Center CEA (Chemical Equilibrium with Applications) software.

There are five steps involved in determining the flammability envelope using an adiabatic flame temperature model for a homogeneous combustion mechanism (where both the fuel and oxidant are in the gaseous state): selection of the desired reactants, selection of the test condition, selection of the limit flame temperature, modification of the reactants, and construction of a flammability envelope from calculations.

In this first step, selection of desired reactants, a decision must be made as to the reactant species that will be present in the system and the quantities of each. In many cases the computer programs used for the calculations have a list of reactant and product species. If any of the data for the species to be studied are not found in the program, they may be obtained from other sources such as the JANAF tables or from the internet. In this current model data for water, nitrogen, oxygen and carbon dioxide were present in the program database. The program database did not have isoprene as a species; therefore the thermodynamic properties were incorporated manually.

The next step is to decide whether the initial pressure and temperature conditions that the combustion process is taking place in. In this model the pressure was 1 atmosphere (absolute) and the temperature was 40° C., the boiling point of isoprene.

The limit flame temperature for combustion can be either selected based on theoretical principles or determined experimentally. Each method has its own limitations.

Based on prior studies, the limit flame temperatures of hydrocarbons fall in the range of 1000 K to 1500 K. For this model, the value of 1500 K was selected. This is the temperature at which the reaction of carbon monoxide to carbon dioxide (a highly exothermic reaction and constitutes a significant proportion of the flame energy) becomes self sustaining.

Once the limit flame temperature has been decided upon, model calculations are performed on the given reactant mixture (species concentrations) and the adiabatic flame temperature is determined. Flame propagation is considered to have occurred only if the temperature is greater than the limit flame temperature. The reactant mixture composition is then modified to create data sets for propagation and non-propagation mixtures.

This type of model shows good agreement with the experimentally determined flammability limits. Regions outside the derived envelope are nonflammable and regions within it are flammable. The shape of the envelope forms a nose. The nose of the envelope is related to the limiting oxygen concentration (LOC) for gaseous fuels.

III. Results from Calculated Adiabatic Flame Temperature (CAFT) Model

Plotted in FIG. 68 through 74 are the CAFT model results for Series A to G, respectively. The figures plot the calculated adiabatic flame temperature (using the NASA CEA program) as a function of fuel concentration (by weight) for several oxygen/nitrogen ratios (by weight). The parts of the curve that are above 1500 K, the selected limit flame temperature, contain fuel levels sufficient for flame propagation. The results may be difficult to interpret in the form presented in FIG. 68 through 74. Additionally, the current form is not conducive to comparison with experimental data which is generally presented in terms of volume percent.

Figure 68:
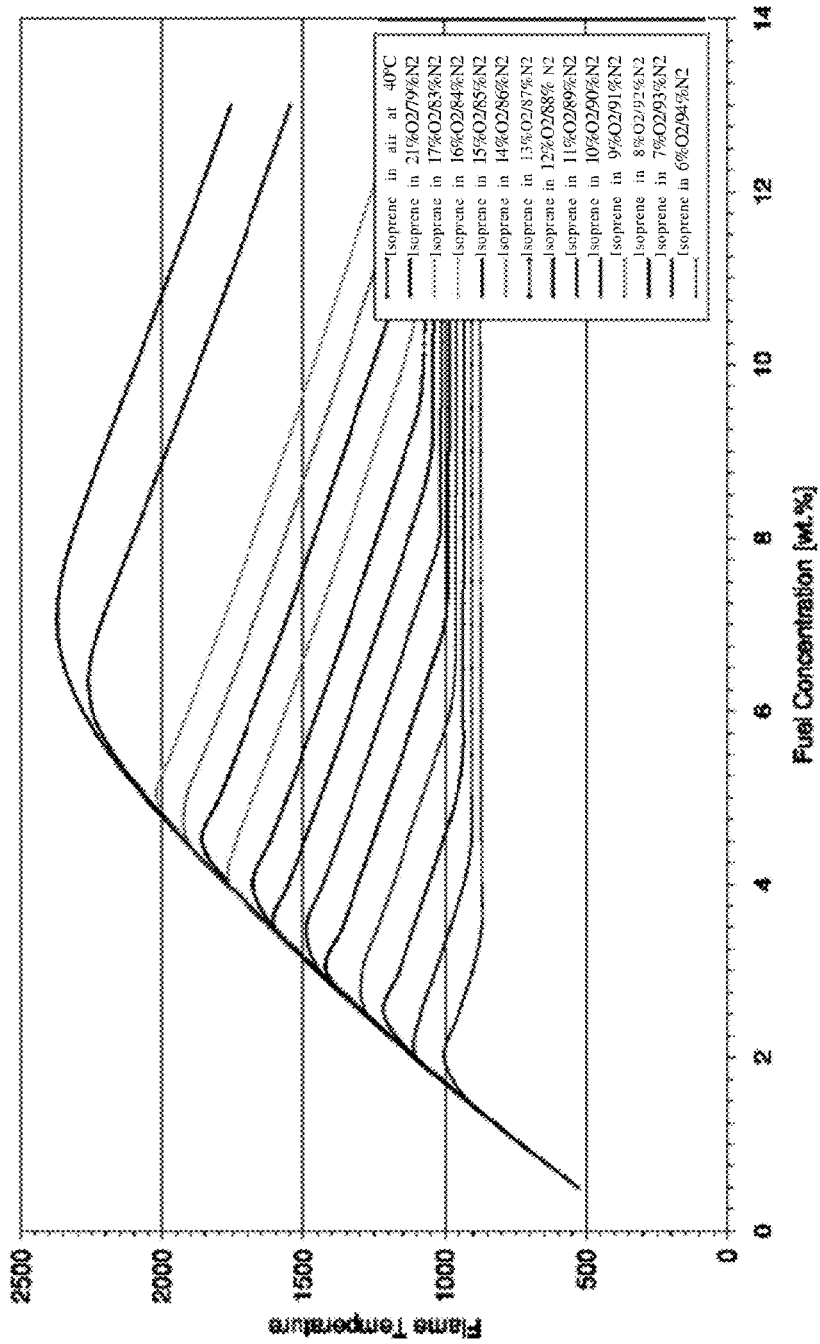
FIG. 68 is a graph of the calculated adiabatic flame temperatures for Series A as a function of fuel concentration for various oxygen levels. The figure legend lists the curves in the order in which they appear in the graph. For example, the first entry in the figure legend (isoprene in air at 40° C.) corresponds to the highest curve in the graph.
Figure 69:
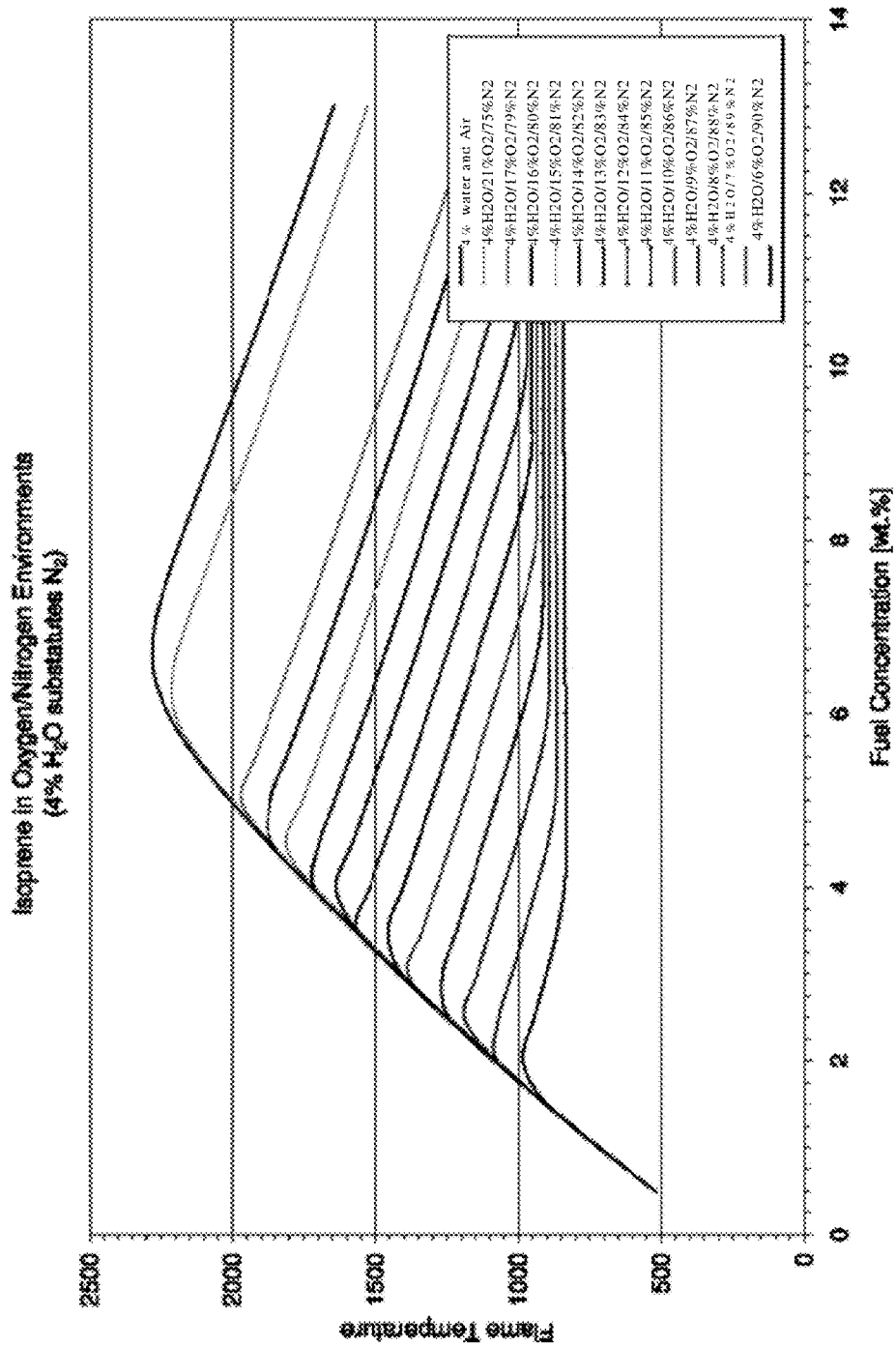
FIG. 69 is a graph of the calculated adiabatic flame temperatures for Series B as a function of fuel concentration for various oxygen levels with 4% water. The figure legend lists the curves in the order in which they appear in the graph.
Figure 70:
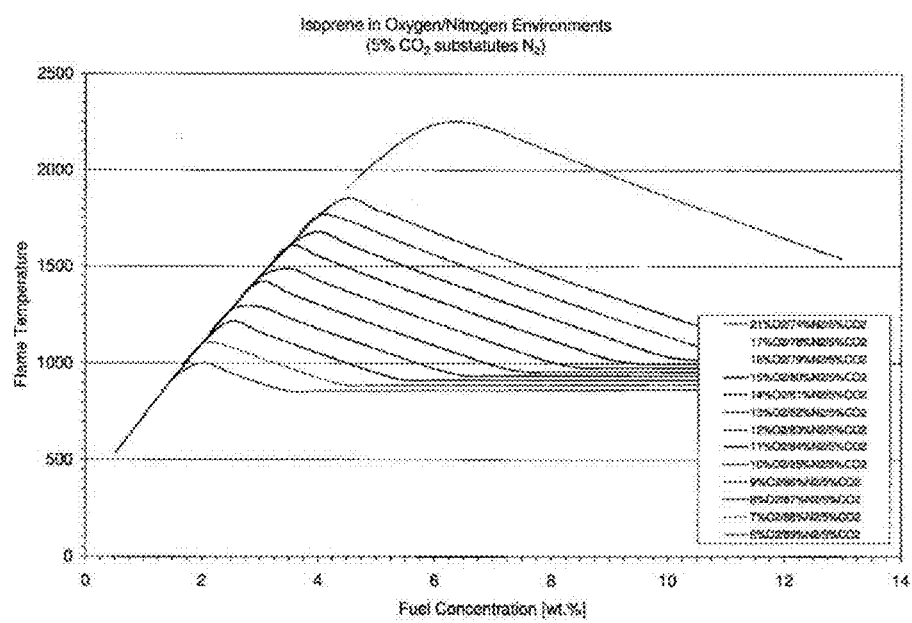
FIG. 70 is a graph of the calculated adiabatic flame temperatures for Series C as a function of fuel concentration for various oxygen levels with 5% $CO_2$. The figure legend lists the curves in the order in which they appear in the graph.
Figure 71:
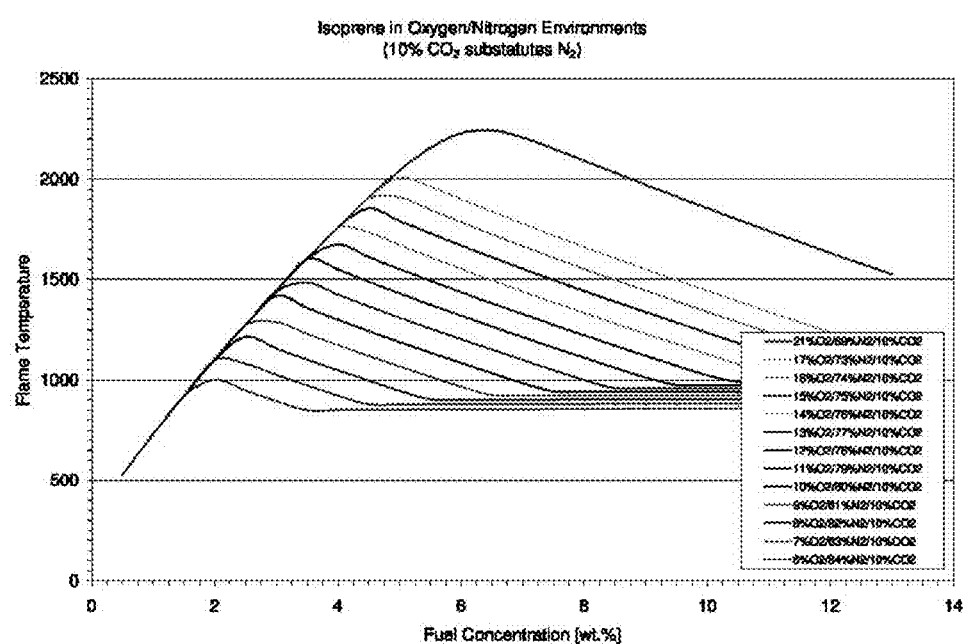
FIG. 71 is a graph of the calculated adiabatic flame temperatures for Series D as a function of fuel concentration for various oxygen levels with 10% $CO_2$. The figure legend lists the curves in the order in which they appear in the graph.
Figure 72:
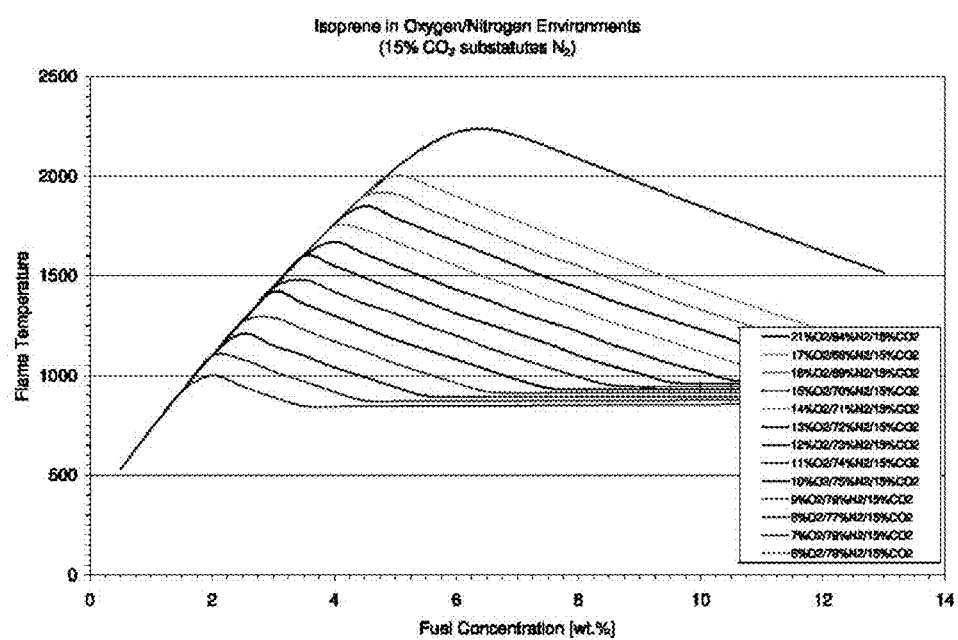
FIG. 72 is a graph of the calculated adiabatic flame temperatures for Series E as a function of fuel concentration for various oxygen levels with 15% $CO_2$. The figure legend lists the curves in the order in which they appear in the graph.
Figure 73:
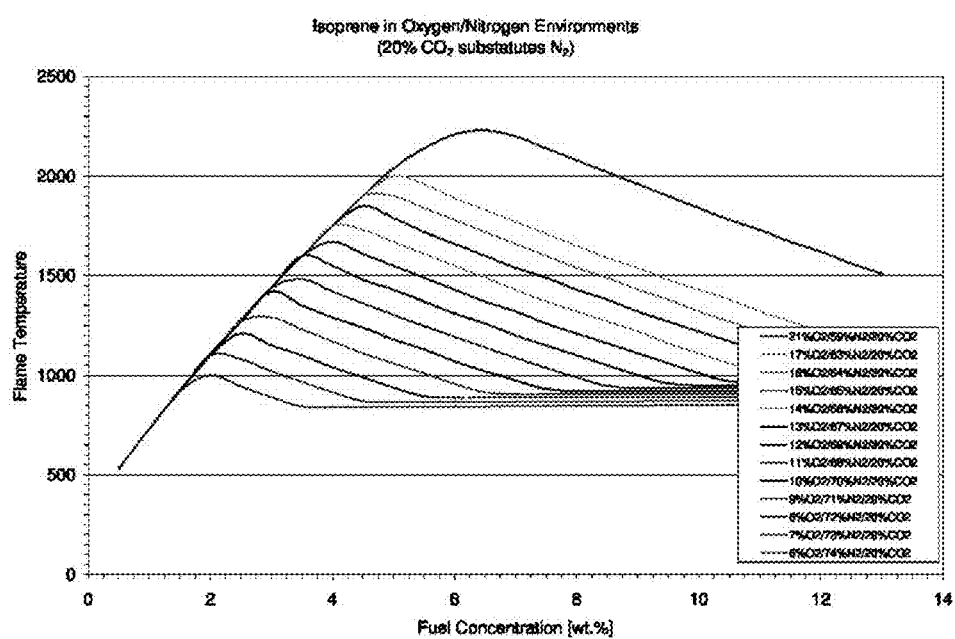
FIG. 73 is a graph of the calculated adiabatic flame temperatures for Series F as a function of fuel concentration for various oxygen levels with 20% $CO_2$. The figure legend lists the curves in the order in which they appear in the graph.
Figure 74:
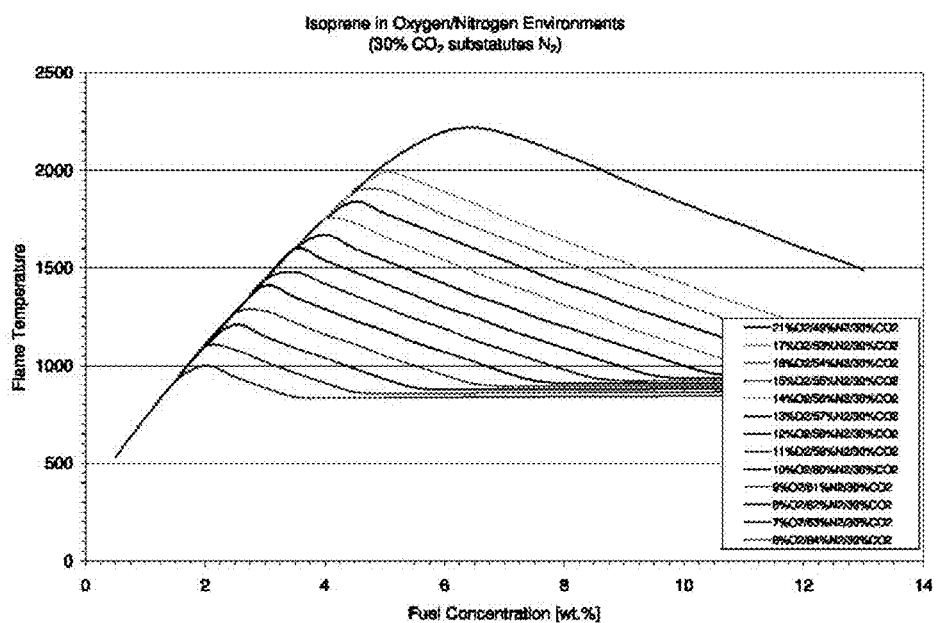
FIG. 74 is a graph of the calculated adiabatic flame temperatures for Series G as a function of fuel concentration for various oxygen levels with 30% $CO_2$. The figure legend lists the curves in the order in which they appear in the graph.

Using Series A as an example the data in FIG. 68 can be plotted in the form of a traditional flammability envelope. Using FIG. 68 and reading across the 1500 K temperature line on the ordinate one can determine the fuel concentration for this limit flame temperature by dropping a tangent to the abscissa for each curve (oxygen to nitrogen ratio) that it intersects. These values can then be tabulated as weight percent of fuel for a given weight percent of oxidizer (FIG. 75A). Then knowing the composition of the fuel (100 wt. % isoprene) and the composition of the oxidizer (relative content of water, oxygen and nitrogen) molar quantities can be established.

Figure 75B:
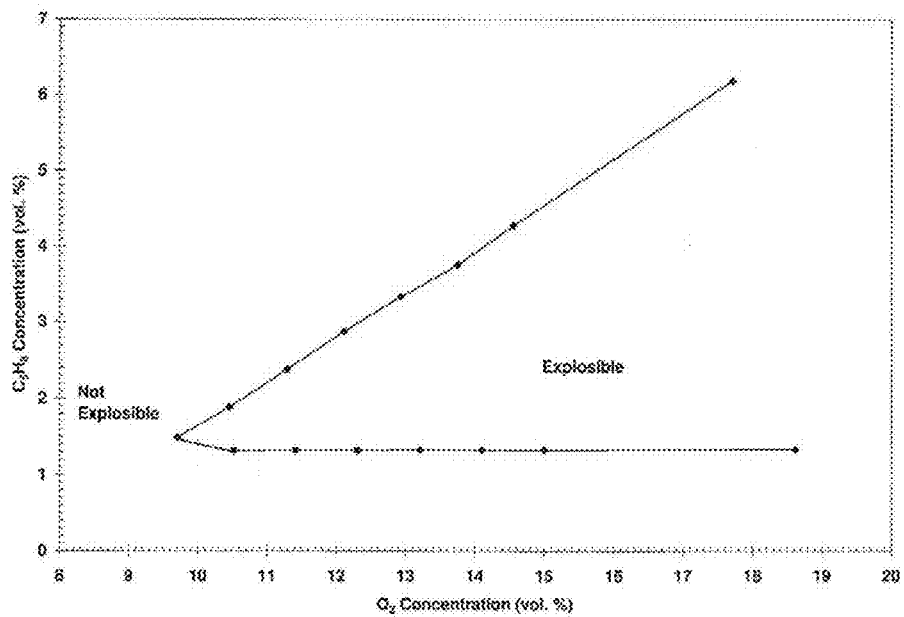
FIG. 75B is a graph of the flammability results from the CAFT model for Series A in FIG. 68 plotted as volume percent.
Figure 76B:
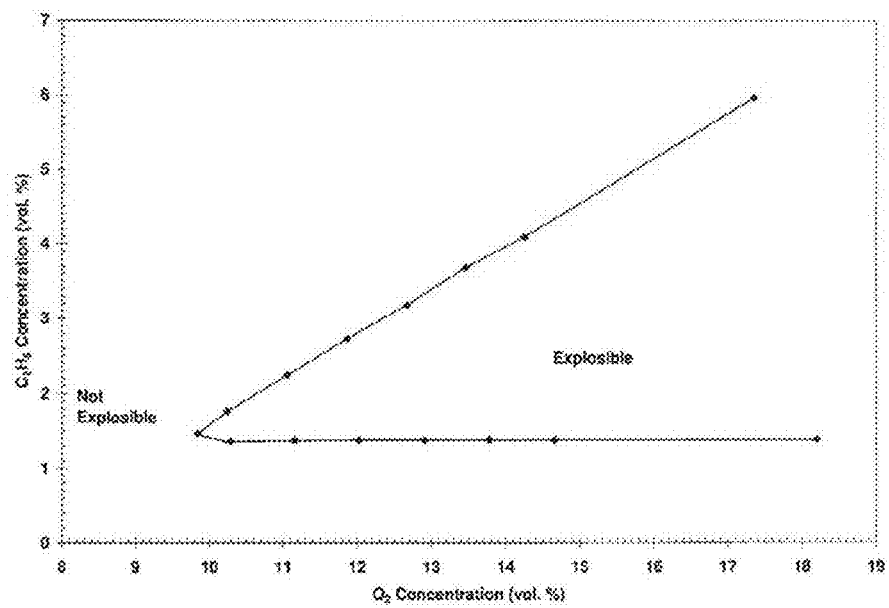
FIG. 76B is a graph of the flammability results from the CAFT model for Series B in FIG. 69 plotted as volume percent.

From these molar quantities percentage volume concentrations can be calculated. The concentrations in terms of volume percent can then be plotted to generate a flammability envelope (FIG. 75B). The area bounded by the envelope is the explosible range and the area excluded is the non-explosible range. The "nose" of the envelope is the limiting oxygen concentration. FIGS. 76A and 76B contain the calculated volume concentrations for the flammability envelope for Series B generated from data presented in FIG. 69. A similar approach can be used on data presented in FIGS. 70-74.

IV. Flammability Testing Experimental Equipment and Procedure

Figure 77:
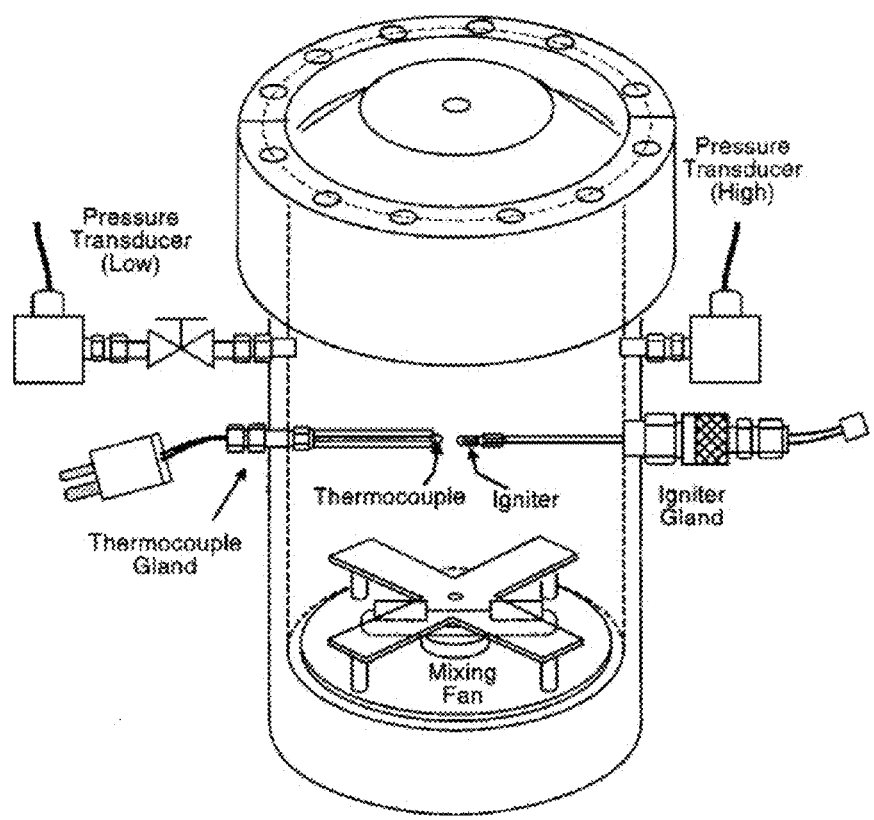
FIG. 77 is a figure of the flammability test vessel.

Flammability testing was conducted in a 4 liter high pressure vessel. The vessel was cylindrical in shape with an inner diameter of 6" and an internal height of 8.625". The temperature of the vessel (and the gases inside) was maintained using external heaters that were controlled by a PID controller. To prevent heat losses, ceramic wool and reflective insulation were wrapped around the pressure vessel. Type K thermocouples were used the measure the temperature of the gas space as well as the temperature of the vessel itself. FIG. 77 illustrates the test vessel.

Before a test was ran, the vessel was evacuated and purged with nitrogen to ensure that any gases from previous tests were removed. A vacuum was then pulled on the vessel. The pressure after this had been done was typically around 0.06 bar(a). Due to the nitrogen purging, the gas responsible for this initial pressure was assumed to be nitrogen. Using partial pressures, water, isoprene, nitrogen, and oxygen were then added in the appropriate amounts to achieve the test conditions in question. A magnetically driven mixing fan within the vessel ensured mixing of the gaseous contents. The gases were allowed to mix for about 2 minutes with the fan being turned off approximately 1 minute prior to ignition.

The igniter was comprised of a 1.5 ohm nicrome coil and an AC voltage source on a timer circuit. Using an oscilloscope, it was determined that 34.4 VAC were delivered to the igniter for 3.2 seconds. A maximum current of 3.8 amps occurred approximately halfway into the ignition cycle. Thus, the maximum power was 131 W and the total energy provided over the ignition cycle was approximately 210 J.

Deflagration data was acquired using a variable reluctance Validyne DP215 pressure transducer connected to a data acquisition system. A gas mixture was considered to have deflagrated if the pressure rise was greater than or equal to 5%.

V. Results of Flammability Testing

The first experimental series (Series 1) was run at 40° C. and 0 psig with no steam. Running tests at varying concentrations of isoprene and oxygen produced the flammability curve shown in FIG. 78A. The data points shown in this curve are only those that border the curve. A detailed list of all the data points taken for this series is shown in FIGS. 80A and 80B.

Figure 78C:
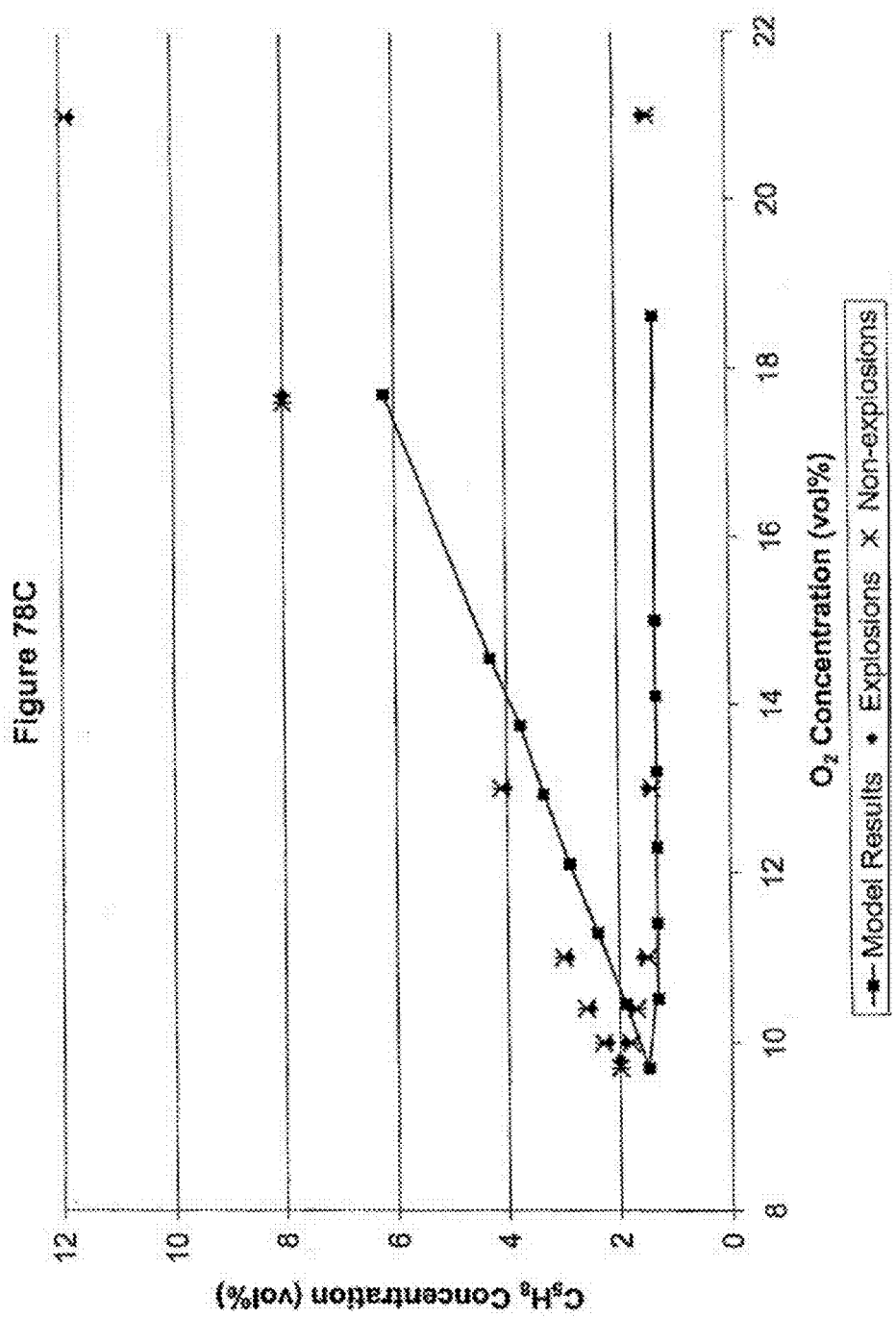
FIG. 78C is a graph of the flammability curve for Test Series 1 compared with the CAFT Model.

FIG. 78B summarizes the explosibility data points shown in FIG. 78A. FIG. 78C is a comparison of the experimental data with the CAFT model predicted flammability envelope. The model agrees very well with the experimental data. Discrepancies may be due to the non-adiabatic nature of the test chamber and limitations of the model. The model looks at an infinite time horizon for the oxidation reaction and does not take into consideration any reaction kinetic limitation.

Additionally, the model is limited by the number of equilibrium chemical species that are in its database and thus may not properly predict pyrolytic species. Also, the flammability envelope developed by the model uses one value for a limit flame temperature (1500K). The limit flame temperature can be a range of values from 1,000K to 1,500K depending on the reacting chemical species. The complex nature of pyrolytic chemical species formed at fuel concentrations above the stoichiometric fuel/oxidizer level is one reason why the model may not accurately predict the upper flammable limit for this system.

The second experimental series (Series 2) was run at 40° C. and 0 psig with a fixed steam concentration of 4%. Running tests at varying concentrations of isoprene and oxygen produced the flammability curve shown in FIG. 79A. The data points shown in this curve are only those that border the curve. A detailed list of all the data points taken for this series is shown in FIG. 81. Due to the similarity between the data in Series 1 only the key points of lower flammable limit, limiting oxygen concentration, and upper flammable limits were tested. The addition of 4% steam to the test mixture did not significantly change the key limits of the flammability envelope. It should be noted that higher concentrations of steam/water and or other inertants may influence the flammability envelope.

Figure 79A:
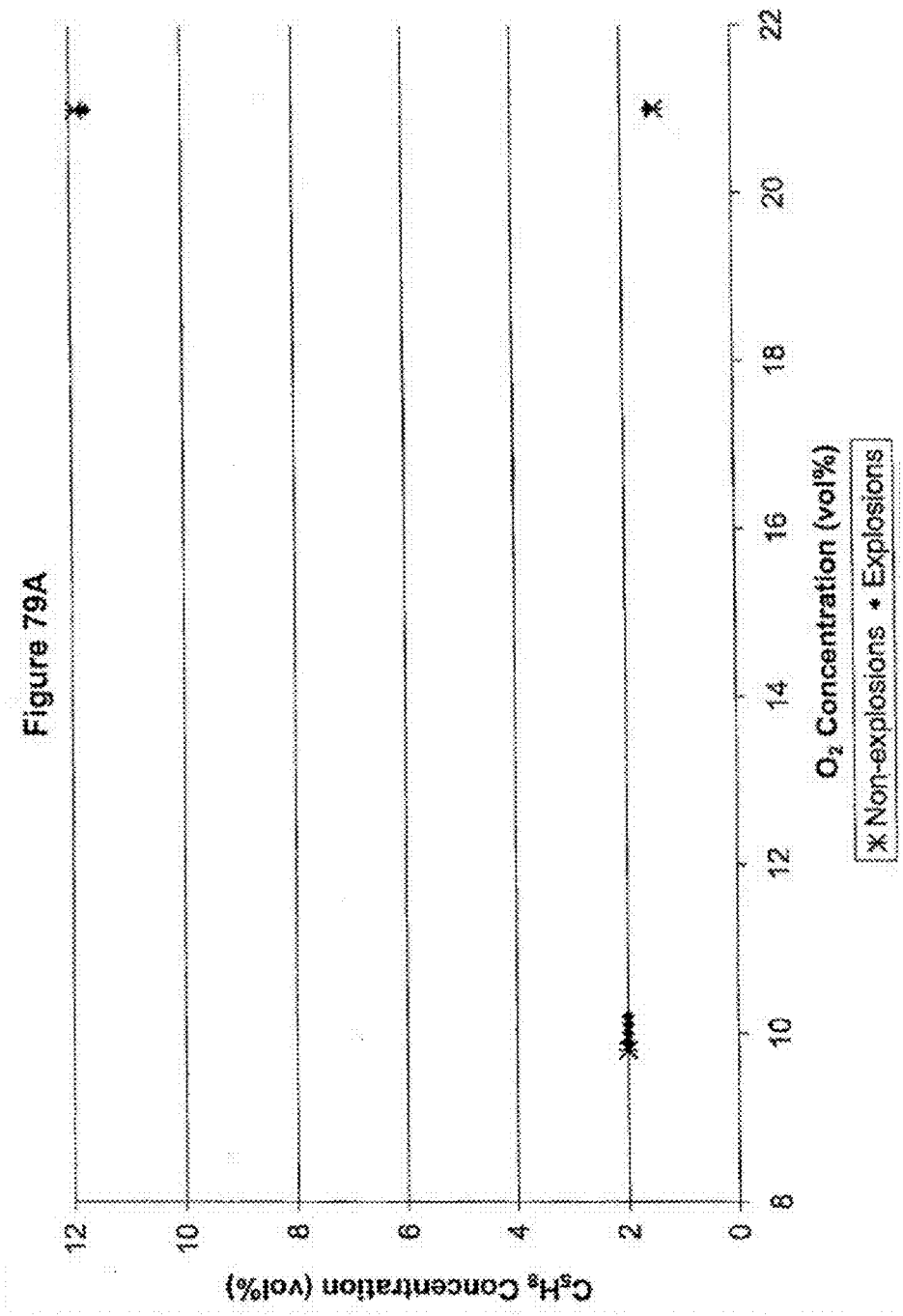
FIG. 79A is a graph of the flammability curve for Test Series 2: 4% Steam, 0 psig, and 40° C.

FIG. 79B summarizes the explosibility data points shown in FIG. 79A. FIG. 79C is a comparison of the experimental data with the CAFT model predicted flammability envelope. The model agrees very well with the experimental data. Discrepancies may be due to the same factors described in Series 1

V. Calculation of Flammability Limits of Isoprene in Air at 3 Atmospheres of Pressure The methods described in Example 13, parts I to IV were also used to calculate the flammability limits of isoprene at an absolute system pressure of 3 atmospheres and 40° C. These results were compared to those of Example 13, parts I to IV at an absolute system pressure of 1 atmosphere and 40° C. This higher pressure was tested because the flammability envelope expands or grows larger as the initial system pressure is increased. The upper flammability limit is affected the most, followed by the limiting oxygen composition. The lower flammability limit is the least affected (see, for example, "Bulletin 627—Flammability Characteristics of Combustible Gases and Vapors" written by Michael G. Zabetakis and published by the former US Bureau of Mines (1965), which is hereby incorporated by reference in its entirety, particular with respect to the calculation of flammability limits).

Figure 82:
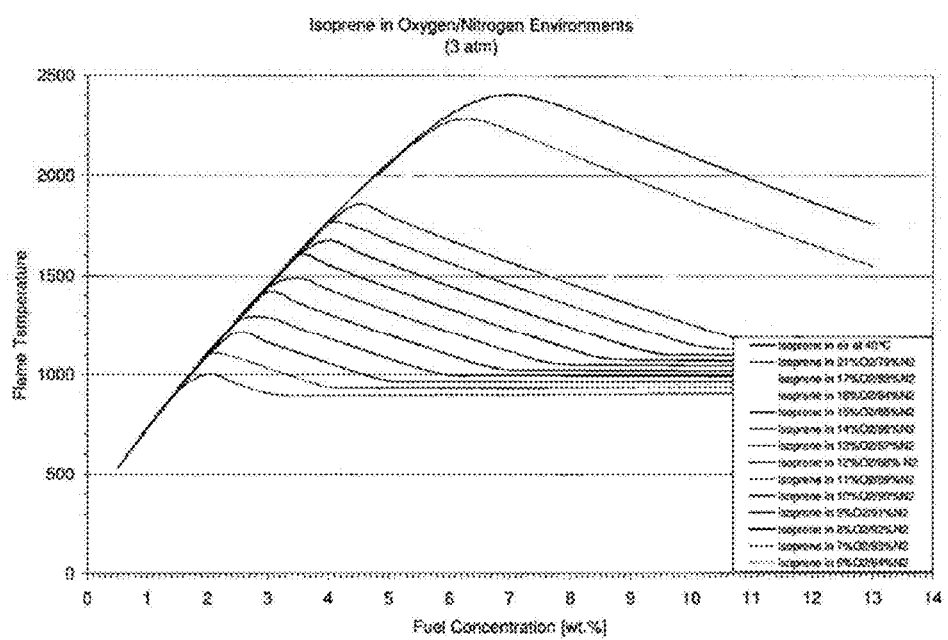
FIG. 82 is a graph of the calculated adiabatic flame temperature plotted as a function of fuel concentration for various nitrogen/oxygen ratios at 3 atmospheres of pressure.
Figure 83:
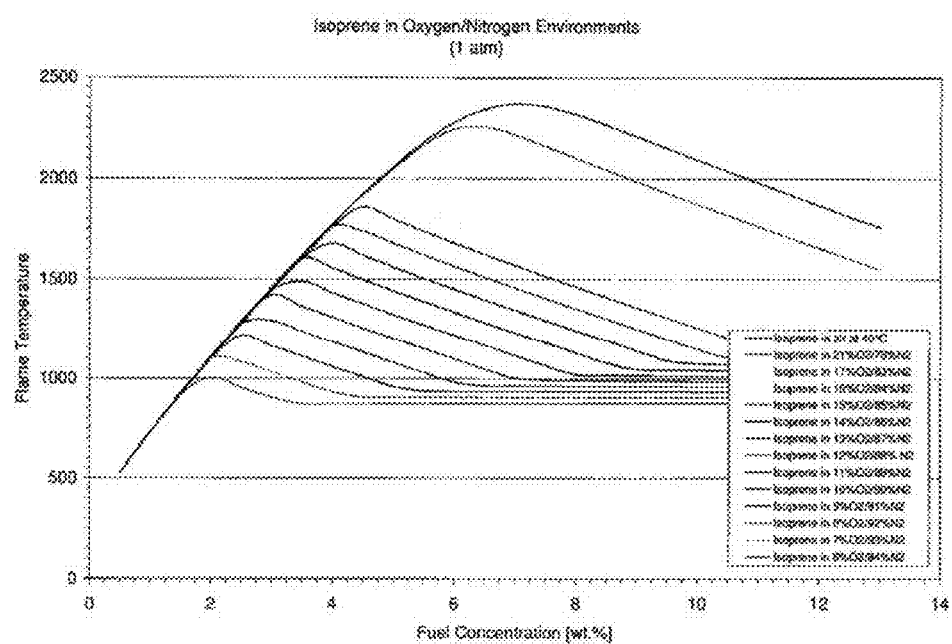
FIG. 83 is a graph of the calculated adiabatic flame temperature plotted as a function of fuel concentration for various nitrogen/oxygen ratios at 1 atmosphere of pressure.
Figure 84:
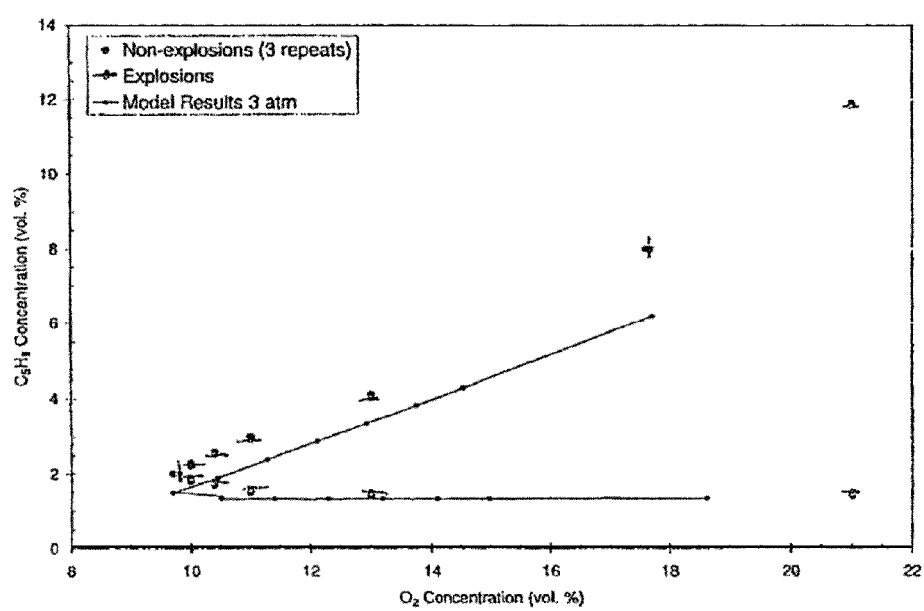
FIG. 84 is a graph of the flammability envelope constructed using data from FIG. 82 and following the methodology described in Example 13. The experimental data points (circles) are from tests described herein that were conducted at 1 atmosphere initial system pressure.
Figure 85:
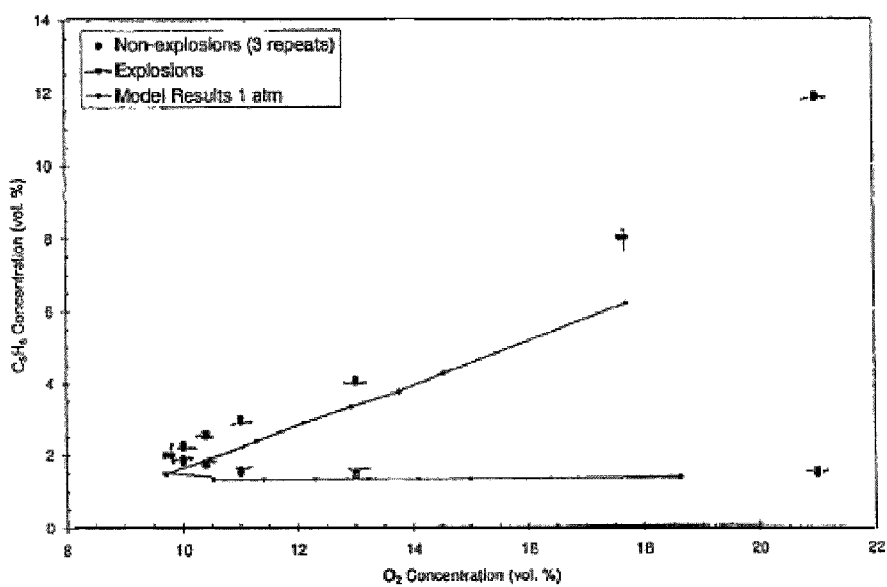
FIG. 85 is a graph of the flammability envelope constructed using data from FIG. 83 and following the methodology described in Example 13. The experimental data points (circles) are from tests described herein that were conducted at 1 atmosphere initial system pressure.

In FIG. 82, the calculated adiabatic flame temperature is plotted as a function of isoprene (fuel) concentration, expressed in weight percent of the total fuel/nitrogen/oxygen, where the system pressure was initially 3 atmospheres. The calculated flame temperatures are very similar to those determined initially in the 1 atmosphere system (FIG. 83). As a result, when flammability envelopes are generated using the calculated adiabatic flammability data, the curves are very similar (see FIGS. 84 and 85). Therefore, based on these theoretical calculations, a system pressure increase from 1 atmosphere to 3 atmosphere does not result in a significant increase/broadening of the flammability envelope. If desired, these model results may be validated using experimental testing (such as the experimental testing described herein at a pressure of 1 atmosphere).

VII. Summary of Flammability Studies

A calculated adiabatic temperature model was developed for the flammability envelope of the isoprene/oxygen/nitrogen/water/carbon dioxide system at 40° C. and 0 psig. The CAFT model that was developed agreed well with the experimental data generated by the tests conducted in this work. The experimental results from Series 1 and 2 validated the model results from Series A and B.

Example 14

Expression Constructs and Strains

I. Construction of Plasmids Encoding Mevalonate Kinase.

A construct encoding the *Methanosarcina mazei* lower MVA pathway (Accession numbers NC_003901.1, NC_003901.1, NC_003901.1, and NC_003901.1, which are each hereby incorporated by reference in their entireties) was synthesized with codon optimization for expression in *E. coli*. This construct is named *M. mazei* archeal Lower Pathway operon (FIGS. 112A-112C; SEQ ID NO:102) and encodes *M. mazei* MVK, a putative decarboxylase, IPK, and IDI enzymes. The gene encoding MVK (Accession number NC_003901.1) was PCR amplified using primers MCM165 and MCM177 (Table 11) using the Strategene Herculase II Fusion kit according to the manufacturer's protocol using 30 cycles with an annealing temperature of 55° C. and extension time of 60 seconds. This amplicon was purified using a Qiagen PCR column and then digested at 37° C. in a 10 μL reaction with PmeI (in the presence of NEB buffer 4 and BSA). After one hour, NsiI and Roche buffer H were added for an additional hour at 37° C. The digested DNA was purified over a Qiagen PCR column and ligated to a similarly digested and purified plasmid MCM29 (MCM29 is *E. coli* TOP10 (Invitrogen) transformed with pTrcKudzu encoding Kudzu isoprene synthase) in an 11 uL reaction 5 uL Roche Quick Ligase buffer 1, 1 uL buffer 2, 1 uL plasmid, 3 uL amplicon, and 1 uL ligase (1 hour at room temperature). MCM 29 is pTrcKudzuKan. The ligation reaction was introduced into Invitrogen TOP10 cells and transformants selected on LA/kan50 plates incubated at 37° C. overnight. The MVK insert in the resulting plasmid MCM382 was sequenced (FIGS. 113A-113C; SEQ ID NO: 103).

TABLE 11

| Oligonucleotides. | | |
|---|---|---|
| MCM161 | *M. mazei* MVK for | CACCATGGTATCCTGTTCTGCG (SEQ ID NO: 104) |
| MCM162 | *M. mazei* MVK rev | TTAATCTACTTTCAGACCTTGC (SEQ ID NO: 105) |
| MCM165 | *M. mazei* MVK for w/ RBS | gcgaacgATGCATaaaggaggtaaaaaaacATGGTATCCTGTTCTG CGCCGGGTAAGATTTACCTG (SEQ ID NO: 106) |
| MCM177 | *M. mazei* MVK rev Pst | gggcccgtttaaactttaactagactTTAATCTACTTTCAGACCTTGC (SEQ ID NO: 107) |

II. Creation of Strains Overexpressing Mevalonate Kinase and Isoprene Synthase.

Plasmid MCM382 was transformed into MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) that had been grown to midlog in LB medium and washed three times in iced, sterile water. One μL of DNA was added to 50 μL of cell suspension, and this mixture was electroporated in a 2 mm cuvette at 2.5 volts, 25 uFd followed immediately by recovery in 500 μL LB medium for one hour at 37° C. Transformant was selected on LA/kan50 and named MCM391. Plasmid MCM82 was introduced into this strain by the same electroporation protocol followed by selection on LA/kan50/spec50. The resulting strain MCM401 contains a cmp-marked chromosomal construct gi1.2KKDyI, kan-marked plasmid MCM382, and spec-marked plasmid MCM82 (which is pCL PtrcUpperPathway encoding *E. faecalis* mvaE and mvaS). See Table 12.

TABLE 12

Strains overexpressing mevalonate kinase and isoprene synthase.

| | |
|---|---|
| MCM382 | *E. coli* BL21 (lambdaDE3) pTrcKudzuMVK(*M. mazei*)GI1.2KKDyI |
| MCM391 | MCM331 pTrcKudzuMVK(*M. mazei*) |
| MCM401 | MCM331pTrcKudzuMVK(*M. mazei*)pCLPtrcUpperpathway |
| MCM396 | MCM333pTrcKudzuMVK(*M. mazei*) |
| MCM406 | MCM333pTrcKudzuMVK(*M. mazei*)pCLPtrcUpperpathway |

III. Construction of Plasmid MCM376-MVK from *M. mazei* Archeal Lower in pET200D.

The MVK ORF from the *M. mazei* archeal Lower Pathway operon (FIGS. 112A-112C; SEQ ID NO:102) was PCR amplified using primers MCM161 and MCM162 (Table 11) using the Invitrogen Platinum HiFi PCR mix. 45 uL of PCR mix was combined with 1 uL template, 1 uL of each primer at 10 uM, and 2 uL water. The reaction was cycled as follows: 94° C. for 2:00; 30 cycles of 94° C. for 0:30, 55° C. for 0:30, and 68° C. for 1:15; and then 72° C. for 7:00, and 4° C. until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 114A-114C; SEQ ID NO:108).

V. Creation of Expression Strain MCM378.

Plasmid MCM376 was transformed into Invitrogen BL21 (DE3) pLysS cells according to the manufacturer's protocol. Transformant MCM378 was selected on LA/kan50.

Example 15

Production of Isoprene by *E. coli* Expressing the Upper Mevalonic Acid (MVA) Pathway, the Integrated Lower MVA Pathway (Gi1.2KkdyI), Mevalonate Kinase from *M. mazei*, and Isoprene Synthase from Kudzu and Grown in Fed-Batch Culture at the 20 mL Batch Scale Medium Recipe (Per Liter Fermentation Medium)

Each liter of fermentation medium contained $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, and 1000× Trace Metal Solution 1 ml. All of the components were added together and dissolved in $diH_2O$. The pH was adjusted to 6.8 with ammonium hydroxide (30%) and brought to volume. Media was filter sterilized with a 0.22 micron filter. Glucose (2.5 g) and antibiotics were added after sterilization and pH adjustment.

1000× Trace Metal Solution:

1000× Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in di $H_2O$, pH to 3.0 with HCl/NaOH, then brought to volume and filter sterilized with a 0.22 micron filter.

Strains:

MCM343 cells are BL21 (DE3) *E. coli* cells containing the upper mevalonic acid (MVA) pathway (pCL Upper), the integrated lower MVA pathway (gi1.2KKDyI), and isoprene synthase from Kudzu (pTrcKudzu).

MCM401 cells are BL21 (DE3) *E. coli* cells containing the upper mevalonic acid (MVA) pathway (pCL PtrcUpperPathway), the integrated lower MVA pathway (gi1.2KKDyI), and high expression of mevalonate kinase from *M. mazei* and isoprene synthase from Kudzu (pTrcKudzuMVK(*M. mazei*)).

Isoprene production was analyzed by growing the strains in 100 mL bioreactors with a 20 mL working volume at a temperature of 30° C. An inoculum of *E. coli* strain taken from a frozen vial was streaked onto an LB broth agar plate (with antibiotics) and incubated at 30° C. A single colony was inoculated into media and grown overnight. The bacteria were diluted into 20 mL of media to reach an optical density of 0.05 measured at 550 nm. The 100 mL bioreactors were sealed, and air was pumped through at a rate of 8 mL/min. Adequate agitation of the media was obtained by stirring at 600 rpm using magnetic stir bars. The off-gas from the bioreactors was analyzed using an on-line Hiden HPR-20 mass spectrometer. Masses corresponding to isoprene, $CO_2$, and other gasses naturally occurring in air were monitored. Accumulated isoprene and $CO_2$ production were calculated by summing the concentration (in percent) of the respective gasses over time. Atmospheric $CO_2$ was subtracted from the total in order to estimate the $CO_2$ released due to metabolic activity.

Isoprene production from a strain expressing the full mevalonic acid pathway and Kudzu isoprene synthase (MCM343) was compared to a strain that in addition over-expressed MVK from *M. mazei* and Kudzu isoprene synthase (MCM401) in 100 mL bioreactors. The bacteria were grown under identical conditions in defined media with glucose as carbon source. Induction of isoprene production was achieved by adding isopropyl-beta-D-1-thiogalactopyranoside (IPTG) to a final concentration of either 100 uM or 200 uM. Off-gas measurements revealed that the strain over-expressing both MVK and isoprene synthase (MCM401) produced significantly more isoprene compared to the strain expressing only the mevalonic acid pathway and Kudzu isoprene synthase (MCM343) as shown in FIGS. 115A-115D. At 100 uM induction, the MCM401 strain produced 2-fold more isoprene compared to the MCM343 strain. At 200 uM IPTG induction, the MCM401 strain produced 3.4-fold more isoprene when compared to the MCM343 strain. Analysis of $CO_2$ in the off-gas from the bioreactors, which is a measure of metabolic activity, indicates that metabolic activity was independent from IPTG induction and isoprene production.

Example 16

Production of Isoprene by *E. coli* Expressing the Upper Mevalonic Acid (MVA) Pathway, the Integrated Lower MVA Pathway (gi1.2KKDyI), Mevalonate Kinase from *M. mazei*, and Isoprene Synthase from Kudzu and Grown in Fed-Batch Culture at the 15-L Scale Medium Recipe (Per Liter Fermentation Medium):

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in DI $H_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, and $NaMoO_4$*$2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L of medium in a 15-L bioreactor.

Glucose was fed at an exponential rate until cells reached the stationary phase. After this time the glucose feed was decreased to meet metabolic demands. The total amount of glucose delivered to the bioreactor during the 68 hour fermentation was 3.8 kg. Induction was achieved by adding isopropyl-beta-D-1-thiogalactopyranoside (IPTG). The IPTG concentration was brought to 51 uM when the optical density at 550 nm ($OD_{550}$) reached a value of 9. The IPTG concentration was raised to 88 uM when $OD_{550}$ reached 149. Additional IPTG additions raised the concentration to 119 uM at $OD_{550}$=195 and 152 uM at $OD_{550}$=210. The $OD_{550}$ profile within the bioreactor over time is shown in FIG. 116. The isoprene level in the off gas from the bioreactor was determined using a Hiden mass spectrometer. The isoprene titer increased over the course of the fermentation to a final value of 23.8 g/L (FIG. 117). The total amount of isoprene produced during the 68 hour fermentation was 227.2 g and the time course of production is shown in FIG. 118. The metabolic activity profile, as measured by TCER, is shown in FIG. 119. The total viable count (total colony forming units) decreased by two orders of magnitude between 10 and 39 hours of fermentation (FIG. 120). The molar yield of utilized carbon that went into producing isoprene during fermentation was 13.0%. The weight percent yield of isoprene from glucose was 6.3%.

Example 17

Production of Isoprene by *E. coli* Expressing the Upper Mevalonic Acid (MVA) Pathway, the Integrated Lower MVA Pathway (gi1.2KKDyI), Mevalonate Kinase from *M. mazei*, and Isoprene Synthase from Kudzu and Grown in Fed-Batch Culture at the 15-L Scale (2×100 µM IPTG Induction)

Medium Recipe (Per Liter Fermentation Medium):

Each liter of fermentation medium contained $K_2HPO_4$ 7.5 g, $MgSO_4$*$7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in DI $H_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, and $NaMoO_4$*$2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L medium in a 15-L bioreactor.

Glucose was fed at an exponential rate until cells reached the stationary phase. After this time the glucose feed was decreased to meet metabolic demands. The total amount of glucose delivered to the bioreactor during the 55 hour fermentation was 1.9 kg. Induction was achieved by adding isopropyl-beta-D-1-thiogalactopyranoside (IPTG). The IPTG concentration was brought to 111 uM when the optical density at 550 nm ($OD_{550}$) reached a value of 9. The IPTG concentration was raised to 193 uM when $OD_{550}$ reached 155. The $OD_{550}$ profile within the bioreactor over time is shown in FIG. 121. The isoprene level in the off gas from the bioreactor was determined using a Hiden mass spectrometer. The isoprene titer increased over the course of the fermentation to a final value of 19.5 g/L (FIG. 122). The total amount of isoprene produced during the 55 hour fermentation was 133.8 g and the time course of production is shown in FIG. 123. Instantaneous volumetric productivity levels reached values as high as 1.5 g isoprene/L broth/hr (FIG. 124). Instantaneous yield levels reached as high as 17.7% w/w (FIG. 125). The metabolic activity profile, as measured by TCER, is shown in FIG. 126. The total viable count (total colony forming units) decreased by two orders of magnitude between 8 and 36 hours of fermentation (FIG. 127). The molar yield of utilized carbon that went into producing isoprene during fermentation was 15.8%. The weight percent yield of isoprene from glucose over the entire fermentation was 7.4%.

In addition, as a control, fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment was carried out to monitor uninduced cell metabolic activity as measured by CER from glucose at the desired fermentation pH 7.0 and temperature 30° C. An inoculum of *E. coli* strain (MCM401 described above) taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L medium in a 15-L bioreactor. Glucose was fed at an exponential rate until cells reached the stationary phase. After this time the glucose feed was decreased to meet metabolic demands.

FIG. 148 compares the CER profiles for the uninduced cells described above and the cells induced by adding isopropyl-beta-D-1-thiogalactopyranoside (IPTG) in Examples 16 and 17.

Example 18

Production of Isoprene by *E. coli* Expressing the Upper Mevalonic Acid (MVA) Pathway, the Integrated Lower MVA Pathway (gi1.2KKDyI), Mevalonate Kinase from *M. mazei*, and Isoprene Synthase from Kudzu and Grown in Fed-Batch Culture at the 15-L Scale (1×50 µM IPTG+150 µM IPTG Fed Induction)

Medium Recipe (Per Liter Fermentation Medium):

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L medium in a 15-L bioreactor.

Glucose was fed at an exponential rate until cells reached the stationary phase. After this time the glucose feed was decreased to meet metabolic demands. The total amount of glucose delivered to the bioreactor during the 55 hour fermentation was 2.2 kg. Induction was achieved by adding isopropyl-beta-D-1-thiogalactopyranoside (IPTG). The IPTG concentration was brought to 51 uM when the optical density at 550 nm ($OD_{550}$) reached a value of 10. In addition to the IPTG spike, at $OD_{550}$=10 a constant feed began and delivered 164 mg of IPTG over 18 hours. The $OD_{550}$ profile within the bioreactor over time is shown in FIG. 128. The isoprene level in the off gas from the bioreactor was determined using a Hiden mass spectrometer. The isoprene titer increased over the course of the fermentation to a final value of 22.0 g/L (FIG. 129). The total amount of isoprene produced during the 55 hour fermentation was 170.5 g and the time course of production is shown in FIG. 130. The metabolic activity profile, as measured by TCER, is shown in FIG. 131. When the airflow to the bioreactor was decreased from 8 slpm to 4 slpm for a period of about 1.7 hours, the concentration of isoprene in the offgas increased from 0.51 to 0.92 w/w % (FIG. 132). These elevated levels of isoprene did not appear to have any negative impact on cell metabolic activity as measured by the total carbon dioxide evolution rate (TCER), since TCER declined only 7% between 37.2 and 39.3 hours (FIG. 132). The total viable count (total colony forming units) decreased by two orders of magnitude between 7 and 36 hours of fermentation (FIG. 133). The molar yield of utilized carbon that went into producing isoprene during fermentation was 16.6%. The weight percent yield of isoprene from glucose over the entire fermentation was 7.7%.

Example 19

The Effect of Externally Applied Isoprene on a Wild-Type *E. coli* Grown in Fed-Batch Culture at the 1-L Scale Medium Recipe (Per Liter Fermentation Medium):

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 1-L bioreactor with BL21 (DE3) *E. coli* cells. This experiment was carried out to monitor the effects of isoprene on cell viability and metabolic activity in a glucose fed-batch bioreactor at the desired fermentation pH 7.0 and temperature 30° C. An inoculum of *E. coli* strain from a frozen vial was inoculated into tryptone-yeast extract medium. After the inoculum grew to OD 1.0, measured at 550 nm, 50 mL was used to inoculate 0.5-L medium in a 1-L bioreactor.

Glucose was fed at an exponential rate until cells reached the stationary phase. After this time the glucose feed was fed to meet metabolic demands. Isoprene was fed into the bioreactor using nitrogen gas as a carrier. The rate of isoprene feeding was 1 g/L/hr during mid-growth phase ($OD_{550}$=31-44) and lasted for a total of 75 minutes (13.2 to 14.4 hours). The $OD_{550}$ profile within the bioreactor over time is shown in FIG. 134. The metabolic activity profile, as measured by TCER, is shown in FIG. 135. The total viable count (total colony forming units) increased by 14-fold during the period when isoprene was introduced into the bioreactor (FIG. 136).

Example 20

Production of Isoprene and Expression of Isoprene Synthase by *Saccharomyces cerevisiae*

The Kudzu isoprene synthase enzyme was optimized for expression according to a hybrid *Saccharomyces cerevisiae/Pichia pastoris* codon usage table, synthesized, and cloned into pDONR221:19430 (by DNA 2.0, FIG. 140 for map and FIG. 141 for sequence (SEQ ID NO:115)). A Gateway® Cloning (Invitrogen) reaction was performed according to the manufacturer's protocol: Since pDONR221:19430 was an "entry" vector, the LR Clonase II enzyme (the LR Reaction) was used to introduce the codon-optimized isoprene synthase into the "destination" vector pYES-DEST52 (Invitrogen).

The LR Reaction was then transformed into Top10 chemically competent cells (Invitrogen) according to the manufacturer's protocol, and bacteria harboring pYES-DEST52 plasmids with the isoprene synthase ORF were selected for on LA plates containing 50 μg/ml carbenicillin. Individual positive transformants were tested by colony PCR (see below for primer concentrations and thermocycling parameters) using illustra PuReTaq Ready-To-Go™ PCR Beads (GE Healthcare) with the T7 forward primer and the Yeast isoprene synthase-Rev2 primer (See Table 13).

To induce isoprene synthase expression, cultures were grown overnight in liquid SC Minimal Medium. The cultures were then diluted to an $OD_{600}$ of approximately 0.2 and grown for 2-3 hours. Cultures were spun by centrifugation, washed once, resuspended in an equal volume (10 ml) of SC minimal medium with 1% raffinose, 2% galactose without uracil, and grown overnight to induce the expression of isoprene synthase. The $OD_{600}$ of the strains was determined (FIG. 144A), and strains were harvested by centrifugation and resuspended in 2 ml of lysis buffer (a 1:1 mix of 50% glycerol and PEB pH 7.4: Tris Base 2.423 g/L, $MgCl_2$ (Anhydrous) 1.904 g/L, KCl 14.910 g/L, DTT 0.154 g/L, Glycerol 50 mL/L).

The lysis mixtures were passed through a french press three times, and lysates were analyzed by SDS-PAGE. For Coomassie gel analysis (FIG. 143A), samples were diluted 1:1 with 2×SDS loading buffer with reducing agent, loaded (20 μl total volume) onto a 4-12% bis-tris gel, run in MES buffer, and stained using SimplyBlue SafeStain according to the manufacturer's protocol (the Invitrogen Novex system).

The WesternBreeze kit (Invitrogen) was used for transfer and chromogenic detection of isoprene synthase on a nitrocellulose membrane. The primary antibody was 1799A 10 week diluted 1:1000 in Invitrogen antibody diluent. Primary antibody binding was followed by development with a secondary antibody labeled with Alexa Fluor 488 (Invitrogen Catalog No. A-11008) to permit quantitative signal determi-

TABLE 13

Primer sequences for amplifying isoprene synthase.

| Primer Name | Sequence (5' to 3') | Purpose |
|---|---|---|
| Yeast HGS-For2 | CACCAAAGACTTCATAGACT (SEQ ID NO: 116) | Forward primer for yeast optimized isoprene synthase |
| Yeast HGS-Rev2 | AGAGATATCTTCCTGCTGCT (SEQ ID NO: 117) | Reverse primer for yeast optimized isoprene synthase |
| T7 Forward | TAATACGACTCACTATAGGG (SEQ ID NO: 118) | PCR and sequencing primer |

Plasmids that yielded a PCR fragment of the correct size (1354 bp) were purified by miniprep (Qiagen) and sent for sequencing (Quintara Biosciences, Berkeley, Calif.) with the T7 Forward and Yeast isoprene synthase-For2 primers (See Table 13). Results from sequencing runs were compared to the known sequence of pDONR221:19430 (using Vector NTI software, Invitrogen), and a single plasmid, pDW14, was selected for further study (FIG. 142A for map and FIGS. 142B and C for the complete sequence (SEQ ID NO:119)). The sequence of pDW14 diverged from that of pDONR221: 19430 by a single nucleotide (marked in bold in FIG. 142B). The single nucleotide change (G to A) did not result in a change in the ORF, since it was in the third position of a lysine-encoding codon.

Purified pDW14 was transformed into *Saccharomyces cerevisiae* strain INVSc-1 using the protocol described in the S. c. EasyComp Transformation kit (Invitrogen). INVSc-1 strains harboring pDW14 or pYES-DEST52 (which contains an intact URA3 gene) were selected for and maintained on SC Minimal Medium with 2% glucose without uracil, as described in the pYES-DEST52 Gateway Vector manual (Invitrogen). Two independent isolates of INVSc-1 containing pDW14 and a single control strain with pYES-DEST52 were chosen for further analysis.

nation. The western blot procedure was carried out as described by Invitrogen. The fluorescence signal was recorded with a Molecular Dynamics Storm instrument using the blue filter setting and quantitatively analyzed with the Molecular Dynamics ImageQuant image analysis software package. Specific activity of the library members was calculated from the ratio of the amount of isoprene produced divided by either the A600 of the induction cultures or the isoprene synthase protein concentration determined by western blot. FIG. 143B shows that isoprene synthase was present in the induced INVSc-1 strains harboring pDW14 (lanes 2 and 3) in comparison to the control harboring pYES-DEST52 (lane 1).

The DMAPP assay for isoprene synthase headspace was performed on 25 uL of the lysate from each strain for which 5 uL 1 M $MgCl_2$, 5 uL 100 mM DMAPP, and 65 uL 50 mM Tris pH 8 were added. The reaction was performed at 30° C. for 15 minutes in a gas tight 1.8 mL GC tube. Reactions were terminated by addition of 100 uL 250 mM EDTA pH 8. FIG. 144B showed the specific activity values (in μg HG/L/OD) of the induced strains harboring pDW14 in comparison to the control. Induced strains harboring pDW14 displayed approximately 20× higher activity than the control lacking isoprene synthase.

PCR Cycling Parameters

Illustra PuReTaq Ready-To-Go™ PCR Beads (GE Healthcare) were used with oligonucleotide primer pairs at a concentration of 0.4 µM each in 25 µl total volume/reaction. For analysis of plasmids resulting from the LR Clonase reaction (Invitrogen), a small amount of bacteria from individual colonies on a selective plate was added to each tube containing the PCR mix described above. The reaction cycle was as follows: 1) 95° C. for 4 minutes; 2) 95° C. for 20 seconds; 3) 52° C. for 20 seconds; 4) 72° C. for 30 seconds; 5 cycles of steps 2 through 4; 5) 95° C. for 20 seconds; 6) 55° C. for 20 seconds; 7) 72° C. for 30 seconds; 25 cycles of steps 5 through 7, 72° C. for 10 minutes, and 4° C. until cool.

Example 21

Production of Isoprene in *Pseudomonas* and Other Gram Negative Bacteria

Construction of pBBR5HGSOpt2_2, Conjugation in *Pseudomonas* and Measurement of Isoprene Synthase Activity A gene encoding isoprene synthase from *Pueraria lobata* (Kudzu plant) was codon-optimized for different microbial species of interest (Table 14; fluo-opt2v2 was the sequence chosen) and was synthesized by DNA2.0, Menlo Park, Calif. The map and sequence of fluo-opt2v2 can be found in FIGS. 145A and 145B (SEQ ID NO:120). HindIII and BamHI restriction sites were added to the synthesized sequence for easier cloning, and a RBS was added in front of the ATG to enhance transcription.

Number of rare codons, as a function of the microbial species, in different versions of codon-optimized isoprene synthase from *Pueraria lobata*. Several rounds of optimization led to a gene with no rare codons in the all the species of interest.

TABLE 14

Number of rare codons.

| Organism | fluo-opt1 (quote) | fluo-opt2 | fluo-opt3 | E. coli opt | fluo-opt2v2 |
|---|---|---|---|---|---|
| *Pseudomonas fluorescens* Pf-5 | 19 | X | X | 57 | 0 |
| *Phodopseudomonas palustris* CGA009 | 37 | 13 | 3 | 74 | 0 |
| *Pseudomonas putida* F1 | 0 | 0 | 0 | 29 | 0 |
| *Corynebacterium glutamicum* (ATCC) | 4 (Ser) | 0 | 0 | 0 | 0 |
| *Pseudomonas fluorescens* PfO-1 | 1 (Val) | 0 | 0 | 57 | 0 |

The gene was provided by DNA2.0 in a cloning vector. The vector was digested with HindIII/BamHI, the band corresponding to the insert of interest was gel-purified, and relegated with HindIII/BamHI-digested pBBR1MCS5 (Kovach et al, *Gene* 166:175-176, 1995, which is incorporated by reference in its entirety, particularly with respect to pBBR1MCS5), FIG. 146A for map and 146B and C for sequence (SEQ ID NO:121). This resulted in plasmid pBBR5HGSOpt2_2 (FIG. 147A for map and 147B and C for sequence (SEQ ID NO:122)) in which isoprene synthase was expressed from the lac promoter presented in pBBR1MCS5.

The vector was transformed in *E. coli* S17-1 and mated with *Pseudomonas putida* F1 ATCC700007 and *Pseudomonas fluorescens* ATCC 13525. After conjugation on LB, selection for plasmid-harboring *Pseudomonas* strains was on M9+16 mM sodium citrate+Gentamicin 50 ug/ml. Presence of the plasmid in the strains thus generated was checked by plasmid preparation using the Qiagen kit (Valencia, Calif.).

Isoprene synthase activities of the recombinant strains *P. putida*, pBBR5HGSOpt2_2 and *P. fluorescens*, pBBR5HGSOpt2_2 were assayed by growing the strains in TM3 medium (as described in Example 1 Part II)+10 g/L glucose, harvesting the biomass in mid-log phase, breaking the cells by French Press and proceeding with the DMAPP assay. Results of the assay were presented in Table 15. The presence of activity measured by the DMAPP assay confirmed that isoprene synthase was expressed in *Pseudomonas*.

Isoprene synthase activity was examined in *Pseudomonas putida* and *Pseudomonas fluorescens* expressing isoprene synthase from the lac promoter, using plasmid pBBR5HGSOpt2_2

TABLE 15

Isoprene synthase activity in *Pseudomonas putida* and *Pseudomonas fluorescens*.

| Strain | OD | Isoprene synthase activity mg isoprene/(L.h.OD) |
|---|---|---|
| *P. fluorescens*, pBBR5HGSOpt2_2 | 1.46 | 0.96 |
| *P. putida*, pBBR5HGSOpt2_2 | 3.44 | 0.65 |
| Control (*P. putida* w/o plasmid) | 8.32 | To be determined |

Example 22

Growth of *E. coli* and *Pseudomonas* Strains on Sugar Cane Compared to Glucose, and Expression of Isoprene Synthase Using Both Substrates I. Preparation of Liquid Sugar Cane Crystallized raw cane sugar was dissolved in water in the following way: 750 g $H_2O$ was added to 250 g sugar. The solution was stirred and gently heated until dissolution. Some material was not soluble. The weight of the solution was adjusted to 1 kg after dissolution to replenish the evaporated water. The volume of the solution was measured to be 940 mL. Hence the concentration of the solution was 265 g/L. The product label claimed 14 g of carbohydrate for 15 g of raw sugar cane. Hence the carbohydrate concentration of the solution was 248 g/L. Dry solids were measured to be 24.03%, close enough of the expected 250 g/kg. pH of the solution was 5.49. Glucose concentration was measured using an enzymatic/spectrophotometric assay, with glucose oxidase. The glucose concentration was 17.4 g/L.

As a majority of microorganisms do not use sucrose, but can use glucose and fructose, the solution was split in two. One half was autoclaved once for 30 minutes (sugar cane as is). Some inversion resulted, as the glucose content increased to 29.75 g/L (See FIG. 149). The other half of the solution was adjusted to pH 4.0 using phosphoric acid, then the solution was inverted by autoclaving (inverted sugar cane). Three cycles of 30 min were sufficient to obtain complete inversion, as shown on FIG. 149. Both solutions were used for the growth curves described below.

II. Growth Curves of Different Strains of *E. coli* and *Pseudomonas* on Sugar Cane Compared to Glucose One colony of each of the strains presented in Table 16 was inoculated in 25 ml TM3+10 g/L glucose, and was grown overnight at 30° C. and 200 rpm. TM3 is described in Example 7, Section II. The morning after, 1 ml of each culture was used to inoculate flasks containing 25 mL TM3 and 10 g/L glucose, 10 g/L sugar cane as is, or 10 g/L inverted sugar cane (sugar cane solutions described above). The flasks were incubated at 30° C. and 200 rpm and samples were taken regularly to measure OD600. FIGS. 150 and 151 show that growth rate and biomass yield were comparable for glucose and inverted sugar cane, both for Pseudomonas and E. coli strains. P. fluorescens showed some signs of being able to use sugar cane which has not been inverted too.

TABLE 16

Strains used in this study.

| | Strain |
|---|---|
| Escherichia coli | BL21 |
| | MG1655 |
| | ATCC11303 |
| | B REL 606 |
| Pseudomonas | putida F1 (ATCC700007) |
| | Fluorescens (ATCC13525) |

III. Comparison of Isoprene Production from E. coli Expressing Isoprene Synthase when Grown on Glucose or Sugar Cane E. coli MCM401 (BL21(DE3)) containing full MVA pathway, mevalonate kinase from M. mazei and isoprene synthase from Pueraria lobata, as described in Example 14, Section II was grown in TM3+either 10 g/L glucose or 10 g/L inverted sugar cane (based on carbohydrate concentration of the syrup). Flasks were inoculated from an overnight culture on TM3+10 g/L glucose at an $OD_{600}$=0.2. Antibiotics were added where needed. After two hours, the E. coli cultures were induced with 400 µM IPTG. After 6 hours of growth, isoprene production and isoprene synthase activities, using the DMAPP assay as described in Example 2B, were measured. Results are presented in Table 17 and illustrate clearly that inverted sugar cane is equivalent to glucose in terms of isoprene and isoprene synthase production on a per cell basis.

TABLE 17

| Strain | Carbon Source | OD | Isoprene synthase activity mg isoprene/ (L.h.OD) | Isoprene production mg isoprene/ (L.h.OD) |
|---|---|---|---|---|
| MCM401 | Glucose | 2.20 | 21.06 | 8.98 |
| MCM401 | Sugar cane inverted | 2.32 | 20.20 | 9.23 |

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

Example 23

Production of Ethylene in E. coli

I. Construction of an Ethylene-Producing E. coli Strain.

The product of the ethylene-forming enzyme (efe) gene from Pseudomonas syringae converts 2-oxoglutarate, an intermediate of the TCA cycle, into ethylene. Primers amplifying the bacterial efe gene were derived from the efe gene of Pseudomonas syringae pv. glycinea strain ICMP2189 (Acc. No. EF175870). The efe gene was amplified by PCR using primer pair efe_rev: 5' CGGACCGTCATGAGCCT-GTCGCGCGGG-3' (SEQ ID NO:127), wherein TCA=stop-codon efe-gene, and efe-Pffh_oe: 5'-CCACCCCAGGC-GAGAGACAATGACCAACCTACAGACTTTC-3' (SEQ ID NO:128), wherein ATG=start-codon efe gene, giving PCR-fragment A. Genomic DNA prepared from Pseudomonas syringae served as template.

The putative promoter region of the ffh gene of E. coli MG1655 encoding the protein component of the signal recognition particle was amplified by PCR using primer pair Pffh_fwd: 5'-CGGTCCGGAAAGAGAAGCAGTATAGCG-3' (SEQ ID NO:129) and Pffh_oe: 5'-GAAAGTCTGTAGGT-TGGTCATTGTCTCTCGCCTGGGGTGG-3' (SEQ ID NO:130), wherein CAT=start codon ffh-gene, to give PCR-fragment B. PCR fragment B covers 147 bp upstream of the start-codon of the ffh-gene and thus the putative ffh-promoter. PCR fragments A and B were spliced by overlap extension PCR generating a DNA fragment that encodes the efe gene under control of the ffh-promoter. After splicing the PCR-fragments A and B using primer pair Pffh_fwd and efe_rev, the blunt ended PCR product was cloned in vector pCR-zero-blunt (Invitrogen) to give plasmid pCR-blunt_Pffh-efe (Seq ID 1x, FIGS. 152A and 152B).

II. Production of Ethylene by E. coli

E. coli DH5α, pCRblunt-Pffh-efe was inoculated in 5 ml LB+50 ppm Kanamycin and incubated overnight at 30° C. and 200 rpm. The morning after, it was inoculated in HM1 medium, pH 6.8 (Table 1x) containing 10 g/L glucose and 1 g/L yeast extract, to an OD600 of 0.1. The culture was incubated at 30° C. and 200 rpm. After 3 h incubation, 4×1 ml and 4×5 ml of culture were transferred in a 20 ml headspace vial sealed with a Teflon cap. After 7.5 h of incubation, another set of 4×5 mL of culture was transferred to a 20 ml headspace vial sealed with a Teflon cap. The vials were incubated at 30° C. and shaking at 200 rpm. At regular time intervals, a vial was removed and analyzed for ethylene concentration in the headspace, OD600 and organic acids.

TABLE 1x

HM1 medium composition

| Compounds | Concentration (g/L) |
|---|---|
| K2HPO4 | 13.6 |
| KH2PO4 | 13.6 |
| MgSO4 * 7H2O | 2 |
| Citric Acid Monohydrate | 2 |
| Ferric Ammonium Citrate | 0.3 |

TABLE 1x-continued

HM1 medium composition

| Compounds | Concentration (g/L) |
|---|---|
| (NH4)2SO4 | 3.2 |
| Trace metal solution | 1 ml |

Ethylene was measured by GC/FID analysis with an Agilent 7890 GC instrument outfitted with a CTC PAL headspace autosampler. The GC column was a GS-GasPro column (30 m×0.25 mm×1 um) interfaced to a FID detector. The carrier gas was helium at a flow rate of 1.076 mL/min (28.8 cm/sec) with the injector port operated at a split ratio of 20:1, and the FID detector held at 260° C. Headspace samples (100 uL/injection) were withdrawn from 20 mL glass vials and analyzed using an isothermal program with an oven temperature set at 90° C. for the 5 min run time. The method was calibrated using a 100 ppm ethylene in nitrogen standard gas mixture obtained from Scott Specialty Gases (PA, USA).

Organic acids were analyzed by HPLC (Ion exclusion column Aminex HPX-87H, 300 mm×7.8 mm, 0.005 M $H_2SO_4$, 0.6 mL/min as the mobile phase). Succinate could not be detected by this method as its peak interfered with a component in the medium.

FIGS. 153, 154 and 155 present ethylene (mg/L headspace), OD, glucose (g/L), acetate (g/L) and lactate (g/L) concentration for the three sets of headspace vials incubation (FIG. 153: 5 mL broth at OD 0.23; FIG. 154: 1 mL broth at OD 0.23; FIG. 155: 5 mL broth at OD 0.45). No ethylene was detected in control vials containing *E. coli* DH5α only, with broth transferred to the vials at same OD and incubated for the same amount of time.

III. Recovery of Ethylene from the Headspace

Ethylene was recovered using adsorption on a silver-modified montmorillonite clay, as described by Cho et al. (*Korean J. Chem. Eng.* (2002) 19(5), 821-826.). Fermentation off-gas was dehumidified and run into a silver-modified clay (Cho (2002)) filter in order to remove ethylene from the off-gas stream. The off-gas stream can be further treated before introduction into the silver-clay filter whereby carbon dioxide is scrubbed from the off-gas stream by sparging through an aqueous sodium hydroxide solution. Ethylene was desorbed from the silver-clay filter using a pressure swing cycle as described by Cho et al.

APPENDIX 1

Exemplary 1-deoxy-D-xylulose-5-phosphate synthase nucleic acids and polypeptides

| | |
|---|---|
| ATH: | AT3G21500(DXPS1) AT4G15560(CLA1) AT5G11380(DXPS3) |
| OSA: | 4338768 4340090 4342614 |
| CME: | CMF089C |
| PFA: | MAL13P1.186 |
| TAN: | TA20470 |
| TPV: | TP01_0516 |
| ECO: | b0420(dxs) |
| ECJ: | JW0410(dxs) |
| ECE: | Z0523(dxs) |
| ECS: | ECs0474 |
| ECC: | c0531(dxs) |
| ECI: | UTI89_C0443(dxs) |
| ECP: | ECP_0479 |
| ECV: | APECO1_1590(dxs) |
| ECW: | EcE24377A_0451(dxs) |
| ECX: | EcHS_A0491 |
| STY: | STY0461(dxs) |
| STT: | t2441(dxs) |
| SPT: | SPA2301(dxs) |
| SEC: | SC0463(dxs) |
| STM: | STM0422(dxs) |
| YPE: | YPO3177(dxs) |
| YPK: | y1008(dxs) |
| YPM: | YP_0754(dxs) |
| YPA: | YPA_2671 |
| YPN: | YPN_0911 |
| YPP: | YPDSF_2812 |
| YPS: | YPTB0939(dxs) |
| YPI: | YpsIP31758_3112(dxs) |
| SFL: | SF0357(dxs) |
| SFX: | S0365(dxs) |
| SFV: | SFV_0385(dxs) |
| SSN: | SSON_0397(dxs) |
| SBO: | SBO_0314(dxs) |
| SDY: | SDY_0310(dxs) |
| ECA: | ECA1131(dxs) |
| PLU: | plu3887(dxs) |
| BUC: | BU464(dxs) |
| BAS: | BUsg448(dxs) |
| WBR: | WGLp144(dxs) |
| SGL: | SG0656 |
| KPN: | KPN_00372(dxs) |
| BFL: | Bfl238(dxs) |
| BPN: | BPEN_244(dxs) |
| HIN: | HI1439(dxs) |
| HIT: | NTHI1691(dxs) |
| HIP: | CGSHiEE_04795 |
| HIQ: | CGSHiGG_01080 |
| HDU: | HD0441(dxs) |
| HSO: | HS_0905(dxs) |
| PMU: | PM0532(dxs) |
| MSU: | MS1059(dxs) |
| APL: | APL_0207(dxs) |
| XFA: | XF2249 |
| XFT: | PD1293(dxs) |
| XCC: | XCC2434(dxs) |
| XCB: | XC_1678 |
| XCV: | XCV2764(dxs) |
| XAC: | XAC2565(dxs) |
| XOO: | XOO2017(dxs) |
| XOM: | XOO_1900(XOO1900) |
| VCH: | VC0889 |
| VVU: | VV1_0315 |
| VVY: | VV0868 |
| VPA: | VP0686 |
| VFI: | VF0711 |
| PPR: | PBPRA0805 |
| PAE: | PA4044(dxs) |
| PAU: | PA14_11550(dxs) |
| PAP: | PSPA7_1057(dxs) |
| PPU: | PP_0527(dxs) |
| PST: | PSPTO_0698(dxs) |
| PSB: | Psyr_0604 |
| PSP: | PSPPH_0599(dxs) |
| PFL: | PFL_5510(dxs) |
| PFO: | Pfl_5007 |
| PEN: | PSEEN0600(dxs) |
| PMY: | Pmen_3844 |
| PAR: | Psyc_0221(dxs) |
| PCR: | Pcryo_0245 |
| ACI: | ACIAD3247(dxs) |
| SON: | SO_1525(dxs) |
| SDN: | Sden_2571 |
| SFR: | Sfri_2790 |
| SAZ: | Sama_2436 |
| SBL: | Sbal_1357 |
| SLO: | Shew_2771 |
| SHE: | Shewmr4_2731 |
| SHM: | Shewmr7_2804 |
| SHN: | Shewana3_2901 |
| SHW: | Sputw3181_2831 |
| ILO: | IL2138(dxs) |
| CPS: | CPS_1088(dxs) |
| PHA: | PSHAa2366(dxs) |
| PAT: | Patl_1319 |

APPENDIX 1

| | |
|---|---|
| SDE: | Sde_3381 |
| PIN: | Ping_2240 |
| MAQ: | Maqu_2438 |
| MCA: | MCA0817(dxs) |
| FTU: | FTT1018c(dxs) |
| FTF: | FTF1018c(dxs) |
| FTW: | FTW_0925(dxs) |
| FTL: | FTL_1072 |
| FTH: | FTH_1047(dxs) |
| FTA: | FTA_1131(dxs) |
| FTN: | FTN_0896(dxs) |
| NOC: | Noc_1743 |
| AEH: | Mlg_1381 |
| HCH: | HCH_05866(dxs) |
| CSA: | Csal_0099 |
| ABO: | ABO_2166(dxs) |
| AHA: | AHA_3321(dxs) |
| BCI: | BCI_0275(dxs) |
| RMA: | Rmag_0386 |
| VOK: | COSY_0360(dxs) |
| NME: | NMB1867 |
| NMA: | NMA0589(dxs) |
| NMC: | NMC0352(dxs) |
| NGO: | NGO0036 |
| CVI: | CV_2692(dxs) |
| RSO: | RSc2221(dxs) |
| REU: | Reut_A0882 |
| REH: | H16_A2732(dxs) |
| RME: | Rmet_2615 |
| BMA: | BMAA0330(dxs) |
| BMV: | BMASAVP1_1512(dxs) |
| BML: | BMA10299_1706(dxs) |
| BMN: | BMA10247_A0364(dxs) |
| BXE: | Bxe_B2827 |
| BUR: | Bcep18194_B2211 |
| BCN: | Bcen_4486 |
| BCH: | Bcen2424_3879 |
| BAM: | Bamb_3250 |
| BPS: | BPSS1762(dxs) |
| BPM: | BURPS1710b_A0842(dxs) |
| BPL: | BURPS1106A_A2392(dxs) |
| BPD: | BURPS668_A2534(dxs) |
| BTE: | BTH_II0614(dxs) |
| BPE: | BP2798(dxs) |
| BPA: | BPP2464(dxs) |
| BBR: | BB1912(dxs) |
| RFR: | Rfer_2875 |
| POL: | Bpro_1747 |
| PNA: | Pnap_1501 |
| AJS: | Ajs_1038 |
| MPT: | Mpe_A2631 |
| HAR: | HEAR0279(dxs) |
| MMS: | mma_0331 |
| NEU: | NE1161(dxs) |
| NET: | Neut_1501 |
| NMU: | Nmul_A0236 |
| EBA: | ebA4439(dxs) |
| AZO: | azo1198(dxs) |
| DAR: | Daro_3061 |
| TBD: | Tbd_0879 |
| MFA: | Mfla_2133 |
| HPY: | HP0354(dxs) |
| HPJ: | jhp0328(dxs) |
| HPA: | HPAG1_0349 |
| HHE: | HH0608(dxs) |
| HAC: | Hac_0968(dxs) |
| WSU: | WS1996 |
| TDN: | Tmden_0475 |
| CJE: | Cj0321(dxs) |
| CJR: | CJE0366(dxs) |
| CJJ: | CJJ81176_0343(dxs) |
| CJU: | C8J_0298(dxs) |
| CJD: | JJD26997_1642(dxs) |
| CFF: | CFF8240_0264(dxs) |
| CCV: | CCV52592_1671(dxs) CCV52592_1722 |
| CHA: | CHAB381_1297(dxs) |
| CCO: | CCC13826_1594(dxs) |
| ABU: | Abu_2139(dxs) |
| NIS: | NIS_0391(dxs) |
| SUN: | SUN_2055(dxs) |
| GSU: | GSU0686(dxs-1) GSU1764(dxs-2) |
| GME: | Gmet_1934 Gmet_2822 |
| PCA: | Pcar_1667 |
| PPD: | Ppro_1191 Ppro_2403 |
| DVU: | DVU1350 |
| DVL: | Dvul_1718 |
| DDE: | Dde_2200 |
| LIP: | LI0408(dsx) |
| DPS: | DP2700 |
| ADE: | Adeh_1097 |
| MXA: | MXAN_4643(dxs) |
| SAT: | SYN_02456 |
| SFU: | Sfum_1418 |
| PUB: | SAR11_0611(dxs) |
| MLO: | mlr7474 |
| MES: | Meso_0735 |
| SME: | SMc00972(dxs) |
| ATU: | Atu0745(dxs) |
| ATC: | AGR_C_1351 |
| RET: | RHE_CH00913(dxs) |
| RLE: | RL0973(dxs) |
| BME: | BMEI1498 |
| BMF: | BAB1_0462(dxs) |
| BMS: | BR0436(dxs) |
| BMB: | BruAb1_0458(dxs) |
| BOV: | BOV_0443(dxs) |
| BJA: | bll2651(dxs) |
| BRA: | BRADO2161(dxs) |
| BBT: | BBta_2479(dxs) |
| RPA: | RPA0952(dxs) |
| RPB: | RPB_4460 |
| RPC: | RPC_1149 |
| RPD: | RPD_4305 |
| RPE: | RPE_1067 |
| NWI: | Nwi_0633 |
| NHA: | Nham_0778 |
| BHE: | BH04350(dxs) |
| BQU: | BQ03540(dxs) |
| BBK: | BARBAKC583_0400(dxs) |
| CCR: | CC_2068 |
| SIL: | SPO0247(dxs) |
| SIT: | TM1040_2920 |
| RSP: | RSP_0254(dxsA) RSP_1134(dxs) |
| JAN: | Jann_0088 Jann_0170 |
| RDE: | RD1_0101(dxs) RD1_0548(dxs) |
| MMR: | Mmar10_0849 |
| HNE: | HNE_1838(dxs) |
| ZMO: | ZMO1234(dxs) ZMO1598(dxs) |
| NAR: | Saro_0161 |
| SAL: | Sala_2354 |
| ELI: | ELI_12520 |
| GOX: | GOX0252 |
| GBE: | GbCGDNIH1_0221 GbCGDNIH1_2404 |
| RRU: | Rru_A0054 Rru_A2619 |
| MAG: | amb2904 |
| MGM: | Mmc1_1048 |
| SUS: | Acid_1783 |
| BSU: | BG11715(dxs) |
| BHA: | BH2779 |
| BAN: | BA4400(dxs) |
| BAR: | GBAA4400(dxs) |
| BAA: | BA_4853 |
| BAT: | BAS4081 |
| BCE: | BC4176(dxs) |
| BCA: | BCE_4249(dxs) |
| BCZ: | BCZK3930(dxs) |
| BTK: | BT9727_3919(dxs) |
| BTL: | BALH_3785(dxs) |
| BLI: | BL01523(dxs) |
| BLD: | BLi02598(dxs) |
| BCL: | ABC2462(dxs) |
| BAY: | RBAM_022600 |
| BPU: | BPUM_2159 |
| GKA: | GK2392 |
| GTN: | GTNG_2322 |
| LMO: | lmo1365(tktB) |

APPENDIX 1

| | |
|---|---|
| LMF: | LMOf2365_1382(dxs) |
| LIN: | lin1402(tktB) |
| LWE: | lwe1380(tktB) |
| LLA: | L108911(dxsA) L123365(dxsB) |
| LLC: | LACR_1572 LACR_1843 |
| LLM: | llmg_0749(dxsB) |
| SAK: | SAK_0263 |
| LPL: | lp_2610(dxs) |
| LJO: | LJ0406 |
| LAC: | LBA0356 |
| LSL: | LSL_0209(dxs) |
| LGA: | LGAS_0350 |
| STH: | STH1842 |
| CAC: | CAC2077 CA_P0106(dxs) |
| CPE: | CPE1819 |
| CPF: | CPF_2073(dxs) |
| CPR: | CPR_1787(dxs) |
| CTC: | CTC01575 |
| CNO: | NT01CX_1983 |
| CTH: | Cthe_0828 |
| CDF: | CD1207(dxs) |
| CBO: | CBO1881(dxs) |
| CBA: | CLB_1818(dxs) |
| CBH: | CLC_1825(dxs) |
| CBF: | CLI_1945(dxs) |
| CKL: | CKL_1231(dxs) |
| CHY: | CHY_1985(dxs) |
| DSY: | DSY2348 |
| DRM: | Dred_1078 |
| PTH: | PTH_1196(dxs) |
| SWO: | Swol_0582 |
| CSC: | Csac_1853 |
| TTE: | TTE1298(dxs) |
| MTA: | Moth_1511 |
| MPE: | MYPE730 |
| MGA: | MGA_1268(dxs) |
| MTU: | Rv2682c(dxsl) Rv3379c(dxs2) |
| MTC: | MT2756(dxs) |
| MBO: | Mb2701c(dxsl) Mb3413c(dxs2) |
| MLE: | ML1038(dxs) |
| MPA: | MAP2803c(dxs) |
| MAV: | MAV_3577(dxs) |
| MSM: | MSMEG_2776(dxs) |
| MMC: | Mmcs_2208 |
| CGL: | NCgl1827(cgl1902) |
| CGB: | cg2083(dxs) |
| CEF: | CE1796 |
| CDI: | DIP1397(dxs) |
| CJK: | jk1078(dxs) |
| NFA: | nfa37410(dxs) |
| RHA: | RHA1_ro06843 |
| SCO: | SCO6013(SC1C3.01) SCO6768(SC6A5.17) |
| SMA: | SAV1646(dxsl) SAV2244(dxs2) |
| TWH: | TWT484 |
| TWS: | TW280(Dxs) |
| LXX: | Lxx10450(dxs) |
| CMI: | CMM_1660(dxsA) |
| AAU: | AAur_1790(dxs) |
| PAC: | PPA1062 |
| TFU: | Tfu_1917 |
| FRA: | Francci3_1326 |
| FAL: | FRAAL2088(dxs) |
| ACE: | Acel_1393 |
| SEN: | SACE_1815(dxs) SACE_4351 |
| BLO: | BL1132(dxs) |
| BAD: | BAD_0513(dxs) |
| FNU: | FN1208 FN1464 |
| RBA: | RB2143(dxs) |
| CTR: | CT331(dxs) |
| CTA: | CTA_0359(dxs) |
| CMU: | TC0608 |
| CPN: | CPn1060(tktB_2) |
| CPA: | CP0790 |
| CPJ: | CPj1060(tktB_2) |
| CPT: | CpB1102 |
| CCA: | CCA00304(dxs) |
| CAB: | CAB301(dxs) |
| CFE: | CF0699(dxs) |
| PCU: | pc0619(dxs) |
| TPA: | TP0824 |
| TDE: | TDE1910(dxs) |
| LIL: | LA3285(dxs) |
| LIC: | LIC10863(dxs) |
| LBJ: | LBJ_0917(dxs) |
| LBL: | LBL_0932(dxs) |
| SYN: | sll1945(dxs) |
| SYW: | SYNW1292(Dxs) |
| SYC: | syc1087_c(dxs) |
| SYF: | Synpcc7942_0430 |
| SYD: | Syncc9605_1430 |
| SYE: | Syncc9902_1069 |
| SYG: | sync_1410(dxs) |
| SYR: | SynRCC307_1390(dxs) |
| SYX: | SynWH7803_1223(dxs) |
| CYA: | CYA_1701(dxs) |
| CYB: | CYB_1983(dxs) |
| TEL: | tll0623 |
| GVI: | gll0194 |
| ANA: | alr0599 |
| AVA: | Ava_4532 |
| PMA: | Pro0928(dxs) |
| PMM: | PMM0907(Dxs) |
| PMT: | PMT0685(dxs) |
| PMN: | PMN2A_0300 |
| PMI: | PMT9312_0893 |
| PMB: | A9601_09541(dxs) |
| PMC: | P9515_09901(dxs) |
| PMF: | P9303_15371(dxs) |
| PMG: | P9301_09521(dxs) |
| PMH: | P9215_09851 |
| PMJ: | P9211_08521 |
| PME: | NATL1_09721(dxs) |
| TER: | Tery_3042 |
| BTH: | BT_1403 BT_4099 |
| BFR: | BF0873 BF4306 |
| BFS: | BF0796(dxs) BF4114 |
| PGI: | PG2217(dxs) |
| CHU: | CHU_3643(dxs) |
| GFO: | GFO_3470(dxs) |
| FPS: | FP0279(dxs) |
| CTE: | CT0337(dxs) |
| CPH: | Cpha266_0671 |
| PVI: | Cvib_0498 |
| PLT: | Plut_0450 |
| DET: | DET0745(dxs) |
| DEH: | cbdb_A720(dxs) |
| DRA: | DR_1475 |
| DGE: | Dgeo_0994 |
| TTH: | TTC1614 |
| TTJ: | TTHA0006 |
| AAE: | aq_881 |
| TMA: | TM1770 |
| PMO: | Pmob_1001 |

Exemplary acetyl-CoA-acetyltransferase nucleic acids and polypeptides

| | |
|---|---|
| HSA: | 38(ACAT1) 39(ACAT2) |
| PTR: | 451528(ACAT1) |
| MCC: | 707653(ACAT1) 708750(ACAT2) |
| MMU: | 110446(Acat1) 110460(Acat2) |
| RNO: | 25014(Acat1) |
| CFA: | 484063(ACAT2) 489421(ACAT1) |
| GGA: | 418968(ACAT1) 421587(RCJMB04_34i5) |
| XLA: | 379569(MGC69098) 414622(MGC81403) 414639(MGC81256) 444457(MGC83664) |
| XTR: | 394562(acat2) |
| DRE: | 30643(acat2) |
| SPU: | 759502(LOC759502) |
| DME: | Dmel_CG10932 Dmel_CG9149 |
| CEL: | T02G5.4 T02G5.7 T02G5.8(kat-1) |
| ATH: | AT5G48230(ACAT2/EMB1276) |
| OSA: | 4326136 4346520 |
| CME: | CMA042C CME087C |
| SCE: | YPL028W(ERG10) |
| AGO: | AGOS_ADR165C |
| PIC: | PICST_31707(ERG10) |

APPENDIX 1

| | |
|---|---|
| CAL: | CaO19.1591(erg10) |
| CGR: | CAGL0L12364g |
| SPO: | SPBC215.09c |
| MGR: | MGG_01755 MGG_13499 |
| ANI: | AN1409.2 |
| AFM: | AFUA_6G14200 AFUA_8G04000 |
| AOR: | AO090103000012 AO090103000406 |
| CNE: | CNC05280 |
| UMA: | UM03571.1 |
| DDI: | DDB_0231621 |
| PFA: | PF14_0484 |
| TET: | TTHERM_00091590 TTHERM_00277470 TTHERM_00926980 |
| TCR: | 511003.60 |
| ECO: | b2224(atoB) |
| ECJ: | JW2218(atoB) JW5453(yqeF) |
| ECE: | Z4164(yqeF) |
| ECS: | ECs3701 |
| ECC: | c2767(atoB) c3441(yqeF) |
| ECI: | UTI89_C2506(atoB) UTI89_C3247(yqeF) |
| ECP: | ECP_2268 ECP_2857 |
| ECV: | APECO1_3662(yqeF) APECO1_4335(atoB) APECO1_43352(atoB) |
| ECX: | EcHS_A2365 |
| STY: | STY3164(yqeF) |
| STT: | t2929(yqeF) |
| SPT: | SPA2886(yqeF) |
| SEC: | SC2958(yqeF) |
| STM: | STM3019(yqeF) |
| SFL: | SF2854(yqeF) |
| SFX: | 53052(yqeF) |
| SFV: | SFV_2922(yqeF) |
| SSN: | SSON_2283(atoB) SSON_3004(yqeF) |
| SBO: | SBO_2736(yqeF) |
| ECA: | ECA1282(atoB) |
| ENT: | Ent638_3299 |
| SPE: | Spro_0592 |
| HIT: | NTHI0932(atoB) |
| XCC: | XCC1297(atoB) |
| XCB: | XC_2943 |
| XCV: | XCV1401(thlA) |
| XAC: | XAC1348(atoB) |
| XOO: | XOO1881(atoB) |
| XOM: | XOO_1778(XOO1778) |
| VCH: | VCA0690 |
| VCO: | VC0395_0630 |
| VVU: | VV2_0494 VV2_0741 |
| VVY: | VVA1043 VVA1210 |
| VPA: | VPA0620 VPA1123 VPA1204 |
| PPR: | PBPRB1112 PBPRB1840 |
| PAE: | PA2001(atoB) PA2553 PA3454 PA3589 PA3925 |
| PAU: | PA14_38630(atoB) |
| PPU: | PP_2051(atoB) PP_2215(fadAx) PP_3754 PP_4636 |
| PPF: | Pput_2009 Pput_2403 Pput_3523 Pput_4498 |
| PST: | PSPTO_0957(phbA-1) PSPTO_3164(phbA-2) |
| PSB: | Psyr_0824 Psyr_3031 |
| PSP: | PSPPH_0850(phbA1) PSPPH_2209(phbA2) |
| PFL: | PFL_1478(atoB-2) PFL_2321 PFL_3066 PFL_4330(atoB-2) PFL_5283 |
| PFO: | Pfl_1269 Pfl_1739 Pfl_2074 Pfl_2868 |
| PEN: | PSEEN3197 PSEEN3547(fadAx) PSEEN4635(phbA) |
| PMY: | Pmen_1138 Pmen_2036 Pmen_3597 Pmen_3662 Pmen_3820 |
| PAR: | Psyc_0252 Psyc_1169 |
| PCR: | Pcryo_0278 Pcryo_1236 Pcryo_1260 |
| PRW: | PsycPRwf_2011 |
| ACI: | ACIAD0694 ACIAD1612 ACIAD2516(atoB) |
| SON: | SO_1677(atoB) |
| SDN: | Sden_1943 |
| SFR: | Sfri_1338 Sfri_2063 |
| SAZ: | Sama_1375 |
| SBL: | Sbal_1495 |
| SBM: | Shew185_1489 |
| SBN: | Sbal195_1525 |
| SLO: | Shew_1667 Shew_2858 |
| SPC: | Sputcn32_1397 |
| SSE: | Ssed_1473 Ssed_3533 |
| SPL: | Spea_2783 |
| SHE: | Shewmr4_2597 |
| SHM: | Shewmr7_2664 |
| SHN: | Shewana3_2771 |
| SHW: | Sputw3181_2704 |
| ILO: | IL0872 |
| CPS: | CPS_1605 CPS_2626 |
| PHA: | PSHAa0908 PSHAa1454(atoB) PSHAa1586(atoB) |
| PAT: | Patl_2923 |
| SDE: | Sde_3149 |
| PIN: | Ping_0659 Ping_2401 |
| MAQ: | Maqu_2117 Maqu_2489 Maqu_2696 Maqu_3162 |
| CBU: | CBU_0974 |
| LPN: | pg1825(atoB) |
| LPF: | lpl1789 |
| LPP: | lpp1788 |
| NOC: | Noc_1891 |
| AEH: | Mlg_0688 Mlg_2706 |
| HHA: | Hhal_1685 |
| HCH: | HCH_05299 |
| CSA: | Csal_0301 Csal_3068 |
| ABO: | ABO_0648(fadAx) |
| MMW: | Mmwyl1_0073 Mmwyl1_3021 Mmwyl1_3053 Mmwyl1_3097 Mmwyl1_4182 |
| AHA: | AHA_2143(atoB) |
| CVI: | CV_2088(atoB) CV_2790(phaA) |
| RSO: | RSc0276(atoB) RSc1632(phbA) RSc1637(bktB) RSc1761(RS02948) |
| REU: | Reut_A0138 Reut_A1348 Reut_A1353 Reut_B4561 Reut_B4738 Reut_B5587 Reut_C5943 Reut_C6062 |
| REH: | H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771 |
| RME: | Rmet_0106 Rmet_1357 Rmet_1362 Rmet_5156 |
| BMA: | BMA1316 BMA1321(phbA) BMA1436 |
| BMV: | BMASAVPLA1805(bktB) BMASAVPLA1810(phbA) |
| BML: | BMA10299_A0086(phbA) BMA10299_A0091 |
| BMN: | BMA10247_1076(bktB) BMA10247_1081(phbA) |
| BXE: | Bxe_A2273 Bxe_A2335 Bxe_A2342 Bxe_A4255 Bxe_B0377 Bxe_B0739 Bxe_C0332 Bxe_C0574 Bxe_C0915 |
| BVI: | Bcep1808_0519 Bcep1808_1717 Bcep1808_2877 Bcep1808_3594 Bcep1808_4015 Bcep1808_5507 Bcep1808_5644 |
| BUR: | Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332 |
| BCN: | Bcen_1553 Bcen_1599 Bcen_2158 Bcen_2563 Bcen_2998 Bcen_6289 |
| BCH: | Bcen2424_0542 Bcen2424_1790 Bcen2424_2772 Bcen2424_5368 Bcen2424_6232 Bcen2424_6276 |
| BAM: | Bamb_0447 Bamb_1728 Bamb_2824 Bamb_4717 Bamb_5771 Bamb_5969 |
| BPS: | BPSL1426 BPSL1535(phbA) BPSL1540 |
| BPM: | BURPS1710b_2325(bktB) BURPS1710b_2330(phbA) BURPS1710b_2453(atoB-2) |
| BPL: | BURPS1106A_2197(bktB) BURPS1106A_2202(phbA) |
| BPD: | BURPS668_2160(bktB) BURPS668_2165(phbA) |
| BTE: | BTH_I2144 BTH_I2256 BTH_I2261 |
| PNU: | Pnuc_0927 |
| BPE: | BP0447 BP0668 BP2059 |
| BPA: | BPP0608 BPP1744 BPP3805 BPP4216 BPP4361 |
| BBR: | BB0614 BB3364 BB4250 BB4804 BB4947 |
| RFR: | Rfer_0272 Rfer_1000 Rfer_1871 Rfer_2273 Rfer_2561 Rfer_2594 Rfer_3839 |
| POL: | Bpro_1577 Bpro_2140 Bpro_3113 Bpro_4187 |
| PNA: | Pnap_0060 Pnap_0458 Pnap_0867 Pnap_1159 Pnap_2136 Pnap_2804 |
| AAV: | Aave_0031 Aave_2478 Aave_3944 Aave_4368 |
| AJS: | Ajs_0014 Ajs_0124 Ajs_1931 Ajs_2073 Ajs_2317 Ajs_3548 Ajs_3738 Ajs_3776 |
| VEI: | Veis_1331 Veis_3818 Veis_4193 |
| DAC: | Daci_0025 Daci_0192 Daci_3601 Daci_5988 |
| MPT: | Mpe_A1536 Mpe_A1776 Mpe_A1869 Mpe_A3367 |
| HAR: | HEAR0577(phbA) |
| MMS: | mma_0555 |
| NEU: | NE2262(bktB) |
| NET: | Neut_0610 |

APPENDIX 1

| | |
|---|---|
| EBA: | ebA5202 p2A409(tioL) |
| AZO: | azo0464(fadA1) azo0469(fadA2) azo2172(thlA) ************** |
| DAR: | Daro_0098 Daro_3022 |
| HPA: | HPAG1_0675 |
| HAC: | Hac_0958(atoB) |
| GME: | Gmet_1719 Gmet_2074 Gmet_2213 Gmet_2268 Gmet_3302 |
| GUR: | Gura_3043 |
| BBA: | Bd0404(atoB) Bd2095 |
| DOL: | Dole_0671 Dole_1778 Dole_160 Dole_2187 |
| ADE: | Adeh_0062 Adeh_2365 |
| AFW: | Anae109_0064 Anae109_1504 |
| MXA: | MXAN_3791 |
| SAT: | SYN_02642 |
| SFU: | Sfum_2280 Sfum_3582 |
| RPR: | RP737 |
| RCO: | RC1134 RC1135 |
| RFE: | RF_0163(paaJ) |
| RBE: | RBE_0139(paaJ) |
| RAK: | A1C_05820 |
| RBO: | A1I_07215 |
| RCM: | A1E_04760 |
| PUB: | SAR11_0428(thlA) |
| MLO: | mlr3847 |
| MES: | Meso_3374 |
| PLA: | Plav_1573 Plav_2783 |
| SME: | SMa1450 SMc03879(phbA) |
| SMD: | Smed_0499 Smed_3117 Smed_5094 Smed_5096 |
| ATU: | Atu2769(atoB) Atu3475 |
| ATC: | AGR_C_5022(phbA) AGR_L_2713 |
| RET: | RHE_CH04018(phbAch) RHE_PC00068(ypc00040) RHE_PF00014(phbAf) |
| RLE: | RL4621(phaA) pRL100301 pRL120369 |
| BME: | BMEI0274 BMEII0817 |
| BMF: | BAB1_1783(phbA-1) BAB2_0790(phbA-2) |
| BMS: | BR1772(phbA-1) BRA0448(phbA-2) |
| BMB: | BruAb1_1756(phbA-1) BruAb2_0774(phbA-2) |
| BOV: | BOV_1707(phbA-1) |
| OAN: | Oant_1130 Oant_3107 Oant_3718 Oant_4020 |
| BJA: | bll0226(atoB) bll3949 b117400 bl7819 blr3724(phbA) |
| BRA: | BRADO0562(phbA) BRADO0983(pimB) BRADO3110 BRADO3134(atoB) |
| BBT: | BBta_3558 BBta_3575(atoB) BBta_5147(pimB) BBta_7072(pimB) BBta_7614(phbA) |
| RPA: | RPA0513(pcaF) RPA0531 RPA3715(pimB) |
| RPB: | RPB_0509 RPB_0525 RPB_1748 |
| RPC: | RPC_0504 RPC_0636 RPC_0641 RPC_0832 RPC_1050 RPC_2005 RPC_2194 RPC_2228 |
| RPD: | RPD_0306 RPD_0320 RPD_3105 RPD_3306 |
| RPE: | RPE_0168 RPE_0248 RPE_3827 |
| NWI: | Nwi_3060 |
| XAU: | Xaut_3108 Xaut_4665 |
| CCR: | CC_0510 CC_0894 CC_3462 |
| SIL: | SPO0142(bktB) SPO0326(phbA) SPO0773 SPO3408 |
| SIT: | TM1040_0067 TM1040_2790 TM1040_3026 TM1040_3735 |
| RSP: | RSP_0745 RSP_1354 RSP_3184 |
| RSH: | Rsph17029_0022 Rsph17029_2401 Rsph17029_3179 Rsph17029_3921 |
| RSQ: | Rsph17025_0012 Rsph17025_2466 Rsph17025_2833 |
| JAN: | Jann_0262 Jann_0493 Jann_4050 |
| RDE: | RD1_0025 RD1_0201(bktB) RD1_3394(phbA) |
| PDE: | Pden_2026 Pden_2663 Pden_2870 Pden_2907 Pden_4811 Pden_5022 |
| DSH: | Dshi_0074 Dshi_3066 Dshi_3331 |
| MMR: | Mmar10_0697 |
| HNE: | HNE_2706 HNE_3065 HNE_3133 |
| NAR: | Saro_0809 Saro_1069 Saro_1222 Saro_2306 Saro_2349 |
| SAL: | Sala_0781 Sala_1244 Sala_2896 Sala_3158 |
| SWI: | Swit_0632 Swit_0752 Swit_2893 Swit_3602 Swit_4887 Swit_5019 Swit_5309 |
| ELI: | ELI_01475 ELI_06705 ELI_12035 |
| GBE: | GbCGDNIH1_0447 |
| ACR: | Acry_1847 Acry_2256 |
| RRU: | Rru_A0274 Rru_A1380 Rru_A1469 Rru_A1946 Rru_A3387 |
| MAG: | amb0842 |
| MGM: | Mmc1_1165 |
| ABA: | Acid345_3239 |
| BSU: | BG11319(mmgA) BG13063(yhfS) |
| BHA: | BH1997 BH2029 BH3801(mmgA) |
| BAN: | BA3687 BA4240 BA5589 |
| BAR: | GBAA3687 GBAA4240 GBAA5589 |
| BAA: | BA_0445 BA_4172 BA_4700 |
| BAT: | BAS3418 BAS3932 BAS5193 |
| BCE: | BC3627 BC4023 BC5344 |
| BCA: | BCE_3646 BCE_4076 BCE_5475 |
| BCZ: | BCZK3329(mmgA) BCZK3780(thl) BCZK5044(atoB) |
| BCY: | Bcer98_2722 Bcer98_3865 |
| BTK: | BT9727_3379(mmgA) BT9727_3765(thl) BT9727_5028(atoB) |
| BTL: | BALH_3262(mmgA) BALH_3642(fadA) BALH_4843(atoB) |
| BLI: | BL03925(mmgA) |
| BLD: | BLi03968(mmgA) |
| BCL: | ABC0345 ABC2989 ABC3617 ABC3891(mmgA) |
| BAY: | RBAM_022450 |
| BPU: | BPUM_2374(yhfS) BPUM_2941 BPUM_3373 |
| OIH: | OB0676 OB0689 OB2632 OB3013 |
| GKA: | GK1658 GK3397 |
| SAU: | SA0342 SA0534(vraB) |
| SAV: | SAV0354 SAV0576(vraB) |
| SAM: | MW0330 MW0531(vraB) |
| SAR: | SAR0351(thl) SAR0581 |
| SAS: | SAS0330 SAS0534 |
| SAC: | SACOL0426 SACOL0622(atoB) |
| SAB: | SAB0304(th1) SAB0526 |
| SAA: | SAUSA300_0355 SAUSA300_0560(vraB) |
| SAO: | SAOUHSC_00336 SAOUHSC_00558 |
| SAJ: | SaudH9_0402 |
| SAH: | SaurJH1_0412 |
| SEP: | SE0346 SE2384 |
| SER: | SERP0032 SERP0220 |
| SHA: | SH0510(mvaC) SH2417 |
| SSP: | SSP0325 SSP2145 |
| LMO: | lmo1414 |
| LMF: | LMOf2365_1433 |
| LIN: | lin1453 |
| LWE: | lwe1431 |
| LLA: | L11745(thiL) L25946(fadA) |
| LLC: | LACR_1665 LACR_1956 |
| LLM: | llmg_0930(thiL) |
| SPY: | SPy_0140 SPy_1637(atoB) |
| SPZ: | M5005_Spy_0119 M5005_Spy_0432 M5005_Spy_1344(atoB) |
| SPM: | spyM18_0136 spyM18_1645(atoB) |
| SPG: | SpyM3_0108 SpyM3_1378(atoB) |
| SPS: | SPs0110 SPs0484 |
| SPH: | MGAS10270_Spy0121 MGAS10270_Spy0433 MGAS10270_Spy1461(atoB) |
| SPI: | MGAS10750_Spy0124 MGAS10750_Spy0452 MGAS10750_Spy1453(atoB) |
| SPJ: | MGAS2096_Spy0123 MGAS2096_Spy0451 MGAS2096_Spy1365(atoB) |
| SPK: | MGAS9429_Spy0121 MGAS9429_Spy0431 MGAS9429_Spy1339(atoB) |
| SPF: | SpyM50447(atoB2) |
| SPA: | M6_Spy0166 M6_Spy0466 M6_Spy1390 |
| SPB: | M28_Spy0117 M28_Spy0420 M28_Spy1385(atoB) |
| SAK: | SAK_0568 |
| LJO: | LJ1609 |
| LAC: | LBA0626(thiL) |
| LSA: | LSA1486 |
| LDB: | Ldb0879 |
| LBU: | LBUL_0804 |
| LBR: | LVIS_2218 |
| LCA: | LSEI_1787 |
| LGA: | LGAS_1374 |
| LRE: | Lreu_0052 |
| EFA: | EF1364 |
| OOE: | OEOE_0529 |
| STH: | STH2913 STH725 STH804 |
| CAC: | CAC2873 CA_P0078(thiL) |
| CPE: | CPE2195(atoB) |
| CPF: | CPF_2460 |
| CPR: | CPR_2170 |
| CTC: | CTC00312 |
| CNO: | NT01CX_0538 NT01CX_0603 |
| CDF: | CD1059(thl1A1) CD2676(thl1A2) |
| CBO: | CBO3200(thl) |
| CBE: | Cbei_0411 Cbei_3630 |
| CKL: | CKL_3696(thlA1) CKL_3697(thlA2) CKL_3698(thlA3) |

APPENDIX 1

| | |
|---|---|
| AMT: | Amet_4630 |
| AOE: | Clos_0084 Clos_0258 |
| CHY: | CHY_1288 CHY_1355(atoB) CHY_1604 CHY_1738 |
| DSY: | DSY0632 DSY0639 DSY1567 DSY1710 DSY2402 DSY3302 |
| DRM: | Dred_0400 Dred_1491 Dred_1784 Dred_1892 |
| SWO: | Swol_0308 Swol_0675 Swol_0789 Swol_1486 Swol_1934 Swol_2051 |
| TTE: | TTE0549(paaJ) |
| MTA: | Moth_1260 |
| MTU: | Rv1135A Rv1323(fadA4) Rv3546(fadA5) |
| MTC: | MT1365(phbA) |
| MBO: | Mb1167 Mb1358(fadA4) Mb3576(fadA5) Mb3586c(fadA6) |
| MBB: | BCG_1197 BCG_1385(fadA4) BCG_3610(fadA5) BCG_3620c(fadA6) |
| MLE: | ML1158(fadA4) |
| MPA: | MAP2407c(fadA3) MAP2436c(fadA4) |
| MAV: | MAV_1544 MAV_1573 MAV_1863 MAV_5081 |
| MSM: | MSMEG_2224 MSMEG_4920 |
| MUL: | MUL_0357 |
| MVA: | Mvan_1976 Mvan_1988 Mvan_4305 Mvan_4677 Mvan_4891 |
| MGI: | Mflv_1347 Mflv_1484 Mflv_2040 Mflv_2340 Mflv_4356 Mflv_4368 |
| MMC: | Mmcs_1758 Mmcs_1769 Mmcs_3796 Mmcs_3864 |
| MKM: | Mkms_0251 Mkms_1540 Mkms_1805 Mkms_1816 Mkms_2836 Mkms_3159 Mkms_3286 Mkms_3869 Mkms_3938 Mkms_4227 Mkms_4411 Mkms_4580 Mkms_4724 Mkms_4764 Mkms_4776 |
| MJL: | Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075 |
| CGL: | NCgl2309(cgl2392) |
| CGB: | cg2625(pcaF) |
| CEF: | CE0731 CE2295 |
| CJK: | jk1543(fadA3) |
| NFA: | nfa10750(fadA4) |
| RHA: | RHA1_ro01455 RHA1_ro01623 RHA1_ro01876 RHA1_ro02517(catF) RHA1ro03022 RHA1ro03024 RHA1ro03391 RHA1ro03892 RHA1ro04599 RHA1ro05257 RHA1ro08871 |
| SCO: | SCO5399(SC8F4.03) |
| SMA: | SAV1384(fadA5) SAV2856(fadA1) |
| ART: | Arth_1160 Arth_2986 Arth_3268 Arth_4073 |
| NCA: | Noca_1371 Noca_1797 Noca_1828 Noca_2764 Noca_4142 |
| TFU: | Tfu_1520 Tfu_2394 |
| FRA: | Francci3_3687 |
| FRE: | Franean1_1044 Franean1_2711 Franean1_2726 Franean1_3929 Franean1_4037 Franean1_4577 |
| FAL: | FRAAL2514 FRAAL2618 FRAAL5910(atoB) |
| ACE: | Acel_0626 Acel_0672 |
| SEN: | SACE_1192(mmgA) SACE_2736(fadA6) SACE_4011(catF) SACE_6236(fadA4) |
| STP: | Strop_3610 |
| SAQ: | Sare_1316 Sare_3991 |
| RXY: | Rxyl_1582 Rxyl_1842 Rxyl_2389 Rxyl_2530 |
| FNU: | FN0495 |
| BGA: | BG0110(fadA) |
| BAF: | BAPKO_0110(fadA) |
| LIL: | LA0457(thiL1) LA0828(thiL2) LA4139(fadA) |
| LIC: | LIC10396(phbA) |
| LBJ: | LBJ_2862(paaJ-4) |
| LBL: | LBL_0209(paaJ-4) |
| SYN: | slr1993(phaA) |
| SRU: | SRU_1211(atoB) SRU_1547 |
| CHU: | CHU_1910(atoB) |
| GFO: | GFO_1507(atoB) |
| FJO: | Fjoh_4612 |
| FPS: | FP0770 FP1586 FP1725 |
| RRS: | RoseRS_3911 RoseRS_4348 |
| RCA: | Rcas_0702 Rcas_3206 |
| HAU: | Haur_0522 |
| DRA: | DR_1072 DR_1428 DR_1960 DR_2480 DR_A0053 |
| DGE: | Dgeo_0755 Dgeo_1305 Dgeo_1441 Dgeo_1883 |
| TTH: | TTC0191 TTC0330 |
| TTJ: | TTHA0559 |
| TME: | Tmel_1134 |
| FNO: | Fnod_0314 |
| PMO: | Pmob_0515 |
| HMA: | rrnAC0896(acaB3) rrnAC2815(aca2) rrnAC3497(yqeF) rrnB0240(aca1) rrnB0242(acaB2) rrnB0309(acaB1) |
| TAC: | Ta0582 |
| TVO: | TVN0649 |
| PTO: | PTO1505 |
| APE: | APE_2108 |
| SSO: | SSO2377(acaB-4) |
| STO: | ST0514 |
| SAI: | Saci_0963 Saci_1361(acaB1) |
| MSE: | Msed_0656 |
| PAI: | PAE1220 |
| PIS: | Pisl_0029 Pisl_1301 |
| PCL: | Pcal_0781 |
| PAS: | Pars_0309 Pars_1071 |
| CMA: | Cmaq_1941 |

Exemplary HMG-CoA synthase nucleic acids and polypeptides

| | |
|---|---|
| HSA: | 3157(HMGCS1) 3158(HMGCS2) |
| PTR: | 457169(HMGCS2) 461892(HMGCS1) |
| MCC: | 702553(HMGCS1) 713541(HMGCS2) |
| MMU: | 15360(Hmgcs2) 208715(Hmgcs1) |
| RNO: | 24450(Hmgcs2) 29637(Hmgcs1) |
| CFA: | 479344(HMGCS1) 607923(HMGCS2) |
| BTA: | 407767(HMGCS1) |
| SSC: | 397673(CH242-38B5.1) |
| GGA: | 396379(HMGCS1) |
| XLA: | 380091(hmgcsl) 447204(MGC80816) |
| DRE: | 394060(hmgcs1) |
| SPU: | 578259(LOC578259) |
| DME: | Dmel_CG4311(Hmgs) |
| CEL: | F25B4.6 |
| ATH: | AT4G11820(BAP1) |
| OSA: | 4331418 4347614 |
| CME: | CMM189C |
| SCE: | YML126C(ERG13) |
| AGO: | AGOS_ADL356C |
| PIC: | PICST_83020 |
| CAL: | CaO19_7312(CaO19.7312) |
| CGR: | CAGL0H04081g |
| SPO: | SPAC4F8.14c(hcs) |
| MGR: | MGG_01026 |
| ANI: | AN4923.2 |
| AFM: | AFUA_3G10660 AFUA_8G07210 |
| AOR: | AO090003000611 AO090010000487 |
| CNE: | CNC05080 CNG02670 |
| UMA: | UM05362.1 |
| ECU: | ECU10_0510 |
| DDI: | DDBDRAFT_0217522 DDB_0219924(hgsA) |
| TET: | TTHERM_00691190 |
| TBR: | Tb927.8.6110 |
| YPE: | YPO1457 |
| YPK: | y2712(pksG) |
| YPM: | YP_1349(pksG) |
| YPA: | YPA_0750 |
| YPN: | YPN_2521 |
| YPP: | YPDSF_1517 |
| YPS: | YPTB1475 |
| CBD: | COXBU7E912_1931 |
| TCX: | Tcr_1719 |
| DNO: | DNO_0799 |
| BMA: | BMAA1212 |
| BPS: | BPSS1002 |
| BPM: | BURPS1710b_A2613 |
| BPL: | BURPS1106A_A1384 |
| BPD: | BURPS668_A1470 |
| BTE: | BTH_II1670 |
| MXA: | MXAN_3948(tac) MXAN_4267(mvaS) |
| BSU: | BG10926(pksG) |
| OIH: | OB2248 |
| SAU: | : SA2334(mvaS) |
| SAV: | SAV2546(mvaS) |
| SAM: | MW2467(mvaS) |
| SAR: | SAR2626(mvaS) |
| SAS: | SAS2432 |
| SAC: | SACOL2561 |
| SAB: | SAB2420(mvaS) |

APPENDIX 1

| | |
|---|---|
| SAA: | SAUSA300_2484 |
| SAO: | SAOUHSC_02860 |
| SAJ: | SaurJH9_2569 |
| SAH: | SaurJH1_2622 |
| SEP: | SE2110 |
| SER: | SERP2122 |
| SHA: | SH0508(mvaS) |
| SSP: | SSP0324 |
| LMO: | lmo1415 |
| LMF: | LMOf2365_1434(mvaS) |
| LIN: | lin1454 |
| LWE: | lwe1432(mvaS) |
| LLA: | L13187(hmcM) |
| LLC: | LACR_1666 |
| LLM: | llmg_0929(hmcM) |
| SPY: | SPy_0881(mvaS.2) |
| SPZ: | M5005_Spy_0687(mvaS.1) |
| SPM: | spyM18_0942(mvaS2) |
| SPG: | SpyM3_0600(mvaS.2) |
| SPS: | SPs1253 |
| SPH: | MGAS10270_Spy0745(mvaS1) |
| SPI: | MGAS10750_Spy0779(mvaS1) |
| SPJ: | MGAS2096_Spy0759(mvaS1) |
| SPK: | MGAS9429_Spy0743(mvaS1) |
| SPF: | SpyM51121(mvaS) |
| SPA: | M6_Spy0704 |
| SPB: | M28_Spy0667(mvaS.1) |
| SPN: | SP_1727 |
| SPR: | spr1571(mvaS) |
| SPD: | SPD_1537(mvaS) |
| SAG: | SAG1316 |
| SAN: | gbs1386 |
| SAK: | SAK_1347 |
| SMU: | SMU.943c |
| STC: | str0577(mvaS) |
| STL: | stu0577(mvaS) |
| STE: | STER_0621 |
| SSA: | SSA_0338(mvaS) |
| SSU: | SSU05_1641 |
| SSV: | SSU98_1652 |
| SGO: | SGO_0244 |
| LPL: | lp_2067(mvaS) |
| LJO: | LJ1607 |
| LAC: | LBA0628(hmcS) |
| LSA: | LSA1484(mvaS) |
| LSL: | LSL_0526 |
| LDB: | Ldb0881(mvaS) |
| LBU: | LBUL_0806 |
| LBR: | LVIS_1363 |
| LCA: | LSEI_1785 |
| LGA: | LGAS_1372 |
| LRE: | Lreu_0676 |
| PPE: | PEPE_0868 |
| EFA: | EF1363 |
| OOE: | OEOE_0968 |
| LME: | LEUM_1184 |
| NFA: | nfa22120 |
| SEN: | SACE_4570(pksG) |
| BBU: | BB0683 |
| BGA: | BG0706 |
| BAF: | BAPK0_0727 |
| FJO: | Fjoh_0678 |
| HAL: | VNG1615G(mvaB) |
| HMA: | rrnAC1740(mvaS) |
| HWA: | HQ2868A(mvaB) |
| NPH: | NP2608A(mvaB_1) NP4836A(mvaB_2) |

Exemplary hydroxymethylglutaryl-CoA reductase nucleic acids and polypeptides

| | |
|---|---|
| HSA: | 3156(HMGCR) |
| PTR: | 471516(HMGCR) |
| MCC: | 705479(HMGCR) |
| MMU: | 15357(Hmgcr) |
| RNO: | 25675(Hmgcr) |
| CFA: | 479182(HMGCR) |
| BTA: | 407159(HMGCR) |
| GGA: | 395145(RCJMB04_14m24) |
| SPU: | 373355(LOC373355) |
| DME: | Dmel_CG10367(Hmgcr) |
| CEL: | F08F8.2 |
| OSA: | 4347443 |
| SCE: | YLR450W(HMG2) YML075C(HMG1) |
| AGO: | AGOS_AER152W |
| CGR: | CAGL0L11506g |
| SPO: | SPCC162.09c(hmg1) |
| ANI: | AN3817.2 |
| AFM: | AFUA_1G11230 AFUA_2G03700 |
| AOR: | A0O90103000311 A0O90120000217 |
| CNE: | CNF04830 |
| UMA: | UM03014.1 |
| ECU: | ECU10_1720 |
| DDI: | DDB_0191125(hmgA) DDB_0215357(hmgB) |
| TBR: | Tb927.6.4540 |
| TCR: | 506831.40 509167.20 |
| LMA: | LmjF30.3190 |
| VCH: | VCA0723 |
| VCO: | VC0395_0662 |
| VVU: | VV2_0117 |
| VVY: | VVA0625 |
| VPA: | VPA0968 |
| VFI: | VFA0841 |
| PAT: | Patl_0427 |
| CBU: | CBU_0030 CBU_0610 |
| CBD: | COXBU7E912_0151 COXBU7E912_0622(hmgA) |
| TCX: | Tcr_1717 |
| DNO: | DNO_0797 |
| CVI: | CV_1806 |
| SUS: | Acid_5728 Acid_6132 |
| SAU: | SA2333(mvaA) |
| SAV: | SAV2545(mvaA) |
| SAM: | MW2466(mvaA) |
| SAB: | SAB2419c(mvaA) |
| SEP: | SE2109 |
| LWE: | lwe0819(mvaA) |
| LLA: | L10433(mvaA) |
| LLC: | LACR_1664 |
| LLM: | llmg_0931(mvaA) |
| SPY: | SPy_0880(mvaS.1) |
| SPM: | spyM18_0941(mvaS1) |
| SPG: | SpyM3_0599(mvaS.1) |
| SPS: | SPs1254 |
| SPH: | MGAS10270_Spy0744 |
| SPI: | MGAS10750_Spy0778 |
| SPJ: | MGAS2096_Spy0758 |
| SPK: | MGAS9429_Spy0742 |
| SPA: | M6_Spy0703 |
| SPN: | SP_1726 |
| SAG: | SAG1317 |
| SAN: | gbs1387 |
| STC: | str0576(mvaA) |
| STL: | stu0576(mvaA) |
| STE: | STER_0620 |
| SSA: | SSA_0337(mvaA) |
| LPL: | lp_0447(mvaA) |
| LJO: | LJ1608 |
| LSL: | LSL_0224 |
| LBR: | LVIS_0450 |
| LGA: | LGAS_1373 |
| EFA: | EF1364 |
| NFA: | nfa22110 |
| BGA: | BG0708(mvaA) |
| SRU: | SRU_2422 |
| FPS: | FP2341 |
| MMP: | MMP0087(hmgA) |
| MMQ: | MmarC5_1589 |
| MAC: | MA3073(hmgA) |
| MBA: | Mbar_A1972 |
| MMA: | MM_0335 |
| MBU: | Mbur_1098 |
| MHU: | Mhun_3004 |
| MEM: | Memar_2365 |
| MBN: | Mboo_0137 |
| MTH: | MTH562 |
| MST: | Msp_0584(hmgA) |
| MSI: | Msm_0227 |
| MKA: | MK0355(HMG1) |

APPENDIX 1

| | |
|---|---|
| AFU: | AF1736(mvaA) |
| HAL: | VNG1875G(mvaA) |
| HMA: | rrnAC3412(mvaA) |
| HWA: | HQ3215A(hmgR) |
| NPH: | NP0368A(mvaA_2) NP2422A(mvaA_1) |
| TAC: | Ta0406m |
| TVO: | TVN1168 |
| PTO: | PTO1143 |
| PAB: | PAB2106(mvaA) |
| PFU: | PF1848 |
| TKO: | TK0914 |
| RCI: | RC1X1027(hmgA) RCIX376(hmgA) |
| APE: | APE_1869 |
| IHO: | Igni_0476 |
| HBU: | Hbut_1531 |
| SSO: | SSO0531 |
| STO: | ST1352 |
| SAI: | Saci_1359 |
| PAI: | PAE2182 |
| PIS: | Pisl_0814 |
| PCL: | Pcal_1085 |
| PAS: | Pars_0796 |

Exemplary mevalonate kinase nucleic acids and polypeptides

| | |
|---|---|
| HSA: | 4598(MVK) |
| MCC: | 707645(MVK) |
| MMU: | 17855(Mvk) |
| RNO: | 81727(Mvk) |
| CFA: | 486309(MVK) |
| BTA: | 505792(MVK) |
| GGA: | 768555(MVK) |
| DRE: | 492477(zgc:103473) |
| SPU: | 585785(LOC585785) |
| DME: | Dmel_CG33671 |
| OSA: | 4348331 |
| SCE: | YMR208W(ERG12) |
| AGO: | AGOS_AER335W |
| PIC: | PICST_40742(ERG12) |
| CGR: | CAGL0F03861g |
| SPO: | SPAC13G6.11c |
| MGR: | MGG_06946 |
| ANI: | AN3869.2 |
| AFM: | AFUA_4G07780 |
| AOR: | AO090023000793 |
| CNE: | CNK01740 |
| ECU: | ECU09_1780 |
| DDI: | DDBDRAFT_0168621 |
| TET: | TTHERM_00637680 |
| TBR: | Tb927.4.4070 |
| TCR: | 436521.9 509237.10 |
| LMA: | LmjF31.0560 |
| CBU: | CBU_0608 CBU_0609 |
| CBD: | COXBU7E912_0620(mvk) |
| LPN: | lpg2039 |
| LPF: | lpl2017 |
| LPP: | lpp2022 |
| BBA: | Bd1027(1mbP) Bd1630(mvk) |
| MXA: | MXAN_5019(mvk) |
| OIH: | OB0225 |
| SAU: | SA0547(mvaK1) |
| SAV: | SAV0590(mvaK1) |
| SAM: | MW0545(mvaK1) |
| SAR: | SAR0596(mvaK1) |
| SAS: | SAS0549 |
| SAC: | SACOL0636(mvk) |
| SAB: | SAB0540(mvaK1) |
| SAA: | SAUSA300_0572(mvk) |
| SAO: | SAOUHSC_00577 |
| SEP: | SE0361 |
| SER: | SERP0238(mvk) |
| SHA: | SH2402(mvaK1) |
| SSP: | SSP2122 |
| LMO: | lmo0010 |
| LMF: | LMOf2365_0011 |
| LIN: | lin0010 |
| LWE: | lwe0011(mvk) |
| LLA: | L7866(yeaG) |
| LLC: | LACR_0454 |
| LLM: | llmg_0425 (mvk) |
| SPY: | SPy_0876(mvaK1) |
| SPZ: | M5005_Spy_0682(mvaK1) |
| SPM: | spyM18_0937(mvaK1) |
| SPG: | SpyM3_0595(mvaK1) |
| SPS: | SPs1258 |
| SPH: | MGAS10270_Spy0740(mvaK1) |
| SPI: | MGAS10750_Spy0774(mvaK1) |
| SPJ: | MGAS2096_Spy0753(mvaK1) |
| SPK: | MGAS9429_Spy0737(mvaK1) |
| SPF: | SpyM51126(mvaK1) |
| SPA: | M6_Spy0699 |
| SPB: | M28_Spy0662(mvaK1) |
| SPN: | SP_0381 |
| SPR: | spr0338(mvk) |
| SPD: | SPD_0346(mvk) |
| SAG: | SAG1326 |
| SAN: | gbs1396 |
| SAK: | SAK_1357(mvk) |
| SMU: | SMU.181 |
| STC: | str0559(mvaK1) |
| STL: | stu0559(mvaK1) |
| STE: | STER_0598 |
| SSA: | SSA_0333(mvaK1) |
| SSU: | SSU05_0289 |
| SSV: | SSU98_0285 |
| SGO: | SGO_0239(mvk) |
| LPL: | lp_1735(mvaK1) |
| LJO: | 111205 |
| LAC: | LBA1167(mvaK) |
| LSA: | LSA0908(mvaK1) |
| LSL: | LSL_0685(eRG) |
| LDB: | Ldb0999(mvk) |
| LBU: | LBUL_0906 |
| LBR: | LVIS_0858 |
| LCA: | LSEI_1491 |
| LGA: | LGAS_1033 |
| LRE: | Lreu_0915 |
| PPE: | PEPE_0927 |
| EFA: | EF0904(mvk) |
| OOE: | OEOE_1100 |
| LME: | LEUM_1385 |
| NFA: | nfa22070 |
| BGA: | BG0711 |
| BAF: | BAPKO_0732 |
| FPS: | FP0313 |
| MMP: | MMP1335 |
| MAE: | Maeo_0775 |
| MAC: | MA0602(mvk) |
| MBA: | Mbar_A1421 |
| MMA: | MM_1762 |
| MBU: | Mbur_2395 |
| MHU: | Mhun_2890 |
| MEM: | Memar_1812 |
| MBN: | Mboo_2213 |
| MST: | Msp_0858(mvk) |
| MSI: | Msm_1439 |
| MKA: | MK0993(ERG12) |
| HAL: | VNG1145G(mv1c) |
| HMA: | rrnAC0077(myk) |
| HWA: | HQ2925A(mvk) |
| NPH: | NP2850A(mvk) |
| PTO: | PTO1352 |
| PHO: | PH1625 |
| PAB: | PAB0372(mvk) |
| PFU: | PF1637(mvk) |
| TKO: | TK1474 |
| RCI: | LRC399(mvk) |
| APE: | APE_2439 |
| HBU: | Hbut_0877 |
| SSO: | SSO0383 |
| STO: | ST2185 |
| SAI: | Saci_2365(mvk) |
| MSE: | Msed_1602 |
| PAI: | PAE3108 |
| PIS: | Pisl_0467 |
| PCL: | Pcal_1835 |

APPENDIX 1

Exemplary phosphomevalonate kinase nucleic acids and polypeptides

| | |
|---|---|
| HSA: | 10654(PMVK) |
| PTR: | 457350(PMVK) |
| MCC: | 717014(PMVK) |
| MMU: | 68603(Pmvk) |
| CFA: | 612251(PMVK) |
| BTA: | 513533(PMVK) |
| DME: | Dmel_CG10268 |
| ATH: | AT1G31910 |
| OSA: | 4332275 |
| SCE: | YMR220W(ERG8) |
| AGO: | AGOS_AER354W |
| PIC: | PICST_52257(ERG8) |
| CGR: | CAGL0F03993g |
| SPO: | SPAC343.01c |
| MGR: | MGG_05812 |
| ANI: | AN2311.2 |
| AFM: | AFUA_5G10680 |
| AOR: | AO090010000471 |
| CNE: | CNM00100 |
| UMA: | UM00760.1 |
| DDI: | DDBDRAFT_0184512 |
| TBR: | Tb09.160.3690 |
| TCR: | 507913.20 508277.140 |
| LMA: | LmjF15.1460 |
| MXA: | MXAN_5017 |
| OIH: | OB0227 |
| SAU: | SA0549(mvaK2) |
| SAV: | SAV0592(mvaK2) |
| SAM: | MW0547(mvaK2) |
| SAR: | SAR0598(mvaK2) |
| SAS: | SAS0551 |
| SAC: | SACOL0638 |
| SAB: | SAB0542(mvaK2) |
| SAA: | SAUSA300_0574 |
| SAO: | SAOUHSC_00579 |
| SAJ: | SaurJH9_0615 |
| SEP: | SE0363 |
| SER: | SERP0240 |
| SHA: | SH2400(mvaK2) |
| SSP: | SSP2120 |
| LMO: | lmo0012 |
| LMF: | LMOf2365_0013 |
| LIN: | lin0012 |
| LWE: | lwe0013 |
| LLA: | L10014(yebA) |
| LLC: | LACR_0456 |
| LLM: | llmg_0427 |
| SPY: | SPy_0878(mvaK2) |
| SPZ: | M5005_Spy_0684(mvaK2) |
| SPM: | spyM18_0939 |
| SPG: | SpyM3_0597(mvaK2) |
| SPS: | SPs1256 |
| SPH: | MGAS10270_Spy0742(mvaK2) |
| SPI: | MGAS10750_Spy0776(mvaK2) |
| SPJ: | MGAS2096_Spy0755(mvaK2) |
| SPK: | MGAS9429_Spy0739(mvaK2) |
| SPF: | SpyM51124(mvaK2) |
| SPA: | M6_Spy0701 |
| SPB: | M28_Spy0664(mvaK2) |
| SPN: | SP_0383 |
| SPR: | spr0340(mvaK2) |
| SPD: | SPD_0348(mvaK2) |
| SAG: | SAG1324 |
| SAN: | gbs1394 |
| SAK: | SAK_1355 |
| SMU: | SMU.938 |
| STC: | str0561(mvaK2) |
| STL: | stu0561(mvaK2) |
| STE: | STER_0600 |
| SSA: | SSA_0335(mvaK2) |
| SSU: | SSU05_0291 |
| SSV: | SSU98_0287 |
| SGO: | SGO_0241 |
| LPL: | lp_1733(mvaK2) |
| LJO: | LJ1207 |
| LAC: | LBA1169 |
| LSA: | LSA0906(mvaK2) |
| LSL: | LSL_0683 |
| LDB: | Ldb0997(mvaK) |
| LBU: | LBUL_0904 |
| LBR: | LVIS_0860 |
| LCA: | LSEI_1092 |
| LGA: | LGAS_1035 |
| LRE: | Lreu_0913 |
| PPE: | PEPE_0925 |
| EFA: | EF0902 |
| NFA: | nfa22090 |
| BGA: | BG0710 |
| BAF: | BAPKO_0731 |
| NPH: | NP2852A |
| SSO: | SSO2988 |
| STO: | ST0978 |
| SAI: | Saci_1244 |

Exemplary diphosphomevalonate decarboxylase nucleic acids and polypeptides

| | |
|---|---|
| HSA: | 4597(MVD) |
| PTR: | 468069(MVD) |
| MCC: | 696865(MVD) |
| MMU: | 192156(Mvd) |
| RNO: | 81726(Mvd) |
| CFA: | 489663(MVD) |
| GGA: | 425359(MVD) |
| DME: | Dmel_CG8239 |
| SCE: | YNR043W(MVD1) |
| AGO: | AGOS_AGL232C |
| PIC: | PICST_90752 |
| CGR: | CAGL0C03630g |
| SPO: | SPAC24C9.03 |
| MGR: | MGG_09750 |
| ANI: | AN4414.2 |
| AFM: | AFUA_4G07130 |
| AOR: | AO090023000862 |
| CNE: | CNL04950 |
| UMA: | UM05179.1 |
| DDI: | DDBDRAFT_0218058 |
| TET: | TTHERM_00849200 |
| TBR: | Tb10.05.0010 Tb10.61.2745 |
| TCR: | 507993.330 511281.40 |
| LMA: | LmjF18.0020 |
| CBU: | CBU_0607(mvaD) |
| CBD: | COXBU7E912_0619(mvaD) |
| LPN: | lpg2040 |
| LPF: | lpl2018 |
| LPP: | lpp2023 |
| TCX: | Tcr_1734 |
| DNO: | DNO_0504(mvaD) |
| BBA: | Bd1629 |
| MXA: | MXAN_5018(mvaD) |
| OIH: | OB0226 |
| SAU: | SA0548(mvaD) |
| SAV: | SAV0591(mvaD) |
| SAM: | MW0546(mvaD) |
| SAR: | SAR0597(mvaD) |
| SAS: | SAS0550 |
| SAC: | SACOL0637(mvaD) |
| SAB: | SAB0541(mvaD) |
| SAA: | SAUSA300_0573(mvaD) |
| SAO: | SAOUHSC_00578 |
| SAJ: | SaurJH9_0614 |
| SAH: | SaurJH1_0629 |
| SEP: | SE0362 |
| SER: | SERP0239(mvaD) |
| SHA: | SH2401(mvaD) |
| SSP: | SSP2121 |
| LMO: | lmo0011 |
| LMF: | LMOf2365_0012(mvaD) |
| LIN: | lin0011 |
| LWE: | lwe0012(mvaD) |
| LLA: | L9089(yeaH) |
| LLC: | LACR_0455 |
| LLM: | llmg_0426(mvaD) |
| SPY: | SPy_0877(mvaD) |

APPENDIX 1

| | |
|---|---|
| SPZ: | M5005_Spy_0683(mvaD) |
| SPM: | spyM18_0938(mvd) |
| SPG: | SpyM3_0596(mvaD) |
| SPS: | SPs1257 |
| SPH: | MGAS10270_Spy0741(mvaD) |
| SPI: | MGAS10750_Spy0775(mvaD) |
| SPJ: | MGAS2096_Spy0754(mvaD) |
| SPK: | MGAS9429_Spy0738(mvaD) |
| SPF: | SpyM51125(mvaD) |
| SPA: | M6_Spy0700 |
| SPB: | M28_Spy0663(mvaD) |
| SPN: | SP_0382 |
| SPR: | spr0339(mvdl) |
| SPD: | SPD_0347(mvaD) |
| SAG: | SAG1325(mvaD) |
| SAN: | gbs1395 |
| SAK: | SAK_1356(mvaD) |
| SMU: | SMU.937 |
| STC: | str0560(mvaD) |
| STL: | stu0560(mvaD) |
| STE: | STER_0599 |
| SSA: | SSA_0334(mvaD) |
| SSU: | SSU05_0290 |
| SSV: | SSU98_0286 |
| SGO: | SGO_0240(mvaD) |
| LPL: | lp_1734(mvaD) |
| LJO: | LJ1206 |
| LAC: | LBA1168(mvaD) |
| LSA: | LSA0907(mvaD) |
| LSL: | LSL_0684 |
| LDB: | Ldb0998(mvaD) |
| LBU: | LBUL_0905 |
| LBR: | LVIS_0859 |
| LCA: | LSEI_1492 |
| LGA: | LGAS_1034 |
| LRE: | Lreu_0914 |
| PPE: | PEPE_0926 |
| EFA: | EF0903(mvaD) |
| LME: | LEUM_1386 |
| NFA: | nfa22080 |
| BBU: | BB0686 |
| BGA: | BG0709 |
| BAF: | BAPKO_0730 |
| GFO: | GFO_3632 |
| FPS: | FP0310(mvaD) |
| HAU: | Haur_1612 |
| HAL: | VNG0593G(dmd) |
| HMA: | rrnAC1489(dmd) |
| HWA: | HQ1525A(mvaD) |
| NPH: | NP1580A(mvaD) |
| PTO: | PTO0478 PTO1356 |
| SSO: | SSO2989 |
| STO: | ST0977 |
| SAI: | Saci_1245(mvd) |
| MSE: | Msed_1576 |

Exemplary isopentenyl phosphate kinases
(IPK) nucleic acids and polypeptides

*Methanobacterium thermoautotrophicum* gi|2621082
*Methanococcus jannaschii* DSM 2661 gi|1590842 ;
*Methanocaldococcus jannaschii* gi|1590842
*Methanothermobacter thermautotrophicus* gi|2621082
*Picrophilus torridus* DSM9790 (IG-57) gi|48477569
*Pyrococcus abyssi* gi|14520758
*Pyrococcus horikoshii* OT3 gi|3258052
*Archaeoglobus fulgidus* DSM4304 gi|2648231

Exemplary isopentenyl-diphosphate Delta-isomerase
(IDI) nucleic acids and polypeptides

| | |
|---|---|
| HSA: | 3422(IDI1) 91734(1DI2) |
| PTR: | 450262(IDI2) 450263(IDI1) |
| MCC: | 710052(LOC710052) 721730(LOC721730) |
| MMU: | :319554(Idi1) |
| RNO: | 89784(Idi1) |
| GGA: | 420459(IDI1) |
| XLA: | 494671(LOC494671) |
| XTR: | 496783(idi2) |
| SPU: | 586184(LOC586184) |
| CEL: | K06H7.9(idi-1) |
| ATH: | AT3G02780(IPP2) |
| OSA: | 4338791 4343523 |
| CME: | CMB062C |
| SCE: | YPL117C(IDI1) |
| AGO: | AGOS_ADL268C |
| PIC: | PICST_68990(IDI1) |
| CGR: | CAGL0J06952g |
| SPO: | SPBC106.15(idi1) |
| ANI: | AN0579.2 |
| AFM: | AFUA_6G11160 |
| AOR: | AO090023000500 |
| CNE: | CNA02550 |
| UMA: | UM04838.1 |
| ECU: | ECU02_0230 |
| DDI: | DDB_0191342(ipi) |
| TET: | TTHERM_00237280 TTHERM_00438860 |
| TBR: | Tb09.211.0700 |
| TCR: | 408799.19 510431.10 |
| LMA: | LmjF35.5330 |
| EHI: | 46.t00025 |
| ECO: | b2889(idi) |
| ECJ: | JW2857(idi) |
| ECE: | Z4227 |
| ECS: | ECs3761 |
| ECC: | c3467 |
| ECI: | UTI89_C3274 |
| ECP: | ECP_2882 |
| ECV: | APECO1_3638 |
| ECW: | EcE24377A_3215(idi) |
| ECX: | EcHS_A3048 |
| STY: | STY3195 |
| STT: | t2957 |
| SPT: | SPA2907(idi) |
| SEC: | SC2979(idi) |
| STM: | STM3039(idi) |
| SFL: | SF2875(idi) |
| SFX: | S3074 |
| SFV: | SFV_2937 |
| SSN: | SSON_3042 SSON_3489(yhfK) |
| SBO: | SBO 3103 |
| SDY: | SDY_3193 |
| ECA: | ECA2789 |
| PLU: | plu3987 |
| ENT: | Ent638_3307 |
| SPE: | Spro_2201 |
| VPA: | VPA0278 |
| VFI: | VF0403 |
| PPR: | PBPRA0469(mvaD) |
| PEN: | PSEEN4850 |
| CBU: | CBU_0607(mvaD) |
| CBD: | COXBU7E912_0619(mvaD) |
| LPN: | lpg2051 |
| LPF: | lpl2029 |
| LPP: | lpp2034 |
| TCX: | Tcr_1718 |
| HHA: | Hhal_1623 |
| DNO: | DNO_0798 |
| EBA: | ebA5678 p2A143 |
| DVU: | DVU1679(idi) |
| DDE: | Dde_1991 |
| LIP: | LI1134 |
| BBA: | Bd1626 |
| AFW: | Anae109_4082 |
| MXA: | MXAN_5021(fni) |
| RPR: | RP452 |
| RTY: | RT0439(idi) |
| RCO: | RC0744 |
| RFE: | RF_0785(fni) |
| RBE: | RBE_0731(fni) |
| RAK: | A1C_04190 |
| RBO: | A1I_04755 |
| RCM: | A1E_02555 |
| RRI: | A1G_04195 |
| MLO: | mlr6371 |
| RET: | RHE_PD00245(ypd00046) |
| XAU: | Xaut_4134 |
| SIL: | SPO0131 |

APPENDIX 1

| | |
|---|---|
| SIT: | TM1040_3442 |
| RSP: | RSP_0276 |
| RSH: | Rsph17029_1919 |
| RSQ: | Rsph17025_1019 |
| JAN: | Jann_0168 |
| RDE: | RD1_0147(idi) |
| DSH: | Dshi_3527 |
| BSU: | BG11440(ypgA) |
| BAN: | BA1520 |
| BAR: | GBAA1520 |
| BAA: | BA_2041 |
| BAT: | BAS1409 |
| BCE: | BC1499 |
| BCA: | BCE_1626 |
| BCZ: | BCZK1380(fni) |
| BCY: | Bcer98_1222 |
| BTK: | BT9727_1381(fni) |
| BTL: | BALH_1354 |
| BLI: | BL02217(fni) |
| BLD: | BLi02426 |
| BAY: | RBAM_021020(fni) |
| BPU: | BPUM_2020(fni) |
| OIH: | OB0537 |
| SAU: | SA2136(fni) |
| SAV: | SAV2346(fni) |
| SAM: | MW2267(fni) |
| SAR: | SAR2431(fni) |
| SAS: | SAS2237 |
| SAC: | SACOL2341(fni) |
| SAB: | SAB2225c(fni) |
| SAA: | SAUSA300_2292(fni) |
| SAO: | SAOUHSC_02623 |
| SEP: | SE1925 |
| SER: | SERP1937(fni-2) |
| SHA: | SH0712(fni) |
| SSP: | SSP0556 |
| LMO: | lmo1383 |
| LMF: | LMOf2365_1402(fni) |
| LIN: | lin1420 |
| LWE: | lwe1399(fni) |
| LLA: | L11083(yebB) |
| LLC: | LACR_0457 |
| LLM: | llmg_0428 (fni) |
| SPY: | SPy_0879 |
| SPZ: | M5005_Spy_0685 |
| SPM: | spyM18_0940 |
| SPG: | SpyM3_0598 |
| SPS: | SPs1255 |
| SPH: | MGAS10270_Spy0743 |
| SPI: | MGAS10750_Spy0777 |
| SPJ: | MGAS2096_Spy0756 |
| SPK: | MGAS9429_Spy0740 |
| SPF: | SpyM51123(fni) |
| SPA: | M6_Spy0702 |
| SPB: | M28_Spy0665 |
| SPN: | SP_0384 |
| SPR: | spr0341(fni) |
| SPD: | SPD_0349(fni) |
| SAG: | SAG1323 |
| SAN: | gbs1393 |
| SAK: | SAK_1354(fni) |
| SMU: | SMU.939 |
| STC: | str0562(idi) |
| STL: | stu0562(idi) |
| STE: | STER_0601 |
| SSA: | SSA_0336 |
| SGO: | SGO_0242 |
| LPL: | lp_1732(idi1) |
| LJO: | LJ1208 |
| LAC: | LBA1171 |
| LSA: | LSA0905(idi) |
| LSL: | LSL_0682 |
| LDB: | Ldb0996(fni) |
| LBU: | LBUL_0903 |
| LBR: | LVIS_0861 |
| LCA: | LSEI_1493 |
| LGA: | LGAS_1036 |
| LRE: | Lreu_0912 |
| EFA: | EF0901 |
| OOE: | OEOE_1103 |
| STH: | STH1674 |
| CBE: | Cbei_3081 |
| DRM: | Dred_0474 |
| SWO: | Swol_1341 |
| MTA: | Moth_1328 |
| MTU: | Rv1745c(idi) |
| MTC: | MT1787(idi) |
| MBO: | Mb1774c(idi) |
| MBB: | BCG_1784c(idi) |
| MPA: | MAP3079c |
| MAV: | MAV_3894(fni) |
| MSM: | MSMEG_1057(fni) MSMEG_2337(fni) |
| MUL: | MUL_0380(idi2) |
| MVA: | Mvan_1582 Mvan_2176 |
| MGI: | Mflv_1842 Mflv_4187 |
| MMC: | Mmcs_1954 |
| MKM: | Mkms_2000 |
| MJL: | Mjls_1934 |
| CGL: | NCgl2223(cgl2305) |
| CGB: | cg2531(idi) |
| CEF: | CE2207 |
| CDI: | DIP1730(idi) |
| NFA: | nfa19790 nfa22100 |
| RHA: | RHA1_ro00239 |
| SCO: | SCO6750(SC5F2A.33c) |
| SMA: | SAV1663(idi) |
| LXX: | Lxx23810(idi) |
| CMI: | CMM_2889(idiA) |
| AAU: | AAur_0321(idi) |
| PAC: | PPA2115 |
| FRA: | Francci3_4188 |
| FRE: | Franean1_5570 |
| FAL: | FRAAL6504(idi) |
| KRA: | Krad_3991 |
| SEN: | SACE_2627(idiB_2) SACE_5210(idi) |
| STP: | Strop_4438 |
| SAQ: | Sare_4564 Sare_4928 |
| RXY: | Rxyl_0400 |
| BBU: | BB0684 |
| BGA: | BG0707 |
| SYN: | sll1556 |
| SYC: | syc2161_c |
| SYF: | Synpcc7942_1933 |
| CYA: | CYA_2395(fni) |
| CYB: | CYB_2691(fni) |
| TEL: | tll1403 |
| ANA: | all4591 |
| AVA: | Ava_2461 Ava_B0346 |
| TER: | Tery_1589 |
| SRU: | SRU_1900(idi) |
| CHU: | CHU_0674(idi) |
| GFO: | GFO_2363(idi) |
| FJO: | Fjoh_0269 |
| FPS: | FP1792(idi) |
| CTE: | CT0257 |
| CCH: | Cag_1445 |
| CPH: | Cpha266_0385 |
| PVI: | Cvib_1545 |
| PLT: | Plut_1764 |
| RRS: | RoseRS_2437 |
| RCA: | Rcas_2215 |
| HAU: | Haur_4687 |
| DRA: | DR_1087 |
| DGE: | Dgeo_1381 |
| TTH: | TT_P0067 |
| TTJ: | TTHB110 |
| MJA: | MJ0862 |
| MMP: | MMP0043 |
| MMQ: | MmarC5_1637 |
| MMX: | MmarC6_0906 |
| MMZ: | MmarC7_1040 |
| MAE: | Maeo_1184 |
| MVN: | Mevan_1058 |
| MAC: | MA0604(idi) |
| MBA: | Mbar_A1419 |
| MMA: | MM_1764 |

APPENDIX 1

| | |
|---|---|
| MBU: | Mbur_2397 |
| MTP: | Mthe_0474 |
| MHU: | Mhun_2888 |
| MLA: | Mlab_1665 |
| MEM: | Memar_1814 |
| MBN: | Mboo_2211 |
| MTH: | MTH48 |
| MST: | Msp_0856(fni) |
| MSI: | Msm_1441 |
| MKA: | MK0776(lldD) |
| AFU: | AF2287 |
| HAL: | VNG1818G(idi) VNG6081G(crt_1) VNG6445G(crt_2) VNG7060 VNG7149 |
| HMA: | rrnAC3484(idi) |
| HWA: | HQ2772A(idiA) HQ2847A(idiB) |
| NPH: | NP0360A(idiB_1) NP4826A(idiA) NP5124A(idiB_2) |
| TAC: | Ta0102 |
| TVO: | TVN0179 |
| PTO: | PTO0496 |
| PHO: | PH1202 |
| PAB: | PAB1662 |
| PFU: | PF0856 |
| TKO: | TK1470 |
| RCI: | LRC397(fni) |
| APE: | APE_1765.1 |
| SMR: | Smar_0822 |
| IHO: | Igni_0804 |
| HBU: | Hbut_0539 |
| SSO: | SSO0063 |
| STO: | ST2059 |
| SAI: | Saci_0091 |
| MSE: | Msed_2136 |
| PAI: | PAE0801 |
| PIS: | Pisl_1093 |
| PCL: | Pcal_0017 |
| PAS: | Pars 0051 |
| TPE: | Tpen_0272 |

Exemplary isoprene synthase nucleic acids and polypeptides Genbank Accession Nos.

AY341431
AY316691
AY279379
AJ457070
AY182241

---

SEQUENCE LISTING

<160> NUMBER OF SEQ ID NOS: 131

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 1

```
atgtgtgcga cctcttctca atttactcag attaccgagc ataattcccg tcgttccgca      60
aactatcagc caaacctgtg gaatttcgaa ttcctgcaat ccctggagaa cgacctgaaa     120
gtggaaaagc tggaggagaa agcgaccaaa ctggaggaag aagttcgctg catgatcaac     180
cgtgtagaca cccagccgct gtccctgctg gagctgatcg acgatgtgca gcgcctgggt     240
ctgacctaca aatttgaaaa agacatcatt aaagccctgg aaaacatcgt actgctggac     300
gaaaacaaaa agaacaaatc tgacctgcac gcaaccgctc tgtctttccg tctgctgcgt     360
cagcacggtt tcgaggtttc tcaggatgtt tttgagcgtt caaggataa agaaggtggt     420 ttcagcggtg aactgaaagg tgacgtccaa ggcctgctga gcctgtatga agcgtcttac     480
ctgggtttcg agggtgagaa cctgctggag gaggcgcgta ccttttccat cacccacctg     540
aagaacaacc tgaaagaagg cattaatacc aaggttcag aacaagtgag ccacgccctg     600
gaactgccat atcaccagcg tctgcaccgt ctggaggcac gttggttcct ggataaatac     660
gaaccgaaag aaccgcatca ccagctgctg ctggagctgg cgaagctgga ttttaacatg     720
gtacagaccc tgcaccagaa agagctgcaa gatctgtccc gctggtggac cgagatgggc     780
ctggctagca aactggattt tgtacgcgac cgcctgatgg aagtttattt ctgggcactg     840
ggtatggcgc cagacccgca gtttgtgaa tgtcgcaaag ctgttactaa aatgtttggt     900
ctggtgacga tcatcgatga cgtgtatgac gtttatggca ctctggacga actgcaactg     960
ttcaccgatg ctgtagagcg ctgggacgtt aacgctatta cacccctgcc ggactatatg    1020
aaactgtgtt tcctggcact gtacaacacc gttaacgaca cgtcctattc tattctgaaa    1080
```

```
gagaaaggtc ataacaacct gtcctatctg acgaaaagct ggcgtgaact gtgcaaagcc      1140
tttctgcaag aggcgaaatg gtccaacaac aaaattatcc cggctttctc caagtacctg      1200
gaaaacgcca gcgtttcctc ctccggtgta gcgctgctgg cgccgtctta cttttccgta      1260
tgccagcagc aggaagacat ctccgaccac gcgctgcgtt ccctgaccga cttccatggt      1320
ctggtgcgtt ctagctgcgt tatcttccgc ctgtgcaacg atctggccac ctctgcggcg      1380
gagctggaac gtggcgagac taccaattct atcattagct acatgcacga aaacgatggt      1440
accagcgagg aacaggcccg cgaagaactg cgtaaactga tcgacgccga atggaaaaag      1500
atgaatcgtg aacgcgttag cgactccacc ctgctgccta aagcgttcat ggaaatcgca      1560
gttaacatgg cacgtgtttc ccactgcacc taccagtatg gcgatggtct gggtcgccca      1620
gactacgcga ctgaaaaccg catcaaactg ctgctgattg accctttccc gattaaccag      1680
ctgatgtatg tctaactgca g                                               1701

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc       120
gcactcccgt tctggataat gttttttgcg ccgacatcat aacggttctg caaatattc        180 tgaaatgagc tgttgacaat taatcatccg gctcgtataa tgtgtggaat tgtgagcgga       240
taacaatttc acacaggaaa cagcgccgct gagaaaaagc gaagcggcac tgctctttaa       300
caatttatca gacaatctgt gtgggcactc gaccggaatt atcgattaac tttattatta       360
aaaattaaag aggtatatat taatgtatcg attaaataag gaggaataaa ccatgtgtgc       420
gacctcttct caatttactc agattaccga gcataattcc cgtcgttccg caaactatca       480
gccaaacctg tggaatttcg aattcctgca atccctggag aacgacctga agtggaaaa       540 gctggaggag aaagcgacca aactggagga agaagttcgc tgcatgatca accgtgtaga       600
cacccagccg ctgtccctgc tggagctgat cgacgatgtg cagcgcctgg gtctgaccta       660
caaatttgaa aaagacatca ttaaagccct ggaaaacatc gtactgctgg acgaaaacaa       720
aaagaacaaa tctgacctgc acgcaaccgc tctgtctttc cgtctgctgc gtcagcacgg       780
tttcgaggtt tctcaggatg ttttgagcg tttcaaggat aaagaaggtg gtttcagcgg       840
tgaactgaaa ggtgacgtcc aaggcctgct gagcctgtat gaagcgtctt acctgggttt       900
cgagggtgag aacctgctgg aggaggcgcg tacctttcc atcacccacc tgaagaacaa       960
cctgaaagaa ggcattaata ccaaggttgc agaacaagtg agccacgccc tggaactgcc      1020
atatcaccag cgtctgcacc gtctggaggc acgttggttc ctggataaat acgaaccgaa      1080
agaaccgcat caccagctgc tgctggagct ggcgaagctg gatttaacaa tggtacagac     1140
cctgcaccag aaagagctgc aagatctgtc ccgctggtgg accgagatgg gcctggctag     1200
caaactggat tttgtacgcg accgcctgat ggaagtttat ttctgggcac tgggtatggc      1260
gccagacccg cagtttggtg aatgtcgcaa agctgttact aaaatgtttg gtctggtgac      1320
gatcatcgat gacgtgtatg acgtttatgg cactctggac gaactgcaac tgttcaccga      1380
tgctgtagag cgctgggacg ttaacgctat taacaccctg ccggactata tgaaactgtg      1440
```

-continued

```
tttcctggca ctgtacaaca ccgttaacga cacgtcctat tctattctga aagagaaagg    1500
tcataacaac ctgtcctatc tgacgaaaag ctggcgtgaa ctgtgcaaag cctttctgca    1560
agaggcgaaa tggtccaaca acaaaattat cccggctttc tccaagtacc tggaaaacgc    1620
cagcgtttcc tcctccggtg tagcgctgct ggcgccgtct tacttttccg tatgccagca    1680
gcaggaagac atctccgacc acgcgctgcg ttccctgacc gacttccatg gtctggtgcg    1740
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
ggaacaggcc cgcgaagaac tgcgtaaact gatcgacgcc gaatggaaaa agatgaatcg    1920
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
gactgaaaac cgcatcaaac tgctgctgat tgacccttc ccgattaacc agctgatgta    2100
tgtctaactg cagctggtac catatgggaa ttcgaagctt tctagaacaa aaactcatct    2160
cagaagagga tctgaatagc gccgtcgacc atcatcatca tcatcattga gtttaaacgg    2220
tctccagctt ggctgttttg gcggatgaga agattttc agcctgatac agattaaatc    2280
agaacgcaga agcggtctga taaaacagaa tttgcctggc ggcagtagcg cggtggtccc    2340
acctgacccc atgccgaact cagaagtgaa acgccgtagc gccgatggta gtgtggggtc    2400
tccccatgcg agagtaggga actgccaggc atcaaataaa acgaaaggct cagtcgaaag    2460
actgggcctt tcgttttatc tgttgtttgt cggtgaacgc tctcctgagt aggacaaatc    2520
cgccgggagc ggatttgaac gttgcgaagc aacggcccgg agggtggcgg caggacgcc    2580 cgccataaac tgccaggcat caaattaagc agaaggccat cctgacggat ggccttttg    2640 cgtttctaca aactcttttt gtttattttt ctaaatacat tcaaatatgt atccgctcat    2700
gagacaataa ccctgataaa tgcttcaata atattgaaaa aggaagagta tgagtattca    2760
acatttccgt gtcgccctta ttcccttttt tgcggcattt tgccttcctg tttttgctca    2820
cccagaaacg ctggtgaaag taaaagatgc tgaagatcag ttgggtgcac gagtgggtta    2880
catcgaactg gatctcaaca gcggtaagat ccttgagagt tttcgccccg aagaacgttt    2940
tccaatgatg agcacttta aagttctgct atgtggcgcg gtattatccc gtgttgacgc    3000
cgggcaagag caactcggtc gccgcataca ctattctcag aatgacttgg ttgagtactc    3060
accagtcaca gaaaagcatc ttacggatgg catgacagta agagaattat gcagtgctgc    3120
cataaccatg agtgataaca ctgcggccaa cttacttctg acaacgatcg gaggaccgaa    3180
ggagctaacc gcttttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat ccttttgat aatctcatga ccaaaatccc    3720
ttaacgtgag ttttcgttcc actgagcgtc agacccgta gaaagatca aaggatcttc    3780 ttgagatcct ttttttctgc gcgtaatctg ctgcttgcaa acaaaaaaac caccgctacc    3840
```

-continued

```
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cgggggttc gtgcacacag cccagcttgg agcgaacgac     4140
ctacaccgaa ctgagatacc tacagcgtga gctatgagaa agcgccacgc ttcccgaagg    4200
gagaaaggcg acaggtatc cggtaagcgg cagggtcgga acaggagagc gcacgaggga     4260
gcttccaggg ggaaacgcct ggtatcttta tagtcctgtc gggtttcgcc acctctgact    4320
tgagcgtcga tttttgtgat gctcgtcagg ggggcggagc ctatggaaaa acgccagcaa    4380
cgcggccttt ttacggttcc tggccttttg ctggcctttt gctcacatgt tctttcctgc    4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca acaccgctg acgcgccctg acgggcttgt     4740
ctgctcccgg catccgctta cagacaagct gtgaccgtct ccgggagctg catgtgtcag    4800
aggttttcac cgtcatcacc gaaacgcgcg aggcagcaga tcaattcgcg cgcgaaggcg    4860
aagcggcatg catttacgtt gacaccatcg aatggtgcaa aacctttcgc ggtatggcat    4920
gatagcgccc ggaagagagt caattcaggg tggtgaatgt gaaaccagta acgttatacg    4980
atgtcgcaga gtatgccggt gtctcttatc agaccgtttc ccgcgtggtg aaccaggcca    5040
gccacgtttc tgcgaaaacg cgggaaaaag tggaagcggc gatggcggag ctgaattaca    5100
ttcccaaccg cgtggcacaa caactggcgg gcaaacagtc gttgctgatt ggcgttgcca    5160
cctccagtct ggccctgcac gcgccgtcgc aaattgtcgc ggcgattaaa tctcgcgccg    5220
atcaactggg tgccagcgtg gtggtgtcga tggtagaacg aagcggcgtc gaagcctgta    5280
aagcggcggt gcacaatctt ctcgcgcaac gcgtcagtgg gctgatcatt aactatccgc    5340
tggatgacca ggatgccatt gctgtggaag ctgcctgcac taatgttccg gcgttatttc    5400
ttgatgtctc tgaccagaca cccatcaaca gtattatttt ctcccatgaa gacggtacgc    5460
gactgggcgt ggagcatctg gtcgcattgg gtcaccagca atcgcgctg ttagcgggcc     5520
cattaagttc tgtctcggcg cgtctgcgtc tggctgctg gcataaatat ctcactcgca    5580
atcaaattca gccgatagcg gaacgggaag gcgactggag tgccatgtcc ggttttcaac    5640
aaaccatgca aatgctgaat gagggcatcg ttcccactgc gatgctggtt gccaacgatc    5700
agatggcgct gggcgcaatg cgcgccatta ccgagtccgg gctgcgcgtt ggtgcggata    5760
tctcggtagt gggatacgac gataccgaag acagctcatg ttatatcccg ccgtcaacca    5820
ccatcaaaca ggattttcgc ctgctggggc aaaccagcgt ggaccgcttg ctgcaactct    5880
ctcagggcca ggcggtgaag gcaatcagc tgttgcccgt ctcactggtg aaaagaaaaa     5940
ccaccctggc gcccaatacg caaaccgcct ctccccgcgc gttggccgat tcattaatgc    6000
agctggcacg acaggtttcc cgactggaaa gcgggcagtg agcgcaacgc aattaatgtg    6060
agttagcgcg aattgatctg                                                 6080
```

<210> SEQ ID NO 3
<211> LENGTH: 37
<212> TYPE: DNA

```
<213> ORGANISM: Artificial Sequence
<220> FEATURE:
<223> OTHER INFORMATION: Synthetic Construct

<400> SEQUENCE: 3
cgtgagatca tatgtgtgcg acctcttctc aatttac                               37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg                              38

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc cggatatagt tcctcctttc agcaaaaaac ccctcaagac ccgtttagag     240
gccccaaggg gttatgctag ttattgctca gcggtggcag cagccaactc agcttccttt     300
cgggctttgt tagcagccgg atccctgcag ttagacatac atcagctggt taatcgggaa     360 aggtcaatc agcagcagtt tgatgcggtt tcagtcgcg tagtctgggc gacccagacc      420
atcgccatac tggtaggtgc agtgggaaac acgtgccatg ttaactgcga tttccatgaa     480
cgctttaggc agcagggtgg agtcgctaac gcgttcacga ttcatctttt tccattcggc     540
gtcgatcagt ttacgcagtt cttcgcgggc ctgttcctcg ctggtaccat cgttttcgtg     600
catgtagcta atgatagaat tggtagtctc gccacgttcc agctccgccg cagaggtggc     660
cagatcgttg cacaggcgga agataacgca gctagaacgc accagaccat ggaagtcggt     720
cagggaacgc agcgcgtggt cggagatgtc ttcctgctgc tggcatacgg aaaagtaaga     780
cggcgccagc agcgctacac cggaggagga aacgctggcg ttttccaggt acttggagaa     840
agccgggata attttgttgt tggaccattt cgcctcttgc agaaaggctt tgcacagttc     900
acgccagctt ttcgtcagat aggacaggtt gttatgacct ttctctttca gaatagaata     960
ggacgtgtcg ttaacggtgt tgtacagtgc caggaaacac agtttcatat agtccggcag    1020
ggtgttaata gcgttaacgt cccagcgctc tacagcatcg gtgaacagtt gcagttcgtc    1080
cagagtgcca taaacgtcat acacgtcatc gatgatcgtc accagaccaa acattttagt    1140
aacagctttg cgacattcac caaactgcgg gtctggcgcc atacccagtg cccagaaata    1200
aacttccatc aggcggtcgc gtacaaaatc cagtttgcta gccaggccca tctcggtcca    1260
ccagcgggac agatcttgca gctctttctg gtgcagggtc tgtaccatgt taaaatccag    1320
cttcgccagc tccagcagca gctggtgatg cggttctttc ggttcgtatt tatccaggaa    1380
ccaacgtgcc tccagacggt gcagacgctg gtgatatggc agttcagggg cgtggctcac    1440
ttgttctgca accttggtat taatgccttc tttcaggttg ttcttcaggt gggtgatgga    1500
```

```
aaaggtacgc gcctcctcca gcaggttctc accctcgaaa cccaggtaag acgcttcata   1560
caggctcagc aggccttgga cgtcaccttt cagttcaccg ctgaaaccac cttctttatc   1620
cttgaaacgc tcaaaaacat cctgagaaac ctcgaaaccg tgctgacgca gcagacggaa   1680
agacagagcg gttgcgtgca ggtcagattt gttcttttg ttttcgtcca gcagtacgat    1740
gttttccagg gctttaatga tgtcttttc aaatttgtag gtcagaccca ggcgctgcac    1800
atcgtcgatc agctccagca gggacagcgg ctgggtgtct acacggttga tcatgcagcg   1860
aacttcttcc tccagtttgg tcgctttctc ctccagcttt tccactttca ggtcgttctc   1920
cagggattgc aggaattcga aattccacag gtttggctga tagtttgcgg aacgacggga   1980
attatgctcg gtaatctgag taaattgaga agaggtcgca cacatatgac gaccttcgat   2040
atggccgctg ctgtgatgat gatgatgatg atgatgatga tggcccatgg tatatctcct   2100
tcttaaagtt aaacaaaatt atttctagag gggaattgtt atccgctcac aattccccta   2160
tagtgagtcg tattaatttc gcgggatcga gatctcgatc ctctacgccg gacgcatcgt   2220
ggccggcatc accggcgcca caggtgcggt tgctggcgcc tatatcgccg acatcaccga   2280 tgggaagat cgggctcgcc acttcgggct catgagcgct tgtttcggcg tgggtatggt    2340
ggcaggcccc gtggccgggg gactgttggg cgccatctcc ttgcatgcac cattccttgc   2400
ggcggcggtg ctcaacggcc tcaacctact actgggctgc ttcctaatgc aggagtcgca   2460
taagggagag cgtcgagatc ccggacacca tcgaatggcg caaaaccttt cgcggtatgg   2520
catgatagcg cccggaagag agtcaattca gggtggtgaa tgtgaaacca gtaacgttat   2580
acgatgtcgc agagtatgcc ggtgtctctt atcagaccgt ttcccgcgtg gtgaaccagg   2640
ccagccacgt ttctgcgaaa acgcgggaaa aagtggaagc ggcgatggcg gagctgaatt   2700
acattcccaa ccgcgtggca caacaactgg cgggcaaaca gtcgttgctg attggcgttg   2760
ccacctccag tctggccctg cacgcgccgt cgcaaattgt cgcggcgatt aaatctcgcg   2820
ccgatcaact gggtgccagc gtggtggtgt cgatggtaga acgaagcggc gtcgaagcct   2880
gtaaagcggc ggtgcacaat cttctcgcgc aacgcgtcag tgggctgatc attaactatc   2940
cgctggatga ccaggatgcc attgctgtgg aagctgcctg cactaatgtt ccggcgttat   3000
ttcttgatgt ctctgaccag acacccatca acagtattat tttctcccat gaagacggta   3060
cgcgactggg cgtggagcat ctggtcgcat tgggtcacca gcaaatcgcg ctgttagcgg   3120
gcccattaag ttctgtctcg gcgcgtctgc gtctggctgg ctggcataaa tatctcactc   3180
gcaatcaaat tcagccgata gcggaacggg aaggcgactg gagtgccatg tccggttttc   3240
aacaaaccat gcaaatgctg aatgagggca tcgttcccac tgcgatgctg gttgccaacg   3300
atcagatggc gctgggcgca atgcgcgcca ttaccgagtc cgggctgcgc gttggtgcgg   3360
atatctcggt agtgggatac gacgataccg aagacagctc atgttatatc cgccgttaa   3420 ccaccatcaa acaggatttt cgcctgctgg ggcaaaccag cgtggaccgc ttgctgcaac   3480
tctctcaggg ccaggcggtg aagggcaatc agctgttgcc cgtctcactg gtgaaaagaa   3540
aaaccaccct ggcgcccaat acgcaaaccg cctctccccg cgcgttggcc gattcattaa   3600
tgcagctggc acgacaggtt tcccgactgg aaagcgggca gtgagcgcaa cgcaattaat   3660
gtaagttagc tcactcatta ggcaccggga tctcgaccga tgcccttgag agccttcaac   3720
ccagtcagct ccttccggtg ggcgcggggc atgactatcg tcgccgcact tatgactgtc   3780
ttctttatca tgcaactcgt aggacaggtg ccggcagcgc tctgggtcat tttcggcgag   3840
gaccgctttc gctggagcgc gacgatgatc ggcctgtcgc ttgcggtatt cggaatcttg   3900
```

```
cacgccctcg ctcaagcctt cgtcactggt cccgccacca aacgtttcgg cgagaagcag    3960
gccattatcg ccggcatggc ggccgacgcg ctgggctacg tcttgctggc gttcgcgacg    4020
cgaggctgga tggccttccc cattatgatt cttctcgctt ccggcggcat cgggatgccc    4080
gcgttgcagg ccatgctgtc caggcaggta gatgacgacc atcagggaca gcttcaagga    4140
tcgctcgcgg ctcttaccag cctaacttcg atcactggac cgctgatcgt cacggcgatt    4200
tatgccgcct cggcgagcac atggaacggg ttggcatgga ttgtaggcgc cgccctatac    4260
cttgtctgcc tccccgcgtt gcgtcgcggt gcatggagcc gggccacctc gacctgaatg    4320
gaagccggcg gcacctcgct aacgattca ccactccaag aattggagcc aatcaattct    4380
tgcggagaac tgtgaatgcg caaaccaacc cttggcagaa catatccatc gcgtccgcca    4440
tctccagcag ccgcacgcgg cgcatctcgg gcagcgttgg gtcctggcca cgggtgcgca    4500
tgatcgtgct cctgtcgttg aggacccggc taggctggcg gggttgcctt actggttagc    4560
agaatgaatc accgatacgc gagcgaacgt gaagcgactg ctgctgcaaa acgtctgcga    4620
cctgagcaac aacatgaatg gtcttcggtt ccgtgtttc gtaaagtctg gaaacgcgga    4680
agtcagcgcc ctgcaccatt atgttccgga tctgcatcgc aggatgctgc tggctaccct    4740
gtggaacacc tacatctgta ttaacgaagc gctggcattg accctgagtg attttttctct   4800 ggtcccgccg catccatacc gccagttgtt taccctcaca acgttccagt aaccgggcat    4860
gttcatcatc agtaacccgt atcgtgagca tcctctctcg tttcatcggt atcattaccc    4920
ccatgaacag aaatcccccct tacacggagg catcagtgac caaacaggaa aaaaccgccc    4980
ttaacatggc ccgctttatc agaagccaga cattaacgct tctggagaaa ctcaacgagc    5040
tggacgcgga tgaacaggca gacatctgtg aatcgcttca cgaccacgct gatgagcttt    5100
accgcagctg cctcgcgcgt ttcggtgatg acggtgaaaa cctctgacac atgcagctcc    5160
cggagacggt cacagcttgt ctgtaagcgg atgccgggag cagacaagcc cgtcagggcg    5220
cgtcagcggg tgttggcggg tgtcggggcg cagccatgac ccagtcacgt agcgatagcg    5280
gagtgtatac tggcttaact atgcggcatc agagcagatt gtactgagag tgcaccatat    5340
atgcggtgtg aaataccgca cagatgcgta aggagaaaat accgcatcag cgctctcc     5400 gcttcctcgc tcactgactc gctgcgctcg gtcgttcggc tgcggcgagc ggtatcagct    5460
cactcaaagg cggtaatacg gttatccaca gaatcagggg ataacgcagg aaagaacatg    5520
tgagcaaaag gccagcaaaa ggccaggaac cgtaaaaagg ccgcgttgct ggcgtttttc    5580
cataggctcc gcccccctga cgagcatcac aaaaatcgac gctcaagtca gaggtggcga    5640
aacccgacag gactataaag ataccaggcg tttccccctg gaagctccct cgtgcgctct    5700
cctgttccga ccctgccgct taccggatac ctgtccgcct ttctcccttc gggaagcgtg    5760
gcgctttctc atagctcacg ctgtaggtat ctcagttcgg tgtaggtcgt tcgctccaag    5820
ctgggctgtg tgcacgaacc ccccgttcag cccgaccgct gcgccttatc cggtaactat    5880
cgtcttgagt ccaacccggt aagacacgac ttatcgccac tggcagcagc cactggtaac    5940
aggattagca gagcgaggta tgtaggcggt gctacagagt tcttgaagtg gtggcctaac    6000
tacggctaca ctagaaggac agtatttggt atctgcgctc tgctgaagcc agttaccttc    6060
ggaaaaagag ttggtagctc ttgatccggc aaacaaacca ccgctggtag cggtggtttt    6120
tttgtttgca agcagcagat tacgcgcaga aaaaaaggat ctcaagaaga tcctttgatc    6180
ttttctacgg ggtctgacgc tcagtggaac gaaaactcac gttaagggat tttggtcatg    6240
agattatcaa aaaggatctt cacctagatc cttttaaatt aaaaatgaag ttttaaatca    6300
```

```
atctaaagta tatatgagta aacttggtct gacagttacc aatgcttaat cagtgaggca    6360
cctatctcag cgatctgtct atttcgttca tccatagttg cctgactccc cgtcgtgtag    6420
ataactacga tacgggaggg cttaccatct ggccccagtg ctgcaatgat accgcgagac    6480
ccacgctcac cggctccaga tttatcagca ataaaccagc cagccggaag ggccgagcgc    6540
agaagtggtc ctgcaacttt atccgcctcc atccagtcta ttaattgttg ccgggaagct    6600
agagtaagta gttcgccagt taatagtttg cgcaacgttg ttgccattgc tgcaggcatc    6660
gtggtgtcac gctcgtcgtt tggtatggct tcattcagct ccggttccca acgatcaagg    6720
cgagttacat gatcccccat gttgtgcaaa aaagcggtta gctccttcgg tcctccgatc    6780
gttgtcagaa gtaagttggc cgcagtgtta tcactcatgg ttatggcagc actgcataat    6840
tctcttactg tcatgccatc cgtaagatgc ttttctgtga ctggtgagta ctcaaccaag    6900
tcattctgag aatagtgtat gcggcgaccg agttgctctt gcccggcgtc aacacgggat    6960
aataccgcgc cacatagcag aactttaaaa gtgctcatca ttggaaaacg ttcttcgggg    7020
cgaaaactct caaggatctt accgctgttg agatccagtt cgatgtaacc cactcgtgca    7080
cccaactgat cttcagcatc ttttactttc accagcgttt ctgggtgagc aaaaacagga    7140
aggcaaaatg ccgcaaaaaa gggaataagg gcgacacgga aatgttgaat actcatactc    7200
ttcctttttc aatattattg aagcatttat cagggttatt gtctcatgag cggatacata    7260
tttgaatgta tttagaaaaa taaacaaata ggggttccgc gcacatttcc ccgaaaagtg    7320
ccacctgacg tctaagaaac cattattatc atgacattaa cctataaaaa taggcgtatc    7380
acgaggccct ttcgtcttca agaa                                          7404

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6
catatgaaag cttgtatcga ttaaataagg aggaataaac c                        41

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7
cccgtcttac tgtcgggaat tcgcgttggc cgattcatta atgcagctgg cacgacaggt    60
ttcccgactg gaaagcgggc agtgagcgca acgcaattaa tgtgagttag ctcactcatt    120
aggcacccca ggctttacac tttatgcttc cggctcgtat gttgtgtgga attgtgagcg    180
gataacaatt tcacacagga aacagctatg accatgatta cgccaagctt gtatcgatta    240 ataaggagg aataaaccat gtgtgcgacc tcttctcaat ttactcagat taccgagcat    300
aattcccgtc gttccgcaaa ctatcagcca aacctgtgga atttcgaatt cctgcaatcc    360
ctggagaacg acctgaaagt ggaaaagctg gaggagaaag cgaccaaact ggaggaagaa    420
gttcgctgca tgatcaaccg tgtagacacc cagccgctgt ccctgctgga gctgatcgac    480
gatgtgcagc gcctgggtct gacctacaaa tttgaaaaag acatcattaa agccctggaa    540
aacatcgtac tgctggacga aaacaaaaag aacaaatctg acctgcacgc aaccgctctg    600
```

```
tctttccgtc tgctgcgtca gcacggtttc gaggtttctc aggatgtttt tgagcgtttc    660
aaggataaag aaggtggttt cagcggtgaa ctgaaaggtg acgtccaagg cctgctgagc    720
ctgtatgaag cgtcttacct gggtttcgag ggtgagaacc tgctggagga ggcgcgtacc    780
ttttccatca cccacctgaa gaacaacctg aaagaaggca ttaataccaa ggttgcagaa    840
caagtgagcc acgccctgga actgccatat caccagcgtc tgcaccgtct ggaggcacgt    900
tggttcctgg ataaatacga accgaaagaa ccgcatcacc agctgctgct ggagctggcg    960
aagctggatt ttaacatggt acagaccctg caccagaaag agctgcaaga tctgtcccgc   1020
tggtggaccg agatgggcct ggctagcaaa ctggattttg tacgcgaccg cctgatggaa   1080
gtttatttct gggcactggg tatggcgcca gacccgcagt ttggtgaatg tcgcaaagct   1140
gttactaaaa tgtttggtct ggtgacgatc atcgatgacg tgtatgacgt ttatggcact   1200
ctggacgaac tgcaactgtt caccgatgct gtagagcgct gggacgttaa cgctattaac   1260
accctgccgg actatatgaa actgtgtttc ctggcactgt acaacaccgt taacgacacg   1320
tcctattcta ttctgaaaga gaaaggtcat aacaacctgt cctatctgac gaaaagctgg   1380
cgtgaactgt gcaaagcctt tctgcaagag gcgaaatggt ccaacaacaa aattatcccg   1440
gctttctcca agtacctgga aaacgccagc gtttcctcct ccggtgtagc gctgctggcg   1500
ccgtcttact tttccgtatg ccagcagcag gaagacatct ccgaccacgc gctgcgttcc   1560
ctgaccgact ccatggtctc ggtgcgttct agctgcgtta tcttccgcct gtgcaacgat   1620
ctggccacct ctgcggcgga gctggaacgt ggcgagacta ccaattctat cattagctac   1680
atgcacgaaa acgatggtac cagcgaggaa caggcccgcg aagaactgcg taaactgatc   1740
gacgccgaat ggaaaaagat gaatcgtgaa cgcgttagcg actccaccct gctgcctaaa   1800
gcgttcatgg aaatcgcagt taacatggca cgtgtttccc actgcaccta ccagtatggc   1860
gatggtctgg gtcgcccaga ctacgcgact gaaaaccgca tcaaactgct gctgattgac   1920
cctttcccga ttaaccagct gatgtatgtc taactgcagg tcgactctag aggatccccg   1980
ggtaccgagc tcgaattcac tggccgtcgt tttacaacgt cgtgactggg aaaaccctgg   2040
cgttacccaa cttaatcgcc ttgcagcaca tccccctttc gccagctggc gtaatagcga   2100
agaggcccgc accgatcgcc cttcccaaca gttgcgcagc ctgaatggcg aatggcgcct   2160
gatgcggtat tttctcctta cgcatctgtg cggtatttca caccgcatat ggtgcactct   2220
cagtacaatc tgctctgatg ccgcatagtt aagccagccc cgacacccgc caacacccgc   2280
tgacgagctt agtaaagccc tcgctagatt ttaatgcgga tgttgcgatt acttcgccaa   2340
ctattgcgat aacaagaaaa agccagcctt tcatgatata tctcccaatt tgtgtagggc   2400
ttattatgca cgcttaaaaa taataaaagc agacttgacc tgatagtttg gctgtgagca   2460
attatgtgct tagtgcatct aacgcttgag ttaagccgcg ccgcgaagcg cgtcggctt    2520 gaacgaattg ttagacatta tttgccgact accttggtga tctcgccttt cacgtagtgg   2580
acaaattctt ccaactgatc tgcgcgcgag gccaagcgat cttcttcttg tccaagataa   2640
gcctgtctag cttcaagtat gacgggctga tactgggccg gcaggcgctc cattgcccag   2700
tcggcagcga catccttcgg cgcgattttg ccggttactg cgctgtacca aatgcgggac   2760
aacgtaagca ctacatttcg ctcatcgcca gcccagtcgg gcggcgagtt ccatagcgtt   2820
aaggtttcat ttagcgcctc aaatagatcc tgttcaggaa ccggatcaaa gagttcctcc   2880
gccgctggac ctaccaaggc aacgctatgt tctcttgctt ttgtcagcaa gatagccaga   2940
tcaatgtcga tcgtggctgg ctcgaagata cctgcaagaa tgtcattgcg ctgccattct   3000
```

-continued

```
ccaaattgca gttcgcgctt agctggataa cgccacggaa tgatgtcgtc gtgcacaaca   3060
atggtgactt ctacagcgcg gagaatctcg ctctctccag gggaagccga agtttccaaa   3120
aggtcgttga tcaaagctcg ccgcgttgtt tcatcaagcc ttacggtcac cgtaaccagc   3180
aaatcaatat cactgtgtgg cttcaggccg ccatccactg cggagccgta caaatgtacg   3240
gccagcaacg tcggttcgag atggcgctcg atgacgccaa ctacctctga tagttgagtc   3300
gatacttcgg cgatcaccgc ttccctcatg atgtttaact ttgttttagg gcgactgccc   3360
tgctgcgtaa catcgttgct gctccataac atcaaacatc gacccacggc gtaacgcgct   3420
tgctgcttgg atgcccgagg catagactgt acccccaaaaa aacagtcata caagccatg   3480
aaaaccgcca ctgcgccgtt accaccgctg cgttcggtca aggttctgga ccagttgcgt   3540
gagcgcatac gctacttgca ttacagctta cgaaccgaac aggcttatgt ccactgggtt   3600
cgtgccttca tccgtttcca cggtgtgcgt cacccggcaa ccttgggcag cagcgaagtc   3660
gaggcatttc tgtcctggct ggcgaacgag cgcaaggttt cggtctccac gcatcgtcag   3720
gcattggcgg ccttgctgtt cttctacggc aaggtgctgt gcacgatct gccctggctt   3780
caggagatcg gaagacctcg gccgtcgcgg cgcttgccgg tggtgctgac cccgatgaa   3840
gtggttcgca tcctcggttt tctggaaggc gagcatcgtt tgttcgccca gcttctgtat   3900
ggaacgggca tgcggatcag tgagggtttg caactgcggg tcaaggatct ggatttcgat   3960
cacggcacga tcatcgtgcg ggagggcaag ggctccaagg atcgggcctt gatgttaccc   4020
gagagcttgg cacccagcct gcgcgagcag gggaattaat tcccacgggt tttgctgccc   4080
gcaaacgggc tgttctggtg ttgctagttt gttatcagaa tcgcagatcc ggcttcagcc   4140
ggtttgccgg ctgaaagcgc tatttcttcc agaattgcca tgattttttc cccacgggag   4200
gcgtcactgg ctcccgtgtt gtcggcagct ttgattcgat aagcagcatc gcctgtttca   4260
ggctgtctat gtgtgactgt tgagctgtaa caagttgtct caggtgttca atttcatgtt   4320
ctagttgctt tgtttactg gtttcacctg ttctattagg tgttacatgc tgttcatctg   4380
ttacattgtc gatctgttca tggtgaacag ctttgaatgc accaaaaact cgtaaaagct   4440
ctgatgtatc tatctttttt acaccgtttt catctgtgca tatggacagt tttccctttg   4500
atatgtaacg gtgaacagtt gttctacttt tgtttgttag tcttgatgct tcactgatag   4560
atacaagagc cataagaacc tcagatcctt ccgtatttag ccagtatgtt ctctagtgtg   4620
gttcgttgtt tttgcgtgag ccatgagaac gaaccattga gatcatactt actttgcatg   4680
tcactcaaaa attttgcctc aaaactggtg agctgaattt ttgcagttaa agcatcgtgt   4740
agtgttttc ttagtccgtt atgtaggtag gaatctgatg taatggttgt tggtattttg   4800
tcaccattca tttttatctg gttgttctca agttcggtta cgagatccat ttgtctatct   4860
agttcaactt ggaaaatcaa cgtatcagtc gggcggcctc gcttatcaac caccaatttc   4920
atattgctgt aagtgtttaa atctttactt attggtttca aaacccattg gttaagcctt   4980
ttaaactcat ggtagttatt ttcaagcatt aacatgaact taaattcatc aaggctaatc   5040
tctatatttg ccttgtgagt tttcttttgt gttagttctt ttaataacca ctcataaatc   5100
ctcatagagt atttgttttc aaaagactta acatgttcca gattatattt tatgaatttt   5160
tttaactgga aaagataagg caatatctct tcactaaaaa ctaattctaa tttttcgctt   5220
gagaacttgg catagttgt ccactggaaa atctcaaagc ctttaaccaa aggattcctg   5280
atttccacag ttctcgtcat cagctctctg gttgctttag ctaatacacc ataagcatt   5340
tccctactga tgttcatcat ctgagcgtat tggttataag tgaacgatac cgtccgttct   5400
```

| | |
|---|---|
| ttccttgtag ggttttcaat cgtggggttg agtagtgcca cacagcataa aattagcttg | 5460 |
| gtttcatgct ccgttaagtc atagcgacta atcgctagtt catttgcttt gaaaacaact | 5520 |
| aattcagaca tacatctcaa ttggtctagg tgattttaat cactatacca attgagatgg | 5580 |
| gctagtcaat gataattact agtccttttc ctttgagttg tgggtatctg taaattctgc | 5640 |
| tagacctttg ctggaaaact tgtaaattct gctagaccct ctgtaaattc cgctagacct | 5700 |
| ttgtgtgttt tttttgttta tattcaagtg gttataattt atagaataaa gaagaataa | 5760 |
| aaaagataa aagaataga tcccagccct gtgtataact cactacttta gtcagttccg | 5820 |
| cagtattaca aaaggatgtc gcaaacgctg tttgctcctc tacaaaacag accttaaaac | 5880 |
| cctaaaggct taagtagcac cctcgcaagc tcggcaaat cgctgaatat tccttttgtc | 5940 |
| tccgaccatc aggcacctga gtcgctgtct ttttcgtgac attcagttcg ctgcgctcac | 6000 |
| ggctctggca gtgaatgggg gtaaatggca ctacaggcgc cttttatgga ttcatgcaag | 6060 |
| gaaactaccc ataatacaag aaaagcccgt cacgggcttc tcagggcgtt ttatggcggg | 6120 |
| tctgctatgt ggtgctatct gactttttgc tgttcagcag ttcctgccct ctgattttcc | 6180 |
| agtctgacca cttcggatta tcccgtgaca ggtcattcag actggctaat gcacccagta | 6240 |
| aggcagcggt atcatcaaca ggctta | 6266 |

<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| atgtgtgcaa cctcctccca gtttactcag attaccgagc ataattctcg acgatctgct | 60 |
| aactaccagc cgaacctttg aactttgag tttctccagt ctctcgaaaa tgacctgaag | 120 |
| gtggaaaagc tcgaggagaa ggcgaccaaa ctcgaggagg aggtgcgatg tatgatcaac | 180 |
| agagttgaca cccaaccccct gtctttgctg gagctgatcg acgatgtgca gcggttgggt | 240 |
| tgacttata aattcgagaa ggacattatc aaggcactgg agaacattgt gctcctcgac | 300 |
| gagaacaaga gaacaagtc tgatcttcac gctaccgctc tctctttccg acttcttcga | 360 |
| caacacggct tcgaggtgtc gcaggacgtc ttcgagagat ttaaggacaa ggagggagga | 420 |
| tttagcggcg agctgaaggg agacgttcag ggtcttctct ccttgtacga ggcgtcctac | 480 |
| ctgggattcg agggagagaa cctcctggag gaagctcgta cattttccat cactcacctt | 540 |
| aagaataacc ttaaggaggg aattaacacc aaggtggccg agcaggtttc tcacgccctg | 600 |
| gagctcccct accaccaacg gctccataga ctggaggctc gttggttcct ggacaaatat | 660 |
| gagccaaagg agcctcatca tcagttgctg ttggagttgg ccaagctgga cttcaatatg | 720 |
| gttcagacgc tgcaccaaaa ggagttgcag gacctgtctc gatggtggac cgagatggga | 780 |
| ttggcctcga agctggattt tgtccgtgac cgacttatgg aggtctattt tgggcccctt | 840 |
| ggaatggcgc ctgaccccca gttcggagag tgccggaagg cggtgacgaa gatgttcggt | 900 |
| cttgtgacta tcatcgacga cgtctacgat gtctacggca cactcgacga gttgcagctg | 960 |
| ttcactgacg ccgtcgagcg atgggatgtg aacgccatta atactctccc tgactatatg | 1020 |
| aagctgtgct tcctggctct gtacaacact gtcaacgata cctcgtactc tatcctcaag | 1080 |
| gagaagggac acaacaatct ctcctacttg accaaatcct ggcgagaact gtgcaaggct | 1140 |
| tttctgcagg aggctaaatg gtccaataac aagatcattc ctgcttttc taaatacctg | 1200 |

-continued

```
gaaaatgcct cggtgtcgag ctctggcgtc gcccttctgg ccccttccta cttctccgtc    1260
tgccagcagc aggaggatat ttccgatcat gctcttagat cgctgaccga ttttcacggc    1320
ctcgtgcgat cttcctgcgt gattttcgg ttgtgtaatg accttgcgac ctctgctgct     1380
gagctggaac gaggcgagac tacaaattcc attatttctt acatgcacga aaacgatgga    1440
acatctgaag aacaggctag agaggaactg cgaaagttga tcgacgccga gtggaagaag    1500
atgaacagag agcgggtgtc cgactctacc ctgcttccca aggccttcat ggagatcgcc    1560
gtgaacatgg ctcgagtttc ccattgtact taccagtacg gtgacggcct gggtcgtccg    1620
gactacgcta cagagaaccg aatcaagctg ctgctcatcg acccctccc tatcaaccaa     1680 ttgatgtacg tgtaa                                                     1695

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
gcttatggat cctctagact attacacgta catcaattgg                           40

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
caccatgtgt gcaacctcct cccagtttac                                      30

<210> SEQ ID NO 11
<211> LENGTH: 8185
<212> TYPE: DNA
<213> ORGANISM: Artificial Sequence
<220> FEATURE:
<223> OTHER INFORMATION: Synthetic Construct

<400> SEQUENCE: 11
cgaccggtga aagaacagc atcgggacaa gggaaggaag aacaaagaca agaaaacaa        60 aagaaagcaa ttgaaaacaa aacaaaacaa ttttcattcc ttctcttatc attcctttc      120 ttttcttttc tctcattcaa cgcactccat cgtatccgta ttcctcttat tttttctctt    180
tctctatatc catttctttc tctctaggtg tgtcctctct ctctcttcaa tttctctact    240
ccgcattcca acgcatcctt cccccaacct cccattcct ccttacggcc cgatagcgat     300
cgtctttccc tcgctatcac tcgctaccgg cccctcctct gcaccgtaac ctcctacgta    360
tttaccatat cataaagttt tttccgacgc ttatcgctga cccccctgtcg ccctcctatt   420 ggcttccgga ttatcttctt gtccataagg tgatccatgc ttcctgaaga ttcccgaaat    480
gtgtccactt tggcggggaa tcattccatc cacttctttc tctctcgctt tcctcattcg    540
gcgctcccct tccgcgtctc attggtcttc cgctccgttt ttgctttgcc gatgttactt    600
ggggagaggt gcgataatcc tttcgcaaaa actcggtttg acgcctccca tggtataaat    660
agtgggtggt ggacaggtgc cttcgctttt ctttaagcaa gagaatccca ttgtcttgac    720
tatcacgaat tcatacacat tatgaagatc accgctgtca ttgccctttt attctcactt    780
gctgctgcct cacctattcc agttgccgat cctggtgtgg tttcagttag caagtcatat    840
```

```
gctgatttcc ttcgtgttta ccaaagttgg aacacttttg ctaatcctga tagacccaac    900
cttaagaaga gaaatgatac acctgcaagt ggatatcaag ttgaaaaagt cgtaattttg    960
tcacgtcacg gtgttagggc ccctacaaaa atgactcaaa ccatgcgtga tgtcactcct   1020
aatacatggc cagaatggcc cgttaaatta ggatatatta caccaagagg tgaacacttg   1080
atatcactta tgggcggttt ttaccgtcaa aaattccagc aacaaggaat cctttctcag   1140
ggctcctgtc ctactcctaa ctccatatat gtctgggctg acgtcgatca gcgtacttta   1200
aaaactggtg aagcattcct tgctggtttg gcaccacaat gtggcttgac aattcatcac   1260
caacaaaatc ttgagaaagc tgatcctctt tttcatcccg ttaaagctgg aacctgctct   1320
atggataaaa ctcaagttca acaagctgtt gagaaggagg cacaaactcc tatagataat   1380
ttgaatcaac attacatccc ctttttagct ttaatgaata caacattaaa ttttagtact   1440
tctgcctggt gccaaaaaca ctctgctgat aaatcctgtg acctaggttt atccatgcct   1500
tctaaattgt ccataaaaga taatggtaac aaggtcgcat ggatggagc tattggtcta   1560
tcctctactt tggccgagat ttttcttctt gaatatgctc aaggcatgcc tcaagctgct   1620
tggggtaaca tccactcaga gcaagagtgg gcttccttgc taaagttgca taatgttcaa   1680
ttcgatttga tggcccgaac accttatatt gctcgacata acggtactcc tttattgcaa   1740
gctatatcaa atgcccttaa tcccaacgcc actgaatcaa aacttccaga tatttcacct   1800
gataacaaaa tattgttcat tgcaggtcat gacacaaata ttgctaatat agccggcatg   1860
ttaaatatgc gttggacatt accaggtcaa ccagataata ctcctccagg tggtgcccta   1920
gtatttgaac gtcttgctga taaaagtgga aaacaatatg tttctgtatc tatggtttat   1980
caaacactag aacaacttcg atcacagact ccccttttctc taaatcagcc tgccggatct   2040
gttcaactta aaattccagg ttgcaatgat caaacagccg agggttactg tcctctttcc   2100
acttttacaa gagttgtttc ccaatctgtt gaacctggat gccaacttca ataatgagga   2160
tccaagtaag ggaatgagaa tgtgatccac ttttaattcc taatgaatac atgcctatag   2220
ttcttttctt ttgttcttta tgtcgttttt cgatggtacg gccgttgtca atctcagttt   2280
gtgtgcttgg ttgcagcttg gtttcaaatc tgttcatctc atgaatcttt taccatttca   2340
ccacacgttt ataccattct ctcatagaat cttcatcaaa ccatctcggg gttagagtgg   2400
aaagaaagtc ttgttctttt atttccttttt ttccatcttc aaggcttttc ttttcttcct   2460
cctcctcgtt catcttgagg tttgacgtgt ctgtttagaa ttttgagctg ttgcagcatc   2520
ttatttttg ttttgcgaaa acgaagcgct ttactctctt catcagttgg acgattgtac   2580
ctttgaaaac caactacttt tgcatgtttt gtatagaaat caatgatatt agaatcccat   2640
cctttaattt cttcaaagt agttgagcta tagttaagtg taagggccct actgcgaaag   2700
catttgccaa ggatgttttc attaatcaag aacgaaagtt aggggatcga agacgatcag   2760
ataccgtcgt agtcttaacc ataaactatg ccgactaggg atcgggcaat gtttcattta   2820
tcgacttgct cggcacctta cgagaaatca agtctttgg gttccggggg gagtatggtc   2880
gcaaggctga aacttaaagg aattgacgga agggcaccac aatggagtgg agcctgcggc   2940
ttaatttgac tcaacacggg gaaactcacc aggtccagac atagtaagga ttgacagatt   3000
gagagctctt tcttgattct atgggtggtg gtgcatggcc gttcttagtt ggtggagtga   3060
tttgtctgct taattgcgat aacgaacgag accttaacct gctaaatagc tggatcagcc   3120
attttggctg atcattagct tcttagaggg actattggca taaagccaat ggaagtttga   3180
ggcaataaca ggtctgtgat gcccttagat gttctgggcc gcacgcgcgc tacactgacg   3240
```

```
gagccaacga gttgaaaaaa atcttttgat tttttatcct tggccggaag gtctgggtaa    3300
tcttgttaaa ctccgtcgtg ctggggatag agcattgcaa ttattgcggc cgctcctcaa    3360
ttcgatgttg cagattttac aagttttttaa aatgtatttc attattactt tttatatgcc   3420
taataaaaaa gccatagttt aatctataga aactttttt tccagtgcac taacggacgt     3480
tacattccca tacaaaactg cgtagttaaa gctaaggaaa agttaatatc atgttaatta    3540
aatacgctat ttacaataag acattgaact catttatatc gttgaatatg ataaccaat     3600 ttcagcgaat ttttaacaaa catcgttcac ctcgtttaag gatatcttgt gtatggggtg    3660
ttgacttgct ttatcgaata attaccgtac ctgtaattgg cttgctggat atagcggtag    3720
tctaatatct agcaaaaatc tttgggtga aaaggcttgc aatttcacga caccgaacta     3780
tttgtcattt tttaataagg aagttttcca taaattcctg taattctcgg ttgatctaat    3840
tgaaaagagt agttttgcat cacgatgagg agggcttttg tagaaagaaa tacgaacgaa    3900
acgaaaatca gcgttgccat cgctttggac aaagctccct tacctgaaga gtcgaattt     3960 attgatgaac ttataacttc caagcatgca aaccaaaagg gagaacaagt aatccaagta    4020
gacacgggaa ttggattctt ggatcacatg tatcatgcac tggctaaaca tgcaggctgg    4080
agcttacgac tttactcaag aggtgattta atcatcgatg atcatcacac tgcagaagat    4140
actgctattg cacttggtat tgcattcaag caggctatgg gtaactttgc cggcgttaaa    4200
agatttggac atgcttattg tccacttgac gaagctcttt ctagaagcgt agttgacttg    4260 tcggacggc cctatgctgt tatcgatttg ggattaaagc gtgaaaaggt tggggaattg     4320
tcctgtgaaa tgatccctca cttactatat tccttttcgg tagcagctgg aattactttg    4380
catgttacct gctatatgg tagtaatgac catcatcgtg ctgaaagcgc ttttaaatct     4440
ctggctgttg ccatgcgcgc ggctactagt cttactggaa gttctgaagt cccaagcacg    4500
aagggagtgt tgtaaagatg aattggatta tgtcaggaaa agaacgacaa ttttgcatcc    4560
aaattgtcta aattttagag ttgcttgaaa acaatagaac cttacttgct ttataattac    4620
gttaattaga agcgttatct cgtgaaggaa tatagtacgt agccgtataa attgaattga    4680
atgttcagct tatagaatag agacactttg ctgttcaatg cgtcgtcact taccatactc    4740
actttattat acgactttaa gtataaactc cgcggttatg gtaaaattaa tgatgcacaa    4800
acgtccgatt ccatatgggt acactacaat taaatacttt taagctgatc ccccacacac    4860
catagcttca aaatgtttct actccttttt tactcttcca gattttctcg gactccgcgc    4920
atcgccgtac cacttcaaaa cacccaagca cagcatacta aatttccct ctttcttcct     4980 ctagggtgtc gttaattacc cgtactaaag gtttggaaaa gaaaaagag accgcctcgt     5040 ttctttttct tcgtcgaaaa aggcaataaa aattttatc acgtttcttt tcttgaaat      5100 tttttttttt agtttttttc tctttcagtg acctccattg atatttaagt taataaacgg    5160
tcttcaattt ctcaagtttc agtttcattt ttcttgttct attacaactt tttttacttc    5220
ttgttcatta gaaagaaagc atagcaatct aatctaaggg cggtgttgac aattaatcat    5280
cggcatagta tatcggcata gtataatacg acaaggtgag gaactaaacc atggccaagt    5340
tgaccagtgc cgttccggtg ctcaccgcgc gcgacgtcgc cggagcggtc gagttctgga    5400
ccgaccggct cgggttctcc cgggacttcg tggaggacga cttcgccggt gtggtccggg    5460
acgacgtgac cctgttcatc agcgcggtcc aggaccaggt ggtgccggac aacaccctgg    5520
cctgggtgtg ggtgcgcggc ctggacgagc tgtacgccga gtggtcggag gtcgtgtcca    5580
cgaacttccg ggacgcctcc gggccggcca tgaccgagat cggcgagcag ccgtggggc     5640
```

-continued

```
gggagttcgc cctgcgcgac ccggccggca actgcgtgca cttcgtggcc gaggagcagg    5700
actgacacgt ccgacggcgg cccacgggtc ccaggcctcg gagatccgtc cccctttttcc   5760
tttgtcgata tcatgtaatt agttatgtca cgcttacatt cacgccctcc ccccacatcc    5820
gctctaaccg aaaaggaagg agttagacaa cctgaagtct aggtccctat ttatttttt    5880
atagttatgt tagtattaag aacgttattt atatttcaaa tttttctttt ttttctgtac   5940
agacgcgagc ttcccagtaa atgtgccatc tcgtaggcag aaaacggttc ccccgtaggg   6000
tctctctctt ggcctccttt ctaggtcggg ctgattgctc ttgaagctct ctagggggc    6060
tcacaccata ggcagataac gttccccacc ggctcgcctc gtaagcgcac aaggactgct   6120
cccaaagatc ctaggcggga ttttgccgat ttcggcctaa aggaaccgga acacgtagaa   6180
agccagtccg cagaaacggt gctgaccccg gatgaatgtc agctactggg ctatctggac   6240
aagggaaaac gcaagcgcaa agagaaagca ggtagcttgc agtgggctta catggcgata   6300
gctagactgg gcggttttat ggacagcaag cgaaccggaa ttgccagctg gggcgccctc   6360
tggtaaggtt gggaagccct gcaaagtaaa ctggatggct ttcttgccgc caaggatctg   6420
atggcgcagg ggatcaagat ctgatcaaga gacaggatga ggatcgtttc gcatgattga   6480
acaagatgga ttgcacgcag gttctccggc cgcttgggtg gagaggctat tcggctatga   6540
ctgggcacaa cagacaatcg gctgctctga tgccgccgtg ttccggctgt cagcgcaggg   6600
gcgcccggtt cttttgtca agaccgacct gtccggtgcc ctgaatgaac tgcaggacga   6660
ggcagcgcgg ctatcgtggc tggccacgac gggcgttcct tgcgcagctg tgctcgacgt   6720
tgtcactgaa gcgggaaggg actggctgct attgggcgaa gtgccggggc aggatctcct   6780
gtcatctcgc cttgctcctg ccagagaaagt atccatcatg gctgatgcaa tgcggcggct   6840
gcatacgctt gatccggcta cctgcccatt cgaccaccaa gcgaaacatc gcatcgagcg   6900
agcacgtact cggatggaag ccggtcttgt cgatcaggat gatctggaca agagcatcag   6960
gggctcgcgc cagccgaact gttcgccagg ctcaaggccg catgcccgac ggcgaggatc   7020
tcgtcgtgat ccatggcgat gcctgctgcc gaatatcatg gtggaaaatg gccgcttttc   7080
tggattaacg actgtggccg gctgggtgtg gcggaccgct atcaggacat agcgtggata   7140
cccgtgatat tgctgaagag cttggcggcg aatgggctga ccgcttcctc gtgctttacg   7200
gtatcgccgc tcccgattcg cagcgcatcg ccttctatcg ccttcttgac gagttcttct   7260
gaattgaaaa aggtaccaag tttactcata tatactttag attgatttaa aacttcattt   7320
ttaatttaaa aggatctagg tgaagatcct ttttgataat ctcatgacca aaatccctta   7380
acgtgagttt tcgttccact gagcgtcaga ccccgtagaa aagatcaaag gatcttcttg   7440
agatcctttt tttctgcgcg taatctgctg cttgcaaaca aaaaaaccac cgctaccagc   7500
ggtggtttgt ttgccggatc aagagctacc aactcttttt ccgaaggtaa ctggcttcag   7560
cagagcgcag ataccaaata ctgtccttct agtgtagccg tagttaggcc accacttcaa   7620
gaactctgta gcaccgccta catacctcgc tctgctaatc ctgttaccag tggctgctgc   7680
cagtggcgat aagtcgtgtc ttaccgggtt ggactcaaga cgatagttac cggataaggc   7740
gcagcggtcg ggctgaacgg ggggttcgtg cacacagccc agcttggagc gaacgaccta   7800
caccgaactg agatacctac agcgtgagca ttgagaaagc gccacgcttc ccgaagggag   7860
aaaggcggac aggtatccgg taagcggcag ggtcggaaca ggagagcgca cgagggagct   7920
tccagggggaa aacgcctggt atctttatag tcctgtcggg tttcgccacc tctgacttga   7980
gcgtcgattt ttgtgatgct cgtcaggggg gcggagccta tggaaaaacg ccagcaacgc   8040
```

-continued

```
ggcctttta cggttcctgg ccttttgctg gccttttgct cacatgttct ttcctgcgtt    8100 atccctgat tctgtggata accgtattac cgcctttgag tgagctgata ccgctcgccg    8160
cagccgaacg accgagcgca gcgag                                         8185
```

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12

```
gaattcaaaa caaaatgtgt gcaacctcct cccagtttac tcagattacc gagcataatt      60
ctcgacgatc tgctaactac cagccgaacc tttggaactt tgagtttctc cagtctctcg     120
aaaatgacct gaaggtggaa aagctcgagg agaaggcgac caaactcgag gaggaggtgc     180
gatgtatgat caacagagtt gacacccaac ccctgtcttt gctggagctg atcgacgatg     240
tgcagcggtt gggtttgact tataaattcg agaaggacat tatcaaggca ctggagaaca     300
ttgtgctcct cgacgagaac aagaagaaca agtctgatct tcacgctacc gctctctctt     360
tccgacttct tcgacaacac ggcttcgagg tgtcgcagga cgtcttcgag agatttaagg     420
acaaggaggg aggatttagc ggcgagctga agggagacgt tcagggtctt ctctccttgt     480
acgaggcgtc ctacctggga ttcgagggag agaacctcct ggaggaagct cgtacatttt     540
ccatcactca ccttaagaat aaccttaagg agggaattaa caccaaggtg ccgagcagg     600 tttctcacgc cctggagctc ccctaccacc aacggctcca tagactggag gctcgttggt     660
tcctggacaa atatgagcca aaggagcctc atcatcagtt gctgttggag ttggccaagc     720
tggacttcaa tatggttcag acgctgcacc aaaaggagtt gcaggacctg tctcgatggt     780
ggaccgagat gggattggcc tcgaagctgg attttgtccg tgaccgactt atggaggtct     840
attttttggc ccttggaatg gcgcctgacc cccagttcgg agagtgccgg aaggcggtga     900
cgaagatgtt cggtcttgtg actatcatcg acgacgtcta cgatgtctac ggcacactcg     960
acgagttgca gctgttcact gacgccgtcg agcgatggga tgtgaacgcc attaatactc    1020
tccctgacta tatgaagctg tgcttcctgg ctctgtacaa cactgtcaac gatacctcgt    1080
actctatcct caaggagaag ggacacaaca atctctccta cttgaccaaa tcctggcgag    1140
aactgtgcaa ggcttttctg caggaggcta atggtccaa taacaagatc attcctgctt    1200
tttctaaata cctggaaaat gcctcggtgt cgagctctgg cgtcgccctt ctggcccctt    1260
cctacttctc cgtctgccag cagcaggagg atatttccga tcatgctctt agatcgctga    1320
ccgattttca cggcctcgtg cgatcttcct gcgtgatttt tcggttgtgt aatgaccttg    1380
cgacctctgc tgctgagctg aacgaggcg agactacaaa ttccattatt tcttacatgc    1440
acgaaaacga tggaacatct gaagaacagg ctagagagga actgcgaaag ttgatcgacg    1500
ccgagtggaa gaagatgaac agagagcggg tgtccgactc taccctgctt cccaaggcct    1560
tcatggagat cgccgtgaac atggctcgag tttcccattg tacttaccag tacggtgacg    1620
gcctgggtcg tccggactac gctacagaga accgaatcaa gctgctgctc atcgaccct    1680 tccctatcaa ccaattgatg tacgtgtaat agtctagagg atcc                    1724
```

<210> SEQ ID NO 13
<211> LENGTH: 1701
<212> TYPE: DNA
<213> ORGANISM: Artificial Sequence
<220> FEATURE:

<223> OTHER INFORMATION: Synthetic Construct

<400> SEQUENCE: 13

```
gaattcaaca aaaatgtgct ctgtttccac tgagaacgtg tcctttactg agactgagac    60
tgaagcacgt agaagcgcca actacgaacc caactcctgg gattatgact ttctgctgtc   120
ttctgacacc gacgagtcga tcgaggttta aaggataag gccaagaaac ttgaggccga    180
ggtcagacga gagattaaca acgagaaggc cgagttcctg acccttcttg agctgatcga   240
caacgttcaa cgacttggtc ttggttaccg tttcgaatcc gatatccgac gtgcattgga   300
tcgatttgtc tcgtccggag gtttcgatgg tgtgactaag acgtcgctgc acgccacagc   360
tctttccttc agactgttgc ggcagcatgg atttgaggtt cccaggaag ccttttctgg    420
tttcaaggat cagaacggaa acttttttgga gaatctcaag gaggacacca aggccatcct   480
gtcgttgtat gaggcctcgt tcctggctct tgagggcgag aatattctgg atgaggctcg   540
ggttttcgct atttcgcacc tgaaggagtt gtcggaggaa aagatcggaa aggaactggc   600
cgagcaggtc aaccatgcac ttgaacttcc cctgcatcga cgtacccagc gactggaggc   660
cgtgtggagc atcgaggcgt acagaaaaaa ggaggatgct aatcaggttc tgctcgaact   720
cgctatcctc gactataaca tgattcagag cgtgtaccag cgtgacttgc gagagacaag   780
ccggtggtgg cgacgggtgg gactggccac gaagctccac tttgctaaag atcgattgat   840
tgagtcgttc tactgggcag tgggtgtggc ctttgagcct cagtactccg actgccgaaa   900
ctccgttgca aagatgtttt cttttgtcac tatcatcgac gacatctacg atgtttacgg   960
cactctcgat gaactcgaac tcttcacgga cgctgtcgag cgatgggatg tgaatgccat  1020
taatgatctg ccagattata tgaagttgtg tttcttggcg ctctacaaca caattaatga  1080
aattgcctac gacaacctca aggacaaggg agagaacatt ctgccctacc ttactaaagc  1140
ctgggccgac ctgtgtaacg ccttttttgca ggaagccaag tggctctata acaaatctac  1200
tcctacattt gatgactact tcggcaacgc ttggaagtct tccagcggcc ctctccagtt  1260
gatcttcgct tactttgcag tggtccagaa catcaagaaa gaggagattg agaacctcca  1320
gaagtatcac gacatcatct cccgaccttc gcacatcttt cgactgtgca atgaccttgc  1380
ctccgcatcc gctgagattg cccgaggaga acagccaat tctgtgtcgt gttacatgcg   1440
tacaaagggc atctccgagg agctggctac cgagtctgtg atgaacctga tcgatgaaac  1500
ctgtaagaag atgaacaaag agaaactggg cggttctctg ttcgccaaac catttgttga  1560
aaccgcgatc aatctggctc gtcagtctca ttgtacttac cataacggtg acgcgcacac  1620
ttcgccggac gaattgaccc gtaagcgtgt gctttcggtg attaccgagc cgatcctgcc  1680
gttcgaaaga taataggatc c                                             1701
```

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14

```
gatcaagctt aaccggaatt gccagctg                                         28
```

<210> SEQ ID NO 15
<211> LENGTH: 33
<212> TYPE: DNA
<213> ORGANISM: Artificial Sequence
<220> FEATURE:

<223> OTHER INFORMATION: Synthetic Construct

<400> SEQUENCE: 15
gatccgatcg tcagaagaac tcgtcaagaa ggc                         33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac                    38

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc                                 26

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg    60

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga t                           31

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc    60
tgaatagcgc cgtcgaccat catcatcatc atcattgagt ttaaacggtc tccagcttgg   120
ctgttttggc ggatgagaga agattttcag cctgatacag attaaatcag aacgcagaag   180
cggtctgata aaacagaatt tgcctggcgg cagtagcgcg gtggtcccac ctgaccccat   240
gccgaactca gaagtgaaac gccgtagcgc cgatggtagt gtggggtctc cccatgcgag   300
agtagggaac tgccaggcat caaataaaac gaaaggctca gtcgaaagac tgggcctttc   360
gttttatctg ttgtttgtcg gtgaacgctc tcctgagtag gacaaatccg ccgggagcgg   420
atttgaacgt tgcgaagcaa cggcccggag ggtggcgggc aggacgcccg ccataaactg   480

```
ccaggcatca aattaagcag aaggccatcc tgacggatgg ccttttgcg tttctacaaa      540 ctctttttgt ttatttttct aaatacattc aaatatgtat ccgcttaacc ggaattgcca      600 gctgggcgc cctctggtaa ggttgggaag ccctgcaaag taaactggat ggctttctcg      660
ccgccaagga tctgatggcg cagggatca agctctgatc aagagacagg atgaggatcg      720
tttcgcatga ttgaacaaga tggattgcac gcaggttctc cggccgcttg ggtggagagg      780
ctattcggct atgactgggc acaacagaca atcggctgct ctgatgccgc cgtgttccgg      840
ctgtcagcgc aggggcgccc ggttcttttt gtcaagaccg acctgtccgg tgccctgaat      900
gaactgcaag acgaggcagc gcggctatcg tggctggcca cgacgggcgt tccttgcgca      960
gctgtgctcg acgttgtcac tgaagcggga agggactggc tgctattggg cgaagtgccg     1020
gggcaggatc tcctgtcatc tcaccttgct cctgccgaga agtatccat catggctgat     1080 gcaatgcggc ggctgcatac gcttgatccg gctacctgcc cattcgacca caagcgaaa     1140 catcgcatcg agcgagcacg tactcggatg aagccggtc ttgtcgatca ggatgatctg     1200
gacgaagagc atcaggggct cgcgccagcc gaactgttcg ccaggctcaa ggcgagcatg     1260
cccgacggcg aggatctcgt cgtgacccat ggcgatgcct gcttgccgaa tatcatggtg     1320
gaaaatggcc gcttttctgg attcatcgac tgtggccggc tgggtgtggc ggaccgctat     1380
caggacatag cgttggctac ccgtgatatt gctgaagagc ttggcggcga atgggctgac     1440
cgcttcctcg tgctttacgg tatcgccgct cccgattcgc agcgcatcgc cttctatcgc     1500
cttcttgacg agttcttctg acatgaccaa aatcccttaa cgtgagtttt cgttccactg     1560
agcgtcagac cccgtagaaa agatcaaagg atcttcttga tcctttttt ttctgcgcgt     1620 aatctgctgc ttgcaaacaa aaaaaccacc gctaccagcg gtggtttgtt tgccggatca     1680
agagctacca actctttttc cgaaggtaac tggcttcagc agagcgcaga taccaaatac     1740
tgtccttcta gtgtagccgt agttaggcca ccacttcaag aactctgtag caccgcctac     1800
atacctcgct ctgctaatcc tgttaccagt ggctgctgcc agtggcgata agtcgtgtct     1860
taccgggttg gactcaagac gatagttacc ggataaggcg cagcggtcgg gctgaacggg     1920
gggttcgtgc acacagccca gcttggagcg aacgacctac accgaactga gatacctaca     1980
gcgtgagcta tgagaaagcg ccacgcttcc cgaagggaga aaggcggaca ggtatccggt     2040
aagcggcagg gtcggaacag gagagcgcac gagggagctt ccaggggaa acgcctggta     2100 tctttatagt cctgtcgggt ttcgccacct ctgacttgag cgtcgatttt tgtgatgctc     2160
gtcagggggg cggagcctat ggaaaaacgc cagcaacgcg gcctttttac ggttcctggc     2220
cttttgctgg ccttttgctc acatgttctt tcctgcgtta tcccctgatt ctgtggataa     2280
ccgtattacc gcctttgagt gagctgatac cgctcgccgc agccgaacga ccgagcgcag     2340
cgagtcagtg agcgaggaag cggaagagcg cctgatgcgg tattttctcc ttacgcatct     2400
gtgcggtatt tcacaccgca tatggtgcac tctcagtaca atctgctctg atgccgcata     2460
gttaagccag tatacactcc gctatcgcta cgtgactggg tcatggctgc gccccgacac     2520
ccgccaacac ccgctgacgc gccctgacgg gcttgtctgc tcccggcatc cgcttacaga     2580
caagctgtga ccgtctccgg gagctgcatg tgtcagaggt tttcaccgtc atcaccgaaa     2640
cgcgcgaggc agcagatcaa ttcgcgcgcg aaggcgaagc ggcatgcatt tacgttgaca     2700
ccatcgaatg gtgcaaaacc tttcgcggta tggcatgata gcgcccggaa gagagtcaat     2760
tcagggtggt gaatgtgaaa ccagtaacgt tatacgatgt cgcagagtat gccggtgtct     2820
cttatcagac cgtttcccgc gtggtgaacc aggccagcca cgtttctgcg aaaacgcggg     2880
```

```
aaaaagtgga agcggcgatg gcggagctga attacattcc caaccgcgtg gcacaacaac    2940
tggcgggcaa acagtcgttg ctgattggcg ttgccacctc cagtctggcc ctgcacgcgc    3000
cgtcgcaaat tgtcgcggcg attaaatctc gcgccgatca actgggtgcc agcgtggtgg    3060
tgtcgatggt agaacgaagc ggcgtcgaag cctgtaaagc ggcggtgcac aatcttctcg    3120
cgcaacgcgt cagtgggctg atcattaact atccgctgga tgaccaggat gccattgctg    3180
tggaagctgc ctgcactaat gttccggcgt tatttcttga tgtctctgac cagacaccca    3240
tcaacagtat tattttctcc catgaagacg gtacgcgact gggcgtggag catctggtcg    3300
cattgggtca ccagcaaatc gcgctgttag cgggcccatt aagttctgtc tcggcgcgtc    3360
tgcgtctggc tggctggcat aaatatctca ctcgcaatca aattcagccg atagcggaac    3420
gggaaggcga ctggagtgcc atgtccggtt ttcaacaaac catgcaaatg ctgaatgagg    3480
gcatcgttcc cactgcgatg ctggttgcca acgatcagat ggcgctgggc gcaatgcgcg    3540
ccattaccga gtccgggctg cgcgttggtg cggatatctc ggtagtggga tacgacgata    3600
ccgaagacag ctcatgttat atcccgccgt caaccaccat caaacaggat tttcgcctgc    3660
tggggcaaac cagcgtggac cgcttgctgc aactctctca gggccaggcg gtgaagggca    3720
atcagctgtt gcccgtctca ctggtgaaaa gaaaaaccac cctggcgccc aatacgcaaa    3780
ccgcctctcc ccgcgcgttg gccgattcat taatgcagct ggcacgacag gtttcccgac    3840
tggaaagcgg gcagtgagcg caacgcaatt aatgtgagtt agcgcgaatt gatctggttt    3900
gacagcttat catcgactgc acggtgcacc aatgcttctg cgtcaggca gccatcggaa    3960
gctgtggtat ggctgtgcag gtcgtaaatc actgcataat tcgtgtcgct caaggcgcac    4020
tcccgttctg gataatgttt tttgcgccga catcataacg gttctggcaa atattctgaa    4080
atgagctgtt gacaattaat catccggctc gtataatgtg tggaattgtg agcggataac    4140
aatttcacac aggaaacagc gccgctgaga aaaagcgaag cggcactgct ctttaacaat    4200
ttatcagaca atctgtgtgg gcactcgacc ggaattatcg attaacttta ttattaaaaa    4260
ttaaagaggt atatattaat gtatcgatta aataaggagg aataaaccat gtgtgcgacc    4320
tcttctcaat ttactcagat taccgagcat aattcccgtc gttccgcaaa ctatcagcca    4380
aacctgtgga atttcgaatt cctgcaatcc ctggagaacg acctgaaagt ggaaaagctg    4440
gaggagaaag cgaccaaact ggaggaagaa gttcgctgca tgatcaaccg tgtagacacc    4500
cagccgctgt ccctgctgga gctgatcgac gatgtgcagc gcctgggtct gacctacaaa    4560
tttgaaaaag acatcattaa agccctggaa aacatcgtac tgctggacga aaacaaaaag    4620
aacaaatctg acctgcacgc aaccgctctg tctttccgtc tgctgcgtca gcacggtttc    4680
gaggtttctc aggatgtttt tgagcgtttc aaggataaag aaggtggttt cagcggtgaa    4740
ctgaaaggtg acgtccaagg cctgctgagc ctgtatgaag cgtcttacct gggtttcgag    4800
ggtgagaacc tgctggagga ggcgcgtacc ttttccatca cccacctgaa gaacaacctg    4860
aaagaaggca ttaataccaa ggttgcagaa caagtgagcc acgccctgga actgccatat    4920
caccagcgtc tgcaccgtct ggaggcacgt tggttcctgg ataaatacga accgaaagaa    4980
ccgcatcacc agctgctgct ggagctggcg aagctggatt taacatggt acagaccctg    5040
caccagaaag agctgcaaga tctgtcccgc tggtggaccg agatgggcct ggctagcaaa    5100
ctggatttg tacgcgaccg cctgatggaa gtttatttct gggcactggg tatggcgcca    5160
gacccgcagt tggtgaatg tcgcaaagct gttactaaaa tgtttggtct ggtgacgatc    5220
atcgatgacg tgtatgacgt ttatggcact ctggacgaac tgcaactgtt caccgatgct    5280
```

```
gtagagcgct gggacgttaa cgctattaac accctgccgg actatatgaa actgtgtttc    5340
ctggcactgt acaacaccgt taacgacacg tcctattcta ttctgaaaga gaaaggtcat    5400
aacaacctgt cctatctgac gaaaagctgg cgtgaactgt gcaaagcctt tctgcaagag    5460
gcgaaatggt ccaacaacaa aattatcccg gctttctcca agtacctgga aaacgccagc    5520
gtttcctcct ccggtgtagc gctgctggcg ccgtcttact tttccgtatg ccagcagcag    5580
gaagacatct ccgaccacgc gctgcgttcc ctgaccgact ccatggtct ggtgcgttct    5640
agctgcgtta tcttccgcct gtgcaacgat ctggccacct ctgcggcgga gctggaacgt    5700
ggcgagacta ccaattctat cattagctac atgcacgaaa acgatggtac cagcgaggaa    5760
caggcccgcg aagaactgcg taaactgatc gacgccgaat ggaaaagat gaatcgtgaa    5820
cgcgttagcg actccaccct gctgcctaaa gcgttcatgg aaatcgcagt taacatggca    5880
cgtgtttccc actgcaccta ccagtatggc gatggtctgg gtcgcccaga ctacgcgact    5940
gaaaaccgca tcaaactgct gctgattgac ccttttcccga ttaaccagct gatgtatgtc    6000
taactgcatc gcccttagga ggtaaaaaaa aatgactgcc gacaacaata gtatgcccca    6060
tggtgcagta tctagttacg ccaaattagt gcaaaaccaa acacctgaag acattttgga    6120
agagtttcct gaaattattc cattacaaca aagacctaat acccgatcta gtgagacgtc    6180
aaatgacgaa agcggagaaa catgtttttc tggtcatgat gaggagcaaa ttaagttaat    6240
gaatgaaaat tgtattgttt tggattggga cgataatgct attggtgccg gtaccaagaa    6300
agtttgtcat ttaatggaaa atattgaaaa gggtttacta catcgtgcat tctccgtctt    6360
tattttcaat gaacaaggtg aattacttt acaacaaaga gccactgaaa aaataacttt    6420
ccctgatctt tggactaaca catgctgctc tcatccacta tgtattgatg acgaattagg    6480
tttgaagggt aagctagacg ataagattaa gggcgctatt actgcggcgg tgagaaaact    6540
agatcatgaa ttaggtattc cagaagatga aactaagaca aggggtaagt ttcacttttt    6600
aaacagaatc cattcatgg caccaagcaa tgaaccatgg ggtgaacatg aaattgatta    6660
catcctattt tataagatca acgctaaaga aaacttgact gtcaacccaa acgtcaatga    6720
agttagagac ttcaaatggg tttccaccaaa tgatttgaaa actatgtttg ctgacccaag    6780
ttacaagttt acgccttggt ttaagattat ttgcgagaat tacttattca actggtggga    6840
gcaattagat gacctttctg aagtggaaaa tgacaggcaa attcatagaa tgctataaca    6900
acgcgtcctg cattcgccct taggaggtaa aaaaacatga gttttgatat tgccaaatac    6960
ccgaccctgg cactggtcga ctccacccag gagttacgac tgttgccgaa agagagttta    7020
ccgaaactct gcgacgaact gcgccgctat ttactcgaca gcgtgagccg ttccagcggg    7080
cacttcgcct ccgggctggg cacggtcgaa ctgaccgtgg cgctgcacta tgtctacaac    7140
accccgtttg accaattgat ttgggatgtg gggcatcagg cttatccgca taaaattttg    7200
accggacgcc gcgacaaaat cggcaccatc cgtcagaaag cggtctgca cccgttcccg    7260
tggcgcggcg aaagcgaata tgacgtatta agcgtcgggc attcatcaac ctccatcagt    7320
gccggaattg gtattgcggt tgctgccgaa aagaaggca aaatcgccg caccgtctgt    7380
gtcattggcg atggcgcgat taccgcaggc atggcgtttg aagcgatgaa tcacgcgggc    7440
gatatccgtc ctgatatgct ggtgattctc aacgacaatg aaatgtcgat tccgaaaaat    7500
gtcggcgcgc tcaacaacca tctggcacag ctgcttccg gtaagcttta ctcttcactg    7560
cgcgaaggcg ggaaaaaagt ttctctggc gtgccgccaa ttaaagagct gctcaaacgc    7620
accgaagaac atattaaagg catggtagtg cctggcacgt tgtttgaaga gctgggcttt    7680
```

```
aactacatcg gcccggtgga cggtcacgat gtgctggggc ttatcaccac gctaaagaac    7740
atgcgcgacc tgaaaggccc gcagttcctg catatcatga ccaaaaaagg tcgtggttat    7800
gaaccggcag aaaaagaccc gatcactttc cacgccgtgc ctaaatttga tccctccagc    7860
ggttgtttgc cgaaaagtag cggcggtttg ccgagctatt caaaaatctt tggcgactgg    7920
ttgtgcgaaa cggcagcgaa agacaacaag ctgatggcga ttactccggc gatgcgtgaa    7980
ggttccggca tggtcgagtt ttcacgtaaa ttcccggatc gctacttcga cgtgcaattt    8040
gccgagcaac acgcggtgac ctttgctgcg ggtctggcga ttggtgggta caacccatt    8100 gtcgcgattt actccacttt cctgcaacgc gcctatgatc aggtgctgca tgacgtggcg    8160
attcaaaagc ttccggtcct gttcgccatc gaccgcgcgg gcattgttgg tgctgacggt    8220
caaacccatc agggtgcttt tgatctctct tacctgcgct gcataccgga atggtcatt    8280 atgaccccga gcgatgaaaa cgaatgtcgc cagatgctct ataccggcta tcactataac    8340 gatgcccgt cagcggtgcg ctacccgcgt ggcaacgcgg tcggcgtgga actgacgccg    8400
ctggaaaaac taccaattgg caaaggcatt gtgaagcgtc gtggcgagaa actggcgatc    8460
cttaactttg gtacgctgat gccagaagcg gcgaaagtcg ccgaatcgct gaacgccacg    8520
ctggtcgata tgcgttttgt gaaaccgctt gatgaagcgt taattctgga aatggccgcc    8580
agccatgaag cgctggtcac cgtagaagaa aacgccatta tgggcggcgc aggcagcggc    8640
gtgaacgaag tgctgatggc ccatcgtaaa ccagtacccg tgctgaacat tggcctgccg    8700
gacttcttta ttccgcaagg aactcaggaa gaaatgcgcg ccgaactcgg cctcgatgcc    8760
gctggtatgg aagccaaaat caaggcctgg ctggcataac tgca                    8804

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21
aggaggtaaa aaaacatgtc attaccgttc ttaacttctg c                        41

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22
atggctgcag gcctatcgca aattagctta tgaagtccat ggtaaattcg tg            52

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
gaattcgccc ttctgcagct acc                                            23

<210> SEQ ID NO 24
<211> LENGTH: 38
<212> TYPE: DNA
<213> ORGANISM: Artificial Sequence
<220> FEATURE:
```

<223> OTHER INFORMATION: Synthetic Construct

<400> SEQUENCE: 24
cgactggtgc acccttaagg aggaaaaaaa catgtcag                      38

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
gtgctggaat tcgcccttct gcagc                                   25

<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

<400> SEQUENCE: 26
gtagatgcat gcagaattcg cccttaagga gg                            32

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc                                  26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac                     38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg                                   25

<210> SEQ ID NO 30
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg                       36

<210> SEQ ID NO 31

```
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact      60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32
cggtcgacgg atccctgcag ttagacatac atcagctg                              38

<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggatcc     420
gagctcggat ccactagtaa cggccgccag tgtgctggaa ttcgccctta ggaggtaaaa     480
aaacatgtca ttaccgttct taacttctgc accgggaaag gttattattt ttggtgaaca     540
ctctgctgtg tacaacaagc ctgccgtcgc tgctagtgtg tctgcgttga aacctacct      600 gctaataagc gagtcatctg caccagatac tattgaattg gacttcccgg acattagctt     660
taatcataag tggtccatca atgatttcaa tgccatcacc gaggatcaag taaactccca     720
aaaattggcc aaggctcaac aagccaccga tggcttgtct caggaactcg ttagtctttt     780
ggatccgttg ttagctcaac tatccgaatc cttccactac catgcagcgt tttgtttcct     840
gtatatgttt gtttgcctat gccccatgc caagaatatt aagttttctt taaagtctac       900
tttacccatc ggtgctgggt tgggctcaag cgcctctatt tctgtatcac tggccttagc     960
tatggcctac ttgggggggt taataggatc taatgacttg gaaaagctgt cagaaaacga    1020
taagcatata gtgaatcaat gggccttcat aggtgaaaag tgtattcacg gtaccccttc    1080
aggaatagat aacgctgtgg ccacttatgg taatgccctg ctatttgaaa agactcaca    1140 taatggaaca ataaacacaa acaattttaa gttcttagat gatttcccag ccattccaat    1200
gatcctaacc tatactagaa ttccaaggtc tacaaaagat cttgttgctc gcgttcgtgt    1260
gttggtcacc gagaaatttc ctgaagttat gaagccaatt ctagatgcca tgggtgaatg    1320
tgccctacaa ggcttagaga tcatgactaa gttaagtaaa tgtaaaggca ccgatgacga    1380
ggctgtagaa actaataatg aactgtatga acaactattg gaattgataa gaataaatca    1440
```

```
tggactgctt gtctcaatcg gtgtttctca tcctggatta gaacttatta aaaatctgag    1500
cgatgatttg agaattggct ccacaaaact taccggtgct ggtggcggcg gttgctcttt    1560
gactttgtta cgaagagaca ttactcaaga gcaaattgac agcttcaaaa agaaattgca    1620
agatgatttt agttacgaga catttgaaac agacttgggt gggactggct gctgtttgtt    1680
aagcgcaaaa aatttgaata aagatcttaa aatcaaatcc ctagtattcc aattatttga    1740
aaataaaact accacaaagc aacaaattga cgatctatta ttgccaggaa acacgaattt    1800
accatggact tcataagcta atttgcgata ggcctgcacc cttaaggagg aaaaaaacat    1860
gtcagagttg agagccttca gtgccccagg gaaagcgtta ctagctggtg gatatttagt    1920
tttagataca aaatatgaag catttgtagt cggattatcg gcaagaatgc atgctgtagc    1980
ccatccttac ggttcattgc aagggtctga taagtttgaa gtgcgtgtga aaagtaaaca    2040
atttaaagat ggggagtggc tgtaccatat aagtcctaaa agtggcttca ttcctgtttc    2100
gataggcgga tctaagaacc cttttcattga aaaagttatc gctaacgtat ttagctactt    2160
taaacctaac atggacgact actgcaatag aaacttgttc gttattgata ttttctctga    2220
tgatgcctac cattctcagg aggatagcgt taccgaacat cgtggcaaca gaagattgag    2280
ttttcattcg cacagaattg aagaagttcc caaaacaggg ctgggctcct cggcaggttt    2340
agtcacagtt ttaactacag cttttggcctc ctttttttgta tcggacctgg aaaataatgt    2400
agacaaatat agagaagtta ttcataattt agcacaagtt gctcattgtc aagctcaggg    2460
taaaattgga agcgggtttg atgtagcggc ggcagcatat ggatctatca gatatagaag    2520
attcccaccc gcattaatct ctaatttgcc agatattgga agtgctactt acggcagtaa    2580
actggcgcat ttggttgatg aagaagactg gaatattacg attaaaagta accatttacc    2640
ttcgggatta actttatgga tgggcgatat taagaatggt tcagaaacag taaaactggt    2700
ccagaaggta aaaaattggt atgattcgca tatgccagaa agcttgaaaa tatatacaga    2760
actcgatcat gcaaattcta gatttatgga tggactatct aaactagatc gcttacacga    2820
gactcatgac gattacagcg atcagatatt tgagtctctt gagaggaatg actgtacctg    2880
tcaaaagtat cctgaaatca cagaagttag agatgcagtt gccacaatta gacgttcctt    2940
tagaaaaata actaaagaat ctggtgccga tatcgaacct cccgtacaaa ctagcttatt    3000
ggatgattgc cagaccttaa aaggagttct tacttgctta atacctggtg ctggtggtta    3060
tgacgccatt gcagtgatta ctaagcaaga tgttgatctt agggctcaaa ccgctaatga    3120
caaaagattt tctaaggttc aatggctgga tgtaactcag gctgactggg gtgttaggaa    3180
agaaaaagat ccggaaactt atcttgataa ataacttaag gtagctgcat gcagaattcg    3240
cccttaagga ggaaaaaaaa atgaccgttt acacagcatc cgttaccgca cccgtcaaca    3300
tcgcaaccct taagtattgg gggaaagggg acacgaagtt gaatctgccc accaattcgt    3360
ccatatcagt gactttatcg caagatgacc tcagaacgtt gacctctgcg gctactgcac    3420
ctgagtttga acgcgacact ttgtggttaa atggagaacc acacagcatc gacaatgaaa    3480
gaactcaaaa ttgtctgcgc gacctacgcc aattaagaaa ggaaatggaa tcgaaggacg    3540
cctcattgcc cacattatct caatggaaac tccacattgt ctccgaaaat aactttccta    3600
cagcagctgg tttagcttcc tccgctgctg gctttgctgc attggtctct gcaattgcta    3660 agttataccca attaccacag tcaacttcag aaatatctag aatagcaaga aagggtctg    3720 gttcagcttg tagatcgttg tttggcggat acgtggcctg ggaaatggga aaagctgaag    3780
atggtcatga ttccatggca gtacaaatcg cagacagctc tgactggcct cagatgaaag    3840
```

```
cttgtgtcct agttgtcagc gatattaaaa aggatgtgag ttccactcag ggtatgcaat    3900
tgaccgtggc aacctccgaa ctatttaaag aaagaattga acatgtcgta ccaaagagat    3960
ttgaagtcat gcgtaaagcc attgttgaaa aagatttcgc cacctttgca aaggaaacaa    4020
tgatggattc caactctttc catgccacat gtttggactc tttccctcca atattctaca    4080
tgaatgacac ttccaagcgt atcatcagtt ggtgccacac cattaatcag ttttacggag    4140
aaacaatcgt tgcatacacg tttgatgcag gtccaaatgc tgtgttgtac tacttagctg    4200
aaaatgagtc gaaactcttt gcatttatct ataaattgtt tggctctgtt cctggatggg    4260
acaagaaatt tactactgag cagcttgagg cttttcaacca tcaatttgaa tcatctaact    4320
ttactgcacg tgaattggat cttgagttgc aaaaggatgt tgccagagtg atttttaactc    4380
aagtcggttc aggcccacaa gaaacaaacg aatctttgat tgacgcaaag actggtctac    4440
caaaggaata agatcaattc gctgcatcgc ccttaggagg taaaaaaaaa tgactgccga    4500
caacaatagt atgccccatg gtgcagtatc tagttacgcc aaattagtgc aaaaccaaac    4560
acctgaagac attttggaag agtttcctga aattattcca ttacaacaaa gacctaatac    4620
ccgatctagt gagacgtcaa atgacgaaag cggagaaaca tgttttttctg gtcatgatga    4680
ggagcaaatt aagttaatga atgaaaattg tattgttttg gattgggacg ataatgctat    4740
tggtgccggt accagaaaag tttgtcattt aatggaaaat attgaaaagg gtttactaca    4800
tcgtgcattc tccgtcttta ttttcaatga acaaggtgaa ttacttttac aacaaagagc    4860
cactgaaaaa ataactttcc ctgatctttg gactaacaca tgctgctctc atccactatg    4920
tattgatgac gaattaggtt tgaagggtaa gctagacgat aagattaagg gcgctattac    4980
tgcggcggtg agaaaactag atcatgaatt aggtattcca gaagatgaaa ctaagacaag    5040
gggtaagttt cacttttttaa acagaatcca ttacatggca ccaagcaatg aaccatgggg    5100
tgaacatgaa attgattaca tcctatttta taagatcaac gctaaagaaa acttgactgt    5160
caacccaaac gtcaatgaag ttagagactt caaatgggtt tcaccaaatg atttgaaaac    5220
tatgtttgct gacccaagtt acaagtttac gccttggttt aagattattt gcgagaatta    5280
cttattcaac tggtgggagc aattagatga cctttctgaa gtggaaaatg acaggcaaat    5340
tcatagaatg ctataacaac gcgtcctgca ttcgccctta ggaggtaaaa aaacatgtgt    5400
gcgacctctt ctcaatttac tcagattacc gagcataatt cccgtcgttc cgcaaactat    5460
cagccaaacc tgtggaattt cgaattcctg caatccctgg agaacgacct gaaagtggaa    5520
aagctggagg agaaagcgac caaactggag gaagaagttc gctgcatgat caaccgtgta    5580
gacacccagc cgctgtccct gctggagctg atcgacgatg tgcagcgcct gggtctgacc    5640
tacaaatttg aaaagacat cattaaagcc ctggaaaaca tcgtactgct ggacgaaaac    5700
aaaaagaaca atctgacct gcacgcaacc gctctgtctt tccgtctgct gcgtcagcac    5760
ggtttcgagg tttctcagga tgttttttgag cgtttcaagg ataaagaagg tggtttcagc    5820
ggtgaactga aggtgacgt ccaaggcctg ctgagcctgt atgaagcgtc ttacctgggt    5880
ttcgagggtc agaacctgct ggaggaggcg cgtacctttt ccatcaccca cctgaagaac    5940
aacctgaaag aaggcattaa taccaaggtt gcagaacaag tgagccacgc cctggaactg    6000
ccatatcacc agcgtctgca ccgtctggag gcacgttggt tcctggataa atacgaaccg    6060
aaagaaccgc atcaccagct gctgctggag ctggcgaagc tggattttaa catggtacag    6120
accctgcacc agaagagct gcaagatctg tcccgctggt ggaccgagat gggcctggct    6180
agcaaactgg attttgtacg cgaccgcctg atggaagttt atttctgggc actgggtatg    6240
```

```
gcgccagacc cgcagtttgg tgaatgtcgc aaagctgtta ctaaaatgtt tggtctggtg    6300
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga atggtccaa caacaaaatt atcccggctt ctccaagta cctggaaaac    6600 gccagcgttt cctcctccgg tgtagcgctg ctggcgccgt cttactttc cgtatgccag    6660 cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
gaggaacagg cccgcgaaga actgcgtaaa ctgatcgacg ccgaatggaa aaagatgaat    6900
cgtgaacgcg ttagcgactc caccctgctg cctaaagcgt tcatggaaat cgcagttaac    6960
atggcacgtg tttcccactg cacctaccag tatggcgatg gtctgggtcg cccagactac    7020
gcgactgaaa accgcatcaa actgctgctg attgacccctt tcccgattaa ccagctgatg    7080
tatgtctaac tgcagctggt accatatggg aattcgaagc tttctagaac aaaaactcat    7140
ctcagaagag gatctgaata gcgccgtcga ccatcatcat catcatcatt gagtttaaac    7200
ggtctccagc ttggctgttt tggcggatga gagaagattt tcagcctgat acagattaaa    7260
tcagaacgca gaagcggtct gataaaacag aatttgcctg gcggcagtag cgcggtggtc    7320
ccacctgacc ccatgccgaa ctcagaagtg aaacgccgta gcgccgatgg tagtgtgggg    7380
tctccccatg cgagagtagg gaactgccag gcatcaaata aaacgaaagg ctcagtcgaa    7440
agactgggcc tttcgtttta tctgttgttt gtcggtgaac gctctcctga gtaggacaaa    7500
tccgccggga gcggatttga acgttgcgaa gcaacggccc ggagggtggc gggcaggacg    7560
cccgccataa actgccaggc atcaaattaa gcagaaggcc atcctgacgg atggccttt    7620 tgcgtttcta caaactcttt ttgtttattt ttctaaatac attcaaatat gtatccgctt    7680
aaccggaatt gccagctggg gcgccctctg gtaaggttgg gaagccctgc aaagtaaact    7740
ggatggcttt ctcgccgcca aggatctgat ggcgcagggg atcaagctct gatcaagaga    7800
caggatgagg atcgtttcgc atgattgaac aagatggatt gcacgcaggt tctccggccg    7860
cttgggtgga gaggctattc ggctatgact gggcacaaca gacaatcggc tgctctgatg    7920
ccgccgtgtt ccgctgtca gcgcagggc gcccggttct ttttgtcaag accgacctgt    7980
ccggtgccct gaatgaactg caagacgagg cagcgcggct atcgtggctg gccacgacgg    8040
gcgttccttg cgcagctgtg ctcgacgttg tcactgaagc gggaagggac tggctgctat    8100
tgggcgaagt gccggggcag gatctcctgt catctcacct tgctcctgcc gagaaagtat    8160
ccatcatggc tgatgcaatg cggcggctgc atacgcttga tccggctacc tgcccattcg    8220
accaccaagc gaaacatcgc atcgagcgag cacgtactcg gatggaagcc ggtcttgtcg    8280
atcaggatga tctggacgaa gagcatcagg ggctcgcgcc agccgaactg ttcgccaggc    8340
tcaaggcgag catgcccgac ggcgaggatc tcgtcgtgac ccatggcgat gcctgcttgc    8400
cgaatatcat ggtggaaaat ggccgctttt ctggattcat cgactgtggc cggctgggtg    8460
tggcggaccg ctatcaggac atagcgttgg ctacccgtga tattgctgaa gagcttggcg    8520
gcgaatgggc tgaccgcttc ctcgtgcttt acggtatcgc cgctcccgat tcgcagcgca    8580
tcgccttcta tcgccttctt gacgagttct tctgacgcat gaccaaaatc ccttaacgtg    8640
```

-continued

```
agttttcgtt ccactgagcg tcagaccccg tagaaaagat caaaggatct tcttgagatc   8700
ctttttttct gcgcgtaatc tgctgcttgc aaacaaaaaa accaccgcta ccagcggtgg   8760
tttgtttgcc ggatcaagag ctaccaactc ttttttccga ggtaactggc ttcagcagag   8820
cgcagatacc aaatactgtc cttcagtgt agccgtagtt aggccaccac ttcaagaact   8880
ctgtagcacc gcctacatac ctcgctctgc taatcctgtt accagtggct gctgccagtg   8940
gcgataagtc gtgtcttacc gggttggact caagacgata gttaccggat aaggcgcagc   9000
ggtcgggctg aacggggggt tcgtgcacac agcccagctt ggagcgaacg acctacaccg   9060
aactgagata cctacagcgt gagctatgag aaagcgccac gcttcccgaa gggagaaagg   9120
cggacaggta tccggtaagc ggcagggtcg aacaggaga gcgcacgagg gagcttccag   9180
ggggaaacgc ctggtatctt tatagtcctg tcgggtttcg ccacctctga cttgagcgtc   9240
gatttttgtg atgctcgtca gggggggcgga gcctatggaa aaacgccagc aacgcggcct   9300
ttttacggtt cctggccttt tgctggcctt ttgctcacat gttctttcct gcgttatccc   9360
ctgattctgt ggataaccgt attaccgcct ttgagtgagc tgataccgct cgccgcagcc   9420
gaacgaccga gcgcagcgag tcagtgagcg aggaagcgga agagcgcctg atgcggtatt   9480
ttctccttac gcatctgtgc ggtatttcac accgcatatg gtgcactctc agtacaatct   9540
gctctgatgc cgcatagtta agccagtata cactccgcta tcgctacgtg actgggtcat   9600
ggctgcgccc cgacacccgc caacacccgc tgacgcgccc tgacgggctt gtctgctccc   9660
ggcatccgct tacagacaag ctgtgaccgt ctccgggagc tgcatgtgtc agaggttttc   9720
accgtcatca ccgaaacgcg cgaggcagca gatcaattcg cgcgcgaagg cgaagcggca   9780
tgcatttacg ttgacaccat cgaatggtgc aaaacctttc gcggtatggc atgatagcgc   9840
ccggaagaga gtcaattcag ggtggtgaat gtgaaaccag taacgttata cgatgtcgca   9900
gagtatgccg gtgtctctta tcagaccgtt tcccgcgtgg tgaaccaggc cagccacgtt   9960
tctgcgaaaa cgcgggaaaa agtggaagcg gcgatggcgg agctgaatta cattcccaac  10020
cgcgtggcac aacaactggc gggcaaacag tcgttgctga ttggcgttgc cacctccagt  10080
ctggccctgc acgcgccgtc gcaaattgtc gcggcgatta atctctcgcg cgatcaactg  10140
ggtgccagcg tggtggtgtc gatggtagaa cgaagcggcg tcgaagcctg taaagcggcg  10200
gtgcacaatc ttctcgcgca acgcgtcagt gggctgatca ttaactatcc gctggatgac  10260
caggatgcca ttgctgtgga agctgcctgc actaatgttc cggcgttatt tcttgatgtc  10320
tctgaccaga cacccatcaa cagtattatt ttctcccatg aagacggtac gcgactgggc  10380
gtggagcatc tggtcgcatt gggtcaccag caaatcgcgc tgttagcggg cccattaagt  10440
tctgtctcgg cgcgtctgcg tctggctggc tggcataaat atctcactcg caatcaaatt  10500
cagccgatag cggaacggga aggcgactgg agtgccatgt ccggttttca acaaaccatg  10560
caaatgctga atgagggcat cgttcccact gcgatgctgg ttgccaacga tcagatggcg  10620
ctgggcgcaa tgcgcgccat taccgagtcc gggctgcgcg ttggtgcgga tatctcggta  10680
gtgggatacg acgataccga agacagctca tgttatatcc gccgtcaac caccatcaaa  10740
caggattttc gcctgctggg gcaaaccagc gtggaccgct tgctgcaact ctctcagggc  10800
caggcggtga agggcaatca gctgttgccc gtctcactgg tgaaagaaa accaccctg   10860
gcgcccaata cgcaaaccgc ctctccccgc gcgttggccg attcattaat gcagctggca  10920
cgacaggttt cccgactgga aagcgggcag tgagcgcaac gcaattaatg tgagttagcg  10980
cgaattgatc tg                                                      10992
```

-continued

<210> SEQ ID NO 34
<211> LENGTH: 50
<212> TYPE: DNA
<213> ORGANISM: Artificial Sequence
<220> FEATURE:
<223> OTHER INFORMATION: Synthetic Construct

<400> SEQUENCE: 34
gagacatgag ctcaggaggt aaaaaaacat gaaaacagta gttattattg        50

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35
tttatcaatc ccaattgtca tgttttttta cctcctttat tgttttctta aatc    54

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36
gatttaagaa acaataaag gaggtaaaaa aacatgacaa ttgggattga taaa      54

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37
gacatgacat agatctttag tttcgataag aacgaacggt                    40

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
atgaaaacag tagttattat tgatgc                                   26

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
atgttattgt tttcttaaat catttaaaat agc                           33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

```
<400> SEQUENCE: 40
atgacaattg ggattgataa aattag                                          26

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41
ttagtttcga taagaacgaa cggt                                            24

<210> SEQ ID NO 42
<211> LENGTH: 23
<212> TYPE: DNA
<213> ORGANISM: Artificial Sequence
<220> FEATURE:
<223> OTHER INFORMATION: Synthetic Construct

<400> SEQUENCE: 42
gaaatagccc cattagaagt atc                                             23

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
ttgccaatca tatgattgaa aatc                                            24

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
gctatgcttc attagatcct tatcg                                           25

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
gaaacctaca tccaatcttt tgccc                                           25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46
cccgtcttac tgtcgggaat tcgcgttggc cgattcatta atgcagattc tgaaatgagc     60
tgttgacaat taatcatccg gctcgtataa tgtgtggaat tgtgagcgga taacaatttc    120
acacaggaaa cagcgccgct gagaaaaagc gaagcggcac tgctctttaa caatttatca    180
```

-continued

| | |
|---|---|
| gacaatctgt gtgggcactc gaccggaatt atcgattaac tttattatta aaaattaaag | 240 |
| aggtatatat taatgtatcg attaaataag gaggaataaa ccatggatcc gagctcagga | 300 |
| ggtaaaaaaa catgaaaaca gtagttatta ttgatgcatt acgaacacca attggaaaat | 360 |
| ataaaggcag cttaagtcaa gtaagtgccg tagacttagg aacacatgtt acaacacaac | 420 |
| ttttaaaaag acattccact atttctgaag aaattgatca agtaatcttt ggaaatgttt | 480 |
| tacaagctgg aaatgccaa atcccgcac gacaaatagc aataaacagc ggtttgtctc | 540 |
| atgaaattcc cgcaatgacg gttaatgagg tctgcggatc aggaatgaag gccgttattt | 600 |
| tggcgaaaca attgattcaa ttaggagaag cggaagtttt aattgctggc gggattgaga | 660 |
| atatgtccca agcacctaaa ttacaacgtt ttaattacga aacagaaagc tacgatgcgc | 720 |
| cttttttctag tatgatgtat gatggattaa cggatgcctt tagtggtcag gcaatgggct | 780 |
| taactgctga aaatgtggcc gaaaagtatc atgtaactag agaagagcaa gatcaatttt | 840 |
| ctgtacattc acaattaaaa gcagctcaag cacaagcaga agggatattc gctgacgaaa | 900 |
| tagcccatt agaagtatca ggaacgcttg tggagaaaga tgaagggatt cgccctaatt | 960 |
| cgagcgttga gaagctagga acgcttaaaa cagttttaa agaagacggt actgtaacag | 1020 |
| cagggaatgc atcaaccatt aatgatgggg cttctgcttt gattattgct tcacaagaat | 1080 |
| atgccgaagc acacggtctt ccttatttag ctattattcg agacagtgtg gaagtcggta | 1140 |
| ttgatccagc ctatatggga atttcgccga ttaaagccat tcaaaaactg ttagcgcgca | 1200 |
| atcaacttac tacggaagaa attgatctgt atgaaatcaa cgaagcattt gcagcaactt | 1260 |
| caatcgtggt ccaaagagaa ctggctttac cagaggaaaa ggtcaacatt tatggtggcg | 1320 |
| gtatttcatt aggtcatgcg attggtgcca caggtgctcg tttattaacg agtttaagtt | 1380 |
| atcaattaaa tcaaaagaa aagaaatatg gagtggcttc tttatgtatc ggcggtggct | 1440 |
| taggactcgc tatgctacta gagagacctc agcaaaaaaa aaacagccga ttttatcaaa | 1500 |
| tgagtcctga ggaacgcctg gcttctcttc ttaatgaagg ccagatttct gctgatacaa | 1560 |
| aaaaagaatt tgaaaatacg gctttatctt cgcagattgc caatcatatg attgaaaatc | 1620 |
| aaatcagtga aacagaagtg ccgatgggcg ttggcttaca tttaacagtg gacgaaactg | 1680 |
| attatttggt accaatggcg acagaagagc cctcagttat tgcggctttg agtaatggtg | 1740 |
| caaaaatagc acaaggattt aaaacagtga atcaacaacg cttaatgcgt ggacaaatcg | 1800 |
| ttttttacga tgttgcagat cccgagtcat tgattgataa actacaagta agagaagcgg | 1860 |
| aagttttca acaagcagag ttaagttatc catctatcgt taaacggggc ggcggcttaa | 1920 |
| gagatttgca atatcgtact tttgatgaat catttgtatc tgtcgacttt ttagtagatg | 1980 |
| ttaaggatgc aatgggggca aatatcgtta acgctatgtt ggaaggtgtg gccgagttgt | 2040 |
| tccgtgaatg gtttgcggag caaaagattt tattcagtat tttaagtaat tatgccacgg | 2100 |
| agtcggttgt tacgatgaaa acggctattc cagtttcacg tttaagtaag gggagcaatg | 2160 |
| gccgggaaat tgctgaaaaa attgttttag cttcacgcta tgcttcatta gatccttatc | 2220 |
| gggcagtcac gcataacaaa ggaatcatga atggcattga agctgtagtt ttagctacag | 2280 |
| gaaatgatac acgcgctgtt agcgcttctt gtcatgcttt tgcggtgaag gaaggtcgct | 2340 |
| accaaggctt gactagttgg acgctggatg gcgaacaact aattggtgaa atttcagttc | 2400 |
| cgcttgctttt agccacggtt ggcggtgcca caaaagtctt acctaaatct caagcagctg | 2460 |
| ctgatttgtt agcagtgacg gatgcaaaag aactaagtcg agtagtagcg ctgttggtt | 2520 |
| tggcacaaaa tttagcggcg ttacgggcct tagtctctga aggaattcaa aaaggacaca | 2580 |

```
tggctctaca agcacgttct ttagcgatga cggtcggagc tactggtaaa gaagttgagg    2640
cagtcgctca acaattaaaa cgtcaaaaaa cgatgaacca agaccgagcc atggctattt    2700
taaatgattt aagaaaacaa taaggaggt aaaaaaacat gacaattggg attgataaaa      2760
ttagtttttt tgtgccccct tattatattg atatgacggc actggctgaa gccagaaatg    2820
tagaccctgg aaaatttcat attggtattg ggcaagacca aatggcggtg aacccaatca    2880
gccaagatat tgtgacattt gcagccaatg ccgcagaagc gatcttgacc aaagaagata    2940
aagaggccat tgatatggtg attgtcggga ctgagtccag tatcgatgag tcaaaagcgg    3000
ccgcagttgt cttacatcgt ttaatgggga ttcaaccttt cgctcgctct ttcgaaatca    3060
aggaagcttg ttacggagca acagcaggct tacagttagc taagaatcac gtagccttac    3120
atccagataa aaaagtcttg gtcgtagcgg cagatattgc aaaatatggc ttaaattctg    3180
gcggtgagcc tacacaagga gctggggcgg ttgcaatgtt agttgctagt gaaccgcgca    3240
ttttggcttt aaaagaggat aatgtgatgc tgacgcaaga tatctatgac ttttggcgtc    3300
caacaggcca cccgtatcct atggtcgatg gtcctttgtc aaacgaaacc tacatccaat    3360
cttttgccca agtctgggat gaacataaaa acgaaccgg tcttgatttt gcagattatg      3420
atgctttagc gttccatatt ccttacacaa aaatgggcaa aaaagcctta ttagcaaaaa    3480
tctccgacca aactgaagca gaacaggaac gaattttagc ccgttatgaa gaaagtatcg    3540
tctatagtcg tcgcgtagga aacttgtata cgggttcact ttatctggga ctcatttccc    3600
ttttagaaaa tgcaacgact ttaaccgcag gcaatcaaat tggtttattc agttatggtt    3660
ctggtgctgt cgctgaattt ttcactggtg aattagtagc tggttatcaa aatcatttac    3720
aaaaagaaac tcatttagca ctgctggata atcggacaga actttctatc gctgaatatg    3780
aagccatgtt tgcagaaact ttagacacag acattgatca aacgttagaa gatgaattaa    3840
aatatagtat ttctgctatt aataataccg ttcgttctta tcgaaactaa gagatctgca    3900
gctggtacca tatgggaatt cgaagcttgg gcccgaacaa aaactcatct cagaagagga    3960
tctgaatagc gccgtcgacc atcatcatca tcatcattga gtttaaacgg tctccagctt    4020
ggctgttttg gcggatgaga gaagattttc agcctgatac agattaaatc agaacgcaga    4080
agcggtctga taaaacagaa tttgcctggc ggcagtagcg cggtggtccc acctgacccc    4140
atgccgaact cagaagtgaa acgccgtagc gccgatggta gtgtggggtc tccccatgcg    4200
agagtaggga actgccaggc atcaaataaa acgaaaggct cagtcgaaag actgggcctt    4260
tcgttttatc tgttgtttgt cggtgaacgc tctcctgagt aggacaaatc cgccgggagc    4320
ggatttgaac gttgcgaagc aacggcccgg agggtggcgg gcaggacgcc cgccataaac    4380
tgccaggcat caaattaagc agaaggccat cctgacggat ggcctttttg cgtttctaca    4440
aactcttttt gtttattttt ctaaatacat tcaaatatgt atccgctcat gagacaataa    4500
ccctgataaa tgcttcaata atctggcgta atagcgaaga ggcccgcacc gatcgccctt    4560
cccaacagtt gcgcagcctg aatggcgaat ggcgcctgat gcggtatttt ctccttacgc    4620
atctgtgcgg tatttcacac cgcatatggt gcactctcag tacaatctgc tctgatgccg    4680
catagttaag ccagccccga cacccgccaa cacccgctga cgagcttagt aaagccctcg    4740
ctagatttta atgcggatgt tgcgattact tcgccaacta ttgcgataac aagaaaaagc    4800
cagcctttca tgatatatct cccaatttgt gtagggctta ttatgcacgc ttaaaaataa    4860
taaaagcaga cttgacctga tagtttggct gtgagcaatt atgtgcttag tgcatctaac    4920
gcttgagtta agccgcgccg cgaagcggcg tcggcttgaa cgaattgtta gacattattt    4980
```

```
gccgactacc ttggtgatct cgcctttcac gtagtggaca aattcttcca actgatctgc    5040
gcgcgaggcc aagcgatctt cttcttgtcc aagataagcc tgtctagctt caagtatgac    5100
gggctgatac tgggccggca ggcgctccat tgcccagtcg gcagcgacat ccttcggcgc    5160
gattttgccg gttactgcgc tgtaccaaat gcgggacaac gtaagcacta catttcgctc    5220
atcgccagcc cagtcgggcg gcgagttcca tagcgttaag gtttcattta gcgcctcaaa    5280
tagatcctgt tcaggaaccg gatcaaagag ttcctccgcc gctggaccta ccaaggcaac    5340
gctatgttct cttgcttttg tcagcaagat agccagatca atgtcgatcg tggctggctc    5400
gaagatacct gcaagaatgt cattgcgctg ccattctcca aattgcagtt cgcgcttagc    5460
tggataacgc cacggaatga tgtcgtcgtg cacaacaatg gtgacttcta cagcgcggag    5520
aatctcgctc tctccagggg aagccgaagt ttccaaaagg tcgttgatca aagctcgccg    5580
cgttgtttca tcaagcctta cggtcaccgt aaccagcaaa tcaatatcac tgtgtggctt    5640
caggccgcca tccactgcgg agccgtacaa atgtacggcc agcaacgtcg gttcgagatg    5700
gcgctcgatg acgccaacta cctctgatag ttgagtcgat acttcggcga tcaccgcttc    5760
cctcatgatg tttaactttg ttttagggcg actgccctgc tgcgtaacat cgttgctgct    5820
ccataacatc aaacatcgac ccacggcgta acgcgcttgc tgcttggatg cccgaggcat    5880
agactgtacc ccaaaaaaac agtcataaca agccatgaaa accgccactg cgccgttacc    5940
accgctgcgt tcggtcaagg ttctggacca gttgcgtgag cgcatacgct acttgcatta    6000
cagcttacga accgaacagg cttatgtcca ctgggttcgt gccttcatcc gtttccacgg    6060
tgtgcgtcac ccggcaacct tgggcagcag cgaagtcgag gcatttctgt cctggctggc    6120
gaacgagcgc aaggtttcgg tctccacgca tcgtcaggca ttggcggcct tgctgttctt    6180
ctacggcaag gtgctgtgca cggatctgcc ctggcttcag gagatcggaa gacctcggcc    6240
gtcgcggcgc ttgccggtgg tgctgacccc ggatgaagtg gttcgcatcc tcggttttct    6300
ggaaggcgag catcgtttgt tcgcccagct tctgtatgga acgggcatgc ggatcagtga    6360
gggtttgcaa ctgcgggtca aggatctgga tttcgatcac ggcacgatca tcgtgcggga    6420
gggcaagggc tccaaggatc gggccttgat gttacccgag agcttggcac ccagcctgcg    6480
cgagcagggg aattaattcc cacgggtttt gctgcccgca aacgggctgt tctggtgttg    6540
ctagtttgtt atcagaatcg cagatccggc ttcagccggt tgccggctg aaagcgctat    6600 ttcttccaga attgccatga ttttttcccc acgggaggcg tcactggctc ccgtgttgtc    6660
ggcagctttg attcgataag cagcatcgcc tgtttcaggc tgtctatgtg tgactgttga    6720
gctgtaacaa gttgtctcag gtgttcaatt tcatgttcta gttgctttgt tttactggtt    6780
tcacctgttc tattaggtgt tacatgctgt tcatctgtta cattgtcgat ctgttcatgg    6840
tgaacagctt tgaatgcacc aaaaactcgt aaaagctctg atgtatctat cttttttaca    6900
ccgttttcat ctgtgcatat ggacagtttt cccctttgata tgtaacggtg aacagttgtt    6960
ctacttttgt ttgttagtct tgatgcttca ctgatagata caagagccat aagaacctca    7020
gatccttccg tatttagcca gtatgttctc tagtgtggtt cgttgttttt gcgtgagcca    7080
tgagaacgaa ccattgagat catacttact ttgcatgtca ctcaaaaatt ttgcctcaaa    7140
actggtgagc tgaattttttg cagttaaagc atcgtgtagt gttttctta gtccgttatg    7200 taggtaggaa tctgatgtaa tggttgttgg tattttgtca ccattcattt ttatctggtt    7260
gttctcaagt tcggttacga gatccatttg tctatctagt tcaacttgga aaatcaacgt    7320
atcagtcggg cggcctcgct tatcaaccac caatttcata ttgctgtaag tgtttaaatc    7380
```

```
tttacttatt ggtttcaaaa cccattggtt aagcctttta aactcatggt agttattttc    7440
aagcattaac atgaacttaa attcatcaag gctaatctct atatttgcct tgtgagtttt    7500
cttttgtgtt agttctttta ataaccactc ataaatcctc atagagtatt tgttttcaaa    7560
agacttaaca tgttccagat tatatttat gaattttttt aactggaaaa gataaggcaa     7620
tatctcttca ctaaaaacta attctaattt ttcgcttgag aacttggcat agtttgtcca    7680
ctggaaaatc tcaaagcctt taaccaaagg attcctgatt tccacagttc tcgtcatcag    7740
ctctctggtt gctttagcta ataccata agcattttcc ctactgatgt tcatcatctg      7800
agcgtattgg ttataagtga acgataccgt ccgttcttc cttgtagggt tttcaatcgt     7860
ggggttgagt agtgccacac agcataaaat tagcttggtt tcatgctccg ttaagtcata    7920
gcgactaatc gctagttcat ttgctttgaa acaactaat tcagacatac atctcaattg     7980
gtctaggtga ttttaatcac tataccaatt gagatgggct agtcaatgat aattactagt    8040
ccttttcctt tgagttgtgg gtatctgtaa attctgctag accttgctg gaaaacttgt     8100 aaattctgct agaccctctg taaattccgc tagacctttg tgtgtttttt ttgtttatat    8160
tcaagtggtt ataatttata gaataaagaa agaataaaaa aagataaaaa gaatagatcc    8220
cagccctgtg tataactcac tactttagtc agttccgcag tattacaaaa ggatgtcgca    8280
aacgctgttt gctcctctac aaaacagacc ttaaaaccct aaaggcttaa gtagcaccct    8340
cgcaagctcg ggcaaatcgc tgaatattcc ttttgtctcc gaccatcagg cacctgagtc    8400
gctgtctttt tcgtgacatt cagttcgctg cgctcacggc tctggcagtg aatggggta    8460 aatggcacta caggcgcctt ttatggattc atgcaaggaa actacccata atacaagaaa    8520
agcccgtcac gggcttctca gggcgtttta tggcgggtct gctatgtggt gctatctgac    8580
tttttgctgt tcagcagttc ctgccctctg attttccagt ctgaccactt cggattatcc    8640
cgtgacaggt cattcagact ggctaatgca cccagtaagg cagcggtatc atcaacaggc    8700
tta                                                                  8703
```

<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47

```
tgtaaccttt gctttcaaat gagtagaaat aatgcacatc catgtttgta tcgtgcaaat      60
aaagtgtttc atccgtagga aaaatgact ttagtatctg ttccgctttt tctgatgaaa      120
tgtgctcccc gacaaaattg aatgaatcat ggacatttgc tggctttgat acagcgaaag    180
cagccgttcc tatgttatat atcggattta acagcaggac aaaaaacacc atgacagcca    240
tcgtcaccca ttattcaca cgcacataaa ccttttcctga cttttggaac agatgatagc     300
tcatcaaaaa tcccgccatt gccaaataaa tcgtatatgg cattactgca ccataatctt    360
ttgagatttg attgggatat ggcgcaagca gcaagacaag cagtccgata atcagcgtat    420
aaaataagcc tagtaagatc ttatccgttc tccaatacag cttgaaaaac actacattca    480
acgcaatggg aagagtgatg atgaaaaaca gaaacacgaa tgcaatcggc tccatcccat    540
ccgggtattc cttccaatac gaaaagaaac taaaaatcat ttgtacgatc ggcaaactga    600
caacagcaag gtcgaacgta taaaacttac cctttccgcc atgatcacgc ggcatcagca    660
tatagtgaaa agccgtcagc agcacatatc cgtataacaa aaaatgcagc agcggcagca    720
```

```
gttcttttcc gtcctctctt aagtaagcgc tggtgaagtt tgttgattgc acctggtgaa      780
taagttcaac agacactccc gccagcagca caatccgcaa tataacaccc gccaagaaca      840
ttgtgcgctg ccggtttatt ttgggatgat gcaccaaaag atataagccc gccagaacaa      900
caattgacca ttgaatcagc agggtgcttt gtctgcttaa tataaaataa cgttcgaaat      960
gcaatacata atgactgaat aactccaaca cgaacaacaa ctccattttc ttctgctatc     1020
aaaataacag actcgtgatt ttccaaacga gctttcaaaa aagcctctgc cccttgcaaa     1080
tcggatgcct gtctataaaa ttcccgatat tggttaaaca gcggcgcaat ggcggccgca     1140
tctgatgtct ttgcttggcg aatgttcatc ttatttcttc ctccctctca ataattttt     1200
cattctatcc cttttctgta aagtttattt ttcagaatac ttttatcatc atgctttgaa     1260
aaaatatcac gataatatcc attgttctca cggaagcaca cgcaggtcat ttgaacgaat     1320
tttttcgaca ggaatttgcc gggactcagg agcatttaac ctaaaaaagc atgacatttc     1380
agcataatga acatttactc atgtctattt tcgttctttt ctgtatgaaa atagttattt     1440
cgagtctcta cggaaatagc gagagatgat atacctaaat agagataaaa tcatctcaaa     1500
aaaatgggtc tactaaaata ttattccatc tattacaata aattcacaga atagtctttt     1560
aagtaagtct actctgaatt tttttaaaag gagagggtaa agagtgtcat taccgttctt     1620
aacttctgca ccgggaaagg ttattatttt tggtgaacac tctgctgtgt acaacaagcc     1680
tgccgtcgct gctagtgtgt ctgcgttgag aacctacctg ctaataagcg agtcatctgc     1740
accagatact attgaattgg acttcccgga cattagcttt aatcataagt ggtccatcaa     1800
tgatttcaat gccatcaccg aggatcaagt aaactcccaa aaattggcca aggctcaaca     1860
agccaccgat ggcttgtctc aggaactcgt tagtcttttg gatccgttgt tagctcaact     1920
atccgaatcc ttccactacc atgcagcgtt ttgtttcctg tatatgtttg tttgcctatg     1980
cccccatgcc aagaatatta agttttcttt aaagtctact ttacccatcg gtgctgggtt     2040
gggctcaagc gcctctattt ctgtatcact ggccttagct atggcctact tgggggggtt     2100
aataggatct aatgacttgg aaaagctgtc agaaaacgat aagcatatag tgaatcaatg     2160
ggccttcata ggtgaaaagt gtattcacgg taccccttca ggaatagata acgctgtggc     2220
cacttatggt aatgccctgc tatttgaaaa agactcacat aatggaacaa taaacacaaa     2280
caattttaag ttcttagatg atttcccagc cattccaatg atcctaacct atactagaat     2340
tccaaggtct acaaaagatc ttgttgctcg cgttcgtgtg ttggtcaccg agaaatttcc     2400
tgaagttatg aagccaattc tagatgccat gggtgaatgt gccctacaag cttagagat     2460
catgactaag ttaagtaaat gtaaaggcac cgatgacgag gctgtagaaa ctaataatga     2520
actgtatgaa caactattgg aattgataag aataaatcat ggactgcttg tctcaatcgg     2580
tgtttctcat cctggattag aacttattaa aaatctgagc gatgatttga gaattggctc     2640
cacaaaactt accggtgctg gtggcggcgg ttgctctttg actttgttac gaagagacat     2700
tactcaagag caaattgaca gcttcaaaaa gaaattgcaa gatgatttta gttacgagac     2760
atttgaaaca gacttgggtg ggactggctg ctgtttgtta agcgcaaaaa atttgaataa     2820
agatcttaaa atcaaatccc tagtattcca attatttgaa aataaaacta ccacaaagca     2880
acaaattgac gatctattat tgccaggaaa cacgaattta ccatggactt cataaaagga     2940
gagggtgtca gagttgagag ccttcagtgc cccagggaaa gcgttactag ctggtggata     3000
tttagtttta gatacaaaat atgaagcatt tgtagtcgga ttatcggcaa gaatgcatgc     3060
tgtagcccat ccttacggtt cattgcaagg gtctgataag tttgaagtgc gtgtgaaaag     3120
```

```
taaacaattt aaagatgggg agtggctgta ccatataagt cctaaaagtg gcttcattcc   3180
tgtttcgata ggcggatcta agaacccttt cattgaaaaa gttatcgcta acgtatttag   3240
ctactttaaa cctaacatgg acgactactg caatagaaac ttgttcgtta ttgatatttt   3300
ctctgatgat gcctaccatt ctcaggagga tagcgttacc gaacatcgtg caacagaag    3360
attgagtttt cattcgcaca gaattgaaga agttcccaaa acagggctgg gctcctcggc   3420
aggtttagtc acagttttaa ctacagcttt ggcctccttt tttgtatcgg acctggaaaa   3480
taatgtagac aaatatagag aagttattca taatttagca caagttgctc attgtcaagc   3540
tcagggtaaa attggaagcg ggtttgatgt agcggcggca gcatatggat ctatcagata   3600
tagaagattc ccacccgcat taatctctaa tttgccagat attggaagtg ctacttacgg   3660
cagtaaactg gcgcatttgg ttgatgaaga agactggaat attacgatta aaagtaacca   3720
tttaccttcg ggattaactt tatggatggg cgatattaag aatggttcag aaacagtaaa   3780
actggtccag aagtaaaaa attggtatga ttcgcatatg ccagaaagct tgaaaatata   3840
tacagaactc gatcatgcaa attctagatt tatggatgga ctatctaaac tagatcgctt   3900
acacgagact catgacgatt acagcgatca gatatttgag tctcttgaga ggaatgactg   3960
tacctgtcaa aagtatcctg aaatcacaga agttagagat gcagttgcca caattagacg   4020
ttcctttaga aaaataacta aagaatctgg tgccgatatc gaacctcccg tacaaactag   4080
cttattggat gattgccaga ccttaaaagg agttcttact tgcttaatac ctggtgctgg   4140
tggttatgac gccattgcag tgattactaa gcaagatgtt gatcttaggg ctcaaaccgc   4200
taatgacaaa agattttcta aggttcaatg gctggatgta actcaggctg actggggtgt   4260
taggaaagaa aaagatccgg aaacttatct tgataaataa aaggagaggg tgaccgttta   4320
cacagcatcc gttaccgcac ccgtcaacat cgcaacccct aagtattggg ggaaaaggga   4380
cacgaagttg aatctgccca ccaattcgtc catatcagtg actttatcgc aagatgacct   4440
cagaacgttg acctctgcgg ctactgcacc tgagtttgaa cgcgacactt tgtggttaaa   4500
tggagaacca cacagcatcg acaatgaaag aactcaaaat tgtctgcgcg acctacgcca   4560
attaagaaag gaaatggaat cgaaggacgc ctcattgccc acattatctc aatgaaaact   4620
ccacattgtc tccgaaaata actttcctac agcagctggt ttagcttcct ccgctgctgg   4680
cttttgctgca ttggtctctg caattgctaa gttataccaa ttccacagt caacttcaga   4740
aatatctaga atagcaagaa aggggtctgg ttcagcttgt agatcgttgt ttggcggata   4800
cgtggcctgg gaaatgggaa aagctgaaga tggtcatgat ccatggcag tacaaatcgc    4860
agacagctct gactggcctc agatgaaagc ttgtgtccta gttgtcagcg atattaaaaa   4920
ggatgtgagt tccactcagg gtatgcaatt gaccgtggca acctccgaac tatttaaga    4980
aagaattgaa catgtcgtac caaagagatt tgaagtcatg cgtaaagcca ttgttgaaaa   5040
agatttcgcc acctttgcaa aggaaacaat gatggattcc aactctttcc atgccacatg   5100
tttggactct ttccctccaa tattctacat gaatgacact tccaagcgta tcatcagttg   5160
gtgccacacc attaatcagt tttacggaga acaatcgtt gcatacacgt ttgatgcagg    5220
tccaaatgct gtgttgtact acttagctga aaatgagtcg aaactctttg catttatcta   5280
taaattgttt ggctctgttc ctggatggga caagaaattt actactgagc agcttgaggc   5340
tttcaaccat caatttgaat catctaactt tactgcacgt gaattggatc ttgagttgca   5400
aaaggatgtt gccagagtga ttttaactca agtcggttca ggcccacaag aaacaaacga   5460
atctttgatt gacgcaaaga ctggtctacc aaaggaataa aaggagaggg tgactgccga   5520
```

| | | | | | |
|---|---|---|---|---|---|
| caacaatagt | atgccccatg | gtgcagtatc | tagttacgcc | aaattagtgc | aaaaccaaac | 5580 |
| acctgaagac | attttggaag | agtttcctga | aattattcca | ttacaacaaa | gacctaatac | 5640 |
| ccgatctagt | gagacgtcaa | atgacgaaag | cggagaaaca | tgtttttctg | gtcatgatga | 5700 |
| ggagcaaatt | aagttaatga | atgaaaattg | tattgttttg | gattgggacg | ataatgctat | 5760 |
| tggtgccggt | accaagaaag | tttgtcattt | aatggaaaat | attgaaaagg | gtttactaca | 5820 |
| tcgtgcattc | tccgtctttta | ttttcaatga | acaaggtgaa | ttacttttac | aacaaagagc | 5880 |
| cactgaaaaa | ataactttcc | ctgatctttg | gactaacaca | tgctgctctc | atccactatg | 5940 |
| tattgatgac | gaattaggtt | tgaagggtaa | gctagacgat | aagattaagg | gcgctattac | 6000 |
| tgcggcggtg | agaaaactag | atcatgaatt | aggtattcca | gaagatgaaa | ctaagacaag | 6060 |
| gggtaagttt | cactttttaa | acagaatcca | ttacatggca | ccaagcaatg | aaccatgggg | 6120 |
| tgaacatgaa | attgattaca | tcctatttta | taagatcaac | gctaaagaaa | acttgactgt | 6180 |
| caacccaaac | gtcaatgaag | ttagagactt | caaatgggtt | tcaccaaatg | atttgaaaac | 6240 |
| tatgtttgct | gacccaagtt | acaagtttac | gccttggttt | aagattattt | gcgagaatta | 6300 |
| cttattcaac | tggtgggagc | aattagatga | cctttctgaa | gtggaaaatg | acaggcaaat | 6360 |
| tcatagaatg | ctataaaaaa | aaccggcctt | ggccccgccg | gttttttatt | attttttcttc | 6420 |
| ctccgcatgt | tcaatccgct | ccataatcga | cggatggctc | cctctgaaaa | ttttaacgag | 6480 |
| aaacggcggg | ttgacccggc | tcagtcccgt | aacggccaag | tcctgaaacg | tctcaatcgc | 6540 |
| cgcttcccgg | tttccggtca | gctcaatgcc | gtaacggtcg | gcggcgtttt | cctgataccg | 6600 |
| ggagacggca | ttcgtaattt | gaatacatac | gaacaaatta | ataaagtgaa | aaaaatactt | 6660 |
| cggaaacatt | taaaaaataa | ccttattggt | acttacatgt | ttggatcagg | agttgagagt | 6720 |
| ggactaaaac | caaatagtga | tcttgacttt | ttagtcgtcg | tatctgaacc | attgacagat | 6780 |
| caaagtaaag | aaatacttat | acaaaaaatt | agacctattt | caaaaaaaat | aggagataaa | 6840 |
| agcaacttac | gatatattga | attaacaatt | attattcagc | aagaaatggt | accgtggaat | 6900 |
| catcctccca | aacaagaatt | tatttatgga | gaatggttac | aagagcttta | tgaacaagga | 6960 |
| tacattcctc | agaaggaatt | aaattcagat | ttaaccataa | tgctttacca | agcaaaacga | 7020 |
| aaaaataaaa | gaatatacgg | aaattatgac | ttagaggaat | tactacctga | tattccattt | 7080 |
| tctgatgtga | gaagagccat | tatggattcg | tcagaggaat | aatagataaa | ttatcaggat | 7140 |
| gatgaaacca | actctatatt | aactttatgc | cgtatgattt | taactatgga | cacgggtaaa | 7200 |
| atcataccaa | aagatattgc | gggaaatgca | gtggctgaat | cttctccatt | agaacatagg | 7260 |
| gagagaattt | tgttagcagt | tcgtagttat | cttggagaga | atattgaatg | gactaatgaa | 7320 |
| aatgtaaatt | taactataaa | ctatttaaat | aacagattaa | aaaaattata | atgtaaccttt | 7380 |
| tgctttcaaa | tgagtagaaa | taatgcacat | ccatgtttgt | atcgtgcaaa | taaagtgttt | 7440 |
| catccgtagg | aaaaaatgac | tttagtatct | gttccgcttt | ttctgatgaa | atgtgctccc | 7500 |
| cgacaaaatt | gaatgaatca | tggacatttg | ctggctttga | tacagcgaaa | gcagccgttc | 7560 |
| ctatgttata | tatcggattt | aacagcagga | caaaaaacac | catgacagcc | atcgtcaccc | 7620 |
| acttattcac | acgcacataa | acctttcctg | acttttggaa | cagatgatag | ctcatcaaaa | 7680 |
| atcccgccat | tgccaaataa | atcgtatatg | gcattactgc | accataatct | tttgagattt | 7740 |
| gattgggata | tggcgcaagc | agcaagacaa | gcagtccgat | aatcagcgta | aaaataagc | 7800 |
| ctagtaagat | cttatccgtt | ctccaataca | gcttgaaaaa | cactacattc | aacgcaatgg | 7860 |
| gaagagtgat | gatgaaaaac | agaaacacga | atgcaatcgg | ctccatccca | tccgggtatt | 7920 |

-continued

```
ccttccaata cgaaaagaaa ctaaaaatca tttgtacgat cggcaaactg acaacagcaa    7980
ggtcgaacgt ataaaactta cccttccgc catgatcacg cggcatcagc atatagtgaa    8040
aagccgtcag cagcacatat ccgtataaca aaaatgcag cagcggcagc agttcttttc    8100
cgtcctctct taagtaagcg ctggtgaagt ttgttgattg cacctggtga ataagttcaa    8160
cagacactcc cgccagcagc acaatccgca atataacacc cgccaagaac attgtgcgct    8220
gccggtttat tttgggatga tgcaccaaaa gatataagcc cgccagaaca caattgacc    8280 attgaatcag cagggtgctt tgtctgctta atataaaata cgttcgaaa tgcaatacat    8340 aatgactgaa taactccaac acgaacaaca aaagtgcgca ttttataaaa gctaatgatt    8400
cagtccacat aattgataga cgaattctgc tacaggtcac gtggctatgt gaaggatcgc    8460
gcgtccagtt aagagcaaaa acattgacaa aaaaatttat ttatgctaaa atttactatt    8520
aatatatttg tatgtataat aagattctcc tggccagggg aatcttattt tttgtggagg    8580
atcatttcat gaggaaaaat gagtccagct taacgtctct aatttcagct tttgcccgtg    8640
catatcacag ccgatatgac acacctctta tttttgatga ttttatcgca aaagatctca    8700
ttaacgaaaa agagtttatc gacatcagta aaaatatgat tcaagaaata tcgtttttca    8760 acaagagat cgccgaacgt cttcaaaatg atcctgaaaa aatattaaaa tgggttgcac    8820
aaatccagct gtctccaacg cccctagcac gtgcttctta ttgtgaaaaa gtcttgcaca    8880
acgaattaat cctgggggca aaacagtatg tcattcttgg agcgggactg gatactttct    8940
gctttcggca tccagaatta gaaaacagct tacaggtttt cgaggttgat catccggcca    9000
cacagcaatt gaaaaaaaat aagctgaagg atgcaaatct gacaattccg ggtcatcttc    9060
attttgttcc tatggatttc accaaaacgt tttcgtatga tcctctctta gatgaaggat    9120
ttaaaaacac aaaaacattc ttcagccttc tcggagtgtc ttattatgta acacgggaag    9180
aaaatgcaag cttgatcagc aatttatttt ctcatgtccc gcctggaagc tctattgttt    9240
ttgattatgc ggacgaaaca cttttttacag caaaagggac gtcgaatcga gttgaacata    9300
tggtgaagat ggctgccgca agcggggaac cgatgaaatc atgtttcact tatcaagaga    9360
ttgaacatct g                                                         9371
```

<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48

```
tagaaaaact catcgagcat caaatgaaac tgcaatttat tcatatcagg attatcaata     60
ccatattttt gaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa ataaggttta tcaagtgaga atcaccatg agtgacgact    240 gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgttttccg gggatcgcag tggtgagtaa ccatgcatca    540
tcaggagtac ggataaaatg cttgatggtc ggaagtggca taaattccgt cagccagttt    600
```

```
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggtgt cgcccttta gtcgctgaac atgtgctctg   1200
tttctaccga gaacgtttcc ttcactgaga cggaaaccga ggcacgtcgt agcgcgaact   1260
acgagccgaa tagctgggac tacgatttcc tgctgtcttc cgatactgac gaatctattg   1320
aggtgtacaa agacaaagca aagaaactgg aggctgaagt gcgccgcgaa attaacaacg   1380
agaaagctga attcctgact ctgctggagc tgatcgataa cgtacagcgc ctgggtctgg   1440
gttaccgctt cgaatctgat atccgtcgcg cactggatcg tttcgtaagc agcggcggtt   1500 tcgatgcgt gaccaaaacg agcctgcacg ctaccgcgct gtccttccgt ctgctgcgtc   1560
agcacggctt cgaagtttct caggaagcat tctccggttt caaagatcaa aacggtaact   1620
tcctggaaaa cctgaaagaa gacactaagg cgatcctgag cctgtatgag gcaagctttc   1680
tggccctgga gggtgagaac atcctggatg aggcgcgcgt attcgccatc tcccatctga   1740
aagagctgtc tgaagagaaa atcggtaagg aactggcaga gcaggttaat cacgcactgg   1800
aactgccgct gcatcgtcgt acccagcgtc tggaggcggt ttggtccatc gaagcgtacc   1860
gcaaaaagga ggatgctaac caggttctgc tggaactggc catcctggac tacaacatga   1920
tccagtccgt ttaccagcgt gatctgcgtg aaacctcccg ttggtggcgc cgtgtgggcc   1980
tggcgaccaa actgcacttc gctaaggacc gcctgattga gtcttttttac tgggcagtcg   2040 gcgttgcgtt cgaacctcag tattctgact gccgtaacag cgttgcgaaa atgttcagct   2100
tcgttactat tatcgacgac atctacgacg tttacggtac tctggacgag ctggaactgt   2160
ttaccgacgc tgtcgaacgt tgggatgtta acgccatcaa cgatctgcct gactacatga   2220
aactgtgctt cctggcactg tataacacga tcaacgaaat tgcatacgac aacctgaaag   2280
acaaaggtga aaacatcctg ccgtacctga ctaaagcgtg gcggatctg tgtaacgctt   2340 ttctgcaaga agcgaaatgg ctgtataaca aatccactcc gacctttgac gattatttcg   2400
gcaatgcctg gaaatccagc tctggcccgc tgcaactgat cttcgcttat tttgcggttg   2460
tccaaaacat caaaaggag gaaattgaaa acctgcaaaa ataccacgat atcattagcc   2520
gtccttctca tatctttcgc ctgtgcaacg acctggcaag cgcgtccgca gagatcgcac   2580
gtggcgaaac cgctaactct gtttcctgct acatgcgcac caagggcatt tccgaagagc   2640
tggcaaccga gagcgtaatg aatctgatcg acgaaacctg taagaaaatg aacaaagaaa   2700
aactgggtgg ctccctgttc gctaaaccgt tcgtagagac tgctattaac ctggcacgtc   2760
agagccactg cacctaccac aatggtgacg cacatactag cccggatgaa ctgactcgta   2820
aacgtgtact gtctgttatc accgaaccga ttctgccgtt cgaacgttaa ctgcagcgtc   2880
aatcgaaagg gcgacacaaa atttattcta aatgcataat aaatactgat aacatcttat   2940
agtttgtatt atattttgta ttatcgttga catgtataat tttgatatca aaaactgatt   3000
```

```
ttcccttat tattttcgag atttattttc ttaattctct ttaacaaact agaaatattg    3060
tatatacaaa aaatcataaa taatagatga atagtttaat tataggtgtt catcaatcga    3120
aaaagcaacg tatcttattt aaagtgcgtt gctttttct catttataag gttaaataat     3180
tctcatatat caagcaaagt gacaggcgcc cttaaatatt ctgacaaatg ctctttccct    3240
aaactccccc cataaaaaaa cccgccgaag cgggttttta cgttatttgc ggattaacga    3300
ttactcgtta tcagaaccgc ccaggggggcc cgagcttaag actggccgtc gttttacaac    3360
acagaaagag tttgtagaaa cgcaaaaagg ccatccgtca ggggccttct gcttagtttg    3420
atgcctggca gttccctact ctcgccttcc gcttcctcgc tcactgactc gctgcgctcg    3480
gtcgttcggc tgcggcgagc ggtatcagct cactcaaagg cggtaatacg gttatccaca    3540
gaatcagggg ataacgcagg aaagaacatg tgagcaaaag gccagcaaaa ggccaggaac    3600
cgtaaaaagg ccgcgttgct ggcgtttttc cataggctcc gcccccctga cgagcatcac    3660
aaaaatcgac gctcaagtca gaggtggcga acccgacag gactataaag ataccaggcg    3720
tttccccctg gaagctccct cgtgcgctct cctgttccga ccctgccgct taccggatac    3780
ctgtccgcct ttctcccttc gggaagcgtg gcgctttctc atagctcacg ctgtaggtat    3840
ctcagttcgg tgtaggtcgt tcgctccaag ctgggctgtg tgcacgaacc ccccgttcag    3900
cccgaccgct gcgccttatc cggtaactat cgtcttgagt ccaacccggt aagacacgac    3960
ttatcgccac tggcagcagc cactggtaac aggattagca gagcgaggta tgtaggcggt    4020
gctacagagt tcttgaagtg gtgggctaac tacggctaca ctagaagaac agtatttggt    4080
atctgcgctc tgctgaagcc agttaccttc ggaaaaagag ttggtagctc ttgatccggc    4140
aaacaaacca ccgctggtag cggtggtttt tttgtttgca agcagcagat tacgcgcaga    4200
aaaaaaggat ctcaagaaga tcctttgatc ttttctacgg ggtctgacgc tcagtggaac    4260
gacgcgcgcg taactcacgt taagggattt tggtcatgag cttgcgccgt cccgtcaagt    4320
cagcgtaatg ctctgctttt                                                4339

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgtgctc    420
tgtttctacc gagaacgttt ccttcactga gacggaaacc gaggcacgtc gtagcgcgaa    480
ctacgagccg aatagctggg actacgattt cctgctgtct tccgatactg acgaatctat    540
tgaggtgtac aaagacaaag caaagaaact ggaggctgaa gtgcgccgcg aaattaacaa    600
cgagaaagct gaattcctga ctctgctgga gctgatcgat aacgtacagc gcctgggtct    660
gggttaccgc ttcgaatctg atatccgtcg cgcactggat cgtttcgtaa gcagcggcgg    720
```

```
tttcgatggc gtgaccaaaa cgagcctgca cgctaccgcg ctgtccttcc gtctgctgcg    780
tcagcacggc ttcgaagttt ctcaggaagc attctccggt ttcaaagatc aaaacggtaa    840
cttcctggaa aacctgaaag aagacactaa ggcgatcctg agcctgtatg aggcaagctt    900
tctggccctg gagggtgaga acatcctgga tgaggcgcgc gtattcgcca tctcccatct    960
gaaagagctg tctgaagaga aaatcggtaa ggaactggca gagcaggtta atcacgcact   1020
ggaactgccg ctgcatcgtc gtacccagcg tctggaggcg gtttggtcca tcgaagcgta   1080
ccgcaaaaag gaggatgcta accaggttct gctggaactg gccatcctgg actacaacat   1140
gatccagtcc gttaccagc gtgatctgcg tgaaacctcc cgttggtggc gccgtgtggg   1200
cctggcgacc aaactgcact tcgctaagga ccgcctgatt gagtcttttt actgggcagt   1260
cggcgttgcg ttcgaacctc agtattctga ctgccgtaac agcgttgcga aaatgttcag   1320
cttcgttact attatcgacg acatctacga cgtttacggt actctggacg agctggaact   1380
gtttaccgac gctgtcgaac gttgggatgt taacgccatc aacgatctgc ctgactacat   1440
gaaactgtgc ttcctggcac tgtataacac gatcaacgaa attgcatacg acaacctgaa   1500
agacaaaggt gaaaacatcc tgccgtacct gactaaagcg tgggcggatc tgtgtaacgc   1560
ttttctgcaa gaagcgaaat ggctgtataa caaatccact ccgacctttg acgattattt   1620
cggcaatgcc tggaaatcca gctctggccc gctgcaactg atcttcgctt attttgcggt   1680
tgtccaaaac atcaaaaagg aggaaattga aaacctgcaa aaataccacg atatcattag   1740
ccgtccttct catatctttc gcctgtgcaa cgacctggca agcgcgtccg cagagatcgc   1800
acgtggcgaa accgctaact ctgtttcctg ctacatgcgc accaagggca tttccgaaga   1860
gctggcaacc gagagcgtaa tgaatctgat cgacgaaacc tgtaagaaaa tgaacaaaga   1920
aaaactgggt ggctccctgt tcgctaaacc gttcgtagag actgctatta acctggcacg   1980
tcagagccac tgcacctacc acaatggtga cgcacatact agcccggatg aactgactcg   2040
taaacgtgta ctgtctgtta tcaccgaacc gattctgccg ttcgaacgtt aactgcagct   2100
ggtaccatat gggaattcga agcttttctag aacaaaaact catctcagaa gaggatctga   2160
atagcgccgt cgaccatcat catcatcatc attgagttta acggtctcc agcttggctg   2220
ttttggcgga tgagaagaa ttttcagcct gatacagatt aaatcagaac gcagaagcgg   2280
tctgataaaa cagaatttgc ctggcggcag tagcgcggtg gtcccacctg accccatgcc   2340
gaactcagaa gtgaaacgcc gtagcgccga tggtagtgtg gggtctcccc atgcgagagt   2400
agggaactgc caggcatcaa ataaaacgaa aggctcagtc gaaagactgg gcctttcgtt   2460
ttatctgttg tttgtcggtg aacgctctcc tgagtaggac aaatccgccg ggagcggatt   2520
tgaacgttgc gaagcaacgg cccggagggt ggcgggcagg acgcccgcca taaactgcca   2580
ggcatcaaat taagcagaag gccatcctga cggatggcct ttttgcgttt ctacaaactc   2640
tttttgttta ttttttctaaa tacattcaaa tatgtatccg ctcatgagac aataaccctg   2700
ataaatgctt caataatatt gaaaaaggaa gagtatgagt attcaacatt tccgtgtcgc   2760
ccttattccc ttttttgcgg cattttgcct tcctgttttt gctcacccag aaacgctggt   2820
gaaagtaaaa gatgctgaag atcagttggg tgcacgagtg ggttacatcg aactggatct   2880
caacagcggt aagatccttg agagttttcg ccccgaagaa cgttttccaa tgatgagcac   2940
ttttaaagtt ctgctatgtg gcgcggtatt atcccgtgtt gacgccgggc aagagcaact   3000
cggtcgccgc atacactatt ctcagaatga cttggttgag tactcaccag tcacagaaaa   3060
gcatcttacg gatggcatga cagtaagaga attatgcagt gctgccataa ccatgagtga   3120
```

```
taacactgcg gccaacttac ttctgacaac gatcggagga ccgaaggagc taaccgcttt    3180
tttgcacaac atgggggatc atgtaactcg ccttgatcgt tgggaaccgg agctgaatga    3240
agccatacca aacgacgagc gtgacaccac gatgcctgta gcaatggcaa caacgttgcg    3300
caaactatta actggcgaac tacttactct agcttcccgg caacaattaa tagactggat    3360
ggaggcggat aaagttgcag gaccacttct gcgctcggcc cttccggctg gctggtttat    3420
tgctgataaa tctggagccg gtgagcgtgg gtctcgcggt atcattgcag cactggggcc    3480
agatggtaag ccctcccgta tcgtagttat ctacacgacg gggagtcagg caactatgga    3540
tgaacgaaat agacagatcg ctgagatagg tgcctcactg attaagcatt ggtaactgtc    3600
agaccaagtt tactcatata ctttagat tgatttaaaa cttcatttt aatttaaaag    3660 gatctaggtg aagatccttt ttgataatct catgaccaaa atcccttaac gtgagttttc    3720
gttccactga gcgtcagacc ccgtagaaaa gatcaaagga tcttcttgag atccttttt    3780 tctgcgcgta atctgctgct tgcaaacaaa aaaaccaccg ctaccagcgg tggtttgttt    3840
gccggatcaa gagctaccaa ctcttttcc gaaggtaact ggcttcagca gagcgcagat    3900
accaaatact gtccttctag tgtagccgta gttaggccac cacttcaaga actctgtagc    3960
accgcctaca tacctcgctc tgctaatcct gttaccagtg gctgctgcca gtggcgataa    4020
gtcgtgtctt accgggttgg actcaagacg atagttaccg gataaggcgc agcggtcggg    4080
ctgaacgggg ggttcgtgca cacagcccag cttggagcga acgacctaca ccgaactgag    4140
atacctacag cgtgagctat gagaaagcgc cacgcttccc gaaggagaa aggcggacag    4200 gtatccggta agcggcaggg tcggaacagg agagcgcacg agggagcttc caggggggaaa    4260 cgcctggtat ctttatagtc ctgtcgggtt cgccacctc tgacttgagc gtcgatttt    4320 gtgatgctcg tcagggggc ggagcctatg gaaaaacgcc agcaacgcgg ccttttacg    4380 gttcctggcc ttttgctggc cttttgctca catgttcttt cctgcgttat ccctgattc    4440 tgtggataac cgtattaccg cctttgagtg agctgatacc gctcgccgca gccgaacgac    4500
cgagcgcagc gagtcagtga gcgaggaagc ggaagagcgc ctgatgcggt attttctcct    4560
tacgcatctg tgcggtattt cacaccgcat atggtgcact ctcagtacaa tctgctctga    4620
tgccgcatag ttaagccagt atacactccg ctatcgctac gtgactgggt catggctgcg    4680
ccccgacacc cgccaacacc cgctgacgcg ccctgacggg cttgtctgct cccggcatcc    4740
gcttacagac aagctgtgac cgtctccggg agctgcatgt gtcagaggtt ttcaccgtca    4800
tcaccgaaac gcgcgaggca gcagatcaat tcgcgcgcga aggcgaagcg gcatgcattt    4860
acgttgacac catcgaatgg tgcaaaacct ttcgcggtat ggcatgatag cgcccggaag    4920
agagtcaatt cagggtggtg aatgtgaaac cagtaacgtt atacgatgtc gcagagtatg    4980
ccggtgtctc ttatcagacc gtttcccgcg tggtgaacca ggccagccac gtttctgcga    5040
aaacgcggga aaaagtggaa gcggcgatgg cggagctgaa ttacattccc aaccgcgtgg    5100
cacaacaact ggcgggcaaa cagtcgttgc tgattggcgt tgccacctcc agtctggccc    5160
tgcacgcgcc gtcgcaaatt gtcgcggcga ttaaatctcg cgccgatcaa ctgggtgcca    5220
gcgtggtggt gtcgatggta gaacgaagcg gcgtcgaagc ctgtaaagcg gcggtgcaca    5280
atcttctcgc gcaacgcgtc agtgggctga tcattaacta tccgctggat gaccaggatg    5340
ccattgctgt ggaagctgcc tgcactaatg ttccggcgtt atttcttgat gtctctgacc    5400
agacacccat caacagtatt attttctccc atgaagacgg tacgcgactg ggcgtggagc    5460
atctggtcgc attgggtcac cagcaaatcg cgctgttagc gggcccatta agttctgtct    5520
```

-continued

| | |
|---|---|
| cggcgcgtct gcgtctggct ggctggcata aatatctcac tcgcaatcaa attcagccga | 5580 |
| tagcggaacg ggaaggcgac tggagtgcca tgtccggttt tcaacaaacc atgcaaatgc | 5640 |
| tgaatgaggg catcgttccc actgcgatgc tggttgccaa cgatcagatg gcgctgggcg | 5700 |
| caatgcgcgc cattaccgag tccggctgc gcgttggtgc ggatatctcg gtagtgggat | 5760 |
| acgacgatac cgaagacagc tcatgttata tcccgccgtc aaccaccatc aaacaggatt | 5820 |
| tcgcctgct ggggcaaacc agcgtggacc gcttgctgca actctctcag gccaggcgg | 5880 |
| tgaagggcaa tcagctgttg cccgtctcac tggtgaaaag aaaaaccacc ctggcgccca | 5940 |
| atacgcaaac cgcctctccc cgcgcgttgg ccgattcatt aatgcagctg gcacgacagg | 6000 |
| tttcccgact ggaaagcggg cagtgagcgc aacgcaatta atgtgagtta gcgcgaattg | 6060 |
| atctg | 6065 |

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50

| | |
|---|---|
| ttgtctgctc ccggcatccg cttacagaca agctgtgacc gtctccggga gctgcatgtg | 60 |
| tcagaggttt tcaccgtcat caccgaaacg cgcgaggcag cagatcaatt cgcgcgcgaa | 120 |
| ggcgaagcgg catgcattta cgttgacacc atcgaatggt gcaaaacctt cgcggtatg | 180 |
| gcatgatagc gcccggaaga gagtcaattc agggtggtga atgtgaaacc agtaacgtta | 240 |
| tacgatgtcg cagagtatgc cggtgtctct tatcagaccg tttcccgcgt ggtgaaccag | 300 |
| gccagccacg tttctgcgaa aacgcgggaa aaagtggaag cggcgatggc ggagctgaat | 360 |
| tacattccca accgcgtggc acaacaactg gcgggcaaac agtcgttgct gattggcgtt | 420 |
| gccacctcca gtctggccct gcacgcgccg tcgcaaattg tcgcggcgat taaatctcgc | 480 |
| gccgatcaac tgggtgccag cgtggtggtg tcgatggtag aacgaagcgg cgtcgaagcc | 540 |
| tgtaaagcgg cggtgcacaa tcttctcgcg caacgcgtca gtgggctgat cattaactat | 600 |
| ccgctggatg accaggatgc cattgctgtg gaagctgcct gcactaatgt tccggcgtta | 660 |
| tttcttgatg tctctgacca gacacccatc aacagtatta ttttctccca tgaagacggt | 720 |
| acgcgactgg gcgtggagca tctggtcgca ttgggtcacc agcaaatcgc gctgttagcg | 780 |
| ggcccattaa gttctgtctc ggcgcgtctg cgtctggctg gctggcataa atatctcact | 840 |
| cgcaatcaaa ttcagccgat agcggaacgg gaaggcgact ggagtgccat gtccggtttt | 900 |
| caacaaacca tgcaaatgct gaatgagggc atcgttccca ctgcgatgct ggttgccaac | 960 |
| gatcagatgg cgctgggcgc aatgcgcgcc attaccgagt ccgggctgcg cgttggtgcg | 1020 |
| gatatctcgg tagtgggata cgacgatacc gaagacagct catgttatat cccgccgtca | 1080 |
| accaccatca aacaggattt cgcctgctg gggcaaacca gcgtggaccg cttgctgcaa | 1140 |
| ctctctcagg ccaggcggt gaagggcaat cagctgttgc ccgtctcact ggtgaaaaga | 1200 |
| aaaaccaccc tggcgcccaa tacgcaaacc gcctctcccc gcgcgttggc cgattcatta | 1260 |
| atgcagctgg cacgacaggt ttcccgactg gaaagcgggc agtgagcgca acgcaattaa | 1320 |
| tgtgagttag cgcgaattga tctggtttga cagcttatca tcgactgcac ggtgcaccaa | 1380 |
| tgcttctggc gtcaggcagc catcggaagc tgtggtatgg ctgtgcaggt cgtaaatcac | 1440 |
| tgcataattc gtgtcgctca aggcgcactc ccgttctgga taatgttttt tgcgccgaca | 1500 |

```
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aagaggtat atattaatgt atcgattaaa    1740
taaggaggaa taaaccatgt gtgcgacctc ttctcaattt actcagatta ccgagcataa   1800
ttcccgtcgt tccgcaaact atcagccaaa cctgtgaat ttcgaattcc tgcaatccct    1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgttttg agcgtttcaa    2160 ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga caacctgaa agaaggcatt aataccaagg ttgcagaaca    2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggatttgta cgcgaccgcc tgatggaagt    2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aggtcataa caacctgtcc tatctgacga aaagctggcg    2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gacccacgcgc tgcgttccct    3060 gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaagatga atcgtgaacg cgttagcgac tccaccctgc tgcctaaagc    3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcatcgc ccttaggagg taaaaaaaaa    3480
tgactgccga caacaatagt atgccccatg gtgcagtatc tagttacgcc aaattagtgc   3540
aaaaccaaac acctgaagac attttggaag agtttcctga aattattcca ttacaacaaa   3600
gacctaatac ccgatctagt gagacgtcaa atgacgaaag cggagaaaca tgttttttctg   3660 gtcatgatga ggagcaaatt aagttaatga atgaaaattg tattgttttg gattgggacg   3720
ataatgctat tggtgccggt accaagaaag tttgtcattt aatggaaaat attgaaaagg   3780
gtttactaca tcgtgcattc tccgtctttta ttttcaatga acaaggtgaa ttacttttac   3840
aacaaagagc cactgaaaaa ataactttcc ctgatctttg gactaacaca tgctgctctc   3900
```

```
atccactatg tattgatgac gaattaggtt tgaagggtaa gctagacgat aagattaagg   3960
gcgctattac tgcggcggtg agaaaactag atcatgaatt aggtattcca gaagatgaaa   4020
ctaagacaag gggtaagttt cacttttta acagaatcca ttacatggca ccaagcaatg    4080
aaccatgggg tgaacatgaa attgattaca tcctatttta taagatcaac gctaaagaaa   4140
acttgactgt caacccaaac gtcaatgaag ttagagactt caaatgggtt tcaccaaatg   4200
atttgaaaac tatgtttgct gacccaagtt acaagtttac gccttggttt aagattattt   4260
gcgagaatta cttattcaac tggtgggagc aattagatga cctttctgaa gtggaaaatg   4320
acaggcaaat tcatagaatg ctataacaac gcgtcctgca gctggtacca tatgggaatt   4380
cgaagctttc tagaacaaaa actcatctca gaagaggatc tgaatagcgc cgtcgaccat   4440
catcatcatc atcattgagt ttaaacggtc tccagcttgg ctgttttggc ggatgagaga   4500
agattttcag cctgatacag attaaatcag aacgcagaag cggtctgata aaacagaatt   4560
tgcctggcgg cagtagcgcg gtggtcccac ctgaccccat gccgaactca gaagtgaaac   4620
gccgtagcgc cgatggtagt gtggggtctc cccatgcgag agtagggaac tgccaggcat   4680
caaataaaac gaaaggctca gtcgaaagac tgggcctttc gttttatctg ttgtttgtcg   4740
gtgaacgctc tcctgagtag gacaaatccg ccgggagcgg atttgaacgt tgcgaagcaa   4800
cggcccggag ggtggcgggc aggacgcccg ccataaactg ccaggcatca aattaagcag   4860
aaggccatcc tgacggatgg cctttttgcg tttctacaaa ctcttttgt ttattttct    4920 aaatacattc aaatatgtat ccgcttaacc ggaattgcca gctggggcgc cctctggtaa   4980
ggttgggaag ccctgcaaag taaactggat ggctttctcg ccgccaagga tctgatggcg   5040
caggggatca agctctgatc aagagacagg atgaggatcg tttcgcatga ttgaacaaga   5100
tggattgcac gcaggttctc cggccgcttg ggtggagagg ctattcggct atgactgggc   5160
acaacagaca atcggctgct ctgatgccgc cgtgttccgg ctgtcagcgc aggggcgccc   5220
ggttcttttt gtcaagaccg acctgtccgg tgccctgaat gaactgcaag acgaggcagc   5280
gcggctatcg tggctggcca cgacgggcgt tccttgcgca gctgtgctcg acgttgtcac   5340
tgaagcggga agggactggc tgctattggg cgaagtgccg gggcaggatc tcctgtcatc   5400
tcaccttgct cctgccgaga agtatccat catggctgat gcaatgcggc ggctgcatac   5460
gcttgatccg gctacctgcc cattcgacca ccaagcgaaa catcgcatcg agcgagcacg   5520
tactcggatg aagccggtc ttgtcgatca ggatgatctg gacgaagagc atcagggct    5580 cgcgccagcc gaactgttcg ccaggctcaa ggcgagcatg cccgacggcg aggatctcgt   5640
cgtgacccat ggcgatgcct gcttgccgaa tatcatggtg gaaaatggcc gcttttctgg   5700
attcatcgac tgtggccggc tgggtgtggc ggaccgctat caggacatag cgttggctac   5760
ccgtgatatt gctgaagagc ttggcggcga atgggctgac cgcttcctcg tgctttacgg   5820
tatcgccgct cccgattcgc agcgcatcgc cttctatcgc cttcttgacg agttcttctg   5880
acatgaccaa aatcccttaa cgtgagtttt cgttccactg agcgtcagac cccgtagaaa   5940
agatcaaagg atcttcttga gatccttttt ttctgcgcgt aatctgctgc ttgcaaacaa   6000
aaaaaccacc gctaccagcg gtggtttgtt tgccggatca agagctacca actctttttc   6060
cgaaggtaac tggcttcagc agagcgcaga taccaaatac tgtccttcta gtgtagccgt   6120
agttaggcca ccacttcaag aactctgtag caccgcctac atacctcgct ctgctaatcc   6180
tgttaccagt ggctgctgcc agtggcgata agtcgtgtct taccgggttg gactcaagac   6240
gatagttacc ggataaggcg cagcggtcgg gctgaacggg gggttcgtgc acacagccca   6300
```

```
gcttggagcg aacgacctac accgaactga gatacctaca gcgtgagcta tgagaaagcg     6360
ccacgcttcc cgaagggaga aaggcggaca ggtatccggt aagcggcagg gtcggaacag     6420
gagagcgcac gagggagctt ccaggggaa acgcctggta tctttatagt cctgtcgggt     6480
ttcgccacct ctgacttgag cgtcgatttt tgtgatgctc gtcagggggg cggagcctat     6540
ggaaaaacgc cagcaacgcg gcctttttac ggttcctggc cttttgctgg ccttttgctc     6600
acatgttctt tcctgcgtta tcccctgatt ctgtggataa ccgtattacc gcctttgagt     6660
gagctgatac cgctcgccgc agccgaacga ccgagcgcag cgagtcagtg agcgaggaag     6720
cggaagagcg cctgatgcgg tattttctcc ttacgcatct gtgcggtatt tcacaccgca     6780
tatggtgcac tctcagtaca atctgctctg atgccgcata gttaagccag tatacactcc     6840
gctatcgcta cgtgactggg tcatggctgc gccccgacac ccgccaacac ccgctgacgc     6900
gccctgacgg gc                                                         6912

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51
ttgtctgctc ccggcatccg cttacagaca agctgtgacc gtctccggga gctgcatgtg       60
tcagaggttt tcaccgtcat caccgaaacg cgcgaggcag cagatcaatt cgcgcgcgaa      120
ggcgaagcgg catgcattta cgttgacacc atcgaatggt gcaaaacctt cgcggtatg      180 gcatgatagc gcccggaaga gagtcaattc agggtggtga atgtgaaacc agtaacgtta      240
tacgatgtcg cagagtatgc cggtgtctct tatcagaccg tttcccgcgt ggtgaaccag      300
gccagccacg tttctgcgaa aacgcgggaa aaagtggaag cggcgatggc ggagctgaat      360
tacattccca accgcgtggc acaacaactg gcgggcaaac agtcgttgct gattggcgtt      420
gccacctcca gtctggccct gcacgcgccg tcgcaaattg tcgcggcgat taaatctcgc      480
gccgatcaac tgggtgccag cgtggtggtg tcgatgctag aacgaagcgg cgtcgaagcc      540
tgtaaagcgg cggtgcacaa tcttctcgcg caacgcgtca gtgggctgat cattaactat      600
ccgctggatg accaggatgc cattgctgtg gaagctgcct gcactaatgt tccggcgtta      660
tttcttgatg tctctgacca gacacccatc aacagtatta ttttctccca tgaagacggt      720
acgcgactgg gcgtggagca tctggtcgca ttgggtcacc agcaaatcgc gctgttagcg      780
ggcccattaa gttctgtctc ggcgcgtctg cgtctggctg gctggcataa atatctcact      840
cgcaatcaaa ttcagccgat agcggaacgg gaaggcgact ggagtgccat gtccggtttt      900
caacaaacca tgcaaatgct gaatgagggc atcgttccca ctgcgatgct ggttgccaac      960
gatcagatgg cgctgggcgc aatgcgcgcc attaccgagt ccgggctgcg cgttggtgcg     1020
gatatctcgg tagtgggata cgacgatacc gaagacagct catgttatat cccgccgtca     1080
accaccatca acaggatttt cgcctgctg ggcaaaccca gcgtggaccg cttgctgcaa     1140
ctctctcagg ccaggcggt gaagggcaat cagctgttgc ccgtctcact ggtgaaaaga     1200
aaaaccaccc tggcgcccaa tacgcaaacc gcctctcccc gcgcgttggc cgattcatta     1260
atgcagctgg cacgacaggt ttcccgactg gaaagcgggc agtgagcgca acgcaattaa     1320
tgtgagttag cgcgaattga tctggtttga cagcttatca tcgactgcac ggtgcaccaa     1380
tgcttctggc gtcaggcagc catcggaagc tgtggtatgg ctgtgcaggt cgtaaatcac     1440
```

-continued

```
tgcataattc gtgtcgctca aggcgcactc ccgttctgga taatgttttt tgcgccgaca    1500
tcataacggt tctggcaaat attctgaaat gagctgttga caattaatca tccggctcgt    1560
ataatgtgtg gaattgtgag cggataacaa tttcacacag gaaacagcgc cgctgagaaa    1620
aagcgaagcg gcactgctct ttaacaattt atcagacaat ctgtgtgggc actcgaccgg    1680
aattatcgat taactttatt attaaaaatt aaagaggtat atattaatgt atcgattaaa    1740
taaggaggaa taaccatgt gtgcgacctc ttctcaattt actcagatta ccgagcataa    1800
ttcccgtcgt tccgcaaact atcagccaaa cctgtggaat tcgaattcc tgcaatccct    1860 ggagaacgac ctgaaagtgg aaaagctgga ggagaaagcg accaaactgg aggaagaagt    1920
tcgctgcatg atcaaccgtg tagacaccca gccgctgtcc ctgctggagc tgatcgacga    1980
tgtgcagcgc ctgggtctga cctacaaatt tgaaaaagac atcattaaag ccctggaaaa    2040
catcgtactg ctggacgaaa acaaaaagaa caaatctgac ctgcacgcaa ccgctctgtc    2100
tttccgtctg ctgcgtcagc acggtttcga ggtttctcag gatgttttg agcgtttcaa    2160 ggataaagaa ggtggtttca gcggtgaact gaaaggtgac gtccaaggcc tgctgagcct    2220
gtatgaagcg tcttacctgg gtttcgaggg tgagaacctg ctggaggagg cgcgtacctt    2280
ttccatcacc cacctgaaga caacctgaa agaaggcatt aataccaagg ttgcagaaca    2340
agtgagccac gccctggaac tgccatatca ccagcgtctg caccgtctgg aggcacgttg    2400
gttcctggat aaatacgaac cgaaagaacc gcatcaccag ctgctgctgg agctggcgaa    2460
gctggatttt aacatggtac agaccctgca ccagaaagag ctgcaagatc tgtcccgctg    2520
gtggaccgag atgggcctgg ctagcaaact ggattttgta cgcgaccgcc tgatggaagt    2580
ttatttctgg gcactgggta tggcgccaga cccgcagttt ggtgaatgtc gcaaagctgt    2640
tactaaaatg tttggtctgg tgacgatcat cgatgacgtg tatgacgttt atggcactct    2700
ggacgaactg caactgttca ccgatgctgt agagcgctgg gacgttaacg ctattaacac    2760
cctgccggac tatatgaaac tgtgtttcct ggcactgtac aacaccgtta acgacacgtc    2820
ctattctatt ctgaaagaga aaggtcataa caacctgtcc tatctgacga aaagctggcg    2880
tgaactgtgc aaagcctttc tgcaagaggc gaaatggtcc aacaacaaaa ttatcccggc    2940
tttctccaag tacctggaaa acgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaagatga atcgtgaacg cgttagcgac tccaccctgc tgcctaaagc    3300
gttcatggaa atcgcagtta acatggcacg tgtttcccac tgcacctacc agtatggcga    3360
tggtctgggt cgcccagact acgcgactga aaaccgcatc aaactgctgc tgattgaccc    3420
tttcccgatt aaccagctga tgtatgtcta actgcattcg cccttaggag gtaaaaaaac    3480
atgagttttg atattgccaa ataccccgacc ctggcactgg tcgactccac ccaggagtta    3540
cgactgttgc cgaaagagag tttaccgaaa ctctgcgacg aactgcgccg ctatttactc    3600
dacagcgtga gccgttccag cgggcacttc gcctccgggc tggcacggt cgaactgacc    3660 gtggcgctgc actatgtcta caacaccccg tttgaccaat tgatttggga tgtggggcat    3720
caggcttatc cgcataaaat tttgaccgga cgccgcgaca aaatcggcac catccgtcag    3780
aaaggcggtc tgcacccgtt cccgtggcgc ggcgaaagcg aatatgacgt attaagcgtc    3840
```

```
gggcattcat caacctccat cagtgccgga attggtattg cggttgctgc cgaaaaagaa   3900
ggcaaaaatc gccgcaccgt ctgtgtcatt ggcgatggcg cgattaccgc aggcatggcg   3960
tttgaagcga tgaatcacgc gggcgatatc cgtcctgata tgctggtgat tctcaacgac   4020
aatgaaatgt cgatttccga aaatgtcggc gcgctcaaca accatctggc acagctgctt   4080
tccggtaagc tttactcttc actgcgcgaa ggcgggaaaa aagttttctc tggcgtgccg   4140
ccaattaaag agctgctcaa acgcaccgaa gaacatatta aaggcatggt agtgcctggc   4200
acgttgtttg aagagctggg ctttaactac atcggcccgg tggacggtca cgatgtgctg   4260
gggcttatca ccacgctaaa gaacatgcgc gacctgaaag gcccgcagtt cctgcatatc   4320
atgaccaaaa aaggtcgtgg ttatgaaccg gcagaaaaag acccgatcac tttccacgcc   4380
gtgcctaaat ttgatccctc cagcggttgt ttgccgaaaa gtagcggcgg tttgccgagc   4440
tattcaaaaa tctttggcga ctggttgtgc gaaacggcag cgaaagacaa caagctgatg   4500
gcgattactc cggcgatgcg tgaaggttcc ggcatggtcg agttttcacg taaattcccg   4560
gatcgctact tcgacgtggc aattgccgag caacacgcgg tgacctttgc tgcgggtctg   4620
gcgattggtg ggtacaaacc cattgtcgcg atttactcca cttccctgca acgcgcctat   4680
gatcaggtgc tgcatgacgt ggcgattcaa aagcttccgg tcctgttcgc catcgaccgc   4740 gcggcattg ttggtgctga cggtcaaacc catcagggtg cttttgatct ctcttacctg   4800
cgctgcatac cggaaatggt cattatgacc ccgagcgatg aaaacgaatg tcgccagatg   4860
ctctataccg gctatcacta taacgatggc ccgtcagcgg tgcgctaccc gcgtggcaac   4920
gcggtcggcg tggaactgac gccgctggaa aaactaccaa ttggcaaagg cattgtgaag   4980
cgtcgtggcg agaaactggc gatccttaac tttggtacgc tgatgccaga agcggcgaaa   5040
gtcgccgaat cgctgaacgc cacgctggtc gatatgcgtt ttgtgaaacc gcttgatgaa   5100
gcgttaattc tggaaatggc cgccagccat gaagcgctgg tcaccgtaga agaaaacgcc   5160
attatgggcg gcgcaggcag cggcgtgaac gaagtgctga tggcccatcg taaaccagta   5220
cccgtgctga acattggcct gccggacttc tttattccgc aaggaactca ggaagaaatg   5280
cgcgccgaac tcgcctcga tgccgctggt atggaagcca aaatcaaggc ctggctggca   5340
taactgcagc tggtaccata tgggaattcg aagctttcta gaacaaaaac tcatctcaga   5400
agaggatctg aatagcgccg tcgaccatca tcatcatcat cattgagttt aaacggtctc   5460
cagcttggct gttttggcgg atgagagaag attttcagcc tgatacagat taaatcagaa   5520
cgcagaagcg gtctgataaa acagaatttg cctggcggca gtagcgcggt ggtcccacct   5580
gaccccatgc cgaactcaga agtgaaacgc cgtagcgccg atggtagtgt ggggtctccc   5640
catgcgagag tagggaactg ccaggcatca aataaaacga aaggctcagt cgaaagactg   5700
ggcctttcgt tttatctgtt gtttgtcggt gaacgctctc ctgagtagga caaatccgcc   5760
gggagcggat ttgaacgttg cgaagcaacg gcccggaggg tggcgggcag gacgcccgcc   5820
ataaactgcc aggcatcaaa ttaagcagaa ggccatcctg acggatggcc ttttctgcgtt   5880 tctacaaact cttttttgttt atttttctaa atacattcaa atatgtatcc gcttaaccgg   5940
aattgccagc tggggcgccc tctggtaagg ttgggaagcc ctgcaaagta aactggatgg   6000
ctttctcgcc gccaaggatc tgatggcgca ggggatcaag ctctgatcaa gagacaggat   6060
gaggatcgtt tcgcatgatt gaacaagatg gattgcacgc aggttctccg gccgcttggg   6120
tggagaggct attcggctat gactgggcac aacagacaat cggctgctct gatgccgccg   6180
tgttccggct gtcagcgcag gggcgcccgg ttcttttgt caagaccgac ctgtccggtg   6240
```

```
ccctgaatga actgcaagac gaggcagcgc ggctatcgtg gctggccacg acgggcgttc    6300
cttgcgcagc tgtgctcgac gttgtcactg aagcgggaag ggactggctg ctattgggcg    6360
aagtgccggg gcaggatctc ctgtcatctc accttgctcc tgccgagaaa gtatccatca    6420
tggctgatgc aatgcggcgg ctgcatacgc ttgatccggc tacctgccca ttcgaccacc    6480
aagcgaaaca tcgcatcgag cgagcacgta ctcggatgga agccggtctt gtcgatcagg    6540
atgatctgga cgaagagcat caggggctcg cgccagccga actgttcgcc aggctcaagg    6600
cgagcatgcc cgacggcgag gatctcgtcg tgacccatgg cgatgcctgc ttgccgaata    6660
tcatggtgga aaatggccgc ttttctggat tcatcgactg tggccggctg ggtgtggcgg    6720
accgctatca ggacatagcg ttggctaccc gtgatattgc tgaagagctt ggcggcgaat    6780
gggctgaccg cttcctcgtg ctttacggta tcgccgctcc cgattcgcag cgcatcgcct    6840
tctatcgcct tcttgacgag ttcttctgac gcatgaccaa aatcccttaa cgtgagtttt    6900
cgttccactg agcgtcagac cccgtagaaa agatcaaagg atcttcttga tccttttttt    6960
ttctgcgcgt aatctgctgc ttgcaaacaa aaaaaccacc gctaccagcg gtggtttgtt    7020
tgccggatca agagctacca actctttttc cgaaggtaac tggcttcagc agagcgcaga    7080
taccaaatac tgtccttcta gtgtagccgt agttaggcca ccacttcaag aactctgtag    7140
caccgcctac atacctcgct ctgctaatcc tgttaccagt ggctgctgcc agtggcgata    7200
agtcgtgtct taccgggttg gactcaagac gatagttacc ggataaggcg cagcggtcgg    7260
gctgaacggg gggttcgtgc acacagccca gcttggagcg aacgacctac accgaactga    7320
gatacctaca gcgtgagcta tgagaaagcg ccacgcttcc cgaagggaga aaggcggaca    7380
ggtatccggt aagcggcagg gtcggaacag gagagcgcac gagggagctt ccaggggdaa    7440
```
(Note: last line value 7440; reading "ccaggggdaa" likely "ccaggggga a" — preserving)
```
acgcctggta tctttatagt cctgtcgggt ttcgccacct ctgacttgag cgtcgatttt    7500
tgtgatgctc gtcagggggg cggagcctat ggaaaaacgc cagcaacgcg gcctttttac    7560
ggttcctggc cttttgctgg ccttttgctc acatgttctt tcctgcgtta tcccctgatt    7620
ctgtggataa ccgtattacc gcctttgagt gagctgatac cgctcgccgc agccgaacga    7680
ccgagcgcag cgagtcagtg agcgaggaag cggaagagcg cctgatgcgg tattttctcc    7740
ttacgcatct gtgcggtatt tcacaccgca tatggtgcac tctcagtaca atctgctctg    7800
atgccgcata gttaagccag tatacactcc gctatcgcta cgtgactggg tcatggctgc    7860
gccccgacac ccgccaacac ccgctgacgc gccctgacgg gc    7902

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52
ctggcgtaat agcgaagagg cccgcaccga tcgcccttcc caacagttgc gcagcctgaa      60
tggcgaatgg cgcctgatgc ggtatttttct ccttacgcat ctgtgcggta tttcacaccg     120
catatggtgc actctcagta caatctgctc tgatgccgca tagttaagcc agccccgaca     180
cccgccaaca cccgctgacg agcttagtaa agccctcgct agattttaat gcggatgttg     240
cgattacttc gccaactatt gcgataacaa gaaaaagcca gcctttcatg atatatctcc     300
caatttgtgt agggcttatt atgcacgctt aaaaataata aaagcagact tgacctgata     360
gtttggctgt gagcaattat gtgcttagtg catctaacgc ttgagttaag ccgcgccgcg     420
```

```
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata cgttaaggt ttcatttagc gcctcaaata gatcctgttc aggaaccgga    780
tcaaagagtt cctccgccgc tggacctacc aaggcaacgc tatgttctct gcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgcttgtttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgttttgc gtgagccatg agaacgaacc attgagatca   2580
tacttactt gcatgtcact caaaatttt gcctcaaaac tggtgagctg aattttgca   2640
gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
```

```
tcaaccacca atttcatatt gctgtaagtg tttaaatctt tacttattgg tttcaaaacc      2880
cattggttaa gccttttaaa ctcatggtag ttattttcaa gcattaacat gaacttaaat      2940
tcatcaaggc taatctctat atttgccttg tgagttttct tttgtgttag ttcttttaat      3000
aaccactcat aaatcctcat agagtatttg ttttcaaaag acttaacatg ttccagatta      3060
tattttatga attttttttaa ctggaaaaga taaggcaata tctcttcact aaaaactaat     3120
tctaattttt cgcttgagaa cttggcatag tttgtccact ggaaaatctc aaagcccttta    3180 accaaaggat tcctgatttc cacagttctc gtcatcagct ctctggttgc tttagctaat      3240
acaccataag catttccct actgatgttc atcatctgag cgtattggtt ataagtgaac       3300
gataccgtcc gttctttcct tgtagggttt tcaatcgtgg ggttgagtag tgccacacag      3360
cataaaatta gcttggtttc atgctccgtt aagtcatagc gactaatcgc tagttcattt      3420
gctttgaaaa caactaattc agacatacat ctcaattggt ctaggtgatt ttaatcacta      3480
taccaattga gatgggctag tcaatgataa ttactagtcc ttttcctttg agttgtgggt      3540
atctgtaaat tctgctagac ctttgctgga aaacttgtaa attctgctag accctctgta      3600
aattccgcta gaccttttgtg tgttttttttt gtttatattc aagtggttat aatttataga    3660 ataagaaag aataaaaaaa gataaaaga atagatccca gccctgtgta taactcacta        3720
ctttagtcag ttccgcagta ttacaaaagg atgtcgcaaa cgctgtttgc tcctctacaa      3780
aacagacctt aaaaccctaa aggcttaagt agcaccctcg caagctcggg caaatcgctg      3840
aatattcctt ttgtctccga ccatcaggca cctgagtcgc tgtcttttc gtgacattca       3900 gttcgctgcg ctcacggctc tggcagtgaa tgggggtaaa tggcactaca ggcgcctttt      3960
atggattcat gcaaggaaac tacccataat acaagaaaag cccgtcacgg gcttctcagg     4020
gcgttttatg gcgggtctgc tatgtggtgc tatctgactt tttgctgttc agcagttcct      4080
gccctctgat tttccagtct gaccacttcg gattatcccg tgacaggtca ttcagactgg     4140
ctaatgcacc cagtaaggca gcggtatcat caacaggctt acccgtctta ctgtcgggaa     4200
ttcgcgttgg ccgattcatt aatgcagatt ctgaaatgag ctgttgacaa ttaatcatcc      4260
ggctcgtata atgtgtggaa ttgtgagcgg ataacaattt cacacaggaa acagcgccgc     4320
tgagaaaaag cgaagcggca ctgctctta caatttatc agacaatctg tgtgggcact       4380
cgaccggaat tatcgattaa ctttattatt aaaaattaaa gaggtatata ttaatgtatc      4440
gattaaataa ggaggaataa accatgtgtg cgacctcttc tcaatttact cagattaccg     4500
agcataattc ccgtcgttcc gcaaactatc agccaaacct gtggaatttc gaattcctgc     4560
aatccctgga gaacgacctg aaagtggaaa agctggagga gaaagcgacc aaactggagg    4620
aagaagttcg ctgcatgatc aaccgtgtag cacccagcc gctgtccctg ctggagctga     4680
tcgacgatgt gcagcgcctg ggtctgacct acaaatttga aaagacatc attaaagccc      4740 tggaaaacat cgtactgctg gacgaaaaca aaaagaacaa atctgacctg cacgcaaccg     4800
ctctgtcttt ccgtctgctg cgtcagcacg gtttcgaggt ttctcaggat gtttttgagc     4860
gtttcaagga taaagaaggt ggtttcagcg gtgaactgaa aggtgacgtc caaggcctgc     4920
tgagcctgta tgaagcgtct tacctgggtt tcgagggtga gaacctgctg gaggaggcgc     4980 gtacctttc catcacccac ctgaagaaca acctgaaaga aggcattaat accaaggttg      5040
cagaacaagt gagccacgcc ctggaactgc catatcacca gcgtctgcac cgtctggagg    5100
cacgttggtt cctggataaa tacgaaccga aagaaccgca tcaccagctg ctgctggagc     5160
tggcgaagct ggatttttaac atggtacaga ccctgcacca gaaagagctg caagatctgt    5220
```

```
cccgctggtg gaccgagatg ggcctggcta gcaaactgga ttttgtacgc gaccgcctga     5280
tggaagttta tttctgggca ctgggtatgg cgccagaccc gcagtttggt gaatgtcgca     5340
aagctgttac taaaatgttt ggtctggtga cgatcatcga tgacgtgtat gacgtttatg     5400
gcactctgga cgaactgcaa ctgttcaccg atgctgtaga gcgctgggac gttaacgcta     5460
ttaacaccct gccggactat atgaaactgt gtttcctggc actgtacaac accgttaacg     5520
acacgtccta ttctattctg aaagagaaag tcataacaa cctgtcctat ctgacgaaaa      5580
gctggcgtga actgtgcaaa gcctttctgc aagaggcgaa atggtccaac aacaaaatta     5640
tcccggcttt ctccaagtac ctggaaaacg ccagcgtttc ctcctccggt gtagcgctgc     5700
tggcgccgtc ttacttttcc gtatgccagc agcaggaaga catctccgac cacgcgctgc     5760
gttccctgac cgacttccat ggtctggtgc gttctagctg cgttatcttc cgcctgtgca     5820
acgatctggc cacctctgcg gcggagctgg aacgtggcga gactaccaat tctatcatta     5880
gctacatgca cgaaaacgat ggtaccagcg aggaacaggc ccgcgaagaa ctgcgtaaac     5940
tgatcgacgc cgaatggaaa aagatgaatc gtgaacgcgt tagcgactcc accctgctgc     6000
ctaaagcgtt catggaaatc gcagttaaca tggcacgtgt ttcccactgc acctaccagt     6060
atggcgatgg tctgggtcgc ccagactacg cgactgaaaa ccgcatcaaa ctgctgctga     6120 ttgaccctt cccgattaac cagctgatgt atgtctaact gcagctggta ccatatggga     6180
attcgaagct ttctagaaca aaaactcatc tcagaagagg atctgaatag cgccgtcgac     6240
catcatcatc atcatcattg agtttaaacg gtctccagct tggctgtttt ggcggatgag     6300
agaagatttt cagcctgata cagattaaat cagaacgcag aagcggtctg ataaaacaga     6360
atttgcctgg cggcagtagc gcggtggtcc cacctgaccc catgccgaac tcagaagtga     6420
aacgccgtag cgccgatggt agtgtggggt ctccccatgc gagagtaggg aactgccagg     6480
catcaaataa aacgaaaggc tcagtcgaaa gactgggcct ttcgttttat ctgttgtttg     6540
tcggtgaacg ctctcctgag taggacaaat ccgccgggag cggatttgaa cgttgcgaag     6600
caacggcccg gagggtggcg ggcaggacgc ccgccataaa ctgccaggca tcaaattaag     6660
cagaaggcca tcctgacgga tggcctttt gcgtttctac aaactctttt tgtttatttt      6720
tctaaataca ttcaaatatg tatccgctca tgagacaata cccctgataa atgcttcaat     6780
aat                                                                    6783
```

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53

```
cccgtcttac tgtcgggaat tcgcgttggc cgattcatta atgcagatta ttgaagcatt       60
tatcagggtt attgtctcat gagcggatac atatttgaat gtatttagaa aaataaacaa      120
aaagagtttg tagaaacgca aaaaggccat ccgtcaggat ggccttctgc ttaatttgat      180
gcctggcagt ttatggcggg cgtcctgccc gccaccctcc gggccgttgc ttcgcaacgt      240
tcaaatccgc tcccggcgga tttgtcctac tcaggagagc gttcaccgac aaacaacaga      300
taaaacgaaa ggcccagtct ttcgactgag cctttcgttt tatttgatgc ctggcagttc      360
cctactctcg catggggaga ccccacacta ccatcggcgc tacggcgttt cacttctgag      420
ttcggcatgg ggtcaggtgg gaccaccgcg ctactgccgc caggcaaatt ctgttttatc      480
```

```
agaccgcttc tgcgttctga tttaatctgt atcaggctga aaatcttctc tcatccgcca    540
aaacagccaa gctggagacc gtttaaactc aatgatgatg atgatgatgg tcgacggcgc    600
tattcagatc ctcttctgag atgagttttt gttctagaaa gcttcgaatt cccatatggt    660
accagctgca gttagacata catcagctgg ttaatcggga aagggtcaat cagcagcagt    720
ttgatgcggt tttcagtcgc gtagtctggg cgacccagac catcgccata ctggtaggtg    780
cagtgggaaa cacgtgccat gttaactgcg atttccatga acgctttagg cagcagggtg    840
gagtcgctaa cgcgttcacg attcatcttt ttccattcgg cgtcgatcag tttacgcagt    900
tcttcgcggg cctgttcctc gctggtacca tcgttttcgt gcatgtagct aatgatagaa    960
ttggtagtct cgccacgttc cagctccgcc gcagaggtgg ccagatcgtt gcacaggcgg   1020
aagataacgc agctagaacg caccagacca tggaagtcgg tcaggaacg  cagcgcgtgg   1080 tcggagatgt cttcctgctg ctggcatacg aaaagtaag  acggcgccag cagcgctaca   1140
ccggaggagg aaacgctggc gttttccagg tacttggaga aagccgggat aattttgttg   1200
ttggaccatt tcgcctcttg cagaaaggct ttgcacagtt cacgccagct tttcgtcaga   1260
taggacaggt tgttatgacc tttctctttc agaatagaat aggacgtgtc gttaacggtg   1320
ttgtacagtg ccaggaaaca cagtttcata tagtccggca gggtgttaat agcgttaacg   1380
tcccagcgct ctacagcatc ggtgaacagt tgcagttcgt ccagagtgcc ataaacgtca   1440
tacacgtcat cgatgatcgt caccagacca aacattttag taacagcttt gcgacattca   1500
ccaaactgcg ggtctggcgc catacccagt gcccagaaat aaacttccat caggcggtcg   1560
cgtacaaaat ccagtttgct agccaggccc atctcggtcc accagcggga cagatcttgc   1620
agctcttcct ggtgcagggt ctgtaccatg ttaaaatcca gcttcgccag ctccagcagc   1680
agctggtgat gcggttcttt cggttcgtat ttatccagga ccaacgtgc  ctccagacgg   1740 tgcagacgct ggtgatatgg cagttccagg gcgtggctca cttgttctgc aaccttggta   1800
ttaatgcctt ctttcaggtt gttcttcagg tgggtgatgg aaaaggtacg cgcctcctcc   1860
agcaggttct caccctcgaa acccaggtaa gacgcttcat acaggctcag caggccttgg   1920
acgtcacctt tcagttcacc gctgaaacca ccttctttat ccttgaaacg ctcaaaaaca   1980
tcctgagaaa cctcgaaacc gtgctgacgc agcagacgga aagacagagc ggttgcgtgc   2040
aggtcagatt tgttcttttt gttttcgtcc agcagtacga tgttttccag ggctttaatg   2100
atgtcttttt caaatttgta ggtcagaccc aggcgctgca catcgtcgat cagctccagc   2160
agggacagcg gctgggtgtc tacacggttg atcatgcagc gaacttcttc ctccagtttg   2220
gtcgctttct cctccagctt ttccactttc aggtcgttct ccagggattg caggaattcg   2280
aaattccaca ggtttggctg atagtttgcg gaacgacggg aattatgctc ggtaatctga   2340
gtaaattgag aagaggtcgc acacatggtt tattcctcct tatttaatcg atacattaat   2400
atatacctct ttaatttta  ataataaagt taatcgataa ttccggtcga gtgcccacac   2460
agattgtctg ataaattgtt aaagagcagt gccgcttcgc ttttctcag  cggcgctgtt   2520 tcctgtgtga aattgttatc cgctcacaat tccacacatt atacgagccg atgattaat   2580 tgtcaacagc tcatttcaga atctggcgta atagcgaaga ggcccgcacc gatcgccctt   2640
cccaacagtt gcgcagcctg aatggcgaat ggcgcctgat gcggtatttt ctccttacgc   2700
atctgtgcgg tatttcacac cgcatatggt gcactctcag tacaatctgc tctgatgccg   2760
catagttaag ccagccccga cacccgccaa cacccgctga cgagcttagt aaagccctcg   2820
ctagatttta atgcggatgt tgcgattact tcgccaacta ttgcgataac aagaaaaagc   2880
```

```
cagcctttca tgatatatct cccaatttgt gtagggctta ttatgcacgc ttaaaaataa    2940
taaaagcaga cttgacctga tagtttggct gtgagcaatt atgtgcttag tgcatctaac    3000
gcttgagtta agccgcgccg cgaagcggcg tcggcttgaa cgaattgtta gacattattt    3060
gccgactacc ttggtgatct cgcctttcac gtagtggaca aattcttcca actgatctgc    3120
gcgcgaggcc aagcgatctt cttcttgtcc aagataagcc tgtctagctt caagtatgac    3180
gggctgatac tgggccggca ggcgctccat gcccagtcg gcagcgacat ccttcggcgc     3240
gattttgccg gttactgcgc tgtaccaaat gcgggacaac gtaagcacta catttcgctc    3300
atcgccagcc cagtcgggcg gcgagttcca tagcgttaag gtttcattta gcgcctcaaa    3360
tagatcctgt tcaggaaccg gatcaaagag ttcctccgcc gctggaccta ccaaggcaac    3420
gctatgttct cttgcttttg tcagcaagat agccagatca atgtcgatcg tggctggctc    3480
gaagatacct gcaagaatgt cattgcgctg ccattctcca aattgcagtt cgcgcttagc    3540
tggataacgc cacggaatga tgtcgtcgtg cacaacaatg gtgacttcta cagcgcggag    3600
aatctcgctc tctccagggg aagccgaagt ttccaaaagg tcgttgatca aagctcgccg    3660
cgttgtttca tcaagcctta cggtcaccgt aaccagcaaa tcaatatcac tgtgtggctt    3720
caggccgcca tccactgcgg agccgtacaa atgtacggcc agcaacgtcg gttcgagatg    3780
gcgctcgatg acgccaacta cctctgatag ttgagtcgat acttcggcga tcaccgcttc    3840
cctcatgatg tttaactttg ttttagggcg actgccctgc tgcgtaacat cgttgctgct    3900
ccataacatc aaacatcgac ccacggcgta acgcgcttgc tgcttggatg cccgaggcat    3960
agactgtacc ccaaaaaaac agtcataaca agccatgaaa accgccactg cgccgttacc    4020
accgctgcgt tcggtcaagg ttctggacca gttgcgtgag cgcatacgct acttgcatta    4080
cagcttacga accgaacagg cttatgtcca ctgggttcgt gccttcatcc gtttccacgg    4140
tgtgcgtcac ccggcaacct tgggcagcag cgaagtcgag gcatttctgt cctggctggc    4200
gaacgagcgc aaggtttcgg tctccacgca tcgtcaggca ttggcggcct tgctgttctt    4260
ctacggcaag gtgctgtgca cggatctgcc ctggcttcag gagatcggaa gacctcggcc    4320
gtcgcggcgc ttgccggtgg tgctgacccc ggatgaagtg gttcgcatcc tcggttttct    4380
ggaaggcgag catcgtttgt tcgcccagct tctgtatgga acgggcatgc ggatcagtga    4440
gggtttgcaa ctgcgggtca aggatctgga tttcgatcac ggcacgatca tcgtgcggga    4500
gggcaagggc tccaaggatc gggccttgat gttacccgag agcttggcac ccagcctgcg    4560
cgagcagggg aattaattcc cacgggtttt gctgcccgca aacgggctgt tctggtgttg    4620
ctagtttgtt atcagaatcg cagatccggc ttcagccggt ttgccggctg aaagcgctat    4680
ttcttccaga attgccatga ttttttcccc acgggaggcg tcactggctc ccgtgttgtc    4740
ggcagctttg attcgataag cagcatcgcc tgtttcaggc tgtctatgtg tgactgttga    4800
gctgtaacaa gttgtctcag gtgttcaatt tcatgttcta gttgctttgt tttactggtt    4860
tcacctgttc tattaggtgt tacatgctgt tcatctgtta cattgtcgat ctgttcatgg    4920
tgaacagctt tgaatgcacc aaaaactcgt aaaagctctg atgtatctat cttttttaca    4980 ccgtttcat ctgtgcatat ggacagtttt ccctttgata tgtaacggtg aacagttgtt    5040 ctactttgt ttgttagtct tgatgcttca ctgatagata caagagccat aagaacctca    5100
gatccttccg tatttagcca gtatgttctc tagtgtggtt cgttgttttt gcgtgagcca    5160
tgagaacgaa ccattgagat catacttact ttgcatgtca ctcaaaaatt ttgcctcaaa    5220
actggtgagc tgaattttg cagttaaagc atcgtgtagt gttttcctta gtccgttatg    5280
```

```
taggtaggaa tctgatgtaa tggttgttgg tattttgtca ccattcattt ttatctggtt    5340
gttctcaagt tcggttacga gatccatttg tctatctagt tcaacttgga aaatcaacgt    5400
atcagtcggg cggcctcgct tatcaaccac caatttcata ttgctgtaag tgtttaaatc    5460
tttacttatt ggtttcaaaa cccattggtt aagcctttta aactcatggt agttattttc    5520
aagcattaac atgaacttaa attcatcaag gctaatctct atatttgcct tgtgagtttt    5580
cttttgtgtt agttctttta ataaccactc ataaatcctc atagagtatt tgttttcaaa    5640
agacttaaca tgttccagat tatattttat gaatttttt aactggaaaa gataaggcaa    5700
tatctcttca ctaaaaacta attctaattt ttcgcttgag aacttggcat agtttgtcca    5760
ctggaaaatc tcaaagcctt taaccaaagg attcctgatt tccacagttc tcgtcatcag    5820
ctctctggtt gctttagcta atacaccata agcattttcc ctactgatgt tcatcatctg    5880
agcgtattgg ttataagtga acgataccgt ccgttctttc cttgtagggt tttcaatcgt    5940
ggggttgagt agtgccacac agcataaaat tagcttggtt tcatgctccg ttaagtcata    6000
gcgactaatc gctagttcat ttgctttgaa aacaactaat tcagacatac atctcaattg    6060
gtctaggtga ttttaatcac tataccaatt gagatgggct agtcaatgat aattactagt    6120 cctttctcctt tgagttgtgg gtatctgtaa attctgctag accttttgctg gaaaacttgt    6180 aaattctgct agaccctctg taaattccgc tagacctttg tgtgttttt ttgtttatat    6240 tcaagtggtt ataatttata gaataaagaa agaataaaaa aagataaaaa gaatagatcc    6300
cagcccgtgt tataactcac tactttagtc agttccgcag tattacaaaa ggatgtcgca    6360
aacgctgttt gctcctctac aaaacagacc ttaaaaccct aaaggcttaa gtagcaccct    6420
cgcaagctcg ggcaaatcgc tgaatattcc ttttgtctcc gaccatcagg cacctgagtc    6480
gctgtctttt tcgtgacatt cagttcgctg cgctcacggc tctggcagtg aatggggta    6540 aatggcacta caggcgcctt ttatggattc atgcaaggaa actacccata atacaagaaa    6600
agcccgtcac gggcttctca gggcgtttta tggcgggtct gctatgtggt gctatctgac    6660 ttttgctgt tcagcagttc ctgccctctg attttccagt ctgaccactt cggattatcc    6720
cgtgacaggt cattcagact ggctaatgca cccagtaagg cagcggtatc atcaacaggc    6780
tta                                                                  6783
```

<210> SEQ ID NO 54  
<211> LENGTH: 7687  
<212> TYPE: DNA  
<213> ORGANISM: Artificial Sequence  
<220> FEATURE:  
<223> OTHER INFORMATION: Synthetic Construct

<400> SEQUENCE: 54

```
ctggcgtaat agcgaagagg cccgcaccga tcgcccttcc caacagttgc gcagcctgaa     60
tggcgaatgg cgcctgatgc ggtatttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
```

-continued

```
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct gcttttgtc     840 agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt aactttgtt    1260 ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gttgcaact gcgggtcaag    1860 gatctggatt tcgatcacgg cacgatcatc gtgcgggagg gcaagggctc caaggatcgg   1920
gccttgatgt acccgagag cttggcaccc agcctgcgcg agcaggggaa ttaattccca    1980
cgggttttgc tgcccgcaaa cgggctgttc tggtgttgct agtttgttat cagaatcgca   2040
gatccggctt cagccggttt gccggctgaa agcgctattt cttccagaat gccatgatt    2100 ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgttttgc gtgagccatg agaacgaacc attgagatca    2580
tacttacttt gcatgtcact caaaaatttt gcctcaaaac tggtgagctg aattttgca    2640 gttaaagcat cgtgtagtgt ttttcttagt ccgttatgta ggtaggaatc tgatgtaatg   2700
gttgttggta ttttgtcacc attcatttt atctggttgt tctcaagttc ggttacgaga    2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttatttcaa gcattaacat gaacttaaat    2940
```

```
tcatcaaggc taatctctat atttgccttg tgagttttct tttgtgttag ttcttttaat    3000
aaccactcat aaatcctcat agagtatttg ttttcaaaag acttaacatg ttccagatta    3060
tattttatga attttttttaa ctggaaaaga taaggcaata tctcttcact aaaaactaat   3120
tctaattttt cgcttgagaa cttggcatag tttgtccact ggaaaatctc aaagcccttta  3180 accaaaggat tcctgatttc acagttctc gtcatcagct ctctggttgc tttagctaat    3240
acaccataag cattttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gaccctttgtg tgtttttttt gtttatattc aagtggttat aatttataga  3660 ataagaaag aataaaaaaa gataaaaaga atagatccca gccctgtgta taactcacta    3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtcttttc gtgacattca    3900 gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat tttccagtct gaccacttcg gattatcccg tgacaggtca ttcagactgg   4140
ctaatgcacc cagtaaggca gcggtatcat caacaggctt accgtctta ctgtcgggaa    4200 ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa cttattattt aaaaattaaa gaggtatata ttaatgtatc    4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaagacatc attaaagccc    4740 tggaaaacat cgtactgctg gacgaaaaca aaaagaacaa atctgacctg cacgcaaccg   4800
ctctgtcttt ccgtctgctg cgtcagcacg gtttcgaggt ttctcaggat gttttttgagc  4860 gtttcaagga taaagaaggt ggtttcagcg gtgaactgaa aggtgacgtc caaggcctgc   4920
tgagcctgta tgaagcgtct tacctggttt cgagggtga aacctgctg gaggaggcgc    4980 gtacctttc catcacccac ctgaagaaca acctgaaaga aggcattaat accaaggttg    5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggattttaac atggtacaga ccctgcacca gaaagagctg caagatctgt   5220
cccgctggtg gaccgagatg ggcctggcta gcaaactgga ttttgtacgc gaccgcctga   5280
tggaagttta tttctgggca ctgggtatgg cgccagaccc gcagtttggt gaatgtcgca   5340
```

```
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt ttcccactgc acctaccagt    6060
atggcgatgg tctgggtcgc ccagactacg cgactgaaaa ccgcatcaaa ctgctgctga    6120
ttgacccttt cccgattaac cagctgatgt atgtctaact gcatcgccct taggaggtaa    6180
aaaaaaatga ctgccgacaa caatagtatg ccccatggtg cagtatctag ttacgccaaa    6240
ttagtgcaaa accaaacacc tgaagacatt tggaagagt ttcctgaaat tattccatta    6300
```
(line 6300 reads: ttagtgcaaa accaaacacc tgaagacatt tggaagagt ttcctgaaat tattccatta)
```
caacaaagac ctaatacccg atctagtgag acgtcaaatg acgaaagcgg agaaacatgt    6360
ttttctggtc atgatgagga gcaaattaag ttaatgaatg aaaattgtat tgttttggat    6420
tgggacgata atgctattgg tgccggtacc aagaaagttt gtcatttaat ggaaaatatt    6480
gaaaagggtt tactacatcg tgcattctcc gtctttatt tcaatgaaca aggtgaatta    6540
```
(line 6540: gaaaagggtt tactacatcg tgcattctcc gtctttatt tcaatgaaca aggtgaatta)
```
cttttacaac aaagagccac tgaaaaaata actttccctg atctttggac taacacatgc    6600
tgctctcatc cactatgtat tgatgacgaa ttaggtttga agggtaagct agacgataag    6660
attaagggcg ctattactgc ggcggtgaga aaactagatc atgaattagg tattccagaa    6720
gatgaaacta agacaagggg taagtttcac tttttaaaca gaatccatta catggcacca    6780
agcaatgaac catggggtga acatgaaatt gattacatcc tattttataa gatcaacgct    6840
aaagaaaact tgactgtcaa cccaaacgtc aatgaagtta gagacttcaa atgggtttca    6900
ccaaatgatt tgaaaactat gtttgctgac ccaagttaca gtttacgcc ttggtttaag    6960
```
(line 6960: ccaaatgatt tgaaaactat gtttgctgac ccaagttaca gtttacgcc ttggtttaag)
```
attatttgcg agaattactt attcaactgg tgggagcaat tagatgacct ttctgaagtg    7020
gaaaatgaca ggcaaattca tagaatgcta taacgacgcg tcctgcagct ggtaccatat    7080
gggaattcga agctttctag aacgaaaact catctcagaa gaggatctga atagcgccgt    7140
cgaccatcat catcatcatc attgagttta acggtctcc agcttggctg ttttggcgga    7200
```
(line 7200: cgaccatcat catcatcatc attgagttta acggtctcc agcttggctg ttttggcgga)
```
tgagagaaga ttttcagcct gatacagatt aaatcagaac gcagaagcgg tctgataaaa    7260
cagaatttgc ctggcggcag tagcgcggtg gtcccacctg accccatgcc gaactcagaa    7320
gtgaaacgcc gtagcgccga tggtagtgtg gggtctcccc atgcgagagt agggaactgc    7380
caggcatcaa ataaaacgaa aggctcagtc gaaagactgg gcctttcgtt ttatctgttg    7440
tttgtcggtg aacgctctcc tgagtaggac aaatccgccg ggagcggatt tgaacgttgc    7500
gaagcaacgg cccggagggt ggcgggcagg acgcccgcca taaactgcca ggcatcaaat    7560
taagcagaag gccatcctga cggatggcct ttttgcgttt ctacaaactc ttttttgttta    7620
```
(line 7620: taagcagaag gccatcctga cggatggcct ttttgcgttt ctacaaactc ttttttgttta)
```
tttttctaaa tacattcaaa tatgtatccg ctcatgagac aataaccctg ataaatgctt    7680
caataat                                                              7687
```

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55

| | | | | | |
|---|---|---|---|---|---|
| cccgtcttac | tgtcgggaat | tcgcgttggc | cgattcatta | atgcagatta | ttgaagcatt | 60 |
| tatcagggtt | attgtctcat | gagcggatac | atatttgaat | gtatttagaa | aaataaacaa | 120 |
| aaagagtttg | tagaaacgca | aaaaggccat | ccgtcaggat | ggccttctgc | ttaatttgat | 180 |
| gcctggcagt | ttatggcggg | cgtcctgccc | gccaccctcc | gggccgttgc | ttcgcaacgt | 240 |
| tcaaatccgc | tcccggcgga | tttgtcctac | tcaggagagc | gttcaccgac | aaacaacaga | 300 |
| taaaacgaaa | ggcccagtct | ttcgactgag | cctttcgttt | tatttgatgc | ctggcagttc | 360 |
| cctactctcg | catggggaga | ccccacacta | ccatcggcgc | tacggcgttt | cacttctgag | 420 |
| ttcggcatgg | ggtcaggtgg | gaccaccgcg | ctactgccgc | caggcaaatt | ctgttttatc | 480 |
| agaccgcttc | tgcgttctga | tttaatctgt | atcaggctga | aaatcttctc | tcatccgcca | 540 |
| aaacagccaa | gctggagacc | gtttaaactc | aatgatgatg | atgatgatgg | tcgacggcgc | 600 |
| tattcagatc | ctcttctgag | atgagttttt | gttctagaaa | gcttcgaatt | cccatatggt | 660 |
| accagctgca | gttatgccag | ccaggccttg | attttggctt | ccataccagc | ggcatcgagg | 720 |
| ccgagttcgg | cgcgcatttc | ttcctgagtt | ccttgcggaa | taagaagtc | cggcaggcca | 780 |
| atgttcagca | cgggtactgg | tttacgatgg | gccatcagca | cttcgttcac | gccgctgcct | 840 |
| gcgccgccca | taatggcgtt | tcttctacg | gtgaccagcg | cttcatggct | ggcggccatt | 900 |
| tccagaatta | acgcttcatc | aagcggtttc | acaaaacgca | tatcgaccag | cgtggcgttc | 960 |
| agcgattcgg | cgactttcgc | cgcttctggc | atcagcgtac | caaagttaag | gatcgccagt | 1020 |
| ttctcgccac | gacgcttcac | aatgcctttg | ccaattggta | gttttccag | cggcgtcagt | 1080 |
| tccacgccga | ccgcgttgcc | acgcgggtag | cgcaccgctg | acgggccatc | gttatagtga | 1140 |
| tagccggtat | agagcatctg | gcgacattcg | ttttcatcgc | tcgggggtcat | aatgaccatt | 1200 |
| tccggtatgc | agcgcaggta | agagagatca | aaagcaccct | gatgggtttg | accgtcagca | 1260 |
| ccaacaatgc | ccgcgcggtc | gatggcgaac | aggaccggaa | gcttttgaat | cgccacgtca | 1320 |
| tgcagcacct | gatcataggc | gcgttgcagg | aaagtggagt | aaatcgcgac | aatgggtttg | 1380 |
| tacccaccaa | tcgccagacc | cgcagcaaag | gtcaccgcgt | gttgctcggc | aattgccacg | 1440 |
| tcgaagtagc | gatccgggaa | tttacgtgaa | aactcgacca | tgccggaacc | ttcacgcatc | 1500 |
| gccggagtaa | tcgccatcag | cttgttgtct | ttcgctgccg | tttcgcacaa | ccagtcgcca | 1560 |
| aagattttg | aatagctcgg | caaaccgccg | ctactttcg | gcaaacaacc | gctggaggga | 1620 |
| tcaaatttag | gcacgcgtg | gaaagtgatc | gggtctttttt | ctgccggttc | ataaccacga | 1680 |
| ccttttttgg | tcatgatatg | caggaactgc | gggcctttca | ggtcgcgcat | gttctttagc | 1740 |
| gtggtgataa | gccccagcac | atcgtgaccg | tccaccgggc | cgatgtagtt | aaagcccagc | 1800 |
| tcttcaaaca | acgtgccagg | cactaccatg | cctttaatat | gttcttcggt | gcgtttgagc | 1860 |
| agctctttaa | ttggcggcac | gccagagaaa | actttttcc | cgccttcgcg | cagtgaagag | 1920 |
| taaagcttac | cggaaagcag | ctgtgccaga | tggttgttga | gcgcgccgac | attttcggaa | 1980 |
| atcgacattt | cattgtcgtt | gagaatcacc | agcatatcag | gacggatatc | gcccgcgtga | 2040 |
| ttcatcgctt | caaacgccat | gcctgcggta | atcgcgccat | cgccaatgac | acagacggtg | 2100 |

```
cggcgatttt tgccttcttt ttcggcagca accgcaatac caattccggc actgatggag    2160
gttgatgaat gcccgacgct taatacgtca tattcgcttt cgccgcgcca cgggaacggg    2220
tgcagaccgc ctttctgacg gatggtgccg attttgtcgc ggcgtccggt caaaatttta    2280
tgcggataag cctgatgccc cacatcccaa atcaattggt caaacggggt gttgtagaca    2340
tagtgcagcg ccacggtcag ttcgaccgtg cccagcccgg aggcgaagtg cccgctggaa    2400
cggctcacgt tgtcgagtaa atagcggcgc agttcgtcgc agagtttcgg taaactctct    2460
ttcggcaaca gtcgtaactc ctgggtggag tcgaccagtg ccagggtcgg gtatttggca    2520
atatcaaaac tcatgttttt ttacctccta agggcgaatg cagttagaca tacatcagct    2580
ggttaatcgg gaaagggtca atcagcagca gtttgatgcg gttttcagtc gcgtagtctg    2640
ggcgacccag accatcgcca tactggtagg tgcagtggga aacacgtgcc atgttaactg    2700
cgatttccat gaacgcttta ggcagcaggg tggagtcgct aacgcgttca cgattcatct    2760
ttttccattc ggcgtcgatc agtttacgca gttcttcgcg ggcctgttcc tcgctggtac    2820
catcgttttc gtgcatgtag ctaatgatag aattggtagt ctcgccacgt ccagctccg    2880 ccgcagaggt ggccagatcg ttgcacaggc ggaagataac gcagctagaa cgcaccagac    2940
catggaagtc ggtcagggaa cgcagcgcgt ggtcggagat gtcttcctgc tgctggcata    3000
cggaaaagta agacggcgcc agcagcgcta caccggagga ggaaacgctg gcgttttcca    3060
ggtacttgga gaaagccggg ataattttgt tgttggacca tttcgcctct tgcagaaagg    3120
ctttgcacag ttcacgccag ctttttcgtca gataggacag gttgttatga cctttctctt    3180
tcagaataga ataggacgtg tcgttaacgg tgttgtacag tgccaggaaa cacagtttca    3240
tatagtccgg cagggtgtta atagcgttaa cgtcccagcg ctctacagca tcggtgaaca    3300
gttgcagttc gtccagagtg ccataaacgt catacacgtc atcgatgatc gtcaccagac    3360
caaacatttt agtaacagct ttgcgacatt caccaaactg cgggtctggc gccatacca    3420 gtgcccagaa ataaacttcc atcaggcggt cgcgtacaaa atccagtttg ctagccaggc    3480
ccatctcggt ccaccagcgg gacagatctt gcagctcttt ctggtgcagg gtctgtacca    3540
tgttaaaatc cagcttcgcc agctccagca gcagctggtg atgcggttct ttcggttcgt    3600
atttatccag gaaccaacgt gcctccagac ggtgcagacg ctggtgatat ggcagttcca    3660
gggcgtggct cacttgttct gcaaccttgg tattaatgcc ttctttcagg ttgttcttca    3720
ggtgggtgat ggaaaaggta cgcgcctcct ccagcaggtt ctcaccctcg aaacccaggt    3780
aagacgcttc atacaggctc agcaggcctt ggacgtcacc tttcagttca ccgctgaaac    3840
caccttcttt atccttgaaa cgctcaaaaa catcctgaga aacctcgaaa ccgtgctgac    3900
gcagcagacg gaaagacaga gcggttgcgt gcaggtcaga tttgttcttt ttgttttcgt    3960
ccagcagtac gatgtttcc agggctttaa tgatgtcttt ttcaaatttg taggtcagac    4020
ccaggcgctg cacatcgtcg atcagctcca gcagggacag cggctgggtg tctacacggt    4080
tgatcatgca gcgaacttct tcctccagtt tggtcgcttt ctcctccagc ttttccactt    4140
tcaggtcgtt ctccagggat tgcaggaatt cgaaattcca caggtttggc tgatagtttg    4200
cggaacgacg ggaattatgc tcggtaatct gagtaaattg agaagaggtc gcacacatgg    4260
tttattcctc cttattaat cgatacatta atatatacct cttaattttt taataataaa    4320
gttaatcgat aattccggtc gagtgcccac acagattgtc tgataaattg ttaaagagca    4380
gtgccgcttc gctttttctc agcggcgctg tttcctgtgt gaaattgtta ccgctcaca    4440 attccacaca ttatacgagc cggatgatta attgtcaaca gctcatttca gaatctggcg    4500
```

```
taatagcgaa gaggcccgca ccgatcgccc ttcccaacag ttgcgcagcc tgaatggcga    4560
atggcgcctg atgcggtatt ttctccttac gcatctgtgc ggtatttcac accgcatatg    4620
gtgcactctc agtacaatct gctctgatgc cgcatagtta agccagcccc gacacccgcc    4680
aacacccgct gacgagctta gtaaagccct cgctagattt taatgcggat gttgcgatta    4740
cttcgccaac tattgcgata acaagaaaaa gccagccttt catgatatat ctcccaattt    4800
gtgtagggct tattatgcac gcttaaaaat aataaaagca gacttgacct gatagtttgg    4860
ctgtgagcaa ttatgtgctt agtgcatcta acgcttgagt taagccgcgc cgcgaagcgg    4920
cgtcggcttg aacgaattgt tagacattat ttgccgacta ccttggtgat ctcgcctttc    4980
acgtagtgga caaattcttc caactgatct gcgcgcgagg ccaagcgatc ttcttcttgt    5040
ccaagataag cctgtctagc ttcaagtatg acgggctgat actgggccgg caggcgctcc    5100
attgcccagt cggcagcgac atccttcggc gcgattttgc cggttactgc gctgtaccaa    5160
atgcgggaca acgtaagcac tacatttcgc tcatcgccag cccagtcggg cggcgagttc    5220
catagcgtta aggtttcatt tagcgcctca aatagatcct gttcaggaac cggatcaaag    5280
agttcctccg ccgctggacc taccaaggca acgctatgtt ctcttgcttt tgtcagcaag    5340
atagccagat caatgtcgat cgtggctggc tcgaagatac ctgcaagaat gtcattgcgc    5400
tgccattctc caaattgcag ttcgcgctta gctggataac gccacggaat gatgtcgtcg    5460
tgcacaacaa tggtgacttc tacagcgcgg agaatctcgc tctctccagg ggaagccgaa    5520
gtttccaaaa ggtcgttgat caaagctcgc cgcgttgttt catcaagcct tacggtcacc    5580
gtaaccagca aatcaatatc actgtgtggc ttcaggccgc catccactgc ggagccgtac    5640
aaatgtacgg ccagcaacgt cggttcgaga tggcgctcga tgacgccaac tacctctgat    5700
agttgagtcg atacttcggc gatcaccgct tccctcatga tgtttaactt tgttttaggg    5760
cgactgccct gctgcgtaac atcgttgctg ctccataaca tcaaacatcg acccacggcg    5820
taacgcgctt gctgcttgga tgcccgaggc atagactgta cccaaaaaaa acagtcataa    5880
caagccatga aaaccgccac tgcgccgtta ccaccgctgc gttcggtcaa ggttctggac    5940
cagttgcgtg agcgcatacg ctacttgcat tacagcttac gaaccgaaca ggcttatgtc    6000
cactgggttc gtgccttcat ccgtttccac ggtgtgcgtc acccggcaac cttgggcagc    6060
agcgaagtcg aggcatttct gtcctggctg gcgaacgagc gcaaggtttc ggtctccacg    6120
catcgtcagg cattggcggc cttgctgttc ttctacggca aggtgctgtg cacggatctg    6180
ccctggcttc aggagatcgg aagacctcgg ccgtcgcggc gcttgccggt ggtgctgacc    6240
ccggatgaag tggttcgcat cctcggtttt ctggaaggcg agcatcgttt gttcgcccag    6300
cttctgtatg gaacgggcat gcggatcagt gagggtttgc aactgcgggt caaggatctg    6360
gatttcgatc acggcacgat catcgtgcgg gagggcaagg gctccaagga tcgggccttg    6420
atgttacccg agagcttggc acccagcctg cgcgagcagg ggaattaatt cccacgggtt    6480
ttgctgcccg caaacgggct gttctggtgt tgctagtttg ttatcagaat cgcagatccg    6540
gcttcagccg gtttgccggc tgaaagcgct atttcttcca gaattgccat gattttttcc    6600
ccacgggagg cgtcactggc tcccgtgttg tcggcagctt tgattcgata agcagcatcg    6660
cctgtttcag gctgtctatg tgtgactgtt gagctgtaac aagttgtctc aggtgttcaa    6720
tttcatgttc tagttgcttt gttttactgg tttcacctgt tctattaggt gttacatgct    6780
gttcatctgt tacattgtcg atctgttcat ggtgaacagc tttgaatgca ccaaaaactc    6840
gtaaaagctc tgatgtatct atctttttta caccgttttc atctgtgcat atggacagtt    6900
```

```
ttcccttttga tatgtaacgg tgaacagttg ttctactttt gtttgttagt cttgatgctt    6960
cactgataga tacaagagcc ataagaacct cagatccttc cgtatttagc cagtatgttc    7020
tctagtgtgg ttcgttgttt ttgcgtgagc catgagaacg aaccattgag atcatactta    7080
ctttgcatgt cactcaaaaa ttttgcctca aaactggtga gctgaatttt tgcagttaaa    7140
gcatcgtgta gtgttttttct tagtccgtta tgtaggtagg aatctgatgt aatggttgtt    7200
ggtattttgt caccattcat ttttatctgg ttgttctcaa gttcggttac gagatccatt    7260
tgtctatcta gttcaacttg gaaaatcaac gtatcagtcg ggcggcctcg cttatcaacc    7320
accaatttca tattgctgta agtgttttaaa tctttactta ttggtttcaa aacccattgg    7380
ttaagccttt taaactcatg gtagttattt tcaagcatta acatgaactt aaattcatca    7440
aggctaatct ctatatttgc cttgtgagtt ttcttttgtg ttagttcttt taataaccac    7500
tcataaatcc tcatagagta tttgttttca aaagacttaa catgttccag attatatttt    7560
atgaattttt ttaactggaa aagataaggc aatatctctt cactaaaaac taattctaat    7620
ttttcgcttg agaacttggc atagtttgtc cactggaaaa tctcaaagcc tttaaccaaa    7680
ggattcctga tttccacagt tctcgtcatc agctctctgg ttgctttagc taatacacca    7740
taagcatttt ccctactgat gttcatcatc tgagcgtatt ggttataagt gaacgatacc    7800
gtccgttctt tccttgtagg gttttcaatc gtggggttga gtagtgccac acagcataaa    7860
attagcttgg tttcatgctc cgttaagtca tagcgactaa tcgctagttc atttgctttg    7920
aaaacaacta attcagacat acatctcaat tggtctaggt gattttaatc actataccaa    7980
ttgagatggg ctagtcaatg ataattacta gtccttttcc tttgagttgt gggtatctgt    8040
aaattctgct agacctttgc tggaaaactt gtaaattctg ctagaccctc tgtaaattcc    8100
gctagacctt tgtgtgtttt ttttgtttat attcaagtgg ttataattta tagaataaag    8160
aaagaataaa aaaagataaa aagaatagat cccagccctg tgtataactc actactttag    8220
tcagttccgc agtattacaa aaggatgtcg caaacgctgt ttgctcctct acaaaacaga    8280
ccttaaaacc ctaaaggctt aagtagcacc ctcgcaagct cgggcaaatc gctgaatatt    8340
ccttttgtct ccgaccatca ggcacctgag tcgctgtctt tttcgtgaca ttcagttcgc    8400
tgcgctcacg gctctggcag tgaatggggg taaatggcac tacaggcgcc ttttatggat    8460
tcatgcaagg aaaactaccca taatacaaga aaagcccgtc acgggcttct cagggcgttt    8520
tatggcgggt ctgctatgtg gtgctatctg acttttttgct gttcagcagt tcctgccctc    8580
tgattttcca gtctgaccac ttcggattat cccgtgacag gtcattcaga ctggctaatg    8640
cacccagtaa ggcagcggta tcatcaacag gctta                               8675
```

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56

```
tcgctgcgct cggtcgttcg gctgcggcga gcggtatcag ctcactcaaa ggcggtaata      60
cggttatcca cagaatcagg ggataacgca ggaaagaaca tgtgagcaaa aggccagcaa     120
aaggccagga accgtaaaaa ggccgcgttg ctggcgtttt tccataggct ccgcccccct     180
gacgagcatc acaaaaatcg acgctcaagt cagaggtggc gaaacccgac aggactataa     240
agataccagg cgtttccccc tggaagctcc ctcgtgcgct ctcctgttcc gaccctgccg     300
```

```
cttaccggat acctgtccgc ctttctccct tcgggaagcg tggcgctttc tcatagctca    360
cgctgtaggt atctcagttc ggtgtaggtc gttcgctcca agctgggctg tgtgcacgaa    420
ccccccgttc agcccgaccg ctgcgcctta tccggtaact atcgtcttga gtccaacccg    480
gtaagacacg acttatcgcc actggcagca gccactggta acaggattag cagagcgagg    540
tatgtaggcg gtgctacaga gttcttgaag tggtggccta actacggcta cactagaaga    600
acagtatttg gtatctgcgc tctgctgaag ccagttacct tcggaaaaag agttggtagc    660
tcttgatccg gcaaacaaac caccgctggt agcggtggtt ttttgtttg caagcagcag    720 attacgcgca gaaaaaaagg atctcaagaa gatcctttga tcttttctac ggggtctgac    780
gctcagtgga acgaaaactc acgttaaggg attttggtca tgagattatc aaaaaggatc    840
ttcacctaga tccttttaaa ttaaaaatga agttttaaat caatctaaag tatatatgag    900
taaacttggt ctgacagtta ccaatgctta atcagtgagg cacctatctc agcgatctgt    960
ctatttcgtt catccatagt tgcctgactc cccgtcgtgt agataactac gatacgggag   1020
ggcttaccat ctggccccag tgctgcaatg ataccgcgag acccacgctc accggctcca   1080
gatttatcag caataaacca gccagccgga agggccgagc gcagaagtgg tcctgcaact   1140
ttatccgcct ccatccagtc tattaattgt tgccgggaag ctagagtaag tagttcgcca   1200
gttaatagtt tgcgcaacgt tgttgccatt gctacaggca tcgtggtgtc acgctcgtcg   1260
tttggtatgg cttcattcag ctccggttcc caacgatcaa ggcgagttac atgatccccc   1320
atgttgtgca aaaagcggt tagctccttc ggtcctccga tcgttgtcag aagtaagttg    1380
gccgcagtgt tatcactcat ggttatggca gcactgcata attctcttac tgtcatgcca   1440
tccgtaagat gcttttctgt gactggtgag tactcaacca agtcattctg agaatagtgt   1500
atgcggcgac cgagttgctc ttgcccggcg tcaatacggg ataataccgc gccacatagc   1560
agaactttaa aagtgctcat cattggaaaa cgttcttcgg ggcgaaaact ctcaaggatc   1620
ttaccgctgt tgagatccag ttcgatgtaa cccactcgtg cacccaactg atcttcagca   1680
tcttttactt tcaccagcgt ttctgggtga gcaaaaacag gaaggcaaaa tgccgcaaaa   1740
aagggaataa gggcgacacg gaaatgttga atactcatac tcttcctttt tcaatattat   1800
tgaagcattt atcagggtta ttgtctcatg agcggataca tatttgaatg tatttagaaa   1860
aataaacaaa taggggttcc gcgcacattt ccccgaaaag tgccacctga cgtctaagaa   1920
accattatta tcatgacatt aacctataaa aataggcgta tcacgaggcc ctttcgtctc   1980
gcgcgtttcg gtgatgacgg tgaaaacctc tgacacatgc agctcccgga gacggtcaca   2040
gcttgtctgt aagcggatgc cgggagcaga caagcccgtc agggcgcgtc agcgggtgtt   2100
ggcgggtgtc ggggctggct taactatgcg gcatcagagc agattgtact gagagtgcac   2160
catagatctg gagctgtaat ataaaaacct tcttcaacta acggggcagg ttagtgacat   2220
tagaaaaccg actgtaaaaa gtacagtcgg cattatctca tattataaaa gccagtcatt   2280
aggcctatct gacaattcct gaatagagtt cataaacaat cctgcatgat aaccatcaca   2340
aacagaatga tgtacctgta aagatagcgg taaatatatt gaattacctt tattaatgaa   2400
ttttcctgct gtaataatgg gtagaaggta attactatta ttattgatat ttaagttaaa   2460
cccagtaaat gaagtccatg gaataataga aagagaaaaa gcattttcag gtataggtgt   2520
tttgggaaac aatttccccg aaccattata tttctctaca tcagaaaggt ataaatcata   2580
aaactctttg aagtcattct ttacaggagt ccaaatacca gagaatgttt tagatacacc   2640
atcaaaaatt gtataaagtg gctctaactt atcccaataa cctaactctc cgtcgctatt   2700
```

```
gtaaccagtt ctaaaagctg tatttgagtt tatcacccett gtcactaaga aaataaatgc    2760
agggtaaaat ttatatcctt cttgttttat gtttcggtat aaaacactaa tatcaatttc    2820
tgtggttata ctaaaagtcg tttgttggtt caaataatga ttaaatatct cttttctctt    2880
ccaattgtct aaatcaattt tattaaagtt catttgatat gcctcctaaa tttttatcta    2940
aagtgaattt aggaggctta cttgtctgct ttcttcatta gaatcaatcc tttttttaaaa   3000
gtcaatatta ctgtaacata aatatatatt ttaaaaatat cccactttat ccaattttcg    3060
tttgttgaac taatgggtgc tttagttgaa gaataaaaga cctatgcggt gtgaaatacc    3120
gcacagatgc gtaaggagaa ataccgcat caggcgccat tcgccattca ggctgcgcaa     3180
ctgttgggaa gggcgatcgg tgcgggcctc ttcgctatta cgccagctgg cgaaagggggg  3240
atgtgctgca aggcgattaa gttgggtaac gccagggttt tcccagtcac gacgttgtaa   3300
aacgacggcc agtgccaagc ttgcatgcct gcactccatt ttcttctgct atcaaaataa   3360
cagactcgtg attttccaaa cgagctttca aaaaagcctc tgcccttgc aaatcggatg    3420
cctgtctata aaattcccga tattggttaa acagcggcgc aatggcggcc gcatctgatg   3480
tctttgcttg gcgaatgttc atcttatttc ttcctcccctc tcaataattt tttcattcta  3540
tcccttttct gtaaagttta ttttttcagaa tactttttatc atcatgcttt gaaaaaatat  3600
cacgataata tccattgttc tcacggaagc acacgcaggt catttgaacg aatttttccg   3660
acaggaattt gccgggactc aggagcattt aacctaaaaa agcatgacat ttcagcataa   3720
tgaacattta ctcatgtcta ttttcgttct tttctgtatg aaaatagtta tttcgagtct   3780
ctacggaaat agcgagagat gatataccta aatagagata aaatcatctc aaaaaaatgg   3840
gtctactaaa atattattcc atctattaca ataaattcac agaatagtct tttaagtaag   3900
tctactctga atttttttaa aaggagaggg taaagagtga aaacagtagt tattattgat   3960
gcattacgaa caccaattgg aaaatataaa ggcagcttaa gtcaagtaag tgccgtagac   4020
ttaggaacac atgttacaac acaactttta aaaagacatt ccactatttc tgaagaaatt  4080
gatcaagtaa tctttggaaa tgttttacaa gctggaaatg gccaaaatcc cgcacgacaa   4140
atagcaataa acagcggttt gtctcatgaa attcccgcaa tgacggttaa tgaggtctgc   4200
ggatcaggaa tgaaggccgt tattttggcg aaacaattga ttcaattagg agaagcggaa   4260
gttttaattg ctggcgggat tgagaatatg tcccaagcac ctaaattaca acgttttaat   4320
tacgaaacag aaagctacga tgcgccttttt tctagtatga tgtatgatgg attaacggat   4380
gcctttagtg gtcaggcaat gggcttaact gctgaaaatg tggccgaaaa gtatcatgta   4440
actagagaag agcaagatca attttctgta cattcacaat taaaagcagc tcaagcacaa   4500
gcagaaggga tattcgctga cgaaatagcc ccattgaag tatcaggaac gcttgtggag   4560
aaagatgaag ggattcgccc taattcgagc gttgagaagc taggaacgct taaaacagtt   4620
tttaaagaag acggtactgt aacagcaggg aatgcatcaa ccattaatga tggggcttct   4680
gctttgatta ttgcttcaca agaatatgcc gaagcacacg gtcttcctta tttagctatt   4740
attcgagaca gtgtggaagt cggtattgat ccagcctata tgggaatttc gccgattaaa  4800
gccattcaaa aactgttagc gcgcaatcaa cttactacgg aagaaattga tctgtatgaa  4860
atcaacgaag catttgcagc aacttcaatc gtggtccaaa gagaactggc tttaccagag  4920
gaaaaggtca acatttatgg tggcggtatt tcattaggtc atgcgattgg tgccacaggt  4980
gctcgtttat taacgagttt aagttatcaa ttaaatcaaa agaaaagaa atatggagtg  5040
gcttctttat gtatcggcgg tggcttagga ctcgctatgc tactagagag acctcagcaa  5100
```

```
aaaaaaaaca gccgatttta tcaaatgagt cctgaggaac gcctggcttc tcttcttaat    5160
gaaggccaga tttctgctga tacaaaaaaa gaatttgaaa atacggcttt atcttcgcag    5220
attgccaatc atatgattga aaatcaaatc agtgaaacag aagtgccgat gggcgttggc    5280
ttacatttaa cagtggacga aactgattat ttggtaccaa tggcgacaga agagccctca    5340
gttattgcgg ctttgagtaa tggtgcaaaa atagcacaag gatttaaaac agtgaatcaa    5400
caacgcttaa tgcgtggaca aatcgttttt tacgatgttg cagatcccga gtcattgatt    5460
gataaactac aagtaagaga agcggaagtt tttcaacaag cagagttaag ttatccatct    5520
atcgttaaac ggggcggcgg cttaagagat ttgcaatatc gtactttga tgaatcattt    5580 gtatctgtcg acttttagt agatgttaag gatgcaatgg gggcaaatat cgttaacgct    5640
atgttggaag gtgtggccga gttgttccgt gaatggtttg cggagcaaaa gattttattc    5700 agtatttaa gtaattatgc cacggagtcg gttgttacga tgaaaacggc tattccagtt    5760
tcacgtttaa gtaaggggag caatggccgg gaaattgctg aaaaaattgt tttagcttca    5820
cgctatgctt cattagatcc ttatcgggca gtcacgcata acaaaggaat catgaatggc    5880
attgaagctg tagttttagc tacaggaaat gatacgcg ctgttagcgc ttcttgtcat    5940
gcttttgcgg tgaaggaagg tcgctaccaa ggcttgacta gttggacgct ggatggcgaa    6000
caactaattg gtgaaatttc agttccgctt gctttagcca cggttggcgg tgccacaaaa    6060
gtcttaccta atctcaagc agctgctgat ttgttagcag tgacggatgc aaaagaacta    6120
agtcgagtag tagcggctgt tggtttggca caaaatttag cggcgttacg ggccttagtc    6180
tctgaaggaa ttcaaaaagg acacatggct ctacaagcac gttctttagc gatgacggtc    6240
ggagctactg gtaaagaagt tgaggcagtc gctcaacaat taaaacgtca aaaaacgatg    6300
aaccaagacc gagccatggc tatttttaaat gatttaagaa aacaataaaa ggagagggtg    6360
acaattggga ttgataaaat tagttttttt gtgccccctt attatattga tatgacggca    6420
ctggctgaag ccagaaatgt agaccctgga aaatttcata ttggtattgg caagaccaa    6480 atggcggtga acccaatcag ccaagatatt gtgacatttg cagccaatgc cgcagaagcg    6540
atcttgacca agaagataa agaggccatt gatatggtga ttgtcgggac tgagtccagt    6600
atcgatgagt caaaagcggc cgcagttgtc ttacatcgtt taatgggat tcaacctttc    6660 gctcgctctt tcgaaatcaa ggaagcttgt acggagcaa cagcaggctt acagttagct    6720
aagaatcacg tagccttaca tccagataaa aaagtcttgg tcgtagcggc agatattgca    6780
aaatatggct taaattctgg cggtgagcct acacaaggac ctggggcggt tgcaatgtta    6840
gttgctagtg aaccgcgcat tttggcttta aaagaggata atgtgatgct gacgcaagat    6900
atctatgact tttggcgtcc aacaggccac ccgtatccta tggtcgatgg tccttttgtca    6960 aacgaaacct acatccaatc tttttgcccaa gtctgggatg aacataaaaa acgaaccggt    7020
cttgattttg cagattatga tgctttagcg ttccatattc cttacacaaa aatgggcaaa    7080
aaagccttat tagcaaaaat ctccgaccaa actgaagcag aacaggaacg aatttttagcc    7140 cgttatgaag aaagtatcgt ctatagtcgt cgcgtaggaa acttgtatac gggttcactt    7200
tatctgggac tcatttccct tttagaaaat gcaacgactt taaccgcagg caatcaaatt    7260
ggtttattca gttatggttc tggtgctgtc gctgaatttt tcactggtga attagtagct    7320
ggttatcaaa atcatttaca aaaagaaact catttagcac tgctggataa tcggacagaa    7380
ctttctatcg ctgaatatga agccatgttt gcagaaactt tagacacaga cattgatcaa    7440
acgttagaag atgaattaaa atatagtatt tctgctatta ataataccgt tcgttcttat    7500
```

```
cgaaactaaa aaaaaccggc cttggccccg ccggtttttt attattttc ttcctccgca       7560 tgttcaatcc gctccataat cgacggatgg ctccctctga aaattttaac gagaaacggc       7620
gggttgaccc ggctcagtcc cgtaacggcc aagtcctgaa acgtctcaat cgccgcttcc       7680
cggtttccgg tcagctcaat gccgtaacgg tcggcggcgt tttcctgata ccgggagacg       7740
gcattcgtaa tcgggatccc cgggtaccga gctcgaattc gtaatcatgt catagctgtt       7800
tcctgtgtga aattgttatc cgctcacaat tccacacaac atacgagccg aagcataaa        7860 gtgtaaagcc tggggtgcct aatgagtgag ctaactcaca ttaattgcgt tgcgctcact       7920
gcccgctttc cagtcgggaa acctgtcgtg ccagctgcat taatgaatcg gccaacgcgc       7980
ggggagaggc ggtttgcgta ttgggcgctc ttccgcttcc tcgctcactg ac              8032

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57
gaattgctcc attttcttct gctatcaaaa taacagactc gtgattttcc aaacgagctt         60
tcaaaaaagc ctctgcccct tgcaaatcgg atgcctgtct ataaaattcc cgatattggt        120
taaacagcgg cgcaatggcg gccgcatctg atgtctttgc ttggcgaatg ttcatcttat        180
ttcttcctcc ctctcaataa ttttttcatt ctatcccttt tctgtaaagt ttatttttca        240
gaatactttt atcatcatgc tttgaaaaaa tatcacgata atatccattg ttctcacgga        300
agcacacgca ggtcatttga acgaattttt tcgacaggaa tttgccggga ctcaggagca        360
tttaacctaa aaaagcatga catttcagca taatgaacat ttactcatgt ctattttcgt        420
tcttttctgt atgaaaatag ttatttcgag tctctacgga aatagcgaga gatgatatac        480
ctaaatagag ataaaatcat ctcaaaaaaa tgggtctact aaaatattat tccatctatt        540
acaataaatt cacagaatag tcttttaagt aagtctactc tgaatttttt taaaaggaga        600
gggtaaagag tgtgtgcgac ctcttctcaa tttactcaga ttaccgagca taattcccgt        660
cgttccgcaa actatcagcc aaacctgtgg aatttcgaat tcctgcaatc cctggagaac        720
gacctgaaag tggaaaagct ggaggagaaa gcgaccaaac tggaggaaga agttcgctgc        780
atgatcaacc gtgtagacac ccagccgctg tccctgctgg agctgatcga cgatgtgcag        840
cgcctgggtc tgacctacaa atttgaaaaa gacatcatta aagccctgga aaacatcgta        900
ctgctggacg aaaacaaaaa gaacaaatct gacctgcacg caaccgctct gtctttccgt        960
ctgctgcgtc agcacggttt cgaggtttct caggatgttt ttgagcgttt caaggataaa       1020
gaaggtggtt tcagcggtga actgaaaggt gacgtccaag gcctgctgag cctgtatgaa       1080
gcgtcttacc tgggtttcga gggtgagaac ctgctggagg aggcgcgtac cttttccatc       1140
acccacctga gaacaacct gaaagaaggc attaatacca aggttgcaga acaagtgagc        1200
cacgccctgg aactgccata tcaccagcgt ctgcaccgtc tggaggcacg ttggttcctg       1260
gataaatacg aaccgaaaga accgcatcac cagctgctgc tggagctggc gaagctggat       1320
tttaacatgg tacagaccct gcaccagaaa gagctgcaag atctgtcccg ctggtggacc       1380
gagatgggcc tggctagcaa actggattt gtacgcgacc gcctgatgga agtttatttc         1440
tgggcactgg gtatggcgcc agacccgcag tttggtgaat gtcgcaaagc tgttactaaa       1500
atgtttggtc tggtgacgat catcgatgac gtgtatgacg tttatggcac tctggacgaa       1560
```

```
ctgcaactgt tcaccgatgc tgtagagcgc tgggacgtta acgctattaa caccctgccg    1620
gactatatga aactgtgttt cctggcactg tacaacaccg ttaacgacac gtcctattct    1680
attctgaaag agaaaggtca taacaacctg tcctatctga cgaaaagctg gcgtgaactg    1740
tgcaaagcct ttctgcaaga ggcgaaatgg tccaacaaca aaattatccc ggctttctcc    1800
aagtacctgg aaaacgccag cgtttcctcc tccggtgtag cgctgctggc gccgtcttac    1860
ttttccgtat gccagcagca ggaagacatc tccgaccacg cgctgcgttc cctgaccgac    1920
ttccatggtc tggtgcgttc tagctgcgtt atcttccgcc tgtgcaacga tctggccacc    1980
tctgcggcgg agctggaacg tggcgagact accaattcta tcattagcta catgcacgaa    2040
aacgatggta ccagcgagga acaggcccgc gaagaactgc gtaaactgat cgacgccgaa    2100
tggaaaaaga tgaatcgtga acgcgttagc gactccaccc tgctgcctaa agcgttcatg    2160
gaaatcgcag ttaacatggc acgtgtttcc cactgcacct accagtatgg cgatggtctg    2220
ggtcgcccag actacgcgac tgaaaaccgc atcaaactgc tgctgattga cccttttccg    2280
attaaccagc tgatgtatgt ctaaaaaaaa ccggccttgg ccccgccggt tttttattat    2340
ttttcttcct ccgcatgttc aatccgctcc ataatcgacg gatggctccc tctgaaaatt    2400
ttaacgagaa acggcgggtt gacccggctc agtcccgtaa cggccaagtc ctgaaacgtc    2460
tcaatcgccg cttcccggtt tccggtcagc tcaatgccgt aacggtcggc ggcgttttcc    2520
tgataccggg agacggcatt cgtaatcgga tcctctagag tcgacctgca ggcatgcaag    2580
ctttgcctcg cgcgtttcgg tgatgacggt gaaaacctct gacacatgca gctcccggag    2640
acggtcacag cttgtctgta agcggatgcc gggagcagac aagcccgtca gggcgcgtca    2700
gcgggtgttg gcgggtgtcg gggcgcagcc atgacccagt cacgtagcga tagcggagtg    2760
tatactggct taactatgcg gcatcagagc agattgtact gagagtgcac catatgcggt    2820
gtgaaatacc gcacagatgc gtaaggagaa aataccgcat caggcgctct tccgcttcct    2880
cgctcactga ctcgctgcgc tcggtcgttc ggctgcggcg agcggtatca gctcactcaa    2940
aggcggtaat acggttatcc acagaatcag gggataacgc aggaaagaac atgtgagcaa    3000
aaggccagca aaaggccagg aaccgtaaaa aggccgcgtt gctggcgttt ttccataggc    3060
tccgcccccc tgacgagcat cacaaaaatc gacgctcaag tcagaggtgg cgaaacccga    3120
caggactata aagataccag gcgtttcccc ctggaagctc cctcgtgcgc tctcctgttc    3180
cgaccctgcc gcttaccgga tacctgtccg cctttctccc ttcgggaagc gtggcgcttt    3240
ctcaatgctc acgctgtagg tatctcagtt cggtgtaggt cgttcgctcc aagctgggct    3300
gtgtgcacga accccccgtt cagcccgacc gctgcgcctt atccggtaac tatcgtcttg    3360
agtccaaccc ggtaagacac gacttatcgc cactggcagc agccactggt aacaggatta    3420
gcagagcgag gtatgtaggc ggtgctacag agttcttgaa gtggtggcct aactacggct    3480
acactagaag gacagtattt ggtatctgcg ctctgctgaa gccagttacc ttcggaaaaa    3540
gagttggtag ctcttgatcc ggcaaacaaa ccaccgctgg tagcggtggt ttttttgttt    3600
gcaagcagca gattacgcgc agaaaaaaag gatctcaaga agatcctttg atcttttcta    3660
cggggtctga cgctcagtgg aacgaaaact cacgttaagg gattttggtc atgagattat    3720
caaaaaggat cgaagtcggt tcagaaaaag aaggatatgg atctggagct gtaatataaa    3780
aaccttcttc aactaacggg gcaggttagt gacattagaa aaccgactgt aaaaagtaca    3840
gtcggcatta tctcatatta taaagccagt cattaggcc tatctgacaa ttcctgaata    3900
gagttcataa acaatcctgc atgataacca tcacaaacag aatgatgtac ctgtaaagat    3960
```

```
agcggtaaat atattgaatt acctttatta atgaattttc ctgctgtaat aatgggtaga    4020
aggtaattac tattattatt gatatttaag ttaaacccag taaatgaagt ccatggaata    4080
atagaaagag aaaaagcatt ttcaggtata ggtgttttgg gaaacaattt aaaagaacca    4140
ttatatttct ctacatcaga aaggtataaa tcataaaact ctttgaagtc attctttaca    4200
ggagtccaaa taccagagaa tgttttagat acaccatcaa aaattgtata aagtggctct    4260
aacttatccc aataacctaa ctctccgtcg ctattgtaac cagttctaaa agctgtattt    4320
gagtttatca cccttgtcac taagaaaata aatgcagggt aaaatttata tccttcttgt    4380
tttatgtttc ggtataaaac actaatatca atttctgtgg ttatactaaa agtcgtttgt    4440
tggttcaaat aatgattaaa tatctctttt ctcttccaat tgtctaaatc aatttttatta   4500 aagttcattt gatatgcctc ctaaattttt atctaaagtg aatttaggag cttacttgt    4560 ctgctttctt cattagaatc aatcctttt taaagtcaat attactgtaa cataaatata     4620
tattttaaaa atatcccact ttatccaatt ttcgtttgtt gaactaatgg gtgctttagt    4680
tgaagaataa agaccacatt aaaaaatgtg gtcttttgtg tttttttaaa ggatttgagc    4740
gtacgcgaaa atcctttc tttctttctt atcttgataa taagggtaac tattgccggt      4800
tgtccattca tggctgaact ctgcttcctc tgttgacatg acacacatca tctcaatatc    4860
cgaatagggc ccatcagtct gacgaccaag agagccataa acaccaatag ccttaacatc    4920
atccccatat ttatccaata ttcgttcctt aatttcatga acaatcttca ttctttcttc    4980
tctagtcatt attattggtc cattcactat tctcattccc ttttcagata attttagatt    5040 tgctttcta aataagaata tttggagagc accgttctta ttcagctatt aataactcgt    5100
cttcctaagc atccttcaat cctttaata acaattatag catctaatct tcaacaaact    5160
ggcccgtttg ttgaactact ctttaataaa ataatttttc cgttcccaat tccacattgc    5220
aataatagaa atccatctt catcggcttt ttcgtcatca tctgtatgaa tcaaatcgcc    5280
ttcttctgtg tcatcaaggt ttaattttt atgtatttct tttaacaaac caccatagga    5340
gattaacctt ttacggtgta aaccttcctc caaatcagac aaacgtttca aattcttttc    5400
ttcatcatcg gtcataaaat ccgtatcctt tacaggatat tttgcagttt cgtcaattgc    5460
cgattgtata tccgatttat atttatttt cggtcgaatc atttgaactt ttacatttgg    5520
atcatagtct aatttcattg cctttttcca aaattgaatc cattgttttt gattcacgta    5580
gttttctgtt attctaaaat aagttggttc cacacatacc attacatgca tgtgctgatt    5640
ataagaatta tctttattat ttattgtcac atccgttgca cgcataaaac caacaagatt    5700
tttattaatt tttttatatt gcatcattcg gcgaaatcct tgagccatat ctgtcaaact    5760
cttatttaat tcttcgccat cataaacatt tttaactgtt aatgtgagaa caaccaacg    5820 aactgttggc ttttgtttaa taacttcagc aacaaccttt tgtgactgaa tgccatgttt    5880
cattgctctc ctccagttgc acattggaca aagcctggat ttgcaaaacc acactcgata    5940
ccactttctt tcgcctgttt cacgattttg tttatactct aatatttcag cacaatcttt    6000
tactctttca gccttttaa attcaagaat atgcagaagt tcaaagtaat caacattagc    6060
gattttcttt tctctccatg gtctcacttt tccactttt gtcttgtcca ctaaaaccct    6120 tgattttca tctgaataaa tgctactatt aggacacata atattaaaag aaaccccat     6180 ctatttagtt atttgtttag tcacttataa ctttaacaga tggggttttt ctgtgcaacc    6240
aattttaagg ttttcaata cttaaaaaca catacatacc aacacttcaa cgcaccttc     6300 agcaactaaa ataaaatga cgttatttct atatgtatca agataagaaa gaacaagttc    6360
```

```
aaaaccatca aaaaaagaca ccttttcagg tgctttttt attttataaa ctcattccct    6420
gatctcgact tcgttctttt tttacctctc ggttatgagt tagttcaaat tcgttctttt    6480
taggttctaa atcgtgtttt tcttggaatt gtgctgtttt atcctttacc ttgtctacaa    6540 acccttaaa aacgttttta aaggctttta agccgtctgt acgttcctta ag             6592
```

<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58

```
gacatcaatt gctccatttt cttctgctat c                                    31
```

<210> SEQ ID NO 59
<211> LENGTH: 41
<212> TYPE: DNA
<213> ORGANISM: Artificial Sequence
<220> FEATURE:
<223> OTHER INFORMATION: Synthetic Construct

<400> SEQUENCE: 59

```
attgagaaga ggtcgcacac actctttacc ctctcctttt a                         41
```

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60

```
taaaaggaga gggtaaagag tgtgtgcgac ctcttctcaa t                         41
```

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61

```
ccaaggccgg ttttttttag acatacatca gctggttaat c                         41
```

<210> SEQ ID NO 62
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62

```
gattaaccag ctgatgtatg tctaaaaaaa accggccttg g                         41
```

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63

```
gacatgacgg atccgattac gaatgccgtc tc                                   32
```

```
<210> SEQ ID NO 64
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c                              31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
gacatgaatt cctccatttt cttctgc                                   27

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct

<400> SEQUENCE: 66
aggagagggt aaagagtgag                                           20

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
cttttccatc acccacctga ag                                        22

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
ggcgaaatgg tccaacaaca aaattatc                                  28

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69
ggtgaattca gtctactggg gattcccaaa tctatatata ctgcaggtga c        51

<210> SEQ ID NO 70
<211> LENGTH: 23
<212> TYPE: DNA
<213> ORGANISM: Artificial Sequence
<220> FEATURE:
<223> OTHER INFORMATION: Synthetic Construct
```

```
<400> SEQUENCE: 70
gcaggtggga aactatgcac tcc                                              23

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71
cctgaattct gttggattgg aggattggat agtggg                                36

<210> SEQ ID NO 72
<211> LENGTH: 30
<212> TYPE: DNA
<213> ORGANISM: Artificial Sequence
<220> FEATURE:
<223> OTHER INFORMATION: Synthetic Construct

<400> SEQUENCE: 72
ggtgtcgacg tacggtcgag cttattgacc                                       30

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
ggtgggcccg cattttgcca cctacaagcc ag                                    32

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
ggtgaattct agaggatccc aacgctgttg cctacaacgg                            40

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg                                36

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
ggtgggccca ttaaatcagt tatcgtttat ttgatag                               37

<210> SEQ ID NO 77
<211> LENGTH: 35
<212> TYPE: DNA
```

```
<213> ORGANISM: Artificial Sequence
<220> FEATURE:
<223> OTHER INFORMATION: Synthetic Construct

<400> SEQUENCE: 77
ggtgaccagc aagtccatgg gtggtttgat catgg                              35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg                              35

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gcggccgcag actaaattta tttcagtctc c                                  31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt                                                              7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg                                                              7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc                                       27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctccttttt aa                     42
```

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84
ttaaaaggag agggtaaaga gtgaaaacag tagttattat tg                            42

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85
cggggccaag gccggttttt tttagtttcg ataagaacga acggt                         45

<210> SEQ ID NO 86
<211> LENGTH: 8000
<212> TYPE: DNA
<213> ORGANISM: Artificial Sequence
<220> FEATURE:
<223> OTHER INFORMATION: Synthetic Construct

<400> SEQUENCE: 86
gtttgacagc ttatcatcga ctgcacggtg caccaatgct tctggcgtca ggcagccatc         60
ggaagctgtg gtatggctgt gcaggtcgta atcactgca taattcgtgt cgctcaaggc         120
gcactcccgt tctggataat gttttttgcg ccgacatcat aacggttctg gcaaatattc        180
tgaaatgagc tgttgacaat taatcatccg gctcgtataa tgtgtggaat tgtgagcgga        240
taacaatttc acacaggaaa cagcgccgct gagaaaaagc gaagcggcac tgctctttaa        300
caatttatca gacaatctgt gtgggcactc gaccggaatt atcgattaac tttattatta       360
aaaattaaag aggtatatat taatgtatcg attaaataag gaggaataaa ccatggatcc        420
gagctcagga ggtaaaaaaa catgaaaaca gtagttatta ttgatgcatt acgaacacca        480
attggaaaat ataaaggcag cttaagtcaa gtaagtgccg tagacttagg aacacatgtt        540
acaacacaac ttttaaaaag acattccact atttctgaag aaattgatca agtaatcttt        600
ggaaatgttt tacaagctgg aaatggccaa atcccgcac gacaaatagc aataaacagc        660
ggtttgtctc atgaaattcc cgcaatgacg gttaatgagg tctgcggatc aggaatgaag        720
gccgttattt tggcgaaaca attgattcaa ttaggagaag cggaagtttt aattgctggc        780
gggattgaga atatgtccca agcacctaaa ttacaacgtt ttaattacga acagaaagc        840 tacgatgcgc ttttttctag tatgatgtat gatggattaa cggatgcctt tagtggtcag        900
gcaatgggct taactgctga aaatgtggcc gaaaagtatc atgtaactag agaagagcaa        960
gatcaatttt ctgtacattc acaattaaaa gcagctcaag cacaagcaga agggatattc        1020
gctgacgaaa tagccccatt agaagtatca ggaacgcttg tggagaaaga tgaagggatt        1080
cgccctaatt cgagcgttga agctagga acgcttaaaa cagtttttaa agaagacggt         1140
actgtaacag cagggaatgc atcaaccatt aatgatgggg cttctgcttt gattattgct        1200
tcacaagaat atgccgaagc acacggtctt ccttatttag ctattattcg agacagtgtg        1260
gaagtcggta ttgatccagc ctatatggga atttcgccga ttaaagccat tcaaaaactg        1320
ttagcgcgca atcaacttac tacggaagaa attgatctgt atgaaatcaa cgaagcattt        1380

```
gcagcaactt caatcgtggt ccaaagagaa ctggctttac cagaggaaaa ggtcaacatt      1440
tatggtggcg gtatttcatt aggtcatgcg attggtgcca caggtgctcg tttattaacg      1500
agtttaagtt atcaattaaa tcaaaaagaa aagaaatatg gagtggcttc tttatgtatc      1560
ggcggtggct taggactcgc tatgctacta gagagacctc agcaaaaaaa aaacagccga      1620
ttttatcaaa tgagtcctga ggaacgcctg gcttctcttc ttaatgaagg ccagatttct      1680
gctgatacaa aaaagaatt tgaaaatacg gctttatctt cgcagattgc caatcatatg      1740
attgaaaatc aaatcagtga aacagaagtg ccgatgggcg ttggcttaca tttaacagtg      1800
gacgaaactg attatttggt accaatggcg acagaagagc cctcagttat tgcggctttg      1860
agtaatggtg caaaaatagc acaaggattt aaaacagtga atcaacaacg cttaatgcgt      1920
ggacaaatcg ttttttacga tgttgcagat cccgagtcat tgattgataa actacaagta      1980
agagaagcgg aagttttcta caagcagag ttaagttatc catctatcgt taaacggggc      2040
ggcggcttaa gagatttgca atatcgtact tttgatgaat catttgtatc tgtcgacttt      2100
ttagtagatg ttaaggatgc aatgggggca aatatcgtta acgctatgtt ggaaggtgtg      2160
gccgagttgt tccgtgaatg gtttgcggag caaaagattt tattcagtat tttaagtaat      2220
tatgccacgg agtcggttgt tacgatgaaa acggctattc cagtttcacg tttaagtaag      2280
gggagcaatg gccgggaaat tgctgaaaaa attgttttag cttcacgcta tgcttcatta      2340
gatccttatc gggcagtcac gcataacaaa ggaatcatga atggcattga agctgtagtt      2400
ttagctacag gaaatgatac acgcgctgtt agcgcttctt gtcatgcttt tgcggtgaag      2460
gaaggtcgct accaaggctt gactagttgg acgctggatg gcgaacaact aattggtgaa      2520
atttcagttc cgcttgcttt agccacggtt ggcggtgcca caaaagtctt acctaaatct      2580
caagcagctg ctgatttgtt agcagtgacg gatgcaaaag aactaagtcg agtagtagcg      2640
gctgttggtt tggcacaaaa tttagcggcg ttacgggcct tagtctctga aggaattcaa      2700
aaaggacaca tggctctaca agcacgttct ttagcgatga cggtcggagc tactggtaaa      2760
gaagttgagg cagtcgctca acaattaaaa cgtcaaaaaa cgatgaacca agaccgagcc      2820
atggctattt taaatgattt aagaaaacaa taaggaggt aaaaaaacat gacaattggg      2880
attgataaaa ttagtttttt tgtgccccct tattatattg atatgacggc actggctgaa      2940
gccagaaatg tagaccctgg aaaatttcat attggtattg gcaagaccca aatggcggtg      3000
aacccaatca gccaagatat tgtgacattt gcagccaatg ccgcagaagc gatcttgacc      3060
aaagaagata aagaggccat tgatatgtg attgtcggga ctgagtccag tatcgatgag      3120
tcaaaagcgg ccgcagttgt cttacatcgt ttaatgggga ttcaacctt cgctcgctct      3180 ttcgaaatca aggaagcttg ttacggagca acagcaggct acagttagc taagaatcac      3240 gtagccttac atccagataa aaaagtcttg gtcgtagcgg cagatattgc aaaatatggc      3300
ttaaattctg gcggtgagcc tacacaagga gctgggggcg ttgcaatgtt agttgctagt      3360
gaaccgcgca ttttggcttt aaaagaggat aatgtgatgc tgacgcaaga tatctatgac      3420
ttttggcgtc caacaggcca cccgtatcct atggtcgatg gtccttttgc aaacgaaacc      3480
tacatccaat cttttgccca gtctgggat gaacataaaa aacgaaccgg tcttgatttt      3540
gcagattatg atgctttagc gttccatat ccttacacaa aaatgggcaa aaaagcctta      3600
ttagcaaaaa tctccgacca aactgaagca gaacaggaac gaattttagc ccgttatgaa      3660
gaaagtatcg tctatagtcg tcgcgtagga aacttgtata cggggttcact ttatctggga      3720 ctcatttccc ttttagaaaa tgcaacgact ttaaccgcag gcaatcaaat tggtttattc      3780
```

```
agttatggtt ctggtgctgt cgctgaattt ttcactggtg aattagtagc tggttatcaa   3840
aatcatttac aaaaagaaac tcatttagca ctgctggata tcggacaga actttctatc    3900
gctgaatatg aagccatgtt tgcagaaact ttagacacag acattgatca aacgttagaa   3960
gatgaattaa aatatagtat ttctgctatt aataataccg ttcgttctta tcgaaactaa   4020
gagatctgca gctggtacca tatgggaatt cgaagcttgg gcccgaacaa aaactcatct   4080
cagaagagga tctgaatagc gccgtcgacc atcatcatca tcatcattga gtttaaacgg   4140
tctccagctt ggctgttttg gcggatgaga agattttc agcctgatac agattaaatc     4200
agaacgcaga agcggtctga taaaacagaa tttgcctggc ggcagtagcg cggtggtccc   4260
acctgacccc atgccgaact cagaagtgaa acgccgtagc gccgatggta gtgtggggtc   4320
tccccatgcg agagtaggga actgccaggc atcaaataaa acgaaaggct cagtcgaaag   4380
actgggcctt tcgttttatc tgttgtttgt cggtgaacgc tctcctgagt aggacaaatc   4440
cgccgggagc ggatttgaac gttgcgaagc aacggcccgg agggtggcgg gcaggacgcc   4500
cgccataaac tgccaggcat caaattaagc agaaggccat cctgacggat ggcctttttg   4560
cgtttctaca aactcttttt gtttattttt ctaaatacat tcaaatatgt atccgctcat   4620
gagacaataa ccctgataaa tgcttcaata atattgaaaa aggaagagta tgagtattca   4680
acatttccgt gtcgccctta ttcccttttt tgcggcattt tgccttcctg tttttgctca   4740
cccagaaacg ctggtgaaag taaaagatgc tgaagatcag ttgggtgcac gagtgggtta   4800
catcgaactg gatctcaaca gcggtaagat ccttgagagt tttcgccccg aagaacgttt   4860
tccaatgatg agcactttta aagttctgct atgtggcgcg gtattatccc gtgttgacgc   4920
cgggcaagag caactcggtc gccgcataca ctattctcag aatgacttgg ttgagtactc   4980
accagtcaca gaaaagcatc ttacggatgg catgacagta agagaattat gcagtgctgc   5040
cataaccatg agtgataaca ctgcggccaa cttacttctg acaacgatcg gaggaccgaa   5100
ggagctaacc gcttttttgc acaacatggg ggatcatgta actcgccttg atcgttggga   5160
accggagctg aatgaagcca taccaaacga cgagcgtgac accacgatgc ctgtagcaat   5220
ggcaacaacg ttgcgcaaac tattaactgg cgaactactt actctagctt cccggcaaca   5280
attaatagac tggatggagg cggataaagt tgcaggacca cttctgcgct cggcccttcc   5340
ggctggctgg tttattgctg ataaatctgg agccggtgag cgtgggtctc gcggtatcat   5400
tgcagcactg gggccagatg gtaagccctc ccgtatcgta gttatctaca cgacggggag   5460
tcaggcaact atggatgaac gaaatagaca gatcgctgag ataggtgcct cactgattaa   5520
gcattggtaa ctgtcagacc aagtttactc atatatactt tagattgatt taaaacttca   5580
tttttaattt aaaaggatct aggtgaagat cctttttgat aatctcatga ccaaaatccc   5640
ttaacgtgag ttttcgttcc actgagcgtc agacccgta gaaaagatca aggatcttc    5700
ttgagatcct ttttttctgc gcgtaatctg ctgcttgcaa acaaaaaaac caccgctacc   5760
agcggtggtt tgtttgccgg atcaagagct accaactctt tttccgaagg taactggctt   5820
cagcagagcg cagataccaa atactgtcct tctagtgtag ccgtagttag gccaccactt   5880
caagaactct gtagcaccgc ctacatacct cgctctgcta atcctgttac cagtggctgc   5940
tgccagtggc gataagtcgt gtcttaccgg gttggactca agacgatagt taccggataa   6000
ggcgcagcgg tcgggctgaa cggggggttc gtgcacacag cccagcttgg agcgaacgac   6060
ctacaccgaa ctgagatacc tacagcgtga gctatgagaa agcgccacgc ttcccgaagg   6120
gagaaaggcg gacaggtatc cggtaagcgg cagggtcgga acaggagagc gcacgaggga   6180
```

-continued

```
gcttccaggg ggaaacgcct ggtatcttta tagtcctgtc gggtttcgcc acctctgact    6240
tgagcgtcga ttttttgtgat gctcgtcagg ggggcggagc ctatggaaaa acgccagcaa    6300
cgcggccttt ttacggttcc tggccttttg ctggcctttt gctcacatgt tctttcctgc    6360
gttatcccct gattctgtgg ataaccgtat taccgccttt gagtgagctg ataccgctcg    6420
ccgcagccga acgaccgagc gcagcgagtc agtgagcgag gaagcggaag agcgcctgat    6480
gcggtatttt ctccttacgc atctgtgcgg tatttcacac cgcatatggt gcactctcag    6540
tacaatctgc tctgatgccg catagttaag ccagtataca ctccgctatc gctacgtgac    6600
tgggtcatgg ctgcgccccg acacccgcca cacccgctg acgcgccctg acgggcttgt    6660
ctgctcccgg catccgctta cagacaagct gtgaccgtct ccgggagctg catgtgtcag    6720
aggttttcac cgtcatcacc gaaacgcgcg aggcagcaga tcaattcgcg cgcgaaggcg    6780
aagcggcatg catttacgtt gacaccatcg aatggtgcaa aacctttcgc ggtatggcat    6840
gatagcgccc ggaagagagt caattcaggg tggtgaatgt gaaaccagta acgttatacg    6900
atgtcgcaga gtatgccggt gtctcttatc agaccgtttc ccgcgtggtg aaccaggcca    6960
gccacgtttc tgcgaaaacg cgggaaaaag tggaagcggc gatggcggag ctgaattaca    7020
ttcccaaccg cgtggcacaa caactggcgg gcaaacagtc gttgctgatt ggcgttgcca    7080
cctccagtct ggccctgcac gcgccgtcgc aaattgtcgc ggcgattaaa tctcgcgccg    7140
atcaactggg tgccagcgtg gtggtgtcga tggtagaacg aagcggcgtc gaagcctgta    7200
aagcggcggt gcacaatctt ctcgcgcaac gcgtcagtgg gctgatcatt aactatccgc    7260
tggatgacca ggatgccatt gctgtggaag ctgcctgcac taatgttccg gcgttatttc    7320
ttgatgtctc tgaccagaca cccatcaaca gtattatttt ctcccatgaa gacggtacgc    7380
gactgggcgt ggagcatctg gtcgcattgg gtcaccagca aatcgcgctg ttagcgggcc    7440
cattaagttc tgtctcggcg cgtctgcgtc tggctggctg gcataaatat ctcactcgca    7500
atcaaattca gccgatagcg gaacgggaag gcgactggag tgccatgtcc ggttttcaac    7560
aaaccatgca aatgctgaat gagggcatcg ttcccactgc gatgctggtt gccaacgatc    7620
agatggcgct gggcgcaatg cgcgccatta ccgagtccgg gctgcgcgtt ggtgcggata    7680
tctcggtagt gggatacgac gataccgaag acagctcatg ttatatcccg ccgtcaacca    7740
ccatcaaaca ggattttcgc ctgctggggc aaaccagcgt ggaccgcttg ctgcaactct    7800
ctcagggcca ggcggtgaag ggcaatcagc tgttgcccgt ctcactggtg aaaagaaaaa    7860
ccaccctggc gcccaatacg caaaccgcct ctccccgcgc gttggccgat tcattaatgc    7920
agctggcacg acaggtttcc cgactggaaa gcgggcagtg agcgcaacgc aattaatgtg    7980
agttagcgcg aattgatctg    8000
```

<210> SEQ ID NO 87
<211> LENGTH: 10432
<212> TYPE: DNA
<213> ORGANISM: Artificial Sequence
<220> FEATURE:
<223> OTHER INFORMATION: Synthetic Construct

<400> SEQUENCE: 87

```
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttaa caatttatca     180
gacaatctgt gtgggcactc gaccggaatt atcgattaac tttattatta aaaattaaag     240
```

```
aggtatatat taatgtatcg attaaataag gaggaataaa ccatggatcc gagctcagga    300
ggtaaaaaaa catgaaaaca gtagttatta ttgatgcatt acgaacacca attggaaaat    360
ataaaggcag cttaagtcaa gtaagtgccg tagacttagg aacacatgtt acaacacaac    420
ttttaaaaag acattccact atttctgaag aaattgatca agtaatcttt ggaaatgttt    480
tacaagctgg aaatggccaa atcccgcac gacaaatagc aataaacagc ggtttgtctc    540
atgaaattcc cgcaatgacg gttaatgagg tctgcggatc aggaatgaag gccgttattt    600
tggcgaaaca attgattcaa ttaggagaag cggaagtttt aattgctggc gggattgaga    660
atatgtccca agcacctaaa ttacaacgtt ttaattacga aacagaaagc tacgatgcgc    720 cttttttctag tatgatgtat gatggattaa cggatgcctt tagtggtcag gcaatgggct    780
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaagggatt cgccctaatt    960
cgagcgttga gaagctagga acgcttaaaa cagttttttaa agaagacggt actgtaacag   1020
cagggaatgc atcaaccatt aatgatgggg cttctgcttt gattattgct tcacaagaat   1080
atgccgaagc acacggtctt ccttatttag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga aacagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800 tttttttacga tgttgcagat cccgagtcat tgattgataa actacaagta agagaagcgg   1860 aagttttttca acaagcagag ttaagttatc catctatcgt taaacggggc ggcggcttaa   1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaaagattt tattcagtat tttaagtaat tatgccacgg   2100
agtcggttgt tacgatgaaa acggctattc cagtttcacg tttaagtaag gggagcaatg   2160
gccgggaaat tgctgaaaaa attgttttag cttcacgcta tgcttcatta gatccttatc   2220
gggcagtcac gcataacaaa ggaatcatga atggcattga agctgtagtt ttagctacag   2280
gaaatgatac acgcgctgtt agcgcttctt gtcatgcttt tgcggtgaag gaaggtcgct   2340
accaaggctt gactagttgg acgctggatg gcgaacaact aattggtgaa atttcagttc   2400
cgcttgcttt agccacggtt ggcggtgcca caaagtcttt acctaaatct caagcagctg   2460
ctgatttgtt agcagtgacg gatgcaaaag aactaagtcg agtagtagcg gctgttggtt   2520
tggcacaaaa tttagcggcg ttacgggcct tagtctctga aggaattcaa aaaggacaca   2580
tggctctaca agcacgttct ttagcgatga cggtcggagc tactggtaaa gaagttgagg   2640
```

```
cagtcgctca acaattaaaa cgtcaaaaaa cgatgaacca agaccgagcc atggctattt    2700
taaatgattt aagaaaacaa taaaggaggt aaaaaaacat gacaattggg attgataaaa    2760 ttagttttt tgtgcccct tattatattg atatgacggc actggctgaa gccagaaatg    2820
tagaccctgg aaaatttcat attggtattg ggcaagacca aatggcggtg aacccaatca    2880
gccaagatat tgtgacattt gcagccaatg ccgcagaagc gatcttgacc aaagaagata    2940
aagaggccat tgatatggtg attgtcggga ctgagtccag tatcgatgag tcaaaagcgg    3000
ccgcagttgt cttacatcgt ttaatgggga ttcaacctt cgctcgctct ttcgaaatca    3060
aggaagcttg ttacggagca acagcaggct tacagttagc taagaatcac gtagccttac    3120
atccagataa aaaagtcttg gtcgtagcgg cagatattgc aaaatatggc ttaaattctg    3180
gcggtgagcc tacacaagga gctgggggcgg ttgcaatgtt agttgctagt gaaccgcgca    3240
ttttggcttt aaaagaggat aatgtgatgc tgacgcaaga tatctatgac ttttggcgtc    3300
caacaggcca cccgtatcct atggtcgatg gtcctttgtc aaacgaaacc tacatccaat    3360
cttttgccca agtctgggat gaacataaaa aacgaaccgg tcttgatttt gcagattatg    3420
atgctttagc gttccatatt ccttacacaa aaatgggcaa aaaagcctta ttagcaaaaa    3480
tctccgacca aactgaagca gaacaggaac gaattttagc ccgttatgaa gaaagtatcg    3540
tctatagtcg tcgcgtagga aacttgtata cgggttcact ttatctggga ctcatttccc    3600
ttttagaaaa tgcaacgact ttaaccgcag gcaatcaaat tggtttattc agttatggtt    3660
ctggtgctgt cgctgaattt ttcactggtg aattagtagc tggttatcaa aatcatttac    3720
aaaaagaaac tcatttagca ctgctggata tcggacaga actttctatc gctgaatatg    3780
aagccatgtt tgcagaaact ttagacacag acattgatca aacgttagaa gatgaattaa    3840
aatatagtat ttctgctatt aataataccg ttcgttctta tcgaaactaa agatctgcat    3900
cctgcattcg cccttaggag gtaaaaaaac atgtgtgcga cctcttctca atttactcag    3960
attaccgagc ataattcccg tcgttccgca aactatcagc caaacctgtg gaatttcgaa    4020
ttcctgcaat ccctggagaa cgacctgaaa gtggaaaagc tggaggagaa agcgaccaaa    4080
ctggaggaag aagttcgctg catgatcaac cgtgtagaca cccagccgct gtccctgctg    4140
gagctgatcg acgatgtgca gcgcctgggt ctgacctaca aatttgaaaa agacatcatt    4200
aaagccctgg aaacatcgt actgctggac gaaaacaaaa agaacaaatc tgacctgcac    4260
gcaaccgctc tgtctttccg tctgctgcgt cagcacggtt tcgaggtttc tcaggatgtt    4320
tttgagcgtt tcaaggataa agaaggtggt ttcagcggtg aactgaaagg tgacgtccaa    4380
ggcctgctga gcctgtatga agcgtcttac ctgggtttcg agggtgagaa cctgctggag    4440
gaggcgcgta ccttttccat cacccacctg aagaacaacc tgaaagaagg cattaatacc    4500
aaggttgcag aacaagtgag ccacgccctg gaactgccat atcaccagcg tctgcaccgt    4560
ctggaggcac gttggttcct ggataaatac gaaccgaaag aaccgcatca ccagctgctg    4620
ctggagctgg cgaagctgga ttttaacatg gtacagaccc tgcaccagaa agagctgcaa    4680
gatctgtccc gctggtggac cgagatgggc ctggctagca aactggattt tgtacgcgac    4740
cgcctgatgg aagtttattt ctgggcactg gtatggcgc cagacccgca gtttggtgaa    4800
tgtcgcaaag ctgttactaa aatgtttggt ctggtgacga tcatcgatga cgtgtatgac    4860
gtttatggca ctctggacga actgcaactg ttcaccgatg ctgtagagcg ctgggacgtt    4920
aacgctatta caccctgcc ggactatatg aaactgtgtt tcctggcact gtacaacacc    4980
gttaacgaca cgtcctattc tattctgaaa gagaaaggtc ataacaacct gtcctatctg    5040
```

```
acgaaaagct ggcgtgaact gtgcaaagcc tttctgcaag aggcgaaatg gtccaacaac    5100
aaaattatcc cggcttttctc caagtacctg gaaaacgcca gcgtttcctc ctccggtgta    5160
gcgctgctgg cgccgtctta cttttccgta tgccagcagc aggaagacat ctccgaccac    5220
gcgctgcgtt ccctgaccga cttccatggt ctggtgcgtt ctagctgcgt tatcttccgc    5280
ctgtgcaacg atctggccac ctctgcggcg gagctggaac gtggcgagac taccaattct    5340
atcattagct acatgcacga aaacgatggt accagcgagg aacaggcccg cgaagaactg    5400
cgtaaactga tcgacgccga atggaaaaag atgaatcgtg aacgcgttag cgactccacc    5460
ctgctgccta aagcgttcat ggaaatcgca gttaacatgg cacgtgtttc ccactgcacc    5520
taccagtatg gcgatggtct gggtcgccca gactacgcga ctgaaaaccg catcaaactg    5580
ctgctgattg acccttttccc gattaaccag ctgatgtatg tctaactgca gctggtacca    5640
tatgggaatt cgaagcttgg gcccgaacaa aaactcatct cagaagagga tctgaatagc    5700
gccgtcgacc atcatcatca tcatcattga gtttaaacgg tctccagctt ggctgttttg    5760
gcggatgaga gaagattttc agcctgatac agattaaatc agaacgcaga gcggtctga    5820 taaaacagaa tttgcctggc ggcagtagcg cggtggtccc acctgacccc atgccgaact    5880
cagaagtgaa acgccgtagc gccgatggta gtgtggggtc tccccatgcg agagtaggga    5940
actgccaggc atcaaataaa acgaaaggct cagtcgaaag actgggcctt tcgttttatc    6000
tgttgtttgt cggtgaacgc tctcctgagt aggacaaatc cgccgggagc ggatttgaac    6060
gttgcgaagc aacggcccgg agggtggcgg gcaggacgcc cgccataaac tgccaggcat    6120
caaattaagc agaaggccat cctgacggat ggcctttttg cgtttctaca aactcttttt    6180
gtttattttt ctaaatacat tcaaatatgt atccgctcat gagacaataa ccctgataaa    6240
tgcttcaata atcggcgta atagcgaaga ggcccgcacc gatcgccctt cccaacagtt    6300
gcgcagcctg aatggcgaat ggcgcctgat gcggtatttt ctccttacgc atctgtgcgg    6360
tatttcacac cgcatatggt gcactctcag tacaatctgc tctgatgccg catagttaag    6420
ccagccccga cacccgccaa cacccgctga cgagcttagt aaagccctcg ctagatttta    6480
atgcggatgt tgcgattact tcgccaacta ttgcgataac aagaaaaagc cagccttttca    6540 tgatatatct cccaatttgt gtagggctta ttatgcacgc ttaaaaataa taaaagcaga    6600
cttgacctga tagtttggct gtgagcaatt atgtgcttag tgcatctaac gcttgagtta    6660
agccgcgccg cgaagcggcg tcggcttgaa cgaattgtta gacattattt gccgactacc    6720
ttggtgatct cgccttttcac gtagtggaca aattcttcca actgatctgc gcgcgaggcc    6780
aagcgatctt cttcttgtcc aagataagcc tgtctagctt caagtatgac gggctgatac    6840
tgggccggca ggcgctccat tgcccagtcg gcagcgacat ccttcggcgc gattttgccg    6900
gttactgcgc tgtaccaaat gcgggacaac gtaagcacta catttcgctc atcgccagcc    6960
cagtcgggcg cgagttcca tagcgttaag gtttcattta gcgcctcaaa tagatcctgt    7020
tcaggaaccg gatcaaagag ttcctccgcc gctggaccta ccaaggcaac gctatgttct    7080
cttgcttttg tcagcaagat agccagatca atgtcgatcg tggctggctc gaagatacct    7140
gcaagaatgt cattgcgctg ccattctcca aattgcagtt cgcgcttagc tggataacgc    7200 cacgaatga tgtcgtcgtg cacaacaatg gtgacttcta cagcgcggag aatctcgctc    7260
tctccagggg aagccgaagt ttccaaaagg tcgttgatca aagctcgccg cgttgtttca    7320
tcaagcctta cggtcaccgt aaccagcaaa tcaatatcac tgtgtggctt caggccgcca    7380
tccactgcgg agccgtacaa atgtacggcc agcaacgtcg gttcgagatg cgctcgatg    7440
```

```
acgccaacta cctctgatag ttgagtcgat acttcggcga tcaccgcttc cctcatgatg    7500
tttaactttg ttttagggcg actgccctgc tgcgtaacat cgttgctgct ccataacatc    7560
aaacatcgac ccacggcgta acgcgcttgc tgcttggatg cccgaggcat agactgtacc    7620
ccaaaaaaac agtcataaca agccatgaaa accgccactg cgccgttacc accgctgcgt    7680
tcggtcaagg ttctggacca gttgcgtgag cgcatacgct acttgcatta cagcttacga    7740
accgaacagg cttatgtcca ctgggttcgt gccttcatcc gtttccacgg tgtgcgtcac    7800
ccggcaacct tgggcagcag cgaagtcgag gcatttctgt cctggctggc gaacgagcgc    7860
aaggtttcgg tctccacgca tcgtcaggca ttggcggcct tgctgttctt ctacggcaag    7920
gtgctgtgca cggatctgcc ctggcttcag gagatcggaa gacctcggcc gtcgcggcgc    7980
ttgccggtgg tgctgacccc ggatgaagtg gttcgcatcc tcggttttct ggaaggcgag    8040
catcgtttgt tcgcccagct tctgtatgga acgggcatgc ggatcagtga gggtttgcaa    8100
ctgcgggtca aggatctgga tttcgatcac ggcacgatca tcgtgcggga gggcaagggc    8160
tccaaggatc gggccttgat gttacccgag agcttggcac ccagcctgcg cgagcagggg    8220
aattaattcc cacgggtttt gctgcccgca acgggctgt tctggtgttg ctagtttgtt      8280
atcagaatcg cagatccggc ttcagccggt ttgccggctg aaagcgctat ttcttccaga    8340
attgccatga tttttcccc acgggaggcg tcactggctc ccgtgttgtc ggcagctttg      8400
attcgataag cagcatcgcc tgtttcaggc tgtctatgtg tgactgttga gctgtaacaa    8460
gttgtctcag gtgttcaatt tcatgttcta gttgctttgt tttactggtt tcacctgttc    8520
tattaggtgt tacatgctgt tcatctgtta cattgtcgat ctgttcatgg tgaacagctt    8580
tgaatgcacc aaaaactcgt aaaagctctg atgtatctat cttttttaca ccgttttcat    8640
ctgtgcatat ggacagtttt cccttgata tgtaacggtg aacagttgtt ctacttttgt      8700
ttgttagtct tgatgcttca ctgatagata caagagccat aagaacctca gatccttccg    8760
tatttagcca gtatgttctc tagtgtggtt cgttgttttt gcgtgagcca tgagaacgaa    8820
ccattgagat catacttact ttgcatgtca ctcaaaaatt ttgcctcaaa actggtgagc    8880 tgaattttg cagttaaagc atcgtgtagt gttttttctta gtccgttatg taggtaggaa     8940
tctgatgtaa tggttgttgg tattttgtca ccattcattt ttatctggtt gttctcaagt    9000
tcggttacga gatccatttg tctatctagt tcaacttgga aaatcaacgt atcagtcggg    9060
cggcctcgct tatcaaccac caatttcata ttgctgtaag tgtttaaatc tttacttatt    9120
ggtttcaaaa cccattggtt aagccttta aactcatggt agttattttc aagcattaac      9180
atgaacttaa attcatcaag gctaatctct atatttgcct tgtgagtttt cttttgtgtt    9240
agttctttta ataccactc ataaatcctc atagagtatt tgttttcaaa agacttaaca     9300
tgttccagat tatattttat gaattttttt aactggaaaa gataaggcaa tatctcttca    9360
ctaaaaacta attctaattt ttcgcttgag aacttggcat agtttgtcca ctggaaaatc    9420
tcaaagcctt taaccaaagg attcctgatt tccacagttc tcgtcatcag ctctctggtt    9480
gctttagcta atacaccata agcatttttcc ctactgatgt tcatcatctg agcgtattgg    9540
ttataagtga acgataccgt ccgttctttc cttgtagggt tttcaatcgt ggggttgagt    9600
agtgccacac agcataaaat tagccttggtt tcatgctccg ttaagtcata gcgactaatc    9660
gctagttcat ttgctttgaa aacaactaat tcagacatac atctcaattg gtctaggtga    9720
ttttaatcac tataccaatt gagatgggct agtcaatgat aattactagt ccttttcctt    9780
tgagttgtgg gtatctgtaa attctgctag acctttgctg gaaaacttgt aaattctgct    9840
```

-continued

| | |
|---|---|
| agaccctctg taaattccgc tagacctttg tgtgtttttt ttgtttatat tcaagtggtt | 9900 |
| ataatttata gaataaagaa agaataaaaa aagataaaaa gaatagatcc cagccctgtg | 9960 |
| tataactcac tactttagtc agttccgcag tattacaaaa ggatgtcgca aacgctgttt | 10020 |
| gctcctctac aaaacagacc ttaaaaccct aaaggcttaa gtagcaccct cgcaagctcg | 10080 |
| ggcaaatcgc tgaatattcc ttttgtctcc gaccatcagg cacctgagtc gctgtctttt | 10140 |
| tcgtgacatt cagttcgctg cgctcacggc tctggcagtg aatgggggta aatggcacta | 10200 |
| caggcgcctt ttatggattc atgcaaggaa actacccata atacaagaaa agcccgtcac | 10260 |
| gggcttctca gggcgtttta tggcgggtct gctatgtggt gctatctgac tttttgctgt | 10320 |
| tcagcagttc ctgccctctg attttccagt ctgaccactt cggattatcc cgtgacaggt | 10380 |
| cattcagact ggctaatgca cccagtaagg cagcggtatc atcaacaggc tt | 10432 |

<210> SEQ ID NO 88
<211> LENGTH: 31
<212> TYPE: DNA
<213> ORGANISM: Artificial Sequence
<220> FEATURE:
<223> OTHER INFORMATION: Synthetic Construct

<400> SEQUENCE: 88
cttgatgcat cctgcattcg cccttaggag g          31

<210> SEQ ID NO 89
<211> LENGTH: 23
<212> TYPE: DNA
<213> ORGANISM: Artificial Sequence
<220> FEATURE:
<223> OTHER INFORMATION: Synthetic Construct

<400> SEQUENCE: 89
ccaggcaaat tctgttttat cag          23

<210> SEQ ID NO 90
<211> LENGTH: 10356
<212> TYPE: DNA
<213> ORGANISM: Artificial Sequence
<220> FEATURE:
<223> OTHER INFORMATION: Synthetic Construct

<400> SEQUENCE: 90

| | |
|---|---|
| caagaaaaat gccccgctta cgcagggcat ccatttatta ctcaaccgta accgattttg | 60 |
| ccaggttacg cggctggtca acgtcggtgc ctttgatcag cgcgacatgg taagccagca | 120 |
| gctgcagcgg aacggtgtag aagatcggtg caatcacctc ttccacatgc ggcatctcga | 180 |
| tgatgtgcat gttatcgcta cttacaaaac ccgcatcctg atcggcgaag acatacaact | 240 |
| gaccgccacg cgcgcgaact tcttcaatgt tggatttcag ttttttccagc aattcgttgt | 300 |
| tcggtgcaac aacaataacc ggcatatcgg catcaattag cgccagcgga ccgtgtttca | 360 |
| gttcgccagc agcgtaggct tcagcgtgaa tgtaagagat ctctttcaac ttcaatgcgc | 420 |
| cttccagcgc gattgggtac tgatcgccac ggcccaggaa cagcgcgtga tgtttgtcag | 480 |
| agaaatcttc tgccagcgct tcaatgcgtt tgtcctgaga cagcatctgc tcaatacggc | 540 |
| tcggcagcgc ctgcagacca tgcacgatgt catgttcaat ggaggcatcc agacctttca | 600 |
| ggcgagacag cttcgccacc agcatcaaca gcacagttaa ctgagtggtg aatgctttag | 660 |
| tggatgccac gccgatttct gtacccgcgt tggtcattag cgccagatcg gattcgcgca | 720 |
| ccagagaaga acccggaacg ttacagattg ccagtgaacc aaggtaaccc agctctttcg | 780 |

```
acagacgcag gccagccagg gtatccgcgg tttcgccaga ctgtgacacg atcgcccttc    840
ccaacagttg cgcagcctat acgtacggca gtttaaggtt tacacctata aagagagag    900 ccgttatcgt ctgtttgtgg atgtacagag tgatattatt gacacgccgg ggcgacggat    960
ggtgatcccc ctggccagtg cacgtctgct gtcagataaa gtctcccgtg aactttaccc   1020
ggtggtgcat atcggggatg aaagctggcg catgatgacc accgatatgg ccagtgtgcc   1080
ggtctccgtt atcggggaag aagtggctga tctcagccac cgcgaaaatg acatcaaaaa   1140
cgccattaac ctgatgttct ggggaatata aatgtcaggc atgagattat caaaaaggat   1200
cttcacctag atccttttca cgtagaaagc cagtccgcag aaacggtgct gaccccggat   1260
gaatgtcagc tactgggcta tctggacaag ggaaaacgca agcgcaaaga gaaagcaggt   1320
agcttgcagt gggcttacat ggcgatagct agactgggcg gttttatgga cagcaagcga   1380
accggaattg ccagctgggg cgccctctgg taaggttggg aagccctgca agtaaactg    1440 gatggctttc tcgccgccaa ggatctgatg gcgcagggga tcaagctctg atcaagagac   1500
aggatgagga tcgtttcgca tgattgaaca agatggattg cacgcaggtt ctccggccgc   1560
ttgggtggag aggctattcg gctatgactg ggcacaacag acaatcggct gctctgatgc   1620
cgccgtgttc cggctgtcag cgcaggggcg cccggttctt tttgtcaaga ccgacctgtc   1680
cggtgccctg aatgaactgc aagacgagga agcgcggcta tcgtggctgg ccacgacggg   1740
cgttccttgc gcagctgtgc tcgacgttgt cactgaagcg ggaagggact ggctgctatt   1800
gggcgaagtg ccggggcagg atctcctgtc atctcacctt gctcctgccg agaaagtatc   1860
catcatggct gatgcaatgc ggcggctgca tacgcttgat ccggctacct gcccattcga   1920
ccaccaagcg aaacatcgca tcgagcgagc acgtactcgg atggaagccg gtcttgtcga   1980
tcaggatgat ctggacgaag agcatcaggg gctcgcgcca gccgaactgt tcgccaggct   2040
caaggcgagc atgcccgacg gcgaggatct cgtcgtgacc catggcgatg cctgcttgcc   2100
gaatatcatg gtggaaaatg gccgcttttc tggattcatc gactgtggcc ggctgggtgt   2160
ggcggaccgc tatcaggaca tagcgttggc tacccgtgat attgctgaag agcttggcgg   2220
cgaatgggct gaccgcttcc tcgtgcttta cggtatcgcc gctcccgatt cgcagcgcat   2280
cgccttctat cgccttcttg acgagttctt ctgaattatt aacgcttaca atttcctgat   2340
gcggtatttt ctccttacgc atctgtgcgg tatttcacac cgcatacagg tggcactttt   2400
cggggaaatg tgcgcggaac ccctatttgt ttatttttct aaatacattc aaatatgtat   2460
ccgctcatga caataaaccc tgataaatgc ttcaataat agcacgtgag gagggccacc     2520
atggccaagt tgaccagtgc cgttccggtg ctcaccgcgc gcgacgtcgc cggagcggtc   2580
gagttctgga ccgaccggct cgggttctcc cctagtaacg gccgccagtg tgctggaatt   2640
caggcagttc aacctgttga tagtacgtac taagctctca tgtttcacgt actaagctct   2700
catgtttaac gtactaagct ctcatgttta cgaactaaa ccctcatggc taacgtacta    2760
agctctcatg gctaacgtac taagctctca tgtttcacgt actaagctct catgtttgaa   2820
caataaaatt aatataaatc agcaacttaa atagcctcta aggttttaag ttttataaga   2880 aaaaaagaa tatataaggc ttttaaagct tttaaggttt aacggttgtg gacaacaagc    2940
cagggatgta acgcactgag aagcccttag agcctctcaa agcaattttc agtgacacag   3000
gaacacttaa cggctgacag cctgaattct gcagatatct gttttccac tcttcgttca    3060 cttcgccag gtagctggtg aagacgaagg aagtcccgga gccatctgcg cggcgtacta    3120
cagcaatgtt ttgtgaaggc agtttcagac ccggattcag tttggcgatg gcttcatcat   3180
```

```
cccacttctt gattttgccc aggtagatgt cgccgagggt tttaccatcc agcaccagtt    3240
cgccagactt cagccctgga atgttaaccg ccagcaccac gccgccaatc acggtcggga    3300
actggaacag accttcctga gccagttttt cgtcagacag cggcgcgtca gaggcaccaa    3360
aatcaacggt attagcgata atctgtttta cgccaccgga agaaccgata ccctggtagt    3420
taactttatt accggtttct ttctggtaag tgtcagccca tttggcatac accggcgcag    3480
ggaaggttgc acctgcacct gtcaggcttg cttctgcaaa cacagagaaa gcactcatcg    3540
ataaggtcgc ggcgacaaca gttgcgacgg tggtacgcat aactttcata atgtctcctg    3600
ggaggattca taaagcattg tttgttggct acgagaagca aaataggaca aacaggtgac    3660
agttatatgt aaggaatatg acagttttat gacagagaga taaagtcttc agtctgattt    3720
aaataagcgt tgatattcag tcaattacaa acattaataa cgaagagatg acagaaaaat    3780
tttcattctg tgacagagaa aaagtagccg aagatgacgg tttgtcacat ggagttggca    3840
ggatgtttga ttaaaagcaa ttaaccctca ctaaagggcg gccgcgaagt tcctattctc    3900
tagaaagtat aggaacttca ttctaccggg taggggaggc gcttttccca aggcagtctg    3960
gagcatgcgc tttagcagcc ccgctgggca cttggcgcta cacaagtggc ctctggcctc    4020
gcacacattc cacatccacc ggtaggcgcc aaccggctcc gttctttggt ggccccttcg    4080
cgccaccttc cactcctccc ctagtcagga agttccccc cgccccgcag ctcgcgtcgt    4140
gcaggacgtg acaaatggaa gtagcacgtc tcactagtct cgtgcagatg acagcaccg    4200 ctgagcaatg gaagcgggta ggcctttggg gcagcggcca atagcagctt tgctccttcg    4260 cttctgggc tcagaggctg ggaaggggtg ggtccggggg cgggctcagg ggcgggctca    4320
ggggcggggc gggcgcccga aggtcctccg gaggcccggc attctgcacg cttcaaaagc    4380
gcacgtctgc cgcgctgttc tcctcttcct catctccggg cctttcgacc tgcagcagca    4440
cgtgttgaca attaatcatc ggcatagtat atcggcatag tataatacga caaggtgagg    4500
aactaaacca tggagaaaaa aatcactgga tataccaccg ttgatatatc ccaatggcat    4560
cgtaaagaac attttgaggc atttcagtca gttgctcaat gtacctataa ccagaccgtt    4620
cagctggata ttacggcctt tttaaagacc gtaaagaaaa ataagcacaa gttttatccg    4680
gcctttattc acattcttgc ccgcctgatg aatgctcatc cggaattccg tatggcaatg    4740
aaagacggtg agctggtgat atgggatagt gttcacccct tgttacaccg tttccatgag    4800
caaactgaaa cgttttcatc gctctggagt gaataccacg acgatttccg gcagtttcta    4860
cacatatatt cgcaagatgt ggcgtgttac ggtgaaaacc tggcctattt ccctaaaggg    4920
tttattgaga atatgttttt cgtctcagcc aatccctggg tgagtttcac cagttttgat    4980
ttaaacgtgg ccaatatgga aacttcttc gcccccgttt tcaccatggg caaatattat    5040
acgcaaggcg acaaggtgct gatgccgctg gcgattcagg ttcatcatgc cgtttgtgat    5100
ggcttccatg tcggcagaat gcttaatgaa ttacaacagt actgcgatga gtggcagggc    5160
ggggcgtaag cgggactctg gggttcgaat aaagaccgac caagcgacgt ctgagagctc    5220
cctggcgaat tcggtaccaa taaaagagct ttattttcat gatctgtgtg ttggtttttg    5280
tgtgcggcgc ggaagttcct attctctaga aagtatagga acttcctcga gccctatagt    5340
gagtcgtatt agcccttgac gatgccacat cctgagcaaa taattcaacc actaattgtg    5400
agcggataac acaaggagga aacagctatg tcattaccgt tcttaacttc tgcaccggga    5460
aaggttatta ttttttggtga acactctgct gtgtacaaca agcctgccgt cgctgctagt    5520
gtgtctgcgt tgagaaccta cctgctaata agcgagtcat ctgcaccaga tactattgaa    5580
```

```
ttggacttcc cggacattag ctttaatcat aagtggtcca tcaatgattt caatgccatc   5640
accgaggatc aagtaaactc ccaaaaattg gccaaggctc aacaagccac cgatggcttg   5700
tctcaggaac tcgttagtct tttggatccg ttgttagctc aactatccga atccttccac   5760
taccatgcag cgttttgttt cctgtatatg tttgtttgcc tatgccccca tgccaagaat   5820
attaagtttt ctttaaagtc tactttaccc atcggtgctg ggttgggctc aagcgcctct   5880
atttctgtat cactggcctt agctatggcc tacttggggg ggttaatagg atctaatgac   5940
ttggaaaagc tgtcagaaaa cgataagcat atagtgaatc aatgggcctt cataggtgaa   6000
aagtgtattc acggtacccc ttcaggaata gataacgctg tggccactta tggtaatgcc   6060
ctgctatttg aaaagactc acataatgga acaataaaca caaacaattt taagttctta   6120
gatgatttcc cagccattcc aatgatccta acctatacta gaattccaag gtctacaaaa   6180
gatcttgttg ctcgcgttcg tgtgttggtc accgagaaat ttcctgaagt tatgaagcca   6240
attctagatg ccatgggtga atgtgcccta caaggcttag agatcatgac taagttaagt   6300
aaatgtaaag gcaccgatga cgaggctgta gaaactaata atgaactgta tgaacaacta   6360
ttggaattga taagaataaa tcatggactg cttgtctcaa tcggtgtttc tcatcctgga   6420
ttagaactta ttaaaaatct gagcgatgat ttgagaattg gctccacaaa acttaccggt   6480
gctggtggcg gcggttgctc tttgactttg ttacgaagag acattactca agagcaaatt   6540
gacagcttca aaagaaatt gcaagatgat tttagttacg agacatttga aacagacttg   6600
ggtgggactg gctgctgttt gttaagcgca aaaaatttga ataagatct taaaatcaaa   6660
tccctagtat tccaattatt tgaaaataaa actaccacaa agcaacaaat tgacgatcta   6720
ttattgccag gaaacacgaa tttaccatgg acttcataag ctaatttgcg ataggcctgc   6780
acccttaagg aggaaaaaaa catgtcagag ttgagagcct tcagtgcccc agggaaagcg   6840
ttactagctg gtggatattt agttttagat acaaaatatg aagcatttgt agtcggatta   6900
tcggcaagaa tgcatgctgt agcccatcct tacggttcat gcaagggtc tgataagttt   6960
gaagtgcgtg tgaaaagtaa acaatttaaa gatggggagt ggctgtacca tataagtcct   7020
aaaagtggct tcattcctgt ttcgataggc ggatctaaga acccttcat tgaaaaagtt   7080
atcgctaacg tatttagcta ctttaaacct aacatggacg actactgcaa tagaaacttg   7140
ttcgttattg atattttctc tgatgatgcc taccattctc aggaggatag cgttaccgaa   7200
catcgtggca acagaagatt gagttttcat tcgcacagaa ttgaagaagt tcccaaaaca   7260
gggctgggct cctcggcagg tttagtcaca gttttaacta cagcttttggc ctccttttt   7320
gtatcggacc tggaaaataa tgtagacaaa tatagagaag ttattcataa tttagcacaa   7380
gttgctcatt gtcaagctca gggtaaaatt ggaagcgggt ttgatgtagc ggcggcagca   7440
tatggatcta tcagatatag aagattccca cccgcattaa tctctaattt gccagatatt   7500
ggaagtgcta cttacggcag taaactggcg catttggttg atgaagaaga ctggaatatt   7560
acgattaaaa gtaaccattt accttcggga ttaactttat ggatgggcga tattaagaat   7620
ggttcagaaa cagtaaaact ggtccagaag gtaaaaaatt ggtatgattc gcatatgcca   7680
gaaagcttga aaatatatac agaactcgat catgcaaatt ctagatttat ggatggacta   7740
tctaaactag atcgcttaca cgagactcat gacgattaca gcgatcagat atttgagtct   7800
cttgagagga atgactgtac ctgtcaaaag tatcctgaaa tcacagaagt tagagatgca   7860
gttgccacaa ttgacgttc cttagaaaa ataactaaag aatctggtgc cgatatcgaa   7920
cctcccgtac aaactagctt attggatgat tgccagacct aaaaggagt tcttacttgc   7980
```

-continued

```
ttaatacctg gtgctggtgg ttatgacgcc attgcagtga ttactaagca agatgttgat    8040
cttagggctc aaaccgctaa tgacaaaaga ttttctaagg ttcaatggct ggatgtaact    8100
caggctgact ggggtgttag gaaagaaaaa gatccggaaa cttatcttga taaataactt    8160
aaggtagctc catgcagaat tcgcccttaa ggaggaaaaa aaaatgaccg tttacacagc    8220
atccgttacc gcacccgtca acatcgcaac ccttaagtat tgggggaaaa gggacacgaa    8280
gttgaatctg cccaccaatt cgtccatatc agtgacttta tcgcaagatg acctcagaac    8340
gttgacctct gcggctactg cacctgagtt tgaacgcgac actttgtggt taaatggaga    8400
accacacagc atcgacaatg aaagaactca aaattgtctg cgcgacctac gccaattaag    8460
aaaggaaatg gaatcgaagg acgcctcatt gcccacatta tctcaatgga aactccacat    8520
tgtctccgaa ataaactttc ctacagcagc tggtttagct tcctccgctg ctggctttgc    8580
tgcattggtc tctgcaattg ctaagttata ccaattacca cagtcaactt cagaaatatc    8640
tagaatagca agaaaggggt ctggttcagc ttgtagatcg ttgtttggcg atacgtggc    8700 ctgggaaatg gaaaagctg aagatggtca tgattccatg gcagtacaaa tcgcagacag    8760
ctctgactgg cctcagatga aagcttgtgt cctagttgtc agcgatatta aaaggatgt    8820 gagttccact cagggtatgc aattgaccgt ggcaacctcc gaactattta agaaagaat    8880 tgaacatgtc gtaccaaga gatttgaagt catgcgtaaa gccattgttg aaaaagattt    8940
cgccaccttt gcaaaggaaa caatgatgga ttccaactct ttccatgcca catgtttgga    9000
ctctttccct ccaatattct acatgaatga cacttccaag cgtatcatca gttggtgcca    9060
caccattaat cagttttacg gagaaacaat cgttgcatac acgtttgatg caggtccaaa    9120
tgctgtgttg tactacttag ctgaaaatga gtcgaaactc tttgcattta tctataaatt    9180
gtttggctct gttcctggat gggacaagaa atttactact gagcagcttg aggctttcaa    9240
ccatcaattt gaatcatcta acttactgc acgtgaattg gatcttgagt tgcaaaagga    9300
tgttgccaga gtgattttaa ctcaagtcgg ttcaggccca caagaaacaa acgaatcttt    9360
gattgacgca aagactggtc taccaaagga ataagatcaa ttcgctgcat cgcccttagg    9420
aggtaaaaaa aaatgactgc cgacaacaat agtatgcccc atggtgcagt atctagttac    9480
gccaaattag tgcaaaacca aacacctgaa gacattttgg aagagtttcc tgaaattatt    9540
ccattacaac aaagacctaa tacccgatct agtgagacgt caaatgacga aagcggagaa    9600
acatgttttt ctggtcatga tgaggagcaa attaagttaa tgaatgaaaa ttgtattgtt    9660
ttggattggg acgataatgc tattggtgcc ggtaccaaga aagtttgtca tttaatgaa    9720 aatattgaaa agggtttact acatcgtgca ttctccgtct ttattttcaa tgaacaaggt    9780
gaattacttt tacaacaaag agccactgaa aaaataactt tccctgatct ttggactaac    9840
acatgctgct ctcatccact atgtattgat gacgaattag gtttgaaggg taagctagac    9900
gataagatta agggcgctat tactgcggcg gtgagaaaac tagatcatga attaggtatt    9960
ccagaagatg aaactaagac aaggggtaag tttcactttt taaacagaat ccattacatg   10020
gcaccaagca tgaaccatg gggtgaacat gaaattgatt acatcctatt ttataagatc   10080
aacgctaaag aaaacttgac tgtcaaccca aacgtcaatg aagttagaga cttcaaatgg   10140
gtttcaccaa atgatttgaa aactatgttt gctgacccaa gttacaagtt tacgccttgg   10200
tttaagatta tttgcgagaa ttacttattc aactggtggg agcaattaga tgacctttct   10260
gaagtggaaa atgacaggca aattcataga atgctataac aacgcgtcta caaataaaaa   10320
aggcacgtca gatgacgtgc cttttttctt ggggcc                             10356
```

```
<210> SEQ ID NO 91
<211> LENGTH: 43
<212> TYPE: DNA
<213> ORGANISM: Artificial Sequence
<220> FEATURE:
<223> OTHER INFORMATION: Synthetic Construct

<400> SEQUENCE: 91
gcatgctcga gcggccgctt ttaatcaaac atcctgccaa ctc            43

<210> SEQ ID NO 92
<211> LENGTH: 37
<212> TYPE: DNA
<213> ORGANISM: Artificial Sequence
<220> FEATURE:
<223> OTHER INFORMATION: Synthetic Construct

<400> SEQUENCE: 92
gatcgaaggg cgatcgtgtc acagtctggc gaaaccg                   37

<210> SEQ ID NO 93
<211> LENGTH: 43
<212> TYPE: DNA
<213> ORGANISM: Artificial Sequence
<220> FEATURE:
<223> OTHER INFORMATION: Synthetic Construct

<400> SEQUENCE: 93
ctgaattctg cagatatctg tttttccact cttcgttcac ttt            43

<210> SEQ ID NO 94
<211> LENGTH: 33
<212> TYPE: DNA
<213> ORGANISM: Artificial Sequence
<220> FEATURE:
<223> OTHER INFORMATION: Synthetic Construct

<400> SEQUENCE: 94
tctagagggc ccaagaaaaa tgccccgctt acg                       33

<210> SEQ ID NO 95
<211> LENGTH: 111
<212> TYPE: DNA
<213> ORGANISM: Artificial Sequence
<220> FEATURE:
<223> OTHER INFORMATION: Synthetic Construct

<400> SEQUENCE: 95
gatcgcggcc gcgcccttga cgatgccaca tcctgagcaa ataattcaac cactaattgt    60
gagcggataa cacaaggagg aaacagctat gtcattaccg ttcttaactt c             111

<210> SEQ ID NO 96
<211> LENGTH: 75
<212> TYPE: DNA
<213> ORGANISM: Artificial Sequence
<220> FEATURE:
<223> OTHER INFORMATION: Synthetic Construct

<400> SEQUENCE: 96
gatcgggccc caagaaaaaa ggcacgtcat ctgacgtgcc tttttatttt gtagacgcgt    60
tgttatagca ttcta                                                    75

<210> SEQ ID NO 97
<211> LENGTH: 81
<212> TYPE: DNA
```

```
<213> ORGANISM: Artificial Sequence
<220> FEATURE:
<223> OTHER INFORMATION: Synthetic Construct

<400> SEQUENCE: 97
aaagtagccg aagatgacgg tttgtcacat ggagttggca ggatgtttga ttaaaagcaa      60
ttaaccctca ctaaagggcg g                                                81

<210> SEQ ID NO 98
<211> LENGTH: 160
<212> TYPE: DNA
<213> ORGANISM: Artificial Sequence
<220> FEATURE:
<223> OTHER INFORMATION: Synthetic Construct

<400> SEQUENCE: 98
agagtgttca ccaaaaataa taacctttcc cggtgcagaa gttaagaacg gtaatgacat      60
agctgtttcc tccttgtgtt atccgctcac aattagtggt tgaattattt gctcaggatg     120
tggcatcgtc aagggctaat acgactcact atagggctcg                           160

<210> SEQ ID NO 99
<211> LENGTH: 60
<212> TYPE: DNA
<213> ORGANISM: Artificial Sequence
<220> FEATURE:
<223> OTHER INFORMATION: Synthetic Construct

<400> SEQUENCE: 99
gatcatgcat tcgcccttag gaggtaaaaa acatgtgtg cgacctcttc tcaatttact       60

<210> SEQ ID NO 100
<211> LENGTH: 38
<212> TYPE: DNA
<213> ORGANISM: Artificial Sequence
<220> FEATURE:
<223> OTHER INFORMATION: Synthetic Construct

<400> SEQUENCE: 100
cggtcgacgg atccctgcag ttagacatac atcagctg                              38

<210> SEQ ID NO 101
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 101
gtgcggccgc aagcttgtcg acggagctcg aattcggatc cctgcagtta gacatacatc      60
agctggttaa tcgggaaagg gtcaatcagc agcagtttga tgcggttttc agtcgcgtag     120
tctgggcgac ccagaccatc gccatactgg taggtgcagt gggaaacacg tgccatgtta     180
actgcgattt ccatgaacgc tttaggcagc agggtggagt cgctaacgcg ttcacgattc     240 atcttttcc attcggcgtc gatcagttta cgcagttctt cgcgggcctg ttcctcgctg     300
gtaccatcgt tttcgtgcat gtagctaatg atagaattgg tagtctcgcc acgttccagc     360
tccgccgcag aggtggccag atcgttcac aggcggaaga taacgcagct agaacgcacc      420
agaccatgga gtcggtcag ggaacgcagc gcgtggtcgg agatgtcttc ctgctgctgg      480
catacggaaa agtaagacgg cgccagcagc gctacaccgg aggaggaaac gctggcgttt     540
tccaggtact tggagaaagc cgggataatt ttgttgttgg accatttcgc ctcttgcaga     600
```

```
aaggctttgc acagttcacg ccagcttttc gtcagatagg acaggttgtt atgacctttc    660
tctttcagaa tagaatagga cgtgtcgtta acggtgttgt acagtgccag gaaacacagt    720
ttcatatagt ccggcagggt gttaatagcg ttaacgtccc agcgctctac agcatcggtg    780
aacagttgca gttcgtccag agtgccataa acgtcataca cgtcatcgat gatcgtcacc    840
agaccaaaca ttttagtaac agctttgcga cattcaccaa actgcgggtc tggcgccata    900
cccagtgccc agaaataaac ttccatcagg cggtcgcgta caaaatccag tttgctagcc    960
aggcccatct cggtccacca gcgggacaga tcttgcagct ctttctggtg cagggtctgt   1020
accatgttaa aatccagctt cgccagctcc agcagcagct ggtgatgcgg ttctttcggt   1080
tcgtatttat ccaggaacca acgtgcctcc agacggtgca gacgctggtg atatggcagt   1140
tccagggcgt ggctcacttg ttctgcaacc ttggtattaa tgccttcttt caggttgttc   1200
ttcaggtggg tgatggaaaa ggtacgcgcc tcctccagca ggttctcacc ctcgaaaccc   1260
aggtaagacg cttcatacag gctcagcagg ccttggacgt cacctttcag ttcaccgctg   1320
aaaccacctt ctttatcctt gaaacgctca aaaacatcct gagaaacctc gaaaccgtgc   1380
tgacgcagca gacggaaaga cagagcggtt cgtgcaggt cagatttgtt cttttttgttt   1440
tcgtccagca gtacgatgtt ttccagggct ttaatgatgt ctttttcaaa tttgtaggtc   1500
agacccaggc gctgcacatc gtcgatcagc tccagcaggg acagcggctg ggtgtctaca   1560
cggttgatca tgcagcgaac ttcttcctcc agtttggtcg ctttctcctc cagcttttcc   1620
actttcaggt cgttctccag ggattgcagg aattcgaaat tccacaggtt tggctgatag   1680
tttgcggaac gacgggaatt atgctcggta atctgagtaa attgagaaga ggtcgcacac   1740
atggtatatc tccttcttaa agttaaacaa aattatttct agaggggaat tgttatccgc   1800
tcacaattcc cctatagtga gtcgtattaa tttcgcggga tcgagatctc gatcctctac   1860
gccggacgca tcgtggccgg catcaccggc gccacaggtg cggttgctgg cgcctatatc   1920
gccgacatca ccgatgggga agatcgggct cgccacttcg ggctcatgag cgcttgtttc   1980
ggcgtgggta tggtggcagg ccccgtggcc ggggggactgt tgggcgccat ctccttgcat   2040
gcaccattcc ttgcggcggc ggtgctcaac ggcctcaacc tactactggg ctgcttccta   2100
atgcaggagt cgcataaggg agagcgtcga gatcccggac accatcgaat ggcgcaaaac   2160
ctttcgcggt atggcatgat agcgcccgga agagagtcaa ttcagggtgg tgaatgtgaa   2220
accagtaacg ttatacgatg tcgcagagta tgccggtgtc tcttatcaga ccgtttcccg   2280
cgtggtgaac caggccagcc acgtttctgc gaaaacgcgg gaaaagtgg aagcggcgat   2340
ggcggagctg aattacattc ccaaccgcgt ggcacaacaa ctggcgggca aacagtcgtt   2400
gctgattggc gttgccacct ccagtctggc cctgcacgcg ccgtcgcaaa ttgtcgcggc   2460
gattaaatct cgcgccgatc aactgggtgc cagcgtggtg gtgtcgatgg tagaacgaag   2520
cggcgtcgaa gcctgtaaag cggcggtgca caatcttctc gcgcaacgcg tcagtgggct   2580
gatcattaac tatccgctgg atgaccagga tgccattgct gtggaagctg cctgcactaa   2640
tgttccggcg ttatttcttg atgtctctga ccagacaccc atcaacagta ttattttctc   2700
ccatgaagac ggtacgcgac tgggcgtgga gcatctggtc gcattgggtc accagcaaat   2760
cgcgctgtta gcgggcccat taagttctgt ctcggcgcgt ctgcgtctgg ctggctggca   2820
taaatatctc actcgcaatc aaattcagcc gatagcggaa cgggaaggcg actggagtgc   2880
catgtccggt tttcaacaaa ccatgcaaat gctgaatgag gcatcgttc ccactgcgat   2940
gctggttgcc aacgatcaga tggcgctggg cgcaatgcgc gccattaccg agtccgggct   3000
```

```
gcgcgttggt gcggatatct cggtagtggg atacgacgat accgaagaca gctcatgtta    3060
tatcccgccg ttaaccacca tcaaacagga ttttcgcctg ctggggcaaa ccagcgtgga    3120
ccgcttgctg caactctctc agggccaggc ggtgaagggc aatcagctgt tgcccgtctc    3180
actggtgaaa agaaaaacca ccctggcgcc caatacgcaa accgcctctc cccgcgcgtt    3240
ggccgattca ttaatgcagc tggcacgaca ggtttcccga ctggaaagcg gcagtgagc    3300 gcaacgcaat taatgtaagt tagctcactc attaggcacc gggatctcga ccgatgccct    3360
tgagagcctt caacccagtc agctccttcc ggtgggcgcg gggcatgact atcgtcgccg    3420
cacttatgac tgtcttcttt atcatgcaac tcgtaggaca ggtgccggca cgctctgggc    3480
tcattttcgg cgaggaccgc tttcgctgga gcgcgacgat gatcggcctg tcgcttgcgg    3540
tattcggaat cttgcacgcc ctcgctcaag ccttcgtcac tggtcccgcc accaaacgtt    3600
tcggcgagaa gcaggccatt atcgccggca tggcggcccc acgggtgcgc atgatcgtgc    3660
tcctgtcgtt gaggacccgg ctaggctggc ggggttgcct tactggttag cagaatgaat    3720
caccgatacg cgagcgaacg tgaagcgact gctgctgcaa aacgtctgcg acctgagcaa    3780
caacatgaat ggtcttcggt ttccgtgttt cgtaaagtct ggaaacgcgg aagtcagcgc    3840
cctgcaccat tatgttccgg atctgcatcg caggatgctg ctggctaccc tgtggaacac    3900
ctacatctgt attaacgaag cgctggcatt gaccctgagt gattttttctc tggtcccgcc    3960 gcatccatac cgccagttgt ttaccctcac aacgttccag taaccgggca tgttcatcat    4020
cagtaacccg tatcgtgagc atcctctctc gtttcatcgg tatcattacc cccatgaaca    4080
gaaatccccc ttacacggag gcatcagtga ccaaacagga aaaaaccgcc cttaacatgg    4140
cccgctttat cagaagccag acattaacgc ttctggagaa actcaacgag ctggacgcgg    4200
atgaacaggc agacatctgt gaatcgcttc acgaccacgc tgatgagctt taccgcagct    4260
gcctcgcgcg tttcggtgat gacggtgaaa acctctgaca catgcagctc ccggagacgg    4320
tcacagcttg tctgtaagcg gatgccggga gcagacaagc ccgtcagggc gcgtcagcgg    4380
gtgttggcgg gtgtcgggcg gcagccatga cccagtcacg tagcgatagc ggagtgtata    4440
ctggcttaac tatgcggcat cagagcagat tgtactgaga gtgcaccata tgcggtgt    4500 gaaataccgc acagatgcgt aaggagaaaa taccgcatca ggcgctcttc cgcttcctcg    4560
ctcactgact cgctgcgctc ggtcgttcgg ctgcggcgag cggtatcagc tcactcaaag    4620
gcggtaatac ggttatccac agaatcaggg gataacgcag gaaagaacat gtgagcaaaa    4680
ggccagcaaa aggccaggaa ccgtaaaaag gccgcgttgc tggcgttttt ccataggctc    4740
cgcccccctg acgagcatca caaaaatcga cgctcaagtc agaggtggcg aaacccgaca    4800
ggactataaa gataccaggc gtttccccct ggaagctccc tcgtgcgctc tcctgttccg    4860
accctgccgc ttaccggata cctgtccgcc tttctccctt cgggaagcgt ggcgctttct    4920
catagctcac gctgtaggta tctcagttcg gtgtaggtcg ttcgctccaa gctgggctgt    4980
gtgcacgaac cccccgttca gcccgaccgc tgcgccttat ccggtaacta tcgtcttgag    5040
tccaacccgg taagacacga cttatcgcca ctggcagcag ccactggtaa caggattagc    5100
agagcgaggt atgtaggcgg tgctacagag ttcttgaagt ggtggcctaa ctacggctac    5160
actagaagga cagtatttgg tatctgcgct ctgctgaagc cagttacctt cggaaaaaga    5220
gttggtagct cttgatccgg caaacaaacc accgctggta gcggtggttt ttttgtttgc    5280
aagcagcaga ttacgcgcag aaaaaaagga tctcaagaag atcctttgat cttttctacg    5340
gggtctgacg ctcagtggaa cgaaaactca cgttaaggga ttttggtcat gacaataaa    5400
```

|   |   |   |   |   |      |
|---|---|---|---|---|------|
| actgtctgct | tacataaaca | gtaatacaag | gggtgttatg | agccatattc aacgggaaac | 5460 |
| gtcttgctct | aggccgcgat | taaattccaa | catggatgct | gatttatatg ggtataaatg | 5520 |
| ggctcgcgat | aatgtcgggc | aatcaggtgc | gacaatctat | cgattgtatg ggaagcccga | 5580 |
| tgcgccagag | ttgtttctga | aacatggcaa | aggtagcgtt | gccaatgatg ttacagatga | 5640 |
| gatggtcaga | ctaaactggc | tgacggaatt | tatgcctctt | ccgaccatca agcattttat | 5700 |
| ccgtactcct | gatgatgcat | ggttactcac | cactgcgatc | cccgggaaaa cagcattcca | 5760 |
| ggtattagaa | gaatatcctg | attcaggtga | aaatattgtt | gatgcgctgg cagtgttcct | 5820 |
| gcgccggttg | cattcgattc | ctgtttgtaa | ttgtcctttt | aacagcgatc gcgtatttcg | 5880 |
| tctcgctcag | gcgcaatcac | gaatgaataa | cggtttggtt | gatgcgagtg attttgatga | 5940 |
| cgagcgtaat | ggctggcctg | ttgaacaagt | ctggaaagaa | atgcataaac ttttgccatt | 6000 |
| ctcaccggat | tcagtcgtca | ctcatggtga | tttctcactt | gataacctta ttttttgacga | 6060 |
| ggggaaatta | ataggttgta | ttgatgttgg | acgagtcgga | atcgcagacc gataccagga | 6120 |
| tcttgccatc | ctatggaact | gcctcggtga | gttttctcct | tcattacaga acggctttt | 6180 |
| tcaaaaatat | ggtattgata | atcctgatat | gaataaattg | cagtttcatt tgatgctcga | 6240 |
| tgagttttc | taagaattaa | ttcatgagcg | gatacatatt | tgaatgtatt tagaaaaata | 6300 |
| aacaaatagg | ggttccgcgc | acatttcccc | gaaaagtgcc | acctgaaatt gtaaacgtta | 6360 |
| atattttgtt | aaaattcgcg | ttaaattttt | gttaaatcag | ctcatttttt aaccaatagg | 6420 |
| ccgaaatcgg | caaaatccct | tataaatcaa | agaatagac | cgagataggg ttgagtgttg | 6480 |
| ttccagtttg | gaacaagagt | ccactattaa | agaacgtgga | ctccaacgtc aaagggcgaa | 6540 |
| aaaccgtcta | tcagggcgat | ggcccactac | gtgaaccatc | accctaatca agttttttgg | 6600 |
| ggtcgaggtg | ccgtaaagca | ctaaatcgga | accctaaagg | gagcccccga tttagagctt | 6660 |
| gacggggaaa | gccggcgaac | gtggcgagaa | aggaagggaa | gaaagcgaaa ggagcgggcg | 6720 |
| ctagggcgct | ggcaagtgta | gcggtcacgc | tgcgcgtaac | caccacaccc gccgcgctta | 6780 |
| atgcgccgct | acagggcgcg | tcccattcgc | caatccggat | atagttcctc ctttcagcaa | 6840 |
| aaaacccctc | aagacccgtt | tagaggcccc | aaggggttat | gctagttatt gctcagcggt | 6900 |
| ggcagcagcc | aactcagctt | cctttcgggc | tttgttagca | gccggatctc agtggtggtg | 6960 |
| gtggtggtgc | tcga |   |   |   | 6974 |

<210> SEQ ID NO 102
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 102

|   |   |   |   |   |     |
|---|---|---|---|---|-----|
| gcggccgcgc | ccttgacgat | gccacatcct | gagcaaataa | ttcaaccact aattgtgagc | 60 |
| ggataacaca | aggaggaaac | agccatggta | tcctgttctg | cgccgggtaa gatttacctg | 120 |
| ttcggtgaac | acgccgtagt | ttatggcgaa | actgcaattg | cgtgtgcggt ggaactgcgt | 180 |
| acccgtgttc | gcgcggaact | caatgactct | atcactattc | agagccagat cggccgcacc | 240 |
| ggtctggatt | tcgaaaagca | cccttatgtg | tctgcggtaa | ttgagaaaat gcgcaaatct | 300 |
| attcctatta | acggtgtttt | cttgaccgtc | gattccgaca | tcccggtggg ctccggtctg | 360 |
| ggtagcagcg | cagccgttac | tatcgcgtct | attggtgcgc | tgaacgagct gttcggcttt | 420 |
| ggcctcagcc | tgcaagaaat | cgctaaactg | ggccacgaaa | tcgaaattaa agtacagggt | 480 |

-continued

| | |
|---|---|
| gccgcgtccc caaccgatac gtatgttct accttcggcg gcgtggttac catcccggaa | 540 |
| cgtcgcaaac tgaaaactcc ggactgcggc attgtgattg gcgataccgg cgttttctcc | 600 |
| tccaccaaag agttagtagc taacgtacgt cagctgcgcg aaagctaccc ggatttgatc | 660 |
| gaaccgctga tgacctctat tggcaaaatc tctcgtatcg gcgaacaact ggttctgtct | 720 |
| ggcgactacg catccatcgg ccgcctgatg aacgtcaacc agggtctcct ggacgccctg | 780 |
| ggcgttaaca tcttagaact gagccagctg atctattccg ctcgtgcggc aggtgcgttt | 840 |
| ggcgctaaaa tcacgggcgc tggcggcggt ggctgtatgg ttgcgctgac cgctccggaa | 900 |
| aaatgcaacc aagtggcaga agcggtagca ggcgctggcg gtaaagtgac tatcactaaa | 960 |
| ccgaccgagc aaggtctgaa agtagattaa gccttgactt aatagctgct tatttcgccc | 1020 |
| ttatggtacc tagtaggagg aaaaaaacat ggaaatgcgt caaccggctg tcgcaggtca | 1080 |
| attctaccca ctgcgttgcg agaacctgga aaacgaactg aaacgctgct cgaaggcct | 1140 |
| ggagatccgc gaacaagaag tgctgggcgc agtctgtccg cacgccggtt atatgtactc | 1200 |
| tggcaaagtt gcggcgcacg tctatgccac tctgccggaa gctgatacct acgtaatctt | 1260 |
| cggcccgaac cacaccggct acggtagccc tgtctctgtg agccgtgaaa cttggaagac | 1320 |
| cccgttgggc aatatcgatg ttgacctgga actggcggac ggcttcctgg gttccatcgt | 1380 |
| agatgcggat gaactcggtc acaaatacga acactctatc gaagttcagc tgccgtttct | 1440 |
| gcaataccgt tttgaacgcg atttcaaaat tctgccaatc tgcatgggta tgcaagacga | 1500 |
| agaaaccgcg gtcgaagtag gtaacctgct ggcggatctg atcagcgagt ccggtaaacg | 1560 |
| tgctgtgatc atcgcaagct ctgatttcac ccactatgag acggctgaac gtgccaaaga | 1620 |
| aatcgattcc gaagttattg attctatcct gaactttgac atctctggca tgtacgatcg | 1680 |
| cctgtatcgc cgtaacgcct ctgtttgcgg ttacggcccg atcaccgcta tgctgacggc | 1740 |
| aagcaaaaag ctgggcggct ctcgtgcgac tttgctgaaa tacgcaaaca gcggtgacgt | 1800 |
| gtccggtgat aaagacgctg tggtgggcta cgccgccatc atcgttgagt aagctgatta | 1860 |
| aaggttgaac agataggatt tcgtcatgga tcctacaagg aggaaaaaaa catgaatgct | 1920 |
| tctaatgaac cggtgattct gaaactgggt ggctctgcta ttaccgacaa aggtgcctac | 1980 |
| gaaggcgtag ttaaggaagc tgatttgctg cgcatcgcac aggaagttag cggtttccgt | 2040 |
| ggcaagatga tcgtggttca tggtgctggt agcttcggcc atacgtacgc gaagaaatac | 2100 |
| ggcctggacc gtaccttcga cccagagggc gcaattgtta ctcatgaatc tgttaaaaag | 2160 |
| ctcgcctcca agttgtagg tgctctgaat agcttcggcg tgcgtgctat cgcggtgcat | 2220 |
| cctatggact gcgcagtatg ccgtaacggt cgtatcgaaa cgatgtatct ggactccatc | 2280 |
| aagttaatgc tggaaaaagg tctggtgccg gttctgcacg gcgacgtcgc aatggatatt | 2340 |
| gaactgggca cttgtatcct gtccggtgat caaatcgttc cttacctggc caaagaactg | 2400 |
| ggtatctccc gcctcggcct gggcagcgca gaggatggtg tgctggatat ggagggcaaa | 2460 |
| cctgtaccgg aaatcacccc agaaactttc gaagagttcc gccactgcat cggtggttct | 2520 |
| ggttctactg atgtaaccgg tggcatgctg gcaaagtgc tggaacttct ggaattgagc | 2580 |
| aaaaattctt ccattactag ctacatttc aacgctggta agcagacaa catctaccgc | 2640 |
| tttctgaatg gtgagtccat cggcactcgc atcagcccgg acaagcgtgt ttaagctagt | 2700 |
| tattaaccta aatgctctaa accagttatg agctctacaa ggaggaaaaa aacatgatta | 2760 |
| acactaccag ccgccgcaaa attgaacacc tgaaactctg cgcagaatcc ccggttgaag | 2820 |
| cgcgtcaggt atctgccggc tttgaagacg ttactctgat ccaccgcgct ttaccggagc | 2880 |

| | |
|---|---|
| tgaacatgga tgaactggac ctcagcgttg atttcctggg taaacgcatc aaagcgccgt | 2940 |
| tcctgattgc gtctatcacg ggtggtcacc cagataccat cccggttaac gctgcgctgg | 3000 |
| cagctgctgc tgaggagctg ggtgttggca tcggcgttgg ctctcagcgc gcggccattg | 3060 |
| atgatccgag ccaggaagac agcttccgtg tagtgcgtga tgaagcccca gatgcgtttg | 3120 |
| tttatggcaa cgtcggcgca gcacagatcc gtcagtatgg tgttgaaggt gttgaaaaac | 3180 |
| tgatcgaaat gattgacgca gatgccttgg caatccacct gaactttctg caagaagcgg | 3240 |
| tccaaccgga aggtgaccgc gacgcgaccg gttgcctgga catgattacc gaaatttgct | 3300 |
| ctcagattaa aactccggta atcgtgaaag aaaccggtgc aggcattagc cgtgaagatg | 3360 |
| cgattctgtt ccagaaagct ggcgtgagcg caatcgacgt tggcggcgcg ggcggcacct | 3420 |
| cctgggctgg cgtcgaggtc taccgtgcta agaaagccg tgactctgtt agcgagcgtt | 3480 |
| taggtgagct gttttgggat tcggcattc cgacggtagc ttctctgatt gaatcccgcg | 3540 |
| tttccttgcc gctgatcgca accggcgta tccgtaacgg tctggacatt gctaaaagca | 3600 |
| tgctctcgg cgcaagcgct gccagcgccg ctctgccgtt cgttggtccg tccctggagg | 3660 |
| gcaaagaatc cgttgtacgt gtgctgagct gcatgctgga agaatttaaa gcagcaatgt | 3720 |
| ttttgtgcgg ttgcggcaac atcaaagacc tgcacaactc tccagtagtg gtaactggtt | 3780 |
| ggacccgcga ataccggag cagcgcggtt ttaacgttaa ggacctctcc ctgccgggca | 3840 |
| acgctctgta agcttcaacg cgtctacaaa taaaaaaggc acgtcagatg acgtgccttt | 3900 |
| tttcttgtct aga | 3913 |

<210> SEQ ID NO 103
<211> LENGTH: 6848
<212> TYPE: DNA
<213> ORGANISM: Artificial Sequence
<220> FEATURE:
<223> OTHER INFORMATION: Synthetic Construct

<400> SEQUENCE: 103

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgtgtgc | 420 |
| gacctcttct caatttactc agattaccga gcataattcc cgtcgttccg caaactatca | 480 |
| gccaaacctg tggaatttcg aattcctgca atccctggag aacgacctga agtggaaaaa | 540 |
| gctggaggag aaagcgacca aactggagga agaagttcgc tgcatgatca accgtgtaga | 600 |
| cacccagccg ctgtccctgc tggagctgat cgacgatgtg cagcgcctgg gtctgaccta | 660 |
| caaatttgaa aaagacatca ttaaagccct ggaaaacatc gtactgctgg acgaaaacaa | 720 |
| aaagaacaaa tctgacctgc acgcaaccgc tctgtctttc cgtctgctgc gtcagcacgg | 780 |
| tttcgaggtt tctcaggatg tttttgagcg tttcaaggat aaagaaggtg gtttcagcgg | 840 |
| tgaactgaaa ggtgacgtcc aaggcctgct gagcctgtat gaagcgtctt acctgggttt | 900 |
| cgagggtgag aacctgctgg aggaggcgcg tacctttttcc atcacccacc tgaagaacaa | 960 |
| cctgaaagaa ggcattaata ccaaggttgc agaacaagtg agccacgccc tggaactgcc | 1020 |

```
atatcaccag cgtctgcacc gtctggaggc acgttggttc ctggataaat acgaaccgaa    1080
agaaccgcat caccagctgc tgctggagct ggcgaagctg gattttaaca tggtacagac    1140
cctgcaccag aaagagctgc aagatctgtc ccgctggtgg accgagatgg gcctggctag    1200
caaactggat tttgtacgcg accgcctgat ggaagtttat ttctgggcac tgggtatggc    1260
gccagacccg cagtttggtg aatgtcgcaa agctgttact aaaatgtttg gtctggtgac    1320
gatcatcgat gacgtgtatg acgttttatgg cactctggac gaactgcaac tgttcaccga    1380
tgctgtagag cgctgggacg ttaacgctat taacaccctg ccggactata tgaaactgtg    1440
tttcctggca ctgtacaaca ccgttaacga cacgtcctat tctattctga aagagaaagg    1500
tcataacaac ctgtcctatc tgacgaaaag ctggcgtgaa ctgtgcaaag cctttctgca    1560
agaggcgaaa tggtccaaca acaaaattat cccggctttc tccaagtacc tggaaaacgc    1620
cagcgtttcc tcctccggtg tagcgctgct ggcgccgtct acttttccg tatgccagca     1680 gcaggaagac atctccgacc acgcgctgcg ttccctgacc gacttccatg gtctggtgcg    1740
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
ggaacaggcc cgcgaagaac tgcgtaaact gatcgacgcc gaatggaaaa agatgaatcg    1920
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
gactgaaaac cgcatcaaac tgctgctgat tgaccctttc ccgattaacc agctgatgta    2100
tgtctaactg cataaaggag gtaaaaaaac atggtatcct gttctgcgcc gggtaagatt    2160
tacctgttcg gtgaacacgc cgtagtttat ggcgaaactg caattgcgtg tgcggtggaa    2220
ctgcgtaccc gtgttcgcgc ggaactcaat gactctatca ctattcagag ccagatcggc    2280
cgcaccggtc tggatttcga aaagcaccct tatgtgtctg cggtaattga aaaatgcgc     2340 aaatctattc ctattaacgg tgttttcttg accgtcgatt ccgacatccc ggtgggctcc    2400
ggtctgggta gcagcgcagc cgttactatc gcgtctattg gtgcgctgaa cgagctgttc    2460
ggctttggcc tcagcctgca agaaatcgct aaactgggcc acgaaatcga aattaaagta    2520
cagggtgccg cgtccccaac cgatacgtat gttttctacct tcggcggcgt ggttaccatc    2580
ccggaacgtc gcaaactgaa aactccggac tgcggcattg tgattggcga taccggcgtt    2640
ttctcctcca ccaaagagtt agtagctaac gtacgtcagc tgcgcgaaag ctacccggat    2700
ttgatcgaac cgctgatgac ctctattggc aaaatctctc gtatcggcga caactggtt     2760 ctgtctggcg actacgcatc catcggccgc ctgatgaacg tcaaccaggg tctcctggac    2820
gccctgggcg ttaacatctt agaactgagc cagctgatct attccgctcg tcggcaggt     2880 gcgtttggcg ctaaaatcac gggcgctggc ggcggtggct gtatggttgc gctgaccgct    2940
ccggaaaaat gcaaccaagt ggcagaagcg gtagcaggcg ctggcggtaa agtgactatc    3000
actaaaccga ccgagcaagg tctgaaagta gattaaagtc tagttaaagt ttaaacggtc    3060
tccagcttgg ctgttttggc ggatgagaga agattttcag cctgatacag attaaatcag    3120
aacgcagaag cggtctgata aaacagaatt tgcctggcgg cagtagcgcg gtggtcccac    3180
ctgaccccat gccgaactca gaagtgaaac gccgtagcgc cgatggtagt gtggggtctc    3240
cccatgcgag agtagggaac tgccaggcat caaataaaac gaaaggctca gtcgaaagac    3300
tgggcctttc gttttatctg ttgtttgtcg gtgaacgctc tcctgagtag acaaatccg     3360 ccgggagcgg atttgaacgt tgcgaagcaa cggcccggag ggtggcgggc aggacgcccg    3420
```

-continued

```
ccataaactg ccaggcatca aattaagcag aaggccatcc tgacggatgg ccttttttgcg    3480 tttctacaaa ctcttttttgt ttatttttct aaatacattc aaatatgtat ccgcttaacc    3540
ggaattgcca gctggggcgc cctctggtaa ggttgggaag ccctgcaaag taaactggat    3600
ggctttctcg ccgccaagga tctgatggcg caggggatca agctctgatc aagagacagg    3660
atgaggatcg tttcgcatga ttgaacaaga tggattgcac gcaggttctc cggccgcttg    3720
ggtggagagg ctattcggct atgactgggc acaacagaca atcggctgct ctgatgccgc    3780
cgtgttccgg ctgtcagcgc aggggcgccc ggttcttttt gtcaagaccg acctgtccgg    3840
tgccctgaat gaactgcaag acgaggcagc gcggctatcg tggctggcca cgacgggcgt    3900
tccttgcgca gctgtgctcg acgttgtcac tgaagcggga agggactggc tgctattggg    3960
cgaagtgccg gggcaggatc tcctgtcatc tcaccttgct cctgccgaga agtatccat    4020 catggctgat gcaatgcggc ggctgcatac gcttgatccg gctacctgcc cattcgacca    4080
ccaagcgaaa catcgcatcg agcgagcacg tactcggatg aagccggtc ttgtcgatca    4140 ggatgatctg gacgaagagc atcaggggct cgcgccagcc gaactgttcg ccaggctcaa    4200
ggcgagcatg cccgacggcg aggatctcgt cgtgacccat ggcgatgcct gcttgccgaa    4260
tatcatggtg gaaaatggcc gcttttctgg attcatcgac tgtggccggc tgggtgtggc    4320
ggaccgctat caggacatag cgttggctac ccgtgatatt gctgaagagc ttggcggcga    4380
atgggctgac cgcttcctcg tgctttacgg tatcgccgct cccgattcgc agcgcatcgc    4440
cttctatcgc cttcttgacg agttcttctg acgcatgacc aaaatccctt aacgtgagtt    4500
ttcgttccac tgagcgtcag accccgtaga aaagatcaaa ggatcttctt gagatccttt    4560
ttttctgcgc gtaatctgct gcttgcaaac aaaaaaacca ccgctaccag cggtggtttg    4620
tttgccggat caagagctac caactctttt tccgaaggta actggcttca gcagagcgca    4680
gataccaaat actgtccttc tagtgtagcc gtagttaggc caccacttca agaactctgt    4740
agcaccgcct acatacctcg ctctgctaat cctgttacca gtggctgctg ccagtggcga    4800
taagtcgtgt cttaccgggt tggactcaag acgatagtta ccggataagg cgcagcggtc    4860
gggctgaacg gggggttcgt gcacacagcc cagcttggag cgaacgacct acaccgaact    4920
gagataccta cagcgtgagc tatgagaaag cgccacgctt cccgaaggga gaaaggcgga    4980
caggtatccg gtaagcggca gggtcggaac aggagagcgc acgagggagc ttccaggggg    5040
aaacgcctgg tatctttata gtcctgtcgg gtttcgccac ctctgacttg agcgtcgatt    5100
tttgtgatgc tcgtcagggg ggcggagcct atggaaaaac gccagcaacg cggcctttttt    5160 acggttcctg gccttttgct ggccttttgc tcacatgttc tttcctgcgt tatcccctga    5220
ttctgtggat aaccgtatta ccgcctttga gtgagctgat accgctcgcc gcagccgaac    5280
gaccgagcgc agcgagtcag tgagcgagga agcggaagag cgcctgatgc ggtatttttct    5340 ccttacgcat ctgtgcggta tttcacaccg catatggtgc actctcagta caatctgctc    5400
tgatgccgca tagttaagcc agtatacact ccgctatcgc tacgtgactg ggtcatggct    5460
gcgccccgac acccgccaac acccgctgac gcgccctgac gggcttgtct gctcccggca    5520
tccgcttaca gacaagctgt gaccgtctcc gggagctgca tgtgtcagag gttttcaccg    5580
tcatcaccga aacgcgcgag gcagcagatc aattcgcgcg cgaaggcgaa gcggcatgca    5640
tttacgttga caccatcgaa tggtgcaaaa cctttcgcgg tatggcatga tagcgcccgg    5700
aagagagtca attcagggtg gtgaatgtga accagtaac gttatacgat gtcgcagagt    5760
atgccggtgt ctcttatcag accgtttccc gcgtggtgaa ccaggccagc cacgtttctg    5820
```

-continued

```
cgaaaacgcg ggaaaaagtg gaagcggcga tggcggagct gaattacatt cccaaccgcg      5880
tggcacaaca actggcgggc aaacagtcgt tgctgattgg cgttgccacc tccagtctgg      5940
ccctgcacgc gccgtcgcaa attgtcgcgg cgattaaatc tcgcgccgat caactgggtg      6000
ccagcgtggt ggtgtcgatg gtagaacgaa gcggcgtcga agcctgtaaa gcggcggtgc      6060
acaatcttct cgcgcaacgc gtcagtgggc tgatcattaa ctatccgctg gatgaccagg      6120
atgccattgc tgtggaagct gcctgcacta atgttccggc gttatttctt gatgtctctg      6180
accagacacc catcaacagt attattttct cccatgaaga cggtacgcga ctgggcgtgg      6240
agcatctggt cgcattgggt caccagcaaa tcgcgctgtt agcgggccca ttaagttctg      6300
tctcggcgcg tctgcgtctg gctggctggc ataaatatct cactcgcaat caaattcagc      6360
cgatagcgga acgggaaggc gactggagtg ccatgtccgg ttttcaacaa accatgcaaa      6420
tgctgaatga gggcatcgtt cccactgcga tgctggttgc caacgatcag atggcgctgg      6480
gcgcaatgcg cgccattacc gagtccgggc tgcgcgttgg tgcggatatc tcggtagtgg      6540
gatacgacga taccgaagac agctcatgtt atatcccgcc gtcaaccacc atcaaacagg      6600
attttcgcct gctggggcaa accagcgtgg accgcttgct gcaactctct cagggccagg      6660
cggtgaaggg caatcagctg ttgcccgtct cactggtgaa agaaaaaacc accctggcgc      6720
ccaatacgca aaccgcctct ccccgcgcgt tggccgattc attaatgcag ctggcacgac      6780
aggtttcccg actggaaagc gggcagtgag cgcaacgcaa ttaatgtgag ttagcgcgaa      6840
ttgatctg                                                              6848
```

```
<210> SEQ ID NO 104
<211> LENGTH: 22
<212> TYPE: DNA
<213> ORGANISM: Artificial Sequence
<220> FEATURE:
<223> OTHER INFORMATION: Synthetic Construct

<400> SEQUENCE: 104
caccatggta tcctgttctg cg                                                22

<210> SEQ ID NO 105
<211> LENGTH: 22
<212> TYPE: DNA
<213> ORGANISM: Artificial Sequence
<220> FEATURE:
<223> OTHER INFORMATION: Synthetic Construct

<400> SEQUENCE: 105
ttaatctact ttcagacctt gc                                                22

<210> SEQ ID NO 106
<211> LENGTH: 66
<212> TYPE: DNA
<213> ORGANISM: Artificial Sequence
<220> FEATURE:
<223> OTHER INFORMATION: Synthetic Construct

<400> SEQUENCE: 106
gcgaacgatg cataaaggag gtaaaaaaac atggtatcct gttctgcgcc gggtaagatt      60
tacctg                                                                 66

<210> SEQ ID NO 107
<211> LENGTH: 48
<212> TYPE: DNA
<213> ORGANISM: Artificial Sequence
<220> FEATURE:
```

<223> OTHER INFORMATION: Synthetic Construct

<400> SEQUENCE: 107
gggcccgttt aaactttaac tagactttaa tctactttca gaccttgc              48

<210> SEQ ID NO 108
<211> LENGTH: 6647
<212> TYPE: DNA
<213> ORGANISM: Artificial Sequence
<220> FEATURE:
<223> OTHER INFORMATION: Synthetic Construct

<400> SEQUENCE: 108

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aaccccctatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact gacaatcggc tgctctgatg ccgccgtgtt | 660 |
| ccggctgtca gcgcagggc gcccggttct ttttgtcaag accgacctgt ccggtgccct | 720 |
| gaatgaactg caggacgagg cagcgcggct atcgtggctg gccacgacgg gcgttccttg | 780 |
| cgcagctgtg ctcgacgttg tcactgaagc gggaagggac tggctgctat tgggcgaagt | 840 |
| gccggggcag gatctcctgt catctcacct tgctcctgcc gagaaagtat ccatcatggc | 900 |
| tgatgcaatg cggcggctgc atacgcttga tccggctacc tgcccattcg accaccaagc | 960 |
| gaaacatcgc atcgagcggg cacgtactcg gatggaagcc ggtcttgtcg atcaggatga | 1020 |
| tctggacgaa gagcatcagg ggctcgcgcc agccgaactg ttcgccaggc tcaaggcgcg | 1080 |
| catgcccgac ggcgaggatc tcgtcgtgac acatggcgat gcctgcttgc cgaatatcat | 1140 |
| ggtggaaaat ggccgctttt ctggattcat cgactgtggc cggctgggtg tggcggaccg | 1200 |
| ctatcaggac atagcgttgg ctacccgtga tattgctgaa gagcttggcg gcgaatgggc | 1260 |
| tgaccgcttc ctcgtgcttt acggtatcgc cgctcccgat tcgcagcgca tcgccttcta | 1320 |
| tcgccttctt gacgagttct tctgagcggg actctggggt tcgaaatgac cgaccaagcg | 1380 |
| acgcctaact gtcagaccaa gtttactcat atactttta gattgattta aacttcatt | 1440 |
| tttaatttaa aaggatctag gtgaagatcc tttttgataa tctcatgacc aaaatccctt | 1500 |
| aacgtgagtt ttcgttccac tgagcgtcag accccgtaga aagatcaaa ggatcttctt | 1560 |
| gagatccttt ttttctgcgc gtaatctgct gcttgcaaac aaaaaaacca ccgctaccag | 1620 |
| cggtggtttg tttgccggat caagagctac caactctttt tccgaaggta actggcttca | 1680 |
| gcagagcgca gataccaaat actgtccttc tagtgtagcc gtagttaggc caccacttca | 1740 |
| agaactctgt agcaccgcct acatacctcg ctctgctaat cctgttacca gtggctgctg | 1800 |
| ccagtggcga taagtcgtgt cttaccgggt tggactcaag acgatagtta ccggataagg | 1860 |
| cgcagcggtc gggctgaacg gggggttcgt gcacacagcc cagcttggag cgaacgacct | 1920 |

```
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggcctttt  acggttcctg gccttttgct ggccttttgc tcacatgttc tttcctgcgt    2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg gccatgttaa gggcggtttt ttcctgtttg    2760
gtcactgatg cctccgtgta agggggattt ctgttcatgg gggtaatgat accgatgaaa    2820
cgagagagga tgctcacgat acgggttact gatgatgaac atgcccggtt actgaacgt     2880
tgtgagggta acaactggc  ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag ggcgctgact ccgcgtttc  cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa     3480
tccatgccaa cccgttccat gtgctcgccg aggcggcata atcgccgtg  acgatcagcg    3540
gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
```

```
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctc ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt ttcccgcgt tttcgcagaa acgtggctgg cctggttcac cacgcgggaa     5100 acgtctgat aagagacacc ggcatactct cgacatcgt ataacgttac tggtttcaca      5160
ttcaccaccc tgaattgact ctcttccggg cgctatcatg ccataccgcg aaaggttttg    5220
cgccattcga tggtgtccgg gatctcgacg ctctcccta tgcgactcct gcattaggaa     5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaattaata cgactcacta tagggaatt gtgagcggat      5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
gccagatcgg ccgcaccggt ctggatttcg aaaagcaccc ttatgtgtct gcggtaattg    5940
agaaaatgcg caaatctatt cctattaacg gtgttttctt gaccgtcgat tccgacatcc    6000
cggtgggctc cggtctgggt agcagcgcag ccgttactat cgcgtctatt ggtgcgctga    6060
acgagctgtt cggctttggc ctcagcctgc aagaaatcgc taaactgggc cacgaaatcg    6120
aaattaaagt acagggtgcc gcgtcccaa ccgatacgta tgtttctacc ttcggcggcg     6180
tggttaccat cccggaacgt cgcaaactga aaactccgga ctgcggcatt gtgattggcg    6240
ataccggcgt tttctcctcc accaaagagt tagtagctaa cgtacgtcag ctgcgcgaaa    6300
gctacccgga tttgatcgaa ccgctgatga cctctattgg caaaatctct cgtatcggcg    6360
aacaactggt tctgtctggc gactacgcat ccatcggccg cctgatgaac gtcaaccagg    6420
gtctcctgga cgccctgggc gttaacatct agaactgag ccagctgatc tattccgctc     6480
gtgcggcagg tgcgtttggc gctaaaatca cgggcgctgg cggcggtggc tgtatggttg    6540
cgctgaccgc tccggaaaaa tgcaaccaag tggcagaagc ggtagcaggc gctggcggta    6600
aagtgactat cactaaaccg accgagcaag gtctgaaagt agattaa                  6647
```

<210> SEQ ID NO 109

```
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 109
```

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aacccatct | cggtctattc | 360 |
| ttttgattta | agggattt | tgccgatttc | ggcctattgg | ttaaaaatg | agctgattta | 420 |
| acaaaattt | aacgcgaatt | ttaacaaaat | attaacgttt | acaattcag | gtggcacttt | 480 |
| tcggggaaat | gtgcgcggaa | cccctatttg | tttattttc | taaatacatt | caaatatgta | 540 |
| tccgctcatg | aattaattct | tagaaaaact | catcgagcat | caaatgaaac | tgcaattat | 600 |
| tcatatcagg | attatcaata | ccatattttt | gaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatccttttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccaggggaa | acgcctggta | tctttatagt | cctgtcgggt | ttcgccacct | ctgacttgag | 2040 |
| cgtcgatttt | tgtgatgctc | gtcaggggg | cggagcctat | ggaaaaacgc | cagcaacgcg | 2100 |
| gccttttac | ggttcctggc | cttttgctgg | ccttttgctc | acatgttctt | tcctgcgtta | 2160 |

```
tccccrgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt tttcctgttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagactttt  3000
cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag ggtggttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat ttgattgcga gtgagatatt tatgccagcc agccagacgc agacgcgccg  4020
agacagaact taatgggccc gctaacagcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccggaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
gggccagact ggaggtggca acgccaatca gcaacgactg tttgcccgcc agttgttgtg  4440
ccacgcggtt gggaatgtaa ttcagctccg ccatcgccgc ttccactttt tcccgcgttt  4500
tcgcagaaac gtggctggcc tggttcacca cgcgggaaac ggtctgataa gagacaccgg  4560
```

```
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg ttttgaggt    5460 ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880 cttttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgaccct tgacgcactac ttcggcaacg catggaaatc    6300
ctcttctggc ccgctgcaac tggtgttcgc ttacttcgct gtcgtgcaga acattaaaaa    6360
ggaagagatc gaaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480 tagcgttttct tgttacatgc gcactaaagg tatctccgaa gaactggcta ccgaaagcgt    6540
gatgaatctg atcgatgaaa cctggaaaaa gatgaacaag gaaaaactgg tggtagcct    6600 gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taacccttg    6900 gggcctctaa acgggtcttg aggggttttt tgctgaaagg aggaactata tccggat    6957
```

<210> SEQ ID NO 110
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 110

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tcccttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | ccctatttg | tttattttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatcctttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccagggggaa | acgcctggta | tctttatagt | cctgtcgggt | ttcgccacct | ctgacttgag | 2040 |
| cgtcgatttt | tgtgatgctc | gtcagggggg | cggagcctat | ggaaaaacgc | cagcaacgcg | 2100 |

```
gcctttttac ggttcctggc cttttgctgg ccttttgctc acatgttctt tcctgcgtta  2160
tccccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt tttcctgttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgccggcacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag ggtggttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat ttgattgcga gtgagatatt tatgccagcc agccagacgc agacgcgccg  4020
agacagaact taatgggccc gctaacagcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccgaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
gggccagact ggaggtggca acgccaatca gcaacgactg tttgcccgcc agttgttgtg  4440
ccacgcggtt gggaatgtaa ttcagctccg ccatcgccgc ttccactttt tcccgcgttt  4500
```

```
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaaacgcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgccg gaactgattg acaacgtcca gcgcctgggc ctgggttacc gtttcgagtc    5340
tgatatccgt cgtgcgctgg atcgcttcgt ttcctccggc ggcttcgatg cggtaaccaa    5400
gacttccctg cacgcgacgg cactgtcttt ccgtctgctg cgtcaacacg gttttgaggt    5460
ttctcaggaa gcgttcagcg gcttcaaaga ccaaaacggc aacttcctga aaaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagatctgg cagaacaggt gaaccatgca ctggaactgc cactgcatcg    5700
ccgtactcag cgtctggaag cagtatggtc tatcgaggcc taccgtaaaa aggaggacgc    5760
ggatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg acgcagttga    6060
gcgttgggac gtaaacgcca tcgacgatct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgacctt tgacgaatac ttcggcaacg catggaaatc    6300
ctcttctggc ccgctgcaac tggtgttcgc ttacttcgct gtcgtgcaga acattaaaaa    6360
ggaagagatc gataacctgc aaaaatacca tgacatcatc tctcgtcctt cccatatctt    6420
ccgtctgtgc aatgacctgg ctagcgcgtc tgcggaaatt gcgcgtggtg aaaccgcaaa    6480 tagcgttttct tgttacatgc gcactaaagg tatctccgaa gaactggcta ccgaaagcgt    6540
gatgaatctg atcgatgaaa cctggaaaaa gatgaacaag gaaaaactgg gtggtagcct    6600
gttcgcgaaa ccgttcgtgg aaaccgcgat caacctggca cgtcaatctc actgcactta    6660
tcataacggc gacgcgcata cctctcccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taaccccttg    6900
```

| | |
|---|---:|
| gggcctctaa acgggtcttg aggggttttt tgctgaaagg aggaactata tccggat | 6957 |

<210> SEQ ID NO 111
<211> LENGTH: 6963
<212> TYPE: DNA
<213> ORGANISM: Artificial Sequence
<220> FEATURE:
<223> OTHER INFORMATION: Synthetic Construct

<400> SEQUENCE: 111

| | |
|---|---:|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta taagggattt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg aattaattct tagaaaaact catcgagcat caaatgaaac tgcaatttat | 600 |
| tcatatcagg attatcaata ccatattttt gaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttcttttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa aatcccttaa | 1440 |
| cgtgagtttt cgttccactg agcgtcagac cccgtagaaa agatcaaagg atcttcttga | 1500 |
| gatcctttt ttctgcgcgt aatctgctgc ttgcaaacaa aaaaaccacc gctaccagcg | 1560 |
| gtggtttgtt tgccggatca agagctacca actcttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata agtcgtgtct taccgggttg gactcaagac gatagttacc ggataaggcg | 1800 |
| cagcggtcgg gctgaacggg gggttcgtgc acacagccca gcttggagcg aacgacctac | 1860 |
| accgaactga gatacctaca gcgtgagcta tgagaaagcg ccacgcttcc cgaagggaga | 1920 |
| aaggcggaca ggtatccggt aagcggcagg gtcggaacag gagagcgcac gagggagctt | 1980 |
| ccaggggaa acgcctggta tctttatagt cctgtcgggt ttcgccacct ctgacttgag | 2040 |

```
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160 tccctgatt  ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
```

```
ccacgcggtt gggaatgtaa ttcagctccg ccatcgccgc ttccacttttt tcccgcgttt    4500 tcgcagaaac gtggctggcc tggttcacca cgcgggaaac ggtctgataa agagacaccgg    4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcatatg cgttgtagcg tgtccaccga    5100
aaatgtgtct ttcaccgaaa ctgaaaccga aacgcgtcgt tctgcgaact acgaacctaa    5160
cagctgggac tatgattacc tgctgtcctc cgacacggac gagtccatcg aagtatacaa    5220
agacaaagcg aaaagctgg aagccgaagt tcgtcgcgag attaataacg aaaaagcaga    5280
atttctgacc ctgctggaac tgattgacaa cgtccagcgc ctgggcctgg gttaccgttt    5340
cgagtctgat atccgtcgtg cgctggatcg cttcgttttcc tccggcggct tcgatgcggt    5400
aaccaagact tccctgcacg cgacggcact gtctttccgt ctgctgcgtc aacacggttt    5460 tgaggttttct caggaagcgt tcagcggctt caaagaccaa aacggcaact tcctggagaa    5520
cctgaaggaa gatatcaaag ctatcctgag cctgtacgag gccagcttcc tggctctgga    5580
aggcgaaaac atcctggacg aggcgaaggt tttcgcaatc tctcatctga agaactgtc    5640 tgaagaaaag atcggtaaag atctggcaga acaggtgaac catgcactgg aactgccact    5700
gcatcgccgt actcagcgtc tggaagcagt actgtctatc gaggcctacc gtaaaaagga    5760
ggacgcggat caggttctgc tggagctggc aattctggat tacaacatga tccagtctgt    5820
ataccagcgt gatctgcgtg aaacgtcccg ttggtggcgt cgtgtgggtc tggcgaccaa    5880
actgcacttt gctcgtgacc gcctgattga gagcttctac tgggccgtgg gtgtagcatt    5940
cgaaccgcaa tactccgact gccgtaactc cgtcgcaaaa atgttttctt tcgtaaccat    6000
tatcgacgat atctacgatg tatacggcac cctggacgaa ctggagctgt ttactaacgc    6060
agttgagcgt tgggacgtaa acgccatcga cgatctgccg gattacatga aactgtgctt    6120
tctggctctg tataacacta ttaacgaaat cgcctacgac aacctgaaag aaaaaggtga    6180
gaacatcctg ccgtatctga ccaaagcctg ggctgacctg tgcaacgctt tcctgcaaga    6240
agccaagtgg ctgtacaaca aatctactcc gacctttgac gaatacttcg gcaacgcatg    6300
gaaatcctct tctggcccgc tgcaactggt gttcgcttac ttcgctgtcg tgcagaacat    6360
taaaaaggaa gagatcgaaa acctgcaaaa ataccatgac atcatctctc gtccttccca    6420
tatcttccgt ctgtgcaatg acctggctag cgcgtctgcg gaaattgcgc gtggtgaaac    6480
cgcaaatagc gtttcttgtt acatgcgcac taaaggtatc tccgaagaac tggctaccga    6540
aagcgtgatg aatctgatcg atgaaacctg gaaaagatg aacaaggaaa aactgggtgg    6600
tagcctgttc gcgaaaccgt tcgtggaaac cgcgatcaac ctggcacgtc aatctcactg    6660
cacttatcat aacggcgacg cgcataacct tccggatgag ctgacccgca aacgcgttct    6720
gtctgtaatc actgaaccga ttctgccgtt gaacgctaa ggatccgaat tcagctccg    6780 tcgacaagct tgcggccgca ctcgagcacc accaccacca ccactgagat ccggctgcta    6840
```

-continued

| | |
|---|---|
| acaaagcccg aaaggaagct gagttggctg ctgccaccgc tgagcaataa ctagcataac | 6900 |
| cccttggggc tctctaaacgg gtcttgaggg gttttttgct gaaaggagga actatatccg | 6960 |
| gat | 6963 |

<210> SEQ ID NO 112
<211> LENGTH: 6966
<212> TYPE: DNA
<213> ORGANISM: Artificial Sequence
<220> FEATURE:
<223> OTHER INFORMATION: Synthetic Construct

<400> SEQUENCE: 112

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcgggggc tcccttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aacctatct cggtctattc | 360 |
| ttttgattta agggatttt tgccgatttc ggcctattgg ttaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga gacgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa atcccttaa | 1440 |
| cgtgagtttt cgttccactg agcgtcagac cccgtagaaa agatcaaagg atcttcttga | 1500 |
| gatccttttt ttctgcgcgt aatctgctgc ttgcaaacaa aaaaaccacc gctaccagcg | 1560 |
| gtggtttgtt tgccggatca agagctacca actcttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata agtcgtgtct taccgggttg gactcaagac gatagttacc ggataaggcg | 1800 |
| cagcggtcgg gctgaacggg gggttcgtgc acacagccca gcttggagcg aacgacctac | 1860 |
| accgaactga gatacctaca gcgtgagcta tgagaaagcg ccacgcttcc cgaagggaga | 1920 |

-continued

```
aaggcggaca ggtatccggt aagcggcagg gtcggaacag gagagcgcac gagggagctt    1980
ccaggggaa  acgcctggta tctttatagt cctgtcgggt ttcgccacct ctgacttgag    2040
cgtcgatttt tgtgatgctc gtcaggggg  cggagcctat ggaaaaacgc cagcaacgcg    2100
gccttttac  ggttcctggc cttttgctgg cctttgctc  acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
```

-continued

```
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgtgctct gtttctaccg agaacgtttc    5100
cttcactgag acgaaaaccg aggcacgtcg tagcgcgaac tacgagccga atagctggga    5160
ctacgatttc ctgctgtctt ccgatactga cgaatctatt gaggtgtaca agacaaagc    5220 aaagaaactg gaggctgaag tgcgccgcga aattaacaac gagaaagctg aattcctgac    5280
tctgctggag ctgatcgata acgtacagcg cctgggtctg ggttaccgct tcgaatctga    5340
tatccgtcgc gcactggatc gtttcgtaag cagcggcggt ttcgatggcg tgaccaaaac    5400
gagcctgcac gctaccgcgc tgtccttccg tctgctgcgt cagcacggct tcgaagtttc    5460
tcaggaagca ttctccggtt tcaaagatca aacggtaac ttcctggaaa acctgaaaga    5520
agacactaag gcgatcctga gcctgtatga ggcaagcttt ctggccctgg agggtgagaa    5580
catcctggat gaggcgcgcg tattctccat ctcccatctg aaagagctgt ctgaagagaa    5640
aatcggtaag gaactggcag agcaggttaa tcacgcactg gaactgccgc tgcatcgtcg    5700
tacccagcgt ctggaggcgg tttggtccat cgaagcgtac cgcaaaaagg aggatgctaa    5760
ccaggttctg ctggaactgg ccatcctgga ctacaacatg atccagtccg tttaccagcg    5820
tgatctgcgt gaaacctccc gttggtggcg ccgtgtgggc ctggcgacca aactgcactt    5880
cgctaaggac cgcctgattg agtcttttta ctgggcagtc ggcgttgcgt tcgaacctca    5940
gtattctgac tgccgtaaca gcgttgcgaa aatgttcagc ttcgttacta ttatcgacga    6000
catctacgac gtttacggta ctctggacga gctggaactg tttaccgacg ctgtcgaacg    6060
ttgggatgtt aacgccatca acgatctgcc tgactacatg aaactgtgct tcctggcact    6120
gtataacacg atcaacgaaa ttgcatacga caacctgaaa gacaaaggtg aaaacatcct    6180
gccgtacctg actaaagcgt gggcggatct gtgtaacgct tttctgcaag aagcgaaatg    6240
gctgtataac aaatccactc cgacctttga cgattatttc ggcaatgcct ggaaatccag    6300
ctctggcccg ctgcaactga tcttcgctta ttttgcggtt gtccaaaaca tcaaaaagga    6360
ggaaattgaa aacctgcaaa ataccacga tatcattagc cgtccttctc atatctttcg    6420
cctgtgcaac gacctggcaa gcgcgtccgc agagatcgca cgtggcgaaa ccgctaactc    6480
tgtttcctgc tacatgcgca ccaagggcat ttccgaagag ctggcaaccg agagcgtaat    6540
gaatctgatc gacgaaacct gtaagaaaat gaacaaagaa aaactgggtg gctccctgtt    6600
cgctaaaccg ttcgtagaga ctgctattaa cctggcacgt cagagccact gcacctacca    6660
caatggtgac gcacatacta gcccggatga actgactcgt aaacgtgtac tgtctgttat    6720
```

```
caccgaaccg attctgccgt tcgaacgtta actgcagctg gtaggatccg aattcgagct    6780
ccgtcgacaa gcttgcggcc gcactcgagc accaccacca ccaccactga gatccggctg    6840
ctaacaaagc ccgaaaggaa gctgagttgg ctgctgccac cgctgagcaa taactagcat    6900
aaccccttgg ggcctctaaa cgggtcttga ggggttttt gctgaaagga ggaactatat    6960
ccggat                                                               6966
```

<210> SEQ ID NO 113
<211> LENGTH: 5679
<212> TYPE: DNA
<213> ORGANISM: Artificial Sequence
<220> FEATURE:
<223> OTHER INFORMATION: Synthetic Construct

<400> SEQUENCE: 113

```
aagggcgaat actgcagata tccatcacac tggcggccgc tcgagcatgc atctagaggg      60
cccaattcgc cctatagtga gtcgtattac aattcactgg ccgtcgtttt acaacgtcgt     120
gactgggaaa accctggcgt tacccaactt aatcgccttg cagcacatcc ccctttcgcc     180
agctggcgta atagcgaaga ggcccgcacc gatcgccctt cccaacagtt gcgcagcctg     240
aatggcgaat ggacgcgccc tgtagcggcg cattaagcgc ggcgggtgtg gtggttacgc     300
gcagcgtgac cgctacactt gccagcgccc tagcgcccgc tcctttcgct ttcttccctt     360
cctttctcgc cacgttcgcc ggctttcccc gtcaagctct aaatcggggg ctcccttag     420 ggttccgatt tagtgcttta cggcacctcg accccaaaaa acttgattag ggtgatggtt     480
cacgtagtgg gccatcgccc tgatagacgg ttttcgccc tttgacgttg gagtccacgt     540
tctttaatag tggactcttg ttccaaactg gaacaacact caaccctatc tcggtctatt     600
cttttgattt ataagggatt ttgccgattt cggcctattg gttaaaaaat gagctgattt     660
aacaaaaatt taacgcgaat tttaacaaaa ttcaggggcgc aagggctgct aaaggaagcg     720
gaacacgtag aaagccagtc gcagaaacg gtgctgaccc cggatgaatg tcagctactg     780
ggctatctgg acaagggaaa acgcaagcgc aaagagaaag caggtagctt gcagtgggct     840
tacatggcga tagctagact gggcggtttt atggacagca agcgaaccgg aattgccagc     900
tggggcgccc tctggtaagg ttgggaagcc ctgcaaagta aactggatgg ctttcttgcc     960
gccaaggatc tgatggcgca ggggatcaag atctgatcaa gagacaggat gaggatcgtt    1020
tcgcatgatt gaacaagatg gattgcacgc aggttctccg gccgcttggg tggagaggct    1080
attcggctat gactgggcac aacagacaat cggctgctct gatgccgccg tgttccggct    1140
gtcagcgcag gggcgcccgg ttcttttttgt caagaccgac ctgtccggtg ccctgaatga    1200
actgcaggac gaggcagcgc ggctatcgtg gctggccacg acgggcgttc cttgcgcagc    1260
tgtgctcgac gttgtcactg aagcgggaag ggactggctg ctattgggcg aagtgccggg    1320
gcaggatccc ctgtcatccc accttgctcc tgccgagaaa gtatccatca tggctgatgc    1380
aatgcggcgg ctgcatacgc ttgatccggc tacctgccca ttcgaccacc aagcgaaaca    1440
tcgcatcgag cgagcacgta ctcggatgga agccggtctt gtcgatcagg atgatctgga    1500
cgaagagcat caggggctcg cgccagccga actgttcgcc aggctcaagg cgcgcatgcc    1560
cgacggcgag gatctcgtcg tgacccatgg cgatgcctgc ttgccgaata tcatggtgga    1620
aaatggccgc ttttctggat tcatcgactg tggccggctg ggtgtggcgg accgctatca    1680
ggacatagcg ttggctaccc gtgatattgc tgaagagctt ggcggcgaat gggctgaccg    1740
cttcctcgtg ctttacggta tcgccgctcc cgattcgcag cgcatcgcct tctatcgcct    1800
```

```
tcttgacgag ttcttctgaa ttgaaaaagg aagagtatga gtattcaaca tttccgtgtc    1860
gcccttattc cctttttgc ggcattttgc cttcctgttt ttgctcaccc agaaacgctg     1920
gtgaaagtaa aagatgctga agatcagttg ggtgcacgag tgggttacat cgaactggat    1980
ctcaacagcg gtaagatcct tgagagtttt cgccccgaag aacgttttcc aatgatgagc    2040
acttttaaag ttctgctatg tggcgcggta ttatcccgta ttgacgccgg gcaagagcaa    2100
ctcggtcgcc gcatacacta ttctcagaat gacttggttg agtactcacc agtcacagaa    2160
aagcatctta cggatggcat gacagtaaga gaattatgca gtgctgccat aaccatgagt    2220
gataacactg cggccaactt acttctgaca acgatcggag gaccgaagga gctaaccgct    2280
tttttgcaca acatggggga tcatgtaact cgccttgatc gttgggaacc ggagctgaat    2340
gaagccatac caaacgacga gcgtgacacc acgatgcctg tagcaatggc aacaacgttg    2400
cgcaaactat taactggcga actacttact ctagcttccc ggcaacaatt aatagactgg    2460
atggaggcgg ataaagttgc aggaccactt ctgcgctcgg cccttccggc tggctggttt    2520
attgctgata atctggagcc ggtgagcgt gggtctcgcg gtatcattgc agcactgggg    2580
ccagatggta agccctcccg tatcgtagtt atctacacga cggggagtca ggcaactatg    2640
gatgaacgaa atagacagat cgctgagata ggtgcctcac tgattaagca ttggtaactg    2700
tcagaccaag tttactcata tatactttag attgatttaa aacttcattt ttaatttaaa    2760
aggatctagg tgaagatcct ttttgataat ctcatgacca aaatccctta acgtgagttt    2820
tcgttccact gagcgtcaga ccccgtagaa aagatcaaag gatcttcttg agatcctttt    2880
tttctgcgcg taatctgctg cttgcaaaca aaaaaaccac cgctaccagc ggtggtttgt    2940
ttgccggatc aagagctacc aactctttt ccgaaggtaa ctggcttcag cagagcgcag    3000
ataccaaata ctgttcttct agtgtagccg tagttaggcc accacttcaa gaactctgta    3060
gcaccgccta catacctcgc tctgctaatc ctgttaccag tggctgctgc cagtggcgat    3120
aagtcgtgtc ttaccgggtt ggactcaaga cgatagttac cggataaggc gcagcggtcg    3180
ggctgaacgg ggggttcgtg cacacagccc agcttggagc gaacgaccta caccgaactg    3240
agatacctac agcgtgagct atgagaaagc gccacgcttc ccgaagggag aaaggcggac    3300
aggtatccgg taagcggcag ggtcggaaca ggagagcgca cgagggagct tccaggggga    3360
aacgcctggt atctttatag tcctgtcggg tttcgccacc tctgacttga gcgtcgattt    3420
ttgtgatgct cgtcaggggg gcggagccta tggaaaaacg ccagcaacgc ggccttttta    3480
cggttcctgg ccttttgctg gccttttgct cacatgttct ttcctgcgtt atcccctgat    3540
tctgtggata accgtattac cgcctttgag tgagctgata ccgctcgccg cagccgaacg    3600
accgagcgca gcgagtcagt gagcgaggaa gcggaagagc gcccaatacg caaaccgcct    3660
ctccccgcgc gttggccgat tcattaatgc agctggcacg acaggtttcc cgactggaaa    3720
gcgggcagtg agcgcaacgc aattaatgtg agttagctca ctcattaggc accccaggct    3780
ttacacttta tgcttccggc tcgtatgttg tgtggaattg tgagcggata acaatttcac    3840
acaggaaaca gctatgacca tgattacgcc aagcttggta ccgagctcgg atccactagt    3900
aacggccgcc agtgtgctgg aattcgccct tgatcatgca ttcgccctta ggaggtaaaa    3960
aaacatgtgt gcgacctctt ctcaatttac tcagattacc gagcataatt cccgtcgttc    4020
cgcaaactat cagccaaacc tgtggaattt cgaattcctg caatccctgg agaacgacct    4080
gaaagtggaa aagctggagg agaaagcgac caaactggag gaagaagttc gctgcatgat    4140
caaccgtgta gacacccagc cgctgtccct gctggagctg atcgacgatg tgcagcgcct    4200
```

-continued

| | |
|---|---|
| gggtctgacc tacaaatttg aaaaagacat cattaaagcc ctggaaaaca tcgtactgct | 4260 |
| ggacgaaaac aaaaagaaca aatctgacct gcacgcaacc gctctgtctt tccgtctgct | 4320 |
| gcgtcagcac ggtttcgagg tttctcagga tgttttgag cgtttcaagg ataaagaagg | 4380 |
| tggtttcagc ggtgaactga aaggtgacgt ccaaggcctg ctgagcctgt atgaagcgtc | 4440 |
| ttacctgggt ttcgagggtg agaacctgct ggaggaggcg cgtacctttt ccatcaccca | 4500 |
| cctgaagaac aacctgaaag aaggcattaa taccaaggtt gcagaacaag tgagccacgc | 4560 |
| cctggaactg ccatatcacc agcgtctgca ccgtctggag gcacgttggt tcctggataa | 4620 |
| atacgaaccg aaagaaccgc atcaccagct gctgctggag ctggcgaagc tggattttaa | 4680 |
| catggtacag accctgcacc agaaagagct gcaagatctg tcccgctggt ggaccgagat | 4740 |
| gggcctggct agcaaactgg attttgtacg cgaccgcctg atggaagttt atttctgggc | 4800 |
| actgggtatg gcgccagacc cgcagtttgg tgaatgtcgc aaagctgtta ctaaaatgtt | 4860 |
| tggtctggtg acgatcatcg atgacgtgta tgacgtttat ggcactctgg acgaactgca | 4920 |
| actgttcacc gatgctgtag agcgctggga cgttaacgct attaacaccc tgccggacta | 4980 |
| tatgaaactg tgtttcctgg cactgtacaa caccgttaac gacacgtcct attctattct | 5040 |
| gaaagagaaa ggtcataaca acctgtccta tctgacgaaa agctggcgtg aactgtgcaa | 5100 |
| agcctttctg caagaggcga aatggtccaa caacaaaatt atcccggctt ctctccaagta | 5160 |
| cctggaaaac gccagcgttt cctcctccgg tgtagcgctg ctggcgccgt cttacttttc | 5220 |
| cgtatgccag cagcaggaag acatctccga ccacgcgctg agttccctga ccgacttcca | 5280 |
| tggtctggtg cgttctagct gcgttatctt ccgcctgtgc aacgatctgg ccacctctgc | 5340 |
| ggcggagctg gaacgtggcg agactaccaa ttctatcatt agctacatgc acgaaaacga | 5400 |
| tggtaccagc gaggaacagg cccgcgaaga actgcgtaaa ctgatcgacg ccgaatggaa | 5460 |
| aaagatgaat cgtgaacgcg ttagcgactc caccctgctg cctaaagcgt tcatggaaat | 5520 |
| cgcagttaac atggcacgtg tttcccactg cacctaccag tatggcgatg gtctgggtcg | 5580 |
| cccagactac gcgactgaaa accgcatcaa actgctgctg attgacccctt tcccgattaa | 5640 |
| ccagctgatg tatgtctaac tgcagggatc cgtcgaccg | 5679 |

<210> SEQ ID NO 114
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 114

| | |
|---|---|
| gtgcggccgc aagcttgtcg acggagctcg aattcggatc cctgcagtta gacatacatc | 60 |
| agctggttaa tcgggaaagg gtcaatcagc agcagtttga tgcggttttc agtcgcgtag | 120 |
| tctgggcgac ccagaccatc gccatactgg taggtgcagt gggaaacacg tgccatgtta | 180 |
| actgcgattt ccatgaacgc tttaggcagc agggtggagt cgctaacgcg ttcacgattc | 240 |
| atcttttttcc attcggcgtc gatcagttta cgcagttctt cgcgggcctg ttcctcgctg | 300 |
| gtaccatcgt tttcgtgcat gtagctaatg atagaattgg tagtctcgcc acgttccagc | 360 |
| tccgccgcag aggtggccag atcgttgcac aggcggaaga taacgcagct agaacgcacc | 420 |
| agaccatgga agtcggtcag ggaacgcagc gcgtggtcgg agatgtcttc ctgctgctgg | 480 |
| catacgaaaa agtaagacgg cgccagcagc gctacaccgg aggaggaaac gctggcgttt | 540 |
| tccaggtact tggagaaagc cgggataatt ttgttgttgg accatttcgc ctcttgcaga | 600 |

```
aaggctttgc acagttcacg ccagcttttc gtcagatagg acaggttgtt atgacctttc    660
tctttcagaa tagaatagga cgtgtcgtta acggtgttgt acagtgccag gaaacacagt    720
ttcatatagt ccggcagggt gttaatagcg ttaacgtccc agcgctctac agcatcggtg    780
aacagttgca gttcgtccag agtgccataa acgtcataca cgtcatcgat gatcgtcacc    840
agaccaaaca ttttagtaac agcattgcga cattcaccaa actgcgggtc tggcgccata    900
cccagtgccc agaaataaac ttccatcagg cggtcgcgta caaaatccag tttgctagcc    960
aggcccatct cggtccacca gcgggacaga tcttgcagct cttcctggtg cagggtctgt   1020
accatgttaa aatccagctt cgccagctcc agcagcagct ggtgatgcgg ttctttcggt   1080
tcgtatttat ccaggaacca acgtgcctcc agacggtgca gacgctggtg atatggcagt   1140
tccagggcgt ggctcacttg ttctgcaacc ttggtattaa tgccttcttt caggttgttc   1200
ttcaggtggg tgatggaaaa ggtacgcgcc tcctccagca ggttctcacc ctcgaaaccc   1260
aggtaagacg cttcatacag gctcagcagg ccttggacgt caccttttcag ttcaccgctg   1320
aaaccaccta ctttaacctt gaaacgcaca aaaacatcct gagaaacctc gaaaccgtgc   1380
tgacgcagca gacggaaaga cagagcggtt gcgtgcaggt cagatttgtt cttttttgttt   1440
tcgtccagca gtacgacgtt ttccagggct ttaatgatgt cttttttcaaa tttgtaggtc   1500
agacccaggc gctgcacatc gtcgatcagc tccagcaggg acagcggctg ggtgtctaca   1560
cggttgatca tgcagcgaac ttcttcctcc agtttggtcg cttctcctc cagcttttcc    1620
actttcaggt cgttctccag ggattgcagg aattcgaaat tccacaggtt tggctgatag   1680
tttgcggaac gacgggaatt atgctcggta atctgagtaa attgagaaga ggtcgcacac   1740
atggtatatc tccttcttaa agttaaacaa aattatttct agaggggaat tgttatccgc   1800
tcacaattcc cctatagtga gtcgtattaa tttcgcggga tcgagatctc gatcctctac   1860
gccggacgca tcgtggccgg catcaccggc gccacaggtg cggttgctgg cgcctatatc   1920
gccgacatca ccgatgggga agatcgggct cgccacttcg ggctcatgag cgcttgtttc   1980
ggcgtgggta tggtggcagg ccccgtggcc ggggactgt tgggcgccat ctccttgcat    2040
gcaccattcc ttgcggcggc ggtgctcaac ggcctcaacc tactactggg ctgcttccta   2100
atgcaggagt cgcataaggg agagcgtcga gatcccggac accatcgaat ggcgcaaaac   2160
ctttcgcggt atggcatgat agcgcccgga agagagtcaa ttcagggtgg tgaatgtgaa   2220
accagtaacg ttatacgatg tcgcagagca tgccggtgtc tcttatcaga ccgtttcccg   2280
cgtggtgaac caggccagcc acgtttctgc gaaaacgcgg gaaaagtgg aagcggcgat    2340
ggcggagctg aattacattc ccaaccgcgt ggcacaacaa ctggcgggca aacagtcgtt   2400
gctgattggc gtagccacct ccagtctggc cctgcacgcg ccgtcgcaaa ttgtcgcggc   2460
gattaaatct cgcgccgatc aactgggtgc cagcgtggtg gtgtcgatgg tagaacgaag   2520
cggcgtcgaa gcctgtaaag cggcggtgca caatcttctc gcgcaacgcg tcagtgggct   2580
gatcattaac tatccgctgg atgaccagga tgccattgct gtggaagctg cctgcactaa   2640
tgttccggcg ttatttcttg atgtctctga ccagacaccc atcaacagta ttattttctc   2700
ccatgaagac ggtacgcgac tgggcgtgga gcatctggtc gcattgggtc accagcaaat   2760
cgcgctgtta gcgggcccat taagttctgt ctcggcgcgt ctgcgtctgg ctggctggca   2820
taaatatctc actcgcaatc aaattcagcc gatagcggaa cgggaaggcg actggagtgc   2880
catgtccggt tttcaacaaa ccatgcaaat gctgaatgag gcatcgttcc ccactgcgat   2940
gctggttgcc aacgatcaga tggcgctggg cgcaatgcgc gccattaccg agtccgggct   3000
```

-continued

```
gcgcgttggt gcggatatct cggtagtggg atacgacgat accgaagaca gctcatgtta    3060
tatcccgccg ttaaccacca tcaaacagga ttttcgcctg ctggggcaaa ccagcgtgga    3120
ccgcttgctg caactctctc agggccaggc ggtgaagggc aatcagctgt tgcccgtctc    3180
actggtgaaa agaaaaacca ccctggcgcc caatacgcaa accgcctctc cccgcgcgtt    3240
ggccgattca ttaatgcagc tggcacgaca ggtttcccga ctggaaagcg ggcagtgagc    3300
gcaacgcaat taatgtaagt tagctcactc attaggcacc gggatctcga ccgatgccct    3360
tgagagcctt caacccagtc agctccttcc ggtgggcgcg gggcatgact atcgtcgccg    3420
cacttatgac tgtcttcttt atcatgcaac tcgtaggaca ggtgccggca gcgctctggg    3480
tcattttcgg cgaggaccgc tttcgctgga gcgcgacgat gatcggcctg tcgcttgcgg    3540
tattcggaat cttgcacgcc ctcgctcaag ccttcgtcac tggtcccgcc accaaacgtt    3600
tcggcgagaa gcaggccatt atcgccggca tggcggcccc acgggtgcgc atgatcgtgc    3660
tcctgtcgtt gaggacccgg ctaggctggc ggggttgcct tactggttag cagaatgaat    3720
caccgatacg cgagcgaacg tgaagcgact gctgctgcaa aacgtctgcg acctgagcaa    3780
caacatgaat ggtcttcggt ttccgtgttt cgtaaagtct ggaaacgcgg aagtcagcgc    3840
cctgcaccat tatgttccgg atctgcatcg caggatgctg ctggctaccc tgtggaacac    3900
ctacatctgt attaacgaag cgctggcatt gaccctgagt gattttctc tggtcccgcc    3960 gcatccatac cgccagttgt ttaccctcac aacgttccag taaccgggca tgttcatcat    4020
cagtaacccg tatcgtgagc atcctctctc gtttcatcgg tatcattacc cccatgaaca    4080
gaaatccccc ttacacggag gcatcagtga ccaaacagga aaaaaccgcc cttaacatgg    4140
cccgctttat cagaagccag acattaacgc ttctggagaa actcaacgag ctggacgcgg    4200
atgaacaggc agacatctgt gaatcgcttc acgaccacgc tgatgagctt taccgcagct    4260
gcctcgcgcg tttcggtgat gacggtgaaa acctctgaca catgcagctc ccggagacgg    4320
tcacagcttg tctgtaagcg gatgccggga gcagacaagc ccgtcagggc gcgtcagcgg    4380
gtgttggcgg gtgtcgggc gcagccatga cccagtcacg tagcgatagc ggagtgtata    4440
ctggcttaac tatgcggcat cagagcagat tgtactgaga gtgcaccata tatgcggtgt    4500
gaaataccgc acagatgcgt aaggagaaaa taccgcatca ggcgctcttc cgcttcctcg    4560
ctcactgact cgctgcgctc ggtcgttcgg ctgcggcgag cggtatcagc tcactcaaag    4620
gcggtaatac ggttatccac agaatcaggg gataacgcag gaaagaacat gtgagcaaaa    4680
ggccagcaaa aggccaggaa ccgtaaaaag gccgcgttgc tggcgttttt ccataggctc    4740
cgcccccctg acgagcatca caaaaatcga cgctcaagtc agaggtggcg aaacccgaca    4800
ggactataaa gataccaggc gtttccccct ggaagctccc tcgtgcgctc tcctgttccg    4860
accctgccgc ttaccggata cctgtccgcc tttctccctt cgggaagcgt ggcgctttct    4920
catagctcac gctgtaggta tctcagttcg gtgtaggtcg atcgctccaa gctgggctgt    4980
gtgcacgaac ccccgttca gcccgaccgc tgcgccttat ccggtaacta tcgtcttgag    5040
tccaacccgg taagacacga cttatcgcca ctggcagcag ccactggtaa caggattagc    5100
agagcgaggt atgtaggcgg tgctacagag ttcttgaagt ggtggcctaa ctacggctac    5160
actagaagga cagtatttgg tatctgcgct ctgctgaagc cagttacctt cggaaaaaga    5220
gttggtagct cttgatccgg caaacaaacc accgctggta gcggtggttt ttttgtttgc    5280
aagcagcaga ttacgcgcag aaaaaaagga tctcaagaag atcctttgat cttttctacg    5340
gggtctgacg ctcagtggaa cgaaaactca cgttaaggga ttttggtcat gaacaataaa    5400
```

| | |
|---|---|
| actgtctgct tacataaaca gtaatacaag gggtgttatg agccatattc aacgggaaac | 5460 |
| gtcttgctct aggccgcgat taaattccaa catggatgct gatttatatg ggtataaatg | 5520 |
| ggctcgcgat aatgtcgggc aatcaggtgc gacaatctat cgattgtatg ggaagcccga | 5580 |
| tgcgccagag ttgtttctga acatggcaa aggtagcgtt gccaatgatg ttacagatga | 5640 |
| gatggtcaga ctaaactggc tgacggaatt tatgcctctt ccgaccatca agcattttat | 5700 |
| ccgtactcct gatgatgcat ggttactcac cactgcgatc cccgggaaaa cagcattcca | 5760 |
| ggtattagaa gaatatcctg attcaggtga aaatattgtt gatgcgctgg cagtgttcct | 5820 |
| gcgccggttg cattcgattc ctgtttgtaa ttgtccttt aacagcgatc gcgtatttcg | 5880 |
| tctcgctcag gcgcaatcac gaatgaataa cggtttggtt gatgcgagtg attttgatga | 5940 |
| cgagcgtaat ggctggcctg ttgaacaagt ctggaaagaa atgcataaac ttttgccatt | 6000 |
| ctcaccggat tcagtcgtca ctcatggtga tttctcactt gataaccta ttttttgacga | 6060 |
| ggggaaatta ataggttgta ttgatgttgg acgagtcgga atcgcagacc gataccagga | 6120 |
| tcttgccatc ctatggaact gcctcggtga gttttctcct tcattacaga acggcttttt | 6180 |
| tcaaaaatat ggtattgata atcctgatat gaataaattg cagtttcatt tgatgctcga | 6240 |
| tgagttttc taagaattaa ttcatgagcg gatacatatt tgaatgtatt tagaaaaata | 6300 |
| aacaaatagg ggttccgcgc acatttcccc gaaaagtgcc acctgaaatt gtaaacgtta | 6360 |
| atattttgtt aaaattcgcg ttaaatttt gttaaatcag ctcatttttt aaccaatagg | 6420 |
| ccgaaatcgg caaaatccct tataaatcaa aagaatagac cgagataggg ttgagtgttg | 6480 |
| ttccagtttg gaacaagagt ccactattaa agaacgtgga ctccaacgtc aaagggcgaa | 6540 |
| aaaccgtcta tcagggcgat ggcccactac gtgaaccatc accctaatca agttttttgg | 6600 |
| ggtcgaggtg ccgtaaagca ctaaatcgga accctaaagg gagcccccga tttagagctt | 6660 |
| gacggggaaa gccggcgaac gtggcgagaa aggaagggaa gaaagcgaaa ggagcgggcg | 6720 |
| ctagggcgct ggcaagtgta gcggtcacgc tgcgcgtaac caccacaccc gccgcgctta | 6780 |
| atgcgccgct acagggcgcg tcccattcgc caatccggat atagttcctc ctttcagcaa | 6840 |
| aaaacccctc aagacccgtt tagaggcccc aaggggttat cgtagttatt gctcagcggt | 6900 |
| ggcagcagcc aactcagctt cctttcgggc tttgttagca gccggatctc agtggtggtg | 6960 |
| gtggtggtgc tcga | 6974 |

<210> SEQ ID NO 115
<211> LENGTH: 1719
<212> TYPE: DNA
<213> ORGANISM: Artificial Sequence
<220> FEATURE:
<223> OTHER INFORMATION: Synthetic Construct

<400> SEQUENCE: 115

| | |
|---|---|
| gaattcaaaa tgtgtgcaac ttcatcccaa ttcactcaaa tcacagagca taattctaga | 60 |
| cgttcagcta actaccaacc aaatctgtgg aattttgaat ttcttcaatc ccttgaaaat | 120 |
| gatttgaaag tggaaaagtt ggaggaaaaa gccacaaaac tagaggaaga agttagatgt | 180 |
| atgataaaca gagtagatac acaacctctg tcactactag aattgattga cgatgtccag | 240 |
| aggctgggtt taacatataa gttcgaaaag gatataatca aagccttaga aaacatagtc | 300 |
| cttctagatg aaaacaagaa gaataagtct gacttgcacg caaccgctct gagttttaga | 360 |
| ttgctgagac aacatggttt tgaagtaagt caagatgtgt ttgaaaggtt caaagacaaa | 420 |
| gagggaggat tctcaggaga attaaaggga gatgtgcagg gtctgttgtc attgtacgag | 480 |

```
gccagttatt tggggtttga aggggaaaat ctactagagg aggccagaac cttctctata      540
acccatctga agaataactt gaaagaaggc atcaatacaa aagtggctga acaagtttca      600
catgcattgg aattgcccta ccaccaaaga cttcatagac ttgaagccag atggttttg       660 gacaagtatg aaccaaagga gcctcaccat caacttttat tggaattagc aaaactggat     720
tttaacatgg ttcagacatt acaccagaaa gaattgcagg acctatcaag atggtggacg    780
gagatgggtt tagccagcaa gttagatttc gttagagata gattgatgga agtttacttt    840
tgggcactgg gaatggcacc agatcctcaa tttggtgaat gtagaaaggc agttacaaag    900
atgtttggtc tagtaacaat cattgatgat gtttatgatg tgtacggaac tttggatgaa    960
ttacaactat tcaccgacgc agttgaacgt tgggatgtaa acgcaataaa cacgttgcct    1020
gattatatga agctgtgttt tctggcattg tacaacacag tcaatgacac ttcttactcc    1080 atttttaaagg agaaagggca taacaatcta tcctatttga caaaatcatg gagggagtta   1140
tgcaaagcat tccttcaaga agctaagtgg tctaacaata agataatccc agcattctcc    1200
aagtatcttg aaaacgcttc cgtatcctcc tccggtgtgg ccctactagc accatcatat    1260
ttttccgtct gccagcagca ggaagatatc tctgatcatg ctttgagatc cttaacagat    1320
tttcatggtc tagtcagatc ctcttgcgtg attttcagat tgtgcaatga tttggctact    1380
tcagccgcag agttagagag gggtgaaacc acgaactcaa ttattagtta tatgcacgag    1440
aatgatggaa catccgaaga acaagcccgt gaagaattaa gaaaactgat cgatgctgaa    1500
tggaagaaga tgaatagaga aagagtttcc gacagcactt tgctgcctaa ggcattcatg    1560
gagatagctg ttaacatggc tagggtttca cactgtacat accaatacgg ggacggtctt    1620
ggaaggcccg actacgccac tgaaaataga attaaactgc tactgattga tccttttcccc    1680 attaaccagt taatgtacgt gtaataggga tccgaattc                            1719

<210> SEQ ID NO 116
<211> LENGTH: 20
<212> TYPE: DNA
<213> ORGANISM: Artificial Sequence
<220> FEATURE:
<223> OTHER INFORMATION: Synthetic Construct

<400> SEQUENCE: 116
caccaaagac ttcatagact                                                   20

<210> SEQ ID NO 117
<211> LENGTH: 20
<212> TYPE: DNA
<213> ORGANISM: Artificial Sequence
<220> FEATURE:
<223> OTHER INFORMATION: Synthetic Construct

<400> SEQUENCE: 117
agagatatct tcctgctgct                                                   20

<210> SEQ ID NO 118
<211> LENGTH: 20
<212> TYPE: DNA
<213> ORGANISM: Artificial Sequence
<220> FEATURE:
<223> OTHER INFORMATION: Synthetic Construct

<400> SEQUENCE: 118
taatacgact cactataggg                                                   20

<210> SEQ ID NO 119
```

<211> LENGTH: 7658
<212> TYPE: DNA
<213> ORGANISM: Artificial Sequence
<220> FEATURE:
<223> OTHER INFORMATION: Synthetic Construct

<400> SEQUENCE: 119

| | | | | | |
|---|---|---|---|---|---|
| acggattaga | agccgccgag | cgggtgacag | ccctccgaag | gaagactctc | ctccgtgcgt | 60 |
| cctcgtcttc | accggtcgcg | ttcctgaaac | gcagatgtgc | ctcgcgccgc | actgctccga | 120 |
| acaataaaga | ttctacaata | ctagctttta | tggttatgaa | gaggaaaaat | tggcagtaac | 180 |
| ctggccccac | aaaccttcaa | atgaacgaat | caaattaaca | accataggat | gataatgcga | 240 |
| ttagtttttt | agccttattt | ctggggtaat | taatcagcga | agcgatgatt | tttgatctat | 300 |
| taacagatat | ataaatgcaa | aaactgcata | accactttaa | ctaatacttt | caacattttc | 360 |
| ggtttgtatt | acttcttatt | caaatgtaat | aaaagtatca | acaaaaaatt | gttaatatac | 420 |
| ctctatactt | taacgtcaag | gagaaaaaac | cccggatcgg | actactagca | gctgtaatac | 480 |
| gactcactat | agggaatatt | aagctatcaa | acaagtttgt | acaaaaaagc | aggctgaatt | 540 |
| caaaatgtgt | gcaacttcat | cccaattcac | tcaaatcaca | gagcataatt | ctagacgttc | 600 |
| agctaactac | caaccaaatc | tgtggaattt | tgaatttctt | caatcccttg | aaaatgattt | 660 |
| gaaagtggaa | aagttggagg | aaaaagccac | aaaactagag | gaagaagtta | gatgtatgat | 720 |
| aaacagagta | gatacacaac | ctctgtcact | actagaattg | attgacgatg | tccagaggct | 780 |
| gggtttaaca | tataagttcg | aaaaggatat | aatcaaagcc | ttagaaaaca | tagtccttct | 840 |
| agatgaaaac | aagaagaata | agtctgactt | gcacgcaacc | gctctgagtt | ttagattgct | 900 |
| gagacaacat | ggttttgaag | taagtcaaga | tgtgtttgaa | aggttcaaag | acaaagaggg | 960 |
| aggattctca | ggagaattaa | agggagatgt | gcagggtctg | ttgtcattgt | acgaggccag | 1020 |
| ttatttgggg | tttgaagggg | aaaatctact | agaggaggcc | agaaccttct | ctataaccca | 1080 |
| tctgaagaat | aacttgaaag | aaggcataaa | tacaaaagtg | gctgaacaag | tttcacatgc | 1140 |
| attggaattg | ccctaccacc | aaagacttca | tagacttgaa | gccagatggt | ttttggacaa | 1200 |
| gtatgaacca | aaggagcctc | accatcaact | tttattggaa | ttagcaaaac | tggattttaa | 1260 |
| catggttcag | acattacacc | agaaagaatt | gcaggaccta | tcaagatggt | ggacggagat | 1320 |
| gggtttagcc | agcaagttag | atttcgttag | agatagattg | atggaagttt | acttttgggc | 1380 |
| actgggaatg | gcaccagatc | ctcaatttgg | tgaatgtaga | aaggcagtta | caaagatgtt | 1440 |
| tggtctagta | acaatcattg | atgatgttta | tgatgtgtac | ggaactttgg | atgaattaca | 1500 |
| actattcacc | gacgcagttg | aacgttggga | tgtaaacgca | ataaacacgt | tgcctgatta | 1560 |
| tatgaagctg | tgttttctgg | cattgtacaa | cacagtcaat | gacacttctt | actccatttt | 1620 |
| aaaggagaaa | gggcataaca | atctatccta | tttgacaaaa | tcatggaggg | agttatgcaa | 1680 |
| agcattcctt | caagaagcta | agtggtctaa | caataagata | atcccagcat | tctccaagta | 1740 |
| tcttgaaaac | gcttccgtat | cctcctccgg | tgtggcccta | ctagcaccat | cattttttc | 1800 |
| cgtctgccag | cagcaggaag | atatctctga | tcatgctttg | agatcccttaa | cagattttca | 1860 |
| tggtctagtc | agatcctctt | gcgtgatttt | cagattgtgc | aatgatttgg | ctacttcagc | 1920 |
| cgcagagtta | gagaggggtg | aaaccacgaa | ctcaattatt | agttatatgc | acgaaatga | 1980 |
| tggaacatcc | gaagaacaag | cccgtgaaga | attaagaaaa | ctgatcgatg | ctgaatggaa | 2040 |
| gaagatgaat | agagaaagag | tttccgacag | cactttgctg | cctaaagcat | tcatggagat | 2100 |
| agctgttaac | atggctaggg | tttcacactg | tacataccaa | tacggggacg | gtcttggaag | 2160 |

```
gcccgactac gccactgaaa atagaattaa actgctactg attgatcctt tccccattaa    2220
ccagttaatg tacgtgtaat agggatccga attcacccag cttctttgta caaagtggtt    2280
cgatctagag ggcccttcga aggtaagcct atccctaacc ctctcctcgg tctcgattct    2340
acgcgtaccg gtcatcatca ccatcaccat tgagtttaaa cccgctgatc ctagagggcc    2400
gcatcatgta attagttatg tcacgcttac attcacgccc tcccccaca tccgctctaa     2460 ccgaaaagga aggagttaga caacctgaag tctaggtccc tatttatttt tttatagtta    2520
tgttagtatt aagaacgtta tttatatttc aaattttttct tttttttctg tacagacgcg    2580
tgtacgcatg taacattata ctgaaaacct tgcttgagaa ggttttggga cgctcgaagg    2640
ctttaatttg caagctgcgg ccctgcatta atgaatcggc caacgcgcgg ggagaggcgg    2700
tttgcgtatt gggcgctctt ccgcttcctc gctcactgac tcgctgcgct cggtcgttcg    2760
gctgcggcga gcggtatcag ctcactcaaa ggcggtaata cggttatcca cagaatcagg    2820
ggataacgca ggaaagaaca tgtgagcaaa aggccagcaa aagcccagga accgtaaaaa    2880
ggccgcgttg ctggcgtttt tccataggct ccgcccccct gacgagcatc acaaaaatcg    2940
acgctcaagt cagaggtggc gaaacccgac aggactataa agataccagg cgtttccccc    3000
tggaagctcc ctcgtgcgct ctcctgttcc gaccctgccg cttaccggat acctgtccgc    3060
ctttctccct tcgggaagcg tggcgctttc tcatagctca cgctgtaggt atctcagttc    3120
ggtgtaggtc gttcgctcca agctgggctg tgtgcacgaa ccccccgttc agcccgaccg    3180
ctgcgcctta tccggtaact atcgtcttga gtccaacccg gtaagacacg acttatcgcc    3240
actggcagca gccactggta acaggattag cagagcgagg tatgtaggcg gtgctacaga    3300
gttcttgaag tggtggccta actacggcta cactagaagg acagtatttg gtatctgcgc    3360
tctgctgaag ccagttacct tcggaaaaag agttggtagc tcttgatccg gcaaacaaac    3420
caccgctggt agcggtggtt tttttgtttg caagcagcag attacgcgca gaaaaaaagg    3480
atctcaagaa gatcctttga tcttttctac ggggtctgac gctcagtgga acgaaaactc    3540
acgttaaggg attttggtca tgagattatc aaaaaggatc ttcacctaga tccttttaaa    3600
ttaaaaatga agttttaaat caatctaaag tatatatgag taaacttggt ctgacagtta    3660
ccaatgctta atcagtgagg cacctatctc agcgatctgt ctatttcgtt catccatagt    3720
tgcctgactc cccgtcgtgt agataactac gatacgggag cgcttaccat ctggccccag    3780
tgctgcaatg ataccgcgag acccacgctc accggctcca gatttatcag caataaacca    3840
gccagccgga agggccgagc gcagaagtgg tcctgcaact ttatccgcct ccatccagtc    3900
tattaattgt tgccgggaag ctagagtaag tagttcgcca gttaatagtt tgcgcaacgt    3960
tgttggcatt gctacaggca tcgtggtgtc actctcgtcg tttggtatgg cttcattcag    4020
ctccggttcc caacgatcaa ggcgagttac atgatccccc atgttgtgca aaaaagcggt    4080
tagctccttc ggtcctccga tcgttgtcag aagtaagttg gccgcagtgt tatcactcat    4140
ggttatggca gcactgcata attctcttac tgtcatgcca tccgtaagat gcttttctgt    4200
gactggtgag tactcaacca agtcattctg agaatagtgt atgcggcgac cgagttgctc    4260
ttgcccggcg tcaatacggg ataatagtgt atcacatagc agaactttaa aagtgctcat    4320
cattggaaaa cgttcttcgg ggcgaaaact ctcaaggatc ttaccgctgt tgagatccag    4380
ttcgatgtaa cccactcgtg cacccaactg atcttcagca tcttttactt tcaccagcgt    4440
ttctgggtga gcaaaacag gaaggcaaaa tgccgcaaaa aagggaataa gggcgacacg    4500
gaaatgttga atactcatac tcttcctttt tcaatgggta ataactgata taattaaatt    4560
```

```
gaagctctaa tttgtgagtt tagtatacat gcatttactt ataatacagt tttttagttt    4620
tgctggccgc atcttctcaa atatgcttcc cagcctgctt ttctgtaacg ttcaccctct    4680
accttagcat cccttccctt tgcaaatagt cctcttccaa caataataat gtcagatcct    4740
gtagagacca catcatccac ggttctatac tgttgaccca atgcgtctcc cttgtcatct    4800
aaacccacac cgggtgtcat aatcaaccaa tcgtaacctt catctcttcc acccatgtct    4860
ctttgagcaa taaagccgat aacaaaatct ttgtcgctct tcgcaatgtc aacagtaccc    4920
ttagtatatt ctccagtaga tagggagccc ttgcatgaca attctgctaa catcaaaagg    4980
cctctaggtt cctttgttac ttcttctgcc gcctgcttca aaccgctaac aatacctggg    5040
cccaccacac cgtgtgcatt cgtaatgtct gcccattctg ctattctgta tacacccgca    5100
gagtactgca atttgactgt attaccaatg tcagcaaatt ttctgtcttc gaagagtaaa    5160
aaattgtact tggcggataa tgcctttagc ggcttaactg tgcctccat ggaaaaatca     5220
gtcaagatat ccacatgtgt ttttagtaaa caaattttgg gacctaatgc ttcaactaac    5280
tccagtaatt ccttggtggt acgaacatcc aatgaagcac acaagtttgt ttgcttttcg    5340
tgcatgatat taaatagctt ggcagcaaca ggactaggat gagtagcagc acgttcctta    5400
tatgtagctt tcgacatgat ttatcttcgt ttcctgcagg ttttttgttct gtgcagttgg    5460
gttaagaata ctgggcaatt tcatgtttct tcaacactac atatgcgtat atataccaat    5520
ctaagtctgt gctccttcct tcgttcttcc ttctgttcgg agattaccga atcaaaaaaa    5580
tttcaaagaa accgaaatca aaaaaaagaa taaaaaaaaa atgatgaatt gaattgaaaa    5640
gctagcttat cgatgataag ctgtcaaaga tgagaattaa ttccacggac tatagactat    5700
actagatact ccgtctactg tacgatacac ttccgctcag gtccttgtcc tttaacgagg    5760
ccttaccact cttttgttac tctattgatc cagctcagca aaggcagtgt gatctaagat    5820
tctatcttcg cgatgtagta aaactagcta gaccgagaaa gagactagaa atgcaaaagg    5880
cacttctaca atggctgcca tcattattat ccgatgtgac gctgcagctt ctcaatgata    5940
ttcgaatacg ctttgaggag atacagccta atatccgaca aactgtttta cagatttacg    6000
atcgtacttg ttacccatca ttgaattttg aacatccgaa cctgggagtt ttccctgaaa    6060
cagatagtat atttgaacct gtataataat atatagtcta gcgctttacg gaagacaatg    6120
tatgtatttc ggttcctgga gaaactattg catctattgc ataggtaatc ttgcacgtcg    6180
catccccggt tcattttctg cgtttccatc ttgcacttca atagcatatc tttgttaacg    6240
aagcatctgt gcttcatttt gtagaacaaa atgcaacgc gagagcgcta attttttcaaa    6300
caaagaatct gagctgcatt tttacagaac agaaatgcaa cgcgaaagcg ctattttacc    6360
aacgaagaat ctgtgcttca ttttttgtaaa acaaaaatgc aacgcgacga gagcgctaat    6420
ttttcaaaca agaatctga gctgcatttt tacagaacag aaatgcaacg cgagagcgct    6480
attttaccaa caaagaatct atacttcttt tttgttctac aaaaatgcat cccgagagcg    6540
ctatttttct aacaaagcat cttagattac tttttttctc ctttgtgcgc tctataatgc    6600
agtctcttga taacttttg cactgtaggt ccgttaaggt tagaagaagg ctactttggt    6660
gtctattttc tcttccataa aaaaagcctg actccacttc ccgcgtttac tgattactag    6720
cgaagctgcg ggtgcatttt ttcaagataa aggcatcccc gattatattc tataccgatg    6780
tggattgcgc atactttgtg aacagaaagt gatagcgttg atgattcttc attggtcaga    6840
aaattatgaa cggtttcttc tattttgtct ctatatacta cgtataggaa atgtttacat    6900
tttcgtattg ttttcgattc actctatgaa tagttcttac tacaattttt ttgtctaaag    6960
```

| | |
|---|---|
| agtaatacta gagataaaca taaaaaatgt agaggtcgag tttagatgca agttcaagga | 7020 |
| gcgaaaggtg gatgggtagg ttatataggg atatagcaca gagatatata gcaaagagat | 7080 |
| acttttgagc aatgtttgtg gaagcggtat tcgcaatggg aagctccacc ccggttgata | 7140 |
| atcagaaaag ccccaaaaac aggaagattg tataagcaaa tatttaaatt gtaaacgtta | 7200 |
| atattttgtt aaaattcgcg ttaaatttt gttaaatcag ctcattttt aacgaatagc | 7260 |
| ccgaaatcgg caaaatccct tataaatcaa agaatagac cgagatagg ttgagtgttg | 7320 |
| ttccagtttc caacaagagt ccactattaa agaacgtgga ctccaacgtc aaagggcgaa | 7380 |
| aaagggtcta tcagggcgat ggcccactac gtgaaccatc accctaatca agtttttgg | 7440 |
| ggtcgaggtg ccgtaaagca gtaaatcgga agggtaaacg gatgccccca tttagagctt | 7500 |
| gacggggaaa gccggcgaac gtggcgagaa aggaagggaa gaaagcgaaa ggagcggggg | 7560 |
| ctagggcggt gggaagtgta ggggtcacgc tgggcgtaac caccacaccc gccgcgctta | 7620 |
| atggggcgct acagggcgcg tgggatgat ccactagt | 7658 |

```
<210> SEQ ID NO 120
<211> LENGTH: 1746
<212> TYPE: DNA
<213> ORGANISM: Artificial Sequence
<220> FEATURE:
<223> OTHER INFORMATION: Synthetic Construct

<400> SEQUENCE: 120
```

| | |
|---|---|
| catcttaagc ttgtttaact ttaagaagga gatatacata tgtgcgccac cagcagccag | 60 |
| ttcacccaga tcaccgagca taatagccgt cggtccgcga actaccagcc caacctgtgg | 120 |
| aacttcgagt tcctgcagag cctggaaaac gacctgaagg tggagaagct cgaagagaag | 180 |
| gccaccaagc tggaggagga ggtgcgttgc atgatcaacc gggtggacac ccagcccctg | 240 |
| agcctgctgg agctcatcga cgacgtgcag cgcctgggcc tgacctacaa gtttgagaaa | 300 |
| gatatcatca aggcgctgga gaacatcgtc ctgctggacg agaataagaa gaacaaaagc | 360 |
| gatctgcacg cgaccgccct gagcttccgc ctgctgcggc agcatggctt tgaggtgagc | 420 |
| caggacgtgt tcgagcgctt caaggacaaa gaaggggct tctccgggga actgaagggt | 480 |
| gacgtgcagg gcctgctgag cctgtacgag gccagctatc tcggtttcga aggcgaaaat | 540 |
| ctgctggagg aggcccgtac cttcagcatc acccatctga gaacaacct caaggagggg | 600 |
| atcaacacga aggtggccga gcaggtgtcc cacgcgctgg agctgccgta tcatcaacgc | 660 |
| ctgcaccgcc tggaggcgcg gtggtttctg gacaagtacg aacccaagga gccgcatcac | 720 |
| cagctgctgc tggaactggc caaactcgat ttcaacatgg tccagaccct gcaccaaaaa | 780 |
| gagctgcagg acctgagccg gtggtggacc gagatgggcc tcgccagcaa gctggatttc | 840 |
| gtgcgggacc gcctgatgga agtgtacttc tgggcgctgg catggcgcc ggacccgcag | 900 |
| ttcggcgaat gccgcaaggc cgtcaccaag atgttcggtc tggtcaccat tatcgatgac | 960 |
| gtctatgacg tgtacggtac cctggacgaa ctgcagctct tcaccgacgc ggtggaacgc | 1020 |
| tgggacgtga acgccatcaa cacgctgccc gactatatga gctgtgctt cctggccctg | 1080 |
| tacaacaccg tgaacgacac gtcctactcc atcctgaagg agaagggcca caataacctg | 1140 |
| agctatctga ccaaaagctg gcgcgaactg tgcaaggcct tcctgcaaga agccaagtgg | 1200 |
| agcaataaca agatcatccc cgccttcagc aagtacctgg agaacgccag cgtgtcctcc | 1260 |
| agcggggtcg cgctgctggc gccgagctac ttctcggtct gccagcagca ggaagatatc | 1320 |
| tcggaccacg ccctccgctc cctgaccgac ttccacggc tggtgcgctc gtcctgcgtg | 1380 |

| | | |
|---|---|---|
| atctttcggc tgtgcaacga tctggcgacc tcggcggcgg aactcgaacg cggcgaaacc | 1440 |
| accaacagca tcatcagcta catgcacgag aacgacggca cgagcgagga acaggcccgc | 1500 |
| gaagagctgc gcaagctgat cgacgccgag tggaagaaaa tgaaccgcga gcgcgtgtcg | 1560 |
| gacagcaccc tgctgccgaa ggcgttcatg gagatcgccg tgaacatggc ccgcgtgagc | 1620 |
| cactgcacct accaatatgg ggacgggctg ggccgcccgg attacgccac cgagaaccgc | 1680 |
| atcaagctgc tgctcatcga cccgttcccc atcaaccagc tgatgtacgt gtgaggatcc | 1740 |
| cgtaac | 1746 |

<210> SEQ ID NO 121
<211> LENGTH: 4768
<212> TYPE: DNA
<213> ORGANISM: Artificial Sequence
<220> FEATURE:
<223> OTHER INFORMATION: Synthetic Construct

<400> SEQUENCE: 121

| | | |
|---|---|---|
| ctcgggccgt ctcttgggct tgatcggcct tcttgcgcat ctcacgcgct cctgcggcgg | 60 |
| cctgtagggc aggctcatac ccctgccgaa ccgcttttgt cagccggtcg gccacggctt | 120 |
| ccggcgtctc aacgcgcttt gagattccca gcttttcggc caatccctgc ggtgcatagg | 180 |
| cgcgtggctc gaccgcttgc gggctgatgg tgacgtggcc cactggtggc cgctccaggg | 240 |
| cctcgtagaa cgcctgaatg cgcgtgtgac gtgccttgct gccctcgatg ccccgttgca | 300 |
| gccctagatc ggccacagcg gccgcaaacg tggtctggtc gcgggtcatc tgcgcttttgt | 360 |
| tgccgatgaa ctccttggcc gacagcctgc cgtcctgcgt cagcggcacc acgaacgcgg | 420 |
| tcatgtgcgg gctggtttcg tcacggtgga tgctggccgt cacgatgcga tccgccccgt | 480 |
| acttgtccgc cagccacttg tgcgccttct cgaagaacgc cgcctgctgt tcttggctgg | 540 |
| ccgacttcca ccattccggg ctggccgtca tgacgtactc gaccgccaac acagcgtcct | 600 |
| tgcgccgctt ctctggcagc aactcgcgca gtcggcccat cgcttcatcg gtgctgctgg | 660 |
| ccgcccagtg ctcgttctct ggcgtcctgc tggcgtcagc gttgggcgtc tcgcgctcgc | 720 |
| ggtaggcgtg cttgagactg gccgccacgt tgcccatttt cgccagcttc ttgcatcgca | 780 |
| tgatcgcgta tgccgccatg cctgcccctc ccttttggtg tccaaccggc tcgacggggg | 840 |
| cagcgcaagg cggtgcctcc ggcgggccac tcaatgcttg agtatactca ctagactttg | 900 |
| cttcgcaaag tcgtgaccgc ctacggcggc tgcggcgccc tacgggcttg ctctccgggc | 960 |
| ttcgccctgc gcggtcgctg cgctcccttg ccagcccgtg gatatgtgga cgatggccgc | 1020 |
| gagcggccac cggctggctc gcttcgctcg gcccgtggac aaccctgctg gacaagctga | 1080 |
| tggacaggct gcgcctgccc acgagcttga ccacagggat tgcccaccgg ctacccagcc | 1140 |
| ttcgaccaca tacccaccgg ctccaactgc gcggcctgcg gccttgcccc atcaattttt | 1200 |
| ttaattttct ctggggaaaa gcctccggcc tgcggcctgc gcgcttcgct tgccggttgg | 1260 |
| acaccaagtg gaaggcgggt caaggctcgc gcagcgaccg cgcagcggct tggccttgac | 1320 |
| gcgcctggaa cgacccaagc ctatgcgagt ggggcagtc gaaggcgaag cccgcccgcc | 1380 |
| tgccccccga gcctcacggc ggcgagtgcg ggggttccaa gggggcagcg ccaccttggg | 1440 |
| caaggccgaa ggccgcgcag tcgatcaaca agccccggag gggccacttt ttgcggagg | 1500 |
| gggagccgcg ccgaaggcgt ggggaaccc cgcagggtg cccttctttg gcaccaaag | 1560 |
| aactagatat agggcgaaat gcgaaagact taaaaatcaa caacttaaaa aaggggggta | 1620 |
| cgcaacagct cattgcggca ccccccgcaa tagctcattg cgtaggttaa agaaaatctg | 1680 |

```
taattgactg ccactttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacgcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg ccacctcga   2580
cctgaatgga agccggcggc acctcgctaa cggattcacc gtttttatca ggctctggga   2640
ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
atcggtgcgg gcctcttcgc tattacgcca gctggcgaaa gggggatgtg ctgcaaggcg   3120
attaagttgg gtaacgccag ggttttccca gtcacgacgt tgtaaaacga cggccagtga   3180
gcgcgcgtaa tacgactcac tatagggcga attggagctc caccgcggtg gcggccgctc   3240
tagaactagt ggatcccccg gctgcagga ttcgatatc aagcttatcg ataccgtcga   3300
cctcgagggg gggcccggta cccagctttt gttccctttta gtgagggtta attgcgcgct   3360
tggcgtaatc atggtcatag ctgtttcctg tgtgaaattg ttatccgctc acaattccac   3420
acaacatacg agccggaagc ataaagtgta aagcctgggg tgcctaatga gtgagctaac   3480
tcacattaat tgcgttgcgc tcactgcccg ctttccagtc gggaaacctg tcgtgccagc   3540
tgcattaatg aatcggccaa cgcgcgggga gaggcggttt gcgtattggg cgcatgcata   3600
aaaactgttg taattcatta agcattctgc cgacatggaa gccatcacaa acggcatgat   3660
gaacctgaat cgccagcggc atcagcacct tgtcgccttg cgtataatat ttgcccatgg   3720
acgcacaccg tggaaacgga tgaaggcacg aacccagttg acataagcct gttcggttcg   3780
taaactgtaa tgcaagtagc gtatgcgctc acgcaactgg tccagaacct tgaccgaacg   3840
cagcggtggt aacggcgcag tggcggtttt catggcttgt tatgactgtt ttttgtaca   3900
gtctatgcct cgggcatcca agcagcaagc gcgttacgcc gtgggtcgat gtttgatgtt   3960
atggagcagc aacgatgtta cgcagcagca acgatgttac gcagcagggc agtcgcccta   4020
aaacaaagtt aggtggctca agtatgggca tcattcgcac atgtaggctc ggccctgacc   4080
```

-continued

| | |
|---|---|
| aagtcaaatc catgcgggct gctcttgatc ttttcggtcg tgagttcgga gacgtagcca | 4140 |
| cctactccca acatcagccg gactccgatt acctcgggaa cttgctccgt agtaagacat | 4200 |
| tcatcgcgct tgctgccttc gaccaagaag cggttgttgg cgctctcgcg cttacgttc | 4260 |
| tgcccaggtt tgagcagccg cgtagtgaga tctatatcta tgatctcgca gtctccggcg | 4320 |
| agcaccggag gcagggcatt gccaccgcgc tcatcaatct cctcaagcat gaggccaacg | 4380 |
| cgcttggtgc ttatgtgatc tacgtgcaag cagattacgg tgacgatccc gcagtggctc | 4440 |
| tctatacaaa gttgggcata cgggaagaag tgatgcactt tgatatcgac ccaagtaccg | 4500 |
| ccacctaaca attcgttcaa gccgagatcg cttcccggc cgcggagttg ttcggtaaat | 4560 |
| tgtcacaacg ccgccaggtg gcactttcg gggaaatgtg cgcgcccgcg ttcctgctgg | 4620 |
| cgctgggcct gtttctggcg ctggactcc cgctgttccg tcagcagctt ttcgcccacg | 4680 |
| gccttgatga tcgcggcggc cttggcctgc atatcccgat tcaacggccc cagggcgtcc | 4740 |
| agaacgggct tcaggcgctc ccgaaggt | 4768 |

<210> SEQ ID NO 122
<211> LENGTH: 6466
<212> TYPE: DNA
<213> ORGANISM: Artificial Sequence
<220> FEATURE:
<223> OTHER INFORMATION: Synthetic Construct

<400> SEQUENCE: 122

| | |
|---|---|
| ctcgggccgt ctcttgggct tgatcggcct tcttgcgcat ctcacgcgct cctgcggcgg | 60 |
| cctgtagggc aggctcatac ccctgccgaa ccgcttttgt cagccggtcg gccacggctt | 120 |
| ccggcgtctc aacgcgcttt gagattccca gcttttcggc caatccctgc ggtgcatagg | 180 |
| cgcgtggctc gaccgcttgc gggctgatgg tgacgtggcc cactggtggc cgctccaggg | 240 |
| cctcgtagaa cgcctgaatg cgcgtgtgac gtgccttgct gccctcgatg ccccgttgca | 300 |
| gccctagatc ggccacagcg gccgcaaacg tggtctggtc gcgggtcatc tgcgctttgt | 360 |
| tgccgatgaa ctccttggcc gacagcctgc cgtcctgcgt cagcggcacc acgaacgcgg | 420 |
| tcatgtgcgg gctggtttcg tcacggtgga tgctggccgt cacgatgcga tccgcccgt | 480 |
| acttgtccgc cagccacttg tgcgccttct cgaagaacgc cgcctgctgt tcttggctgg | 540 |
| ccgacttcca ccattccggg ctggccgtca tgacgtactc gaccgccaac acagcgtcct | 600 |
| tgcgccgctt ctctggcagc aactcgcgca gtcggcccat cgcttcatcg gtgctgctgg | 660 |
| ccgcccagtc tcgttctct ggcgtcctgc tggcgtcagc gttgggcgtc tcgcgctcgc | 720 |
| ggtaggcgtg cttgagactg gccgccacgt tgcccatttt cgccagcttc ttgcatcgca | 780 |
| tgatcgcgta tgccgccatg cctgcccctc ccttttggtg tccaaccggc tcgacggggg | 840 |
| cagcgcaagg cggtgcctcc ggcgggccac tcaatgcttg agtatactca ctagactttg | 900 |
| cttcgcaaag tcgtgaccgc ctacggcgg tgcggcgccc tacggcttg ctctccgggc | 960 |
| ttcgccctgc gcggtcgctg cgctcccttg ccagcccgtg gatatgtgga cgatggccgc | 1020 |
| gagcggccac cggctggctc gcttcgctcg gccgtggac aaccctgctg gacaagctga | 1080 |
| tggacaggct gcgcctgccc acgagcttga ccacagggat tgcccaccgg ctacccagcc | 1140 |
| ttcgaccaca tacccaccgg ctccaactgc gcggcctgcg gccttgcccc atcaattttt | 1200 |
| ttaattttct ctggggaaaa gcctccggcc tgcggcctgc gcgcttcgct tgccggttgg | 1260 |
| acaccaagtg gaaggcgggt caaggctcgc gcagcgaccg cgcagcggct tggccttgac | 1320 |
| gcgcctggaa cgacccaagc ctatgcgagt gggggcagtc gaaggcgaag cccgccccgcc | 1380 |

```
tgcccccga gcctcacggc ggcgagtgcg ggggttccaa gggggcagcg ccaccttggg    1440
caaggccgaa ggccgcgcag tcgatcaaca agccccggag gggccacttt ttgccggagg    1500
gggagccgcg ccgaaggcgt gggggaaccc cgcagggtg cccttctttg gcaccaaag     1560
aactagatat agggcgaaat gcgaaagact taaaaatcaa caacttaaaa aagggggta    1620
cgcaacagct cattgcggca cccccccgcaa tagctcattg cgtaggttaa agaaaatctg   1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacggcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg gccaccctcga  2580
cctgaatgga agccggcggc acctcgctaa cggattcacc gttttttatca ggctctggga  2640
ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
atcggtgcgg gcctcttcgc tattacgcca gctggcgaaa gggggatgtg ctgcaaggcg   3120
attaagttgg gtaacgccag ggttttccca gtcacgacgt tgtaaaacga cggccagtga   3180
gcgcgcgtaa tacgactcac tatagggcga attggagctc caccgcggtg gcggccgctc   3240
tagaactagt ggatcctcac acgtacatca gctggttgat ggggaacggg tcgatgagca   3300
gcagcttgat gcggttctcg gtggcgtaat ccggcggcc cagcccgtcc ccatattggt    3360
aggtgcagtg gctcacgcgg gccatgttca cggcgatctc catgaacgcc ttcggcagca   3420
gggtgctgtc cgacacgcgc tcgcggttca ttttcttcca ctcggcgtcg atcagcttgc   3480
gcagctcttc gcgggcctgt cctcgctcg tgccgtcgtt ctcgtgcatg tagctgatga   3540
tgctgttggt ggtttcgccg cgttcgagtt ccgccgccga ggtcgccaga tcgttgcaca  3600
gccgaaagat cacgcaggac gagcgcacca ggccgtggaa gtcggtcagg gagcggaggg   3660
cgtggtccga gatatcttcc tgctgctggc agaccgagaa gtagctcggc gccagcagcg   3720
cgaccccgct ggaggacacg ctggcgttct ccaggtactt gctgaaggcg gggatgatct   3780
```

```
tgttattgct ccacttggct tcttgcagga aggccttgca cagttcgcgc cagcttttgg    3840
tcagatagct caggttattg tggcccttct ccttcaggat ggagtaggac gtgtcgttca    3900
cggtgttgta cagggccagg aagcacagct tcatatagtc gggcagcgtg ttgatggcgt    3960
tcacgtccca gcgttccacc gcgtcggtga agagctgcag ttcgtccagg gtaccgtaca    4020
cgtcatagac gtcatcgata atggtgacca gaccgaacat cttggtgacg gccttgcggc    4080
attcgccgaa ctgcgggtcc ggcgccatgc ccagcgccca gaagtacact tccatcaggc    4140
ggtcccgcac gaaatccagc ttgctggcga ggcccatctc ggtccaccac cggctcaggt    4200
cctgcagctc ttttggtgc agggtctgga ccatgttgaa atcgagtttg ccagttcca     4260
gcagcagctg gtgatgcggc tccttgggtt cgtacttgtc cagaaaccac cgcgcctcca    4320
ggcggtgcag gcgttgatga tacgcagct ccagcgcgtg ggacacctgc tcggccacct    4380
tcgtgttgat ccctccttg aggttgttct tcagatgggt gatgctgaag gtacgggcct    4440
cctccagcag atttcgcct tcgaaaccga gatagctggc ctcgtacagg ctcagcaggc    4500
cctgcacgtc acccttcagt tccccggaga agccccttc tttgtccttg aagcgctcga    4560
acacgtcctg gctcacctca aagccatgct gccgcagcag gcggaagctc agggcggtcg    4620
cgtgcagatc gcttttgttc ttcttattct cgtccagcag gacgatgttc tccagcgcct    4680
tgatgatatc tttctcaaac ttgtaggtca ggcccaggcg ctgcacgtcg tcgatgagct    4740
ccagcaggct caggggctgg gtgtccaccc ggttgatcat gcaacgcacc tcctcctcca    4800
gcttggtggc cttctcttcg agcttctcca ccttcaggtc gttttccagg ctctgcagga    4860
actcgaagtt ccacaggttg ggctggtagt tcgcggaccg acggctatta tgctcggtga    4920
tctgggtgaa ctggctgctg gtggcgcaca tatgtatatc tccttcttaa agttaaacaa    4980
gcttatcgat accgtcgacc tcgagggggg gcccggtacc cagcttttgt tccctttagt    5040
gagggttaat tgcgcgcttg gcgtaatcat ggtcatagct gtttcctgtg tgaaattgtt    5100
atccgctcac aattccacac aacatacgag ccggaagcat aaagtgtaaa gcctggggtg    5160
cctaatgagt gagctaactc acattaattg cgttgcgctc actgcccgct ttccagtcgg    5220
gaaacctgtc gtgccagctg cattaatgaa tcggccaacg cgcggggaga ggcggtttgc    5280
gtattgggcg catgcataaa aactgttgta attcattaag cattctgccg acatggaagc    5340
catcacaaac ggcatgatga acctgaatcg ccagcggcat cagcaccttg tcgccttgcg    5400
tataatattt gcccatggac gcacaccgtg gaaacggatg aaggcacgaa cccagttgac    5460
ataagcctgt tcggttcgta aactgtaatg caagtagcgt atgcgctcac gcaactggtc    5520
cagaaccttg accgaacgca gcggtggtaa cggcgcagtg gcggttttca tggcttgtta    5580
tgactgtttt tttgtacagt ctatgcctcg ggcatccaag cagcaagcgc gttacgccgt    5640
gggtcgatgt ttgatgttat ggagcagcaa cgatgttacg cagcagcaac gatgttacgc    5700
agcagggcag tcgccctaaa acaaagttag gtggctcaag tatgggcatc attcgcacat    5760
gtaggctcgg ccctgaccaa gtcaaatcca tgcgggctgc tcttgatctt ttcggtcgtg    5820
agttcggaga cgtagccacc tactcccaac atcagccgga ctccgattac ctcgggaact    5880
tgctccgtag taagacattc atcgcgcttg ctgccttcga ccaagaagcg gttgttggcg    5940
ctctcgcggc ttacgttctg cccaggtttg agcagccgcg tagtgagatc tatatctatg    6000
atctcgcagt ctccggcgag caccggaggc agggcattgc caccgcgctc atcaatctcc    6060
tcaagcatga ggccaacgcg cttggtgctt atgtgatcta cgtgcaagca gattacggtg    6120
acgatcccgc agtggctctc tatacaaagt tgggcatacg gaagaagtg atgcactttg    6180
```

-continued

| | |
|---|---|
| atatcgaccc aagtaccgcc acctaacaat tcgttcaagc cgagatcggc ttcccggccg | 6240 |
| cggagttgtt cggtaaattg tcacaacgcc gccaggtggc acttttcggg gaaatgtgcg | 6300 |
| cgcccgcgtt cctgctggcg ctgggcctgt ttctggcgct ggacttcccg ctgttccgtc | 6360 |
| agcagctttt cgcccacggc cttgatgatc gcggcggcct tggcctgcat atcccgattc | 6420 |
| aacggcccca gggcgtccag aacgggcttc aggcgctccc gaaggt | 6466 |

<210> SEQ ID NO 123
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 123

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta tagggatttt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatacg cgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa atcccttaa | 1440 |
| cgtgagtttt cgttccactg agcgtcagac cccgtagaaa agatcaaagg atcttcttga | 1500 |
| gatcctttt ttctgcgcgt aatctgctgc ttgcaaacaa aaaaaccacc gctaccagcg | 1560 |
| gtggtttgtt tgccggatca agagctacca actcttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata agtcgtgtct taccgggttg gactcaagac gatagttacc ggataaggcg | 1800 |

```
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag agagcgcac gagggagctt    1980 ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttttac ggttcctggc cttttgctgg ccttttgctc acatgttctt tcctgcgtta  2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataagaaga cagtcataag tgcggcgacg atagtcatgc cccgcgccca    3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc gttccgcta   3960 tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
```

-continued

```
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccacttttt tcccgcgttt   4500 tcgcagaaac gtggctggcc tggttcacca cgcggaaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttctct gaaactgaaa ccgaaacgcg tcgttctgcg aactacgaac ctaacagctg   5160
ggactatgat tacctgctgt cctccgacac ggacgagtcc atcgaagtac acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt cgtgcgctgg atcgcttcgt ttcctccggc ggcttcgatg gcgtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gtcccatgca ctggaactgc cactgcatcg   5700
ccgtactcag cgtctggaag cagtatggtc tatcgaggcc taccgtaaaa aggaggacgc   5760
gaaccaggtt ctgctggagc tggcaattct ggattacaac atgatccagt ctgtatacca   5820
gcgtgatctg cgtgaaacgt cccgttggtg gcgtcgtgtg ggtctggcga ccaaactgca   5880 cttttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tgatcttcgc ttacttcgct gtcgtgcaga acattaaaaa   6360
ggaagagatc gaaaacctgc aaaaatacca tgacatcatc tctcgtcctt cccatatctt   6420
ccgtctgtgc aatgacctgg ctagcgcgtc tgcggaaatt gcgcgtggtg aaaccgcaaa   6480
tagcgtttct tgttacatgc gcactaaagg tatctccgaa gaactggcta ccgaaagcgt   6540
gatgaatctg atcgatgaaa cctggaaaaa gatgaacaag gaaaaactgg gtggtagcct   6600
```

-continued

```
gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taaccccttg    6900
gggcctctaa acgggtcttg agggttttt tgctgaaagg aggaactata tccggat        6957
```

<210> SEQ ID NO 124
<211> LENGTH: 560
<212> TYPE: PRT
<213> ORGANISM: Populus tremuloides

<400> SEQUENCE: 124

```
Met Arg Cys Ser Val Ser Thr Glu Asn Val Ser Phe Ser Glu Thr Glu
1               5                   10                  15

Thr Glu Thr Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val His Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Arg Ala Leu
                85                  90                  95

Asp Arg Phe Val Ser Ser Gly Gly Phe Asp Gly Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Ser His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320
```

```
Glu Leu Glu Leu Phe Thr Asp Ala Val Glu Arg Trp Asp Val Asn Ala
            325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
            355                 360                 365

Asn Ile Leu Pro Tyr Leu Thr Lys Ala Trp Ala Asp Leu Cys Asn Ala
            370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
            405                 410                 415

Leu Ile Phe Ala Tyr Phe Ala Val Val Gln Asn Ile Lys Lys Glu Glu
            420                 425                 430

Ile Glu Asn Leu Gln Lys Tyr His Asp Ile Ile Ser Arg Pro Ser His
            435                 440                 445

Ile Phe Arg Leu Cys Asn Asp Leu Ala Ser Ala Ser Ala Glu Ile Ala
            450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
            485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
            515                 520                 525

Thr Tyr His Asn Gly Asp Ala His Thr Ser Pro Asp Glu Leu Thr Arg
            530                 535                 540

Lys Arg Val Leu Ser Val Ile Thr Glu Pro Ile Leu Pro Phe Glu Arg
545                 550                 555                 560

<210> SEQ ID NO 125
<211> LENGTH: 4719
<212> TYPE: DNA
<213> ORGANISM: Artificial Sequence
<220> FEATURE:
<223> OTHER INFORMATION: Synthetic Construct

<400> SEQUENCE: 125
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
ttaggtgacg cgttagaata ctcaagctat gcatcaagct tggtaccgag ctcggatcca     300
ctagtaacgg ccgccagtgt gctggaattc aggcggtccg gaaagagaag cagtatagcg     360
tcaggtgaac gctgctccaa ccgttgcata caacaaaga cgccttcatg ttatactgcg      420
gcaaaatact gatgatgtgt cgcgattgcg gccaaccgtt ccaccccag gcgagagaca      480 atgaccaacc tacagacttt cgagttacct accgaggtaa ccggctgcgc cgccgatatc     540
tcattgggaa gggcgctgat ccaagcctgg caaaaagatg gcatttttca gatcaagacc     600
gatagtgagc aggatcgcaa aacgcaggaa gcaatggctg ctagcaagca gttttgcaag     660
gaaccgctga cttttaagag tagctgcgtt agcgatctga cctacagcgg ctatgttgcg     720
tcaggcgagg aagtcacagc tggtaaacct gatttccctg aaatcttcac tgtctgcaag     780
```

```
gacttgtcgg taggcgatca gcgtgtaaaa gccggctggc cttgccatgg tccggtgcca    840
tggccaaata acacctatca gaaaagcatg aagaccttca tggaagagct gggtttagcg    900
ggcgaacggt tgctcaaact gacagcgctc ggctttgaac tacccatcaa cacgttcacc    960
gacttaactc gcgatggttg gcaccacatg cgtgtattac gcttcccgcc ccaaacatcc   1020
acgctgtccc gtggaattgg tgcgcacact gactatgggt tgttggtaat tgccgctcag   1080
gacgatgttg gtggcttata tattcgccct ccagtcgagg gagagaagcg taatcgtaac   1140
tggttgcctg gtgagagctc agcaggcatg tttgagcacg atgaaccttg gaccttcgtg   1200
acgcccaccc caggcgtgtg gacagttttc ccaggtgata tcttgcagtt catgaccggc   1260
ggccagctgc tttccactcc gcacaaggtt aagctcaata cccgcgaacg tttcgcctgc   1320
gcttattttc atgagcctaa ttttgaagca tccgcctatc cgttgttcga gcccagcgcc   1380
aatgagcgta ttcattatgg tgagcacttt accaacatgt ttatgcgttg ctatccagat   1440
cggatcacca cccagagcat caacaaggag aatcgcctgg cgcacttgga ggacttgaag   1500
aagtattcgg acacccgcgc gacaggctca tgacggtccg cctgaattct gcagatatcc   1560
atcacactgg cggccgctcg agcatgcatc tagagggccc aattcgccct atagtgagtc   1620
gtattacaat tcactggccg tcgttttaca acgtcgtgac tgggaaaacc ctggcgttac   1680
ccaacttaat cgccttgcag cacatccccc tttcgccagc tggcgtaata gcgaagaggc   1740
ccgcaccgat cgcccttccc aacagttgcg cagcctatac gtacggcagt ttaaggttta   1800
cacctataaa agagagagcc gttatcgtct gtttgtggat gtacagagtg atattattga   1860
cacgccgggg cgacggatgg tgatccccct ggccagtgca cgtctgctgt cagataaagt   1920
ctcccgtgaa ctttacccgg tggtgcatat cggggatgaa agctggcgca tgatgaccac   1980
cgatatggcc agtgtgccgg tctccgttat cggggaagaa gtggctgatc tcagccaccg   2040
cgaaaatgac atcaaaaacg ccattaacct gatgttctgg ggaatataaa tgtcaggcat   2100
gagattatca aaaaggatct tcacctagat ccttttcacg tagaaagcca gtccgcagaa   2160
acggtgctga ccccggatga atgtcagcta ctgggctatc tggacaaggg aaaacgcaag   2220
cgcaaagaga agcaggtag cttgcagtgg gcttacatgg cgatagctag actgggcggt   2280
tttatgctga gcaagcgaac cggaattgcc agctggggcg ccctctggta aggttgggaa   2340
gccctgcaaa gtaaactgga tggctttctt gccgccaagg atctgatggc gcagggatc   2400
aagctctgat caagacag gatgaggatc gtttcgcatg attgaacaag atggattgca   2460
cgcaggttct ccggccgctt gggtggagag gctattcggc tatgactggg cacaacagac   2520
aatcggctgc tctgatgccg ccgtgttccg gctgtcagcg caggggcgcc cggttctttt   2580
tgtcaagacc gacctgtccg gtgccctgaa tgaactgcaa gacgaggcag cgcggctatc   2640
gtggctggcc acgacgggcg ttccttgcgc agctgtgctc gacgttgtca ctgaagcggg   2700
aagggactgg ctgctattgg gcgaagtgcc ggggcaggat ctcctgtcat ctcaccttgc   2760
tcctgccgag aaagtatcca tcatggctga tgcaatgcgg cggctgcata cgcttgatcc   2820
ggctacctgc ccattcgacc accaagcgaa acatcgcatc gagcgagcac gtactcggat   2880
ggaagccggt cttgtcgatc aggatgatct ggacgaagag catcaggggc tcgcgccagc   2940
cgaactgttc gccaggctca aggcgagcat gcccgacggc gaggatctcg tcgtgaccca   3000
tggcgatgcc tgcttgccga atatcatggt ggaaaatggc cgcttttctg gattcatcga   3060
ctgtggccgc tgggtgtgg cggaccgcta tcaggacata gcgttggcta cccgtgatat   3120
tgctgaagag cttggcggcg aatgggctga ccgcttcctc gtgctttacg gtatcgccgc   3180
```

-continued

```
tcccgattcg cagcgcatcg ccttctatcg ccttcttgac gagttcttct gaattattaa    3240
cgcttacaat ttcctgatgc ggtattttct ccttacgcat ctgtgcggta tttcacaccg    3300
catcaggtgg cacttttcgg ggaaatgtgc gcggaacccc tatttgttta tttttctaaa    3360
tacattcaaa tatgtatccg ctcatgagac aataaccctg ataaatgctt caataatagc    3420
acgtgaggag ggccaccatg gccaagttga ccagtgccgt tccggtgctc accgcgcgcg    3480
acgtcgccgg agcggtcgag ttctggaccg accggctcgg gttctcccgg gacttcgtgg    3540
aggacgactt cgccggtgtg gtccgggacg acgtgaccct gttcatcagc gcggtccagg    3600
accaggtggt gccggacaac accctggcct gggtgtgggt gcgcggcctg gacgagctgt    3660
acgccgagtg gtcggaggtc gtgtccacga acttccggga cgcctccggg ccggccatga    3720
ccgagatcgg cgagcagccg tgggggcggg agttcgccct gcgcgacccg gccggcaact    3780
gcgtgcactt cgtggccgag gagcaggact gacacgtgct aaaacttcat ttttaattta    3840
aaaggatcta ggtgaagatc cttttttgata atctcatgac caaaatccct taacgtgagt    3900
tttcgttcca ctgagcgtca gaccccgtag aaaagatcaa aggatcttct tgagatcctt    3960
ttttttctgcg cgtaatctgc tgcttgcaaa caaaaaaacc accgctacca gcggtggttt    4020
gtttgccgga tcaagagcta ccaactcttt ttccgaaggt aactggcttc agcagagcgc    4080
agataccaaa tactgttctt ctagtgtagc cgtagttagg ccaccacttc aagaactctg    4140
tagcaccgcc tacatacctc gctctgctaa tcctgttacc agtggctgct gccagtggcg    4200
ataagtcgtg tcttaccggg ttggactcaa gacgatagtt accggataag gcgcagcggt    4260
cgggctgaac ggggggttcg tgcacacagc ccagcttgga gcgaacgacc tacaccgaac    4320
tgagatacct acagcgtgag ctatgagaaa gcgccacgct tcccgaaggg agaaaggcgg    4380
acaggtatcc ggtaagcggc agggtcggaa caggagagcg cacgagggag cttccagggg    4440
gaaacgcctg gtatctttat agtcctgtcg ggtttcgcca cctctgactt gagcgtcgat    4500
ttttgtgatg ctcgtcaggg gggcggagcc tatggaaaaa cgccagcaac gcggcctttt    4560
tacggttcct ggccttttgc tggccttttg ctcacatgtt ctttcctgcg ttatcccctg    4620
attctgtgga taaccgtatt accgcctttg agtgagctga taccgctcgc cgcagccgaa    4680
cgaccgagcg cagcgagtca gtgagcgagg aagcggaag                           4719
```

<210> SEQ ID NO 126
<211> LENGTH: 45
<212> TYPE: DNA
<213> ORGANISM: Artificial Sequence
<220> FEATURE:
<223> OTHER INFORMATION: Synthetic Construct

<400> SEQUENCE: 126
accgttcgtt cttatcgaaa ctaaaaaaaa ccggccttgg ccccg                   45

<210> SEQ ID NO 127
<211> LENGTH: 28
<212> TYPE: DNA
<213> ORGANISM: Artificial Sequence
<220> FEATURE:
<223> OTHER INFORMATION: Synthetic Construct

<400> SEQUENCE: 127
cggaccgtca tgagcctgtc gcgcgggg                                      28

<210> SEQ ID NO 128
<211> LENGTH: 40

-continued

```
<212> TYPE: DNA
<213> ORGANISM: Artificial Sequence
<220> FEATURE:
<223> OTHER INFORMATION: Synthetic Construct

<400> SEQUENCE: 128
ccaccccagg cgagagacaa tgaccaacct acagactttc                                40

<210> SEQ ID NO 129
<211> LENGTH: 27
<212> TYPE: DNA
<213> ORGANISM: Artificial Sequence
<220> FEATURE:
<223> OTHER INFORMATION: Synthetic Construct

<400> SEQUENCE: 129
cggtccggaa agagaagcag tatagcg                                             27

<210> SEQ ID NO 130
<211> LENGTH: 40
<212> TYPE: DNA
<213> ORGANISM: Artificial Sequence
<220> FEATURE:
<223> OTHER INFORMATION: Synthetic Construct

<400> SEQUENCE: 130
gaaagtctgt aggttggtca ttgtctctcg cctggggtgg                               40

<210> SEQ ID NO 131
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4, 5, 6, 7, 8, 9
<223> OTHER INFORMATION: n = A,T,C or G

<400> SEQUENCE: 131
ccannnnnnt gg                                                             12
```

What is claimed is:

1. A method of producing a compound, wherein the compound has one or more characteristics selected from the group consisting of (a) a Henry's law coefficient of less than 250 M/atm and (b) a solubility in water of less than 100 g/L, the method comprising:
   a) culturing cells comprising one or more nucleic acids encoding for an isoprene synthase polypeptide;
   b) adding an oxygen-containing gas to the culture at a gas sparging rate between about 0.01 vvm to about 2 vvm, thereby producing the compound; and
   c) recovering the compound made in step (b).

2. The method of claim 1, wherein the compound produced is ethylene.

3. The method of claim 1, wherein the compound produced is isoprene.

4. A method of producing a compound, wherein the compound has one or more characteristics selected from the group consisting of (a) a Henry's law coefficient of less than 250 M/atm and (b) a solubility in water of less than 100 g/L, the method comprising:
   a) culturing cells comprising one or more nucleic acids encoding for an isoprene synthase polypeptide;
   b) adding an oxygen-containing gas to the culture at a gas sparging rate of at least 0.1 vvm, thereby producing the compound; and
   c) recovering the compound from the gas phase.

5. The method of claim 4, wherein the compound produced is ethylene.

6. The method of claim 4, wherein the compound is isoprene.

7. The method of claim 1, wherein the cells further comprise one or more heterologous nucleic acids or one or more additional copies of an endogenous nucleic acid encoding an isopentenyl-diphosphate-delta-isomerase (IDI) polypeptide, a mevalonic acid (MVA) pathway enzyme, or a deoxyxylulose-5-phosphate synthase (DXP) pathway enzyme.

8. The method of claim 7 wherein the MVA pathway enzyme is one or more enzymes selected from the group consisting of acetyl-CoA acetyltransferase (AA-CoA thiolase), 3-hydroxy-3-methylglutaryl-CoA synthase (HMG-CoA synthase), 3-hydroxy-3-methylglutaryl-CoA reductase (HMG-CoA reductase), mevalonate kinase (MVK), phosphomevalonate kinase (PMK), diphosphomevalonate decarboxylase (MVD), phosphomevalonate decarboxylase (PMDC), and isopentenyl diphosphate isomerase (IDI).

9. The method of claim 1, wherein the isoprene synthase polypeptide is from *Pueraria* or *Populus* or the hybrid *Populus alba×Populus tremula*, or variants thereof.

10. The method of claim 9, wherein the isoprene synthase polypeptide is selected from the group consisting of *Pueraria montana, Pueraria lobata, Populus tremuloides, Populus alba, Populus nigra, Populus trichocarpa*, and variants thereof.

11. The method of claim 1, wherein the cells are gram-positive bacterial cells, *Streptomyces* cells, gram-negative bacterial cells, *Escherichia* cells, *Pantoea* cells, fungal cells, filamentous fungal cells, *Trichoderma* cells, *Corynebacterium* cells, *Aspergillus* cells, or yeast cells.

12. The method of claim 11, wherein the cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae, Aspergillus niger, Saccharomyces cerevisiae, Corynebacterium glutamicum*, and *Yarrowia lipolytica*.

13. The method of claim 3, wherein the cells produce greater than 400 nmole/gwcm/hour of isoprene and the carbon dioxide evolution rate of the cells is greater than $1\times10^{-18}$ mmol/L/hour.

14. The method of claim 4, wherein the cells further comprise one or more heterologous nucleic acids or one or more additional copies of an endogenous nucleic acid encoding an isopentenyl-diphosphate-delta-isomerase (IDI) polypeptide, a mevalonic acid (MVA) pathway enzyme, or a deoxyxylulose-5-phosphate synthase (DXP) pathway enzyme.

15. The method of claim 14 wherein the MVA pathway enzyme is one or more enzymes selected from the group consisting of acetyl-CoA acetyltransferase (AA-CoA thiolase), 3-hydroxy-3-methylglutaryl-CoA synthase (HMG-CoA synthase), 3-hydroxy-3-methylglutaryl-CoA reductase (HMG-CoA reductase), mevalonate kinase (MVK), phosphomevalonate kinase (PMK), diphosphomevalonate decarboxylase (MVD), phosphomevalonate decarboxylase (PMDC), and isopentenyl diphosphate isomerase (IDI).

16. The method of claim 4, wherein the isoprene synthase polypeptide is from *Pueraria* or *Populus* or the hybrid *Populus alba×Populus tremula*, or variants thereof.

17. The method of claim 16, wherein the isoprene synthase polypeptide is selected from the group consisting of *Pueraria montana, Pueraria lobata, Populus tremuloides, Populus alba, Populus nigra, Populus trichocarpa*, and variants thereof.

18. The method of claim 4, wherein the cells are gram-positive bacterial cells, *Streptomyces* cells, gram-negative bacterial cells, *Escherichia* cells, *Pantoea* cells, fungal cells, filamentous fungal cells, *Trichoderma* cells, *Corynebacterium* cells, *Aspergillus* cells, or yeast cells.

19. The method of claim 18, wherein the cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae, Aspergillus niger, Saccharomyces cerevisiae, Corynebacterium glutamicum*, and *Yarrowia lipolytica*.

20. The method of claim 6, wherein the cells produce greater than 400 nmole/gwcm/hour of isoprene and the carbon dioxide evolution rate of the cells is greater than $1\times10^{-18}$ mmol/L/hour.

* * * * *